US008715686B2

(12) United States Patent
Kwong et al.

(10) Patent No.: US 8,715,686 B2
(45) Date of Patent: *May 6, 2014

(54) CONFORMATIONALLY STABILIZED HIV ENVELOPE IMMUNOGENS

(75) Inventors: Peter Kwong, Washington, DC (US); John Mascola, Rockville, MD (US); Gary Nabel, Washington, DC (US); Richard Wyatt, Rockville, MD (US); Barna Dey, Germantown, MD (US); Ling Xu, Potomac, MD (US); Tongqing Zhou, Boyds, MD (US); Joseph Sodroski, Boston, MA (US); Wen Yuan, Brighton, MA (US); Shi-Hua Xiang, Boston, MA (US)

(73) Assignees: The United States of America, as represented by the Secretary, Department of Health and Human Services, Washington, DC (US); Dana-Faber Cancer Institute, Inc., Boston, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/585,700

(22) Filed: Aug. 14, 2012

(65) Prior Publication Data

US 2012/0328641 A1 Dec. 27, 2012

Related U.S. Application Data

(60) Continuation of application No. 13/232,775, filed on Sep. 14, 2011, now Pat. No. 8,268,323, which is a division of application No. 12/065,894, filed as application No. PCT/US2006/034681 on Sep. 6, 2006, now Pat. No. 8,044,185.

(60) Provisional application No. 60/713,725, filed on Sep. 6, 2005, provisional application No. 60/729,878, filed on Oct. 24, 2005, provisional application No. 60/731,627, filed on Oct. 28, 2005, provisional application No. 60/832,458, filed on Jul. 20, 2006.

(51) Int. Cl.
*A61K 39/21* (2006.01)

(52) U.S. Cl.
USPC ...................... 424/188.1; 424/208.1

(58) Field of Classification Search
None
See application file for complete search history.

(56) References Cited

U.S. PATENT DOCUMENTS

| 5,869,624 | A | 2/1999 | Hasel et al. |
| 5,922,325 | A | 7/1999 | Tilley et al. |
| 6,432,675 | B1 | 8/2002 | Crea |
| 6,710,173 | B1 | 3/2004 | Binley et al. |
| 6,716,429 | B1 | 4/2004 | Sodroski et al. |
| 6,908,617 | B1 | 6/2005 | Wyatt et al. |
| 7,022,324 | B2 | 4/2006 | Binley et al. |
| 7,048,929 | B1 | 5/2006 | Sodroski et al. |
| 8,268,323 | B2 * | 9/2012 | Kwong et al. ............. 424/188.1 |
| 2005/0025779 | A1 | 2/2005 | Berman et al. |

FOREIGN PATENT DOCUMENTS

| WO | WO 99/24465 | 5/1999 |
| WO | WO 99/24553 | 5/1999 |
| WO | WO 00/58438 | 10/2000 |
| WO | WO 01/72123 | 10/2001 |
| WO | WO 2007/030637 | 3/2007 |

OTHER PUBLICATIONS

Ashish et al., "Binding of Full-length HIV-1 gp120 to CD4 Induces Structural Reorientation Around the gp120 Core," *Biophysical Journal-Biophysical Letters*, pp. L01-L03 (2006).
Burton et al., HIV vaccine design and the neutralizing antibody problem, *Nature Immunology*, 5(3):233-236 (2004).
Burton, Dennis R., "Antibodies, viruses and vaccines," *Nature Review*, 2:706-713 (2002).
Chen et al., "Determining the Structure of an Unliganded and Fully Glycosylated SIV gp120 Envelope Glycoprotein," *Structure, Current Biology Ltd.*, 13(2):197-211 (2005).
Desrosiers, "Prospects for an AIDS vaccine," *Nature Medicine*, vol. 10, pp. 221-223 (2004).
Dey et al., "Neutralizing of Human Immunodeficiency Virus Type 1 by sCD4-17b, a Single-Chain Chimeric Protein, Based on Sequential Interaction of gp120 with CD4 and Coreceptor," *Journal of Virology*, 77(5):2859-2865 (2003).
Huang et al., "Scorpion-Toxin Mimics of CD4 in Complex with Human Immunodeficiency Virus gp120: Crystal Structures, Molecular Mimicry, and Neutralization Breadth," *Structure*, 13:755-768 (2005).
Huang et al., "Structure of a V3-Containing HIV-1 gp120 Core," *Science*, 310:1025-1028 (2005).
Korber et al., "Numbering Positions in HIV Relative to HXB2CG," *Human Retroviruses and AIDS*, pp. III-102 to III-111 (1998).
Kwong et al., "HIV-1 GP120 Core Complexed with CD4 and a Neutralizing Human Antibody," *Nature*, 393(648):1-105 (1998).
Kwong et al., "Structure of an HIV GP 120 Envelope Glycoprotein in Complex with the CD4 Receptor and a Neutralizing Human Antibody," *Nature*, 393:648-659 (1998).
Kwong et al., "Structures of HIV-1 gp120 envelope glycoprotein from laboratory-adapted and primary isolates," *Structures, Current Biology Ltd.*, 8(12):1329-1339 (2000).
Moulard et al., "Broadly cross-reactive HIV-1-neutralizing human monocolonal Fab selected for binding to gp120-CD4-CCR5 complexes," *PNAS*, 99(10):6913-6918 (2002).
Myszka et al., "Energetics of the HIV gp120-CD4 binding reaction," *PNAS*, 97(16):9026-9031 (2000).
Pan et al., "CD4 Binding Partially Locks the Bridging Sheet in gp120 but Leaves the beta2/3 Strands Flexible," *Journal of Molecular Biology*, 350(3):514-527 (2005).

(Continued)

*Primary Examiner* — Jeffrey Parkin
(74) *Attorney, Agent, or Firm* — Klarquist Sparkman, LLP

(57) ABSTRACT

Isolated immunogens including a HIV-1 gp120 polypeptide or immunogenic fragment thereof stabilized in a CD4 bound confirmation by crosslinked cysteines, and methods of their use are disclosed. The immunogens are useful, for example, for generating an immune response to HIV-1 gp120 in a subject.

20 Claims, 32 Drawing Sheets

(56) References Cited

OTHER PUBLICATIONS

Reynard et al., "HIV-1 acute infection env glycomutants designed from 3D model: effects on processing, antigenicity, and neutralization sensitivity," *Virology*, 324(1):90-102 (2004).

Satoh et al., "Bioactive Peptide Design Based on Protein Surface Epitopes," *The Journal of Biological Chemistry*, 272(18): 12175-12180 (1997).

Schülke et al., "Oligomeric and Conformational Properties of a Proteolytically Mature Disulfide-Stabilized Human Immunodeficiency Virus Type 1 gp140 Envelope Glycoprotein," *Journal of Virology*, 76(15):7760-7776 (2002).

Stanfield et al., "Recurring conformation of the human immunodeficiency virus type 1 gp120 V3 loop," *Virology*, 315(1):159-173 (2003). Abstract only.

Wang et al., "Uncommon gp120 Cysteine Residues Found in Primary HIV-1 Isolates," *Aids Research and Human Retroviruses*, 11(1):185-188 (1995).

Wyatt et al., "Structure of the Core of the HIV-1 gp120 Exterior Envelope Glycoprotein," *Analysis*, pp. III-3-III-9 (1998).

Wyatt et al., "The Antigenic Structure of the HIV gp120 Envelope Glycoprotein," *Nature*, 393:705-711 (1998).

Xiang et al., "CD4-Bound Conformation of HIV-1 gp120 Improved by Introduced Disulfide Bonds," 9th Conference on Retroviruses and Opportunistic Infections, 2002 <http://www.retroconference.org/2002/Abstract/12607.htm>.

Xiang et al., "Mutagenic Stabilization and/or Disruption of a CD4-Bound State Reveals Distinct Conformations of the Human Immunodeficiency Virus Type 1 gp120 Envelope Glycoprotein," *Journal of Virology*, 76(19):9888-9899 (2002).

Yang et al., "Characterization of the Outer Domain of the gp120 Glycoprotein from Human Immunodeficiency Virus Type 1," *Journal of Virology*, 78(23):12975-12986 (2004).

\* cited by examiner

HxBc2 Core 8b=C123S12

Animal 60594

| Serum Dilution | BD-1 Sera | Peptide | % Neut | fraction remain. virus | % inhib | fold effect |
|---|---|---|---|---|---|---|
| 1:10 | 30594 HxBc2 Core - 8b mutan | Mock | 82 | 0.183 | | |
| | | V3 Scr | 79 | 0.214 | 4% | 1.169 |
| | | YU2 V3 peptide | 27 | 0.727 | 67% | 3.977 |
| | | YU2 V1/2 pool 1 | 81 | 0.191 | 1% | 1.046 |
| | | YU2 V1/2 pool 2 | 81 | 0.192 | 1% | 1.050 |
| 1:40 | 30594 HxBc2 Core - 8b mutan | Mock | 58 | 0.419 | | |
| | | V3 Scr | 58 | 0.424 | 1% | 1.011 |
| | | YU2 V3 peptide | 16 | 0.835 | 72% | 1.994 |
| | | YU2 V1/2 pool 1 | 59 | 0.410 | -2% | 0.978 |
| | | YU2 V1/2 pool 2 | 57 | 0.429 | 2% | 1.024 |
| 1:160 | 30594 HxBc2 Core - 8b mutan | Mock | 29 | 0.713 | | |
| | | V3 Scr | 27 | 0.732 | 6% | 97% |
| | | YU2 V3 peptide | 7 | 0.932 | 75% | 97% |
| | | YU2 V1/2 pool 1 | 32 | 0.678 | -12% | 98% |
| | | YU2 V1/2 pool 2 | 28 | 0.716 | 1% | 98% |
| 1:640 | 30594 HxBc2 Core - 8b mutan | Mock | 5 | 0.947 | | |
| | | V3 Scr | 10 | 0.896 | -97% | 0.946 |
| | | YU2 V3 peptide | 8 | 0.923 | -46% | 0.974 |
| | | YU2 V1/2 pool 1 | 19 | 0.806 | -265% | 0.852 |
| | | YU2 V1/2 pool 2 | 13 | 0.868 | -150% | 0.916 |

Virus: YU2.SG3
Peptides: YU2 V3, YU2 V1/V2 Pools 1 and 2 all 20 µg/ml
Cells: TZM-BL cells
Sera: BD-1 Rabbit Sera Post-5

Animal 60595

| Serum Dilution | BD-1 Sera | Peptide | % Neut | fraction remain. virus | % inhib | fold effect |
|---|---|---|---|---|---|---|
| 1:10 | 30595 HxBc2 Core - 8b mutan | Mock | 73 | 0.269 | | |
| | | V3 Scr | 69 | 0.305 | 5% | 1.133 |
| | | YU2 V3 peptide | 26 | 0.743 | 65% | 2.757 |
| | | YU2 V1/2 pool 1 | 69 | 0.306 | 5% | 1.136 |
| | | YU2 V1/2 pool 2 | 70 | 0.298 | 4% | 1.108 |
| 1:40 | 30595 HxBc2 Core - 8b mutan | Mock | 44 | 0.563 | | |
| | | V3 Scr | 44 | 0.559 | -1% | 0.993 |
| | | YU2 V3 peptide | 16 | 0.836 | 63% | 1.485 |
| | | YU2 V1/2 pool 1 | 41 | 0.592 | 6% | 1.050 |
| | | YU2 V1/2 pool 2 | 43 | 0.566 | 1% | 1.006 |
| | | V3 Scr | 8 | 0.918 | 50% | 1.100 |
| | | YU2 V3 peptide | 2 | 0.980 | 88% | 1.174 |
| | | YU2 V1/2 pool 1 | 21 | 0.795 | -24% | 0.952 |
| | | YU2 V1/2 pool 2 | 17 | 0.833 | -1% | 0.998 |
| 1:640 | 30595 HxBc2 Core - 8b mutan | Mock | 9 | 0.908 | | |
| | | V3 Scr | 8 | 0.923 | 16% | 1.105 |
| | | YU2 V3 peptide | 2 | 0.977 | 75% | 1.170 |
| | | YU2 V1/2 pool 1 | 8 | 0.924 | 17% | 1.107 |
| | | YU2 V1/2 pool 2 | 5 | 0.953 | 49% | 1.141 |

A
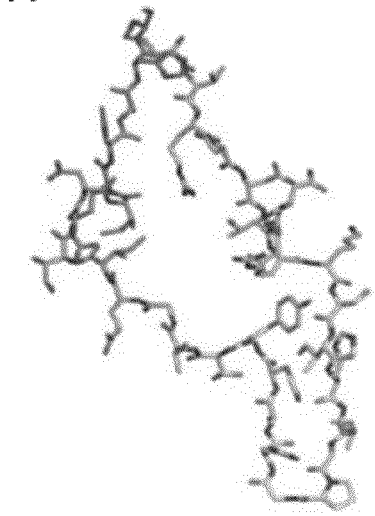
JR-FL(core+V3):d1d2:X5
50.1
447-52D
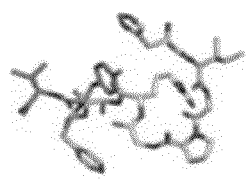
59.1
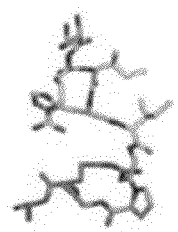
83.1
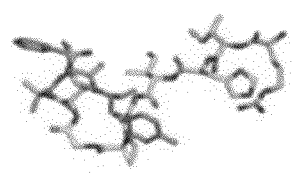
58.2
B
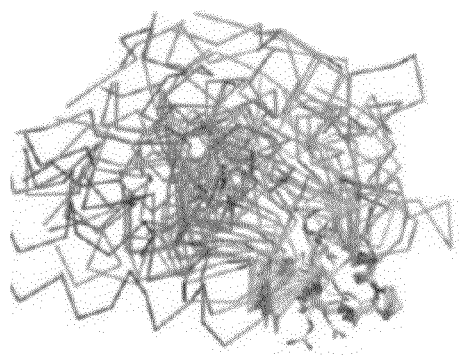
Free V3
0.5β
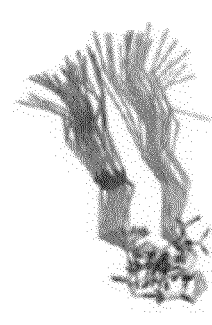
447-52D
FIG. 11

New V1/2 for HxBc2 9c mutant

B-turn after Leu125

B-turn right after Cys123

FIG. 13

```
New hxbc2 core gp120 with shorter V1/V1 and new V3

9596           109            123
                                         ||             |              |
Hxbc2_core_      EVVLVNVTENFNMWKNDMVEQMHEDIISLWDQSLKPCVKLTPLCVGAGSCNTSVITQACP
New_9c_          EVVLVNVTENFNWCKNDMVEQMHEDICSLWDQSLKPCVKLCPLA-----GATSVITQACP
                 ************  ************ *************          *********
                                                                      257
                                                                       |
Hxbc2_core_      KVSFEPIPIHYCAPAGFAILKCNNKTFNGTGPCTNVSTVQCTHGIRPVVSTQLLLNGSLA
New_9c_          KVSFEPIPIHYCAPAGFAILKCNNKTFNGTGPCTNVSTVQCTHGIRPVVSSQLLLNGSLA
                 **************************************************:*********
                       275
                        |
Hxbc2_core_      EEEVVIRSVNFTDNAKTIIVQLNTSVEINCT-------GAG-------------------
New_9c_          EEEVVIRSCNFTDNAKTIIVQLNTSVEINCTRPNNGGSGSG-----------------GN
                 ******** *********************       *:*
                                                                375
                                                                 |
Hxbc2_core_      ----HCNISRAKWNNTLKQIASKLREQFGNNKTIIFKQSSGGDPEIVTHSFNCGGEFFYC
New_9c_          MRQAHCNISRAKWNNTLKQIASKLREQFGNNKTIIFKQSSGGDPEIVTHWFNCGGEFFYC
                     ******************************************** **********
                                                             428 431
                                                               |  |
Hxbc2_core_      NSTQLFNSTWFNSTWSTEGSNNTEGSDTITLPCRIKQIINMWQKVGKAMYAPPISGQIRC
New_9c_          NSTQLFNSTWFNSTWSTEGSNNTEGSDTITLPCRIKQIINMWCKVCKAMYAPPISGQIRC
                 ***************************************** ** **************

Hxbc2_core_      SSNITGLLLTRDGGNSNNESEIFRPGGGDMRDNWRSELYKYKVVKIE
New_9c_          SSNITGLLLTRDGGNSNNESEIFRPGGGDMRDNWRSELYKYKVVKIE
                 ***********************************************

Labels: 9c mutations, old core sequence, new design
```

DM or C2
Gtgaagagagggctctgctgtgtgctgctgctgtgtggagcagtcttcgtttcgcccagccaggaaatccatgc
ccgattcagaagaggagccagatctgaggtggtgctggtgaacgtgaccgagaacttcaacatgtggaagaacg
acatggtggagcagatgcacgaggacatcatcagcctgtgggaccagagcctgaagccctgcgtgaagctgacc
cccctgtgcgtgggcgccggcagctgcaacaccagcgtgatcacccaggcctgccccaaggtgagcttcgagcc
catccccatccactactgcgcccccgccggcttcgccatcctgaagtgcaacaacaagaccttcaacggcaccg
gcccctgcaccaacgtgagcaccgtgcagtgcacccacggcatccgccccgtggtgagcagtcagctgctgctg
aacggcagcctggccgaggaggaggtggtgatccgcagcgtgaacttcaccgacaacgccaagaccatcatcgt
gcagctgaacaccagcgtggagatcaactgcaccggcgccggccactgcaacatcgcccgcgccaagtggaaca
acaccctgaagcagatcgccagcaagctgcgcgagcagttcggcaacaacaagaccatcatcttcaagcagagc
agcggcggcgaccccgagatcgtgacccactggttcaactgcggcggcgagttcttctactgcaacagcaccca
gctgttcaacagcacctggttcaacagcacctggagcaccgagggcagcaacaacaccgagggcagcgacacca
tcaccctgccctgccgcatcaagcagatcatcaacatgtggcagaaggtgggcaaggccatgtacgccccccc
atcagcggccagatccgctgcagcagcaacatcaccggcctgctgctgacccgcgacggcggcaacagcaacaa
cgagagcgagatcttccgtccgggcggcggcgacatgcgcgacaactggcgcagcgagctgtacaagtacaagg
tggtgaagatcgagtga (SEQ ID NO:3)

4a or C2S2
Gtgaagagagggctctgctgtgtgctgctgctgtgtggagcagtcttcgtttcgcccagccaggaaatccatgc
ccgattcagaagaggagccagatctgaggtggtgctggtgaacgtgaccgagaacttcaacatgtggaagaacg
acatggtggagcagatgcacgaggacatctgtagcctgtgggaccagagcctgaagccctgcgtgaagctgacc
cccctgtgcgtgggcgccggcagctgcaacaccagcgtgatcacccaggcctgccccaaggtgagcttcgagcc
catccccatccactactgcgcccccgccggcttcgccatcctgaagtgcaacaacaagaccttcaacggcaccg
gcccctgcaccaacgtgagcaccgtgcagtgcacccacggcatccgccccgtggtgagcagtcagctgctgctg
aacggcagcctggccgaggaggaggtggtgatccgcagcgtgaacttcaccgacaacgccaagaccatcatcgt
gcagctgaacaccagcgtggagatcaactgcaccggcgccggccactgcaacatcgcccgcgccaagtggaaca
acaccctgaagcagatcgccagcaagctgcgcgagcagttcggcaacaacaagaccatcatcttcaagcagagc
agcggcggcgaccccgagatcgtgacccactggttcaactgcggcggcgagttcttctactgcaacagcaccca
gctgttcaacagcacctggttcaacagcacctggagcaccgagggcagcaacaacaccgagggcagcgacacca
tcaccctgccctgccgcatcaagcagatcatcaacatgtggtgtaaggtgggcaaggccatgtacgccccccc
atcagcggccagatccgctgcagcagcaacatcaccggcctgctgctgacccgcgacggcggcaacagcaacaa
cgagagcgagatcttccgtccgggcggcggcgacatgcgcgacaactggcgcagcgagctgtacaagtacaagg
tggtgaagatcgagtga (SEQ ID NO: 4)

4b or C2S4
Gtgaagagagggctctgctgtgtgctgctgctgtgtggagcagtcttcgtttcgcccagccaggaaatccatgc
ccgattcagaagaggagccagatctgaggtggtgctggtgaacgtgaccgagaacttcaacatgtggaagaacg
acatggtggagcagatgcacgaggacatcatcagcctgtgggaccagagcctgaagccctgcgtgaagctgacc
cccctgtgcgtgggcgccggcagctgcaacaccagcgtgatcacccaggcctgccccaaggtgagcttcgagcc
catccccatccactactgcgcccccgccggcttcgccatcctgaagtgcaacaactgtaccttcaacggctaccg
gcccctgcaccaacgtgagcaccgtgcagtgcacccacggcatccgccccgtggtgagcagtcagctgctgctg
aacggcagcctggcatgcgaggaggtggtgatccgcagcgtgaacttcaccgacaacgccaagaccatcatcgt
gcagctgaacaccagcgtggagatcaactgcaccggcgccggccactgcaacatcgcccgcgccaagtggaaca
acaccctgaagcagatcgccagcaagctgcgcgagcagttcggcaacaacaagaccatcatcttcaagcagagc
agcggcggcgaccccgagatcgtgacccactggttcaactgcggcggcgagttcttctactgcaacagcaccca
gctgttcaacagcacctggttcaacagcacctggagcaccgagggcagcaacaacaccgagggcagcgacacca
tcaccctgccctgccgcatcaagcagatcatcaacatgtggcagaaggtgggcaaggccatgtacgccccccc
atcagcggccagatccgctgcagcagcaacatcaccggcctgctgctgacccgcgacggcggcaacagcaacaa
cgagagcgagatcttccgtccgggcggcggcgacatgcgcgacaactggcgcagcgagctgtacaagtacaagg
tggtgaagatcgagtga (SEQ ID NO: 5)

FIG. 14A 4c or C2S3
Gtgaagagagggctctgctgtgtgctgctgctgtgtggagcagtcttcgtttcgcccagccaggaaatc
catgcccgattcagaagaggagccagatctgaggtggtgctggtgaacgtgaccgagaacttcaacatg
tggaagaacgacatggtggagcagatgcacgaggacatcatcagcctgtgggaccagagcctgaagccc
tgcgtgaagctgtgtcccctgtgcgtgggcgccggcagctgcaacaccagcgtgatcacccaggcctgc
cccaaggtgagcttcgagcccatccccatccactactgcgccccgccggcttcgccatcctgaagtgc
aacaacaagaccttcaacggcaccggcccctgcaccaacgtgagcaccgtgcagtgcacccacggcatc
cgccccgtggtgagcagtcagctgctgctgaacggcagcctggccgaggaggaggtggtgatccgcagc
gtgaacttcaccgacaacgccaagaccatcatcgtgcagctgaacaccagcgtggagatcaactgcacc
ggcgccggccactgcaacatcgcccgcgccaagtggaacaacaccctgaagcagatcgccagcaagctg
cgcgagcagttcggcaacaacaagaccatcatcttcaagcagagcagcggcggcgaccccgagatcgtg
acccactggttcaactgcggcggcgagttcttctactgcaacagcacccagctgttcaacagcacctgg
ttcaacagcacctggagcaccgagggcagcaacaacaccgagggcagcgacaccatcaccctgccctgc
cgcatcaagcagatcatcaacatgtggcagaaggtgtgtaaggccatgtacgccccccccatcagcggc
cagatccgctgcagcagcaacatcaccggcctgctgctgacccgcgacggcggcaacagcaacaacgag
agcgagatcttccgtccgggcggcggcgacatgcgcgacaactggcgcagcgagctgtacaagtacaag
gtggtgaagatcgagtga (SEQ ID NO:6)

6a or C123S1
Gtgaagagagggctctgctgtgtgctgctgctgtgtggagcagtcttcgtttcgcccagccaggaaatc
catgcccgattcagaagaggagccagatctgaggtggtgctggtgaacgtgaccgagaacttcaactgg
tgcaagaacgacatggtggagcagatgcacgaggacatctgtagcctgtgggaccagagcctgaagccc
tgcgtgaagctgacccccctgtgcgtgggcgccggcagctgcaacaccagcgtgatcacccaggcctgc
cccaaggtgagcttcgagcccatccccatccactactgcgccccgccggcttcgccatcctgaagtgc
aacaacaagaccttcaacggcaccggcccctgcaccaacgtgagcaccgtgcagtgcacccacggcatc
cgccccgtggtgagcagtcagctgctgctgaacggcagcctggccgaggaggaggtggtgatcagatct
tgcaacttcaccgacaacgccaagaccatcatcgtgcagctgaacaccagcgtggagatcaactgcacc
ggcgccggccactgcaacatcgcccgcgccaagtggaacaacaccctgaagcagatcgccagcaagctg
cgcgagcagttcggcaacaacaagaccatcatcttcaagcagagcagcggcggcgaccccgagatcgtg
acccactggttcaactgcggcggcgagttcttctactgcaacagcacccagctgttcaacagcacctgg
ttcaacagcacctggagcaccgagggcagcaacaacaccgagggcagcgacaccatcaccctgccctgc
cgcatcaagcagatcattaatatgtggtgtaaggtgggcaagatgatgtacgccccccccatcagcggc
cagatccgctgcagcagcaacatcaccggcctgctgctgacccgcgacggcggcaacagcaacaacgag
agcgagatcttccgtccgggcggcggcgacatgcgcgacaactggcgcagcgagctgtacaagtacaag
gtggtgaagatcgagtga (SEQ ID NO: 7)

6b or C2S24
Gtgaagagagggctctgctgtgtgctgctgctgtgtggagcagtcttcgtttcgcccagccaggaaatc
catgcccgattcagaagaggagccagatctgaggtggtgctggtgaacgtgaccgagaacttcaacatg
tggaagaacgacatggtggagcagatgcacgaggacatctgtagcctgtgggaccagagcctgaagccc
tgcgtgaagctgacccccctgtgcgtgggcgccggcagctgcaacaccagcgtgatcacccaggcctgc
cccaaggtgagcttcgagcccatccccatccactactgcgccccgccggcttcgccatcctgaagtgc
aacaactgtaccttcaacgtaccggcccctgcaccaacgtgagcaccgtgcagtgcacccacggcatc
cgccccgtggtgagcagtcagctgctgctgaacggcagcctggcatgcgaggaggtggtgatccgcagc
gtgaacttcaccgacaacgccaagaccatcatcgtgcagctgaacaccagcgtggagatcaactgcacc
ggcgccggccactgcaacatcgcccgcgccaagtggaacaacaccctgaagcagatcgccagcaagctg
cgcgagcagttcggcaacaacaagaccatcatcttcaagcagagcagcggcggcgaccccgagatcgtg
acccactggttcaactgcggcggcgagttcttctactgcaacagcacccagctgttcaacagcacctgg
ttcaacagcacctggagcaccgagggcagcaacaacaccgagggcagcgacaccatcaccctgccctgc
cgcatcaagcagatcattaatatgtggtgtaaggtgggcaaggccatgtacgccccccccatcagcggc
cagatccgctgcagcagcaacatcaccggcctgctgctgacccgcgacggcggcaacagcaacaacgag
agcgagatcttccgtccgggcggcggcgacatgcgcgacaactggcgcagcgagctgtacaagtacaag
gtggtgaagatcgagtga (SEQ ID NO: 8)

FIG. 14B 8a or C123S14
Gtgaagagagggctctgctgtgtgctgctgctgtgtggagcagtcttcgtttcgcccagccaggaaatccatg
cccgattcagaagaggagccagatctgaggtggtgctggtgaacgtgaccgagaacttcaactggtgcaagaa
cgacatggtggagcagatgcacgaggacatcatcagcctgtgggaccagagcctgaagccctgcgtgaagctg
acccccctgtgcgtgggcgccggcagctgcaacaccagcgtgatcacccaggcctgccccaaggtgagcttcg
agcccatccccatccactactgcgccccgccggcttcgccatcctgaagtgcaacaactgtaccttcaacgg
taccggccctgcaccaacgtgagcaccgtgcagtgcacccacggcatccgcccgtggtgagcagtcagctg
ctgctgaacggcagcctggcatgcgaggaggtggtgatcagatcttgcaacttcaccgacaacgccaagacca
tcatcgtgcagctgaacaccagcgtggagatcaactgcaccggcgccggccactgcaacatcgcccgcgccaa
gtggaacaacaccctgaagcagatcgccagcaagctgcgcgagcagttcggcaacaacaagaccatcatcttc
aagcagagcagcggcggcgaccccgagatcgtgacccactggttcaactgcggcggcgagttcttctactgca
acagcacccagctgttcaacagcacctggttcaacagcacctggagcaccgagggcagcaacaacaccgaggg
cagcgacaccatcaccctgccctgccgcatcaagcagatcatcaatatgtggcagaaggtgggcaagatgatg
tacgcccccccatcagcggccagatccgctgcagcagcaacatcaccggcctgctgctgacccgcgacggcg
gcaacagcaacaacgagagcgagatcttccgtccgggcggcggcgacatgcgcgacaactggcgcagcgagct
gtacaagtacaaggtggtgaagatcgagtga (SEQ ID NO: 9)

8b or C123S12
Gtgaagagagggctctgctgtgtgctgctgctgtgtggagcagtcttcgtttcgcccagccaggaaatccatg
cccgattcagaagaggagccagatctgaggtggtgctggtgaacgtgaccgagaacttcaactggtgcaagaa
cgacatggtggagcagatgcacgaggacatctgtagcctgtgggaccagagcctgaagccctgcgtgaagctg
acccccctgtgcgtgggcgccggcagctgcaacaccagcgtgatcacccaggcctgccccaaggtgagcttcg
agcccatccccatccactactgcgccccgccggcttcgccatcctgaagtgcaacaacaagaccttcaacgg
caccggccctgcaccaacgtgagcaccgtgcagtgcacccacggcatccgcccgtggtgagcagtcagctg
ctgctgaacggcagcctggccgaggaggaggtggtgatcagatcttgcaacttcaccgacaacgccaagacca
tcatcgtgcagctgaacaccagcgtggagatcaactgcaccggcgccggccactgcaacatcgcccgcgccaa
gtggaacaacaccctgaagcagatcgccagcaagctgcgcgagcagttcggcaacaacaagaccatcatcttc
aagcagagcagcggcggcgaccccgagatcgtgacccactggttcaactgcggcggcgagttcttctactgca
acagcacccagctgttcaacagcacctggttcaacagcacctggagcaccgagggcagcaacaacaccgaggg
cagcgacaccatcaccctgccctgccgcatcaagcagatcattaatatgtggtgtaaggtgggcaagatgatg
tacgcccccccatcagcggccagatccgctgcagcagcaacatcaccggcctgctgctgacccgcgacggcg
gcaacagcaacaacgagagcgagatcttccgtccgggcggcggcgacatgcgcgacaactggcgcagcgagct
gtacaagtacaaggtggtgaagatcgagtga (SEQ ID NO: 10)

8c or C2S234
Gtgaagagagggctctgctgtgtgctgctgctgtgtggagcagtcttcgtttcgcccagccaggaaatccatg
cccgattcagaagaggagccagatctgaggtggtgctggtgaacgtgaccgagaacatgtggaagaa
cgacatggtggagcagatgcacgaggacatctgtagcctgtgggaccagagcctgaagccctgcgtgaagctt
tgtcccctgtgcgtgggcgccggcagctgcaacaccagcgtgatcacccaggcctgccccaaggtgagcttcg
agcccatccccatccactactgcgccccgccggcttcgccatcctgaagtgcaacaactgtaccttcaacgg
taccggccctgcaccaacgtgagcaccgtgcagtgcacccacggcatccgcccgtggtgagcagtcagctg
ctgctgaacggcagcctggcatgcgaggaggtggtgatccgcagcgtgaacttcaccgacaacgccaagacca
tcatcgtgcagctgaacaccagcgtggagatcaactgcaccggcgccggccactgcaacatcgcccgcgccaa
gtggaacaacaccctgaagcagatcgccagcaagctgcgcgagcagttcggcaacaacaagaccatcatcttc
aagcagagcagcggcggcgaccccgagatcgtgacccactggttcaactgcggcggcgagttcttctactgca
acagcacccagctgttcaacagcacctggttcaacagcacctggagcaccgagggcagcaacaacaccgaggg
cagcgacaccatcaccctgccctgccgcatcaagcagatcattaatatgtggtgtaaggtgtgtaaggccatg
tacgcccccccatcagcggccagatccgctgcagcagcaacatcaccggcctgctgctgacccgcgacggcg
gcaacagcaacaacgagagcgagatcttccgtccgggcggcggcgacatgcgcgacaactggcgcagcgagct
gtacaagtacaaggtggtgaagatcgagtga (SEQ ID NO: 11)

FIG. 14C 9a or C23S234
Gtgaagagagggctctgctgtgtgctgctgctgtgtggagcagtcttcgtttcgcccagccaggaaatcc
atgcccgattcagaagaggagccagatctgaggtggtgctggtgaacgtgaccgagaacttcaacatgtg
gaagaacgacatggtggagcagatgcacgaggacatctgtagcctgtgggaccagagcctgaagccctgc
gtgaagctttgtccctgtgcgtgggcgccggcagctgcaacaccagcgtgatcacccaggcctgcccca
aggtgagcttcgagcccatccccatccactactgcgccccgccggcttcgccatcctgaagtgcaacaa
ctgtaccttcaacggtaccggccctgcaccaacgtgagcaccgtgcagtgcacccacggcatccgcccc
gtggtgagcagtcagctgctgctgaacggcagcctggcatgcgaggaggtggtgatccgcagcgtgaact
tcaccgacaacgccaagaccatcatcgtgcagctgaacaccagcgtggagatcaactgcaccggcgccgg
ccactgcaacatcgcccgcgccaagtggaacaaccctgaagcagatcgccagcaagctgcgcgagcag
ttcggcaacaacaagaccatcatcttcaagcagagcagcggcggcgaccccgagatcgtgacccactggt
tcaactgcggcggcgagttcttctactgcaacagcacccagctgttcaacagcacctggttcaacagcac
ctggagcaccgagggcagcaacaacaccgagggcagcgacaccatcaccctgccctgccgcatcaagcag
atcattaatatgtggtgtaaggtgtgtaagatgatgtacgccccccgatatcaggccagatccgctgca
gcagcaacatcaccggcctgctgctgacccgcgacggcggcaacagcaacaacgagagcgagatcttccg
tccgggcggcggcgacatgcgcgacaactggcgcagcgagctgtacaagtacaaggtggtgaagatcgag
tga (SEQ ID NO:12)

9b or C12S134
Gtgaagagagggctctgctgtgtgctgctgctgtgtggagcagtcttcgtttcgcccagccaggaaatcc
atgcccgattcagaagaggagccagatctgaggtggtgctggtgaacgtgaccgagaacttcaactggtg
caagaacgacatggtggagcagatgcacgaggacatcatcagcctgtgggaccagagcctgaagccctgc
gtgaagctttgtccctgtgcgtgggcgccggcagctgcaacaccagcgtgatcacccaggcctgcccca
aggtgagcttcgagcccatccccatccactactgcgccccgccggcttcgccatcctgaagtgcaacaa
ctgtaccttcaacggtaccggccctgcaccaacgtgagcaccgtgcagtgcacccacggcatccgcccc
gtggtgagcagtcagctgctgctgaacggcagcctggcatgcgaggaggtggtgatcagatcttgcaact
tcaccgacaacgccaagaccatcatcgtgcagctgaacaccagcgtggagatcaactgcaccggcgccgg
ccactgcaacatcgcccgcgccaagtggaacaaccctgaagcagatcgccagcaagctgcgcgagcag
ttcggcaacaacaagaccatcatcttcaagcagagcagcggcggcgaccccgagatcgtgacccactggt
tcaactgcggcggcgagttcttctactgcaacagcacccagctgttcaacagcacctggttcaacagcac
ctggagcaccgagggcagcaacaacaccgagggcagcgacaccatcaccctgccctgccgcatcaagcag
atcatcaacatgtggcagaaggtgtgtaaggccatgtacgccccccccatcagcggccagatccgctgca
gcagcaacatcaccggcctgctgctgacccgcgacggcggcaacagcaacaacgagagcgagatcttccg
tccgggcggcggcgacatgcgcgacaactggcgcagcgagctgtacaagtacaaggtggtgaagatcgag
tga (SEQ ID NO:13)

9c or C12S123
Gtgaagagagggctctgctgtgtgctgctgctgtgtggagcagtcttcgtttcgcccagccaggaaatcc
atgcccgattcagaagaggagccagatctgaggtggtgctggtgaacgtgaccgagaacttcaactggtg
caagaacgacatggtggagcagatgcacgaggacatctgtagcctgtgggaccagagcctgaagccctgc
gtgaagctgtgtccctgtgcgtgggcgccggcagctgcaacaccagcgtgatcacccaggcctgcccca
aggtgagcttcgagcccatccccatccactactgcgccccgctggcttcgccatcctgaagtgcaacaa
caagaccttcaacggcaccggccctgcaccaacgtgagcaccgtgcagtgcacccacggcatccgcccc
gtggtgagcagtcagctgctgctgaacggcagcctggccgaggaggaggtggtgatcagatcttgcaact
tcaccgacaacgccaagaccatcatcgtgcagctgaacaccagcgtggagatcaactgcaccggcgccgg
ccactgcaacatcgcccgcgccaagtggaacaaccctgaagcagatcgccagcaagctgcgcgagcag
ttcggcaacaacaagaccatcatcttcaagcagagcagcggcggcgaccccgagatcgtgacccactggt
tcaactgcggcggcgagttcttctactgcaacagcacccagctgttcaacagcacctggttcaacagcac
ctggagcaccgagggcagcaacaacaccgagggcagcgacaccatcaccctgccctgccgcatcaagcag
atcatcaacatgtggtgtaaggtgtgtaaggccatgtacgccccccccatcagcggccagatccgctgca
gcagcaacatcaccggcctgctgctgacccgcgacggcggcaacagcaacaacgagagcgagatcttccg
tccgggcggcggcgacatgcgcgacaactggcgcagcgagctgtacaagtacaaggtggtgaagatcgag
tga (SEQ ID NO: 14)

FIG. 14D 10a or C123S124
Gtgaagagagggctctgctgtgctgctgctgtgtggagcagtcttcgtttcgcccagccaggaaatccatgcccgattcagaaga
ggagccagatctgaggtggtgctggtgaacgtgaccgagaacttcaactggtgcaagaacgacatggtggagcagatgcacga
ggacatctgtagcctgtgggaccagagcctgaagccctgcgtgaagctgacccctgtgcgtgggcgccggcagctgcaacac
cagcgtgatcacccaggcctgccccaaggtgagcttcgagcccatccccatccactactgcgccccgccggcttcgccatcctg
aagtgcaacaactgtaccttcaacggtaccggcccctgcaccaacgtgagcacgtgcagtgcacccacggcatccgccccgtg
gtgagcagtcagctgctgctgaacggcagcctggcatgcgaggaggtggtgatcagatcttgcaacttcaccgacaacgccaag
accatcatcgtgcagctgaacaccagcgtggagatcaactgcaccggcgccggccactgcaacatcgcccgcgccaagtgga
acaacaccctgaagcagatcgccagcaagctgcgcgagcagttcggcaacaacaagaccatcatcttcaagcagagcagcg
gcggcgaccccgagatcgtgacccactggttcaactgcggcggcgagttcttctactgcaacagcacccagctgttcaacagcac
ctggttcaacagcacctggagcaccgagggcagcaacaacaccgagggcagcgacaccatcaccctgccctgccgcatcaa
gcagatcattaatatgtggtgtaaggtgggcaagatgatgtacgccccccccatcagcggccagatccgctgcagcagcaacatc
accggcctgctgctgaccccgcgacggcggcaacagcaacaacgagagcgagatcttccgtccgggcggcggcgacatgcgc
gacaactggcgcagcgagctgtacaagtacaaggtggtgaagatcgagtga (SEQ ID NO: 15)

10b or C123S123
Atgaagagagggctctgctgtgctgctgctgtgtggagcagtcttcgtttcgcccagccaggaaatccatgcccgattcagaaga
ggagccagatctgaggtggtgctggtgaacgtgaccgagaacttcaactggtgcaagaacgacatggtggagcagatgcacga
ggacatctgtagcctgtgggaccagagcctgaagccctgcgtgaagctgtgtccctgtgcgtgggcgccggcagctgcaacacc
agcgtgatcacccaggcctgccccaaggtgagcttcgagcccatccccatccactactgcgcccccgctggcttcgccatcctga
agtgcaacaacaagaccttcaacggcaccggcccctgcaccaacgtgagcacgtgcagtgcacccacggcatccgccccgt
ggtgagcagtcagctgctgctgaacggcagcctggcgaggaggaggtggtgatcagatcttgcaacttcaccgacaacgccaa
gaccatcatcgtgcagctgaacaccagcgtggagatcaactgcaccggcgccggccactgcaacatgcccgcgccaagtgg
aacaacaccctgaagcagatcgccagcaagctgcgcgagcagttcggcaacaacaagaccatcatcttcaagcagagcagc
ggcggcgaccccgagatcgtgacccactggttcaactgcggcggcgagttcttctactgcaacagcacccagctgttcaacagca
cctggttcaacagcacctggagcaccgagggcagcaacaacacgagggcagcgacaccatcaccctgccctgccgcatcaa
gcagatcatcaacatgtggtgtaaggtgtgtaagatgatgtacgccccccccatcagcggccagatccgctgcagcagcaacatc
accggcctgctgctgaccccgcgacggcggcaacagcaacaacgagagcgagatcttccgtccgggcggcggcgacatgcgc
gacaactggcgcagcgagctgtacaagtacaaggtggtgaagatcgagtgag (SEQ ID NO: 16)

10c or C123S134
Gtgaagagagggctctgctgtgctgctgctgtgtggagcagtcttcgtttcgcccagccaggaaatccatgcccgattcagaaga
ggagccagatctgaggtggtgctggtgaacgtgaccgagaacttcaactggtgcaagaacgacatggtggagcagatgcacga
ggacatcatcagcctgtgggaccagagcctgaagccctgcgtgaagctttgtccctgtgcgtgggcgccggcagctgcaacacc
agcgtgatcacccaggcctgccccaaggtgagcttcgagcccatccccatccactactgcgcccccgccggcttcgccatcctga
agtgcaacaactgtaccttcaacggtaccggccctgcaccaacgtgagcacgtgcagtgcacccacggcatccgccccgtgg
tgagcagtcagctgctgctgaacggcagcctggcatgcgaggaggtggtgatcagatcttgcaacttcaccgacaacgccaaga
ccatcatcgtgcagctgaacaccagcgtggagatcaactgcaccggcgccggccactgcaacatcgcccgcgccaagtggaa
caacaccctgaagcagatcgccagcaagctgcgcgagcagttcggcaacaacaagaccatcatcttcaagcagagcagcggc
ggcgaccccgagatcgtgacccactggttcaactgcggcggcgagttcttctactgcaacagcacccagctgttcaacagcacct
ggttcaacagcacctggagcaccgagggcagcaacaacaccgagggcagcgacaccatcaccctgccctgccgcatcaagc
agatcatcaatatgtggcagaaggtgtgtaaggccatgtacgccccccccatcagcggccagatccgctgcagcagcaacatca
ccggcctgctgctgaccccgcgacggcggcaacagcaacaacgagagcgagatcttccgtccggcggcggcgacatgcgcg
acaactggcgcagcgagctgtacaagtacaaggtggtgaagatcgagtga (SEQ ID NO: 17)

FIG. 14E 11a or C12S1234
Gtgaagagagggctctgctgtgtgctgctgctgtgtggagcagtcttcgtttcgcccagccaggaaat
ccatgcccgattcagaagaggagccagatctgaggtggtgctggtgaacgtgaccgagaacttcaact
ggtgcaagaacgacatggtggagcagatgcacgaggacatctgtagcctgtgggaccagagcctgaag
ccctgcgtgaagctgtgtcccctgtgcgtgggcgccggcagctgcaacaccagcgtgatcacccaggc
ctgccccaaggtgagcttcgagcccatccccatccactactgcgccccgccggcttcgccatcctga
agtgcaacaactgtaccttcaacggtaccggccctgcaccaacgtgagcaccgtgcagtgcacccac
ggcatccgcccgtggtgagcagtcagctgctgctgaacggcagcctggcatgcgaggaggtggtgat
cagatcttgcaacttcaccgacaacgccaagaccatcatcgtgcagctgaacaccagcgtggagatca
actgcaccggcgccggccactgcaacatcgcccgcgccaagtggaacaacaccctgaagcagatcgcc
agcaagctgcgcgagcagttcggcaacaacaagaccatcatcttcaagcagagcagcggcggcgaccc
cgagatcgtgacccactggttcaactgcggcggcgagttcttctactgcaacagcacccagctgttca
acagcacctggttcaacagcacctggagcaccgagggcagcaacaacaccgagggcagcgacaccatc
accctgccctgccgcatcaagcagatcatcaacatgtggtgtaaggtgtgtaaggccatgtacgcccc
ccccatcagcggccagatccgctgcagcagcaacatcaccggcctgctgctgacccgcgacggcggca
acagcaacaacgagagcgagatcttccgtccgggcggcggcgacatgcgcgacaactggcgcagcgag
ctgtacaagtacaaggtggtgaagatcgagtga (SEQ ID NO: 18)

HxBc2Core wt
Gtgaagagagggctctgctgtgtgctgctgctgtgtggagcagtcttcgtttcgcccagccaggaaat
ccatgcccgattcagaagaggagccagatctgaggtggtgctggtgaacgtgaccgagaacttcaaca
tgtggaagaacgacatggtggagcagatgcacgaggacatcatcagcctgtgggaccagagcctgaag
ccctgcgtgaagctgaccccctgtgcgtgggcgccggcagctgcaacaccagcgtgatcacccaggc
ctgccccaaggtgagcttcgagcccatccccatccactactgcgccccgccggcttcgccatcctga
agtgcaacaacaagaccttcaacggcaccggccctgcaccaacgtgagcaccgtgcagtgcacccac
ggcatccgcccgtggtgagcacccagctgctgctgaacggcagcctggccgaggaggaggtggtgat
ccgcagcgtgaacttcaccgacaacgccaagaccatcatcgtgcagctgaacaccagcgtggagatca
actgcaccggcgccggccactgcaacatcgcccgcgccaagtggaacaacaccctgaagcagatcgcc
agcaagctgcgcgagcagttcggcaacaacaagaccatcatcttcaagcagagcagcggcggcgaccc
cgagatcgtgacccacagcttcaactgcggcggcgagttcttctactgcaacagcacccagctgttca
acagcacctggttcaacagcacctggagcaccgagggcagcaacaacaccgagggcagcgacaccatc
accctgccctgccgcatcaagcagatcatcaacatgtggcagaaggtgggcaaggccatgtacgcccc
ccccatcagcggccagatccgctgcagcagcaacatcaccggcctgctgctgacccgcgacggcggca
acagcaacaacgagagcgagatcttccgtccgggcggcggcgacatgcgcgacaactggcgcagcgag
ctgtacaagtacaaggtggtgaagatcgagtga (SEQ ID NO: 19)

New Core9c
Gtgaagagagggctctgctgtgtgctgctgctgtgtggagcagtcttcgtttcgcccagccaggaaat
ccatgcccgattcagaagaggagccagatctgaggtggtgctggtgaacgtgaccgagaacttcaact
ggtgcaagaacgacatggtggagcagatgcacgaggacatctgtagcctgtgggaccagagcctgaag
ccctgcgtgaagctgtgtcctctggccggcgccaccagcgtgatcacccaggcctgccccaaggtgag
cttcgagcccatccccatccactactgcgccccgctggcttcgccatcctgaagtgcaacaacaaga
ccttcaacggcaccggccctgcaccaacgtgagcaccgtgcagtgcacccacggcatccgcccgtg
gtgagcagtcagctgctgctgaacggcagcctggccgaggaggaggtggtgatcagatcttgcaactt
caccgacaacgccaagaccatcatcgtgcagctgaacaccagcgtggagatcaactgcacccgcccca
acaacggcggcagcggcagcggcggcaacatgcgccaggcccactgcaacatcagccgcgccaagtgg
aacaacaccctgaagcagatcgccagcaagctgcgcgagcagttcggcaacaacaagaccatcatctt
caagcagagcagcggcggcgaccccgagatcgtgacccactggttcaactgcggcggcgagttcttct
actgcaacagcacccagctgttcaacagcacctggttcaacagcacctggagcaccgagggcagcaac
aacaccgagggcagcgacaccatcaccctgccctgccgcatcaagcagatcatcaacatgtggtgtaa
ggtgtgtaaggccatgtacgcccccccatcagcggccagatccgctgcagcagcaacatcaccggcc
tgctgctgacccgcgacggcggcaacagcaacaacgagagcgagatcttccgtccgggcggcggcgac
atgcgcgacaactggcgcagcgagctgtacaagtacaaggtggtgaagatcgagtga (SEQ ID
NO: 26)

FIG. 14F

Measurement of thermodynamic properties of p120 upon ligand binding (by ITC)

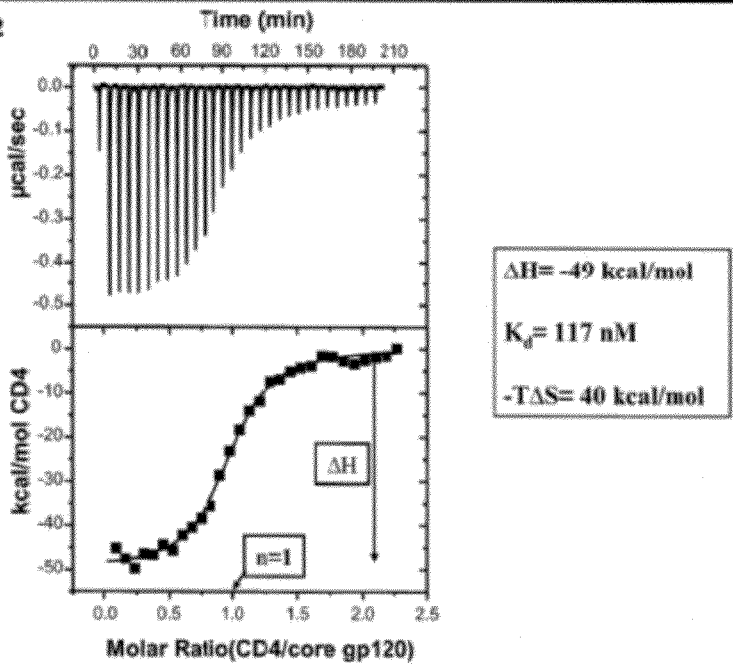

Titration of HXBc2 core with sCD4(D1D2) at 37°C $\Delta H = -49$ kcal/mol $K_d = 117$ nM $-T\Delta S = 40$ kcal/mol

Comparison of thermodynamic values of CD4-gp10 binding

| Protein | $\Delta H$ (kcal/mol) | $-T\Delta S$ (kcal/mol) | $K_d$ (nM) to sCD4 |
|---|---|---|---|
| HXcore WT | -49.7 +/- 1.77 | 40.0 +/- 1.77 | 87 |
| C2 | -51.3 +/- 1.82 | 39.0 +/- 1.81 | 1.5 |
| C2S2 | -29.3 +/- 1.04 | 17.2 +/- 1.04 | 2.5 |
| C2S3 | -46.4 +/- 1.97 | 26.8 +/- 1.97 | 1 |
| C2S4 | -39.4 +/- 2.32 | 34.2 +/- 2.32 | 3 |
| C123S1 | -38.8 +/- 2.06 | 28.3 +/- 2.06 | 35 |
| C123S12 | -30.0 +/- 1.07 | 18.5 +/- 1.08 | 6 |
| C12S123 | -31.4 +/- 1.60 | 18.9 +/- 1.60 | 1 |
| New C12S123 | -27.75 +/- 1.11 | 15.62 +/- 1.11 | 3 |
| NewC12S1234 | -27.47 +/- 1.39 | 15.24 +/- 1.39 | 2 |

FIG. 15

447 – V3 mAb
39F – V3 mAb
82-2 – GP sera from dCFldV12 clade (BaL)
9427 – Baboon sera; gp140GCN-4 (YU2)

6535

H

Percent Neutralization based on sCD4 baseline

I

J

ADA
Percent Neutralization based on sCD4 baseline

Effect of sCD4
- 447 (10 ug/ml)
- % inhibition by sCD4

K

Effect of sCD4
- Sera 82-2 (1:10)
- Sera 82-4 (1:10)
- % inhibition by sCD4

82-2, 82-4 are each GP sera from dCFIdV12 clade (BaL)

FIGs. 16J-16K 5-2, 21-4 are each GP sera from dCFI clade C

ZA12

N
Effect of sCD4
- 17b (10 ug/ml)
- % inh. by sCD4

O
Effect of sCD4
- Sera 5-2 (1:10)
- Sera 21-2 (1:5)
- % inh. by sCD4

5-2, 21-4 are each GP sera from dCFI clade C

Q 5-2, 21-4 are each GP sera from dCFI clade C

CONFORMATIONALLY STABILIZED HIV ENVELOPE IMMUNOGENS

CROSS REFERENCE TO RELATED APPLICATION

This application is a continuation application of U.S. patent application Ser. No. 13/232,775, filed Sep. 14, 2011, now U.S. Pat. No. 8,268,323, which is a divisional application of U.S. patent application Ser. No. 12/065,894, filed Mar. 5, 2008, now U.S. Pat. No. 8,044,185, which is the U.S. §371 National Stage of International Application No. PCT/US2006/034681, filed Sep. 6, 2006, published in English under PCT Article 21(2), which in turn claims the benefit of U.S. Provisional Application No: 60/713,725, filed Sep. 6, 2005; U.S. Provisional Application No: 60/729,878, filed Oct. 24, 2005; U.S. Provisional Application No: 60/731,627, filed Oct. 28, 2005; and U.S. Provisional Application No: 60/832,458, filed Jul. 20, 2006. All of the prior applications are incorporated by reference herein in their entirety.

FIELD

The present disclosure relates to stabilized forms of human immunodeficiency virus gp120 envelope protein, specifically to crystalline forms of gp120, high resolution structures obtained from these crystals, and use thereof.

BACKGROUND

The primary immunologic abnormality resulting from infection by human immunodeficiency virus (HIV) is the progressive depletion and functional impairment of T lymphocytes expressing the CD4 cell surface glycoprotein. The loss of CD4 helper/inducer T cell function probably underlies the profound defects in cellular and humoral immunity leading to the opportunistic infections and malignancies characteristic of the acquired immunodeficiency syndrome (AIDS) (Lane et al., *Ann. Rev. Immunol.* 3:477, 1985). Studies of HIV-1 infection of fractionated CD4 and CD8 T cells from normal donors and AIDS patients have revealed that depletion of CD4 T cells results from the ability of HIV-1 to selectively infect, replicate in, and ultimately destroy this T lymphocyte subset (Klatzmann et al., *Science* 225:59, 1984). The possibility that CD4 itself is an essential component of the cellular receptor for HIV-1 was first indicated by the observation that monoclonal antibodies directed against CD4 block HIV-1 infection and syncytia induction (Dalgleish et al., *Nature* 312:767, 1984; McDougal et al., *J. Immunol.* 135:3151, 1985). This hypothesis has been confirmed by the demonstration that a molecular complex forms between CD4 and the major envelope glycoprotein of HIV-1 (McDougal et al., *Science* 231:382, 1986)

The major envelope protein of HIV-1 is a glycoprotein of approximately 160 kD (160). During infection proteases of the host cell cleave gp160 into gp120 and gp41. gp41 is an integral membrane protein, while gp120 protrudes from the mature virus. Together gp120 and gp41 make up the HIV envelope spike.

The HIV envelope spike mediates binding to receptors and virus entry (Wyatt and Sodroski, *Science* 280:188, 1998). The spike is trimeric and composed of three gp120 exterior and three gp41 transmembrane envelope glycoproteins. CD4 binding to gp120 in the spike induces conformational changes that allow binding to a coreceptor, either CCR5 or CXCR4, which is required for viral entry (Dalgleish et al., *Nature* 312:763, 1984; Sattentau and Moore, *J. Exp. Med.* 174:407, 1991; Feng at al., *Science* 272:872, 1996; Wu et al., *Nature* 384:179, 1996; Trkola et al., *Nature* 384:184, 1996).

The mature gp120 glycoprotein is approximately 470-490 amino acids long depending on the HIV strain of origin. N-linked glycosylation at approximately 20-25 sites makes up nearly half of the mass of the molecule. Sequence analysis shows that the polypeptide is composed of five conserved regions (C1-C5) and five regions of high variability (V1-V5).

With the number of individuals infected by HIV-1 approaching 1% of the world's population, an effective vaccine is urgently needed. An enveloped virus, HIV-1 hides from humoral recognition behind a protective lipid bilayer. An available viral target for neutralizing antibodies is the envelope spike. Genetic, immunologic and structural studies of the HIV-1 envelope glycoproteins have revealed extraordinary diversity as well as multiple overlapping mechanisms of humoral evasion, including self-masquerading glycan, immunodominant variable loops, and conformational masking. These evolutionarily honed bathers of diversity and evasion have confounded traditional means of vaccine development. It is believed that immunization with effectively immunogenic HIV gp120 envelope glycoprotein can elicit a neutralizing response directed against gp120, and thus HIV. The need exists for immunogens that are capable of eliciting an immunogenic response in a suitable subject. In order to be effective, the antibodies raised must be capable of neutralizing a broad range of HIV strains and subtypes.

SUMMARY OF THE DISCLOSURE

Disclosed herein are gp120 polypeptides and nucleic acid molecules encoding gp120 polypeptides, which are useful to induce an immunogenic response to a lentivirus, such as SIV or HIV (for example HIV-1 and HIV-II) in a subject. In several embodiments, the gp120 polypeptides are stabilized in a CD4 bound conformation by the introduction of a plurality of non-naturally occurring cross-linking cysteine residues. In other examples, the gp120 polypeptide has the V3 loop in an extended conformation.

Immunogenic compositions containing a therapeutically effective amount of gp120 polypeptides and nucleic acid molecules encoding gp120 polypeptides are also disclosed. Also disclosed are methods for eliciting and/or enhancing an immune response in a subject, for example by administering an immunogenic composition.

Crystalline forms of gp120 are disclosed as are crystal structures of gp120 polypeptides obtained from these structures. Methods are also disclosed for identifying an immunogen that induces an immune response to gp120 using these crystal structures. Also provided by this disclosure is a machine readable data storage medium including a data storage material encoded with machine readable data corresponding to the coordinates of the crystal structures disclosed herein. A computer system is disclosed for displaying the coordinate data from these crystal structures of gp120, such as the atomic positions, surface, domain, or region of the gp120 polypeptide.

The foregoing and other objects, features, and advantages of the invention will become more apparent from the following detailed description, which proceeds with reference to the accompanying figures.

BRIEF DESCRIPTION OF THE DRAWINGS

FIG. 11 is a set of computer generated images that show the alignment of V3 peptide:antibody structures with V3 in the context of core gp120. FIG. 11 (A) X-ray structures. The structures of V3 are shown either in the context of core gp120 or bound to antibody 50.1, 447-52D, 59.1, 83.1, or 58.2. FIG. 11 (B) Nuclear magnetic resonance (NMR) structures. The NMR ensembles are shown for free V3), as well as for V3 peptides bound to antibodies, 0.5β and 447-52D. All structures are aligned with the conserved Pro-Gly of the tip.

FIG. 13 is an alignment of the amino acid sequences of the HXBc2 core (SEQ ID NO: 20) with the New HXBc2 9c (SEQ ID NO: 1).

FIG. 14 are nucleotide sequences that encode HXBc2 gp120 WT and stabilized forms thereof. FIG. 14A is a nucleotide sequence of gp120 HXBc2 DM (SEQ ID NO: 3), a nucleotide sequence of gp120 HXBc2 Core4a (SEQ ID NO: 4), and a nucleotide sequence of gp120 HXBc2 Core 4b (SEQ ID NO: 5). FIG. 14 B is a nucleotide sequence of gp120 HXBc2 Core4c (SEQ ID NO: 6), a nucleotide sequence of gp120 HXBc2 Core6a (SEQ ID NO: 7), and a nucleotide sequence of gp120 HXBc2 Core6b (SEQ ID NO: 8). FIG. 14C is a nucleotide sequence of gp120 HXBc2 Core8a (SEQ ID NO: 9), a nucleotide sequence of gp120 HXBc2 Core8b (SEQ ID NO: 10), and a nucleotide sequence of gp120 HXBc2 Core8c (SEQ ID NO: 11). FIG. 14D is a nucleotide sequence of gp120 HXBc2 Core9a (SEQ ID NO: 12), a nucleotide sequence of gp120 HXBc2 Core9b (SEQ ID NO: 13), and a nucleotide sequence of gp120 HXBc2 Core9c (SEQ ID NO: 14). FIG. 14E is a nucleotide sequence of gp120 HXBc2 Core10a (SEQ ID NO: 15), a nucleotide sequence of gp120 HXBc2 Core10b (SEQ ID NO: 16), and a nucleotide sequence of gp120 HXBc2 Core10c (SEQ ID NO: 17). FIG. 14F is a nucleotide sequence of gp120 HXBc2 Core11a (SEQ ID NO: 18), a nucleotide sequence of wild type (WT) gp120 HXBc2 (SEQ ID NO: 19), and a nucleotide sequence of gp120 HXBc2 Core New 9c.

FIG. 15 is an example of an isothermal titration calorimetry curve for the binding of a soluble form of CD4 to a gp120 polypeptide. Thermodynamic properties describing this molecular interaction can be extracted from such a curve. The table shows the extracted thermodynamic parameters of a selected set of gp120 polypeptides binding to a soluble form of gp120. The collection of such data and the extraction thermodynamic parameters is well known in the art.

FIG. 16 D is a line graph shows percent neutralization of mAb 447 with the indicated amount of sCD4 present (x-axis), calculated after affect of sCD4 is taken into account. The diamonds (♦) show the affect of sCD4 alone. The circles (●) show the combined effect of sCD4 plus mAb 447. The diamonds (♦) show the percent neutralization calculated based on the level of virus entry with sCD4 present. FIG. 16 H is a line graph of the neutralization of virus 6535 by mAbs 447 and 17b.

SEQUENCE LISTING AND NOMENCLATURE

Figure 1:
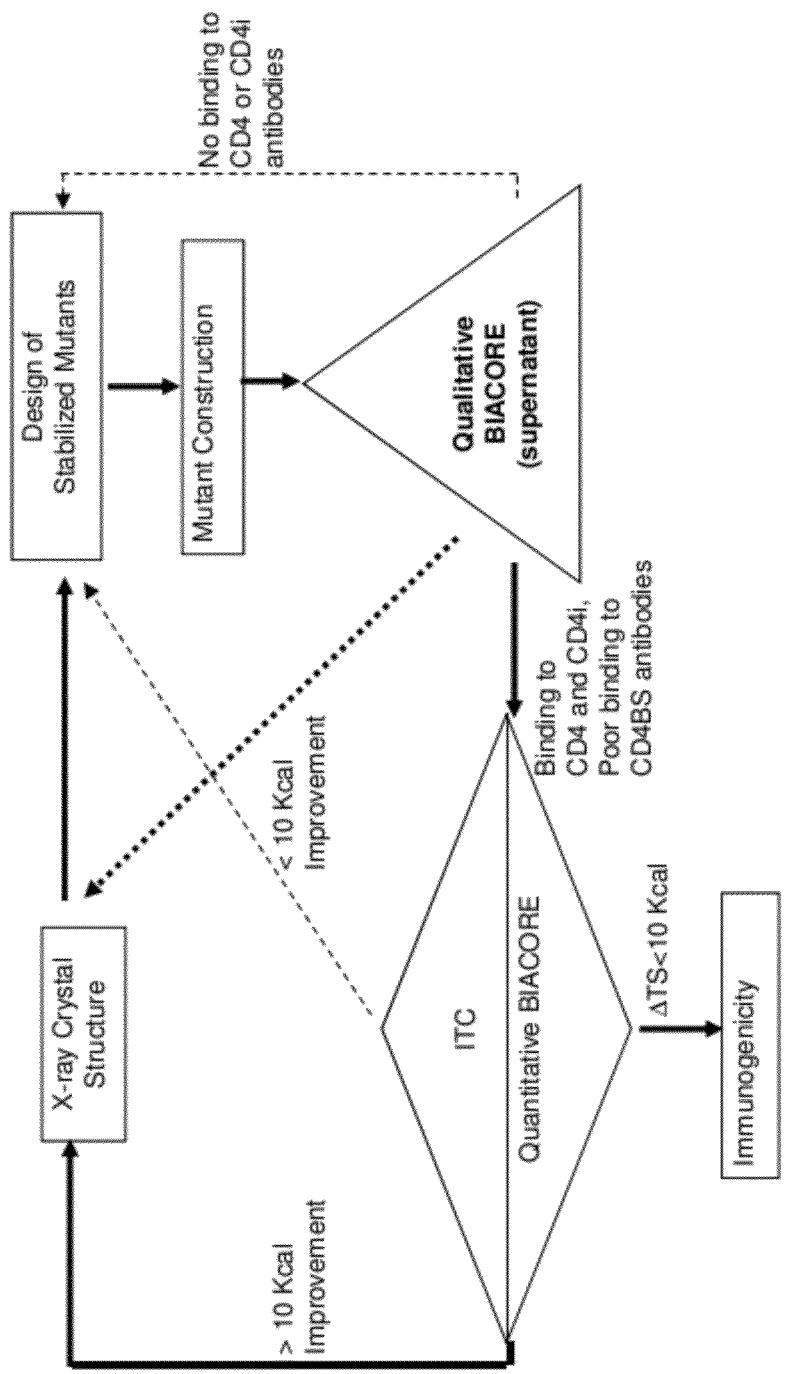
FIG. 1 is a schematic representation of the development cycle for gp120 immunogens stabilized in the CD4-bound conformation. Qualitative Biacore analysis was used as an initial screen to determine if CD4 and the CD4 induced (CD4i) antibodies still bound. Isothermal titration calorimetry (ITC) and crystal structure determination were used to refine the gp120 immunogens.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the amino acid sequence of gp120 HXBc2 Core New 9c.
SEQ ID NO: 2 the amino acid sequence of the gp120 with an extended V3 loop.
SEQ ID NO: 3 is a nucleotide sequence of gp120 HXBc2 DM.
SEQ ID NOs: 4-18 are nucleotide sequences of stabilized HXBc2 Core gp120.
SEQ ID NO: 19 is a nucleotide sequence of wild type (WT) HXBc2.
SEQ ID NO: 20 is the amino acid sequence of wild type (WT) HXBc2.
SEQ ID NO: 21-25 are amino acid sequences of V3 loops.
SEQ ID NO: 26 is a nucleotide sequence of gp120 HXBc2 Core New 9c.
SEQ ID NO: 27 is the amino acid sequence of gp120 HXB2CG.

Nomenclature Conversion for Conformationally Stabilized HXBc2 Mutants

| Mutant Name WT core | New name WT core | T257S S375W C2 | A433M C3 | M95W W96C V275C C1S1 | I109C Q428C S2 | T123C G431C S3 | K231C E267C S4 | K231C E268C S5 |
|---|---|---|---|---|---|---|---|---|
| 2a | C2 | x | | | | | | |
| 4-0 | C2S5 | x | | | | | | x |
| 4a | C2S2 | x | | | x | | | |
| 4b | C2S4 | x | | | | | x | |
| 4c | C2S3 | x | | | | x | | |
| 5mut | C12S1 | x | | x | | | | |
| 6a | C123S1 | x | x | x | | | | |
| 6b | C2S24 | x | | | x | | x | |
| 8a | C123S14 | x | x | x | | | x | |
| 8b | C123S12 | x | x | x | x | | | |
| 9a | C23S234 | x | x | | | x | x | x |
| 8c | C2S234 | x | | | x | x | x | |
| 10a | C123S124 | x | x | x | x | | x | |
| 9b | C12S134 | x | | x | | x | x | |
| 10c | C123S134 | x | x | x | | x | x | |
| 9c | C12S123 | x | | x | x | x | | |
| 10b | C123S123 | x | x | x | x | x | | |
| 11a | C12S1234 | x | | x | x | x | x | |

DETAILED DESCRIPTION

I. Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Terms describing protein structure and structural elements of proteins can be found in Creighton, Proteins, Structures and Molecular Properties, W.H. Freeman & Co., New York, 1993 (ISBN 0-717-7030) which is incorporated by reference herein in its entirety.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All publications, patent applications, patents, and other references mentioned herein are incorporated by reference in their entirety. In case of conflict, the present specification, including explanations of terms, will control. In addition, all the materials, methods, and examples are illustrative and not intended to be limiting. In order to facilitate review of the various embodiments of the disclosure, the following explanations of specific terms are provided:

Adjuvant: A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides.

Administration: The introduction of a composition into a subject by a chosen route. For example, if the chosen route is intravenous, the composition is administered by introducing the composition into a vein of the subject.

Antibody: A polypeptide substantially encoded by an immunoglobulin gene or immunoglobulin genes, or fragments thereof, which specifically binds and recognizes an analyte (antigen) such as gp120 or an antigenic fragment of gp120. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (SCFvs) that bind to gp120 or fragments of gp120 would be gp120-specific binding agents. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies such as bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

Antigenic gp120 polypeptide: An "antigenic gp120 polypeptide" includes a gp120 molecule or a portion thereof that is capable of provoking an immune response in a mammal, such as a mammal with or without an HIV infection. Administration of an antigenic gp120 polypeptide that provokes an immune response preferably leads to protective immunity against HIV.

Antigenic surface: A surface of a molecule, for example a protein such as a gp120 protein or polypeptide, capable of eliciting an immune response. An antigenic surface includes the defining features of that surface, for example the three-dimensional shape and the surface charge. An antigenic surface includes both surfaces that occur on gp120 polypeptides as well as surfaces of compounds that mimic the surface of a gp120 polypeptide (mimetics).

CD4: Cluster of differentiation factor 4 polypeptide, a T-cell surface protein that mediates interaction with the MHC class II molecule. CD4 also serves as the primary receptor site for HIV on T-cells during HIV-1 infection.

The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

The term "CD4" includes polypeptide molecules that are derived from CD4 include fragments of CD4, generated either by chemical (for example enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., *Proc. Natl. Acad. Sci.* 92:6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4.

CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles that maintain the ability to functionally bind to a target molecule.

CD4BS antibodies: Antibodies that bind to or substantially overlap the CD4 binding surface of a gp120 polypeptide. The antibodies interfere with or prevent CD4 from binding to a gp120 polypeptide.

CD4i antibodies: Antibodies that bind to a conformation of gp120 induced by CD4 binding.

Contacting: Placement in direct physical association; includes both in solid and liquid form.

Computer readable media: Any medium or media, which can be read and accessed directly by a computer, so that the media is suitable for use in a computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Computer system: Hardware that can be used to analyze atomic coordinate data. The minimum hardware of a computer-based system typically comprises a central processing unit (CPU), an input device, for example a mouse, keyboard, and the like, an output device, and a data storage device. Desirably a monitor is provided to visualize structure data. The data storage device may be RAM or other means for accessing computer readable. Examples of such systems are microcomputer workstations available from Silicon Graphics Incorporated and Sun Microsystems running Unix based Windows NT or IBM OS/2 operating systems.

Degenerate variant and conservative variant: A polynucleotide encoding a polypeptide or an antibody that includes a sequence that is degenerate as a result of the genetic code. For example, a polynucleotide encoding a gp120 polypeptide or an antibody that binds gp120 that includes a sequence that is degenerate as a result of the genetic code. There are 20 natural amino acids, most of which are specified by more than one codon. Therefore, all degenerate nucleotide sequences are included as long as the amino acid sequence of the gp120 polypeptide or antibody that binds gp120 encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

Epitope: An antigenic determinant. These are particular chemical groups or peptide sequences on a molecule that are antigenic, such that they elicit a specific immune response. An antibody binds a particular antigenic epitope, such as an epitope of a gp120 polypeptide.

Expression: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

gp120: The envelope protein from Human Immunodeficiency Virus (HIV). The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (such as CCR5).

The mature gp120 wildtype polypeptides have about 500 amino acids in the primary sequence. Gp120 is heavily N-glycosylated giving rise to an apparent molecular weight of 120 kD. The polypeptide is comprised of five conserved regions (C1-C5) and five regions of high variability (V1-V5). Exemplary sequence of wt gp160 polypeptides are shown on GEN-BANK, for example accession numbers AAB05604 and AAD12142

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core comprises 25 beta strands, 5 alpha helices, and 10 defined loop segments.

"Stabilized gp120" is a form of gp120 polypeptide from HIV-1, characterized by an increase in $T_m$ over the wild type gp120. In some examples the gp120 is stabilized by the replacement of at least two amino acids of gp120 with cysteines such that a disulfide bond can form, wherein the gp120 protein has a $T_m$ of greater than about 53.8° C. The stabilized gp120 mutants may contain amino acid substitutions that fill cavities present in the core of native gp120. The stabilized gp120 can bind CD4. Stabilized forms of gp120 may include forms that have synthetic amino acids. Several exemplary stabilized gp120 proteins are disclosed herein.

Gp120 polypeptides also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants), genetic alleles, fusions proteins of gp120, or combinations thereof.

The third variable region referred to herein as the V3 loop is a loop of about 35 amino acids critical for the binding of the co-receptor and determination of which of the co-receptors will bind. In certain examples the V3 loop comprises residues 296-331.

The numbering used in gp120 polypeptides disclosed herein is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex. which is incorporated by reference herein in its entirety. For reference, the amino acid sequence of HXB2CG is given below as SEQ ID NO: 27:
lwvtvyygvpvwkeatttlfcasdakaydtevhnvwathacvptdpnpqevv
lvnvtenfnmwkndmveqmhediislwdqslkpcvkltplcvslkctdlk ndtntnsssgrmimekgeikncsfnistsirgkvqkeyaffykldiipidndtt sykltscntsvitqacpkvsfepipihycapagfailkcnnktfngtgpctnvstv qcthgirpvvstqlllngslaeeevvirsvnftdnaktiivqlntsveinctrpnnn trkririqrgpgrafvtigkignmrqahcnisrak wnntlkqiasklreqfgnnk-tiifkqssggdpeivthsfncggeffycnstqlfnstwfnstwstegsnntegsdt itlpcrikqiinmwqkvgkamyapp isgqircssnitglllltrdggnsnnese-ifrpgggdmrdnwrselykykvvkieplgvaptkakrrvvqrekr (SEQ ID NO: 27). HXB2 is also known as: HXBc2, for HXB clone 2; HXB2R, in the Los Alamos HIV database, with the R for revised, as it was slightly revised relative to the original HXB2 sequence; and HXB2CG in GenBank, for HXB2 complete genome.

Heavy atom derivatization: A method of producing a chemically modified form of a protein crystal, for example a crystal containing gp120. In practice, a crystal is soaked in a solution containing heavy metal atom salts, or organometallic compounds, such as lead chloride, gold thiomalate, thimerosal or uranyl acetate, which can diffuse through the solvent channels of the crystal and bind the surface of the protein. The location(s) of the bound heavy metal atom(s) can be determined by X-ray diffraction analysis of the soaked crystal. This information, in turn, is used to generate the phase information used to construct three-dimensional structure of the enzyme (see Blundel and Johnson, Protein Crystallography, Academic Press (1976).

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

In silico: A process performed virtually within a computer. For example, using a computer, a virtual compound can be screened for surface similarity or conversely surface complementarity to a virtual representation of the atomic positions at least a portion of a gp120 polypeptide, for example as stabilized gp120, such as defined in Table 1 or a gp120 with an extended V3 loop, such as defined in Table 2.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (for example antibody production) against the antigen from which the immunogenic peptide is derived.

In one embodiment, immunogenic peptides are identified using sequence motifs or other methods, such as neural net or polynomial determinations known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of gp120, or a fragment thereof.

Immunogenic composition: A composition comprising an immunogenic peptide that induces a measurable CTL response against virus expressing the immunogenic peptide, or induces a measurable B cell response (such as production of antibodies) against the immunogenic peptide. In one example an "immunogenic composition" is composition comprising a gp120 polypeptide that induces a measurable CTL response against virus expressing gp120 polypeptide, or induces a measurable B cell response (such as production of antibodies) against a gp120 polypeptide. It further refers to isolated nucleic acids encoding an immunogenic peptide, such as a nucleic acid that can be used to express the gp120 polypeptide (and thus be used to elicit an immune response against this polypeptide).

For in vitro use, an immunogenic composition may consist of the isolated protein, peptide epitope, or nucleic acid encoding the protein, or peptide epitope. For in vivo use, the immunogenic composition will typically comprise the protein or immunogenic peptide in pharmaceutically acceptable carriers, and/or other agents. Any particular peptide, such as a gp120 polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment is normally about pH 7 (such as from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Immunotherapy: A method of evoking an immune response against a virus based on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Inhibiting or treating a disease: Inhibiting the full development of a disease or condition, for example, in a subject who is at risk for a disease such as acquired immune deficiency syndrome (AIDS), AIDS related conditions, HIV-1 infection, or combinations thereof. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid, peptide or protein) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids.

$K_d$: The dissociation constant for a given interaction, such as a polypeptide ligand interaction. For example, for the bimolecular interaction of CD4 and gp120 it is the concentration of the individual components of the bimolecular interaction divided by the concentration of the complex.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes).

Ligand: Any molecule which specifically binds a protein, such as a gp120 protein, and includes, inter alia, antibodies that specifically bind a gp120 protein. In alternative embodiments, the ligand is a protein or a small molecule (one with a molecular weight less than 6 kiloDaltons).

Mimetic: A molecule (such as an organic chemical compound) that mimics the activity of an agent, such as the activity of a gp120 protein, for example by inducing an immune response to gp120. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid side chains in the peptide, resulting in such peptido- and organomimetics of the peptides having substantial specific activity. For computer modeling applications, a pharmacophore is an idealized, three-dimensional definition of the structural requirements for biological activity. Peptido- and organomimetics can be designed to fit each pharmacophore with computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in computer assisted drug design.

Molecular Replacement: A method that involves generating a preliminary model, such as a model of a gp120 polypeptide, whose structure coordinates are unknown, by orienting and positioning a molecule whose structure coordinates are known (such as coordinates from Table 1) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown molecule (see Lattman, Methods in Enzymology, 115:55-77, 1985; Rossmann, ed., "The Molecular Replacement Method", Int. Sci. Rev. Ser., No. 13, Gordon & Breach, New York, 1972). Using the structure coordinates of gp120, such as a stabilized gp120 provided herein; molecular replacement may be used to determine the structure coordinates of a crystalline mutant or homologue of gp120, a different crystal form of gp120, or gp120 in complex with another molecule, such as an antibody, cell surface receptor, or combination thereof.

Naturally Occurring Amino Acids: L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, gamma.-carboxyglutamic acid, arginine, ornithine and lysine. Unless specifically indicated, all amino acids referred to in this application are in the L-form. "Synthetic amino acids" refers to amino acids that are not naturally found in proteins. Examples of synthetic amino acids used herein, include racemic mixtures of selenocysteine and selenomethionine. In addition, unnatural amino acids include the D or L forms of nor-leucine, para-nitrophenylalanine, homophenylalanine, para-fluorophenylalanine, 3-amino-2-benzylpropionic acid, homoarginine, and D-phenylalanine. The term "positively charged amino acid" refers to any naturally occurring or synthetic amino acid having a positively charged side chain under normal physiological conditions. Examples of positively charged naturally occurring amino acids are arginine, lysine and histidine. The term "negatively charged amino acid" refers to any naturally occurring or synthetic amino acid having a negatively charged side chain under normal physiological conditions. Examples of negatively charged naturally occurring amino acids are aspartic acid and glutamic acid. The term "hydrophobic amino acid" refers to any amino acid having an uncharged, nonpolar side chain that is relatively insoluble in water. Examples of naturally occurring hydrophobic amino acids are alanine, leucine, isoleucine, valine, proline, phenylalanine, tryptophan and methionine. The term "hydrophilic amino acid" refers to any amino acid having an uncharged, polar side chain that is relatively soluble in water. Examples of naturally occurring hydrophilic amino acids are serine, threonine, tyrosine, asparagine, glutamine, and cysteine.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide. A gp120 polynucleotide is a nucleic acid encoding a gp120 polypeptide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences and amino acids sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I. Theory and Nucleic Acid Preparation*, Laboratory Techniques in Biochemistry and Molecular Biology, Elsevier Science Ltd., NY, N.Y., 1993 and Ausubel et al. *Short Protocols in Molecular Biology*, 4th ed., John Wiley & Sons, Inc., 1999.

"Stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid. For example, a nucleic acid construct can include a polynucleotide sequence that hybridizes under high stringency or very high stringency, or even higher stringency conditions to a polynucleotide sequence that encodes SEQ ID NO: 1.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide Modifications: The present disclosure includes mutant gp120 peptides, as well as synthetic embodiments. In addition, analogues (non-peptide organic molecules), derivatives (chemically functionalized peptide molecules obtained starting with the disclosed peptide sequences) and variants (homologs) of gp120 can be utilized in the methods described herein. The peptides disclosed herein include a sequence of amino acids that can be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques. In one example, a mimetic mimics the antigenic activity generated by gp120 a mutant, a variant, fragment, or fusion thereof.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (such as glycosylation or phosphorylation). "Polypeptide" applies to amino acid polymers to naturally occurring amino acid polymers and non-naturally occurring amino acid polymer as well as in which one or more amino acid residue is a non-natural amino acid, for example an artificial chemical mimetic of a corresponding naturally occurring amino acid. In one embodiment, the polypeptide is a gp120 polypeptide, such as a stabilized gp120. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used interchangeably herein to refer to a polymer of amino acid residues.

Protein core: The protein core refers to the interior of a folded protein, which is substantially free of solvent exposure, such as solvent in the form of water molecules in solution. Typically, the protein core is predominately composed of hydrophobic or apolar amino acids. In some examples, a protein core may contain charged amino acids, for example aspartic acid, glutamic acid, arginine, and/or lysine. The inclusion of uncompensated charged amino acids (a compensated charged amino can be in the form of a salt bridge) in the protein core can lead to a destabilized protein. That is, a protein with a lower $T_m$ then a similar protein without an uncompensated charged amino acid in the protein core. In other examples, a protein core may have a cavity with in the protein core. Cavities are essentially voids within a folded protein where amino acids or amino acid side chains are not present. Such cavities can also destabilize a protein relative to a similar protein without a cavity. Thus, when creating a stabilized form of a protein, for example a stabilized form of gp120, it may be advantageous to substitute amino acid residues within the core in order to fill cavities present in the wild-type protein.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

The gp120 polypeptides disclosed herein, or antibodies that specifically bind gp120, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Space Group: The arrangement of symmetry elements of a crystal.

Structure coordinates: Mathematical coordinates derived from mathematical equations related to the patterns obtained on diffraction of a monochromatic beam of X-rays by the atoms (scattering centers) such as a gp120, a gp120:CD4 complex, a gp120:antibody complex, or combinations thereof in a crystal in crystal form. The diffraction data are used to calculate an electron density map of the repeating unit of the crystal. The electron density maps are used to establish the positions of the individual atoms within the unit cell of the crystal. In one example, the term "structure coordinates" refers to Cartesian coordinates derived from mathematical equations related to the patterns obtained on diffraction of a monochromatic beam of X-rays, such as by the atoms of a stabilized form of gp120 in crystal form.

Atomic coordinate data, such as that in Table 1 and Table 2 lists each atom by a unique number (column 2); the atom name in the context of the residue to which it belongs (column 3), for example CA refers to the alpha carbon of the peptide backbone (detailed descriptions of the atom identifiers for each residue can be found for example in Creighton, Proteins, Structures and Molecular Properties, W.H. Freeman & Co., New York, 1993); the amino acid residue in which the atom is located (column 4); the chain identifier (column 4') which may or may not be included, the number of the residue (column 5); the coordinates (for example, X, Y, Z) which define with respect to the crystallographic axes the atomic position (in Å) of the respective atom (columns 6, 7, and 8); the occupancy of the atom in the respective position (column 9); the "B-factor", which is the isotropic displacement parameter (in Å$^2$) and accounts for movement of the atom around its atomic center (column 10).

Those of ordinary skill in the art understand that a set of structure coordinates determined by X-ray crystallography is not without standard error. For the purpose of this disclosure, any set of structure coordinates for a stabilized form of gp120 or a gp120 with an extended V3 loop that have a root mean square deviation of protein backbone atoms (N, Cα, C and 0) of less than about 1.0 Angstroms when superimposed, such as about 0.75, or about 0.5, or about 0.25 Angstroms, using backbone atoms, on the structure coordinates listed in Table 1 or Table 2 shall (in the absence of an explicit statement to the contrary) be considered identical.

Subject: Living multi-cellular vertebrate organisms, a category that includes both human and veterinary subjects, including human and non-human mammals.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: Used in a generic sense, it includes treating agents, prophylactic agents, and replacement agents.

$T_m$: The temperature at which a change of state occurs. For example, the temperature at which gp120 undergoes a transition from the folded form to the unfolded form. Essentially this is the temperature at which the structure melts away.

Stabilized gp120 has a higher $T_m$ than native gp120. Another example would be the temperature at which a DNA duplex melts.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Unit Cell: The smallest building block of a crystal. The entire volume of a crystal may be constructed by regular assembly of such blocks. Each unit cell comprises a complete representation of the unit of pattern, the repetition of which builds produces a crystal lattice Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

HIV-1 is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

X5: An antibody that bonds a conformation of gp120 induced by the binding of CD4. Antibodies that bind to gp120 in a conformation induced by CD4 binding are termed CD4i antibodies.

ΔS: The change in entropy, such as the change in entropy upon the association of gp120 and CD4 or an antibody or antibody fragment, for example X5.

ΔH: The change in the enthalpy, such as the change in enthalpy upon the association of gp120 and CD4 or an antibody.

II. Overview of Several Embodiments

Provided herein in various embodiments are gp120 polypeptides, which are useful to induce immunogenic response in vertebrate animals (such as mammals, for example primates, such as humans) to lentivirus, such as SIV or HIV (for example HIV-1 and HIV-2).

In several embodiments, the gp120 polypeptides are stabilized in a CD4 bound conformation. In several disclosed examples, the gp120 polypeptides are stabilized by modification. In certain examples, these modifications can be the introduction of a plurality of non-naturally occurring cross-linking cysteine residues. In certain examples, the modification can be the introduction of at least one amino acid substitution in the protein core of gp120.

In several disclosed examples, cysteines are introduced into the gp120 polypeptide at position 96, 109, 123, 231, 267, 275, 428, 431 or in combinations thereof. In some examples of gp120 polypeptides disclosed herein, the plurality of non-naturally occurring cross-linking cysteine residues are defined by the interaction and crosslinking of at least one of residue pairs 96 and 275; 109 and 428; 123 and 431; and 231 and 267. In some embodiments, all of the residue pairs 96 and 275; 109 and 428; 123 and 431; and 231 and 267 are crosslinked.

In some embodiments, the stabilized gp120 polypeptide contains one or more amino acid substitutions in the protein core. In several examples, the substitution is made at position 95, 257, 375, 433, or a combination thereof. In specific examples, the substitution is a serine to tryptophan substitution at position 95, a threonine to serine substitution at position 257, a serine to tryptophan substitution at position 375, an alanine to methionine substitution at position 433, or a combination thereof.

In specific examples, the stabilized gp120 polypeptide includes the amino acid sequence set forth as SEQ ID NO: 1 or is encoded by one of SEQ ID NO: 4, 5, 6, 7, 8, 10, 11, 12, 13, 14, 15, 16, 17, 18, or degenerate variants thereof. In still other embodiments, the stabilized gp120 contains a portion of the amino acid sequence set forth as SEQ ID NO: 1 or as encoded by any one of SEQ NOs: 4-18, for example, a domain such as the outer domain, or a contiguous stretch of about 5 or more amino acids, such as about 6, about 7, about 8, about 9, about 10, about 15, about 20, about 25, or more amino acids.

In other examples, the gp120 polypeptide has the V3 loop in an extended conformation. In one example, the gp120 polypeptide with the V3 loop in an extended conformation contains the amino acid sequence set forth as SEQ ID NO: 2. In other embodiments, the gp120 polypeptide with an extended v3 loop contains a portion of the amino acid sequence set forth as SED ID NO: 2, for example, a domain such as the outer domain, or a contiguous stretch of about 5 or more amino acids, such as about 6, about 7, about 8, about 9, about 10, about 15, about 20, about 25, or more amino acids wherein the domain or contiguous stretch of amino acids includes a portion of the V3 loop.

Other embodiments are compositions containing a therapeutically effective amount of at least one gp120 polypeptide, such as a stabilized gp120 polypeptide (such as set forth as SEQ ID NO: 1 or as encoded by the nucleotide sequence set forth as one of SEQ ID NO: 4, 5, 6, 7, 8, 10, 11, 12, 13, 14 15, 16, 17, and 18, or a degenerate variant thereof) or a gp120 polypeptide with the V3 loop in an extended conformation, such as the amino acid sequence set forth as SEQ NO: 2. In some embodiments, the composition can contain pharmaceutically acceptable carriers, adjuvants, or combinations thereof.

This disclosure further provides methods for eliciting and/or enhancing an immune response in a subject (such as a primate subject, for example a human subject). In some embodiments, these methods involve administering to the subject a composition including a gp120 polypeptide as disclosed herein, for example a stabilized gp120 such as set forth as SEQ ID NO: 1 or as encoded by the nucleotide sequence set forth as one of SEQ ID NO: 4, 5, 6, 7, 8, 10, 11, 12, 13, 14 15, 16, 17, and 18, or a degenerate variant thereof. In some embodiments, these methods involve administering to the subject a composition including a gp120 polypeptide with an extended V3 loop such as set forth as SEQ ID NO: 2. In one specific, non-limiting example, the subject is infected with a lentivirus, for example SIV or HIV, such as HIV-1 or HIV-2. In some embodiments, the immune response is a B cell response, a T cell response, or a combination thereof.

In other embodiments, the subject is further administered a therapeutically effective amount of a monomeric or trimeric gp140 polypeptide, an unmodified monomeric or trimeric gp120 polypeptide, or a combination thereof.

Other embodiments of this disclosure are isolated polynucleotides (nucleic acid molecules) which encode the gp120 polypeptides described herein. Specific examples of such nucleic acid molecules contain nucleic acids encoding the amino acid sequence set forth as one of SEQ ID NO: 1 or 2, the nucleotide sequences set forth as one of SEQ ID NOs: 4-18, or degenerate variants thereof. In other embodiments, the isolated polynucleotides consist of nucleic acid molecules encoding the amino acid sequence set forth as one of SEQ ID NO: 1 or 2, the nucleotide sequences set forth as one of SEQ ID NOs: 4-18, or degenerate variants thereof. In certain embodiments, the nucleic acid encoding a gp120 polypeptide is operably linked to a promoter. Vectors comprising such polynucleotides are also disclosed, as are host cells transformed with such vectors.

Other embodiments are compositions containing a therapeutically effective amount of a polynucleotide containing a nucleic acid encoding a gp120 polypeptide disclosed herein. In certain embodiments, the nucleic acid encodes the amino acid sequence set forth as SEQ ID NO: 1 and 2. In other embodiments the nucleic acid contains the one of the nucleotide sequences set forth as SEQ ID NO: 4-18 or a degenerate variant thereof. In some embodiments, the composition can contain pharmaceutically acceptable carriers, adjuvants, or combinations thereof.

This disclosure further provides methods for eliciting and/or enhancing an immune response in a subject (such as a primate subject, for example a human subject). The methods involve administering to the subject a composition containing a nucleic acid encoding a gp120 polypeptide of this disclosure. In one specific, non-limiting example, the subject is infected with a lentivirus, for example SIV or HIV, such as HIV-1 or HIV-2. In some embodiments, the immune response is a B cell response, a T cell response, or a combination thereof.

In other embodiments, the subject is further administered a therapeutically effective amount of a plasmid vector expressing a polypeptide containing a monomeric or trimeric gp140 polypeptide, an unmodified monomeric or trimeric gp120 polypeptide; or combination thereof.

Also disclosed herein are methods for identifying an immunogen that induces an immune response to gp120, for example gp120 from a lentivirus, such as SIV or HIV such as HIV-1 or HIV-2. Typically the immune response is a B cell response, a T cell response, or a combination thereof. These methods involve using a three-dimensional structure of gp120 as defined by atomic coordinates set forth in Table 1, Table 2, or a portion thereof to design or select the immunogen, synthesizing the immunogen, immunizing a subject with the immunogen; and determining if an immune response to gp120 is induced in the subject. In some embodiments, the immunogen is designed from the gp120 amino acid sequence. In certain embodiments, the immunogen is designed or selected using a three-dimensional structure of gp120 as defined by atomic coordinates set forth in Table 1, Table 2, or a portion thereof and an amino acid sequence is assembled to provide an immunogen, for example by synthesizing the amino acid sequence or producing a nucleic acid encoding the immunogen. In other embodiments the is selected from a database of compounds or is designed de novo.

Also provided by this disclosure is a machine readable data storage medium including a data storage material encoded with machine readable data corresponding to the coordinates of a stabilized form of gp120 as defined by Table 1 or a portion thereof or a form of gp120 having an extended conformation of the V3 loop as defined by Table 2 or a portion thereof.

Also provided for are computer systems including data and a data processor, wherein the system forms a representation of the three-dimensional structure gp120 protein as defined by Table 1, Table 2, or a portion thereof, such as the atomic positions, surface, domain, or region of the gp120 polypeptide.

Also disclosed herein is the use of stabilized gp120 molecules as crystallization tools. A crystalline form of a stabilized gp120 also is disclosed, for example the crystalline form of gp120 as defined by the coordinates as given in Table 1, or with coordinates having a root mean square deviation therefrom, wherein the distance between the residues is less than about 0.75 Å. A crystalline form of a gp120 with an extended V3 loop also is disclosed, for example the crystalline form of gp120 as defined by the coordinates as given in Table 2, or with coordinates having a root mean square deviation therefrom, wherein the distance between the residues is less than about 0.75 Å.

III. gp120 Immunogens and Nucleic Acids Encoding gp120 Immunogens

The present disclosure relates to gp120 polypeptides and nucleic acids encoding these gp120 polypeptides. The gp120 polypeptides of this disclosure are capable of eliciting an immune response to a gp120 protein in a subject, such as a human subject. In some embodiments, the gp120 polypeptides of this disclosure are stabilized in a CD4 bound conformation.

Using a combination of atomic level structural information with biophysical techniques novel gp120 polypeptides were designed that are stabilized in the conformation substantially identical to the CD4 bound polypeptide. For example, the three-dimensional structure of the wild-type polypeptide was analyzed to determine where cysteine residues could be introduced such that they would form disulfide bonds in the folded molecule. This methodology is not specific to cysteine residues; other natural or non-natural amino acids could be used. In some embodiments, the stabilized gp120 has a $K_d$ for CD4 of less than or equal to about 10 nM, such as less than or equal to about 5 nM, less than or equal to about 3 nM, or less than or equal to about 1 nM. In some embodiments the stabilized gp120 has $-T\Delta S$ for CD4 binding of about less than or equal to 40 kcal/mol, such as about less than or equal to 30 kcal/mol, about less than or equal to 15 kcal/mol, or about less than or equal to 10 kcal/mol.

The stability of folded polypeptides can be measured using techniques such as thermal denaturation. The temperature of the unfolding transition ($T_m$) is an accepted measure of the stability of the folded polypeptide, where increases in $T_m$ indicate an increase in the stability of the folded polypeptide. In some embodiments, the stabilized gp120 polypeptides has a $T_m$ value greater than about 52° C., such as greater than about 53° C., greater than about 54° C. (such as 53.8° C.), greater than about 55° C., greater than about 56° C., greater than about 57° C., greater than about 58° C., or even greater than about 59° C.

In some embodiments, the stabilized gp120 polypeptides are stabilized by a plurality of non-naturally occurring cross-linking cysteine residues. By plurality it is meant that there are at least 2, such as at least 4, at least 6, or at least 8 cysteines introduced by mutation into a gp120 polypeptide, such that pairs of cysteines form at least 1, such as at least 2, at least 3, or at least 4 disulfide bonds. Each disulfide bond is formed by a pair of cysteines.

In some embodiments, the mutationally introduced cysteines are introduced into the gp120 polypeptide at positions 96, 109, 123, 231, 267, 275, 428, 431, or in a sub-combination thereof. In some examples of the stabilized gp120 polypeptides, the plurality of non-naturally occurring cross-linking cysteine residues are defined by the interaction of at least one of residue pairs 96 and 275; 109 and 428; 123 and 431; and 231 and 267. Thus, the stabilized gp120 polypeptides of this disclosure may have any combination of the crosslinked cysteines defined by the interaction of 96 and 275; 109 and 428; 123 and 431; and 231 and 267.

In some embodiments, the stabilized gp120 polypeptide contains one or more amino acid substitutions in the protein core. In several disclosed examples, the substitution is made at position 95, 257, 375, 433, or a combination thereof. Thus, a stabilized gp120 polypeptide may have one, two, three, or four substitutions in the protein core. In specific examples, the substitution is a serine to tryptophan substitution at position 95, a threonine to serine substitution at position 257, a serine to tryptophan substitution at position 375, an alanine to methionine substitution at position 433, or various combinations thereof.

In one embodiment, the stabilized gp120 polypeptide (new_9c) includes the amino acid sequence set forth as:

sequence set forth as one of SEQ ID NO: 4, 5, 6, 7, 8, 10, 11, 12, 13, 14 15, 16, 17, and 18, or a degenerate variant thereof. In some embodiments, a stabilized gp120 polypeptide is an immunogenic fragment of SEQ ID NO: 1 or as encoded by the nucleotide sequence set forth as one of SEQ ID NO: 4, 5, 6, 7, 8, 10, 11, 12, 13, 14 15, 16, 17, and 18, or a degenerate variant thereof, such that the immunogenic fragment is stabilized in a CD4 binding conformation. In some embodiments, the stabilized gp120 includes the outer-domain. In one example, the outer domain includes residues 255-421 and 436-474 of gp120. Thus, the outer domain can contain residues 109-246 and 261-299 of SEQ ID NO: 1, the amino acid sequence encoded by SEQ ID NO: 4-18 or a degenerate variant thereof. In some examples residues 246 and 261 are covalently linked, for example by a peptide linker. In some examples, the peptide linker is residues 247-260 of SEQ ID NO: 1, the amino acid sequence encoded by SEQ ID NO: 4-18 or a degenerate variant thereof. Ideally the linker should be of sufficient length such that the folded protein is a conformation that can be bound by CD4. In some embodiments, the linker is a peptide linker and the peptide linker is about 2 to about 20 amino acids in length, such as about 2, about 3, about 4, about 5, about 6, about 7, about 8, about 10, about 12, about 15, or about 20 amino acids in length. In some embodiments, the immunogenic fragment of gp120 consists of residues 109-246 and 261-299, and a linker In some embodiments the linker does not contain a sequence form gp120.

In other embodiments, the stabilized gp120 fragment is truncated on the carboxy terminal end. For example, the carboxy terminal end can be truncated to about amino acid residue 433. In addition, portions of the amino terminus of gp120 can also be eliminated from the stabilized gp120 fragment. The truncated gp120 sequence can be free from the carboxy terminus through amino acid residue 95. In one embodiment, the truncated gp120 sequence is free from the amino terminus of gp120 through residue 95 and residue 433 through the carboxy terminus of gp120. Thus, in some embodiments the stabilized gp120 contains a portion of the (SEQ ID NO: 1)
EVVLVNVTENFNWCKNDMVEQMHEDICSLWDQSLKPCVKLCPLAGATSVITQACPKVSFEPIPIHY

CAPAGFAILKCNNKTFNGTGPCTNVSTVQCTHGIRPVVSSQLLLNGSLAEEEVVIRSCNFTDNAKTII

VQLNTSVEINCTRPNNGGSGSGGNMRQAHCNISRAKWNNTLKQIASKLREQFGNNKTIIFKQSSGG

DPEIVTHWFNCGGEFFYCNSTQLFNSTWFNSTWSTEGSNNTEGSDTITLPCRIKQIINMWCKVCKA

MYAPPISGQIRCSSNITGLLLTRDGGNSNNESEIFRPGGGDMRDNWRSELYKYKVVKIE.

In other embodiments, the stabilized gp120 includes the amino acid sequence encoded by one of SEQ ID NO: 4, 5, 6, 7, 8, 10, 11, 12, 13, 14, 15, 16, 17, and 18, or degenerate variants thereof. In still other embodiments, the stabilized gp120 polypeptide consists of the amino acid sequence set forth as SEQ ID NO: 1 or as encoded by the nucleotide amino acid sequence set forth as SEQ ID NO: 1 or as encoded by any one of SED NOs:4-18.

In other embodiments, the gp120 polypeptide has the V3 loop in an extended conformation. An exemplary sequence of a gp120 with an extended loop is set forth as:

(SEQ ID NO: 2)
GARSEVVLENVTEHFNMWKNDMVEQMQEDIISLWDQSLKPCVKLTPLCVGAGSCDTSVITQACPKI

SFEPIPIHYCAPAGFAILKCNDKTFNGKGPCKNVSTVQCTHGIRPVVSTQLLLNGSLAEEEVVIRSDNF

TNNAKTIIVQLKESVEINCTRPNQNTRKSIHIGPGRAFYTTGEIIGDIRQAHCNISRAKWNDTLKQIVIK

LREQFENKTIVFNHSSGGDPEIVMHSFNCGGEFFYCNSAQLFNSTWNNNTEGSNNTEGNTITLPCRIK

QIINMWQEVGKAMYAPPIRGQIRCSSNITGLLLTRDGGINENGTEIFRPGGGDMRDNWRSELYKYKV

VKIE.

Thus, a gp120 polypeptide with an extended V3 loop can contain the amino acid sequence set forth as SEQ ID NO: 2 or a fragment thereof. In one example, the gp120 polypeptide with the V3 loop in an extended conformation consists of the amino acid sequence set forth as SEQ ID NO: 2 or a fragment thereof. In still other embodiments, the gp120 polypeptide with an extended V3 loop contains a portion of the amino acid sequence set forth as SED ID NO: 2. In some embodiments, the stabilized gp120 includes the outer-domain. In one example, the outer domain includes residues 255-421 and 436-474 of gp120. Thus, the outer domain can include residues 109-246 and 261-299 of SEQ ID NO: 2.

In other embodiments, the gp120 polypeptide has the V3 loop in an extended conformation is truncated on the carboxy terminal end. For example, the carboxy terminal end can be truncated to about amino acid residue 433. In addition, portions of the amino terminus of gp120 can also be eliminated from the gp120 polypeptide has the V3 loop in an extended conformation fragment. The truncated gp120 sequence can be free from the carboxy terminus through amino acid residue 95. In one embodiment, the truncated gp120 sequence is free from the amino terminus of gp120 through residue 95 and residue 433 through the carboxy terminus of gp120. Thus, in some embodiments the gp120 polypeptide has the V3 loop in an extended conformation contains a portion of the amino acid sequence set forth as SEQ ID NO: 2.

In other embodiments, the gp120 polypeptide has an amino acid sequence least 90% identical to SEQ ID NO: 1, SEQ ID NO: 2, or the amino acid sequence encoded by any one of SEQ ID NO: 4-18, for example a polypeptide that has about 91%, 92%, 93%, 94%, 95%, 96%, 97%, 98%, 99% or even higher sequence identity to SEQ ID NO: 1, SEQ ID NO: 2, or the amino acid sequence encoded by any one of SEQ ID NO: 4-18.

The immunogenic gp120 polypeptides or immunogenic fragments of the gp120 polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

In other embodiments, fusion proteins are provided including a first and second polypeptide moiety in which one of the protein moieties includes an amino acid sequence as set forth in SEQ ID NO: 1 or 2, or a fragment thereof. In other embodiments, fusion proteins are provided comprising a first and second polypeptide moiety in which one of the protein moieties includes an amino acid sequence encoded by one of the nucleotide sequences as set forth as SEQ ID NO: 4-18, or a fragment thereof. The other moiety is a heterologous protein such as can be a carrier protein and/or an immunogenic protein. Such fusions also are useful to evoke an immune response against gp120. In certain embodiments the gp120 polypeptides disclosed herein are covalent or non-covalent addition of TLR ligands or dendritic cell or B cell targeting moieties.

A gp120 polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Most antigenic epitopes of HIV proteins are relatively small in size, such as about 5 to 100 amino acids in size, for example about 5, about 6, about 7, about 8, about 9, about 10, about 15, about 20, about 25, about 30, about 40, about 50, about 60, about 70, about 80, about 90, or about 100. Thus, fragments (for example, epitopes or other antigenic fragments) of a gp120 polypeptide, such as any of the gp120 polypeptides described herein or a fragment thereof, can be used as an immunogen.

In some embodiments, the disclosed gp120 polypeptides are modified by glycosylation, for example by N-linked glycans. Thus, the immune response can be focused on a region interest of a gp120 polypeptide by masking other regions with non-immunogenic glycans. Glycosylation sites can be introduced into the gp120 polypeptides by site directed mutagenesis. This straggly can be utilized to focus the immune response to regions of interest in the gp120 polypeptide, for example the CD4 binding site or the binding site for a neutralizing antibody, for example a the b12 antibody. Examples of glycan masking can be found in Pantophlet and Burton, *Trends Mol Med.* 9(11):468-73, 2003, which is incorporated by reference herein in its entirety.

Another strategy to focus the immune response on the CD4 binding region or b12 epitope region is to use SIV and HIVgp120 core glycoproteins (such as the stabilized gp120 polypeptides disclosed herein) that possess an endogenous CD4 binding site or to scaffold the heterologous HIV-1 CD4 binding region onto cores derived from selected SIV or HIV-2 strains. The gp120 core can be derived from the envelope glycoproteins of lentivirus, for example SIV such as SIV mac239 and HIV, such as HIV-2 7132A. The residues required for CD4BS antibody recognition, for example the site of b12 binding, are transplanted by site-directed mutagenesis of the appropriate codon-optimized plasmid sequences. In some embodiments, extra N-glycans are added to these cores to eliminate the elicitation of non-cross reactive antibodies directed against regions outside the antibody binding site, for example the binding site of a neutralizing antibody such as CD4BS antibody.

The present disclosure concerns nucleic acid constructs including polynucleotide sequences that encode antigenic gp120 polypeptides of HIV-1. These polynucleotides include DNA, cDNA and RNA sequences which encode the polypeptide of interest.

Methods for the manipulation and insertion of the nucleic acids of this disclosure into vectors are well known in the (see for example, Sambrook et al., *Molecular Cloning, a Laboratory Manual,* 2d edition, Cold Spring Harbor Press, Cold Spring Harbor, N.Y., 1989, and Ausubel et al., *Current Protocols in Molecular Biology,* Greene Publishing Associates and John Wiley & Sons, New York, N.Y., 1994).

Typically, the nucleic acid constructs encoding the gp120 polypeptides of this disclosure are plasmids. However, other vectors (for example, viral vectors, phage, cosmids, etc.) can be utilized to replicate the nucleic acids. In the context of this disclosure, the nucleic acid constructs typically are expression vectors that contain a promoter sequence which facilitates the efficient transcription of the inserted genetic sequence of the host. The expression vector typically contains an origin of replication, a promoter, as well as specific nucleic acid sequences that allow phenotypic selection of the transformed cells.

More generally, polynucleotide sequences encoding the gp120 polypeptides of this disclosure can be operably linked to any promoter and/or enhancer that is capable of driving expression of the nucleic acid following introduction into a host cell. A promoter is an array of nucleic acid control sequences that directs transcription of a nucleic acid. A promoter includes necessary nucleic acid sequences (which can be) near the start site of transcription, such as in the case of a polymerase II type promoter (a TATA element). A promoter also can include distal enhancer or repressor elements which can be located as much as several thousand base pairs from the start site of transcription. Both constitutive and inducible promoters are included (see, for example, Bitter et al., *Methods in Enzymology* 153:516-544, 1987).

To produce such nucleic acid constructs, polynucleotide sequences encoding gp120 polypeptides are inserted into a suitable expression vector, such as a plasmid expression vector. Procedures for producing polynucleotide sequences encoding gp120 polypeptides and for manipulating them in vitro are well known to those of skill in the art, and can be found, for example in Sambrook and Ausubel, supra.

In addition to the polynucleotide sequences encoding the polypeptides set forth as SEQ ID NOs:1-2 disclosed herein and nucleic acids encoding gp120 polypeptides as set forth as SEQ ID NOs:4-18 as disclosed herein, the nucleic acid constructs can include variant polynucleotide sequences that encode polypeptides that are substantially similar to SEQ ID NOs: 1-2 and nucleic acids encoding gp120 polypeptides as set forth as SEQ ID NOs: 4-18. Similarly, the nucleic acid constructs can include polynucleotides that encode chimeric polypeptides, for example fusion proteins. For enhanced immunogenicity, it may be advantageous to include the sequence encoding for heterologous T helper sequences derived from HIV or other heterologous sources.

The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. Thus, the nucleic acid constructs can include polynucleotides that encode polypeptides that are at least about 90%, or 95%, 98%, or 99% identical to one of SEQ ID NOs: 1-2 with respect to amino acid sequence, or that have at least about 90%, 95%, 98%, or 99% sequence identity to one or more of SEQ ID NOs: 4-18 and/or that differ from one of these sequences by the substitution of degenerate codons.

DNA sequences encoding an immunogenic gp120 polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The polynucleotide sequences encoding an immunogenic gp120 polypeptide can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques that are well known to those of ordinary skill in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an immunogenic gp120 polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

IV. Immunogenic Compositions and Therapeutic Methods

Any of the gp120 polypeptides and nucleic acid molecules encoding the gp120 polypeptides disclosed herein can be used as immunogens, or to produce immunogens to elicit an immune response (immunogenic compositions) to gp120 such as to a gp120 expressing virus, for example to reduce HIV-1 infection or a symptom of HIV-1 infection. Following administration of a therapeutically effective amount of the disclosed therapeutic compositions, the subject can be monitored for HIV-1 infection, symptoms associated with HIV-1 infection, or both. Disclosed herein are methods of administering the therapeutic molecules disclosed herein (such as gp120 polypeptides and nucleic acids encoding gp120 polypeptides) to reduce HIV-1 infection. In several examples, a therapeutically effective amount of a gp120 polypeptide including SEQ ID NO: 1, a therapeutically effective amount of a gp120 polypeptide including SEQ ID NO: 2, a therapeutically effective amount of a gp120 polypeptide encoded by one of SEQ ID NOs: 4-18 or a degenerate variant thereof, or a combination thereof is administered to a subject.

In certain embodiments, the immunogenic composition includes an adjuvant. An adjuvant can be a suspension of minerals, such as alum, aluminum hydroxide, aluminum phosphate, on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif.

In one example, the immunogenic composition is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference herein in their entirety. A stabilizing detergent is any detergent that allows the components of the emulsion to remain as a stable emulsion. Such detergents include polysorbate 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

Immunogenic compositions can be formulated with an appropriate solid or liquid carrier, depending upon the particular mode of administration chosen. If desired, the disclosed pharmaceutical compositions can also contain minor amounts of non-toxic auxiliary substances, such as wetting or emulsifying agents, preservatives, and pH buffering agents and the like, for example sodium acetate or sorbitan monolaurate. Excipients that can be included in the disclosed compositions include flow conditioners and lubricants, for example silicic acid, talc, stearic acid or salts thereof, such as magnesium or calcium stearate, and/or polyethylene glycol, or derivatives thereof.

Immunogenic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

A form of repository or "depot" slow release preparation can be used so that therapeutically effective amounts of the preparation are delivered into the bloodstream over many hours or days following transdermal injection or delivery. Such long acting formulations can be administered by implantation (for example subcutaneously or intramuscularly) or by intramuscular injection. The compounds can be formulated with suitable polymeric or hydrophobic materials (for example as an emulsion in an acceptable oil) or ion exchange resins, or as sparingly soluble derivatives, for example, as a sparingly soluble salt.

Immunogenic compositions that include a disclosed therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, immunogenic compositions including a disclosed therapeutic agent are administered by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

Immunogenic compositions can be administered for therapeutic treatments. In therapeutic applications, a therapeutically effective amount of the immunogenic composition is administered to a subject suffering from a disease, such as HIV-1 infection or AIDS. The immunogenic composition can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle (see, for example, Banga, supra). A particulate carrier based on a synthetic polymer has been shown to act as an adjuvant to enhance the immune response, in addition to providing a controlled release. Aluminum salts can also be used as adjuvants to produce an immune response.

Immunogenic compositions can be formulated in unit dosage form, suitable for individual administration of precise dosages. In pulse doses, a bolus administration of an immunogenic composition that includes a disclosed immunogen is provided, followed by a time-period wherein no disclosed immunogen is administered to the subject, followed by a second bolus administration. A therapeutically effective amount of an immunogenic composition can be administered in a single dose, or in multiple doses, for example daily, during a course of treatment. In specific, non-limiting examples, pulse doses of an immunogenic composition that include a disclosed immunogen are administered during the course of a day, during the course of a week, or during the course of a month.

Immunogenic compositions can be administered whenever the effect (such as decreased signs, symptom, or laboratory results of HIV-1 infection) is desired. Generally, the dose is sufficient to treat or ameliorate symptoms or signs of disease without producing unacceptable toxicity to the subject. Systemic or local administration can be utilized.

Amounts effective for therapeutic use can depend on the severity of the disease and the age, weight, general state of the patient, and other clinical factors. Thus, the final determination of the appropriate treatment regimen will be made by the attending clinician. Typically, dosages used in vitro can provide useful guidance in the amounts useful for in situ administration of the pharmaceutical composition, and animal models may be used to determine effective dosages for treatment of particular disorders. Various considerations are described, for example in Gilman et al., eds., Goodman and Gilman: The Pharmacological Bases of Therapeutics, 8th ed., Pergamon Press, 1990; and Remington's Pharmaceutical Sciences, 17th ed., Mack Publishing Co., Easton, Pa., 1990. Typically, the dose range for a gp120 polypeptide is from about 0.1 µg/kg body weight to about 100 mg/kg body weight. Other suitable ranges include doses of from about 1 µg/kg to 10 mg/kg body weight. In one example, the dose is about 1.0 µg to about 50 mg, for example, 1 µg to 1 mg, such as 1 mg peptide per subject. The dosing schedule can vary from daily to as seldom as once a year, depending on clinical factors, such as the subject's sensitivity to the peptide and tempo of their disease. Therefore, a subject can receive a first dose of a disclosed therapeutic molecule, and then receive a second dose (or even more doses) at some later time(s), such as at least one day later, such as at least one week later.

The pharmaceutical compositions disclosed herein can be prepared and administered in dose units. Solid dose units include tablets, capsules, transdermal delivery systems, and suppositories. The administration of a therapeutic amount can be carried out both by single administration in the form of an individual dose unit or else several smaller dose units and also by multiple administrations of subdivided doses at specific intervals. Suitable single or divided doses include, but are not limited to about 0.01, 0.1, 0.5, 1, 3, 5, 10, 15, 30, or 50 µg protein/kg/day The nucleic acid constructs encoding antigenic gp120 polypeptides described herein are used, for example, in combination, as pharmaceutical compositions (medicaments) for use in therapeutic, for example, prophylactic regimens (such as vaccines) and administered to subjects (for example, primate subjects such as human subjects) to elicit an immune response against one or more clade or strain of HIV. For example, the compositions described herein can be administered to a human (or non-human) subject prior to infection with HIV to inhibit infection by or replication of the virus. Thus, the pharmaceutical compositions described above can be administered to a subject to elicit a protective immune response against HIV. To elicit an immune response, a therapeutically effective (for example, immunologically effective) amount of the nucleic acid constructs are administered to a subject, such as a human (or non-human) subject.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin).

For administration of gp120 nucleic acid molecules, the nucleic acid can be delivered intracellularly, for example by expression from an appropriate nucleic acid expression vector which is administered so that it becomes intracellular, such as by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., Proc. Natl. Acad. Sci. USA 1991, 88:1864-8). The present disclosure includes all forms of nucleic acid delivery, including synthetic oligos, naked DNA, plasmid and viral, integrated into the genome or not.

In another approach to using nucleic acids for immunization, an immunogenic gp120 polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, Nature 351:456-460, 1991).

In one example, a viral vector is utilized. These vectors include, but are not limited to, adenovirus, herpes virus, vaccinia, or an RNA virus such as a retrovirus. In one example, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding a gp120 polypeptide into the viral vector, along with another gene that encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the polynucleotide encoding a gp120 polypeptide.

Since recombinant retroviruses are defective, they need assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Suitable formulations for the nucleic acid constructs, include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the composition for use in the inventive method is formulated to protect the nucleic acid constructs from damage prior to administration. For example, the composition can be formulated to reduce loss of the adenoviral vectors on devices used to prepare, store, or administer the expression vector, such as glassware, syringes, or needles. The compositions can be formulated to decrease the light sensitivity and/or temperature sensitivity of the components. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof.

In therapeutic applications, a therapeutically effective amount of the composition is administered to a subject prior to or following exposure to or infection by HIV. When administered prior to exposure, the therapeutic application can be referred to as a prophylactic administration (such as in the form of a vaccine). Single or multiple administrations of the compositions are administered depending on the dosage and frequency as required and tolerated by the subject. In one embodiment, the dosage is administered once as a bolus, but in another embodiment can be applied periodically until a therapeutic result, such as a protective immune response, is achieved. Generally, the dose is sufficient to treat or ameliorate symptoms or signs of disease without producing unacceptable toxicity to the subject. Systemic or local administration can be utilized.

In the context of nucleic acid vaccines, naturally occurring or synthetic immunostimulatory compositions that bind to and stimulate receptors involved in innate immunity can be administered along with nucleic acid constructs encoding the gp120 polypeptides. For example, agents that stimulate certain Toll-like receptors (such as TLR7, TLR8 and TLR9) can be administered in combination with the nucleic acid constructs encoding gp120 polypeptides. In some embodiments, the nucleic acid construct is administered in combination with immunostimulatory CpG oligonucleotides.

Nucleic acid constructs encoding gp120 polypeptides can be introduced in vivo as naked DNA plasmids. DNA vectors can be introduced into the desired host cells by methods known in the art, including but not limited to transfection, electroporation (for example, transcutaneous electroporation), microinjection, transduction, cell fusion, DEAE dextran, calcium phosphate precipitation, use of a gene gun, or use of a DNA vector transporter (See for example, Wu et al. *J. Biol. Chem.,* 267:963-967, 1992; Wu and Wu *J. Biol. Chem.,* 263:14621-14624, 1988; and Williams et al. *Proc. Natl. Acad. Sci. USA* 88:2726-2730, 1991). As described in detail in the Examples, a needleless delivery device, such as a BIOJECTOR® needleless injection device can be utilized to introduce the therapeutic nucleic acid constructs in vivo. Receptor-mediated DNA delivery approaches can also be used (Curiel et al. *Hum. Gene Ther.,* 3:147-154, 1992; and Wu and Wu, J. *Biol. Chem.*, 262:4429-4432, 1987). Methods for formulating and administering naked DNA to mammalian muscle tissue are disclosed in U.S. Pat. Nos. 5,580,859 and 5,589,466, both of which are herein incorporated by reference. Other molecules are also useful for facilitating transfection of a nucleic acid in vivo, such as a cationic oligopeptide (for example, WO95/21931), peptides derived from DNA binding proteins (for example, WO96/25508), or a cationic polymer (for example, WO95/21931).

Another well-known method that can be used to introduce nucleic acid constructs encoding gp120 immunogens into host cells is particle bombardment (also known as biolistic transformation). Biolistic transformation is commonly accomplished in one of several ways. One common method involves propelling inert or biologically active particles at cells. This technique is disclosed in, for example, U.S. Pat. Nos. 4,945,050, 5,036,006; and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. *Proc. Natl. Acad. Sci. USA* 84:7413-7417, 1987; Mackey, et al. *Proc. Natl. Acad. Sci. USA* 85:8027-8031, 1988; Ulmer et al. *Science* 259:1745-1748, 1993). The use of cationic lipids can promote encapsulation of negatively charged nucleic acids, and also promote fusion with negatively charged cell membranes (Felgner and Ringoid *Science* 337:387-388, 1989). Particularly useful lipid compounds and compositions for transfer of nucleic acids are described in WO95/18863 and WO96/17823, and in U.S. Pat. No. 5,459,127, herein incorporated by reference.

As with the immunogenic polypeptide, the nucleic acid compositions may be administered in a single dose, or multiple doses separated by a time interval can be administered to elicit an immune response against HIV. For example, two doses, or three doses, or four doses, or five doses, or six doses or more can be administered to a subject over a period of several weeks, several months or even several years, to optimize the immune response.

It may be advantageous to administer the immunogenic compositions disclosed herein with other agents such as proteins, peptides, antibodies, and other anti-HIV agents. Examples of such anti-HIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir osamprenavir, ritonavir, saquinavir, tipranavir, and the like, and fusion protein inhibitors such as enfuvirtide and the like. In certain embodiments, immunonogenic compositions are administered concurrently with other anti-HIV therapeutic agents. In certain embodiments, the immunonogenic compositions are administered sequentially with other anti-HIV therapeutic agents, such as before or after the other agent. One of ordinary skill in the art would know that sequential administration can mean immediately following or after an appropriate period of time, such as hours days, weeks, months, or even years later.

While not being bound by theory, it is believed that CD4 binding to gp120 triggers the exposure of the immunodominant V3 loop. Thus, co-administration of soluble forms of CD4, such as the fragments described herein, or an antibody that binds to the CD4 binding site, can lead to enhanced elicitation of an immunogenic response to gp120.

In certain embodiments, immunonogenic compositions disclosed herein are administered with a soluble portion of CD4, for example a sufficient portion of the CD4 to bind to the CD4 binding site on gp120. Such soluble fragments typically include both the D1 and D2 extracellular domains of CD4 (D1D2) or sCD4 (which is comprised of D1 D2 D3 and D4 domains of CD4), although smaller fragments may also provide specific and functional CD4-like binding. In certain embodiments, the gp120 polypeptide with an extended V3 loop or a nucleic acid encoding the same is administered concurrently with a soluble portion of CD4. In other embodiments, the gp120 polypeptide with an extended V3 loop or a nucleic acid encoding the same is administered concurrently with an antibody that binds to the CD4 binding site on gp120.

The immunogenic gp120 polypeptides and nucleic acid encoding these polypeptides (such as stabilized gp120 polypeptides, gp120 polypeptides with an extended V3 loop) can be used in a novel multistep immunization regime. Typically, this regime includes administering to a subject a therapeutically effective amount of a gp120 polypeptide as disclosed herein (the prime) and boosting the immunogenic response with stabilized gp140 trimer (Yang et al. *J Virol.* 76(9):4634-42, 2002) after an appropriate period of time. The method of eliciting such an immune reaction is what is known as "prime-boost." In this method, a gp120 polypeptide is initially administered to a subject and at periodic times thereafter stabilized gp140 trimer boosts are administered. Examples of stabilized gp140 or gp120 trimers can be found for example in U.S. Pat. No. 6,911,205 which is incorporated herein in its entirely.

The prime can be administered as a single dose or multiple doses, for example two doses, three doses, four doses, five doses, six doses or more can be administered to a subject over day week or months. The boost can be administered as a single dose or multiple doses, for example two to six doses, or more can be administered to a subject over a day, a week or months. Multiple boosts can also be given, such one to five, or more.

The boosts can be an identical molecule or a somewhat different, but related, molecule. For example, one preferred strategy with the gp120 polypeptides of the present disclosure would be to prime using a stabilized gp120 polypeptide or a gp120 polypeptide with an extended V3 and boosting periodically with stabilized trimers where the gp120 units are designed to come closer and closer to the wild type gp120 over the succession of boosts. For example, the first prime could be a stabilized gp120 polypeptide, with a boost by a stabilized trimer form with the same stabilized gp120 or a trimer with less deletions or changes from the native gp120 conformation, with subsequent boosts using trimers that had still less deletions or changes from the native gp120 conformation until the boosts were finally being given by trimers with a gp120 portion based on the native wild type HIV gp120.

One can also use cocktails containing a variety of different HIV strains to prime and boost with trimers from a variety of different HIV strains or with trimers that are a mixture of multiple HIV strains For example, the first prime could be with a gp120 polypeptide from one primary HIV isolate, with subsequent boosts using trimers from different primary isolates.

In certain embodiments, the prime is a nucleic acid construct comprising a nucleic acid sequence encoding a gp120 immunogen as disclosed herein, for example an nucleotide sequence encoding the amino acid sequence set forth as SEQ ID NO: 1 or SEQ ID NO: 2, or the nucleotide sequence as set forth as one of SEQ ID NO: 4-18 or a degenerate variant thereof. In certain embodiments the boost comprises a nucleic acid sequence encoding a stabilized gp140 trimer.

V. Crystal Structures

The stabilized gp120 polypeptides and the gp120 polypeptides with an extended V3 loop disclosed herein can be used to produce detailed models of gp120 polypeptide atomic structure. Exemplary coordinate data is given in Table 1 and Table 2. The atomic coordinate data is disclosed herein, or the coordinate data derived from homologous proteins may be used to build a three-dimensional model of a gp120 polypeptide or a portion thereof, for example by providing a sufficient number of atoms of the stabilized form of gp120 or the gp120 with the V3 loop in the extended conformation as defined by the coordinates of Table 1 or Table 2 which represent a surface or three-dimensional region of interest, such as an antigenic surface or ligand binding site. Thus, there can be provided the coordinates of at least about 5, such at least about 10, at least about 20, at least about 30, at least at least about 40, at least about 50, at least about 60, at least about 70, at least about 80, at least about 90, at least about 100, at least about 150, at least about 200, at least about 250, at least about 300, at least about 350, at least about 400, at least about 450, at least about 500 or more atoms of the structure, such as defined by the coordinates of Table 1 or Table 2. Thus, a sub-domain, region, or fragment of interest of the stabilized form of gp120 or the gp120 with the extended V3 loop which is in the vicinity of the antigenic surface, can be provided for identifying or rationally designing a compound or drug, such as an immunogen. A "sub-domain," "region," or "fragment" can mean at least one, for example, one, two, three, four, or more, element(s) of secondary structure of particular regions of the stabilized form of gp120 or the gp120 with the extended V3 loop gp120 with the extended V3 loop, and includes those set forth in Table 1 and Table 2.

Any available computational methods may be used to build the three dimensional model. As a starting point, the X-ray diffraction pattern obtained from the assemblage of the molecules or atoms in a crystalline version of a gp120 polypeptide can be used to build an electron density map using tools well known to those skilled in the art of crystallography and X-ray diffraction techniques. Additional phase information extracted either from the diffraction data and available in the published literature and/or from supplementing experiments may then used to complete the reconstruction.

For an overview of the procedures of collecting, analyzing, and utilizing X-ray diffraction data for the construction of electron densities see, for example, Campbell et al., *Biological Spectroscopy*, The Benjamin/Cummings Publishing Co., Inc., Menlo Park, Calif., 1984; Cantor et al., Biophysical Chemistry, Part II: Techniques for the study of biological structure and function, W.H. Freeman and Co., San Francisco, Calif. 1980; A. T. Brunger, X-plor Version 3.1: A system for X-ray crystallography and NMR, Yale Univ. Pr., New Haven, Conn. 1993; M. M. Woolfson, An Introduction to X-ray Crystallography, Cambridge Univ. Pr., Cambridge, UK, 1997; J. Drenth, Principles of Protein X-ray Crystallography (Springer Advanced Texts in Chemistry), Springer Verlag; Berlin, 1999; Tsirelson et al, Electron Density and Bonding in Crystals: Principles, Theory and X-ray Diffraction Experiments in Solid State Physics and Chemistry, Inst. of Physics Pub., 1996; each of which is herein specifically incorporated by reference in their entirety.

Information on molecular modeling can be found for example in, M. Schlecht, Molecular Modeling on the PC, 1998, John Wiley & Sons; Gans et al., Fundamental Principals of Molecular Modeling, Plenum Pub. Corp., 1996; N.C. Cohen (editor), Guidebook on Molecular Modeling in Drug Design, Academic Press, 1996; and W. B. Smith, Introduction to Theoretical Organic Chemistry and Molecular Modeling, 1996.

Typically, a well-ordered crystal that will diffract x-rays strongly is used to solve the three-dimensional structure of a protein by x-ray crystallography. The crystallographic method directs a beam of x-rays onto a regular, repeating array of many identical molecules. The x-rays are diffracted from it in a pattern from which the atomic positions of the atom that make up the molecule of interest can be determined.

Substantially pure and homogeneous protein samples are usually used for crystallization. Typically, crystals form when molecules are precipitated very slowly from supersaturated solutions. A typical procedure for making protein crystals is the hanging-drop method, in which a drop of protein solution is brought very gradually to supersaturation by loss of water from the droplet to the larger reservoir that contains salt, polyethylene glycol, or other solution that functions as a hydroattractant, although any other method that generates diffraction quality crystals can be used. In some examples diffraction quality crystals are obtained by seeding the supersaturated solution with smaller crystals that serve as templates.

Powerful x-ray beams can be produced from synchrotron storage rings where electrons (or positrons) travel close to the speed of light. These particles emit very strong radiation at all wavelengths from short gamma rays to visible light. When used as an x-ray source, only radiation within a window of suitable wavelengths is channeled from the storage ring.

In diffraction experiments a narrow and parallel beam of x-rays is taken out from the x-ray source and directed onto the crystal to produce diffracted beams. The incident x-ray beam causes damage to both protein and solvent molecules. The crystal is, therefore, usually cooled to prolong its lifetime (for example to −220° to −50° C.). In some examples, single crystals are used to obtain a data set, while in other examples, multiple crystals are used to obtain a data set. The x-ray beam must strike the crystal from many different directions to produce all possible diffraction spots, thereby creating a complete data set. Therefore, the crystal is rotated relative to the beam during data collection. The diffracted spots are recorded either on a film, or by an electronic detector, both of which are commercially available.

When the primary beam from an x-ray source strikes the crystal, x-rays interact with the electrons on each atom in the crystal and cause them to oscillate. The oscillating electrons serve as a new source of x-rays, which are emitted in almost all directions in a process referred to as scattering. When atoms (and hence their electrons) are arranged in a regular three-dimensional array, as in a crystal, the x-rays emitted from the oscillating electrons interfere with one another. In most cases, these x-rays, colliding from different directions, cancel each other out; those from certain directions, however, will add together to produce diffracted beams of radiation that can be recorded as a pattern on a photographic plate or detector.

The diffraction pattern obtained in an x-ray experiment is related to the crystal that caused the diffraction. X-rays that are reflected from adjacent planes travel different distances, and diffraction only occurs when the difference in distance is equal to the wavelength of the x-ray beam. This distance is dependent on the reflection angle, which is equal to the angle between the primary beam and the planes.

Each atom in a crystal scatters x-rays in all directions, and only those that positively interfere with one another, according to Bragg's law ($2d \sin \theta = \lambda$), give rise to diffracted beams that can be recorded as a distinct diffraction spot above background. Each diffraction spot is the result of interference of all x-rays with the same diffraction angle emerging from all atoms. To extract information about individual atoms from such a system requires considerable computation. The mathematical tool that is used to handle such problems is called the Fourier transform.

Each diffracted beam, which is recorded as a spot on the film, is defined by three properties: the amplitude, which is measured as the intensity of the spot; the wavelength, which is determined by the x-ray source; and the phase information, which is lost in x-ray experiments and must be calculated. All three properties are used for all of the diffracted beams, in order to determine the position of the atoms giving rise to the diffracted beams. Methods of determining the phases are well known in the art.

For example, phase differences between diffracted spots can be determined from intensity changes following heavy atom derivatization. Another example would be determining the phases by molecular replacement.

The amplitudes and the phases of the diffraction data from the protein crystals are used to calculate an electron-density map of the repeating unit of the crystal. A model of the particular amino acid sequence is built to approximate the electron density map.

The initial model will contain some errors. Provided the protein crystals diffract to high enough resolution (e.g., better than 3.5 Å), most or substantially all of the errors can be removed by crystallographic refinement of the model using computer algorithms. In this process, the model is changed to minimize the difference between the experimentally observed diffraction amplitudes and those calculated for a hypothetical crystal containing the model. This difference is expressed as an R factor (residual disagreement) which is 0.0 for exact agreement and about 0.59 for total disagreement.

Typically, the R factor of a refined model is preferably between 0.15 and 0.35 (such as less than about 0.24-0.28) for a well-determined protein structure. The residual difference is a consequence of errors and imperfections in the data. These derive from various sources, including slight variations in the conformation of the protein molecules, as well as inaccurate corrections both for the presence of solvent and for differences in the orientation of the microcrystals from which the crystal is built. Thus, the final model represents an average of molecules that are slightly different in both conformation and orientation.

In refined structures at high resolution, there are usually no major errors in the orientation of individual residues, and the estimated errors in atomic positions are usually around 0.1-0.2 Å, provided the amino acid sequence is known.

Most x-ray structures are determined to a resolution between 1.7 Å. and 3.5 Å. Electron-density maps with this resolution range are preferably interpreted by fitting the known amino acid sequences into regions of electron density in which individual atoms are not resolved.

VI. Crystals Structure of Stabilized gp120

The present disclosure also relates to the crystals obtained from stabilized forms of gp120, the crystal structures of the stabilized forms of gp120, the three-dimensional coordinates of the stabilized forms of gp120 polypeptide and three-dimensional structures of models of stabilized forms of gp120. Table 1 provides the atomic coordinates of the crystal structure of the polypeptide encoded by SEQ ID NO: 14.

TABLE 1

The structural coordinates of an exemplary stabilized form of gp120 at atomic resolution

| | | | | | | | | | |
|---|---|---|---|---|---|---|---|---|---|
| ATOM | 1 | CB | GLU | 83 | 18.617 | −44.257 | 86.334 | 1.00 | 108.57 |
| ATOM | 2 | CG | GLU | 83 | 17.192 | −44.735 | 86.515 | 1.00 | 108.41 |
| ATOM | 3 | CD | GLU | 83 | 16.205 | −43.880 | 85.755 | 1.00 | 108.12 |
| ATOM | 4 | OE1 | GLU | 83 | 16.358 | −43.762 | 84.524 | 1.00 | 108.57 |
| ATOM | 5 | OE2 | GLU | 83 | 15.280 | −43.327 | 86.385 | 1.00 | 107.50 |
| ATOM | 6 | C | GLU | 83 | 19.772 | −46.457 | 86.717 | 1.00 | 109.62 |
| ATOM | 7 | O | GLU | 83 | 18.985 | −47.321 | 87.117 | 1.00 | 110.00 |
| ATOM | 8 | N | GLU | 83 | 20.954 | −44.298 | 87.129 | 1.00 | 108.79 |
| ATOM | 9 | CA | GLU | 83 | 19.642 | −45.003 | 87.189 | 1.00 | 109.16 |
| ATOM | 10 | N | VAL | 84 | 20.768 | −46.714 | 85.869 | 1.00 | 109.52 |
| ATOM | 11 | CA | VAL | 84 | 21.044 | −48.053 | 85.341 | 1.00 | 109.11 |
| ATOM | 12 | CB | VAL | 84 | 20.172 | −48.376 | 84.093 | 1.00 | 108.87 |
| ATOM | 13 | CG1 | VAL | 84 | 18.713 | −48.542 | 84.498 | 1.00 | 108.27 |
| ATOM | 14 | CG2 | VAL | 84 | 20.302 | −47.271 | 83.061 | 1.00 | 109.39 |
| ATOM | 15 | C | VAL | 84 | 22.526 | −48.185 | 84.964 | 1.00 | 108.77 |
| ATOM | 16 | O | VAL | 84 | 22.925 | −47.846 | 83.851 | 1.00 | 108.35 |
| ATOM | 17 | N | VAL | 85 | 23.332 | −48.684 | 85.900 | 1.00 | 108.71 |
| ATOM | 18 | CA | VAL | 85 | 24.774 | −48.848 | 85.689 | 1.00 | 108.45 |
| ATOM | 19 | CB | VAL | 85 | 25.515 | −49.032 | 87.038 | 1.00 | 108.05 |
| ATOM | 20 | CG1 | VAL | 85 | 25.521 | −47.724 | 87.807 | 1.00 | 108.41 |
| ATOM | 21 | CG2 | VAL | 85 | 24.837 | −50.110 | 87.862 | 1.00 | 107.81 |
| ATOM | 22 | C | VAL | 85 | 25.175 | −49.994 | 84.754 | 1.00 | 108.29 |
| ATOM | 23 | O | VAL | 85 | 24.757 | −51.138 | 84.941 | 1.00 | 108.64 |
| ATOM | 24 | N | LEU | 86 | 25.997 | −49.670 | 83.755 | 1.00 | 107.51 |
| ATOM | 25 | CA | LEU | 86 | 26.483 | −50.644 | 82.774 | 1.00 | 106.03 |
| ATOM | 26 | CB | LEU | 86 | 26.839 | −49.943 | 81.458 | 1.00 | 104.36 |
| ATOM | 27 | CG | LEU | 86 | 25.737 | −49.391 | 80.552 | 1.00 | 103.07 |
| ATOM | 28 | CD1 | LEU | 86 | 24.750 | −48.544 | 81.333 | 1.00 | 102.61 |
| ATOM | 29 | CD2 | LEU | 86 | 26.390 | −48.575 | 79.450 | 1.00 | 101.71 |
| ATOM | 30 | C | LEU | 86 | 27.720 | −51.369 | 83.298 | 1.00 | 105.81 |
| ATOM | 31 | O | LEU | 86 | 28.354 | −50.916 | 84.254 | 1.00 | 105.88 |

TABLE 1-continued The structural coordinates of an exemplary stabilized form of gp120 at atomic resolution

| ATOM | 32 | N | VAL | 87 | 28.065 | −52.490 | 82.668 | 1.00 | 105.43 |
|---|---|---|---|---|---|---|---|---|---|
| ATOM | 33 | CA | VAL | 87 | 29.231 | −53.263 | 83.083 | 1.00 | 104.73 |
| ATOM | 34 | CB | VAL | 87 | 28.827 | −54.553 | 83.805 | 1.00 | 104.68 |
| ATOM | 35 | CG1 | VAL | 87 | 28.000 | −54.214 | 85.032 | 1.00 | 104.54 |
| ATOM | 36 | CG2 | VAL | 87 | 28.057 | −55.462 | 82.857 | 1.00 | 105.03 |
| ATOM | 37 | C | VAL | 87 | 30.119 | −53.643 | 81.910 | 1.00 | 104.29 |
| ATOM | 38 | O | VAL | 87 | 29.635 | −53.933 | 80.813 | 1.00 | 103.86 |
| ATOM | 39 | N | ASN | 88 | 31.425 | −53.652 | 82.166 | 1.00 | 104.01 |
| ATOM | 40 | CA | ASN | 88 | 32.428 | −53.982 | 81.155 | 1.00 | 103.78 |
| ATOM | 41 | CB | ASN | 88 | 32.360 | −55.474 | 80.781 | 1.00 | 104.65 |
| ATOM | 42 | CG | ASN | 88 | 32.859 | −56.393 | 81.902 | 1.00 | 105.20 |
| ATOM | 43 | OD1 | ASN | 88 | 33.953 | −56.199 | 82.445 | 1.00 | 104.86 |
| ATOM | 44 | ND2 | ASN | 88 | 32.056 | −57.399 | 82.235 | 1.00 | 104.99 |
| ATOM | 45 | C | ASN | 88 | 32.252 | −53.117 | 79.909 | 1.00 | 102.44 |
| ATOM | 46 | O | ASN | 88 | 32.505 | −53.561 | 78.787 | 1.00 | 101.94 |
| ATOM | 47 | N | VAL | 89 | 31.822 | −51.875 | 80.122 | 1.00 | 100.88 |
| ATOM | 48 | CA | VAL | 89 | 31.614 | −50.931 | 79.032 | 1.00 | 98.81 |
| ATOM | 49 | CB | VAL | 89 | 30.231 | −50.258 | 79.127 | 1.00 | 98.28 |
| ATOM | 50 | CG1 | VAL | 89 | 30.035 | −49.322 | 77.953 | 1.00 | 97.33 |
| ATOM | 51 | CG2 | VAL | 89 | 29.139 | −51.310 | 79.151 | 1.00 | 98.08 |
| ATOM | 52 | C | VAL | 89 | 32.679 | −49.841 | 79.051 | 1.00 | 97.94 |
| ATOM | 53 | O | VAL | 89 | 33.180 | −49.461 | 80.113 | 1.00 | 97.43 |
| ATOM | 54 | N | THR | 90 | 33.020 | −49.348 | 77.864 | 1.00 | 96.73 |
| ATOM | 55 | CA | THR | 90 | 34.020 | −48.295 | 77.724 | 1.00 | 95.18 |
| ATOM | 56 | CB | THR | 90 | 35.403 | −48.891 | 77.319 | 1.00 | 95.36 |
| ATOM | 57 | OG1 | THR | 90 | 36.380 | −47.845 | 77.263 | 1.00 | 95.05 |
| ATOM | 58 | CG2 | THR | 90 | 35.324 | −49.591 | 75.962 | 1.00 | 95.57 |
| ATOM | 59 | C | THR | 90 | 33.551 | −47.260 | 76.686 | 1.00 | 93.85 |
| ATOM | 60 | O | THR | 90 | 33.505 | −47.539 | 75.481 | 1.00 | 93.47 |
| ATOM | 61 | N | GLU | 91 | 33.196 | −46.069 | 77.177 | 1.00 | 91.35 |
| ATOM | 62 | CA | GLU | 91 | 32.707 | −44.963 | 76.347 | 1.00 | 87.86 |
| ATOM | 63 | CB | GLU | 91 | 31.343 | −44.504 | 76.865 | 1.00 | 88.15 |
| ATOM | 64 | CG | GLU | 91 | 30.189 | −44.701 | 75.899 | 1.00 | 89.11 |
| ATOM | 65 | CD | GLU | 91 | 30.231 | −43.732 | 74.737 | 1.00 | 90.17 |
| ATOM | 66 | OE1 | GLU | 91 | 29.248 | −43.679 | 73.968 | 1.00 | 90.39 |
| ATOM | 67 | OE2 | GLU | 91 | 31.249 | −43.023 | 74.591 | 1.00 | 90.88 |
| ATOM | 68 | C | GLU | 91 | 33.676 | −43.781 | 76.358 | 1.00 | 85.11 |
| ATOM | 69 | O | GLU | 91 | 34.317 | −43.509 | 77.369 | 1.00 | 85.37 |
| ATOM | 70 | N | ASN | 92 | 33.783 | −43.076 | 75.235 | 1.00 | 81.78 |
| ATOM | 71 | CA | ASN | 92 | 34.683 | −41.928 | 75.151 | 1.00 | 78.41 |
| ATOM | 72 | CB | ASN | 92 | 35.342 | −41.832 | 73.778 | 1.00 | 79.10 |
| ATOM | 73 | CG | ASN | 92 | 36.358 | −42.903 | 73.549 | 1.00 | 79.88 |
| ATOM | 74 | OD1 | ASN | 92 | 36.973 | −43.404 | 74.492 | 1.00 | 80.64 |
| ATOM | 75 | ND2 | ASN | 92 | 36.568 | −43.252 | 72.285 | 1.00 | 80.59 |
| ATOM | 76 | C | ASN | 92 | 34.001 | −40.602 | 75.405 | 1.00 | 75.77 |
| ATOM | 77 | O | ASN | 92 | 33.114 | −40.198 | 74.650 | 1.00 | 75.80 |
| ATOM | 78 | N | PHE | 93 | 34.426 | −39.915 | 76.455 | 1.00 | 71.82 |
| ATOM | 79 | CA | PHE | 93 | 33.870 | −38.608 | 76.751 | 1.00 | 68.48 |
| ATOM | 80 | CB | PHE | 93 | 33.622 | −38.429 | 78.244 | 1.00 | 67.44 |
| ATOM | 81 | CG | PHE | 93 | 32.495 | −39.245 | 78.781 | 1.00 | 67.39 |
| ATOM | 82 | CD1 | PHE | 93 | 32.554 | −40.629 | 78.775 | 1.00 | 68.23 |
| ATOM | 83 | CD2 | PHE | 93 | 31.396 | −38.629 | 79.358 | 1.00 | 68.44 |
| ATOM | 84 | CE1 | PHE | 93 | 31.537 | −41.393 | 79.346 | 1.00 | 68.02 |
| ATOM | 85 | CE2 | PHE | 93 | 30.373 | −39.382 | 79.931 | 1.00 | 69.14 |
| ATOM | 86 | CZ | PHE | 93 | 30.446 | −40.768 | 79.926 | 1.00 | 68.02 |
| ATOM | 87 | C | PHE | 93 | 34.888 | −37.568 | 76.319 | 1.00 | 66.64 |
| ATOM | 88 | O | PHE | 93 | 36.094 | −37.801 | 76.418 | 1.00 | 66.70 |
| ATOM | 89 | N | ASN | 94 | 34.405 | −36.436 | 75.821 | 1.00 | 63.67 |
| ATOM | 90 | CA | ASN | 94 | 35.277 | −35.344 | 75.439 | 1.00 | 61.19 |
| ATOM | 91 | CB | ASN | 94 | 35.618 | −35.387 | 73.950 | 1.00 | 61.27 |
| ATOM | 92 | CG | ASN | 94 | 36.609 | −34.300 | 73.550 | 1.00 | 61.92 |
| ATOM | 93 | OD1 | ASN | 94 | 37.602 | −34.062 | 74.241 | 1.00 | 61.52 |
| ATOM | 94 | ND2 | ASN | 94 | 36.351 | −33.647 | 72.422 | 1.00 | 61.78 |
| ATOM | 95 | C | ASN | 94 | 34.442 | −34.119 | 75.767 | 1.00 | 59.74 |
| ATOM | 96 | O | ASN | 94 | 33.882 | −33.482 | 74.893 | 1.00 | 60.53 |
| ATOM | 97 | N | TRP | 95 | 34.345 | −33.831 | 77.055 | 1.00 | 57.77 |
| ATOM | 98 | CA | TRP | 95 | 33.579 | −32.719 | 77.567 | 1.00 | 55.79 |
| ATOM | 99 | CB | TRP | 95 | 33.948 | −32.471 | 79.030 | 1.00 | 53.78 |
| ATOM | 100 | CG | TRP | 95 | 35.277 | −31.803 | 79.223 | 1.00 | 49.89 |
| ATOM | 101 | CD2 | TRP | 95 | 35.534 | −30.615 | 79.971 | 1.00 | 50.17 |
| ATOM | 102 | CE2 | TRP | 95 | 36.913 | −30.357 | 79.903 | 1.00 | 49.60 |
| ATOM | 103 | CE3 | TRP | 95 | 34.727 | −29.734 | 80.707 | 1.00 | 50.04 |
| ATOM | 104 | CD1 | TRP | 95 | 36.474 | −32.211 | 78.737 | 1.00 | 49.33 |
| ATOM | 105 | NE1 | TRP | 95 | 37.468 | −31.354 | 79.134 | 1.00 | 49.08 |
| ATOM | 106 | CZ2 | TRP | 95 | 37.513 | −29.263 | 80.533 | 1.00 | 49.33 |
| ATOM | 107 | CZ3 | TRP | 95 | 35.316 | −28.650 | 81.335 | 1.00 | 49.36 |
| ATOM | 108 | CH2 | TRP | 95 | 36.696 | −28.424 | 81.246 | 1.00 | 50.29 |
| ATOM | 109 | C | TRP | 95 | 33.733 | −31.432 | 76.782 | 1.00 | 55.51 |

TABLE 1-continued

The structural coordinates of an exemplary stabilized form of gp120 at atomic resolution

| ATOM | 110 | O | TRP | 95 | 32.832 | −30.588 | 76.793 | 1.00 | 55.05 |
|---|---|---|---|---|---|---|---|---|---|
| ATOM | 111 | N | CYS | 96 | 34.876 | −31.286 | 76.114 | 1.00 | 55.79 |
| ATOM | 112 | CA | CYS | 96 | 35.183 | −30.109 | 75.309 | 1.00 | 56.39 |
| ATOM | 113 | C | CYS | 96 | 34.565 | −30.210 | 73.922 | 1.00 | 55.35 |
| ATOM | 114 | O | CYS | 96 | 35.144 | −29.765 | 72.935 | 1.00 | 55.34 |
| ATOM | 115 | CB | CYS | 96 | 36.705 | −29.935 | 75.183 | 1.00 | 59.56 |
| ATOM | 116 | SG | CYS | 96 | 37.516 | −29.511 | 76.772 | 1.00 | 65.71 |
| ATOM | 117 | N | LYS | 97 | 33.370 | −30.781 | 73.863 | 1.00 | 54.38 |
| ATOM | 118 | CA | LYS | 97 | 32.641 | −30.968 | 72.619 | 1.00 | 53.06 |
| ATOM | 119 | CB | LYS | 97 | 33.439 | −31.832 | 71.655 | 1.00 | 54.39 |
| ATOM | 120 | CG | LYS | 97 | 34.407 | −31.101 | 70.750 | 1.00 | 57.02 |
| ATOM | 121 | CD | LYS | 97 | 35.090 | −32.103 | 69.834 | 1.00 | 59.38 |
| ATOM | 122 | CE | LYS | 97 | 36.181 | −31.488 | 68.980 | 1.00 | 60.34 |
| ATOM | 123 | NZ | LYS | 97 | 36.872 | −32.554 | 68.187 | 1.00 | 60.06 |
| ATOM | 124 | C | LYS | 97 | 31.366 | −31.691 | 72.967 | 1.00 | 52.61 |
| ATOM | 125 | O | LYS | 97 | 31.042 | −32.698 | 72.363 | 1.00 | 53.46 |
| ATOM | 126 | N | ASN | 98 | 30.653 | −31.195 | 73.965 | 1.00 | 52.56 |
| ATOM | 127 | CA | ASN | 98 | 29.410 | −31.833 | 74.362 | 1.00 | 52.14 |
| ATOM | 128 | CB | ASN | 98 | 29.300 | −31.911 | 75.889 | 1.00 | 50.77 |
| ATOM | 129 | CG | ASN | 98 | 28.087 | −32.706 | 76.342 | 1.00 | 49.63 |
| ATOM | 130 | OD1 | ASN | 98 | 26.961 | −32.405 | 75.957 | 1.00 | 48.41 |
| ATOM | 131 | ND2 | ASN | 98 | 28.314 | −33.723 | 77.168 | 1.00 | 48.49 |
| ATOM | 132 | C | ASN | 98 | 28.232 | −31.056 | 73.788 | 1.00 | 52.73 |
| ATOM | 133 | O | ASN | 98 | 28.181 | −29.825 | 73.873 | 1.00 | 52.21 |
| ATOM | 134 | N | ASP | 99 | 27.286 | −31.780 | 73.202 | 1.00 | 53.95 |
| ATOM | 135 | CA | ASP | 99 | 26.107 | −31.160 | 72.601 | 1.00 | 55.38 |
| ATOM | 136 | CB | ASP | 99 | 25.354 | −32.184 | 71.745 | 1.00 | 58.50 |
| ATOM | 137 | CG | ASP | 99 | 25.615 | −32.009 | 70.253 | 1.00 | 60.48 |
| ATOM | 138 | OD1 | ASP | 99 | 25.206 | −32.892 | 69.462 | 1.00 | 61.59 |
| ATOM | 139 | OD2 | ASP | 99 | 26.222 | −30.982 | 69.877 | 1.00 | 61.09 |
| ATOM | 140 | C | ASP | 99 | 25.142 | −30.546 | 73.608 | 1.00 | 54.26 |
| ATOM | 141 | O | ASP | 99 | 24.342 | −29.676 | 73.260 | 1.00 | 54.68 |
| ATOM | 142 | N | MET | 100 | 25.208 | −31.008 | 74.851 | 1.00 | 51.85 |
| ATOM | 143 | CA | MET | 100 | 24.331 | −30.496 | 75.889 | 1.00 | 49.13 |
| ATOM | 144 | CB | MET | 100 | 24.357 | −31.424 | 77.094 | 1.00 | 48.72 |
| ATOM | 145 | CG | MET | 100 | 24.159 | −32.873 | 76.743 | 1.00 | 49.12 |
| ATOM | 146 | SD | MET | 100 | 24.699 | −33.947 | 78.077 | 1.00 | 48.08 |
| ATOM | 147 | CE | MET | 100 | 23.233 | −33.971 | 79.064 | 1.00 | 49.17 |
| ATOM | 148 | C | MET | 100 | 24.783 | −29.110 | 76.308 | 1.00 | 47.86 |
| ATOM | 149 | O | MET | 100 | 23.969 | −28.274 | 76.678 | 1.00 | 48.48 |
| ATOM | 150 | N | VAL | 101 | 26.085 | −28.867 | 76.253 | 1.00 | 46.25 |
| ATOM | 151 | CA | VAL | 101 | 26.616 | −27.569 | 76.641 | 1.00 | 45.39 |
| ATOM | 152 | CB | VAL | 101 | 28.145 | −27.522 | 76.472 | 1.00 | 45.11 |
| ATOM | 153 | CG1 | VAL | 101 | 28.654 | −26.126 | 76.755 | 1.00 | 44.71 |
| ATOM | 154 | CG2 | VAL | 101 | 28.801 | −28.517 | 77.401 | 1.00 | 43.94 |
| ATOM | 155 | C | VAL | 101 | 25.994 | −26.455 | 75.800 | 1.00 | 45.33 |
| ATOM | 156 | O | VAL | 101 | 25.579 | −25.426 | 76.318 | 1.00 | 45.54 |
| ATOM | 157 | N | GLU | 102 | 25.918 | −26.676 | 74.498 | 1.00 | 45.19 |
| ATOM | 158 | CA | GLU | 102 | 25.371 | −25.685 | 73.599 | 1.00 | 46.23 |
| ATOM | 159 | CB | GLU | 102 | 25.770 | −26.016 | 72.167 | 1.00 | 49.62 |
| ATOM | 160 | CG | GLU | 102 | 27.168 | −26.621 | 72.070 | 1.00 | 55.61 |
| ATOM | 161 | CD | GLU | 102 | 28.245 | −25.679 | 72.588 | 1.00 | 59.03 |
| ATOM | 162 | OE1 | GLU | 102 | 29.297 | −26.166 | 73.077 | 1.00 | 59.85 |
| ATOM | 163 | OE2 | GLU | 102 | 28.034 | −24.448 | 72.489 | 1.00 | 60.10 |
| ATOM | 164 | C | GLU | 102 | 23.869 | −25.627 | 73.715 | 1.00 | 45.67 |
| ATOM | 165 | O | GLU | 102 | 23.278 | −24.568 | 73.567 | 1.00 | 45.84 |
| ATOM | 166 | N | GLN | 103 | 23.244 | −26.764 | 73.982 | 1.00 | 45.79 |
| ATOM | 167 | CA | GLN | 103 | 21.795 | −26.786 | 74.101 | 1.00 | 47.31 |
| ATOM | 168 | CB | GLN | 103 | 21.271 | −28.220 | 74.156 | 1.00 | 48.93 |
| ATOM | 169 | CG | GLN | 103 | 19.750 | −28.313 | 74.345 | 1.00 | 52.63 |
| ATOM | 170 | CD | GLN | 103 | 18.929 | −27.662 | 73.216 | 1.00 | 53.89 |
| ATOM | 171 | OE1 | GLN | 103 | 17.703 | −27.566 | 73.309 | 1.00 | 54.70 |
| ATOM | 172 | NE2 | GLN | 103 | 19.600 | −27.222 | 72.154 | 1.00 | 52.85 |
| ATOM | 173 | C | GLN | 103 | 21.416 | −26.066 | 75.363 | 1.00 | 47.02 |
| ATOM | 174 | O | GLN | 103 | 20.494 | −25.260 | 75.390 | 1.00 | 46.84 |
| ATOM | 175 | N | MET | 104 | 22.146 | −26.369 | 76.418 | 1.00 | 48.58 |
| ATOM | 176 | CA | MET | 104 | 21.902 | −25.752 | 77.703 | 1.00 | 49.89 |
| ATOM | 177 | CB | MET | 104 | 22.985 | −26.182 | 78.694 | 1.00 | 52.33 |
| ATOM | 178 | CG | MET | 104 | 22.741 | −25.743 | 80.137 | 1.00 | 56.81 |
| ATOM | 179 | SD | MET | 104 | 22.286 | −27.119 | 81.216 | 1.00 | 60.04 |
| ATOM | 180 | CE | MET | 104 | 20.594 | −27.574 | 80.517 | 1.00 | 58.09 |
| ATOM | 181 | C | MET | 104 | 21.975 | −24.255 | 77.483 | 1.00 | 49.53 |
| ATOM | 182 | O | MET | 104 | 20.998 | −23.535 | 77.676 | 1.00 | 50.52 |
| ATOM | 183 | N | HIS | 105 | 23.146 | −23.808 | 77.048 | 1.00 | 48.30 |
| ATOM | 184 | CA | HIS | 105 | 23.409 | −22.403 | 76.807 | 1.00 | 47.10 |
| ATOM | 185 | CB | HIS | 105 | 24.712 | −22.250 | 76.031 | 1.00 | 46.50 |
| ATOM | 186 | CG | HIS | 105 | 25.181 | −20.836 | 75.913 | 1.00 | 45.38 |
| ATOM | 187 | CD2 | HIS | 105 | 25.468 | −20.082 | 74.828 | 1.00 | 44.97 |

TABLE 1-continued

The structural coordinates of an exemplary stabilized form of gp120 at atomic resolution

| ATOM | 188 | ND1 | HIS | 105 | 25.431 | −20.044 | 77.010 | 1.00 | 45.09 |
|---|---|---|---|---|---|---|---|---|---|
| ATOM | 189 | CE1 | HIS | 105 | 25.855 | −18.859 | 76.607 | 1.00 | 45.28 |
| ATOM | 190 | NE2 | HIS | 105 | 25.887 | −18.858 | 75.289 | 1.00 | 45.84 |
| ATOM | 191 | C | HIS | 105 | 22.306 | −21.664 | 76.077 | 1.00 | 47.03 |
| ATOM | 192 | O | HIS | 105 | 22.185 | −20.458 | 76.222 | 1.00 | 47.98 |
| ATOM | 193 | N | GLU | 106 | 21.506 | −22.362 | 75.283 | 1.00 | 47.46 |
| ATOM | 194 | CA | GLU | 106 | 20.439 | −21.680 | 74.564 | 1.00 | 48.81 |
| ATOM | 195 | CB | GLU | 106 | 20.203 | −22.323 | 73.203 | 1.00 | 51.42 |
| ATOM | 196 | CG | GLU | 106 | 21.432 | −22.305 | 72.320 | 1.00 | 57.65 |
| ATOM | 197 | CD | GLU | 106 | 21.126 | −22.632 | 70.870 | 1.00 | 61.26 |
| ATOM | 198 | OE1 | GLU | 106 | 20.441 | −23.656 | 70.619 | 1.00 | 63.05 |
| ATOM | 199 | OE2 | GLU | 106 | 21.583 | −21.866 | 69.985 | 1.00 | 62.41 |
| ATOM | 200 | C | GLU | 106 | 19.153 | −21.679 | 75.356 | 1.00 | 48.72 |
| ATOM | 201 | O | GLU | 106 | 18.369 | −20.731 | 75.281 | 1.00 | 47.67 |
| ATOM | 202 | N | ASP | 107 | 18.928 | −22.747 | 76.109 | 1.00 | 49.07 |
| ATOM | 203 | CA | ASP | 107 | 17.733 | −22.828 | 76.921 | 1.00 | 49.88 |
| ATOM | 204 | CB | ASP | 107 | 17.606 | −24.210 | 77.535 | 1.00 | 52.08 |
| ATOM | 205 | CG | ASP | 107 | 17.469 | −25.283 | 76.484 | 1.00 | 55.84 |
| ATOM | 206 | OD1 | ASP | 107 | 16.638 | −25.099 | 75.569 | 1.00 | 56.69 |
| ATOM | 207 | OD2 | ASP | 107 | 18.186 | −26.304 | 76.566 | 1.00 | 58.55 |
| ATOM | 208 | C | ASP | 107 | 17.834 | −21.775 | 78.000 | 1.00 | 49.32 |
| ATOM | 209 | O | ASP | 107 | 16.845 | −21.127 | 78.340 | 1.00 | 50.32 |
| ATOM | 210 | N | ILE | 108 | 19.043 | −21.595 | 78.524 | 1.00 | 48.00 |
| ATOM | 211 | CA | ILE | 108 | 19.285 | −20.600 | 79.562 | 1.00 | 46.04 |
| ATOM | 212 | CB | ILE | 108 | 20.713 | −20.686 | 80.102 | 1.00 | 45.64 |
| ATOM | 213 | CG2 | ILE | 108 | 20.891 | −19.691 | 81.234 | 1.00 | 43.75 |
| ATOM | 214 | CG1 | ILE | 108 | 21.024 | −22.119 | 80.550 | 1.00 | 46.19 |
| ATOM | 215 | CD1 | ILE | 108 | 20.330 | −22.579 | 81.803 | 1.00 | 46.61 |
| ATOM | 216 | C | ILE | 108 | 19.082 | −19.204 | 78.979 | 1.00 | 45.89 |
| ATOM | 217 | O | ILE | 108 | 18.185 | −18.483 | 79.396 | 1.00 | 47.43 |
| ATOM | 218 | N | CYS | 109 | 19.913 | −18.824 | 78.015 | 1.00 | 44.32 |
| ATOM | 219 | CA | CYS | 109 | 19.773 | −17.518 | 77.413 | 1.00 | 43.51 |
| ATOM | 220 | C | CYS | 109 | 18.334 | −17.218 | 77.154 | 1.00 | 41.47 |
| ATOM | 221 | O | CYS | 109 | 17.860 | −16.135 | 77.471 | 1.00 | 40.35 |
| ATOM | 222 | CB | CYS | 109 | 20.550 | −17.422 | 76.110 | 1.00 | 46.91 |
| ATOM | 223 | SG | CYS | 109 | 22.213 | −16.826 | 76.488 | 1.00 | 54.67 |
| ATOM | 224 | N | SER | 110 | 17.643 | −18.198 | 76.585 | 1.00 | 41.43 |
| ATOM | 225 | CA | SER | 110 | 16.227 | −18.094 | 76.252 | 1.00 | 42.22 |
| ATOM | 226 | CB | SER | 110 | 15.780 | −19.377 | 75.551 | 1.00 | 43.14 |
| ATOM | 227 | OG | SER | 110 | 14.365 | −19.448 | 75.485 | 1.00 | 46.83 |
| ATOM | 228 | C | SER | 110 | 15.347 | −17.839 | 77.473 | 1.00 | 41.93 |
| ATOM | 229 | O | SER | 110 | 14.414 | −17.037 | 77.438 | 1.00 | 40.88 |
| ATOM | 230 | N | LEU | 111 | 15.646 | −18.534 | 78.557 | 1.00 | 42.29 |
| ATOM | 231 | CA | LEU | 111 | 14.881 | −18.369 | 79.773 | 1.00 | 43.38 |
| ATOM | 232 | CB | LEU | 111 | 15.370 | −19.376 | 80.807 | 1.00 | 41.89 |
| ATOM | 233 | CG | LEU | 111 | 14.309 | −19.802 | 81.813 | 1.00 | 42.18 |
| ATOM | 234 | CD1 | LEU | 111 | 13.052 | −20.245 | 81.083 | 1.00 | 42.84 |
| ATOM | 235 | CD2 | LEU | 111 | 14.863 | −20.926 | 82.659 | 1.00 | 43.66 |
| ATOM | 236 | C | LEU | 111 | 15.061 | −16.935 | 80.279 | 1.00 | 45.09 |
| ATOM | 237 | O | LEU | 111 | 14.095 | −16.253 | 80.633 | 1.00 | 44.96 |
| ATOM | 238 | N | TRP | 112 | 16.307 | −16.476 | 80.290 | 1.00 | 46.31 |
| ATOM | 239 | CA | TRP | 112 | 16.613 | −15.131 | 80.744 | 1.00 | 48.17 |
| ATOM | 240 | CB | TRP | 112 | 18.126 | −14.922 | 80.779 | 1.00 | 49.91 |
| ATOM | 241 | CG | TRP | 112 | 18.747 | −15.516 | 82.010 | 1.00 | 52.44 |
| ATOM | 242 | CD2 | TRP | 112 | 19.544 | −14.840 | 82.984 | 1.00 | 53.45 |
| ATOM | 243 | CE2 | TRP | 112 | 19.851 | −15.778 | 83.999 | 1.00 | 53.54 |
| ATOM | 244 | CE3 | TRP | 112 | 20.031 | −13.532 | 83.102 | 1.00 | 54.72 |
| ATOM | 245 | CD1 | TRP | 112 | 18.613 | −16.796 | 82.453 | 1.00 | 52.57 |
| ATOM | 246 | NE1 | TRP | 112 | 19.269 | −16.964 | 83.647 | 1.00 | 51.79 |
| ATOM | 247 | CZ2 | TRP | 112 | 20.619 | −15.454 | 85.121 | 1.00 | 55.71 |
| ATOM | 248 | CZ3 | TRP | 112 | 20.797 | −13.204 | 84.217 | 1.00 | 56.51 |
| ATOM | 249 | CH2 | TRP | 112 | 21.083 | −14.165 | 85.215 | 1.00 | 57.71 |
| ATOM | 250 | C | TRP | 112 | 15.951 | −14.044 | 79.914 | 1.00 | 49.45 |
| ATOM | 251 | O | TRP | 112 | 15.497 | −13.047 | 80.459 | 1.00 | 50.46 |
| ATOM | 252 | N | ASP | 113 | 15.889 | −14.222 | 78.603 | 1.00 | 50.27 |
| ATOM | 253 | CA | ASP | 113 | 15.257 | −13.220 | 77.765 | 1.00 | 51.73 |
| ATOM | 254 | CB | ASP | 113 | 15.386 | −13.594 | 76.291 | 1.00 | 53.23 |
| ATOM | 255 | CG | ASP | 113 | 16.821 | −13.541 | 75.807 | 1.00 | 55.73 |
| ATOM | 256 | OD1 | ASP | 113 | 17.504 | −12.529 | 76.078 | 1.00 | 56.27 |
| ATOM | 257 | OD2 | ASP | 113 | 17.270 | −14.506 | 75.152 | 1.00 | 57.05 |
| ATOM | 258 | C | ASP | 113 | 13.788 | −13.064 | 78.125 | 1.00 | 52.99 |
| ATOM | 259 | O | ASP | 113 | 13.250 | −11.953 | 78.091 | 1.00 | 52.81 |
| ATOM | 260 | N | GLN | 114 | 13.144 | −14.173 | 78.483 | 1.00 | 54.06 |
| ATOM | 261 | CA | GLN | 114 | 11.727 | −14.145 | 78.837 | 1.00 | 54.67 |
| ATOM | 262 | CB | GLN | 114 | 11.018 | −15.408 | 78.318 | 1.00 | 56.60 |
| ATOM | 263 | CG | GLN | 114 | 11.793 | −16.710 | 78.507 | 1.00 | 61.03 |
| ATOM | 264 | CD | GLN | 114 | 11.135 | −17.906 | 77.812 | 1.00 | 63.04 |
| ATOM | 265 | OE1 | GLN | 114 | 10.062 | −18.362 | 78.210 | 1.00 | 64.12 |

TABLE 1-continued

The structural coordinates of an exemplary stabilized form of gp120 at atomic resolution

| ATOM | 266 | NE2 | GLN | 114 | 11.780 | −18.411 | 76.764 | 1.00 | 63.49 |
|------|-----|-----|-----|-----|--------|---------|--------|------|-------|
| ATOM | 267 | C | GLN | 114 | 11.441 | −13.953 | 80.321 | 1.00 | 53.71 |
| ATOM | 268 | O | GLN | 114 | 10.316 | −14.158 | 80.766 | 1.00 | 54.68 |
| ATOM | 269 | N | SER | 115 | 12.449 | −13.547 | 81.086 | 1.00 | 52.50 |
| ATOM | 270 | CA | SER | 115 | 12.265 | −13.308 | 82.519 | 1.00 | 51.69 |
| ATOM | 271 | CB | SER | 115 | 13.038 | −14.336 | 83.348 | 1.00 | 51.04 |
| ATOM | 272 | OG | SER | 115 | 12.621 | −15.652 | 83.056 | 1.00 | 52.93 |
| ATOM | 273 | C | SER | 115 | 12.746 | −11.913 | 82.901 | 1.00 | 51.57 |
| ATOM | 274 | O | SER | 115 | 12.011 | −11.142 | 83.520 | 1.00 | 52.69 |
| ATOM | 275 | N | LEU | 116 | 13.989 | −11.604 | 82.532 | 1.00 | 49.90 |
| ATOM | 276 | CA | LEU | 116 | 14.603 | −10.315 | 82.825 | 1.00 | 48.45 |
| ATOM | 277 | CB | LEU | 116 | 16.022 | −10.529 | 83.343 | 1.00 | 47.47 |
| ATOM | 278 | CG | LEU | 116 | 16.268 | −10.161 | 84.806 | 1.00 | 48.17 |
| ATOM | 279 | CD1 | LEU | 116 | 17.715 | −10.461 | 85.176 | 1.00 | 47.96 |
| ATOM | 280 | CD2 | LEU | 116 | 15.955 | −8.686 | 85.019 | 1.00 | 47.70 |
| ATOM | 281 | C | LEU | 116 | 14.645 | −9.431 | 81.581 | 1.00 | 48.28 |
| ATOM | 282 | O | LEU | 116 | 15.644 | −9.414 | 80.858 | 1.00 | 48.83 |
| ATOM | 283 | N | LYS | 117 | 13.571 | −8.682 | 81.345 | 1.00 | 46.85 |
| ATOM | 284 | CA | LYS | 117 | 13.479 | −7.817 | 80.170 | 1.00 | 45.19 |
| ATOM | 285 | CB | LYS | 117 | 12.012 | −7.662 | 79.768 | 1.00 | 45.35 |
| ATOM | 286 | CG | LYS | 117 | 11.377 | −8.958 | 79.341 | 1.00 | 45.38 |
| ATOM | 287 | CD | LYS | 117 | 9.987 | −8.733 | 78.809 | 1.00 | 45.69 |
| ATOM | 288 | CE | LYS | 117 | 9.621 | −9.864 | 77.882 | 1.00 | 45.39 |
| ATOM | 289 | NZ | LYS | 117 | 10.704 | −10.041 | 76.876 | 1.00 | 44.68 |
| ATOM | 290 | C | LYS | 117 | 14.100 | −6.440 | 80.351 | 1.00 | 43.15 |
| ATOM | 291 | O | LYS | 117 | 14.002 | −5.846 | 81.410 | 1.00 | 43.84 |
| ATOM | 292 | N | PRO | 118 | 14.764 | −5.920 | 79.315 | 1.00 | 41.84 |
| ATOM | 293 | CD | PRO | 118 | 15.467 | −6.711 | 78.301 | 1.00 | 41.18 |
| ATOM | 294 | CA | PRO | 118 | 15.377 | −4.594 | 79.428 | 1.00 | 42.68 |
| ATOM | 295 | CB | PRO | 118 | 16.611 | −4.708 | 78.532 | 1.00 | 41.64 |
| ATOM | 296 | CG | PRO | 118 | 16.852 | −6.184 | 78.446 | 1.00 | 41.32 |
| ATOM | 297 | C | PRO | 118 | 14.452 | −3.444 | 78.977 | 1.00 | 44.00 |
| ATOM | 298 | O | PRO | 118 | 13.547 | −3.631 | 78.155 | 1.00 | 43.14 |
| ATOM | 299 | N | CYS | 119 | 14.688 | −2.258 | 79.528 | 1.00 | 44.26 |
| ATOM | 300 | CA | CYS | 119 | 13.911 | −1.082 | 79.177 | 1.00 | 45.33 |
| ATOM | 301 | C | CYS | 119 | 14.328 | −0.688 | 77.776 | 1.00 | 44.84 |
| ATOM | 302 | O | CYS | 119 | 13.536 | −0.157 | 76.996 | 1.00 | 45.02 |
| ATOM | 303 | CB | CYS | 119 | 14.212 | 0.059 | 80.148 | 1.00 | 48.41 |
| ATOM | 304 | SG | CYS | 119 | 14.000 | −0.390 | 81.904 | 1.00 | 55.41 |
| ATOM | 305 | N | VAL | 120 | 15.595 | −0.946 | 77.476 | 1.00 | 43.63 |
| ATOM | 306 | CA | VAL | 120 | 16.165 | −0.669 | 76.166 | 1.00 | 42.72 |
| ATOM | 307 | CB | VAL | 120 | 16.807 | 0.719 | 76.110 | 1.00 | 40.94 |
| ATOM | 308 | CG1 | VAL | 120 | 17.494 | 0.914 | 74.784 | 1.00 | 38.51 |
| ATOM | 309 | CG2 | VAL | 120 | 15.740 | 1.773 | 76.293 | 1.00 | 40.48 |
| ATOM | 310 | C | VAL | 120 | 17.217 | −1.734 | 75.897 | 1.00 | 43.68 |
| ATOM | 311 | O | VAL | 120 | 17.932 | −2.162 | 76.811 | 1.00 | 42.94 |
| ATOM | 312 | N | LYS | 121 | 17.292 | −2.168 | 74.643 | 1.00 | 44.39 |
| ATOM | 313 | CA | LYS | 121 | 18.232 | −3.197 | 74.237 | 1.00 | 45.78 |
| ATOM | 314 | CB | LYS | 121 | 17.498 | −4.530 | 74.119 | 1.00 | 46.75 |
| ATOM | 315 | CG | LYS | 121 | 18.292 | −5.667 | 73.498 | 1.00 | 48.39 |
| ATOM | 316 | CD | LYS | 121 | 17.477 | −6.942 | 73.525 | 1.00 | 49.47 |
| ATOM | 317 | CE | LYS | 121 | 18.214 | −8.075 | 72.855 | 1.00 | 52.19 |
| ATOM | 318 | NZ | LYS | 121 | 17.391 | −9.321 | 72.815 | 1.00 | 54.57 |
| ATOM | 319 | C | LYS | 121 | 18.834 | −2.829 | 72.897 | 1.00 | 46.81 |
| ATOM | 320 | O | LYS | 121 | 18.119 | −2.708 | 71.913 | 1.00 | 47.70 |
| ATOM | 321 | N | LEU | 122 | 20.146 | −2.641 | 72.864 | 1.00 | 48.66 |
| ATOM | 322 | CA | LEU | 122 | 20.828 | −2.293 | 71.629 | 1.00 | 51.53 |
| ATOM | 323 | CB | LEU | 122 | 21.795 | −1.138 | 71.841 | 1.00 | 50.96 |
| ATOM | 324 | CG | LEU | 122 | 21.169 | 0.187 | 72.235 | 1.00 | 51.52 |
| ATOM | 325 | CD1 | LEU | 122 | 22.202 | 1.272 | 72.015 | 1.00 | 52.75 |
| ATOM | 326 | CD2 | LEU | 122 | 19.930 | 0.468 | 71.403 | 1.00 | 51.31 |
| ATOM | 327 | C | LEU | 122 | 21.613 | −3.454 | 71.075 | 1.00 | 54.29 |
| ATOM | 328 | O | LEU | 122 | 22.385 | −4.069 | 71.794 | 1.00 | 55.82 |
| ATOM | 329 | N | CYS | 123 | 21.422 | −3.756 | 69.796 | 1.00 | 57.66 |
| ATOM | 330 | CA | CYS | 123 | 22.156 | −4.844 | 69.161 | 1.00 | 61.99 |
| ATOM | 331 | C | CYS | 123 | 22.651 | −4.401 | 67.790 | 1.00 | 65.95 |
| ATOM | 332 | O | CYS | 123 | 21.868 | −3.977 | 66.952 | 1.00 | 66.42 |
| ATOM | 333 | CB | CYS | 123 | 21.261 | −6.068 | 69.001 | 1.00 | 61.14 |
| ATOM | 334 | SG | CYS | 123 | 20.636 | −6.863 | 70.520 | 1.00 | 64.65 |
| ATOM | 335 | N | PRO | 124 | 23.962 | −4.486 | 67.543 | 1.00 | 70.34 |
| ATOM | 336 | CD | PRO | 124 | 25.032 | −4.644 | 68.538 | 1.00 | 71.39 |
| ATOM | 337 | CA | PRO | 124 | 24.526 | −4.079 | 66.255 | 1.00 | 74.44 |
| ATOM | 338 | CB | PRO | 124 | 25.915 | −3.586 | 66.640 | 1.00 | 73.49 |
| ATOM | 339 | CG | PRO | 124 | 26.298 | −4.577 | 67.678 | 1.00 | 72.11 |
| ATOM | 340 | C | PRO | 124 | 24.600 | −5.151 | 65.170 | 1.00 | 78.68 |
| ATOM | 341 | O | PRO | 124 | 25.007 | −6.289 | 65.435 | 1.00 | 78.97 |
| ATOM | 342 | N | LEU | 125 | 24.216 | −4.754 | 63.952 | 1.00 | 83.43 |
| ATOM | 343 | CA | LEU | 125 | 24.246 | −5.602 | 62.755 | 1.00 | 87.97 |

TABLE 1-continued

The structural coordinates of an exemplary stabilized form of gp120 at atomic resolution

| ATOM | 344 | CB  | LEU | 125 | 22.826 | −5.802 | 62.199 | 1.00 | 85.90  |
|------|-----|-----|-----|-----|--------|--------|--------|------|--------|
| ATOM | 345 | CG  | LEU | 125 | 22.682 | −6.595 | 60.892 | 1.00 | 85.01  |
| ATOM | 346 | CD1 | LEU | 125 | 23.501 | −7.878 | 60.933 | 1.00 | 84.72  |
| ATOM | 347 | CD2 | LEU | 125 | 21.223 | −6.908 | 60.673 | 1.00 | 84.26  |
| ATOM | 348 | C   | LEU | 125 | 25.136 | −4.880 | 61.723 | 1.00 | 91.79  |
| ATOM | 349 | O   | LEU | 125 | 24.645 | −4.294 | 60.751 | 1.00 | 92.07  |
| ATOM | 350 | N   | CYS | 126 | 26.449 | −4.932 | 61.963 | 1.00 | 95.81  |
| ATOM | 351 | CA  | CYS | 126 | 27.456 | −4.274 | 61.128 | 1.00 | 99.93  |
| ATOM | 352 | C   | CYS | 126 | 27.478 | −4.610 | 59.639 | 1.00 | 101.72 |
| ATOM | 353 | O   | CYS | 126 | 26.500 | −5.115 | 59.075 | 1.00 | 101.70 |
| ATOM | 354 | CB  | CYS | 126 | 28.860 | −4.525 | 61.702 | 1.00 | 101.65 |
| ATOM | 355 | SG  | CYS | 126 | 29.830 | −3.024 | 62.094 | 1.00 | 105.44 |
| ATOM | 356 | N   | VAL | 127 | 28.627 | −4.317 | 59.026 | 1.00 | 103.91 |
| ATOM | 357 | CA  | VAL | 127 | 28.873 | −4.528 | 57.601 | 1.00 | 105.90 |
| ATOM | 358 | CB  | VAL | 127 | 29.149 | −6.029 | 57.278 | 1.00 | 105.47 |
| ATOM | 359 | CG1 | VAL | 127 | 29.583 | −6.188 | 55.822 | 1.00 | 104.28 |
| ATOM | 360 | CG2 | VAL | 127 | 30.240 | −6.563 | 58.196 | 1.00 | 104.81 |
| ATOM | 361 | C   | VAL | 127 | 27.668 | −4.011 | 56.817 | 1.00 | 107.53 |
| ATOM | 362 | O   | VAL | 127 | 27.187 | −2.905 | 57.086 | 1.00 | 107.44 |
| ATOM | 363 | N   | GLY | 128 | 27.171 | −4.801 | 55.869 | 1.00 | 108.79 |
| ATOM | 364 | CA  | GLY | 128 | 26.041 | −4.358 | 55.076 | 1.00 | 110.07 |
| ATOM | 365 | C   | GLY | 128 | 26.390 | −3.033 | 54.422 | 1.00 | 111.37 |
| ATOM | 366 | O   | GLY | 128 | 25.543 | −2.144 | 54.318 | 1.00 | 111.70 |
| ATOM | 367 | N   | ALA | 129 | 27.653 | −2.909 | 54.007 | 1.00 | 112.10 |
| ATOM | 368 | CA  | ALA | 129 | 28.187 | −1.712 | 53.350 | 1.00 | 112.06 |
| ATOM | 369 | CB  | ALA | 129 | 27.246 | −1.268 | 52.213 | 1.00 | 112.16 |
| ATOM | 370 | C   | ALA | 129 | 28.491 | −0.520 | 54.272 | 1.00 | 111.66 |
| ATOM | 371 | O   | ALA | 129 | 27.895 |  0.551 | 54.125 | 1.00 | 111.99 |
| ATOM | 372 | N   | GLY | 194 | 29.418 | −0.709 | 55.215 | 1.00 | 110.69 |
| ATOM | 373 | CA  | GLY | 194 | 29.815 |  0.358 | 56.129 | 1.00 | 108.83 |
| ATOM | 374 | C   | GLY | 194 | 28.806 |  0.894 | 57.136 | 1.00 | 107.51 |
| ATOM | 375 | O   | GLY | 194 | 29.136 |  1.040 | 58.316 | 1.00 | 106.82 |
| ATOM | 376 | N   | SER | 195 | 27.596 |  1.212 | 56.672 | 1.00 | 106.32 |
| ATOM | 377 | CA  | SER | 195 | 26.529 |  1.737 | 57.529 | 1.00 | 104.42 |
| ATOM | 378 | CB  | SER | 195 | 25.342 |  2.211 | 56.684 | 1.00 | 104.28 |
| ATOM | 379 | OG  | SER | 195 | 25.728 |  3.205 | 55.752 | 1.00 | 103.83 |
| ATOM | 380 | C   | SER | 195 | 26.050 |  0.664 | 58.497 | 1.00 | 103.36 |
| ATOM | 381 | O   | SER | 195 | 24.927 |  0.164 | 58.381 | 1.00 | 103.62 |
| ATOM | 382 | N   | CYS | 196 | 26.917 |  0.317 | 59.446 | 1.00 | 101.48 |
| ATOM | 383 | CA  | CYS | 196 | 26.631 | −0.696 | 60.461 | 1.00 | 98.25  |
| ATOM | 384 | C   | CYS | 196 | 25.391 | −0.331 | 61.275 | 1.00 | 93.82  |
| ATOM | 385 | O   | CYS | 196 | 25.496 |  0.258 | 62.352 | 1.00 | 93.50  |
| ATOM | 386 | CB  | CYS | 196 | 27.846 | −0.843 | 61.390 | 1.00 | 100.91 |
| ATOM | 387 | SG  | CYS | 196 | 29.301 | −1.683 | 60.659 | 1.00 | 104.77 |
| ATOM | 388 | N   | ASN | 197 | 24.219 | −0.688 | 60.758 | 1.00 | 88.40  |
| ATOM | 389 | CA  | ASN | 197 | 22.973 | −0.380 | 61.444 | 1.00 | 82.77  |
| ATOM | 390 | CB  | ASN | 197 | 21.770 | −0.728 | 60.566 | 1.00 | 85.03  |
| ATOM | 391 | CG  | ASN | 197 | 21.187 |  0.494 | 59.868 | 1.00 | 87.21  |
| ATOM | 392 | OD1 | ASN | 197 | 20.801 |  1.465 | 60.529 | 1.00 | 88.02  |
| ATOM | 393 | ND2 | ASN | 197 | 21.120 |  0.450 | 58.539 | 1.00 | 88.02  |
| ATOM | 394 | C   | ASN | 197 | 22.863 | −1.088 | 62.780 | 1.00 | 77.50  |
| ATOM | 395 | O   | ASN | 197 | 23.334 | −2.210 | 62.943 | 1.00 | 77.29  |
| ATOM | 396 | N   | THR | 198 | 22.227 | −0.413 | 63.730 | 1.00 | 71.01  |
| ATOM | 397 | CA  | THR | 198 | 22.048 | −0.929 | 65.075 | 1.00 | 63.96  |
| ATOM | 398 | CB  | THR | 198 | 22.715 |  0.006 | 66.085 | 1.00 | 64.25  |
| ATOM | 399 | OG1 | THR | 198 | 24.118 |  0.085 | 65.802 | 1.00 | 64.31  |
| ATOM | 400 | CG2 | THR | 198 | 22.496 | −0.496 | 67.500 | 1.00 | 64.07  |
| ATOM | 401 | C   | THR | 198 | 20.575 | −1.056 | 65.427 | 1.00 | 58.97  |
| ATOM | 402 | O   | THR | 198 | 19.859 | −0.065 | 65.448 | 1.00 | 58.60  |
| ATOM | 403 | N   | SER | 199 | 20.136 | −2.279 | 65.709 | 1.00 | 53.41  |
| ATOM | 404 | CA  | SER | 199 | 18.747 | −2.559 | 66.067 | 1.00 | 48.39  |
| ATOM | 405 | CB  | SER | 199 | 18.470 | −4.051 | 65.915 | 1.00 | 47.89  |
| ATOM | 406 | OG  | SER | 199 | 17.306 | −4.425 | 66.627 | 1.00 | 48.16  |
| ATOM | 407 | C   | SER | 199 | 18.439 | −2.134 | 67.495 | 1.00 | 45.34  |
| ATOM | 408 | O   | SER | 199 | 19.174 | −2.470 | 68.403 | 1.00 | 45.45  |
| ATOM | 409 | N   | VAL | 200 | 17.340 | −1.414 | 67.691 | 1.00 | 42.99  |
| ATOM | 410 | CA  | VAL | 200 | 16.955 | −0.932 | 69.016 | 1.00 | 40.63  |
| ATOM | 411 | CB  | VAL | 200 | 16.927 |  0.610 | 69.046 | 1.00 | 39.79  |
| ATOM | 412 | CG1 | VAL | 200 | 16.500 |  1.098 | 70.404 | 1.00 | 39.65  |
| ATOM | 413 | CG2 | VAL | 200 | 18.290 |  1.164 | 68.702 | 1.00 | 38.60  |
| ATOM | 414 | C   | VAL | 200 | 15.583 | −1.440 | 69.449 | 1.00 | 40.29  |
| ATOM | 415 | O   | VAL | 200 | 14.629 | −1.400 | 68.678 | 1.00 | 40.35  |
| ATOM | 416 | N   | ILE | 201 | 15.482 | −1.905 | 70.689 | 1.00 | 40.20  |
| ATOM | 417 | CA  | ILE | 201 | 14.217 | −2.417 | 71.219 | 1.00 | 41.32  |
| ATOM | 418 | CB  | ILE | 201 | 14.249 | −3.956 | 71.405 | 1.00 | 42.65  |
| ATOM | 419 | CG2 | ILE | 201 | 12.921 | −4.441 | 71.989 | 1.00 | 41.02  |
| ATOM | 420 | CG1 | ILE | 201 | 14.543 | −4.646 | 70.070 | 1.00 | 43.17  |
| ATOM | 421 | CD1 | ILE | 201 | 14.834 | −6.135 | 70.211 | 1.00 | 44.46  |

TABLE 1-continued

The structural coordinates of an exemplary stabilized form of gp120 at atomic resolution

| ATOM | 422 | C | ILE | 201 | 13.874 | −1.810 | 72.577 | 1.00 | 41.94 |
|---|---|---|---|---|---|---|---|---|---|
| ATOM | 423 | O | ILE | 201 | 14.654 | −1.896 | 73.532 | 1.00 | 41.41 |
| ATOM | 424 | N | THR | 202 | 12.690 | −1.214 | 72.657 | 1.00 | 41.95 |
| ATOM | 425 | CA | THR | 202 | 12.226 | −0.601 | 73.889 | 1.00 | 42.08 |
| ATOM | 426 | CB | THR | 202 | 11.969 | 0.892 | 73.696 | 1.00 | 41.25 |
| ATOM | 427 | OG1 | THR | 202 | 13.082 | 1.490 | 73.027 | 1.00 | 40.91 |
| ATOM | 428 | CG2 | THR | 202 | 11.788 | 1.560 | 75.031 | 1.00 | 41.52 |
| ATOM | 429 | C | THR | 202 | 10.918 | −1.251 | 74.318 | 1.00 | 43.20 |
| ATOM | 430 | O | THR | 202 | 9.948 | −1.241 | 73.563 | 1.00 | 43.24 |
| ATOM | 431 | N | GLN | 203 | 10.890 | −1.818 | 75.524 | 1.00 | 44.57 |
| ATOM | 432 | CA | GLN | 203 | 9.679 | −2.464 | 76.037 | 1.00 | 45.88 |
| ATOM | 433 | CB | GLN | 203 | 9.752 | −3.978 | 75.850 | 1.00 | 45.18 |
| ATOM | 434 | CG | GLN | 203 | 10.718 | −4.635 | 76.792 | 1.00 | 46.99 |
| ATOM | 435 | CD | GLN | 203 | 11.663 | −5.579 | 76.093 | 1.00 | 48.26 |
| ATOM | 436 | OE1 | GLN | 203 | 11.253 | −6.602 | 75.541 | 1.00 | 47.41 |
| ATOM | 437 | NE2 | GLN | 203 | 12.945 | −5.236 | 76.109 | 1.00 | 49.20 |
| ATOM | 438 | C | GLN | 203 | 9.526 | −2.169 | 77.515 | 1.00 | 46.24 |
| ATOM | 439 | O | GLN | 203 | 10.416 | −1.575 | 78.126 | 1.00 | 46.33 |
| ATOM | 440 | N | ALA | 204 | 8.395 | −2.576 | 78.086 | 1.00 | 46.69 |
| ATOM | 441 | CA | ALA | 204 | 8.169 | −2.376 | 79.510 | 1.00 | 47.75 |
| ATOM | 442 | CB | ALA | 204 | 6.754 | −2.731 | 79.869 | 1.00 | 47.77 |
| ATOM | 443 | C | ALA | 204 | 9.155 | −3.326 | 80.193 | 1.00 | 49.20 |
| ATOM | 444 | O | ALA | 204 | 9.282 | −4.492 | 79.799 | 1.00 | 50.45 |
| ATOM | 445 | N | CYS | 205 | 9.854 | −2.830 | 81.209 | 1.00 | 49.03 |
| ATOM | 446 | CA | CYS | 205 | 10.870 | −3.618 | 81.895 | 1.00 | 47.82 |
| ATOM | 447 | C | CYS | 205 | 10.596 | −3.914 | 83.372 | 1.00 | 47.00 |
| ATOM | 448 | O | CYS | 205 | 11.342 | −3.464 | 84.244 | 1.00 | 47.48 |
| ATOM | 449 | CB | CYS | 205 | 12.214 | −2.899 | 81.749 | 1.00 | 49.40 |
| ATOM | 450 | SG | CYS | 205 | 12.089 | −1.097 | 82.038 | 1.00 | 52.40 |
| ATOM | 451 | N | PRO | 206 | 9.535 | −4.692 | 83.671 | 1.00 | 45.36 |
| ATOM | 452 | CD | PRO | 206 | 8.592 | −5.258 | 82.690 | 1.00 | 44.00 |
| ATOM | 453 | CA | PRO | 206 | 9.142 | −5.069 | 85.037 | 1.00 | 43.93 |
| ATOM | 454 | CB | PRO | 206 | 8.083 | −6.135 | 84.797 | 1.00 | 42.82 |
| ATOM | 455 | CG | PRO | 206 | 7.423 | −5.660 | 83.552 | 1.00 | 42.86 |
| ATOM | 456 | C | PRO | 206 | 10.294 | −5.603 | 85.890 | 1.00 | 43.70 |
| ATOM | 457 | O | PRO | 206 | 11.013 | −6.495 | 85.458 | 1.00 | 43.27 |
| ATOM | 458 | N | LYS | 207 | 10.471 | −5.059 | 87.094 | 1.00 | 44.28 |
| ATOM | 459 | CA | LYS | 207 | 11.533 | −5.521 | 87.992 | 1.00 | 45.36 |
| ATOM | 460 | CB | LYS | 207 | 11.664 | −4.626 | 89.235 | 1.00 | 43.66 |
| ATOM | 461 | CG | LYS | 207 | 12.061 | −3.179 | 89.019 | 1.00 | 42.40 |
| ATOM | 462 | CD | LYS | 207 | 13.436 | −3.046 | 88.429 | 1.00 | 41.07 |
| ATOM | 463 | CE | LYS | 207 | 14.481 | −3.725 | 89.264 | 1.00 | 40.58 |
| ATOM | 464 | NZ | LYS | 207 | 15.758 | −3.685 | 88.510 | 1.00 | 40.89 |
| ATOM | 465 | C | LYS | 207 | 11.157 | −6.913 | 88.481 | 1.00 | 47.60 |
| ATOM | 466 | O | LYS | 207 | 10.126 | −7.086 | 89.126 | 1.00 | 49.38 |
| ATOM | 467 | N | VAL | 208 | 11.975 | −7.910 | 88.185 | 1.00 | 49.19 |
| ATOM | 468 | CA | VAL | 208 | 11.669 | −9.248 | 88.654 | 1.00 | 50.40 |
| ATOM | 469 | CB | VAL | 208 | 11.317 | −10.192 | 87.512 | 1.00 | 49.17 |
| ATOM | 470 | CG1 | VAL | 208 | 10.947 | −11.548 | 88.072 | 1.00 | 48.47 |
| ATOM | 471 | CG2 | VAL | 208 | 10.171 | −9.621 | 86.720 | 1.00 | 49.94 |
| ATOM | 472 | C | VAL | 208 | 12.867 | −9.800 | 89.379 | 1.00 | 52.48 |
| ATOM | 473 | O | VAL | 208 | 13.950 | −9.895 | 88.820 | 1.00 | 53.30 |
| ATOM | 474 | N | SER | 209 | 12.667 | −10.153 | 90.638 | 1.00 | 55.82 |
| ATOM | 475 | CA | SER | 209 | 13.744 | −10.701 | 91.442 | 1.00 | 59.23 |
| ATOM | 476 | CB | SER | 209 | 14.271 | −9.657 | 92.433 | 1.00 | 60.00 |
| ATOM | 477 | OG | SER | 209 | 13.294 | −9.300 | 93.397 | 1.00 | 59.59 |
| ATOM | 478 | C | SER | 209 | 13.251 | −11.912 | 92.205 | 1.00 | 60.56 |
| ATOM | 479 | O | SER | 209 | 12.328 | −11.819 | 93.015 | 1.00 | 61.51 |
| ATOM | 480 | N | PHE | 210 | 13.863 | −13.054 | 91.927 | 1.00 | 61.88 |
| ATOM | 481 | CA | PHE | 210 | 13.509 | −14.293 | 92.596 | 1.00 | 62.55 |
| ATOM | 482 | CB | PHE | 210 | 12.163 | −14.831 | 92.088 | 1.00 | 62.36 |
| ATOM | 483 | CG | PHE | 210 | 12.173 | −15.247 | 90.645 | 1.00 | 62.80 |
| ATOM | 484 | CD1 | PHE | 210 | 12.312 | −14.303 | 89.634 | 1.00 | 63.22 |
| ATOM | 485 | CD2 | PHE | 210 | 12.044 | −16.588 | 90.295 | 1.00 | 63.02 |
| ATOM | 486 | CE1 | PHE | 210 | 12.321 | −14.690 | 88.294 | 1.00 | 62.99 |
| ATOM | 487 | CE2 | PHE | 210 | 12.052 | −16.980 | 88.957 | 1.00 | 63.02 |
| ATOM | 488 | CZ | PHE | 210 | 12.191 | −16.027 | 87.956 | 1.00 | 62.16 |
| ATOM | 489 | C | PHE | 210 | 14.624 | −15.285 | 92.317 | 1.00 | 62.59 |
| ATOM | 490 | O | PHE | 210 | 15.231 | −15.266 | 91.245 | 1.00 | 62.81 |
| ATOM | 491 | N | GLU | 211 | 14.908 | −16.138 | 93.291 | 1.00 | 62.66 |
| ATOM | 492 | CA | GLU | 211 | 15.963 | −17.120 | 93.127 | 1.00 | 62.85 |
| ATOM | 493 | CB | GLU | 211 | 16.274 | −17.768 | 94.490 | 1.00 | 63.27 |
| ATOM | 494 | CG | GLU | 211 | 17.354 | −16.985 | 95.278 | 1.00 | 65.06 |
| ATOM | 495 | CD | GLU | 211 | 17.291 | −17.160 | 96.800 | 1.00 | 65.99 |
| ATOM | 496 | OE1 | GLU | 211 | 17.055 | −18.299 | 97.267 | 1.00 | 66.91 |
| ATOM | 497 | OE2 | GLU | 211 | 17.497 | −16.153 | 97.528 | 1.00 | 63.93 |
| ATOM | 498 | C | GLU | 211 | 15.645 | −18.161 | 92.036 | 1.00 | 61.85 |
| ATOM | 499 | O | GLU | 211 | 14.538 | −18.703 | 91.965 | 1.00 | 61.07 |

TABLE 1-continued

The structural coordinates of an exemplary stabilized form of gp120 at atomic resolution

| ATOM | 500 | N | PRO | 212 | 16.617 | −18.406 | 91.136 | 1.00 | 60.73 |
|------|-----|-----|-----|-----|--------|---------|--------|------|-------|
| ATOM | 501 | CD | PRO | 212 | 17.853 | −17.606 | 91.033 | 1.00 | 60.13 |
| ATOM | 502 | CA | PRO | 212 | 16.529 | −19.355 | 90.019 | 1.00 | 60.07 |
| ATOM | 503 | CB | PRO | 212 | 17.865 | −19.151 | 89.295 | 1.00 | 60.56 |
| ATOM | 504 | CG | PRO | 212 | 18.190 | −17.724 | 89.579 | 1.00 | 58.99 |
| ATOM | 505 | C | PRO | 212 | 16.318 | −20.824 | 90.424 | 1.00 | 59.13 |
| ATOM | 506 | O | PRO | 212 | 17.062 | −21.371 | 91.241 | 1.00 | 58.14 |
| ATOM | 507 | N | ILE | 213 | 15.308 | −21.454 | 89.834 | 1.00 | 58.39 |
| ATOM | 508 | CA | ILE | 213 | 14.999 | −22.851 | 90.111 | 1.00 | 57.51 |
| ATOM | 509 | CB | ILE | 213 | 13.582 | −23.226 | 89.634 | 1.00 | 57.45 |
| ATOM | 510 | CG2 | ILE | 213 | 12.936 | −24.123 | 90.645 | 1.00 | 58.00 |
| ATOM | 511 | CG1 | ILE | 213 | 12.716 | −21.978 | 89.461 | 1.00 | 58.13 |
| ATOM | 512 | CD1 | ILE | 213 | 12.426 | −21.230 | 90.750 | 1.00 | 58.27 |
| ATOM | 513 | C | ILE | 213 | 15.995 | −23.705 | 89.330 | 1.00 | 57.45 |
| ATOM | 514 | O | ILE | 213 | 16.398 | −23.335 | 88.225 | 1.00 | 57.51 |
| ATOM | 515 | N | PRO | 214 | 16.406 | −24.863 | 89.888 | 1.00 | 56.69 |
| ATOM | 516 | CD | PRO | 214 | 16.153 | −25.380 | 91.240 | 1.00 | 55.47 |
| ATOM | 517 | CA | PRO | 214 | 17.361 | −25.729 | 89.193 | 1.00 | 55.78 |
| ATOM | 518 | CB | PRO | 214 | 17.614 | −26.845 | 90.197 | 1.00 | 54.06 |
| ATOM | 519 | CG | PRO | 214 | 17.405 | −26.184 | 91.489 | 1.00 | 54.24 |
| ATOM | 520 | C | PRO | 214 | 16.789 | −26.257 | 87.894 | 1.00 | 56.50 |
| ATOM | 521 | O | PRO | 214 | 15.620 | −26.637 | 87.820 | 1.00 | 55.06 |
| ATOM | 522 | N | ILE | 215 | 17.640 | −26.271 | 86.878 | 1.00 | 58.07 |
| ATOM | 523 | CA | ILE | 215 | 17.286 | −26.745 | 85.555 | 1.00 | 58.99 |
| ATOM | 524 | CB | ILE | 215 | 17.892 | −25.815 | 84.461 | 1.00 | 60.28 |
| ATOM | 525 | CG2 | ILE | 215 | 17.752 | −26.442 | 83.088 | 1.00 | 61.12 |
| ATOM | 526 | CG1 | ILE | 215 | 17.218 | −24.435 | 84.499 | 1.00 | 61.06 |
| ATOM | 527 | CD1 | ILE | 215 | 15.713 | −24.448 | 84.230 | 1.00 | 60.70 |
| ATOM | 528 | C | ILE | 215 | 17.846 | −28.153 | 85.391 | 1.00 | 59.41 |
| ATOM | 529 | O | ILE | 215 | 18.987 | −28.418 | 85.754 | 1.00 | 58.13 |
| ATOM | 530 | N | HIS | 216 | 17.019 | −29.051 | 84.866 | 1.00 | 61.77 |
| ATOM | 531 | CA | HIS | 216 | 17.403 | −30.436 | 84.617 | 1.00 | 63.93 |
| ATOM | 532 | CB | HIS | 216 | 16.393 | −31.403 | 85.235 | 1.00 | 64.72 |
| ATOM | 533 | CG | HIS | 216 | 16.375 | −31.414 | 86.730 | 1.00 | 67.28 |
| ATOM | 534 | CD2 | HIS | 216 | 15.441 | −30.977 | 87.609 | 1.00 | 67.94 |
| ATOM | 535 | ND1 | HIS | 216 | 17.375 | −31.987 | 87.483 | 1.00 | 68.72 |
| ATOM | 536 | CE1 | HIS | 216 | 17.057 | −31.908 | 88.766 | 1.00 | 68.43 |
| ATOM | 537 | NE2 | HIS | 216 | 15.890 | −31.300 | 88.868 | 1.00 | 69.02 |
| ATOM | 538 | C | HIS | 216 | 17.378 | −30.655 | 83.105 | 1.00 | 65.39 |
| ATOM | 539 | O | HIS | 216 | 16.331 | −30.504 | 82.474 | 1.00 | 65.51 |
| ATOM | 540 | N | TYR | 217 | 18.517 | −31.002 | 82.517 | 1.00 | 66.95 |
| ATOM | 541 | CA | TYR | 217 | 18.562 | −31.260 | 81.081 | 1.00 | 67.77 |
| ATOM | 542 | CB | TYR | 217 | 19.964 | −30.971 | 80.530 | 1.00 | 69.80 |
| ATOM | 543 | CG | TYR | 217 | 20.183 | −31.360 | 79.076 | 1.00 | 72.85 |
| ATOM | 544 | CD1 | TYR | 217 | 20.066 | −32.688 | 78.656 | 1.00 | 73.62 |
| ATOM | 545 | CE1 | TYR | 217 | 20.306 | −33.062 | 77.332 | 1.00 | 73.91 |
| ATOM | 546 | CD2 | TYR | 217 | 20.543 | −30.408 | 78.124 | 1.00 | 74.21 |
| ATOM | 547 | CE2 | TYR | 217 | 20.787 | −30.774 | 76.791 | 1.00 | 75.39 |
| ATOM | 548 | CZ | TYR | 217 | 20.664 | −32.105 | 76.407 | 1.00 | 75.03 |
| ATOM | 549 | OH | TYR | 217 | 20.905 | −32.476 | 75.101 | 1.00 | 75.25 |
| ATOM | 550 | C | TYR | 217 | 18.198 | −32.726 | 80.881 | 1.00 | 67.53 |
| ATOM | 551 | O | TYR | 217 | 18.779 | −33.611 | 81.512 | 1.00 | 66.37 |
| ATOM | 552 | N | CYS | 218 | 17.220 | −32.977 | 80.021 | 1.00 | 68.26 |
| ATOM | 553 | CA | CYS | 218 | 16.801 | −34.345 | 79.736 | 1.00 | 69.95 |
| ATOM | 554 | C | CYS | 218 | 17.146 | −34.676 | 78.291 | 1.00 | 70.18 |
| ATOM | 555 | O | CYS | 218 | 17.368 | −33.768 | 77.483 | 1.00 | 71.00 |
| ATOM | 556 | CB | CYS | 218 | 15.299 | −34.515 | 79.952 | 1.00 | 70.79 |
| ATOM | 557 | SG | CYS | 218 | 14.717 | −34.185 | 81.647 | 1.00 | 73.86 |
| ATOM | 558 | N | ALA | 219 | 17.190 | −35.969 | 77.972 | 1.00 | 69.23 |
| ATOM | 559 | CA | ALA | 219 | 17.525 | −36.418 | 76.622 | 1.00 | 67.68 |
| ATOM | 560 | CB | ALA | 219 | 17.950 | −37.874 | 76.651 | 1.00 | 68.44 |
| ATOM | 561 | C | ALA | 219 | 16.367 | −36.224 | 75.644 | 1.00 | 66.31 |
| ATOM | 562 | O | ALA | 219 | 15.224 | −36.577 | 75.937 | 1.00 | 64.91 |
| ATOM | 563 | N | PRO | 220 | 16.657 | −35.652 | 74.462 | 1.00 | 65.58 |
| ATOM | 564 | CD | PRO | 220 | 17.955 | −35.074 | 74.079 | 1.00 | 65.63 |
| ATOM | 565 | CA | PRO | 220 | 15.657 | −35.394 | 73.420 | 1.00 | 64.40 |
| ATOM | 566 | CB | PRO | 220 | 16.352 | −34.386 | 72.500 | 1.00 | 64.51 |
| ATOM | 567 | CG | PRO | 220 | 17.515 | −33.858 | 73.317 | 1.00 | 65.89 |
| ATOM | 568 | C | PRO | 220 | 15.298 | −36.670 | 72.676 | 1.00 | 63.38 |
| ATOM | 569 | O | PRO | 220 | 16.095 | −37.609 | 72.625 | 1.00 | 63.61 |
| ATOM | 570 | N | ALA | 221 | 14.104 | −36.691 | 72.090 | 1.00 | 61.61 |
| ATOM | 571 | CA | ALA | 221 | 13.645 | −37.852 | 71.345 | 1.00 | 59.16 |
| ATOM | 572 | CB | ALA | 221 | 12.397 | −37.503 | 70.558 | 1.00 | 57.25 |
| ATOM | 573 | C | ALA | 221 | 14.751 | −38.323 | 70.407 | 1.00 | 58.51 |
| ATOM | 574 | O | ALA | 221 | 15.303 | −37.532 | 69.645 | 1.00 | 58.11 |
| ATOM | 575 | N | GLY | 222 | 15.092 | −39.608 | 70.492 | 1.00 | 58.44 |
| ATOM | 576 | CA | GLY | 222 | 16.121 | −40.163 | 69.632 | 1.00 | 58.13 |
| ATOM | 577 | C | GLY | 222 | 17.508 | −40.316 | 70.229 | 1.00 | 58.27 |

TABLE 1-continued

The structural coordinates of an exemplary stabilized form of gp120 at atomic resolution

| ATOM | 578 | O   | GLY | 222 | 18.405 | −40.830 | 69.560 | 1.00 | 57.97 |
|------|-----|-----|-----|-----|--------|---------|--------|------|-------|
| ATOM | 579 | N   | PHE | 223 | 17.700 | −39.888 | 71.475 | 1.00 | 58.69 |
| ATOM | 580 | CA  | PHE | 223 | 19.020 | −39.989 | 72.102 | 1.00 | 58.31 |
| ATOM | 581 | CB  | PHE | 223 | 19.711 | −38.625 | 72.073 | 1.00 | 59.64 |
| ATOM | 582 | CG  | PHE | 223 | 20.030 | −38.136 | 70.690 | 1.00 | 60.13 |
| ATOM | 583 | CD1 | PHE | 223 | 19.032 | −37.613 | 69.873 | 1.00 | 59.78 |
| ATOM | 584 | CD2 | PHE | 223 | 21.330 | −38.222 | 70.197 | 1.00 | 59.77 |
| ATOM | 585 | CE1 | PHE | 223 | 19.323 | −37.182 | 68.588 | 1.00 | 60.31 |
| ATOM | 586 | CE2 | PHE | 223 | 21.632 | −37.797 | 68.919 | 1.00 | 60.24 |
| ATOM | 587 | CZ  | PHE | 223 | 20.626 | −37.273 | 68.107 | 1.00 | 61.40 |
| ATOM | 588 | C   | PHE | 223 | 19.052 | −40.530 | 73.527 | 1.00 | 57.51 |
| ATOM | 589 | O   | PHE | 223 | 18.016 | −40.708 | 74.165 | 1.00 | 56.31 |
| ATOM | 590 | N   | ALA | 224 | 20.261 | −40.787 | 74.021 | 1.00 | 57.34 |
| ATOM | 591 | CA  | ALA | 224 | 20.447 | −41.309 | 75.373 | 1.00 | 58.31 |
| ATOM | 592 | CB  | ALA | 224 | 20.842 | −42.773 | 75.311 | 1.00 | 58.16 |
| ATOM | 593 | C   | ALA | 224 | 21.517 | −40.514 | 76.116 | 1.00 | 58.54 |
| ATOM | 594 | O   | ALA | 224 | 22.404 | −39.945 | 75.491 | 1.00 | 59.61 |
| ATOM | 595 | N   | ILE | 225 | 21.436 | −40.486 | 77.444 | 1.00 | 57.96 |
| ATOM | 596 | CA  | ILE | 225 | 22.401 | −39.751 | 78.255 | 1.00 | 57.94 |
| ATOM | 597 | CB  | ILE | 225 | 21.699 | −38.763 | 79.225 | 1.00 | 58.15 |
| ATOM | 598 | CG2 | ILE | 225 | 22.734 | −38.081 | 80.114 | 1.00 | 58.23 |
| ATOM | 599 | CG1 | ILE | 225 | 20.904 | −37.712 | 78.444 | 1.00 | 58.02 |
| ATOM | 600 | CD1 | ILE | 225 | 20.136 | −36.737 | 79.329 | 1.00 | 55.55 |
| ATOM | 601 | C   | ILE | 225 | 23.278 | −40.666 | 79.101 | 1.00 | 58.42 |
| ATOM | 602 | O   | ILE | 225 | 22.794 | −41.341 | 80.006 | 1.00 | 59.16 |
| ATOM | 603 | N   | LEU | 226 | 24.572 | −40.686 | 78.815 | 1.00 | 58.75 |
| ATOM | 604 | CA  | LEU | 226 | 25.484 | −41.509 | 79.597 | 1.00 | 59.39 |
| ATOM | 605 | CB  | LEU | 226 | 26.569 | −42.109 | 78.699 | 1.00 | 57.81 |
| ATOM | 606 | CG  | LEU | 226 | 26.083 | −42.866 | 77.461 | 1.00 | 56.08 |
| ATOM | 607 | CD1 | LEU | 226 | 27.257 | −43.550 | 76.802 | 1.00 | 55.05 |
| ATOM | 608 | CD2 | LEU | 226 | 25.039 | −43.886 | 77.838 | 1.00 | 55.26 |
| ATOM | 609 | C   | LEU | 226 | 26.101 | −40.612 | 80.667 | 1.00 | 60.63 |
| ATOM | 610 | O   | LEU | 226 | 26.257 | −39.412 | 80.453 | 1.00 | 60.94 |
| ATOM | 611 | N   | LYS | 227 | 26.448 | −41.197 | 81.810 | 1.00 | 62.31 |
| ATOM | 612 | CA  | LYS | 227 | 27.022 | −40.452 | 82.930 | 1.00 | 63.91 |
| ATOM | 613 | CB  | LYS | 227 | 25.940 | −40.230 | 84.000 | 1.00 | 63.10 |
| ATOM | 614 | CG  | LYS | 227 | 26.440 | −39.783 | 85.373 | 1.00 | 62.19 |
| ATOM | 615 | CD  | LYS | 227 | 25.292 | −39.708 | 86.391 | 1.00 | 61.38 |
| ATOM | 616 | CE  | LYS | 227 | 25.767 | −39.220 | 87.765 | 1.00 | 61.56 |
| ATOM | 617 | NZ  | LYS | 227 | 24.653 | −39.044 | 88.746 | 1.00 | 59.42 |
| ATOM | 618 | C   | LYS | 227 | 28.208 | −41.169 | 83.560 | 1.00 | 65.80 |
| ATOM | 619 | O   | LYS | 227 | 28.038 | −42.199 | 84.205 | 1.00 | 67.24 |
| ATOM | 620 | N   | CYS | 228 | 29.409 | −40.631 | 83.387 | 1.00 | 68.12 |
| ATOM | 621 | CA  | CYS | 228 | 30.578 | −41.262 | 83.983 | 1.00 | 70.64 |
| ATOM | 622 | C   | CYS | 228 | 30.444 | −41.156 | 85.496 | 1.00 | 70.41 |
| ATOM | 623 | O   | CYS | 228 | 30.085 | −40.107 | 86.019 | 1.00 | 70.19 |
| ATOM | 624 | CB  | CYS | 228 | 31.871 | −40.590 | 83.511 | 1.00 | 73.46 |
| ATOM | 625 | SG  | CYS | 228 | 33.366 | −41.502 | 84.026 | 1.00 | 78.70 |
| ATOM | 626 | N   | ASN | 229 | 30.733 | −42.243 | 86.200 | 1.00 | 71.33 |
| ATOM | 627 | CA  | ASN | 229 | 30.600 | −42.255 | 87.647 | 1.00 | 71.92 |
| ATOM | 628 | CB  | ASN | 229 | 29.857 | −43.508 | 88.082 | 1.00 | 72.45 |
| ATOM | 629 | CG  | ASN | 229 | 28.411 | −43.492 | 87.652 | 1.00 | 73.11 |
| ATOM | 630 | OD1 | ASN | 229 | 27.647 | −42.610 | 88.051 | 1.00 | 72.87 |
| ATOM | 631 | ND2 | ASN | 229 | 28.022 | −44.465 | 86.830 | 1.00 | 72.92 |
| ATOM | 632 | C   | ASN | 229 | 31.867 | −42.109 | 88.469 | 1.00 | 72.51 |
| ATOM | 633 | O   | ASN | 229 | 31.785 | −42.025 | 89.688 | 1.00 | 72.22 |
| ATOM | 634 | N   | ASN | 230 | 33.033 | −42.089 | 87.829 | 1.00 | 74.40 |
| ATOM | 635 | CA  | ASN | 230 | 34.272 | −41.910 | 88.582 | 1.00 | 76.62 |
| ATOM | 636 | CB  | ASN | 230 | 35.455 | −41.654 | 87.648 | 1.00 | 77.04 |
| ATOM | 637 | CG  | ASN | 230 | 35.879 | −42.887 | 86.894 | 1.00 | 78.06 |
| ATOM | 638 | OD1 | ASN | 230 | 36.745 | −42.818 | 86.020 | 1.00 | 78.68 |
| ATOM | 639 | ND2 | ASN | 230 | 35.278 | −44.024 | 87.232 | 1.00 | 78.86 |
| ATOM | 640 | C   | ASN | 230 | 34.064 | −40.685 | 89.458 | 1.00 | 77.81 |
| ATOM | 641 | O   | ASN | 230 | 33.496 | −39.687 | 89.010 | 1.00 | 78.44 |
| ATOM | 642 | N   | LYS | 231 | 34.507 | −40.754 | 90.706 | 1.00 | 79.00 |
| ATOM | 643 | CA  | LYS | 231 | 34.338 | −39.623 | 91.608 | 1.00 | 80.19 |
| ATOM | 644 | CB  | LYS | 231 | 34.648 | −40.048 | 93.049 | 1.00 | 81.06 |
| ATOM | 645 | CG  | LYS | 231 | 33.678 | −41.098 | 93.576 | 1.00 | 81.81 |
| ATOM | 646 | CD  | LYS | 231 | 34.028 | −41.600 | 94.968 | 1.00 | 82.80 |
| ATOM | 647 | CE  | LYS | 231 | 33.081 | −42.740 | 95.376 | 1.00 | 83.45 |
| ATOM | 648 | NZ  | LYS | 231 | 33.385 | −43.321 | 96.720 | 1.00 | 82.56 |
| ATOM | 649 | C   | LYS | 231 | 35.235 | −38.474 | 91.169 | 1.00 | 80.35 |
| ATOM | 650 | O   | LYS | 231 | 35.008 | −37.321 | 91.536 | 1.00 | 80.46 |
| ATOM | 651 | N   | THR | 232 | 36.245 | −38.803 | 90.368 | 1.00 | 80.83 |
| ATOM | 652 | CA  | THR | 232 | 37.188 | −37.817 | 89.843 | 1.00 | 81.48 |
| ATOM | 653 | CB  | THR | 232 | 38.552 | −37.900 | 90.545 | 1.00 | 81.81 |
| ATOM | 654 | OG1 | THR | 232 | 38.381 | −37.665 | 91.947 | 1.00 | 82.72 |
| ATOM | 655 | CG2 | THR | 232 | 39.515 | −36.865 | 89.965 | 1.00 | 81.15 |

TABLE 1-continued

The structural coordinates of an exemplary stabilized form of gp120 at atomic resolution

| ATOM | 656 | C | THR | 232 | 37.399 | −38.103 | 88.367 | 1.00 | 81.71 |
| ATOM | 657 | O | THR | 232 | 38.174 | −38.987 | 87.998 | 1.00 | 82.58 |
| ATOM | 658 | N | PHE | 233 | 36.706 | −37.350 | 87.526 | 1.00 | 81.77 |
| ATOM | 659 | CA | PHE | 233 | 36.807 | −37.537 | 86.089 | 1.00 | 81.98 |
| ATOM | 660 | CB | PHE | 233 | 35.426 | −37.881 | 85.532 | 1.00 | 80.95 |
| ATOM | 661 | CG | PHE | 233 | 35.448 | −38.347 | 84.117 | 1.00 | 80.20 |
| ATOM | 662 | CD1 | PHE | 233 | 36.242 | −39.423 | 83.746 | 1.00 | 79.86 |
| ATOM | 663 | CD2 | PHE | 233 | 34.675 | −37.713 | 83.153 | 1.00 | 80.45 |
| ATOM | 664 | CE1 | PHE | 233 | 36.269 | −39.865 | 82.434 | 1.00 | 80.01 |
| ATOM | 665 | CE2 | PHE | 233 | 34.692 | −38.145 | 81.840 | 1.00 | 80.85 |
| ATOM | 666 | CZ | PHE | 233 | 35.493 | −39.226 | 81.477 | 1.00 | 80.97 |
| ATOM | 667 | C | PHE | 233 | 37.351 | −36.276 | 85.428 | 1.00 | 82.46 |
| ATOM | 668 | O | PHE | 233 | 36.918 | −35.172 | 85.749 | 1.00 | 82.61 |
| ATOM | 669 | N | ASN | 234 | 38.304 | −36.432 | 84.513 | 1.00 | 83.24 |
| ATOM | 670 | CA | ASN | 234 | 38.874 | −35.271 | 83.841 | 1.00 | 84.16 |
| ATOM | 671 | CB | ASN | 234 | 40.354 | −35.499 | 83.532 | 1.00 | 86.83 |
| ATOM | 672 | CG | ASN | 234 | 40.574 | −36.548 | 82.469 | 1.00 | 90.05 |
| ATOM | 673 | OD1 | ASN | 234 | 39.934 | −36.527 | 81.421 | 1.00 | 91.19 |
| ATOM | 674 | ND2 | ASN | 234 | 41.507 | −37.457 | 82.725 | 1.00 | 92.74 |
| ATOM | 675 | C | ASN | 234 | 38.117 | −34.914 | 82.559 | 1.00 | 83.56 |
| ATOM | 676 | O | ASN | 234 | 38.633 | −34.196 | 81.697 | 1.00 | 83.14 |
| ATOM | 677 | N | GLY | 235 | 36.897 | −35.433 | 82.444 | 1.00 | 82.91 |
| ATOM | 678 | CA | GLY | 235 | 36.049 | −35.147 | 81.300 | 1.00 | 81.77 |
| ATOM | 679 | C | GLY | 235 | 36.479 | −35.646 | 79.936 | 1.00 | 80.76 |
| ATOM | 680 | O | GLY | 235 | 35.687 | −35.623 | 78.996 | 1.00 | 80.76 |
| ATOM | 681 | N | THR | 236 | 37.722 | −36.095 | 79.808 | 1.00 | 79.92 |
| ATOM | 682 | CA | THR | 236 | 38.203 | −36.583 | 78.521 | 1.00 | 78.75 |
| ATOM | 683 | CB | THR | 236 | 39.368 | −35.722 | 77.992 | 1.00 | 79.46 |
| ATOM | 684 | OG1 | THR | 236 | 39.526 | −35.948 | 76.586 | 1.00 | 79.72 |
| ATOM | 685 | CG2 | THR | 236 | 40.671 | −36.091 | 78.698 | 1.00 | 79.62 |
| ATOM | 686 | C | THR | 236 | 38.676 | −38.020 | 78.618 | 1.00 | 77.39 |
| ATOM | 687 | O | THR | 236 | 38.821 | −38.564 | 79.706 | 1.00 | 77.35 |
| ATOM | 688 | N | GLY | 237 | 38.926 | −38.628 | 77.469 | 1.00 | 76.80 |
| ATOM | 689 | CA | GLY | 237 | 39.390 | −39.998 | 77.455 | 1.00 | 76.72 |
| ATOM | 690 | C | GLY | 237 | 38.283 | −40.994 | 77.729 | 1.00 | 76.45 |
| ATOM | 691 | O | GLY | 237 | 37.106 | −40.659 | 77.589 | 1.00 | 76.57 |
| ATOM | 692 | N | PRO | 238 | 38.634 | −42.235 | 78.113 | 1.00 | 75.99 |
| ATOM | 693 | CD | PRO | 238 | 40.000 | −42.777 | 78.002 | 1.00 | 75.67 |
| ATOM | 694 | CA | PRO | 238 | 37.689 | −43.311 | 78.413 | 1.00 | 75.71 |
| ATOM | 695 | CB | PRO | 238 | 38.456 | −44.544 | 77.980 | 1.00 | 75.43 |
| ATOM | 696 | CG | PRO | 238 | 39.824 | −44.215 | 78.454 | 1.00 | 75.46 |
| ATOM | 697 | C | PRO | 238 | 37.247 | −43.404 | 79.876 | 1.00 | 75.60 |
| ATOM | 698 | O | PRO | 238 | 38.014 | −43.116 | 80.795 | 1.00 | 74.29 |
| ATOM | 699 | N | CYS | 239 | 35.996 | −43.811 | 80.065 | 1.00 | 76.23 |
| ATOM | 700 | CA | CYS | 239 | 35.401 | −43.978 | 81.386 | 1.00 | 77.64 |
| ATOM | 701 | C | CYS | 239 | 35.078 | −45.462 | 81.561 | 1.00 | 77.75 |
| ATOM | 702 | O | CYS | 239 | 34.724 | −46.151 | 80.602 | 1.00 | 77.99 |
| ATOM | 703 | CB | CYS | 239 | 34.114 | −43.136 | 81.511 | 1.00 | 78.55 |
| ATOM | 704 | SG | CYS | 239 | 33.201 | −43.307 | 83.092 | 1.00 | 79.98 |
| ATOM | 705 | N | THR | 240 | 35.205 | −45.950 | 82.789 | 1.00 | 77.99 |
| ATOM | 706 | CA | THR | 240 | 34.936 | −47.352 | 83.086 | 1.00 | 77.29 |
| ATOM | 707 | CB | THR | 240 | 36.156 | −47.984 | 83.808 | 1.00 | 77.48 |
| ATOM | 708 | OG1 | THR | 240 | 36.642 | −47.088 | 84.817 | 1.00 | 77.79 |
| ATOM | 709 | CG2 | THR | 240 | 37.276 | −48.253 | 82.812 | 1.00 | 76.21 |
| ATOM | 710 | C | THR | 240 | 33.651 | −47.555 | 83.914 | 1.00 | 76.52 |
| ATOM | 711 | O | THR | 240 | 32.878 | −48.482 | 83.653 | 1.00 | 76.31 |
| ATOM | 712 | N | ASN | 241 | 33.427 | −46.683 | 84.898 | 1.00 | 74.90 |
| ATOM | 713 | CA | ASN | 241 | 32.239 | −46.740 | 85.760 | 1.00 | 72.80 |
| ATOM | 714 | CB | ASN | 241 | 32.617 | −46.258 | 87.171 | 1.00 | 72.80 |
| ATOM | 715 | CG | ASN | 241 | 31.621 | −46.691 | 88.241 | 1.00 | 72.83 |
| ATOM | 716 | OD1 | ASN | 241 | 30.404 | −46.657 | 88.031 | 1.00 | 73.02 |
| ATOM | 717 | ND2 | ASN | 241 | 32.142 | −47.079 | 89.402 | 1.00 | 71.56 |
| ATOM | 718 | C | ASN | 241 | 31.195 | −45.797 | 85.132 | 1.00 | 71.45 |
| ATOM | 719 | O | ASN | 241 | 31.185 | −44.601 | 85.419 | 1.00 | 70.59 |
| ATOM | 720 | N | VAL | 242 | 30.323 | −46.333 | 84.278 | 1.00 | 69.95 |
| ATOM | 721 | CA | VAL | 242 | 29.319 | −45.512 | 83.591 | 1.00 | 68.27 |
| ATOM | 722 | CB | VAL | 242 | 29.779 | −45.171 | 82.153 | 1.00 | 68.44 |
| ATOM | 723 | CG1 | VAL | 242 | 30.532 | −46.343 | 81.548 | 1.00 | 68.10 |
| ATOM | 724 | CG2 | VAL | 242 | 28.574 | −44.842 | 81.286 | 1.00 | 68.72 |
| ATOM | 725 | C | VAL | 242 | 27.911 | −46.091 | 83.494 | 1.00 | 66.92 |
| ATOM | 726 | O | VAL | 242 | 27.736 | −47.279 | 83.258 | 1.00 | 67.05 |
| ATOM | 727 | N | SER | 243 | 26.908 | −45.231 | 83.650 | 1.00 | 65.86 |
| ATOM | 728 | CA | SER | 243 | 25.513 | −45.657 | 83.568 | 1.00 | 65.72 |
| ATOM | 729 | CB | SER | 243 | 24.911 | −45.773 | 84.975 | 1.00 | 64.61 |
| ATOM | 730 | OG | SER | 243 | 25.167 | −44.631 | 85.765 | 1.00 | 62.69 |
| ATOM | 731 | C | SER | 243 | 24.655 | −44.729 | 82.700 | 1.00 | 65.75 |
| ATOM | 732 | O | SER | 243 | 25.138 | −43.719 | 82.195 | 1.00 | 66.44 |
| ATOM | 733 | N | THR | 244 | 23.386 | −45.089 | 82.523 | 1.00 | 65.22 |

TABLE 1-continued

The structural coordinates of an exemplary stabilized form of gp120 at atomic resolution

| ATOM | 734 | CA  | THR | 244 | 22.440 | −44.307 | 81.722 | 1.00 | 64.94 |
|------|-----|-----|-----|-----|--------|---------|--------|------|-------|
| ATOM | 735 | CB  | THR | 244 | 21.692 | −45.202 | 80.714 | 1.00 | 65.14 |
| ATOM | 736 | OG1 | THR | 244 | 22.448 | −45.286 | 79.501 | 1.00 | 65.13 |
| ATOM | 737 | CG2 | THR | 244 | 20.294 | −44.655 | 80.422 | 1.00 | 64.17 |
| ATOM | 738 | C   | THR | 244 | 21.408 | −43.644 | 82.614 | 1.00 | 65.03 |
| ATOM | 739 | O   | THR | 244 | 20.913 | −44.262 | 83.550 | 1.00 | 66.14 |
| ATOM | 740 | N   | VAL | 245 | 21.065 | −42.397 | 82.310 | 1.00 | 64.75 |
| ATOM | 741 | CA  | VAL | 245 | 20.089 | −41.669 | 83.112 | 1.00 | 64.42 |
| ATOM | 742 | CB  | VAL | 245 | 20.777 | −40.574 | 83.939 | 1.00 | 64.72 |
| ATOM | 743 | CG1 | VAL | 245 | 21.922 | −41.172 | 84.732 | 1.00 | 64.56 |
| ATOM | 744 | CG2 | VAL | 245 | 21.291 | −39.477 | 83.019 | 1.00 | 65.00 |
| ATOM | 745 | C   | VAL | 245 | 19.008 | −41.016 | 82.264 | 1.00 | 64.37 |
| ATOM | 746 | O   | VAL | 245 | 19.148 | −40.887 | 81.052 | 1.00 | 62.59 |
| ATOM | 747 | N   | GLN | 246 | 17.927 | −40.600 | 82.910 | 1.00 | 65.67 |
| ATOM | 748 | CA  | GLN | 246 | 16.839 | −39.947 | 82.195 | 1.00 | 67.31 |
| ATOM | 749 | CB  | GLN | 246 | 15.528 | −40.083 | 82.972 | 1.00 | 69.55 |
| ATOM | 750 | CG  | GLN | 246 | 15.009 | −41.514 | 83.055 | 1.00 | 72.91 |
| ATOM | 751 | CD  | GLN | 246 | 14.973 | −42.189 | 81.691 | 1.00 | 74.79 |
| ATOM | 752 | OE1 | GLN | 246 | 14.414 | −41.645 | 80.737 | 1.00 | 76.33 |
| ATOM | 753 | NE2 | GLN | 246 | 15.568 | −43.381 | 81.593 | 1.00 | 74.80 |
| ATOM | 754 | C   | GLN | 246 | 17.174 | −38.477 | 81.991 | 1.00 | 67.14 |
| ATOM | 755 | O   | GLN | 246 | 17.049 | −37.952 | 80.887 | 1.00 | 67.40 |
| ATOM | 756 | N   | CYS | 247 | 17.603 | −37.819 | 83.064 | 1.00 | 67.11 |
| ATOM | 757 | CA  | CYS | 247 | 17.981 | −36.408 | 83.009 | 1.00 | 66.41 |
| ATOM | 758 | C   | CYS | 247 | 19.173 | −36.223 | 83.942 | 1.00 | 64.14 |
| ATOM | 759 | O   | CYS | 247 | 19.394 | −37.048 | 84.834 | 1.00 | 63.44 |
| ATOM | 760 | CB  | CYS | 247 | 16.821 | −35.516 | 83.465 | 1.00 | 68.57 |
| ATOM | 761 | SG  | CYS | 247 | 15.192 | −35.863 | 82.704 | 1.00 | 72.95 |
| ATOM | 762 | N   | THR | 248 | 19.943 | −35.155 | 83.736 | 1.00 | 61.65 |
| ATOM | 763 | CA  | THR | 248 | 21.115 | −34.882 | 84.571 | 1.00 | 58.60 |
| ATOM | 764 | CB  | THR | 248 | 22.015 | −33.789 | 83.953 | 1.00 | 58.51 |
| ATOM | 765 | OG1 | THR | 248 | 21.401 | −32.506 | 84.118 | 1.00 | 58.42 |
| ATOM | 766 | CG2 | THR | 248 | 22.224 | −34.048 | 82.472 | 1.00 | 57.39 |
| ATOM | 767 | C   | THR | 248 | 20.649 | −34.404 | 85.938 | 1.00 | 56.78 |
| ATOM | 768 | O   | THR | 248 | 19.460 | −34.479 | 86.248 | 1.00 | 56.77 |
| ATOM | 769 | N   | HIS | 249 | 21.575 | −33.914 | 86.759 | 1.00 | 54.48 |
| ATOM | 770 | CA  | HIS | 249 | 21.204 | −33.423 | 88.085 | 1.00 | 52.32 |
| ATOM | 771 | CB  | HIS | 249 | 22.408 | −33.455 | 89.036 | 1.00 | 50.67 |
| ATOM | 772 | CG  | HIS | 249 | 23.557 | −32.617 | 88.581 | 1.00 | 50.88 |
| ATOM | 773 | CD2 | HIS | 249 | 23.960 | −31.378 | 88.951 | 1.00 | 51.06 |
| ATOM | 774 | ND1 | HIS | 249 | 24.418 | −33.016 | 87.582 | 1.00 | 52.07 |
| ATOM | 775 | CE1 | HIS | 249 | 25.300 | −32.059 | 87.354 | 1.00 | 52.55 |
| ATOM | 776 | NE2 | HIS | 249 | 25.043 | −31.053 | 88.171 | 1.00 | 51.62 |
| ATOM | 777 | C   | HIS | 249 | 20.648 | −31.997 | 88.000 | 1.00 | 51.12 |
| ATOM | 778 | O   | HIS | 249 | 20.672 | −31.366 | 86.943 | 1.00 | 50.41 |
| ATOM | 779 | N   | GLY | 250 | 20.120 | −31.504 | 89.112 | 1.00 | 50.12 |
| ATOM | 780 | CA  | GLY | 250 | 19.589 | −30.158 | 89.128 | 1.00 | 48.39 |
| ATOM | 781 | C   | GLY | 250 | 20.738 | −29.188 | 89.013 | 1.00 | 47.71 |
| ATOM | 782 | O   | GLY | 250 | 21.720 | −29.274 | 89.754 | 1.00 | 47.82 |
| ATOM | 783 | N   | ILE | 251 | 20.631 | −28.262 | 88.075 | 1.00 | 47.08 |
| ATOM | 784 | CA  | ILE | 251 | 21.692 | −27.295 | 87.898 | 1.00 | 47.14 |
| ATOM | 785 | CB  | ILE | 251 | 22.386 | −27.494 | 86.533 | 1.00 | 46.53 |
| ATOM | 786 | CG2 | ILE | 251 | 23.380 | −26.363 | 86.268 | 1.00 | 46.08 |
| ATOM | 787 | CG1 | ILE | 251 | 23.100 | −28.845 | 86.534 | 1.00 | 46.01 |
| ATOM | 788 | CD1 | ILE | 251 | 23.697 | −29.231 | 85.209 | 1.00 | 46.76 |
| ATOM | 789 | C   | ILE | 251 | 21.222 | −25.856 | 88.050 | 1.00 | 47.08 |
| ATOM | 790 | O   | ILE | 251 | 20.219 | −25.439 | 87.479 | 1.00 | 46.45 |
| ATOM | 791 | N   | ARG | 252 | 21.953 | −25.114 | 88.868 | 1.00 | 47.74 |
| ATOM | 792 | CA  | ARG | 252 | 21.651 | −23.722 | 89.101 | 1.00 | 48.23 |
| ATOM | 793 | CB  | ARG | 252 | 22.398 | −23.209 | 90.335 | 1.00 | 49.56 |
| ATOM | 794 | CG  | ARG | 252 | 21.642 | −23.363 | 91.631 | 1.00 | 52.05 |
| ATOM | 795 | CD  | ARG | 252 | 21.428 | −24.816 | 91.987 | 1.00 | 55.46 |
| ATOM | 796 | NE  | ARG | 252 | 20.534 | −24.934 | 93.127 | 1.00 | 58.57 |
| ATOM | 797 | CZ  | ARG | 252 | 20.800 | −24.438 | 94.330 | 1.00 | 61.06 |
| ATOM | 798 | NH1 | ARG | 252 | 21.942 | −23.796 | 94.547 | 1.00 | 61.62 |
| ATOM | 799 | NH2 | ARG | 252 | 19.917 | −24.568 | 95.313 | 1.00 | 62.98 |
| ATOM | 800 | C   | ARG | 252 | 22.125 | −22.965 | 87.877 | 1.00 | 47.35 |
| ATOM | 801 | O   | ARG | 252 | 23.322 | −22.949 | 87.577 | 1.00 | 48.58 |
| ATOM | 802 | N   | PRO | 253 | 21.194 | −22.354 | 87.134 | 1.00 | 45.23 |
| ATOM | 803 | CD  | PRO | 253 | 19.728 | −22.423 | 87.233 | 1.00 | 44.55 |
| ATOM | 804 | CA  | PRO | 253 | 21.595 | −21.604 | 85.949 | 1.00 | 43.24 |
| ATOM | 805 | CB  | PRO | 253 | 20.288 | −21.483 | 85.179 | 1.00 | 42.38 |
| ATOM | 806 | CG  | PRO | 253 | 19.293 | −21.350 | 86.272 | 1.00 | 43.19 |
| ATOM | 807 | C   | PRO | 253 | 22.182 | −20.256 | 86.375 | 1.00 | 41.47 |
| ATOM | 808 | O   | PRO | 253 | 21.744 | −19.199 | 85.926 | 1.00 | 42.48 |
| ATOM | 809 | N   | VAL | 254 | 23.179 | −20.305 | 87.255 | 1.00 | 39.38 |
| ATOM | 810 | CA  | VAL | 254 | 23.822 | −19.092 | 87.751 | 1.00 | 37.91 |
| ATOM | 811 | CB  | VAL | 254 | 24.819 | −19.384 | 88.879 | 1.00 | 37.89 |

TABLE 1-continued

The structural coordinates of an exemplary stabilized form of gp120 at atomic resolution

| ATOM | 812 | CG1 | VAL | 254 | 25.491 | −18.100 | 89.330 | 1.00 | 36.95 |
|---|---|---|---|---|---|---|---|---|---|
| ATOM | 813 | CG2 | VAL | 254 | 24.107 | −20.023 | 90.030 | 1.00 | 40.36 |
| ATOM | 814 | C | VAL | 254 | 24.589 | −18.384 | 86.661 | 1.00 | 36.14 |
| ATOM | 815 | O | VAL | 254 | 25.346 | −19.000 | 85.913 | 1.00 | 37.64 |
| ATOM | 816 | N | VAL | 255 | 24.399 | −17.078 | 86.588 | 1.00 | 32.62 |
| ATOM | 817 | CA | VAL | 255 | 25.090 | −16.278 | 85.607 | 1.00 | 30.04 |
| ATOM | 818 | CB | VAL | 255 | 24.103 | −15.366 | 84.867 | 1.00 | 31.25 |
| ATOM | 819 | CG1 | VAL | 255 | 24.783 | −14.073 | 84.437 | 1.00 | 31.11 |
| ATOM | 820 | CG2 | VAL | 255 | 23.571 | −16.105 | 83.654 | 1.00 | 32.07 |
| ATOM | 821 | C | VAL | 255 | 26.165 | −15.463 | 86.298 | 1.00 | 26.49 |
| ATOM | 822 | O | VAL | 255 | 25.878 | −14.632 | 87.144 | 1.00 | 24.49 |
| ATOM | 823 | N | SER | 256 | 27.412 | −15.706 | 85.931 | 1.00 | 24.46 |
| ATOM | 824 | CA | SER | 256 | 28.486 | −14.982 | 86.556 | 1.00 | 23.46 |
| ATOM | 825 | CB | SER | 256 | 28.585 | −15.389 | 88.010 | 1.00 | 22.73 |
| ATOM | 826 | OG | SER | 256 | 29.018 | −16.727 | 88.096 | 1.00 | 21.19 |
| ATOM | 827 | C | SER | 256 | 29.846 | −15.182 | 85.915 | 1.00 | 23.86 |
| ATOM | 828 | O | SER | 256 | 30.047 | −16.034 | 85.038 | 1.00 | 22.73 |
| ATOM | 829 | N | SER | 257 | 30.787 | −14.384 | 86.401 | 1.00 | 23.62 |
| ATOM | 830 | CA | SER | 257 | 32.159 | −14.423 | 85.941 | 1.00 | 23.31 |
| ATOM | 831 | CB | SER | 257 | 32.559 | −13.053 | 85.417 | 1.00 | 22.82 |
| ATOM | 832 | OG | SER | 257 | 32.592 | −12.107 | 86.466 | 1.00 | 20.86 |
| ATOM | 833 | C | SER | 257 | 33.063 | −14.804 | 87.106 | 1.00 | 23.53 |
| ATOM | 834 | O | SER | 257 | 32.629 | −14.829 | 88.250 | 1.00 | 23.12 |
| ATOM | 835 | N | GLN | 258 | 34.313 | −15.119 | 86.792 | 1.00 | 24.34 |
| ATOM | 836 | CA | GLN | 258 | 35.327 | −15.475 | 87.785 | 1.00 | 26.23 |
| ATOM | 837 | CB | GLN | 258 | 35.699 | −14.223 | 88.565 | 1.00 | 25.47 |
| ATOM | 838 | CG | GLN | 258 | 35.659 | −13.014 | 87.684 | 1.00 | 25.81 |
| ATOM | 839 | CD | GLN | 258 | 36.430 | −11.876 | 88.256 | 1.00 | 26.39 |
| ATOM | 840 | OE1 | GLN | 258 | 36.368 | −11.623 | 89.454 | 1.00 | 27.90 |
| ATOM | 841 | NE2 | GLN | 258 | 37.163 | −11.168 | 87.407 | 1.00 | 23.70 |
| ATOM | 842 | C | GLN | 258 | 34.995 | −16.601 | 88.757 | 1.00 | 26.10 |
| ATOM | 843 | O | GLN | 258 | 35.661 | −17.630 | 88.785 | 1.00 | 27.43 |
| ATOM | 844 | N | LEU | 259 | 33.965 | −16.397 | 89.559 | 1.00 | 26.43 |
| ATOM | 845 | CA | LEU | 259 | 33.563 | −17.382 | 90.538 | 1.00 | 25.71 |
| ATOM | 846 | CB | LEU | 259 | 33.304 | −16.692 | 91.865 | 1.00 | 25.10 |
| ATOM | 847 | CG | LEU | 259 | 34.388 | −15.692 | 92.261 | 1.00 | 24.45 |
| ATOM | 848 | CD1 | LEU | 259 | 33.952 | −14.868 | 93.466 | 1.00 | 20.24 |
| ATOM | 849 | CD2 | LEU | 259 | 35.672 | −16.457 | 92.530 | 1.00 | 26.19 |
| ATOM | 850 | C | LEU | 259 | 32.295 | −18.068 | 90.083 | 1.00 | 26.56 |
| ATOM | 851 | O | LEU | 259 | 31.402 | −17.423 | 89.533 | 1.00 | 27.02 |
| ATOM | 852 | N | LEU | 260 | 32.236 | −19.377 | 90.310 | 1.00 | 26.59 |
| ATOM | 853 | CA | LEU | 260 | 31.076 | −20.199 | 89.977 | 1.00 | 25.55 |
| ATOM | 854 | CB | LEU | 260 | 31.528 | −21.570 | 89.490 | 1.00 | 21.73 |
| ATOM | 855 | CG | LEU | 260 | 32.353 | −21.522 | 88.222 | 1.00 | 20.50 |
| ATOM | 856 | CD1 | LEU | 260 | 32.904 | −22.888 | 87.902 | 1.00 | 21.75 |
| ATOM | 857 | CD2 | LEU | 260 | 31.485 | −21.036 | 87.102 | 1.00 | 19.68 |
| ATOM | 858 | C | LEU | 260 | 30.306 | −20.347 | 91.282 | 1.00 | 26.59 |
| ATOM | 859 | O | LEU | 260 | 30.823 | −20.923 | 92.233 | 1.00 | 28.36 |
| ATOM | 860 | N | LEU | 261 | 29.076 | −19.847 | 91.330 | 1.00 | 27.70 |
| ATOM | 861 | CA | LEU | 261 | 28.283 | −19.905 | 92.557 | 1.00 | 28.07 |
| ATOM | 862 | CB | LEU | 261 | 27.611 | −18.555 | 92.769 | 1.00 | 28.66 |
| ATOM | 863 | CG | LEU | 261 | 28.555 | −17.374 | 92.533 | 1.00 | 28.66 |
| ATOM | 864 | CD1 | LEU | 261 | 27.784 | −16.071 | 92.672 | 1.00 | 28.33 |
| ATOM | 865 | CD2 | LEU | 261 | 29.722 | −17.433 | 93.517 | 1.00 | 28.00 |
| ATOM | 866 | C | LEU | 261 | 27.233 | −21.004 | 92.632 | 1.00 | 28.30 |
| ATOM | 867 | O | LEU | 261 | 26.633 | −21.362 | 91.635 | 1.00 | 27.56 |
| ATOM | 868 | N | ASN | 262 | 27.022 | −21.538 | 93.831 | 1.00 | 30.19 |
| ATOM | 869 | CA | ASN | 262 | 26.026 | −22.589 | 94.062 | 1.00 | 30.65 |
| ATOM | 870 | CB | ASN | 262 | 24.627 | −21.988 | 93.972 | 1.00 | 30.68 |
| ATOM | 871 | CG | ASN | 262 | 24.446 | −20.825 | 94.915 | 1.00 | 32.60 |
| ATOM | 872 | OD1 | ASN | 262 | 25.131 | −20.716 | 95.937 | 1.00 | 32.65 |
| ATOM | 873 | ND2 | ASN | 262 | 23.506 | −19.952 | 94.590 | 1.00 | 33.30 |
| ATOM | 874 | C | ASN | 262 | 26.107 | −23.820 | 93.158 | 1.00 | 29.62 |
| ATOM | 875 | O | ASN | 262 | 25.084 | −24.400 | 92.777 | 1.00 | 27.50 |
| ATOM | 876 | N | GLY | 263 | 27.328 | −24.226 | 92.835 | 1.00 | 29.42 |
| ATOM | 877 | CA | GLY | 263 | 27.501 | −25.384 | 91.983 | 1.00 | 30.33 |
| ATOM | 878 | C | GLY | 263 | 27.889 | −26.635 | 92.734 | 1.00 | 29.97 |
| ATOM | 879 | O | GLY | 263 | 27.951 | −26.638 | 93.954 | 1.00 | 30.00 |
| ATOM | 880 | N | SER | 264 | 28.148 | −27.704 | 91.991 | 1.00 | 31.78 |
| ATOM | 881 | CA | SER | 264 | 28.540 | −28.977 | 92.579 | 1.00 | 32.91 |
| ATOM | 882 | CB | SER | 264 | 28.367 | −30.119 | 91.576 | 1.00 | 32.66 |
| ATOM | 883 | OG | SER | 264 | 27.014 | −30.289 | 91.197 | 1.00 | 33.12 |
| ATOM | 884 | C | SER | 264 | 29.992 | −28.926 | 92.992 | 1.00 | 33.65 |
| ATOM | 885 | O | SER | 264 | 30.813 | −28.339 | 92.288 | 1.00 | 34.68 |
| ATOM | 886 | N | LEU | 265 | 30.301 | −29.537 | 94.133 | 1.00 | 34.04 |
| ATOM | 887 | CA | LEU | 265 | 31.667 | −29.588 | 94.627 | 1.00 | 34.32 |
| ATOM | 888 | CB | LEU | 265 | 31.689 | −29.585 | 96.155 | 1.00 | 32.99 |
| ATOM | 889 | CG | LEU | 265 | 31.346 | −28.271 | 96.859 | 1.00 | 33.66 |

TABLE 1-continued

The structural coordinates of an exemplary stabilized form of gp120 at atomic resolution

| ATOM | 890 | CD1 | LEU | 265 | 31.307 | −28.477 | 98.352 | 1.00 | 34.03 |
|---|---|---|---|---|---|---|---|---|---|
| ATOM | 891 | CD2 | LEU | 265 | 32.379 | −27.219 | 96.520 | 1.00 | 34.44 |
| ATOM | 892 | C | LEU | 265 | 32.297 | −30.869 | 94.098 | 1.00 | 35.56 |
| ATOM | 893 | O | LEU | 265 | 31.596 | −31.751 | 93.607 | 1.00 | 34.43 |
| ATOM | 894 | N | ALA | 266 | 33.622 | −30.951 | 94.176 | 1.00 | 38.30 |
| ATOM | 895 | CA | ALA | 266 | 34.352 | −32.128 | 93.725 | 1.00 | 40.59 |
| ATOM | 896 | CB | ALA | 266 | 35.769 | −31.751 | 93.302 | 1.00 | 38.89 |
| ATOM | 897 | C | ALA | 266 | 34.372 | −33.070 | 94.920 | 1.00 | 43.62 |
| ATOM | 898 | O | ALA | 266 | 34.755 | −32.677 | 96.026 | 1.00 | 44.02 |
| ATOM | 899 | N | GLU | 267 | 33.961 | −34.314 | 94.691 | 1.00 | 46.39 |
| ATOM | 900 | CA | GLU | 267 | 33.868 | −35.303 | 95.754 | 1.00 | 49.11 |
| ATOM | 901 | CB | GLU | 267 | 33.263 | −36.593 | 95.198 | 1.00 | 51.72 |
| ATOM | 902 | CG | GLU | 267 | 32.103 | −36.352 | 94.222 | 1.00 | 56.02 |
| ATOM | 903 | CD | GLU | 267 | 31.126 | −37.527 | 94.130 | 1.00 | 57.75 |
| ATOM | 904 | OE1 | GLU | 267 | 30.292 | −37.680 | 95.053 | 1.00 | 58.56 |
| ATOM | 905 | OE2 | GLU | 267 | 31.190 | −38.294 | 93.139 | 1.00 | 58.03 |
| ATOM | 906 | C | GLU | 267 | 35.125 | −35.625 | 96.554 | 1.00 | 49.70 |
| ATOM | 907 | O | GLU | 267 | 35.031 | −35.933 | 97.736 | 1.00 | 50.00 |
| ATOM | 908 | N | GLU | 268 | 36.299 | −35.552 | 95.944 | 1.00 | 51.35 |
| ATOM | 909 | CA | GLU | 268 | 37.510 | −35.879 | 96.691 | 1.00 | 53.41 |
| ATOM | 910 | CB | GLU | 268 | 38.332 | −36.923 | 95.940 | 1.00 | 55.13 |
| ATOM | 911 | CG | GLU | 268 | 37.589 | −38.222 | 95.692 | 1.00 | 59.90 |
| ATOM | 912 | CD | GLU | 268 | 38.264 | −39.115 | 94.650 | 1.00 | 61.80 |
| ATOM | 913 | OE1 | GLU | 268 | 37.689 | −40.179 | 94.332 | 1.00 | 62.83 |
| ATOM | 914 | OE2 | GLU | 268 | 39.358 | −38.756 | 94.154 | 1.00 | 62.29 |
| ATOM | 915 | C | GLU | 268 | 38.381 | −34.672 | 96.964 | 1.00 | 53.78 |
| ATOM | 916 | O | GLU | 268 | 38.293 | −34.046 | 98.023 | 1.00 | 54.54 |
| ATOM | 917 | N | GLU | 269 | 39.232 | −34.355 | 96.000 | 1.00 | 53.53 |
| ATOM | 918 | CA | GLU | 269 | 40.139 | −33.231 | 96.132 | 1.00 | 53.58 |
| ATOM | 919 | CB | GLU | 269 | 41.564 | −33.689 | 95.841 | 1.00 | 55.20 |
| ATOM | 920 | CG | GLU | 269 | 41.923 | −35.009 | 96.487 | 1.00 | 57.76 |
| ATOM | 921 | CD | GLU | 269 | 43.335 | −35.450 | 96.151 | 1.00 | 59.84 |
| ATOM | 922 | OE1 | GLU | 269 | 43.678 | −36.621 | 96.416 | 1.00 | 59.87 |
| ATOM | 923 | OE2 | GLU | 269 | 44.109 | −34.623 | 95.626 | 1.00 | 62.07 |
| ATOM | 924 | C | GLU | 269 | 39.746 | −32.126 | 95.162 | 1.00 | 52.41 |
| ATOM | 925 | O | GLU | 269 | 38.749 | −32.252 | 94.452 | 1.00 | 53.19 |
| ATOM | 926 | N | VAL | 270 | 40.530 | −31.049 | 95.138 | 1.00 | 50.34 |
| ATOM | 927 | CA | VAL | 270 | 40.269 | −29.926 | 94.241 | 1.00 | 48.54 |
| ATOM | 928 | CB | VAL | 270 | 41.091 | −28.663 | 94.633 | 1.00 | 47.63 |
| ATOM | 929 | CG1 | VAL | 270 | 41.172 | −27.707 | 93.467 | 1.00 | 45.74 |
| ATOM | 930 | CG2 | VAL | 270 | 40.424 | −27.950 | 95.806 | 1.00 | 47.67 |
| ATOM | 931 | C | VAL | 270 | 40.631 | −30.337 | 92.823 | 1.00 | 47.45 |
| ATOM | 932 | O | VAL | 270 | 41.651 | −30.994 | 92.606 | 1.00 | 47.66 |
| ATOM | 933 | N | VAL | 271 | 39.790 | −29.948 | 91.864 | 1.00 | 45.27 |
| ATOM | 934 | CA | VAL | 271 | 40.012 | −30.290 | 90.461 | 1.00 | 42.45 |
| ATOM | 935 | CB | VAL | 271 | 38.878 | −31.202 | 89.925 | 1.00 | 41.54 |
| ATOM | 936 | CG1 | VAL | 271 | 39.220 | −31.677 | 88.530 | 1.00 | 39.33 |
| ATOM | 937 | CG2 | VAL | 271 | 38.663 | −32.380 | 90.857 | 1.00 | 40.44 |
| ATOM | 938 | C | VAL | 271 | 40.123 | −29.071 | 89.535 | 1.00 | 40.87 |
| ATOM | 939 | O | VAL | 271 | 39.324 | −28.132 | 89.623 | 1.00 | 41.07 |
| ATOM | 940 | N | ILE | 272 | 41.130 | −29.096 | 88.662 | 1.00 | 37.99 |
| ATOM | 941 | CA | ILE | 272 | 41.342 | −28.035 | 87.691 | 1.00 | 35.44 |
| ATOM | 942 | CB | ILE | 272 | 42.724 | −27.352 | 87.867 | 1.00 | 32.95 |
| ATOM | 943 | CG2 | ILE | 272 | 42.894 | −26.892 | 89.302 | 1.00 | 30.53 |
| ATOM | 944 | CG1 | ILE | 272 | 43.857 | −28.308 | 87.528 | 1.00 | 30.50 |
| ATOM | 945 | CD1 | ILE | 272 | 45.218 | −27.694 | 87.759 | 1.00 | 28.89 |
| ATOM | 946 | C | ILE | 272 | 41.226 | −28.705 | 86.329 | 1.00 | 36.01 |
| ATOM | 947 | O | ILE | 272 | 41.804 | −29.760 | 86.104 | 1.00 | 36.26 |
| ATOM | 948 | N | ARG | 273 | 40.436 | −28.100 | 85.444 | 1.00 | 36.70 |
| ATOM | 949 | CA | ARG | 273 | 40.173 | −28.629 | 84.107 | 1.00 | 36.68 |
| ATOM | 950 | CB | ARG | 273 | 38.711 | −29.077 | 83.996 | 1.00 | 34.08 |
| ATOM | 951 | CG | ARG | 273 | 38.209 | −30.035 | 85.056 | 1.00 | 32.56 |
| ATOM | 952 | CD | ARG | 273 | 36.708 | −30.273 | 84.871 | 1.00 | 32.51 |
| ATOM | 953 | NE | ARG | 273 | 36.253 | −31.508 | 85.502 | 1.00 | 31.47 |
| ATOM | 954 | CZ | ARG | 273 | 36.149 | −31.672 | 86.811 | 1.00 | 32.01 |
| ATOM | 955 | NH1 | ARG | 273 | 36.458 | −30.672 | 87.615 | 1.00 | 34.75 |
| ATOM | 956 | NH2 | ARG | 273 | 35.771 | −32.835 | 87.323 | 1.00 | 30.95 |
| ATOM | 957 | C | ARG | 273 | 40.409 | −27.566 | 83.030 | 1.00 | 39.20 |
| ATOM | 958 | O | ARG | 273 | 40.272 | −26.364 | 83.288 | 1.00 | 41.19 |
| ATOM | 959 | N | SER | 274 | 40.757 | −28.013 | 81.823 | 1.00 | 40.06 |
| ATOM | 960 | CA | SER | 274 | 40.969 | −27.114 | 80.691 | 1.00 | 40.76 |
| ATOM | 961 | CB | SER | 274 | 42.332 | −26.436 | 80.763 | 1.00 | 36.80 |
| ATOM | 962 | OG | SER | 274 | 42.480 | −25.540 | 79.681 | 1.00 | 32.87 |
| ATOM | 963 | C | SER | 274 | 40.867 | −27.899 | 79.399 | 1.00 | 43.92 |
| ATOM | 964 | O | SER | 274 | 41.114 | −29.100 | 79.372 | 1.00 | 45.39 |
| ATOM | 965 | N | CYS | 275 | 40.480 | −27.230 | 78.325 | 1.00 | 47.15 |
| ATOM | 966 | CA | CYS | 275 | 40.377 | −27.916 | 77.055 | 1.00 | 51.92 |
| ATOM | 967 | C | CYS | 275 | 41.737 | −27.968 | 76.403 | 1.00 | 52.82 |

TABLE 1-continued

The structural coordinates of an exemplary stabilized form of gp120 at atomic resolution

| ATOM | 968 | O | CYS | 275 | 41.890 | −28.485 | 75.303 | 1.00 | 54.44 |
|---|---|---|---|---|---|---|---|---|---|
| ATOM | 969 | CB | CYS | 275 | 39.375 | −27.207 | 76.154 | 1.00 | 55.95 |
| ATOM | 970 | SG | CYS | 275 | 37.681 | −27.472 | 76.771 | 1.00 | 66.91 |
| ATOM | 971 | N | ASN | 276 | 42.730 | −27.439 | 77.106 | 1.00 | 53.33 |
| ATOM | 972 | CA | ASN | 276 | 44.104 | −27.397 | 76.624 | 1.00 | 52.97 |
| ATOM | 973 | CB | ASN | 276 | 44.161 | −26.855 | 75.186 | 1.00 | 55.96 |
| ATOM | 974 | CG | ASN | 276 | 45.584 | −26.683 | 74.685 | 1.00 | 61.01 |
| ATOM | 975 | OD1 | ASN | 276 | 46.331 | −25.861 | 75.210 | 1.00 | 63.58 |
| ATOM | 976 | ND2 | ASN | 276 | 45.980 | −27.485 | 73.701 | 1.00 | 64.98 |
| ATOM | 977 | C | ASN | 276 | 44.864 | −26.475 | 77.571 | 1.00 | 51.50 |
| ATOM | 978 | O | ASN | 276 | 44.876 | −25.251 | 77.398 | 1.00 | 50.11 |
| ATOM | 979 | N | PHE | 277 | 45.483 | −27.074 | 78.584 | 1.00 | 49.28 |
| ATOM | 980 | CA | PHE | 277 | 46.235 | −26.309 | 79.570 | 1.00 | 47.85 |
| ATOM | 981 | CB | PHE | 277 | 46.763 | −27.231 | 80.675 | 1.00 | 46.32 |
| ATOM | 982 | CG | PHE | 277 | 45.689 | −27.794 | 81.567 | 1.00 | 44.69 |
| ATOM | 983 | CD1 | PHE | 277 | 45.136 | −29.050 | 81.321 | 1.00 | 43.74 |
| ATOM | 984 | CD2 | PHE | 277 | 45.235 | −27.070 | 82.667 | 1.00 | 43.64 |
| ATOM | 985 | CE1 | PHE | 277 | 44.149 | −29.577 | 82.163 | 1.00 | 41.58 |
| ATOM | 986 | CE2 | PHE | 277 | 44.249 | −27.590 | 83.511 | 1.00 | 42.49 |
| ATOM | 987 | CZ | PHE | 277 | 43.707 | −28.848 | 83.258 | 1.00 | 40.91 |
| ATOM | 988 | C | PHE | 277 | 47.397 | −25.526 | 78.959 | 1.00 | 47.27 |
| ATOM | 989 | O | PHE | 277 | 47.758 | −24.456 | 79.451 | 1.00 | 46.87 |
| ATOM | 990 | N | THR | 278 | 47.972 | −26.069 | 77.890 | 1.00 | 47.46 |
| ATOM | 991 | CA | THR | 278 | 49.103 | −25.462 | 77.189 | 1.00 | 48.47 |
| ATOM | 992 | CB | THR | 278 | 49.612 | −26.414 | 76.092 | 1.00 | 48.42 |
| ATOM | 993 | OG1 | THR | 278 | 50.438 | −27.415 | 76.691 | 1.00 | 48.33 |
| ATOM | 994 | CG2 | THR | 278 | 50.410 | −25.659 | 75.038 | 1.00 | 49.75 |
| ATOM | 995 | C | THR | 278 | 48.784 | −24.103 | 76.562 | 1.00 | 48.99 |
| ATOM | 996 | O | THR | 278 | 49.596 | −23.168 | 76.609 | 1.00 | 48.80 |
| ATOM | 997 | N | ASP | 279 | 47.600 | −24.021 | 75.964 | 1.00 | 48.66 |
| ATOM | 998 | CA | ASP | 279 | 47.094 | −22.816 | 75.315 | 1.00 | 48.23 |
| ATOM | 999 | CB | ASP | 279 | 45.819 | −23.178 | 74.547 | 1.00 | 50.23 |
| ATOM | 1000 | CG | ASP | 279 | 45.261 | −22.025 | 73.742 | 1.00 | 51.68 |
| ATOM | 1001 | OD1 | ASP | 279 | 44.294 | −22.275 | 72.986 | 1.00 | 51.77 |
| ATOM | 1002 | OD2 | ASP | 279 | 45.778 | −20.890 | 73.870 | 1.00 | 51.55 |
| ATOM | 1003 | C | ASP | 279 | 46.792 | −21.801 | 76.414 | 1.00 | 47.12 |
| ATOM | 1004 | O | ASP | 279 | 45.827 | −21.958 | 77.168 | 1.00 | 47.67 |
| ATOM | 1005 | N | ASN | 280 | 47.609 | −20.758 | 76.507 | 1.00 | 43.96 |
| ATOM | 1006 | CA | ASN | 280 | 47.410 | −19.775 | 77.559 | 1.00 | 41.43 |
| ATOM | 1007 | CB | ASN | 280 | 48.671 | −18.910 | 77.722 | 1.00 | 39.74 |
| ATOM | 1008 | CG | ASN | 280 | 49.007 | −18.101 | 76.485 | 1.00 | 36.68 |
| ATOM | 1009 | OD1 | ASN | 280 | 48.755 | −18.525 | 75.364 | 1.00 | 36.56 |
| ATOM | 1010 | ND2 | ASN | 280 | 49.604 | −16.931 | 76.692 | 1.00 | 33.53 |
| ATOM | 1011 | C | ASN | 280 | 46.174 | −18.916 | 77.364 | 1.00 | 41.24 |
| ATOM | 1012 | O | ASN | 280 | 45.970 | −17.927 | 78.058 | 1.00 | 40.99 |
| ATOM | 1013 | N | ALA | 281 | 45.321 | −19.315 | 76.434 | 1.00 | 41.19 |
| ATOM | 1014 | CA | ALA | 281 | 44.117 | −18.547 | 76.192 | 1.00 | 40.89 |
| ATOM | 1015 | CB | ALA | 281 | 44.119 | −18.045 | 74.777 | 1.00 | 42.27 |
| ATOM | 1016 | C | ALA | 281 | 42.859 | −19.356 | 76.463 | 1.00 | 40.32 |
| ATOM | 1017 | O | ALA | 281 | 41.764 | −18.949 | 76.090 | 1.00 | 41.07 |
| ATOM | 1018 | N | LYS | 282 | 43.012 | −20.500 | 77.115 | 1.00 | 39.16 |
| ATOM | 1019 | CA | LYS | 282 | 41.864 | −21.334 | 77.423 | 1.00 | 38.60 |
| ATOM | 1020 | CB | LYS | 282 | 42.116 | −22.773 | 76.970 | 1.00 | 39.99 |
| ATOM | 1021 | CG | LYS | 282 | 41.897 | −22.990 | 75.479 | 1.00 | 41.46 |
| ATOM | 1022 | CD | LYS | 282 | 40.523 | −22.473 | 75.048 | 1.00 | 43.09 |
| ATOM | 1023 | CE | LYS | 282 | 40.172 | −22.875 | 73.625 | 1.00 | 41.82 |
| ATOM | 1024 | NZ | LYS | 282 | 39.986 | −24.349 | 73.519 | 1.00 | 42.86 |
| ATOM | 1025 | C | LYS | 282 | 41.488 | −21.310 | 78.897 | 1.00 | 37.93 |
| ATOM | 1026 | O | LYS | 282 | 42.336 | −21.477 | 79.777 | 1.00 | 38.22 |
| ATOM | 1027 | N | THR | 283 | 40.200 | −21.110 | 79.149 | 1.00 | 36.68 |
| ATOM | 1028 | CA | THR | 283 | 39.648 | −21.049 | 80.494 | 1.00 | 35.31 |
| ATOM | 1029 | CB | THR | 283 | 38.117 | −20.944 | 80.447 | 1.00 | 34.66 |
| ATOM | 1030 | OG1 | THR | 283 | 37.745 | −19.702 | 79.850 | 1.00 | 37.62 |
| ATOM | 1031 | CG2 | THR | 283 | 37.523 | −21.018 | 81.833 | 1.00 | 34.32 |
| ATOM | 1032 | C | THR | 283 | 39.982 | −22.263 | 81.340 | 1.00 | 35.03 |
| ATOM | 1033 | O | THR | 283 | 39.808 | −23.396 | 80.896 | 1.00 | 35.94 |
| ATOM | 1034 | N | ILE | 284 | 40.461 | −22.026 | 82.558 | 1.00 | 33.55 |
| ATOM | 1035 | CA | ILE | 284 | 40.750 | −23.115 | 83.481 | 1.00 | 32.06 |
| ATOM | 1036 | CB | ILE | 284 | 42.087 | −22.926 | 84.220 | 1.00 | 29.94 |
| ATOM | 1037 | CG2 | ILE | 284 | 42.264 | −24.025 | 85.253 | 1.00 | 25.00 |
| ATOM | 1038 | CG1 | ILE | 284 | 43.234 | −22.964 | 83.225 | 1.00 | 28.55 |
| ATOM | 1039 | CD1 | ILE | 284 | 44.563 | −22.787 | 83.859 | 1.00 | 28.55 |
| ATOM | 1040 | C | ILE | 284 | 39.609 | −23.124 | 84.502 | 1.00 | 33.37 |
| ATOM | 1041 | O | ILE | 284 | 39.398 | −22.149 | 85.237 | 1.00 | 32.79 |
| ATOM | 1042 | N | ILE | 285 | 38.867 | −24.227 | 84.516 | 1.00 | 33.28 |
| ATOM | 1043 | CA | ILE | 285 | 37.740 | −24.413 | 85.412 | 1.00 | 32.89 |
| ATOM | 1044 | CB | ILE | 285 | 36.657 | −25.259 | 84.734 | 1.00 | 31.95 |
| ATOM | 1045 | CG2 | ILE | 285 | 35.537 | −25.555 | 85.697 | 1.00 | 32.46 |

TABLE 1-continued

The structural coordinates of an exemplary stabilized form of gp120 at atomic resolution

| ATOM | 1046 | CG1 | ILE | 285 | 36.113 | −24.517 | 83.527 | 1.00 | 32.81 |
|---|---|---|---|---|---|---|---|---|---|
| ATOM | 1047 | CD1 | ILE | 285 | 34.981 | −25.242 | 82.844 | 1.00 | 35.28 |
| ATOM | 1048 | C | ILE | 285 | 38.158 | −25.122 | 86.695 | 1.00 | 34.13 |
| ATOM | 1049 | O | ILE | 285 | 38.440 | −26.313 | 86.690 | 1.00 | 35.08 |
| ATOM | 1050 | N | VAL | 286 | 38.206 | −24.398 | 87.799 | 1.00 | 34.62 |
| ATOM | 1051 | CA | VAL | 286 | 38.566 | −25.024 | 89.056 | 1.00 | 34.98 |
| ATOM | 1052 | CB | VAL | 286 | 39.403 | −24.051 | 89.931 | 1.00 | 34.50 |
| ATOM | 1053 | CG1 | VAL | 286 | 39.593 | −24.600 | 91.335 | 1.00 | 31.43 |
| ATOM | 1054 | CG2 | VAL | 286 | 40.743 | −23.843 | 89.292 | 1.00 | 34.26 |
| ATOM | 1055 | C | VAL | 286 | 37.276 | −25.413 | 89.788 | 1.00 | 36.26 |
| ATOM | 1056 | O | VAL | 286 | 36.276 | −24.683 | 89.736 | 1.00 | 36.24 |
| ATOM | 1057 | N | GLN | 287 | 37.290 | −26.581 | 90.425 | 1.00 | 35.78 |
| ATOM | 1058 | CA | GLN | 287 | 36.151 | −27.041 | 91.210 | 1.00 | 36.32 |
| ATOM | 1059 | CB | GLN | 287 | 35.441 | −28.214 | 90.547 | 1.00 | 35.89 |
| ATOM | 1060 | CG | GLN | 287 | 34.369 | −28.830 | 91.444 | 1.00 | 35.81 |
| ATOM | 1061 | CD | GLN | 287 | 33.732 | −30.067 | 90.834 | 1.00 | 35.51 |
| ATOM | 1062 | OE1 | GLN | 287 | 34.394 | −30.838 | 90.141 | 1.00 | 34.61 |
| ATOM | 1063 | NE2 | GLN | 287 | 32.446 | −30.269 | 91.102 | 1.00 | 34.71 |
| ATOM | 1064 | C | GLN | 287 | 36.673 | −27.444 | 92.595 | 1.00 | 36.79 |
| ATOM | 1065 | O | GLN | 287 | 37.691 | −28.131 | 92.728 | 1.00 | 35.75 |
| ATOM | 1066 | N | LEU | 288 | 35.955 | −27.011 | 93.623 | 1.00 | 37.06 |
| ATOM | 1067 | CA | LEU | 288 | 36.357 | −27.248 | 94.996 | 1.00 | 37.17 |
| ATOM | 1068 | CB | LEU | 288 | 36.146 | −25.962 | 95.805 | 1.00 | 34.97 |
| ATOM | 1069 | CG | LEU | 288 | 36.614 | −24.630 | 95.206 | 1.00 | 32.83 |
| ATOM | 1070 | CD1 | LEU | 288 | 35.969 | −23.494 | 95.955 | 1.00 | 31.53 |
| ATOM | 1071 | CD2 | LEU | 288 | 38.120 | −24.514 | 95.268 | 1.00 | 31.88 |
| ATOM | 1072 | C | LEU | 288 | 35.653 | −28.405 | 95.707 | 1.00 | 38.46 |
| ATOM | 1073 | O | LEU | 288 | 34.553 | −28.817 | 95.334 | 1.00 | 38.22 |
| ATOM | 1074 | N | ASN | 289 | 36.322 | −28.898 | 96.748 | 1.00 | 39.95 |
| ATOM | 1075 | CA | ASN | 289 | 35.855 | −29.984 | 97.605 | 1.00 | 40.45 |
| ATOM | 1076 | CB | ASN | 289 | 37.057 | −30.772 | 98.117 | 1.00 | 40.55 |
| ATOM | 1077 | CG | ASN | 289 | 38.027 | −29.893 | 98.867 | 1.00 | 42.68 |
| ATOM | 1078 | OD1 | ASN | 289 | 38.080 | −28.692 | 98.600 | 1.00 | 43.84 |
| ATOM | 1079 | ND2 | ASN | 289 | 38.797 | −30.451 | 99.798 | 1.00 | 45.54 |
| ATOM | 1080 | C | ASN | 289 | 35.136 | −29.342 | 98.793 | 1.00 | 40.56 |
| ATOM | 1081 | O | ASN | 289 | 34.426 | −30.011 | 99.534 | 1.00 | 41.39 |
| ATOM | 1082 | N | THR | 290 | 35.334 | −28.037 | 98.971 | 1.00 | 40.82 |
| ATOM | 1083 | CA | THR | 290 | 34.716 | −27.293 | 100.075 | 1.00 | 39.80 |
| ATOM | 1084 | CB | THR | 290 | 35.738 | −26.968 | 101.168 | 1.00 | 40.22 |
| ATOM | 1085 | OG1 | THR | 290 | 36.425 | −28.160 | 101.564 | 1.00 | 40.45 |
| ATOM | 1086 | CG2 | THR | 290 | 35.038 | −26.345 | 102.361 | 1.00 | 40.96 |
| ATOM | 1087 | C | THR | 290 | 34.141 | −25.953 | 99.630 | 1.00 | 38.45 |
| ATOM | 1088 | O | THR | 290 | 34.790 | −25.211 | 98.898 | 1.00 | 38.51 |
| ATOM | 1089 | N | SER | 291 | 32.941 | −25.626 | 100.093 | 1.00 | 37.41 |
| ATOM | 1090 | CA | SER | 291 | 32.334 | −24.349 | 99.735 | 1.00 | 36.56 |
| ATOM | 1091 | CB | SER | 291 | 30.834 | −24.367 | 100.019 | 1.00 | 37.11 |
| ATOM | 1092 | OG | SER | 291 | 30.126 | −25.014 | 98.978 | 1.00 | 40.14 |
| ATOM | 1093 | C | SER | 291 | 32.965 | −23.232 | 100.537 | 1.00 | 35.66 |
| ATOM | 1094 | O | SER | 291 | 33.504 | −23.480 | 101.604 | 1.00 | 36.84 |
| ATOM | 1095 | N | VAL | 292 | 32.919 | −22.012 | 100.002 | 1.00 | 35.35 |
| ATOM | 1096 | CA | VAL | 292 | 33.432 | −20.806 | 100.682 | 1.00 | 34.01 |
| ATOM | 1097 | CB | VAL | 292 | 34.734 | −20.239 | 100.018 | 1.00 | 32.71 |
| ATOM | 1098 | CG1 | VAL | 292 | 35.059 | −18.859 | 100.597 | 1.00 | 27.63 |
| ATOM | 1099 | CG2 | VAL | 292 | 35.907 | −21.193 | 100.257 | 1.00 | 29.57 |
| ATOM | 1100 | C | VAL | 292 | 32.306 | −19.784 | 100.537 | 1.00 | 33.54 |
| ATOM | 1101 | O | VAL | 292 | 31.983 | −19.374 | 99.426 | 1.00 | 33.35 |
| ATOM | 1102 | N | GLU | 293 | 31.691 | −19.379 | 101.639 | 1.00 | 33.37 |
| ATOM | 1103 | CA | GLU | 293 | 30.580 | −18.440 | 101.519 | 1.00 | 34.15 |
| ATOM | 1104 | CB | GLU | 293 | 29.834 | −18.262 | 102.846 | 1.00 | 37.09 |
| ATOM | 1105 | CG | GLU | 293 | 29.612 | −19.536 | 103.649 | 1.00 | 44.11 |
| ATOM | 1106 | CD | GLU | 293 | 30.893 | −20.000 | 104.321 | 1.00 | 50.19 |
| ATOM | 1107 | OE1 | GLU | 293 | 31.452 | −19.216 | 105.135 | 1.00 | 53.93 |
| ATOM | 1108 | OE2 | GLU | 293 | 31.350 | −21.131 | 104.033 | 1.00 | 51.72 |
| ATOM | 1109 | C | GLU | 293 | 31.013 | −17.077 | 101.036 | 1.00 | 32.44 |
| ATOM | 1110 | O | GLU | 293 | 32.131 | −16.632 | 101.270 | 1.00 | 32.48 |
| ATOM | 1111 | N | ILE | 294 | 30.112 | −16.419 | 100.334 | 1.00 | 31.24 |
| ATOM | 1112 | CA | ILE | 294 | 30.371 | −15.080 | 99.858 | 1.00 | 31.02 |
| ATOM | 1113 | CB | ILE | 294 | 30.909 | −15.060 | 98.407 | 1.00 | 28.57 |
| ATOM | 1114 | CG2 | ILE | 294 | 29.896 | −15.631 | 97.459 | 1.00 | 28.94 |
| ATOM | 1115 | CG1 | ILE | 294 | 31.228 | −13.627 | 97.999 | 1.00 | 26.61 |
| ATOM | 1116 | CD1 | ILE | 294 | 31.771 | −13.513 | 96.622 | 1.00 | 26.35 |
| ATOM | 1117 | C | ILE | 294 | 29.018 | −14.391 | 99.953 | 1.00 | 32.34 |
| ATOM | 1118 | O | ILE | 294 | 28.050 | −14.785 | 99.293 | 1.00 | 31.74 |
| ATOM | 1119 | N | ASN | 295 | 28.943 | −13.381 | 100.811 | 1.00 | 33.69 |
| ATOM | 1120 | CA | ASN | 295 | 27.694 | −12.666 | 101.002 | 1.00 | 36.46 |
| ATOM | 1121 | CB | ASN | 295 | 27.305 | −12.678 | 102.484 | 1.00 | 36.40 |
| ATOM | 1122 | CG | ASN | 295 | 27.390 | −14.059 | 103.099 | 1.00 | 36.18 |
| ATOM | 1123 | OD1 | ASN | 295 | 26.783 | −15.025 | 102.619 | 1.00 | 32.60 |

TABLE 1-continued

The structural coordinates of an exemplary stabilized form of gp120 at atomic resolution

| ATOM | 1124 | ND2 | ASN | 295 | 28.148 | −14.155 | 104.180 | 1.00 | 37.07 |
|---|---|---|---|---|---|---|---|---|---|
| ATOM | 1125 | C | ASN | 295 | 27.801 | −11.230 | 100.513 | 1.00 | 37.74 |
| ATOM | 1126 | O | ASN | 295 | 28.729 | −10.512 | 100.889 | 1.00 | 37.01 |
| ATOM | 1127 | N | CYS | 296 | 26.852 | −10.822 | 99.672 | 1.00 | 39.54 |
| ATOM | 1128 | CA | CYS | 296 | 26.853 | −9.467 | 99.142 | 1.00 | 40.74 |
| ATOM | 1129 | C | CYS | 296 | 25.546 | −8.761 | 99.438 | 1.00 | 39.17 |
| ATOM | 1130 | O | CYS | 296 | 24.554 | −9.388 | 99.804 | 1.00 | 37.88 |
| ATOM | 1131 | CB | CYS | 296 | 27.051 | −9.468 | 97.637 | 1.00 | 43.38 |
| ATOM | 1132 | SG | CYS | 296 | 28.393 | −10.504 | 96.984 | 1.00 | 50.13 |
| ATOM | 1133 | N | THR | 297 | 25.548 | −7.450 | 99.241 | 1.00 | 38.11 |
| ATOM | 1134 | CA | THR | 297 | 24.368 | −6.654 | 99.498 | 1.00 | 38.11 |
| ATOM | 1135 | CB | THR | 297 | 24.326 | −6.200 | 100.953 | 1.00 | 39.36 |
| ATOM | 1136 | OG1 | THR | 297 | 23.087 | −5.522 | 101.209 | 1.00 | 40.89 |
| ATOM | 1137 | CG2 | THR | 297 | 25.500 | −5.261 | 101.241 | 1.00 | 37.42 |
| ATOM | 1138 | C | THR | 297 | 24.348 | −5.412 | 98.629 | 1.00 | 37.88 |
| ATOM | 1139 | O | THR | 297 | 25.400 | −4.820 | 98.356 | 1.00 | 37.71 |
| ATOM | 1140 | N | GLY | 298 | 23.144 | −5.011 | 98.218 | 1.00 | 36.98 |
| ATOM | 1141 | CA | GLY | 298 | 22.990 | −3.829 | 97.389 | 1.00 | 36.14 |
| ATOM | 1142 | C | GLY | 298 | 23.541 | −2.583 | 98.058 | 1.00 | 35.80 |
| ATOM | 1143 | O | GLY | 298 | 23.479 | −1.486 | 97.499 | 1.00 | 35.86 |
| ATOM | 1144 | N | ALA | 299 | 24.079 | −2.752 | 99.262 | 1.00 | 35.67 |
| ATOM | 1145 | CA | ALA | 299 | 24.648 | −1.644 | 100.018 | 1.00 | 34.99 |
| ATOM | 1146 | CB | ALA | 299 | 24.757 | −2.001 | 101.506 | 1.00 | 35.85 |
| ATOM | 1147 | C | ALA | 299 | 26.014 | −1.346 | 99.450 | 1.00 | 34.21 |
| ATOM | 1148 | O | ALA | 299 | 26.628 | −0.354 | 99.809 | 1.00 | 34.18 |
| ATOM | 1149 | N | GLY | 329 | 26.503 | −2.232 | 98.591 | 1.00 | 34.17 |
| ATOM | 1150 | CA | GLY | 329 | 27.785 | −1.988 | 97.965 | 1.00 | 35.52 |
| ATOM | 1151 | C | GLY | 329 | 28.940 | −2.931 | 98.199 | 1.00 | 36.98 |
| ATOM | 1152 | O | GLY | 329 | 30.059 | −2.611 | 97.805 | 1.00 | 37.25 |
| ATOM | 1153 | N | HIS | 330 | 28.709 | −4.086 | 98.817 | 1.00 | 39.63 |
| ATOM | 1154 | CA | HIS | 330 | 29.827 | −5.002 | 99.058 | 1.00 | 40.25 |
| ATOM | 1155 | CB | HIS | 330 | 30.600 | −4.559 | 100.305 | 1.00 | 39.30 |
| ATOM | 1156 | CG | HIS | 330 | 29.818 | −4.666 | 101.578 | 1.00 | 40.80 |
| ATOM | 1157 | CD2 | HIS | 330 | 30.171 | −5.105 | 102.807 | 1.00 | 42.00 |
| ATOM | 1158 | ND1 | HIS | 330 | 28.516 | −4.227 | 101.693 | 1.00 | 41.71 |
| ATOM | 1159 | CE1 | HIS | 330 | 28.105 | −4.386 | 102.936 | 1.00 | 41.88 |
| ATOM | 1160 | NE2 | HIS | 330 | 29.090 | −4.918 | 103.636 | 1.00 | 42.53 |
| ATOM | 1161 | C | HIS | 330 | 29.536 | −6.504 | 99.162 | 1.00 | 40.37 |
| ATOM | 1162 | O | HIS | 330 | 28.388 | −6.961 | 99.125 | 1.00 | 38.87 |
| ATOM | 1163 | N | CYS | 331 | 30.630 | −7.255 | 99.255 | 1.00 | 41.78 |
| ATOM | 1164 | CA | CYS | 331 | 30.620 | −8.702 | 99.394 | 1.00 | 42.53 |
| ATOM | 1165 | C | CYS | 331 | 31.656 | −9.068 | 100.444 | 1.00 | 41.74 |
| ATOM | 1166 | O | CYS | 331 | 32.783 | −8.569 | 100.418 | 1.00 | 40.56 |
| ATOM | 1167 | CB | CYS | 331 | 31.022 | −9.387 | 98.105 | 1.00 | 44.95 |
| ATOM | 1168 | SG | CYS | 331 | 29.923 | −9.199 | 96.679 | 1.00 | 48.68 |
| ATOM | 1169 | N | ASN | 332 | 31.273 | −9.945 | 101.359 | 1.00 | 40.38 |
| ATOM | 1170 | CA | ASN | 332 | 32.189 | −10.364 | 102.386 | 1.00 | 40.12 |
| ATOM | 1171 | CB | ASN | 332 | 31.556 | −10.224 | 103.766 | 1.00 | 42.37 |
| ATOM | 1172 | CG | ASN | 332 | 31.322 | −8.777 | 104.151 | 1.00 | 44.33 |
| ATOM | 1173 | OD1 | ASN | 332 | 32.169 | −7.911 | 103.909 | 1.00 | 44.82 |
| ATOM | 1174 | ND2 | ASN | 332 | 30.175 | −8.509 | 104.768 | 1.00 | 44.71 |
| ATOM | 1175 | C | ASN | 332 | 32.586 | −11.795 | 102.141 | 1.00 | 39.72 |
| ATOM | 1176 | O | ASN | 332 | 31.793 | −12.607 | 101.661 | 1.00 | 38.64 |
| ATOM | 1177 | N | ILE | 333 | 33.834 | −12.088 | 102.472 | 1.00 | 40.00 |
| ATOM | 1178 | CA | ILE | 333 | 34.387 | −13.416 | 102.317 | 1.00 | 40.51 |
| ATOM | 1179 | CB | ILE | 333 | 35.109 | −13.544 | 100.985 | 1.00 | 40.85 |
| ATOM | 1180 | CG2 | ILE | 333 | 35.936 | −14.821 | 100.957 | 1.00 | 42.34 |
| ATOM | 1181 | CG1 | ILE | 333 | 34.089 | −13.520 | 99.855 | 1.00 | 40.11 |
| ATOM | 1182 | CD1 | ILE | 333 | 34.709 | −13.314 | 98.515 | 1.00 | 41.51 |
| ATOM | 1183 | C | ILE | 333 | 35.381 | −13.647 | 103.432 | 1.00 | 40.36 |
| ATOM | 1184 | O | ILE | 333 | 36.201 | −12.780 | 103.723 | 1.00 | 40.87 |
| ATOM | 1185 | N | ALA | 334 | 35.299 | −14.812 | 104.060 | 1.00 | 39.60 |
| ATOM | 1186 | CA | ALA | 334 | 36.204 | −15.156 | 105.147 | 1.00 | 38.54 |
| ATOM | 1187 | CB | ALA | 334 | 35.762 | −16.471 | 105.757 | 1.00 | 41.22 |
| ATOM | 1189 | C | ALA | 334 | 37.614 | −15.275 | 104.590 | 1.00 | 36.87 |
| ATOM | 1190 | O | ALA | 334 | 37.883 | −16.097 | 103.715 | 1.00 | 33.76 |
| ATOM | 1191 | N | ARG | 335 | 38.510 | −14.444 | 105.102 | 1.00 | 36.58 |
| ATOM | 1192 | CA | ARG | 335 | 39.883 | −14.434 | 104.628 | 1.00 | 37.37 |
| ATOM | 1193 | CB | ARG | 335 | 40.669 | −13.333 | 105.326 | 1.00 | 36.39 |
| ATOM | 1194 | CG | ARG | 335 | 42.094 | −13.213 | 104.847 | 1.00 | 38.55 |
| ATOM | 1195 | CD | ARG | 335 | 42.801 | −12.047 | 105.516 | 1.00 | 42.33 |
| ATOM | 1196 | NE | ARG | 335 | 42.268 | −10.762 | 105.079 | 1.00 | 44.44 |
| ATOM | 1197 | CZ | ARG | 335 | 42.375 | −10.305 | 103.837 | 1.00 | 45.53 |
| ATOM | 1198 | NH1 | ARG | 335 | 42.999 | −11.034 | 102.924 | 1.00 | 46.03 |
| ATOM | 1199 | NH2 | ARG | 335 | 41.856 | −9.127 | 103.509 | 1.00 | 46.38 |
| ATOM | 1200 | C | ARG | 335 | 40.558 | −15.774 | 104.855 | 1.00 | 38.44 |
| ATOM | 1201 | O | ARG | 335 | 41.318 | −16.259 | 104.012 | 1.00 | 39.73 |
| ATOM | 1202 | N | ALA | 336 | 40.276 | −16.375 | 106.000 | 1.00 | 38.31 |

TABLE 1-continued

The structural coordinates of an exemplary stabilized form of gp120 at atomic resolution

| ATOM | 1203 | CA  | ALA | 336 | 40.849 | −17.664 | 106.347 | 1.00 | 38.08 |
|------|------|-----|-----|-----|--------|---------|---------|------|-------|
| ATOM | 1204 | CB  | ALA | 336 | 40.436 | −18.025 | 107.750 | 1.00 | 38.47 |
| ATOM | 1205 | C   | ALA | 336 | 40.393 | −18.754 | 105.371 | 1.00 | 38.68 |
| ATOM | 1206 | O   | ALA | 336 | 41.214 | −19.420 | 104.728 | 1.00 | 37.19 |
| ATOM | 1207 | N   | LYS | 337 | 39.078 | −18.934 | 105.271 | 1.00 | 39.27 |
| ATOM | 1208 | CA  | LYS | 337 | 38.523 | −19.932 | 104.376 | 1.00 | 39.56 |
| ATOM | 1209 | CB  | LYS | 337 | 37.003 | −19.839 | 104.339 | 1.00 | 40.15 |
| ATOM | 1210 | CG  | LYS | 337 | 36.316 | −20.161 | 105.642 | 1.00 | 42.29 |
| ATOM | 1211 | CD  | LYS | 337 | 34.875 | −20.564 | 105.373 | 1.00 | 44.78 |
| ATOM | 1212 | CE  | LYS | 337 | 34.130 | −20.917 | 106.647 | 1.00 | 46.19 |
| ATOM | 1213 | NZ  | LYS | 337 | 32.829 | −21.580 | 106.331 | 1.00 | 47.33 |
| ATOM | 1214 | C   | LYS | 337 | 39.066 | −19.744 | 102.974 | 1.00 | 39.65 |
| ATOM | 1215 | O   | LYS | 337 | 39.464 | −20.699 | 102.329 | 1.00 | 39.54 |
| ATOM | 1216 | N   | TRP | 338 | 39.086 | −18.506 | 102.501 | 1.00 | 41.16 |
| ATOM | 1217 | CA  | TRP | 338 | 39.585 | −18.252 | 101.159 | 1.00 | 43.17 |
| ATOM | 1218 | CB  | TRP | 338 | 39.319 | −16.817 | 100.725 | 1.00 | 40.60 |
| ATOM | 1219 | CG  | TRP | 338 | 39.685 | −16.593 | 99.290  | 1.00 | 37.38 |
| ATOM | 1220 | CD2 | TRP | 338 | 38.950 | −17.042 | 98.154  | 1.00 | 36.44 |
| ATOM | 1221 | CE2 | TRP | 338 | 39.646 | −16.608 | 97.004  | 1.00 | 36.35 |
| ATOM | 1222 | CE3 | TRP | 338 | 37.765 | −17.774 | 97.993  | 1.00 | 35.17 |
| ATOM | 1223 | CD1 | TRP | 338 | 40.777 | −15.928 | 98.803  | 1.00 | 36.91 |
| ATOM | 1224 | NE1 | TRP | 338 | 40.761 | −15.930 | 97.427  | 1.00 | 35.85 |
| ATOM | 1225 | CZ2 | TRP | 338 | 39.194 | −16.878 | 95.714  | 1.00 | 36.13 |
| ATOM | 1226 | CZ3 | TRP | 338 | 37.316 | −18.044 | 96.712  | 1.00 | 34.19 |
| ATOM | 1227 | CH2 | TRP | 338 | 38.028 | −17.596 | 95.588  | 1.00 | 35.36 |
| ATOM | 1228 | C   | TRP | 338 | 41.069 | −18.515 | 101.032 | 1.00 | 46.01 |
| ATOM | 1229 | O   | TRP | 338 | 41.523 | −19.094 | 100.045 | 1.00 | 46.74 |
| ATOM | 1230 | N   | ASN | 339 | 41.836 | −18.083 | 102.020 | 1.00 | 48.56 |
| ATOM | 1231 | CA  | ASN | 339 | 43.260 | −18.298 | 101.949 | 1.00 | 51.16 |
| ATOM | 1232 | CB  | ASN | 339 | 43.957 | −17.688 | 103.143 | 1.00 | 56.16 |
| ATOM | 1233 | CG  | ASN | 339 | 45.435 | −17.890 | 103.080 | 1.00 | 63.56 |
| ATOM | 1234 | OD1 | ASN | 339 | 46.073 | −17.445 | 102.132 | 1.00 | 64.19 |
| ATOM | 1235 | ND2 | ASN | 339 | 45.995 | −18.566 | 104.079 | 1.00 | 71.86 |
| ATOM | 1236 | C   | ASN | 339 | 43.605 | −19.777 | 101.860 | 1.00 | 50.86 |
| ATOM | 1237 | O   | ASN | 339 | 44.597 | −20.144 | 101.242 | 1.00 | 50.87 |
| ATOM | 1238 | N   | ASN | 340 | 42.800 | −20.634 | 102.478 | 1.00 | 50.99 |
| ATOM | 1239 | CA  | ASN | 340 | 43.071 | −22.067 | 102.407 | 1.00 | 51.70 |
| ATOM | 1240 | CB  | ASN | 340 | 42.192 | −22.862 | 103.371 | 1.00 | 54.49 |
| ATOM | 1241 | CG  | ASN | 340 | 42.634 | −22.724 | 104.808 | 1.00 | 58.41 |
| ATOM | 1242 | OD1 | ASN | 340 | 43.787 | −23.014 | 105.151 | 1.00 | 60.24 |
| ATOM | 1243 | ND2 | ASN | 340 | 41.719 | −22.288 | 105.666 | 1.00 | 60.46 |
| ATOM | 1244 | C   | ASN | 340 | 42.781 | −22.540 | 101.004 | 1.00 | 50.85 |
| ATOM | 1245 | O   | ASN | 340 | 43.537 | −23.331 | 100.433 | 1.00 | 51.84 |
| ATOM | 1246 | N   | THR | 341 | 41.669 | −22.058 | 100.456 | 1.00 | 48.01 |
| ATOM | 1247 | CA  | THR | 341 | 41.269 | −22.434 | 99.116  | 1.00 | 45.14 |
| ATOM | 1248 | CB  | THR | 341 | 39.989 | −21.678 | 98.686  | 1.00 | 44.64 |
| ATOM | 1249 | OG1 | THR | 341 | 38.964 | −21.883 | 99.667  | 1.00 | 42.76 |
| ATOM | 1250 | CG2 | THR | 341 | 39.488 | −22.189 | 97.334  | 1.00 | 42.30 |
| ATOM | 1251 | C   | THR | 341 | 42.416 | −22.124 | 98.163  | 1.00 | 44.38 |
| ATOM | 1252 | O   | THR | 341 | 42.821 | −22.977 | 97.377  | 1.00 | 42.42 |
| ATOM | 1253 | N   | LEU | 342 | 42.959 | −20.911 | 98.249  | 1.00 | 44.37 |
| ATOM | 1254 | CA  | LEU | 342 | 44.061 | −20.531 | 97.373  | 1.00 | 44.41 |
| ATOM | 1255 | CB  | LEU | 342 | 44.506 | −19.087 | 97.635  | 1.00 | 43.85 |
| ATOM | 1256 | CG  | LEU | 342 | 43.507 | −17.950 | 97.335  | 1.00 | 44.37 |
| ATOM | 1257 | CD1 | LEU | 342 | 44.162 | −16.606 | 97.623  | 1.00 | 43.63 |
| ATOM | 1258 | CD2 | LEU | 342 | 43.050 | −17.996 | 95.894  | 1.00 | 43.05 |
| ATOM | 1259 | C   | LEU | 342 | 45.245 | −21.489 | 97.514  | 1.00 | 44.72 |
| ATOM | 1260 | O   | LEU | 342 | 45.858 | −21.851 | 96.515  | 1.00 | 45.32 |
| ATOM | 1261 | N   | LYS | 343 | 45.567 | −21.917 | 98.735  | 1.00 | 44.30 |
| ATOM | 1262 | CA  | LYS | 343 | 46.678 | −22.854 | 98.921  | 1.00 | 43.59 |
| ATOM | 1263 | CB  | LYS | 343 | 46.928 | −23.141 | 100.406 | 1.00 | 44.40 |
| ATOM | 1264 | CG  | LYS | 343 | 48.240 | −23.898 | 100.658 | 1.00 | 46.15 |
| ATOM | 1265 | CD  | LYS | 343 | 48.413 | −24.323 | 102.114 | 1.00 | 49.16 |
| ATOM | 1266 | CE  | LYS | 343 | 48.578 | −23.136 | 103.080 | 1.00 | 52.93 |
| ATOM | 1267 | NZ  | LYS | 343 | 49.893 | −22.400 | 103.011 | 1.00 | 53.31 |
| ATOM | 1268 | C   | LYS | 343 | 46.388 | −24.173 | 98.206  | 1.00 | 42.93 |
| ATOM | 1269 | O   | LYS | 343 | 47.242 | −24.709 | 97.493  | 1.00 | 42.92 |
| ATOM | 1270 | N   | GLN | 344 | 45.179 | −24.693 | 98.396  | 1.00 | 42.56 |
| ATOM | 1271 | CA  | GLN | 344 | 44.778 | −25.957 | 97.777  | 1.00 | 42.99 |
| ATOM | 1272 | CB  | GLN | 344 | 43.385 | −26.373 | 98.241  | 1.00 | 41.89 |
| ATOM | 1273 | CG  | GLN | 344 | 43.168 | −26.344 | 99.725  | 1.00 | 42.51 |
| ATOM | 1274 | CD  | GLN | 344 | 41.735 | −26.664 | 100.081 | 1.00 | 43.88 |
| ATOM | 1275 | OE1 | GLN | 344 | 41.243 | −27.736 | 99.755  | 1.00 | 45.09 |
| ATOM | 1276 | NE2 | GLN | 344 | 41.052 | −25.728 | 100.744 | 1.00 | 44.66 |
| ATOM | 1277 | C   | GLN | 344 | 44.762 | −25.908 | 96.254  | 1.00 | 43.37 |
| ATOM | 1278 | O   | GLN | 344 | 44.870 | −26.952 | 95.612  | 1.00 | 44.99 |
| ATOM | 1279 | N   | ILE | 345 | 44.602 | −24.714 | 95.679  | 1.00 | 43.39 |
| ATOM | 1280 | CA  | ILE | 345 | 44.559 | −24.567 | 94.218  | 1.00 | 42.52 |

TABLE 1-continued

The structural coordinates of an exemplary stabilized form of gp120 at atomic resolution

| ATOM | 1281 | CB  | ILE | 345 | 43.705 | −23.359 | 93.765 | 1.00 | 40.62 |
|------|------|-----|-----|-----|--------|---------|--------|------|-------|
| ATOM | 1282 | CG2 | ILE | 345 | 43.479 | −23.434 | 92.280 | 1.00 | 39.28 |
| ATOM | 1283 | CG1 | ILE | 345 | 42.332 | −23.377 | 94.419 | 1.00 | 40.32 |
| ATOM | 1284 | CD1 | ILE | 345 | 41.517 | −22.134 | 94.104 | 1.00 | 40.02 |
| ATOM | 1285 | C   | ILE | 345 | 45.946 | −24.394 | 93.611 | 1.00 | 43.06 |
| ATOM | 1286 | O   | ILE | 345 | 46.281 | −25.050 | 92.626 | 1.00 | 42.31 |
| ATOM | 1287 | N   | ALA | 346 | 46.745 | −23.496 | 94.184 | 1.00 | 44.37 |
| ATOM | 1288 | CA  | ALA | 346 | 48.097 | −23.273 | 93.683 | 1.00 | 45.42 |
| ATOM | 1289 | CB  | ALA | 346 | 48.836 | −22.275 | 94.556 | 1.00 | 43.26 |
| ATOM | 1290 | C   | ALA | 346 | 48.771 | −24.630 | 93.743 | 1.00 | 46.84 |
| ATOM | 1291 | O   | ALA | 346 | 49.582 | −24.981 | 92.886 | 1.00 | 47.39 |
| ATOM | 1292 | N   | SER | 347 | 48.408 | −25.396 | 94.765 | 1.00 | 47.70 |
| ATOM | 1293 | CA  | SER | 347 | 48.950 | −26.722 | 94.934 | 1.00 | 49.50 |
| ATOM | 1294 | CB  | SER | 347 | 48.337 | −27.376 | 96.160 | 1.00 | 51.28 |
| ATOM | 1295 | OG  | SER | 347 | 48.850 | −28.685 | 96.317 | 1.00 | 56.57 |
| ATOM | 1296 | C   | SER | 347 | 48.662 | −27.558 | 93.683 | 1.00 | 49.94 |
| ATOM | 1297 | O   | SER | 347 | 49.586 | −28.029 | 93.030 | 1.00 | 50.34 |
| ATOM | 1298 | N   | LYS | 348 | 47.382 | −27.728 | 93.351 | 1.00 | 50.78 |
| ATOM | 1299 | CA  | LYS | 348 | 46.962 | −28.494 | 92.170 | 1.00 | 51.63 |
| ATOM | 1300 | CB  | LYS | 348 | 45.432 | −28.577 | 92.098 | 1.00 | 51.50 |
| ATOM | 1301 | CG  | LYS | 348 | 44.791 | −29.584 | 93.032 | 1.00 | 51.75 |
| ATOM | 1302 | CD  | LYS | 348 | 45.064 | −30.988 | 92.556 | 1.00 | 50.85 |
| ATOM | 1303 | CE  | LYS | 348 | 44.542 | −32.004 | 93.543 | 1.00 | 50.69 |
| ATOM | 1304 | NZ  | LYS | 348 | 44.944 | −33.375 | 93.137 | 1.00 | 50.94 |
| ATOM | 1305 | C   | LYS | 348 | 47.463 | −27.869 | 90.869 | 1.00 | 52.28 |
| ATOM | 1306 | O   | LYS | 348 | 47.585 | −28.535 | 89.840 | 1.00 | 52.16 |
| ATOM | 1307 | N   | LEU | 349 | 47.738 | −26.579 | 90.908 | 1.00 | 53.08 |
| ATOM | 1308 | CA  | LEU | 349 | 48.203 | −25.921 | 89.713 | 1.00 | 55.10 |
| ATOM | 1309 | CB  | LEU | 349 | 48.002 | −24.402 | 89.824 | 1.00 | 53.88 |
| ATOM | 1310 | CG  | LEU | 349 | 46.572 | −23.855 | 89.720 | 1.00 | 50.78 |
| ATOM | 1311 | CD1 | LEU | 349 | 46.600 | −22.369 | 89.985 | 1.00 | 49.11 |
| ATOM | 1312 | CD2 | LEU | 349 | 45.977 | −24.134 | 88.345 | 1.00 | 47.99 |
| ATOM | 1313 | C   | LEU | 349 | 49.655 | −26.259 | 89.402 | 1.00 | 57.08 |
| ATOM | 1314 | O   | LEU | 349 | 49.959 | −26.620 | 88.270 | 1.00 | 57.54 |
| ATOM | 1315 | N   | ARG | 350 | 50.555 | −26.159 | 90.383 | 1.00 | 59.82 |
| ATOM | 1316 | CA  | ARG | 350 | 51.961 | −26.476 | 90.114 | 1.00 | 63.18 |
| ATOM | 1317 | CB  | ARG | 350 | 52.866 | −26.042 | 91.266 | 1.00 | 64.31 |
| ATOM | 1318 | CG  | ARG | 350 | 52.410 | −26.471 | 92.624 | 1.00 | 68.34 |
| ATOM | 1319 | CD  | ARG | 350 | 53.595 | −26.540 | 93.563 | 1.00 | 72.56 |
| ATOM | 1320 | NE  | ARG | 350 | 54.525 | −25.427 | 93.375 | 1.00 | 76.31 |
| ATOM | 1321 | CZ  | ARG | 350 | 55.714 | −25.343 | 93.974 | 1.00 | 78.63 |
| ATOM | 1322 | NH1 | ARG | 350 | 56.113 | −26.308 | 94.798 | 1.00 | 78.98 |
| ATOM | 1323 | NH2 | ARG | 350 | 56.511 | −24.301 | 93.751 | 1.00 | 79.29 |
| ATOM | 1324 | C   | ARG | 350 | 52.125 | −27.968 | 89.851 | 1.00 | 64.33 |
| ATOM | 1325 | O   | ARG | 350 | 53.102 | −28.405 | 89.234 | 1.00 | 65.71 |
| ATOM | 1326 | N   | GLU | 351 | 51.148 | −28.741 | 90.312 | 1.00 | 64.55 |
| ATOM | 1327 | CA  | GLU | 351 | 51.126 | −30.180 | 90.112 | 1.00 | 63.62 |
| ATOM | 1328 | CB  | GLU | 351 | 49.963 | −30.778 | 90.898 | 1.00 | 66.10 |
| ATOM | 1329 | CG  | GLU | 351 | 49.896 | −32.290 | 90.914 | 1.00 | 70.44 |
| ATOM | 1330 | CD  | GLU | 351 | 48.652 | −32.811 | 91.628 | 1.00 | 72.67 |
| ATOM | 1331 | OE1 | GLU | 351 | 47.536 | −32.631 | 91.090 | 1.00 | 74.72 |
| ATOM | 1332 | OE2 | GLU | 351 | 48.787 | −33.397 | 92.726 | 1.00 | 73.74 |
| ATOM | 1333 | C   | GLU | 351 | 50.941 | −30.456 | 88.615 | 1.00 | 61.98 |
| ATOM | 1334 | O   | GLU | 351 | 51.096 | −31.588 | 88.162 | 1.00 | 61.55 |
| ATOM | 1335 | N   | GLN | 352 | 50.602 | −29.409 | 87.861 | 1.00 | 60.65 |
| ATOM | 1336 | CA  | GLN | 352 | 50.397 | −29.505 | 86.415 | 1.00 | 59.13 |
| ATOM | 1337 | CB  | GLN | 352 | 48.942 | −29.191 | 86.053 | 1.00 | 56.49 |
| ATOM | 1338 | CG  | GLN | 352 | 48.699 | −29.115 | 84.545 | 1.00 | 53.84 |
| ATOM | 1339 | CD  | GLN | 352 | 47.501 | −29.931 | 84.092 | 1.00 | 52.61 |
| ATOM | 1340 | OE1 | GLN | 352 | 47.280 | −30.122 | 82.895 | 1.00 | 49.99 |
| ATOM | 1341 | NE2 | GLN | 352 | 46.722 | −30.416 | 85.048 | 1.00 | 52.71 |
| ATOM | 1342 | C   | GLN | 352 | 51.320 | −28.619 | 85.563 | 1.00 | 59.46 |
| ATOM | 1343 | O   | GLN | 352 | 51.494 | −28.873 | 84.375 | 1.00 | 58.99 |
| ATOM | 1344 | N   | PHE | 353 | 51.908 | −27.585 | 86.152 | 1.00 | 60.32 |
| ATOM | 1345 | CA  | PHE | 353 | 52.796 | −26.714 | 85.390 | 1.00 | 62.07 |
| ATOM | 1346 | CB  | PHE | 353 | 52.262 | −25.277 | 85.366 | 1.00 | 61.62 |
| ATOM | 1347 | CG  | PHE | 353 | 50.957 | −25.129 | 84.641 | 1.00 | 61.43 |
| ATOM | 1348 | CD1 | PHE | 353 | 49.752 | −25.258 | 85.316 | 1.00 | 61.91 |
| ATOM | 1349 | CD2 | PHE | 353 | 50.930 | −24.905 | 83.268 | 1.00 | 62.10 |
| ATOM | 1350 | CE1 | PHE | 353 | 48.532 | −25.168 | 84.633 | 1.00 | 62.04 |
| ATOM | 1351 | CE2 | PHE | 353 | 49.717 | −24.815 | 82.576 | 1.00 | 61.69 |
| ATOM | 1352 | CZ  | PHE | 353 | 48.516 | −24.948 | 83.261 | 1.00 | 61.58 |
| ATOM | 1353 | C   | PHE | 353 | 54.229 | −26.713 | 85.915 | 1.00 | 64.18 |
| ATOM | 1354 | O   | PHE | 353 | 55.046 | −25.880 | 85.511 | 1.00 | 65.29 |
| ATOM | 1355 | N   | GLY | 354 | 54.540 | −27.642 | 86.812 | 1.00 | 64.51 |
| ATOM | 1356 | CA  | GLY | 354 | 55.888 | −27.697 | 87.340 | 1.00 | 65.83 |
| ATOM | 1357 | C   | GLY | 354 | 55.948 | −27.501 | 88.838 | 1.00 | 67.15 |
| ATOM | 1358 | O   | GLY | 354 | 55.746 | −26.395 | 89.346 | 1.00 | 67.01 |

TABLE 1-continued

The structural coordinates of an exemplary stabilized form of gp120 at atomic resolution

| ATOM | 1359 | N | ASN | 355 | 56.237 | −28.589 | 89.544 | 1.00 | 67.83 |
|---|---|---|---|---|---|---|---|---|---|
| ATOM | 1360 | CA | ASN | 355 | 56.329 | −28.576 | 90.994 | 1.00 | 68.59 |
| ATOM | 1361 | CB | ASN | 355 | 56.573 | −29.995 | 91.513 | 1.00 | 70.55 |
| ATOM | 1362 | CG | ASN | 355 | 55.301 | −30.841 | 91.533 | 1.00 | 72.72 |
| ATOM | 1363 | OD1 | ASN | 355 | 55.353 | −32.048 | 91.776 | 1.00 | 74.24 |
| ATOM | 1364 | ND2 | ASN | 355 | 54.155 | −30.208 | 91.290 | 1.00 | 72.93 |
| ATOM | 1365 | C | ASN | 355 | 57.413 | −27.644 | 91.509 | 1.00 | 68.43 |
| ATOM | 1366 | O | ASN | 355 | 57.574 | −27.480 | 92.716 | 1.00 | 69.01 |
| ATOM | 1367 | N | ASN | 356 | 58.155 | −27.032 | 90.597 | 1.00 | 67.89 |
| ATOM | 1368 | CA | ASN | 356 | 59.214 | −26.114 | 90.988 | 1.00 | 67.81 |
| ATOM | 1369 | CB | ASN | 356 | 60.495 | −26.427 | 90.209 | 1.00 | 68.67 |
| ATOM | 1370 | CG | ASN | 356 | 61.021 | −27.836 | 90.475 | 1.00 | 68.82 |
| ATOM | 1371 | OD1 | ASN | 356 | 62.067 | −28.223 | 89.956 | 1.00 | 68.37 |
| ATOM | 1372 | ND2 | ASN | 356 | 60.294 | −28.605 | 91.282 | 1.00 | 69.10 |
| ATOM | 1373 | C | ASN | 356 | 58.756 | −24.690 | 90.698 | 1.00 | 67.61 |
| ATOM | 1374 | O | ASN | 356 | 59.399 | −23.719 | 91.109 | 1.00 | 68.06 |
| ATOM | 1375 | N | LYS | 357 | 57.632 | −24.588 | 89.989 | 1.00 | 66.72 |
| ATOM | 1376 | CA | LYS | 357 | 57.028 | −23.308 | 89.603 | 1.00 | 64.44 |
| ATOM | 1377 | CB | LYS | 357 | 55.979 | −23.528 | 88.503 | 1.00 | 65.55 |
| ATOM | 1378 | CG | LYS | 357 | 56.524 | −23.915 | 87.138 | 1.00 | 66.86 |
| ATOM | 1379 | CD | LYS | 357 | 57.287 | −22.758 | 86.511 | 1.00 | 68.57 |
| ATOM | 1380 | CE | LYS | 357 | 57.563 | −22.990 | 85.033 | 1.00 | 69.07 |
| ATOM | 1381 | NZ | LYS | 357 | 56.297 | −23.017 | 84.250 | 1.00 | 69.35 |
| ATOM | 1382 | C | LYS | 357 | 56.353 | −22.582 | 90.769 | 1.00 | 61.58 |
| ATOM | 1383 | O | LYS | 357 | 55.735 | −23.211 | 91.630 | 1.00 | 61.43 |
| ATOM | 1384 | N | THR | 358 | 56.463 | −21.257 | 90.778 | 1.00 | 57.89 |
| ATOM | 1385 | CA | THR | 358 | 55.851 | −20.434 | 91.817 | 1.00 | 54.10 |
| ATOM | 1386 | CB | THR | 358 | 56.721 | −19.218 | 92.155 | 1.00 | 53.27 |
| ATOM | 1387 | OG1 | THR | 358 | 57.983 | −19.666 | 92.659 | 1.00 | 52.66 |
| ATOM | 1388 | CG2 | THR | 358 | 56.045 | −18.358 | 93.202 | 1.00 | 53.26 |
| ATOM | 1389 | C | THR | 358 | 54.500 | −19.944 | 91.317 | 1.00 | 51.75 |
| ATOM | 1390 | O | THR | 358 | 54.412 | −19.332 | 90.257 | 1.00 | 51.73 |
| ATOM | 1391 | N | ILE | 359 | 53.452 | −20.221 | 92.084 | 1.00 | 48.72 |
| ATOM | 1392 | CA | ILE | 359 | 52.100 | −19.832 | 91.707 | 1.00 | 45.84 |
| ATOM | 1393 | CB | ILE | 359 | 51.054 | −20.849 | 92.247 | 1.00 | 44.27 |
| ATOM | 1394 | CG2 | ILE | 359 | 49.667 | −20.470 | 91.782 | 1.00 | 43.26 |
| ATOM | 1395 | CG1 | ILE | 359 | 51.387 | −22.258 | 91.767 | 1.00 | 42.29 |
| ATOM | 1396 | CD1 | ILE | 359 | 51.461 | −22.383 | 90.264 | 1.00 | 42.14 |
| ATOM | 1397 | C | ILE | 359 | 51.732 | −18.450 | 92.228 | 1.00 | 45.04 |
| ATOM | 1398 | O | ILE | 359 | 51.703 | −18.231 | 93.438 | 1.00 | 44.85 |
| ATOM | 1399 | N | ILE | 360 | 51.451 | −17.528 | 91.309 | 1.00 | 44.16 |
| ATOM | 1400 | CA | ILE | 360 | 51.058 | −16.163 | 91.667 | 1.00 | 43.62 |
| ATOM | 1401 | CB | ILE | 360 | 51.930 | −15.086 | 90.968 | 1.00 | 41.87 |
| ATOM | 1402 | CG2 | ILE | 360 | 51.486 | −13.711 | 91.399 | 1.00 | 41.80 |
| ATOM | 1403 | CG1 | ILE | 360 | 53.401 | −15.280 | 91.297 | 1.00 | 40.00 |
| ATOM | 1404 | CD1 | ILE | 360 | 54.176 | −15.839 | 90.143 | 1.00 | 41.00 |
| ATOM | 1405 | C | ILE | 360 | 49.620 | −15.898 | 91.231 | 1.00 | 43.95 |
| ATOM | 1406 | O | ILE | 360 | 49.205 | −16.302 | 90.139 | 1.00 | 43.81 |
| ATOM | 1407 | N | PHE | 361 | 48.859 | −15.215 | 92.076 | 1.00 | 43.88 |
| ATOM | 1408 | CA | PHE | 361 | 47.486 | −14.886 | 91.721 | 1.00 | 45.05 |
| ATOM | 1409 | CB | PHE | 361 | 46.510 | −15.333 | 92.818 | 1.00 | 44.55 |
| ATOM | 1410 | CG | PHE | 361 | 46.421 | −16.832 | 92.991 | 1.00 | 43.16 |
| ATOM | 1411 | CD1 | PHE | 361 | 47.047 | −17.463 | 94.059 | 1.00 | 41.83 |
| ATOM | 1412 | CD2 | PHE | 361 | 45.723 | −17.609 | 92.074 | 1.00 | 41.08 |
| ATOM | 1413 | CE1 | PHE | 361 | 46.978 | −18.835 | 94.207 | 1.00 | 39.99 |
| ATOM | 1414 | CE2 | PHE | 361 | 45.650 | −18.978 | 92.216 | 1.00 | 39.19 |
| ATOM | 1415 | CZ | PHE | 361 | 46.280 | −19.591 | 93.284 | 1.00 | 39.63 |
| ATOM | 1416 | C | PHE | 361 | 47.370 | −13.381 | 91.521 | 1.00 | 45.78 |
| ATOM | 1417 | O | PHE | 361 | 47.599 | −12.619 | 92.456 | 1.00 | 48.15 |
| ATOM | 1418 | N | LYS | 362 | 47.032 | −12.946 | 90.310 | 1.00 | 44.97 |
| ATOM | 1419 | CA | LYS | 362 | 46.880 | −11.519 | 90.044 | 1.00 | 45.08 |
| ATOM | 1420 | CB | LYS | 362 | 47.836 | −11.058 | 88.946 | 1.00 | 46.05 |
| ATOM | 1421 | CG | LYS | 362 | 49.297 | −11.075 | 89.307 | 1.00 | 46.12 |
| ATOM | 1422 | CD | LYS | 362 | 50.116 | −10.559 | 88.147 | 1.00 | 44.35 |
| ATOM | 1423 | CE | LYS | 362 | 51.572 | −10.516 | 88.524 | 1.00 | 45.15 |
| ATOM | 1424 | NZ | LYS | 362 | 51.752 | −9.677 | 89.742 | 1.00 | 45.33 |
| ATOM | 1425 | C | LYS | 362 | 45.461 | −11.179 | 89.611 | 1.00 | 45.45 |
| ATOM | 1426 | O | LYS | 362 | 44.719 | −12.042 | 89.138 | 1.00 | 45.50 |
| ATOM | 1427 | N | GLN | 363 | 45.102 | −9.907 | 89.759 | 1.00 | 45.24 |
| ATOM | 1428 | CA | GLN | 363 | 43.781 | −9.411 | 89.380 | 1.00 | 44.82 |
| ATOM | 1429 | CB | GLN | 363 | 43.639 | −7.954 | 89.818 | 1.00 | 44.59 |
| ATOM | 1430 | CG | GLN | 363 | 44.807 | −7.064 | 89.415 | 1.00 | 45.02 |
| ATOM | 1431 | CD | GLN | 363 | 44.428 | −5.595 | 89.372 | 1.00 | 45.87 |
| ATOM | 1432 | OE1 | GLN | 363 | 43.555 | −5.199 | 88.600 | 1.00 | 47.42 |
| ATOM | 1433 | NE2 | GLN | 363 | 45.079 | −4.780 | 90.199 | 1.00 | 44.92 |
| ATOM | 1434 | C | GLN | 363 | 43.527 | −9.506 | 87.872 | 1.00 | 45.01 |
| ATOM | 1435 | O | GLN | 363 | 44.459 | −9.717 | 87.090 | 1.00 | 44.87 |
| ATOM | 1436 | N | SER | 364 | 42.263 | −9.350 | 87.470 | 1.00 | 44.60 |

TABLE 1-continued

The structural coordinates of an exemplary stabilized form of gp120 at atomic resolution

| ATOM | 1437 | CA | SER | 364 | 41.895 | −9.394 | 86.052 | 1.00 | 43.07 |
|---|---|---|---|---|---|---|---|---|---|
| ATOM | 1438 | CB | SER | 364 | 40.444 | −8.956 | 85.850 | 1.00 | 41.38 |
| ATOM | 1439 | OG | SER | 364 | 40.073 | −9.076 | 84.487 | 1.00 | 39.74 |
| ATOM | 1440 | C | SER | 364 | 42.803 | −8.436 | 85.297 | 1.00 | 43.26 |
| ATOM | 1441 | O | SER | 364 | 43.104 | −7.347 | 85.793 | 1.00 | 43.43 |
| ATOM | 1442 | N | SER | 365 | 43.234 | −8.829 | 84.102 | 1.00 | 42.44 |
| ATOM | 1443 | CA | SER | 365 | 44.116 | −7.979 | 83.312 | 1.00 | 41.33 |
| ATOM | 1444 | CB | SER | 365 | 45.140 | −8.846 | 82.566 | 1.00 | 41.58 |
| ATOM | 1445 | OG | SER | 365 | 44.530 | −10.000 | 82.013 | 1.00 | 44.41 |
| ATOM | 1446 | C | SER | 365 | 43.445 | −6.996 | 82.328 | 1.00 | 40.25 |
| ATOM | 1447 | O | SER | 365 | 44.132 | −6.413 | 81.491 | 1.00 | 42.93 |
| ATOM | 1448 | N | GLY | 366 | 42.130 | −6.794 | 82.424 | 1.00 | 36.76 |
| ATOM | 1449 | CA | GLY | 366 | 41.473 | −5.860 | 81.524 | 1.00 | 32.05 |
| ATOM | 1450 | C | GLY | 366 | 40.321 | −6.445 | 80.741 | 1.00 | 31.17 |
| ATOM | 1451 | O | GLY | 366 | 40.099 | −7.652 | 80.762 | 1.00 | 31.00 |
| ATOM | 1452 | N | GLY | 367 | 39.581 | −5.585 | 80.044 | 1.00 | 30.27 |
| ATOM | 1453 | CA | GLY | 367 | 38.441 | −6.040 | 79.258 | 1.00 | 29.70 |
| ATOM | 1454 | C | GLY | 367 | 37.117 | −5.504 | 79.777 | 1.00 | 29.80 |
| ATOM | 1455 | O | GLY | 367 | 37.087 | −4.691 | 80.702 | 1.00 | 31.08 |
| ATOM | 1456 | N | ASP | 368 | 36.015 | −5.954 | 79.192 | 1.00 | 29.13 |
| ATOM | 1457 | CA | ASP | 368 | 34.699 | −5.507 | 79.626 | 1.00 | 31.89 |
| ATOM | 1458 | CB | ASP | 368 | 33.604 | −6.305 | 78.909 | 1.00 | 35.79 |
| ATOM | 1459 | CG | ASP | 368 | 33.588 | −6.073 | 77.397 | 1.00 | 39.65 |
| ATOM | 1460 | OD1 | ASP | 368 | 32.826 | −6.784 | 76.700 | 1.00 | 40.00 |
| ATOM | 1461 | OD2 | ASP | 368 | 34.328 | −5.187 | 76.908 | 1.00 | 42.73 |
| ATOM | 1462 | C | ASP | 368 | 34.527 | −5.663 | 81.144 | 1.00 | 32.13 |
| ATOM | 1463 | O | ASP | 368 | 35.139 | −6.527 | 81.757 | 1.00 | 32.82 |
| ATOM | 1464 | N | PRO | 369 | 33.684 | −4.821 | 81.766 | 1.00 | 31.85 |
| ATOM | 1465 | CD | PRO | 369 | 32.993 | −3.693 | 81.120 | 1.00 | 30.96 |
| ATOM | 1466 | CA | PRO | 369 | 33.404 | −4.838 | 83.207 | 1.00 | 31.36 |
| ATOM | 1467 | CB | PRO | 369 | 32.265 | −3.842 | 83.337 | 1.00 | 31.63 |
| ATOM | 1468 | CG | PRO | 369 | 32.613 | −2.833 | 82.289 | 1.00 | 31.18 |
| ATOM | 1469 | C | PRO | 369 | 33.007 | −6.203 | 83.739 | 1.00 | 30.91 |
| ATOM | 1470 | O | PRO | 369 | 33.485 | −6.649 | 84.778 | 1.00 | 31.90 |
| ATOM | 1471 | N | GLU | 370 | 32.112 | −6.858 | 83.023 | 1.00 | 30.62 |
| ATOM | 1472 | CA | GLU | 370 | 31.627 | −8.162 | 83.415 | 1.00 | 31.59 |
| ATOM | 1473 | CB | GLU | 370 | 30.534 | −8.585 | 82.440 | 1.00 | 32.54 |
| ATOM | 1474 | CG | GLU | 370 | 29.303 | −7.659 | 82.445 | 1.00 | 34.81 |
| ATOM | 1475 | CD | GLU | 370 | 29.452 | −6.366 | 81.622 | 1.00 | 34.63 |
| ATOM | 1476 | OE1 | GLU | 370 | 28.495 | −5.567 | 81.601 | 1.00 | 34.16 |
| ATOM | 1477 | OE2 | GLU | 370 | 30.503 | −6.142 | 80.991 | 1.00 | 35.90 |
| ATOM | 1478 | C | GLU | 370 | 32.718 | −9.245 | 83.519 | 1.00 | 32.22 |
| ATOM | 1479 | O | GLU | 370 | 32.528 | −10.259 | 84.194 | 1.00 | 33.09 |
| ATOM | 1480 | N | ILE | 371 | 33.857 | −9.016 | 82.864 | 1.00 | 31.32 |
| ATOM | 1481 | CA | ILE | 371 | 34.999 | −9.943 | 82.861 | 1.00 | 28.31 |
| ATOM | 1482 | CB | ILE | 371 | 35.579 | −10.085 | 81.422 | 1.00 | 28.08 |
| ATOM | 1483 | CG2 | ILE | 371 | 37.098 | −10.089 | 81.437 | 1.00 | 27.78 |
| ATOM | 1484 | CG1 | ILE | 371 | 35.037 | −11.343 | 80.779 | 1.00 | 28.02 |
| ATOM | 1485 | CD1 | ILE | 371 | 33.555 | −11.407 | 80.819 | 1.00 | 30.47 |
| ATOM | 1486 | C | ILE | 371 | 36.133 | −9.506 | 83.797 | 1.00 | 27.21 |
| ATOM | 1487 | O | ILE | 371 | 36.974 | −10.315 | 84.191 | 1.00 | 26.14 |
| ATOM | 1488 | N | VAL | 372 | 36.158 | −8.224 | 84.138 | 1.00 | 26.33 |
| ATOM | 1489 | CA | VAL | 372 | 37.194 | −7.676 | 85.007 | 1.00 | 27.67 |
| ATOM | 1490 | CB | VAL | 372 | 37.487 | −6.200 | 84.678 | 1.00 | 27.14 |
| ATOM | 1491 | CG1 | VAL | 372 | 38.468 | −5.636 | 85.687 | 1.00 | 24.67 |
| ATOM | 1492 | CG2 | VAL | 372 | 38.035 | −6.078 | 83.258 | 1.00 | 26.38 |
| ATOM | 1493 | C | VAL | 372 | 36.807 | −7.739 | 86.467 | 1.00 | 28.75 |
| ATOM | 1494 | O | VAL | 372 | 37.662 | −7.792 | 87.355 | 1.00 | 29.82 |
| ATOM | 1495 | N | THR | 373 | 35.506 | −7.734 | 86.709 | 1.00 | 29.47 |
| ATOM | 1496 | CA | THR | 373 | 34.983 | −7.770 | 88.066 | 1.00 | 28.66 |
| ATOM | 1497 | CB | THR | 373 | 34.079 | −6.554 | 88.296 | 1.00 | 27.96 |
| ATOM | 1498 | OG1 | THR | 373 | 32.916 | −6.668 | 87.472 | 1.00 | 28.85 |
| ATOM | 1499 | CG2 | THR | 373 | 34.801 | −5.285 | 87.888 | 1.00 | 26.32 |
| ATOM | 1500 | C | THR | 373 | 34.166 | −9.042 | 88.221 | 1.00 | 28.00 |
| ATOM | 1501 | O | THR | 373 | 33.806 | −9.658 | 87.211 | 1.00 | 28.23 |
| ATOM | 1502 | N | HIS | 374 | 33.902 | −9.453 | 89.466 | 1.00 | 27.55 |
| ATOM | 1503 | CA | HIS | 374 | 33.075 | −10.642 | 89.723 | 1.00 | 26.55 |
| ATOM | 1504 | CB | HIS | 374 | 33.245 | −11.149 | 91.162 | 1.00 | 25.93 |
| ATOM | 1505 | CG | HIS | 374 | 32.187 | −12.121 | 91.591 | 1.00 | 26.09 |
| ATOM | 1506 | CD2 | HIS | 374 | 31.358 | −12.121 | 92.663 | 1.00 | 26.47 |
| ATOM | 1507 | ND1 | HIS | 374 | 31.866 | −13.243 | 90.863 | 1.00 | 27.70 |
| ATOM | 1508 | CE1 | HIS | 374 | 30.881 | −13.892 | 91.463 | 1.00 | 25.87 |
| ATOM | 1509 | NE2 | HIS | 374 | 30.555 | −13.232 | 92.557 | 1.00 | 25.26 |
| ATOM | 1510 | C | HIS | 374 | 31.654 | −10.153 | 89.476 | 1.00 | 25.07 |
| ATOM | 1511 | O | HIS | 374 | 31.071 | −9.423 | 90.268 | 1.00 | 25.98 |
| ATOM | 1512 | N | TRP | 375 | 31.132 | −10.546 | 88.332 | 1.00 | 24.08 |
| ATOM | 1513 | CA | TRP | 375 | 29.829 | −10.142 | 87.866 | 1.00 | 24.74 |
| ATOM | 1514 | CB | TRP | 375 | 29.960 | −9.781 | 86.383 | 1.00 | 25.04 |

TABLE 1-continued

The structural coordinates of an exemplary stabilized form of gp120 at atomic resolution

| ATOM | 1515 | CG  | TRP | 375 | 28.702 | −9.478  | 85.662 | 1.00 | 25.75 |
|------|------|-----|-----|-----|--------|---------|--------|------|-------|
| ATOM | 1516 | CD2 | TRP | 375 | 28.096 | −10.271 | 84.645 | 1.00 | 25.29 |
| ATOM | 1517 | CE2 | TRP | 375 | 26.916 | −9.609  | 84.235 | 1.00 | 24.75 |
| ATOM | 1518 | CE3 | TRP | 375 | 28.430 | −11.488 | 84.037 | 1.00 | 26.21 |
| ATOM | 1519 | CD1 | TRP | 375 | 27.896 | −8.390  | 85.828 | 1.00 | 26.87 |
| ATOM | 1520 | NE1 | TRP | 375 | 26.819 | −8.457  | 84.972 | 1.00 | 25.73 |
| ATOM | 1521 | CZ2 | TRP | 375 | 26.075 | −10.111 | 83.256 | 1.00 | 25.28 |
| ATOM | 1522 | CZ3 | TRP | 375 | 27.591 | −11.996 | 83.057 | 1.00 | 25.89 |
| ATOM | 1523 | CH2 | TRP | 375 | 26.424 | −11.307 | 82.678 | 1.00 | 26.36 |
| ATOM | 1524 | C   | TRP | 375 | 28.844 | −11.268 | 88.060 | 1.00 | 26.93 |
| ATOM | 1525 | O   | TRP | 375 | 29.098 | −12.411 | 87.687 | 1.00 | 27.40 |
| ATOM | 1526 | N   | PHE | 376 | 27.707 | −10.946 | 88.646 | 1.00 | 28.62 |
| ATOM | 1527 | CA  | PHE | 376 | 26.693 | −11.954 | 88.863 | 1.00 | 31.15 |
| ATOM | 1528 | CB  | PHE | 376 | 26.989 | −12.736 | 90.130 | 1.00 | 30.11 |
| ATOM | 1529 | CG  | PHE | 376 | 27.135 | −11.877 | 91.332 | 1.00 | 30.51 |
| ATOM | 1530 | CD1 | PHE | 376 | 28.310 | −11.162 | 91.547 | 1.00 | 30.86 |
| ATOM | 1531 | CD2 | PHE | 376 | 26.090 | −11.754 | 92.241 | 1.00 | 30.19 |
| ATOM | 1532 | CE1 | PHE | 376 | 28.448 | −10.331 | 92.652 | 1.00 | 29.71 |
| ATOM | 1533 | CE2 | PHE | 376 | 26.209 | −10.929 | 93.352 | 1.00 | 30.22 |
| ATOM | 1534 | CZ  | PHE | 376 | 27.393 | −10.213 | 93.560 | 1.00 | 30.89 |
| ATOM | 1535 | C   | PHE | 376 | 25.355 | −11.279 | 88.996 | 1.00 | 32.83 |
| ATOM | 1536 | O   | PHE | 376 | 25.280 | −10.086 | 89.252 | 1.00 | 33.02 |
| ATOM | 1537 | N   | ASN | 377 | 24.299 | −12.051 | 88.809 | 1.00 | 35.69 |
| ATOM | 1538 | CA  | ASN | 377 | 22.963 | −11.521 | 88.929 | 1.00 | 40.61 |
| ATOM | 1539 | CB  | ASN | 377 | 22.046 | −12.178 | 87.913 | 1.00 | 44.38 |
| ATOM | 1540 | CG  | ASN | 377 | 20.647 | −11.597 | 87.940 | 1.00 | 48.66 |
| ATOM | 1541 | OD1 | ASN | 377 | 20.426 | −10.443 | 87.542 | 1.00 | 48.26 |
| ATOM | 1542 | ND2 | ASN | 377 | 19.689 | −12.393 | 88.420 | 1.00 | 51.13 |
| ATOM | 1543 | C   | ASN | 377 | 22.491 | −11.855 | 90.327 | 1.00 | 42.23 |
| ATOM | 1544 | O   | ASN | 377 | 22.892 | −12.864 | 90.876 | 1.00 | 44.30 |
| ATOM | 1545 | N   | CYS | 378 | 21.643 | −11.009 | 90.901 | 1.00 | 44.55 |
| ATOM | 1546 | CA  | CYS | 378 | 21.117 | −11.220 | 92.251 | 1.00 | 45.14 |
| ATOM | 1547 | C   | CYS | 378 | 19.934 | −10.282 | 92.488 | 1.00 | 43.00 |
| ATOM | 1548 | O   | CYS | 378 | 20.075 | −9.066  | 92.377 | 1.00 | 41.28 |
| ATOM | 1549 | CB  | CYS | 378 | 22.203 | −10.950 | 93.302 | 1.00 | 49.09 |
| ATOM | 1550 | SG  | CYS | 378 | 21.506 | −11.015 | 94.982 | 1.00 | 57.12 |
| ATOM | 1551 | N   | GLY | 379 | 18.773 | −10.842 | 92.819 | 1.00 | 41.22 |
| ATOM | 1552 | CA  | GLY | 379 | 17.600 | −10.011 | 93.025 | 1.00 | 40.83 |
| ATOM | 1553 | C   | GLY | 379 | 17.246 | −9.244  | 91.753 | 1.00 | 40.79 |
| ATOM | 1554 | O   | GLY | 379 | 16.556 | −8.222  | 91.784 | 1.00 | 41.26 |
| ATOM | 1555 | N   | GLY | 380 | 17.718 | −9.738  | 90.619 | 1.00 | 39.72 |
| ATOM | 1556 | CA  | GLY | 380 | 17.442 | −9.059  | 89.372 | 1.00 | 39.79 |
| ATOM | 1557 | C   | GLY | 380 | 18.461 | −7.986  | 89.005 | 1.00 | 39.81 |
| ATOM | 1558 | O   | GLY | 380 | 18.544 | −7.578  | 87.842 | 1.00 | 39.98 |
| ATOM | 1559 | N   | GLU | 381 | 19.243 | −7.524  | 89.979 | 1.00 | 39.10 |
| ATOM | 1560 | CA  | GLU | 381 | 20.244 | −6.489  | 89.712 | 1.00 | 38.16 |
| ATOM | 1561 | CB  | GLU | 381 | 20.440 | −5.607  | 90.940 | 1.00 | 38.52 |
| ATOM | 1562 | CG  | GLU | 381 | 19.162 | −5.139  | 91.601 | 1.00 | 41.28 |
| ATOM | 1563 | CD  | GLU | 381 | 18.327 | −4.226  | 90.728 | 1.00 | 43.40 |
| ATOM | 1564 | OE1 | GLU | 381 | 18.904 | −3.420  | 89.963 | 1.00 | 44.79 |
| ATOM | 1565 | OE2 | GLU | 381 | 17.083 | −4.303  | 90.827 | 1.00 | 44.94 |
| ATOM | 1566 | C   | GLU | 381 | 21.583 | −7.123  | 89.353 | 1.00 | 36.75 |
| ATOM | 1567 | O   | GLU | 381 | 21.890 | −8.228  | 89.796 | 1.00 | 34.31 |
| ATOM | 1568 | N   | PHE | 382 | 22.382 | −6.421  | 88.556 | 1.00 | 34.93 |
| ATOM | 1569 | CA  | PHE | 382 | 23.684 | −6.937  | 88.174 | 1.00 | 34.11 |
| ATOM | 1570 | CB  | PHE | 382 | 23.955 | −6.685  | 86.699 | 1.00 | 35.03 |
| ATOM | 1571 | CG  | PHE | 382 | 23.062 | −7.450  | 85.796 | 1.00 | 35.63 |
| ATOM | 1572 | CD1 | PHE | 382 | 21.868 | −6.901  | 85.351 | 1.00 | 37.48 |
| ATOM | 1573 | CD2 | PHE | 382 | 23.392 | −8.740  | 85.415 | 1.00 | 37.08 |
| ATOM | 1574 | CE1 | PHE | 382 | 21.007 | −7.628  | 84.534 | 1.00 | 38.27 |
| ATOM | 1575 | CE2 | PHE | 382 | 22.543 | −9.482  | 84.600 | 1.00 | 38.30 |
| ATOM | 1576 | CZ  | PHE | 382 | 21.343 | −8.924  | 84.156 | 1.00 | 38.80 |
| ATOM | 1577 | C   | PHE | 382 | 24.800 | −6.316  | 88.992 | 1.00 | 33.85 |
| ATOM | 1578 | O   | PHE | 382 | 25.066 | −5.122  | 88.892 | 1.00 | 33.66 |
| ATOM | 1579 | N   | PHE | 383 | 25.463 | −7.145  | 89.788 | 1.00 | 33.72 |
| ATOM | 1580 | CA  | PHE | 383 | 26.557 | −6.694  | 90.628 | 1.00 | 33.09 |
| ATOM | 1581 | CB  | PHE | 383 | 26.646 | −7.546  | 91.895 | 1.00 | 34.99 |
| ATOM | 1582 | CG  | PHE | 383 | 25.462 | −7.409  | 92.806 | 1.00 | 38.33 |
| ATOM | 1583 | CD1 | PHE | 383 | 24.183 | −7.730  | 92.364 | 1.00 | 39.48 |
| ATOM | 1584 | CD2 | PHE | 383 | 25.619 | −6.928  | 94.103 | 1.00 | 40.16 |
| ATOM | 1585 | CE1 | PHE | 383 | 23.079 | −7.568  | 93.195 | 1.00 | 39.96 |
| ATOM | 1586 | CE2 | PHE | 383 | 24.517 | −6.762  | 94.942 | 1.00 | 39.80 |
| ATOM | 1587 | CZ  | PHE | 383 | 23.247 | −7.082  | 94.484 | 1.00 | 40.07 |
| ATOM | 1588 | C   | PHE | 383 | 27.876 | −6.775  | 89.887 | 1.00 | 31.86 |
| ATOM | 1589 | O   | PHE | 383 | 28.064 | −7.627  | 89.024 | 1.00 | 30.97 |
| ATOM | 1590 | N   | TYR | 384 | 28.779 | −5.870  | 90.233 | 1.00 | 31.42 |
| ATOM | 1591 | CA  | TYR | 384 | 30.102 | −5.818  | 89.646 | 1.00 | 32.51 |
| ATOM | 1592 | CB  | TYR | 384 | 30.197 | −4.673  | 88.643 | 1.00 | 33.51 |

TABLE 1-continued

The structural coordinates of an exemplary stabilized form of gp120 at atomic resolution

| ATOM | 1593 | CG  | TYR | 384 | 29.350 | −4.850  | 87.399  | 1.00 | 35.33 |
|------|------|-----|-----|-----|--------|---------|---------|------|-------|
| ATOM | 1594 | CD1 | TYR | 384 | 27.961 | −4.728  | 87.451  | 1.00 | 36.88 |
| ATOM | 1595 | CE1 | TYR | 384 | 27.177 | −4.891  | 86.311  | 1.00 | 36.38 |
| ATOM | 1596 | CD2 | TYR | 384 | 29.938 | −5.145  | 86.170  | 1.00 | 35.34 |
| ATOM | 1597 | CE2 | TYR | 384 | 29.165 | −5.311  | 85.023  | 1.00 | 36.36 |
| ATOM | 1598 | CZ  | TYR | 384 | 27.784 | −5.185  | 85.102  | 1.00 | 37.21 |
| ATOM | 1599 | OH  | TYR | 384 | 27.008 | −5.351  | 83.971  | 1.00 | 37.53 |
| ATOM | 1600 | C   | TYR | 384 | 31.033 | −5.558  | 90.815  | 1.00 | 33.55 |
| ATOM | 1601 | O   | TYR | 384 | 31.207 | −4.404  | 91.217  | 1.00 | 32.94 |
| ATOM | 1602 | N   | CYS | 385 | 31.619 | −6.631  | 91.356  | 1.00 | 34.77 |
| ATOM | 1603 | CA  | CYS | 385 | 32.509 | −6.549  | 92.525  | 1.00 | 34.65 |
| ATOM | 1604 | C   | CYS | 385 | 33.971 | −6.626  | 92.216  | 1.00 | 34.20 |
| ATOM | 1605 | O   | CYS | 385 | 34.433 | −7.558  | 91.565  | 1.00 | 35.22 |
| ATOM | 1606 | CB  | CYS | 385 | 32.217 | −7.658  | 93.521  | 1.00 | 34.87 |
| ATOM | 1607 | SG  | CYS | 385 | 30.526 | −7.663  | 94.168  | 1.00 | 40.52 |
| ATOM | 1608 | N   | ASN | 386 | 34.705 | −5.653  | 92.727  | 1.00 | 33.25 |
| ATOM | 1609 | CA  | ASN | 386 | 36.129 | −5.598  | 92.521  | 1.00 | 33.13 |
| ATOM | 1610 | CB  | ASN | 386 | 36.645 | −4.259  | 93.011  | 1.00 | 35.09 |
| ATOM | 1611 | CG  | ASN | 386 | 38.103 | −4.104  | 92.775  | 1.00 | 39.37 |
| ATOM | 1612 | OD1 | ASN | 386 | 38.880 | −4.983  | 93.117  | 1.00 | 41.53 |
| ATOM | 1613 | ND2 | ASN | 386 | 38.506 | −2.990  | 92.194  | 1.00 | 43.99 |
| ATOM | 1614 | C   | ASN | 386 | 36.802 | −6.744  | 93.280  | 1.00 | 32.07 |
| ATOM | 1615 | O   | ASN | 386 | 36.891 | −6.718  | 94.507  | 1.00 | 33.16 |
| ATOM | 1616 | N   | SER | 387 | 37.288 | −7.746  | 92.555  | 1.00 | 30.06 |
| ATOM | 1617 | CA  | SER | 387 | 37.922 | −8.895  | 93.196  | 1.00 | 29.26 |
| ATOM | 1618 | CB  | SER | 387 | 37.505 | −10.178 | 92.478  | 1.00 | 28.12 |
| ATOM | 1619 | OG  | SER | 387 | 37.730 | −10.093 | 91.087  | 1.00 | 26.31 |
| ATOM | 1620 | C   | SER | 387 | 39.443 | −8.867  | 93.337  | 1.00 | 29.50 |
| ATOM | 1621 | O   | SER | 387 | 40.063 | −9.889  | 93.624  | 1.00 | 29.39 |
| ATOM | 1622 | N   | THR | 388 | 40.045 | −7.702  | 93.159  | 1.00 | 29.97 |
| ATOM | 1623 | CA  | THR | 388 | 41.488 | −7.586  | 93.273  | 1.00 | 31.62 |
| ATOM | 1624 | CB  | THR | 388 | 41.929 | −6.116  | 93.190  | 1.00 | 32.80 |
| ATOM | 1625 | OG1 | THR | 388 | 41.734 | −5.630  | 91.849  | 1.00 | 31.68 |
| ATOM | 1626 | CG2 | THR | 388 | 43.392 | −5.980  | 93.590  | 1.00 | 31.85 |
| ATOM | 1627 | C   | THR | 388 | 42.038 | −8.194  | 94.561  | 1.00 | 33.05 |
| ATOM | 1628 | O   | THR | 388 | 43.100 | −8.816  | 94.553  | 1.00 | 33.91 |
| ATOM | 1629 | N   | GLN | 389 | 41.320 | −8.027  | 95.667  | 1.00 | 34.67 |
| ATOM | 1630 | CA  | GLN | 389 | 41.792 | −8.574  | 96.944  | 1.00 | 37.35 |
| ATOM | 1631 | CB  | GLN | 389 | 40.957 | −8.065  | 98.124  | 1.00 | 36.04 |
| ATOM | 1632 | CG  | GLN | 389 | 40.860 | −6.578  | 98.266  | 1.00 | 34.05 |
| ATOM | 1633 | CD  | GLN | 389 | 39.773 | −6.202  | 99.241  | 1.00 | 34.91 |
| ATOM | 1634 | OE1 | GLN | 389 | 39.964 | −6.271  | 100.451 | 1.00 | 37.19 |
| ATOM | 1635 | NE2 | GLN | 389 | 38.609 | −5.826  | 98.720  | 1.00 | 36.20 |
| ATOM | 1636 | C   | GLN | 389 | 41.779 | −10.101 | 97.011  | 1.00 | 38.08 |
| ATOM | 1637 | O   | GLN | 389 | 42.422 | −10.687 | 97.882  | 1.00 | 40.01 |
| ATOM | 1638 | N   | LEU | 390 | 41.042 | −10.752 | 96.124  | 1.00 | 37.43 |
| ATOM | 1639 | CA  | LEU | 390 | 40.994 | −12.199 | 96.175  | 1.00 | 38.01 |
| ATOM | 1640 | CB  | LEU | 390 | 39.663 | −12.699 | 95.613  | 1.00 | 37.92 |
| ATOM | 1641 | CG  | LEU | 390 | 38.396 | −12.318 | 96.392  | 1.00 | 37.01 |
| ATOM | 1642 | CD1 | LEU | 390 | 37.175 | −12.765 | 95.614  | 1.00 | 35.68 |
| ATOM | 1643 | CD2 | LEU | 390 | 38.399 | −12.959 | 97.764  | 1.00 | 35.67 |
| ATOM | 1644 | C   | LEU | 390 | 42.163 | −12.816 | 95.415  | 1.00 | 39.31 |
| ATOM | 1645 | O   | LEU | 390 | 42.692 | −13.863 | 95.801  | 1.00 | 40.54 |
| ATOM | 1646 | N   | PHE | 391 | 42.583 | −12.150 | 94.347  | 1.00 | 39.70 |
| ATOM | 1647 | CA  | PHE | 391 | 43.680 | −12.644 | 93.528  | 1.00 | 38.54 |
| ATOM | 1648 | CB  | PHE | 391 | 43.206 | −12.794 | 92.092  | 1.00 | 37.22 |
| ATOM | 1649 | CG  | PHE | 391 | 41.913 | −13.532 | 91.984  | 1.00 | 37.31 |
| ATOM | 1650 | CD1 | PHE | 391 | 40.707 | −12.871 | 92.177  | 1.00 | 38.01 |
| ATOM | 1651 | CD2 | PHE | 391 | 41.897 | −14.907 | 91.784  | 1.00 | 37.44 |
| ATOM | 1652 | CE1 | PHE | 391 | 39.507 | −13.565 | 92.179  | 1.00 | 37.83 |
| ATOM | 1653 | CE2 | PHE | 391 | 40.699 | −15.613 | 91.786  | 1.00 | 37.13 |
| ATOM | 1654 | CZ  | PHE | 391 | 39.501 | −14.939 | 91.986  | 1.00 | 38.34 |
| ATOM | 1655 | C   | PHE | 391 | 44.848 | −11.691 | 93.622  | 1.00 | 39.15 |
| ATOM | 1656 | O   | PHE | 391 | 45.093 | −10.874 | 92.724  | 1.00 | 37.81 |
| ATOM | 1657 | N   | ASN | 392 | 45.554 | −11.808 | 94.742  | 1.00 | 40.04 |
| ATOM | 1658 | CA  | ASN | 392 | 46.709 | −10.980 | 95.038  | 1.00 | 40.61 |
| ATOM | 1659 | CB  | ASN | 392 | 46.243 | −9.647  | 95.650  | 1.00 | 40.52 |
| ATOM | 1660 | CG  | ASN | 392 | 47.401 | −8.713  | 95.990  | 1.00 | 42.11 |
| ATOM | 1661 | OD1 | ASN | 392 | 48.388 | −8.643  | 95.255  | 1.00 | 42.90 |
| ATOM | 1662 | ND2 | ASN | 392 | 47.272 | −7.978  | 97.093  | 1.00 | 42.11 |
| ATOM | 1663 | C   | ASN | 392 | 47.615 | −11.736 | 96.006  | 1.00 | 40.17 |
| ATOM | 1664 | O   | ASN | 392 | 47.771 | −11.336 | 97.148  | 1.00 | 40.62 |
| ATOM | 1665 | N   | SER | 393 | 48.205 | −12.837 | 95.558  | 1.00 | 40.28 |
| ATOM | 1666 | CA  | SER | 393 | 49.085 | −13.598 | 96.436  | 1.00 | 41.43 |
| ATOM | 1667 | CB  | SER | 393 | 48.261 | −14.448 | 97.403  | 1.00 | 40.63 |
| ATOM | 1668 | OG  | SER | 393 | 47.328 | −15.262 | 96.718  | 1.00 | 40.80 |
| ATOM | 1669 | C   | SER | 393 | 50.077 | −14.479 | 95.687  | 1.00 | 42.79 |
| ATOM | 1670 | O   | SER | 393 | 49.819 | −14.908 | 94.556  | 1.00 | 42.31 |

TABLE 1-continued

The structural coordinates of an exemplary stabilized form of gp120 at atomic resolution

| ATOM | 1671 | N | THR | 394 | 51.212 | −14.737 | 96.333 | 1.00 | 43.79 |
|---|---|---|---|---|---|---|---|---|---|
| ATOM | 1672 | CA | THR | 394 | 52.277 | −15.551 | 95.756 | 1.00 | 45.04 |
| ATOM | 1673 | CB | THR | 394 | 53.574 | −14.737 | 95.642 | 1.00 | 45.96 |
| ATOM | 1674 | OG1 | THR | 394 | 53.333 | −13.573 | 94.833 | 1.00 | 46.10 |
| ATOM | 1675 | CG2 | THR | 394 | 54.688 | −15.584 | 95.026 | 1.00 | 45.27 |
| ATOM | 1676 | C | THR | 394 | 52.541 | −16.790 | 96.602 | 1.00 | 45.64 |
| ATOM | 1677 | O | THR | 394 | 52.906 | −16.684 | 97.769 | 1.00 | 44.76 |
| ATOM | 1678 | N | TRP | 395 | 52.378 | −17.964 | 95.996 | 1.00 | 47.09 |
| ATOM | 1679 | CA | TRP | 395 | 52.548 | −19.228 | 96.705 | 1.00 | 47.76 |
| ATOM | 1680 | CB | TRP | 395 | 51.288 | −20.068 | 96.527 | 1.00 | 41.92 |
| ATOM | 1681 | CG | TRP | 395 | 50.107 | −19.326 | 96.976 | 1.00 | 38.28 |
| ATOM | 1682 | CD2 | TRP | 395 | 49.405 | −19.506 | 98.205 | 1.00 | 36.22 |
| ATOM | 1683 | CE2 | TRP | 395 | 48.415 | −18.503 | 98.268 | 1.00 | 36.46 |
| ATOM | 1684 | CE3 | TRP | 395 | 49.514 | −20.414 | 99.258 | 1.00 | 33.85 |
| ATOM | 1685 | CD1 | TRP | 395 | 49.532 | −18.258 | 96.357 | 1.00 | 37.38 |
| ATOM | 1686 | NE1 | TRP | 395 | 48.517 | −17.754 | 97.126 | 1.00 | 36.41 |
| ATOM | 1687 | CZ2 | TRP | 395 | 47.539 | −18.387 | 99.348 | 1.00 | 34.01 |
| ATOM | 1688 | CZ3 | TRP | 395 | 48.647 | −20.297 | 100.324 | 1.00 | 33.66 |
| ATOM | 1689 | CH2 | TRP | 395 | 47.670 | −19.290 | 100.361 | 1.00 | 33.40 |
| ATOM | 1690 | C | TRP | 395 | 53.761 | −20.066 | 96.339 | 1.00 | 51.43 |
| ATOM | 1691 | O | TRP | 395 | 54.159 | −20.124 | 95.170 | 1.00 | 52.73 |
| ATOM | 1692 | N | PHE | 396 | 54.339 | −20.710 | 97.358 | 1.00 | 54.22 |
| ATOM | 1693 | CA | PHE | 396 | 55.491 | −21.589 | 97.190 | 1.00 | 56.04 |
| ATOM | 1694 | CB | PHE | 396 | 55.138 | −22.681 | 96.186 | 1.00 | 54.94 |
| ATOM | 1695 | CG | PHE | 396 | 53.790 | −23.305 | 96.422 | 1.00 | 55.63 |
| ATOM | 1696 | CD1 | PHE | 396 | 53.083 | −23.883 | 95.373 | 1.00 | 56.03 |
| ATOM | 1697 | CD2 | PHE | 396 | 53.226 | −23.325 | 97.699 | 1.00 | 56.08 |
| ATOM | 1698 | CE1 | PHE | 396 | 51.830 | −24.480 | 95.591 | 1.00 | 56.77 |
| ATOM | 1699 | CE2 | PHE | 396 | 51.974 | −23.917 | 97.930 | 1.00 | 56.41 |
| ATOM | 1700 | CZ | PHE | 396 | 51.275 | −24.495 | 96.872 | 1.00 | 56.06 |
| ATOM | 1701 | C | PHE | 396 | 56.708 | −20.813 | 96.713 | 1.00 | 58.81 |
| ATOM | 1702 | O | PHE | 396 | 57.523 | −21.322 | 95.938 | 1.00 | 59.35 |
| ATOM | 1703 | N | ASN | 397 | 56.815 | −19.570 | 97.172 | 1.00 | 61.45 |
| ATOM | 1704 | CA | ASN | 397 | 57.932 | −18.717 | 96.802 | 1.00 | 63.89 |
| ATOM | 1705 | CB | ASN | 397 | 57.462 | −17.262 | 96.713 | 1.00 | 65.82 |
| ATOM | 1706 | CG | ASN | 397 | 58.568 | −16.310 | 96.270 | 1.00 | 68.51 |
| ATOM | 1707 | OD1 | ASN | 397 | 58.333 | −15.112 | 96.075 | 1.00 | 69.99 |
| ATOM | 1708 | ND2 | ASN | 397 | 59.782 | −16.839 | 96.110 | 1.00 | 68.62 |
| ATOM | 1709 | C | ASN | 397 | 59.052 | −18.854 | 97.837 | 1.00 | 64.94 |
| ATOM | 1710 | O | ASN | 397 | 59.583 | −19.946 | 98.065 | 1.00 | 64.91 |
| ATOM | 1711 | N | GLY | 410 | 45.948 | −11.180 | 107.879 | 1.00 | 61.02 |
| ATOM | 1712 | CA | GLY | 410 | 45.413 | −9.847 | 107.656 | 1.00 | 62.50 |
| ATOM | 1713 | C | GLY | 410 | 44.155 | −9.569 | 108.466 | 1.00 | 62.44 |
| ATOM | 1714 | O | GLY | 410 | 44.097 | −9.849 | 109.668 | 1.00 | 63.35 |
| ATOM | 1715 | N | SER | 411 | 43.145 | −9.007 | 107.814 | 1.00 | 61.14 |
| ATOM | 1716 | CA | SER | 411 | 41.893 | −8.720 | 108.488 | 1.00 | 60.04 |
| ATOM | 1717 | CB | SER | 411 | 41.252 | −7.461 | 107.913 | 1.00 | 61.29 |
| ATOM | 1718 | OG | SER | 411 | 39.982 | −7.232 | 108.499 | 1.00 | 62.93 |
| ATOM | 1719 | C | SER | 411 | 40.959 | −9.902 | 108.295 | 1.00 | 59.15 |
| ATOM | 1720 | O | SER | 411 | 40.857 | −10.448 | 107.197 | 1.00 | 59.05 |
| ATOM | 1721 | N | ASP | 412 | 40.278 | −10.285 | 109.369 | 1.00 | 57.82 |
| ATOM | 1722 | CA | ASP | 412 | 39.338 | −11.406 | 109.376 | 1.00 | 56.24 |
| ATOM | 1723 | CB | ASP | 412 | 38.360 | −11.213 | 110.532 | 1.00 | 59.37 |
| ATOM | 1724 | CG | ASP | 412 | 37.032 | −11.908 | 110.298 | 1.00 | 63.07 |
| ATOM | 1725 | OD1 | ASP | 412 | 37.031 | −13.136 | 110.041 | 1.00 | 64.07 |
| ATOM | 1726 | OD2 | ASP | 412 | 35.990 | −11.214 | 110.371 | 1.00 | 65.25 |
| ATOM | 1727 | C | ASP | 412 | 38.556 | −11.681 | 108.082 | 1.00 | 53.55 |
| ATOM | 1728 | O | ASP | 412 | 38.694 | −12.746 | 107.475 | 1.00 | 52.85 |
| ATOM | 1729 | N | THR | 413 | 37.715 | −10.735 | 107.680 | 1.00 | 50.45 |
| ATOM | 1730 | CA | THR | 413 | 36.918 | −10.892 | 106.472 | 1.00 | 46.99 |
| ATOM | 1731 | CB | THR | 413 | 35.415 | −10.527 | 106.742 | 1.00 | 46.65 |
| ATOM | 1732 | OG1 | THR | 413 | 34.929 | −9.666 | 105.703 | 1.00 | 46.90 |
| ATOM | 1733 | CG2 | THR | 413 | 35.247 | −9.813 | 108.078 | 1.00 | 44.53 |
| ATOM | 1734 | C | THR | 413 | 37.456 | −10.014 | 105.337 | 1.00 | 44.78 |
| ATOM | 1735 | O | THR | 413 | 38.021 | −8.954 | 105.580 | 1.00 | 45.19 |
| ATOM | 1736 | N | ILE | 414 | 37.311 | −10.471 | 104.099 | 1.00 | 41.90 |
| ATOM | 1737 | CA | ILE | 414 | 37.744 | −9.684 | 102.949 | 1.00 | 39.73 |
| ATOM | 1738 | CB | ILE | 414 | 38.299 | −10.564 | 101.813 | 1.00 | 38.13 |
| ATOM | 1739 | CG2 | ILE | 414 | 38.798 | −9.697 | 100.690 | 1.00 | 36.56 |
| ATOM | 1740 | CG1 | ILE | 414 | 39.464 | −11.408 | 102.316 | 1.00 | 37.94 |
| ATOM | 1741 | CD1 | ILE | 414 | 39.966 | −12.403 | 101.300 | 1.00 | 34.67 |
| ATOM | 1742 | C | ILE | 414 | 36.474 | −9.007 | 102.444 | 1.00 | 39.45 |
| ATOM | 1743 | O | ILE | 414 | 35.541 | −9.682 | 102.008 | 1.00 | 38.16 |
| ATOM | 1744 | N | THR | 415 | 36.420 | −7.683 | 102.526 | 1.00 | 39.33 |
| ATOM | 1745 | CA | THR | 415 | 35.237 | −6.956 | 102.071 | 1.00 | 39.02 |
| ATOM | 1746 | CB | THR | 415 | 34.868 | −5.782 | 103.045 | 1.00 | 40.55 |
| ATOM | 1747 | OG1 | THR | 415 | 34.451 | −6.313 | 104.313 | 1.00 | 41.85 |
| ATOM | 1748 | CG2 | THR | 415 | 33.731 | −4.942 | 102.483 | 1.00 | 39.85 |

TABLE 1-continued

The structural coordinates of an exemplary stabilized form of gp120 at atomic resolution

| ATOM | 1749 | C   | THR | 415 | 35.487 | −6.410 | 100.671 | 1.00 | 37.52 |
|------|------|-----|-----|-----|--------|--------|---------|------|-------|
| ATOM | 1750 | O   | THR | 415 | 36.386 | −5.592 | 100.458 | 1.00 | 36.96 |
| ATOM | 1751 | N   | LEU | 416 | 34.683 | −6.887 | 99.722  | 1.00 | 35.70 |
| ATOM | 1752 | CA  | LEU | 416 | 34.772 | −6.480 | 98.323  | 1.00 | 33.93 |
| ATOM | 1753 | CB  | LEU | 416 | 34.459 | −7.669 | 97.422  | 1.00 | 35.45 |
| ATOM | 1754 | CG  | LEU | 416 | 35.609 | −8.553 | 96.946  | 1.00 | 36.03 |
| ATOM | 1755 | CD1 | LEU | 416 | 36.708 | −8.616 | 98.004  | 1.00 | 35.17 |
| ATOM | 1756 | CD2 | LEU | 416 | 35.046 | −9.933 | 96.610  | 1.00 | 35.12 |
| ATOM | 1757 | C   | LEU | 416 | 33.831 | −5.340 | 97.949  | 1.00 | 31.99 |
| ATOM | 1758 | O   | LEU | 416 | 32.631 | −5.392 | 98.222  | 1.00 | 31.87 |
| ATOM | 1759 | N   | PRO | 417 | 34.366 | −4.285 | 97.319  | 1.00 | 29.92 |
| ATOM | 1760 | CD  | PRO | 417 | 35.782 | −3.965 | 97.067  | 1.00 | 27.19 |
| ATOM | 1761 | CA  | PRO | 417 | 33.507 | −3.169 | 96.929  | 1.00 | 28.26 |
| ATOM | 1762 | CB  | PRO | 417 | 34.509 | −2.052 | 96.705  | 1.00 | 24.49 |
| ATOM | 1763 | CG  | PRO | 417 | 35.678 | −2.776 | 96.162  | 1.00 | 23.69 |
| ATOM | 1764 | C   | PRO | 417 | 32.747 | −3.548 | 95.654  | 1.00 | 28.94 |
| ATOM | 1765 | O   | PRO | 417 | 33.305 | −4.215 | 94.781  | 1.00 | 29.04 |
| ATOM | 1766 | N   | CYS | 418 | 31.476 | −3.166 | 95.553  | 1.00 | 30.16 |
| ATOM | 1767 | CA  | CYS | 418 | 30.702 | −3.472 | 94.348  | 1.00 | 33.10 |
| ATOM | 1768 | C   | CYS | 418 | 29.782 | −2.338 | 93.978  | 1.00 | 32.71 |
| ATOM | 1769 | O   | CYS | 418 | 29.610 | −1.387 | 94.731  | 1.00 | 33.13 |
| ATOM | 1770 | CB  | CYS | 418 | 29.808 | −4.704 | 94.510  | 1.00 | 35.70 |
| ATOM | 1771 | SG  | CYS | 418 | 30.459 | −6.095 | 95.454  | 1.00 | 40.35 |
| ATOM | 1772 | N   | ARG | 419 | 29.167 | −2.479 | 92.812  | 1.00 | 33.12 |
| ATOM | 1773 | CA  | ARG | 419 | 28.226 | −1.499 | 92.315  | 1.00 | 33.48 |
| ATOM | 1774 | CB  | ARG | 419 | 28.937 | −0.474 | 91.418  | 1.00 | 35.57 |
| ATOM | 1775 | CG  | ARG | 419 | 28.028 | 0.673  | 91.009  | 1.00 | 42.11 |
| ATOM | 1776 | CD  | ARG | 419 | 28.395 | 1.296  | 89.654  | 1.00 | 47.71 |
| ATOM | 1777 | NE  | ARG | 419 | 29.270 | 2.464  | 89.754  | 1.00 | 50.54 |
| ATOM | 1778 | CZ  | ARG | 419 | 30.576 | 2.412  | 90.009  | 1.00 | 50.62 |
| ATOM | 1779 | NH1 | ARG | 419 | 31.178 | 1.240  | 90.189  | 1.00 | 50.07 |
| ATOM | 1780 | NH2 | ARG | 419 | 31.279 | 3.538  | 90.093  | 1.00 | 49.54 |
| ATOM | 1781 | C   | ARG | 419 | 27.163 | −2.223 | 91.501  | 1.00 | 31.21 |
| ATOM | 1782 | O   | ARG | 419 | 27.453 | −3.223 | 90.848  | 1.00 | 28.57 |
| ATOM | 1783 | N   | ILE | 420 | 25.929 | −1.736 | 91.567  | 1.00 | 30.97 |
| ATOM | 1784 | CA  | ILE | 420 | 24.845 | −2.301 | 90.759  | 1.00 | 31.92 |
| ATOM | 1785 | CB  | ILE | 420 | 23.459 | −2.255 | 91.482  | 1.00 | 31.58 |
| ATOM | 1786 | CG2 | ILE | 420 | 22.341 | −2.527 | 90.491  | 1.00 | 29.56 |
| ATOM | 1787 | CG1 | ILE | 420 | 23.396 | −3.308 | 92.583  | 1.00 | 32.48 |
| ATOM | 1788 | CD1 | ILE | 420 | 24.525 | −3.201 | 93.579  | 1.00 | 35.47 |
| ATOM | 1789 | C   | ILE | 420 | 24.793 | −1.378 | 89.542  | 1.00 | 31.56 |
| ATOM | 1790 | O   | ILE | 420 | 24.866 | −0.161 | 89.687  | 1.00 | 31.84 |
| ATOM | 1791 | N   | LYS | 421 | 24.687 | −1.938 | 88.349  | 1.00 | 30.80 |
| ATOM | 1792 | CA  | LYS | 421 | 24.626 | −1.104 | 87.163  | 1.00 | 31.04 |
| ATOM | 1793 | CB  | LYS | 421 | 25.808 | −1.418 | 86.259  | 1.00 | 32.69 |
| ATOM | 1794 | CG  | LYS | 421 | 27.164 | −1.194 | 86.883  | 1.00 | 32.84 |
| ATOM | 1795 | CD  | LYS | 421 | 28.220 | −1.316 | 85.790  | 1.00 | 33.11 |
| ATOM | 1796 | CE  | LYS | 421 | 29.583 | −0.872 | 86.271  | 1.00 | 32.74 |
| ATOM | 1797 | NZ  | LYS | 421 | 30.553 | −0.859 | 85.147  | 1.00 | 32.81 |
| ATOM | 1798 | C   | LYS | 421 | 23.320 | −1.330 | 86.401  | 1.00 | 30.54 |
| ATOM | 1799 | O   | LYS | 421 | 22.720 | −2.408 | 86.503  | 1.00 | 30.70 |
| ATOM | 1800 | N   | GLN | 422 | 22.879 | −0.319 | 85.651  | 1.00 | 29.64 |
| ATOM | 1801 | CA  | GLN | 422 | 21.652 | −0.428 | 84.859  | 1.00 | 30.52 |
| ATOM | 1802 | CB  | GLN | 422 | 20.803 | 0.838  | 84.969  | 1.00 | 30.67 |
| ATOM | 1803 | CG  | GLN | 422 | 20.065 | 0.997  | 86.279  | 1.00 | 32.13 |
| ATOM | 1804 | CD  | GLN | 422 | 20.998 | 1.157  | 87.466  | 1.00 | 33.77 |
| ATOM | 1805 | OE1 | GLN | 422 | 21.823 | 2.081  | 87.514  | 1.00 | 30.92 |
| ATOM | 1806 | NE2 | GLN | 422 | 20.869 | 0.255  | 88.438  | 1.00 | 34.85 |
| ATOM | 1807 | C   | GLN | 422 | 21.989 | −0.669 | 83.395  | 1.00 | 31.34 |
| ATOM | 1808 | O   | GLN | 422 | 21.162 | −1.159 | 82.630  | 1.00 | 31.50 |
| ATOM | 1809 | N   | ILE | 423 | 23.213 | −0.321 | 83.017  | 1.00 | 32.09 |
| ATOM | 1810 | CA  | ILE | 423 | 23.681 | −0.501 | 81.650  | 1.00 | 31.47 |
| ATOM | 1811 | CB  | ILE | 423 | 24.220 | 0.825  | 81.125  | 1.00 | 30.44 |
| ATOM | 1812 | CG2 | ILE | 423 | 24.767 | 0.662  | 79.725  | 1.00 | 29.43 |
| ATOM | 1813 | CG1 | ILE | 423 | 23.084 | 1.842  | 81.151  | 1.00 | 29.90 |
| ATOM | 1814 | CD1 | ILE | 423 | 23.454 | 3.193  | 80.628  | 1.00 | 30.47 |
| ATOM | 1815 | C   | ILE | 423 | 24.727 | −1.625 | 81.564  | 1.00 | 32.00 |
| ATOM | 1816 | O   | ILE | 423 | 25.905 | −1.453 | 81.856  | 1.00 | 33.10 |
| ATOM | 1817 | N   | ILE | 424 | 24.241 | −2.785 | 81.149  | 1.00 | 33.21 |
| ATOM | 1818 | CA  | ILE | 424 | 24.995 | −4.022 | 81.017  | 1.00 | 33.92 |
| ATOM | 1819 | CB  | ILE | 424 | 24.055 | −5.212 | 81.346  | 1.00 | 34.97 |
| ATOM | 1820 | CG2 | ILE | 424 | 24.828 | −6.487 | 81.526  | 1.00 | 35.83 |
| ATOM | 1821 | CG1 | ILE | 424 | 23.264 | −4.900 | 82.605  | 1.00 | 37.56 |
| ATOM | 1822 | CD1 | ILE | 424 | 24.141 | −4.483 | 83.764  | 1.00 | 40.47 |
| ATOM | 1823 | C   | ILE | 424 | 25.529 | −4.276 | 79.609  | 1.00 | 33.77 |
| ATOM | 1824 | O   | ILE | 424 | 25.094 | −3.670 | 78.644  | 1.00 | 34.71 |
| ATOM | 1825 | N   | ASN | 425 | 26.481 | −5.194 | 79.515  | 1.00 | 34.13 |
| ATOM | 1826 | CA  | ASN | 425 | 27.033 | −5.649 | 78.244  | 1.00 | 33.45 |

TABLE 1-continued

The structural coordinates of an exemplary stabilized form of gp120 at atomic resolution

| ATOM | 1827 | CB  | ASN | 425 | 28.559 | −5.655  | 78.279 | 1.00 | 33.20 |
|------|------|-----|-----|-----|--------|---------|--------|------|-------|
| ATOM | 1828 | CG  | ASN | 425 | 29.174 | −4.556  | 77.438 | 1.00 | 32.66 |
| ATOM | 1829 | OD1 | ASN | 425 | 28.619 | −4.149  | 76.414 | 1.00 | 30.45 |
| ATOM | 1830 | ND2 | ASN | 425 | 30.346 | −4.087  | 77.855 | 1.00 | 32.53 |
| ATOM | 1831 | C   | ASN | 425 | 26.536 | −7.081  | 78.347 | 1.00 | 33.79 |
| ATOM | 1832 | O   | ASN | 425 | 27.053 | −7.826  | 79.167 | 1.00 | 33.77 |
| ATOM | 1833 | N   | MET | 426 | 25.539 | −7.471  | 77.554 | 1.00 | 35.05 |
| ATOM | 1834 | CA  | MET | 426 | 24.974 | −8.827  | 77.653 | 1.00 | 36.48 |
| ATOM | 1835 | CB  | MET | 426 | 23.788 | −8.980  | 76.698 | 1.00 | 37.46 |
| ATOM | 1836 | CG  | MET | 426 | 22.690 | −7.954  | 76.921 | 1.00 | 42.17 |
| ATOM | 1837 | SD  | MET | 426 | 21.033 | −8.496  | 76.443 | 1.00 | 47.19 |
| ATOM | 1838 | CE  | MET | 426 | 21.110 | −8.248  | 74.701 | 1.00 | 47.57 |
| ATOM | 1839 | C   | MET | 426 | 25.928 | −10.006 | 77.447 | 1.00 | 37.83 |
| ATOM | 1840 | O   | MET | 426 | 27.017 | −9.867  | 76.885 | 1.00 | 37.54 |
| ATOM | 1841 | N   | TRP | 427 | 25.506 | −11.176 | 77.916 | 1.00 | 39.73 |
| ATOM | 1842 | CA  | TRP | 427 | 26.304 | −12.386 | 77.770 | 1.00 | 41.17 |
| ATOM | 1843 | CB  | TRP | 427 | 26.323 | −13.179 | 79.085 | 1.00 | 42.99 |
| ATOM | 1844 | CG  | TRP | 427 | 24.959 | −13.556 | 79.621 | 1.00 | 45.82 |
| ATOM | 1845 | CD2 | TRP | 427 | 24.303 | −14.822 | 79.485 | 1.00 | 46.80 |
| ATOM | 1846 | CE2 | TRP | 427 | 23.034 | −14.709 | 80.100 | 1.00 | 47.00 |
| ATOM | 1847 | CE3 | TRP | 427 | 24.662 | −16.044 | 78.899 | 1.00 | 47.97 |
| ATOM | 1848 | CD1 | TRP | 427 | 24.087 | −12.748 | 80.300 | 1.00 | 47.03 |
| ATOM | 1849 | NE1 | TRP | 427 | 22.929 | −13.434 | 80.591 | 1.00 | 47.49 |
| ATOM | 1850 | CZ2 | TRP | 427 | 22.124 | −15.763 | 80.143 | 1.00 | 47.71 |
| ATOM | 1851 | CZ3 | TRP | 427 | 23.756 | −17.097 | 78.944 | 1.00 | 48.88 |
| ATOM | 1852 | CH2 | TRP | 427 | 22.500 | −16.947 | 79.562 | 1.00 | 49.07 |
| ATOM | 1853 | C   | TRP | 427 | 25.812 | −13.284 | 76.632 | 1.00 | 41.19 |
| ATOM | 1854 | O   | TRP | 427 | 26.607 | −13.964 | 76.000 | 1.00 | 41.60 |
| ATOM | 1855 | N   | CYS | 428 | 24.509 | −13.272 | 76.363 | 1.00 | 42.00 |
| ATOM | 1856 | CA  | CYS | 428 | 23.922 | −14.101 | 75.308 | 1.00 | 44.36 |
| ATOM | 1857 | C   | CYS | 428 | 24.410 | −13.749 | 73.917 | 1.00 | 44.00 |
| ATOM | 1858 | O   | CYS | 428 | 24.887 | −14.616 | 73.176 | 1.00 | 44.48 |
| ATOM | 1859 | CB  | CYS | 428 | 22.394 | −14.023 | 75.381 | 1.00 | 47.62 |
| ATOM | 1860 | SG  | CYS | 428 | 21.874 | −14.854 | 76.914 | 1.00 | 57.16 |
| ATOM | 1861 | N   | LYS | 429 | 24.290 | −12.479 | 73.557 | 1.00 | 43.21 |
| ATOM | 1862 | CA  | LYS | 429 | 24.750 | −12.015 | 72.263 | 1.00 | 41.60 |
| ATOM | 1863 | CB  | LYS | 429 | 23.569 | −11.882 | 71.307 | 1.00 | 42.35 |
| ATOM | 1864 | CG  | LYS | 429 | 22.384 | −11.156 | 71.883 | 1.00 | 43.72 |
| ATOM | 1865 | CD  | LYS | 429 | 21.248 | −11.148 | 70.901 | 1.00 | 45.78 |
| ATOM | 1866 | CE  | LYS | 429 | 20.053 | −10.418 | 71.475 | 1.00 | 47.56 |
| ATOM | 1867 | NZ  | LYS | 429 | 18.901 | −10.405 | 70.517 | 1.00 | 50.92 |
| ATOM | 1868 | C   | LYS | 429 | 25.423 | −10.673 | 72.495 | 1.00 | 40.41 |
| ATOM | 1869 | O   | LYS | 429 | 25.256 | −10.073 | 73.553 | 1.00 | 40.49 |
| ATOM | 1870 | N   | VAL | 430 | 26.193 | −10.213 | 71.521 | 1.00 | 39.52 |
| ATOM | 1871 | CA  | VAL | 430 | 26.879 | −8.944  | 71.645 | 1.00 | 39.11 |
| ATOM | 1872 | CB  | VAL | 430 | 27.937 | −8.791  | 70.532 | 1.00 | 37.84 |
| ATOM | 1873 | CG1 | VAL | 430 | 28.489 | −7.380  | 70.507 | 1.00 | 39.67 |
| ATOM | 1874 | CG2 | VAL | 430 | 29.073 | −9.761  | 70.743 | 1.00 | 35.62 |
| ATOM | 1875 | C   | VAL | 430 | 25.914 | −7.764  | 71.573 | 1.00 | 40.33 |
| ATOM | 1876 | O   | VAL | 430 | 25.783 | −7.136  | 70.539 | 1.00 | 42.24 |
| ATOM | 1877 | N   | CYS | 431 | 25.211 | −7.470  | 72.657 | 1.00 | 41.16 |
| ATOM | 1878 | CA  | CYS | 431 | 24.291 | −6.326  | 72.682 | 1.00 | 43.40 |
| ATOM | 1879 | C   | CYS | 431 | 24.499 | −5.530  | 73.970 | 1.00 | 42.17 |
| ATOM | 1880 | O   | CYS | 431 | 25.000 | −6.062  | 74.964 | 1.00 | 43.09 |
| ATOM | 1881 | CB  | CYS | 431 | 22.835 | −6.780  | 72.668 | 1.00 | 48.10 |
| ATOM | 1882 | SG  | CYS | 431 | 22.257 | −7.836  | 71.299 | 1.00 | 60.95 |
| ATOM | 1883 | N   | LYS | 432 | 24.119 | −4.257  | 73.960 | 1.00 | 38.87 |
| ATOM | 1884 | CA  | LYS | 432 | 24.226 | −3.454  | 75.164 | 1.00 | 36.15 |
| ATOM | 1885 | CB  | LYS | 432 | 24.860 | −2.104  | 74.846 | 1.00 | 35.67 |
| ATOM | 1886 | CG  | LYS | 432 | 25.975 | −1.723  | 75.807 | 1.00 | 37.19 |
| ATOM | 1887 | CD  | LYS | 432 | 26.857 | −0.647  | 75.192 | 1.00 | 39.70 |
| ATOM | 1888 | CE  | LYS | 432 | 28.075 | −0.335  | 76.058 | 1.00 | 42.82 |
| ATOM | 1889 | NZ  | LYS | 432 | 28.992 | −1.509  | 76.255 | 1.00 | 42.87 |
| ATOM | 1890 | C   | LYS | 432 | 22.794 | −3.297  | 75.680 | 1.00 | 35.02 |
| ATOM | 1891 | O   | LYS | 432 | 21.888 | −3.024  | 74.909 | 1.00 | 35.60 |
| ATOM | 1892 | N   | ALA | 433 | 22.574 | −3.497  | 76.972 | 1.00 | 33.36 |
| ATOM | 1893 | CA  | ALA | 433 | 21.226 | −3.385  | 77.500 | 1.00 | 33.09 |
| ATOM | 1894 | CB  | ALA | 433 | 20.714 | −4.753  | 77.881 | 1.00 | 33.61 |
| ATOM | 1895 | C   | ALA | 433 | 21.156 | −2.460  | 78.696 | 1.00 | 34.02 |
| ATOM | 1896 | O   | ALA | 433 | 22.129 | −2.309  | 79.420 | 1.00 | 35.31 |
| ATOM | 1897 | N   | MET | 434 | 20.006 | −1.830  | 78.908 | 1.00 | 34.39 |
| ATOM | 1898 | CA  | MET | 434 | 19.853 | −0.927  | 80.043 | 1.00 | 34.19 |
| ATOM | 1899 | CB  | MET | 434 | 19.688 | 0.522   | 79.577 | 1.00 | 34.29 |
| ATOM | 1900 | CG  | MET | 434 | 19.537 | 1.519   | 80.722 | 1.00 | 35.19 |
| ATOM | 1901 | SD  | MET | 434 | 18.772 | 3.088   | 80.230 | 1.00 | 38.57 |
| ATOM | 1902 | CE  | MET | 434 | 17.017 | 2.778   | 80.598 | 1.00 | 37.43 |
| ATOM | 1903 | C   | MET | 434 | 18.626 | −1.328  | 80.841 | 1.00 | 34.05 |
| ATOM | 1904 | O   | MET | 434 | 17.522 | −1.387  | 80.307 | 1.00 | 35.74 |

TABLE 1-continued

The structural coordinates of an exemplary stabilized form of gp120 at atomic resolution

| ATOM | 1905 | N | TYR | 435 | 18.817 | −1.602 | 82.123 | 1.00 | 32.51 |
|---|---|---|---|---|---|---|---|---|---|
| ATOM | 1906 | CA | TYR | 435 | 17.709 | −1.984 | 82.973 | 1.00 | 30.96 |
| ATOM | 1907 | CB | TYR | 435 | 18.106 | −3.184 | 83.822 | 1.00 | 29.29 |
| ATOM | 1908 | CG | TYR | 435 | 18.339 | −4.417 | 82.992 | 1.00 | 25.84 |
| ATOM | 1909 | CD1 | TYR | 435 | 19.560 | −4.636 | 82.365 | 1.00 | 25.45 |
| ATOM | 1910 | CE1 | TYR | 435 | 19.745 | −5.711 | 81.524 | 1.00 | 24.61 |
| ATOM | 1911 | CD2 | TYR | 435 | 17.311 | −5.314 | 82.760 | 1.00 | 23.29 |
| ATOM | 1912 | CE2 | TYR | 435 | 17.482 | −6.382 | 81.924 | 1.00 | 24.52 |
| ATOM | 1913 | CZ | TYR | 435 | 18.699 | −6.581 | 81.305 | 1.00 | 24.68 |
| ATOM | 1914 | OH | TYR | 435 | 18.847 | −7.648 | 80.450 | 1.00 | 26.95 |
| ATOM | 1915 | C | TYR | 435 | 17.313 | −0.828 | 83.859 | 1.00 | 32.33 |
| ATOM | 1916 | O | TYR | 435 | 18.001 | 0.195 | 83.892 | 1.00 | 33.56 |
| ATOM | 1917 | N | ALA | 436 | 16.203 | −0.984 | 84.576 | 1.00 | 32.62 |
| ATOM | 1918 | CA | ALA | 436 | 15.736 | 0.067 | 85.473 | 1.00 | 33.64 |
| ATOM | 1919 | CB | ALA | 436 | 14.236 | −0.064 | 85.698 | 1.00 | 31.13 |
| ATOM | 1920 | C | ALA | 436 | 16.494 | −0.003 | 86.813 | 1.00 | 35.55 |
| ATOM | 1921 | O | ALA | 436 | 17.025 | −1.058 | 87.199 | 1.00 | 36.85 |
| ATOM | 1922 | N | PRO | 437 | 16.580 | 1.132 | 87.527 | 1.00 | 35.03 |
| ATOM | 1923 | CD | PRO | 437 | 16.171 | 2.473 | 87.084 | 1.00 | 34.29 |
| ATOM | 1924 | CA | PRO | 437 | 17.270 | 1.198 | 88.817 | 1.00 | 34.44 |
| ATOM | 1925 | CB | PRO | 437 | 17.150 | 2.665 | 89.182 | 1.00 | 35.20 |
| ATOM | 1926 | CG | PRO | 437 | 17.130 | 3.339 | 87.833 | 1.00 | 35.19 |
| ATOM | 1927 | C | PRO | 437 | 16.572 | 0.287 | 89.825 | 1.00 | 35.06 |
| ATOM | 1928 | O | PRO | 437 | 15.471 | −0.200 | 89.562 | 1.00 | 36.23 |
| ATOM | 1929 | N | PRO | 438 | 17.188 | 0.051 | 90.994 | 1.00 | 33.79 |
| ATOM | 1930 | CD | PRO | 438 | 18.576 | 0.364 | 91.356 | 1.00 | 33.35 |
| ATOM | 1931 | CA | PRO | 438 | 16.587 | −0.820 | 92.008 | 1.00 | 34.09 |
| ATOM | 1932 | CB | PRO | 438 | 17.729 | −1.028 | 92.994 | 1.00 | 33.97 |
| ATOM | 1933 | CG | PRO | 438 | 18.947 | −0.849 | 92.167 | 1.00 | 33.01 |
| ATOM | 1934 | C | PRO | 438 | 15.343 | −0.263 | 92.694 | 1.00 | 35.40 |
| ATOM | 1935 | O | PRO | 438 | 15.116 | 0.945 | 92.706 | 1.00 | 35.71 |
| ATOM | 1936 | N | ILE | 439 | 14.524 | −1.151 | 93.253 | 1.00 | 36.30 |
| ATOM | 1937 | CA | ILE | 439 | 13.333 | −0.707 | 93.962 | 1.00 | 36.39 |
| ATOM | 1938 | CB | ILE | 439 | 12.008 | −1.142 | 93.261 | 1.00 | 34.37 |
| ATOM | 1939 | CG2 | ILE | 439 | 12.003 | −0.699 | 91.836 | 1.00 | 34.23 |
| ATOM | 1940 | CG1 | ILE | 439 | 11.845 | −2.653 | 93.288 | 1.00 | 35.39 |
| ATOM | 1941 | CD1 | ILE | 439 | 10.469 | −3.098 | 92.843 | 1.00 | 34.29 |
| ATOM | 1942 | C | ILE | 439 | 13.367 | −1.242 | 95.393 | 1.00 | 37.68 |
| ATOM | 1943 | O | ILE | 439 | 12.507 | −0.911 | 96.204 | 1.00 | 39.13 |
| ATOM | 1944 | N | SER | 440 | 14.364 | −2.062 | 95.705 | 1.00 | 37.37 |
| ATOM | 1945 | CA | SER | 440 | 14.491 | −2.584 | 97.057 | 1.00 | 39.32 |
| ATOM | 1946 | CB | SER | 440 | 14.604 | −4.104 | 97.054 | 1.00 | 40.44 |
| ATOM | 1947 | OG | SER | 440 | 14.933 | −4.568 | 98.362 | 1.00 | 40.66 |
| ATOM | 1948 | C | SER | 440 | 15.707 | −2.011 | 97.774 | 1.00 | 40.33 |
| ATOM | 1949 | O | SER | 440 | 16.679 | −1.597 | 97.135 | 1.00 | 41.36 |
| ATOM | 1950 | N | GLY | 441 | 15.646 | −1.994 | 99.102 | 1.00 | 40.54 |
| ATOM | 1951 | CA | GLY | 441 | 16.752 | −1.482 | 99.890 | 1.00 | 42.17 |
| ATOM | 1952 | C | GLY | 441 | 17.425 | −2.604 | 100.659 | 1.00 | 43.06 |
| ATOM | 1953 | O | GLY | 441 | 18.367 | −2.392 | 101.437 | 1.00 | 42.78 |
| ATOM | 1954 | N | GLN | 442 | 16.920 | −3.811 | 100.439 | 1.00 | 43.64 |
| ATOM | 1955 | CA | GLN | 442 | 17.445 | −4.997 | 101.085 | 1.00 | 44.67 |
| ATOM | 1956 | CB | GLN | 442 | 16.475 | −5.475 | 102.175 | 1.00 | 45.38 |
| ATOM | 1957 | CG | GLN | 442 | 16.864 | −5.030 | 103.587 | 1.00 | 47.90 |
| ATOM | 1958 | CD | GLN | 442 | 15.750 | −5.219 | 104.621 | 1.00 | 49.44 |
| ATOM | 1959 | OE1 | GLN | 442 | 14.751 | −4.495 | 104.599 | 1.00 | 50.66 |
| ATOM | 1960 | NE2 | GLN | 442 | 15.921 | −6.190 | 105.530 | 1.00 | 47.39 |
| ATOM | 1961 | C | GLN | 442 | 17.679 | −6.080 | 100.035 | 1.00 | 44.84 |
| ATOM | 1962 | O | GLN | 442 | 16.909 | −7.032 | 99.904 | 1.00 | 44.57 |
| ATOM | 1963 | N | ILE | 443 | 18.755 | −5.908 | 99.278 | 1.00 | 45.49 |
| ATOM | 1964 | CA | ILE | 443 | 19.132 | −6.851 | 98.236 | 1.00 | 46.47 |
| ATOM | 1965 | CB | ILE | 443 | 19.492 | −6.092 | 96.941 | 1.00 | 45.56 |
| ATOM | 1966 | CG2 | ILE | 443 | 20.064 | −7.039 | 95.908 | 1.00 | 44.09 |
| ATOM | 1967 | CG1 | ILE | 443 | 18.238 | −5.392 | 96.411 | 1.00 | 45.07 |
| ATOM | 1968 | CD1 | ILE | 443 | 18.433 | −4.604 | 95.153 | 1.00 | 44.19 |
| ATOM | 1969 | C | ILE | 443 | 20.328 | −7.651 | 98.744 | 1.00 | 47.21 |
| ATOM | 1970 | O | ILE | 443 | 21.449 | −7.142 | 98.782 | 1.00 | 47.84 |
| ATOM | 1971 | N | ARG | 444 | 20.087 | −8.899 | 99.135 | 1.00 | 47.05 |
| ATOM | 1972 | CA | ARG | 444 | 21.150 | −9.732 | 99.681 | 1.00 | 48.36 |
| ATOM | 1973 | CB | ARG | 444 | 20.856 | −10.036 | 101.152 | 1.00 | 50.00 |
| ATOM | 1974 | CG | ARG | 444 | 20.436 | −8.837 | 101.994 | 1.00 | 52.86 |
| ATOM | 1975 | CD | ARG | 444 | 21.439 | −8.535 | 103.105 | 1.00 | 55.04 |
| ATOM | 1976 | NE | ARG | 444 | 20.951 | −7.500 | 104.017 | 1.00 | 59.88 |
| ATOM | 1977 | CZ | ARG | 444 | 20.629 | −6.255 | 103.659 | 1.00 | 61.86 |
| ATOM | 1978 | NH1 | ARG | 444 | 20.193 | −5.391 | 104.570 | 1.00 | 62.57 |
| ATOM | 1979 | NH2 | ARG | 444 | 20.741 | −5.862 | 102.395 | 1.00 | 62.40 |
| ATOM | 1980 | C | ARG | 444 | 21.361 | −11.052 | 98.948 | 1.00 | 48.73 |
| ATOM | 1981 | O | ARG | 444 | 20.405 | −11.671 | 98.481 | 1.00 | 49.67 |
| ATOM | 1982 | N | CYS | 445 | 22.619 | −11.479 | 98.849 | 1.00 | 48.63 |

TABLE 1-continued

The structural coordinates of an exemplary stabilized form of gp120 at atomic resolution

| ATOM | 1983 | CA  | CYS | 445 | 22.956 | −12.749 | 98.212  | 1.00 | 47.62 |
|------|------|-----|-----|-----|--------|---------|---------|------|-------|
| ATOM | 1984 | C   | CYS | 445 | 24.029 | −13.502 | 98.946  | 1.00 | 45.78 |
| ATOM | 1985 | O   | CYS | 445 | 25.207 | −13.129 | 98.931  | 1.00 | 45.76 |
| ATOM | 1986 | CB  | CYS | 445 | 23.392 | −12.574 | 96.762  | 1.00 | 50.80 |
| ATOM | 1987 | SG  | CYS | 445 | 21.966 | −12.871 | 95.692  | 1.00 | 57.24 |
| ATOM | 1988 | N   | SER | 446 | 23.595 | −14.574 | 99.589  | 1.00 | 42.24 |
| ATOM | 1989 | CA  | SER | 446 | 24.471 | −15.438 | 100.339 | 1.00 | 39.56 |
| ATOM | 1990 | CB  | SER | 446 | 23.764 | −15.885 | 101.600 | 1.00 | 40.45 |
| ATOM | 1991 | OG  | SER | 446 | 22.870 | −14.868 | 102.024 | 1.00 | 43.28 |
| ATOM | 1992 | C   | SER | 446 | 24.667 | −16.613 | 99.417  | 1.00 | 37.50 |
| ATOM | 1993 | O   | SER | 446 | 23.767 | −17.424 | 99.252  | 1.00 | 37.85 |
| ATOM | 1994 | N   | SER | 447 | 25.833 | −16.693 | 98.795  | 1.00 | 34.81 |
| ATOM | 1995 | CA  | SER | 447 | 26.095 | −17.780 | 97.881  | 1.00 | 33.45 |
| ATOM | 1996 | CB  | SER | 447 | 26.331 | −17.227 | 96.485  | 1.00 | 34.56 |
| ATOM | 1997 | OG  | SER | 447 | 25.323 | −16.307 | 96.128  | 1.00 | 36.68 |
| ATOM | 1998 | C   | SER | 447 | 27.300 | −18.588 | 98.300  | 1.00 | 32.91 |
| ATOM | 1999 | O   | SER | 447 | 28.088 | −18.178 | 99.151  | 1.00 | 33.16 |
| ATOM | 2000 | N   | ASN | 448 | 27.432 | −19.755 | 97.697  | 1.00 | 32.65 |
| ATOM | 2001 | CA  | ASN | 448 | 28.561 | −20.620 | 97.970  | 1.00 | 33.16 |
| ATOM | 2002 | CB  | ASN | 448 | 28.088 | −22.019 | 98.361  | 1.00 | 35.97 |
| ATOM | 2003 | CG  | ASN | 448 | 27.950 | −22.184 | 99.852  | 1.00 | 41.24 |
| ATOM | 2004 | OD1 | ASN | 448 | 28.938 | −22.162 | 100.574 | 1.00 | 42.95 |
| ATOM | 2005 | ND2 | ASN | 448 | 26.727 | −22.357 | 100.331 | 1.00 | 46.28 |
| ATOM | 2006 | C   | ASN | 448 | 29.444 | −20.706 | 96.731  | 1.00 | 31.71 |
| ATOM | 2007 | O   | ASN | 448 | 29.005 | −21.162 | 95.668  | 1.00 | 30.58 |
| ATOM | 2008 | N   | ILE | 449 | 30.675 | −20.222 | 96.862  | 1.00 | 29.84 |
| ATOM | 2009 | CA  | ILE | 449 | 31.645 | −20.292 | 95.772  | 1.00 | 27.37 |
| ATOM | 2010 | CB  | ILE | 449 | 32.980 | −19.595 | 96.137  | 1.00 | 25.12 |
| ATOM | 2011 | CG2 | ILE | 449 | 34.005 | −19.817 | 95.040  | 1.00 | 24.87 |
| ATOM | 2012 | CG1 | ILE | 449 | 32.766 | −18.110 | 96.374  | 1.00 | 22.91 |
| ATOM | 2013 | CD1 | ILE | 449 | 34.006 | −17.435 | 96.882  | 1.00 | 20.04 |
| ATOM | 2014 | C   | ILE | 449 | 31.929 | −21.784 | 95.734  | 1.00 | 27.61 |
| ATOM | 2015 | O   | ILE | 449 | 32.203 | −22.373 | 96.785  | 1.00 | 29.12 |
| ATOM | 2016 | N   | THR | 450 | 31.854 | −22.409 | 94.567  | 1.00 | 25.09 |
| ATOM | 2017 | CA  | THR | 450 | 32.134 | −23.836 | 94.501  | 1.00 | 24.31 |
| ATOM | 2018 | CB  | THR | 450 | 30.832 | −24.667 | 94.295  | 1.00 | 24.01 |
| ATOM | 2019 | OG1 | THR | 450 | 30.135 | −24.223 | 93.121  | 1.00 | 23.07 |
| ATOM | 2020 | CG2 | THR | 450 | 29.927 | −24.523 | 95.489  | 1.00 | 22.78 |
| ATOM | 2021 | C   | THR | 450 | 33.108 | −24.109 | 93.368  | 1.00 | 24.60 |
| ATOM | 2022 | O   | THR | 450 | 33.469 | −25.248 | 93.088  | 1.00 | 23.80 |
| ATOM | 2023 | N   | GLY | 451 | 33.542 | −23.042 | 92.718  | 1.00 | 25.04 |
| ATOM | 2024 | CA  | GLY | 451 | 34.470 | −23.200 | 91.620  | 1.00 | 26.73 |
| ATOM | 2025 | C   | GLY | 451 | 34.924 | −21.855 | 91.118  | 1.00 | 26.65 |
| ATOM | 2026 | O   | GLY | 451 | 34.370 | −20.828 | 91.505  | 1.00 | 27.30 |
| ATOM | 2027 | N   | LEU | 452 | 35.945 | −21.851 | 90.273  | 1.00 | 26.29 |
| ATOM | 2028 | CA  | LEU | 452 | 36.439 | −20.592 | 89.739  | 1.00 | 27.72 |
| ATOM | 2029 | CB  | LEU | 452 | 37.798 | −20.211 | 90.351  | 1.00 | 25.03 |
| ATOM | 2030 | CG  | LEU | 452 | 37.865 | −19.937 | 91.850  | 1.00 | 23.22 |
| ATOM | 2031 | CD1 | LEU | 452 | 37.792 | −21.248 | 92.592  | 1.00 | 22.91 |
| ATOM | 2032 | CD2 | LEU | 452 | 39.150 | −19.225 | 92.198  | 1.00 | 22.12 |
| ATOM | 2033 | C   | LEU | 452 | 36.602 | −20.720 | 88.249  | 1.00 | 27.91 |
| ATOM | 2034 | O   | LEU | 452 | 36.381 | −21.784 | 87.678  | 1.00 | 30.44 |
| ATOM | 2035 | N   | LEU | 453 | 36.983 | −19.620 | 87.626  | 1.00 | 25.60 |
| ATOM | 2036 | CA  | LEU | 453 | 37.223 | −19.605 | 86.211  | 1.00 | 24.90 |
| ATOM | 2037 | CB  | LEU | 453 | 36.071 | −18.936 | 85.473  | 1.00 | 21.07 |
| ATOM | 2038 | CG  | LEU | 453 | 34.724 | −19.652 | 85.532  | 1.00 | 16.96 |
| ATOM | 2039 | CD1 | LEU | 453 | 33.754 | −18.930 | 84.649  | 1.00 | 17.51 |
| ATOM | 2040 | CD2 | LEU | 453 | 34.850 | −21.061 | 85.077  | 1.00 | 13.58 |
| ATOM | 2041 | C   | LEU | 453 | 38.485 | −18.790 | 86.124  | 1.00 | 27.06 |
| ATOM | 2042 | O   | LEU | 453 | 38.458 | −17.568 | 86.262  | 1.00 | 28.02 |
| ATOM | 2043 | N   | LEU | 454 | 39.602 | −19.480 | 85.936  | 1.00 | 28.63 |
| ATOM | 2044 | CA  | LEU | 454 | 40.889 | −18.809 | 85.862  | 1.00 | 30.83 |
| ATOM | 2045 | CB  | LEU | 454 | 41.898 | −19.483 | 86.789  | 1.00 | 29.19 |
| ATOM | 2046 | CG  | LEU | 454 | 41.646 | −19.667 | 88.277  | 1.00 | 28.21 |
| ATOM | 2047 | CD1 | LEU | 454 | 42.802 | −20.460 | 88.863  | 1.00 | 28.15 |
| ATOM | 2048 | CD2 | LEU | 454 | 41.527 | −18.331 | 88.961  | 1.00 | 28.25 |
| ATOM | 2049 | C   | LEU | 454 | 41.474 | −18.815 | 84.465  | 1.00 | 32.86 |
| ATOM | 2050 | O   | LEU | 454 | 41.103 | −19.631 | 83.622  | 1.00 | 33.87 |
| ATOM | 2051 | N   | THR | 455 | 42.415 | −17.904 | 84.248  | 1.00 | 34.41 |
| ATOM | 2052 | CA  | THR | 455 | 43.123 | −17.791 | 82.984  | 1.00 | 37.13 |
| ATOM | 2053 | CB  | THR | 455 | 42.759 | −16.519 | 82.250  | 1.00 | 38.41 |
| ATOM | 2054 | OG1 | THR | 455 | 41.340 | −16.467 | 82.075  | 1.00 | 41.71 |
| ATOM | 2055 | CG2 | THR | 455 | 43.438 | −16.491 | 80.893  | 1.00 | 38.74 |
| ATOM | 2056 | C   | THR | 455 | 44.591 | −17.716 | 83.344  | 1.00 | 38.29 |
| ATOM | 2057 | O   | THR | 455 | 44.943 | −17.138 | 84.367  | 1.00 | 38.34 |
| ATOM | 2058 | N   | ARG | 456 | 45.450 | −18.289 | 82.508  | 1.00 | 39.99 |
| ATOM | 2059 | CA  | ARG | 456 | 46.881 | −18.277 | 82.783  | 1.00 | 41.61 |
| ATOM | 2060 | CB  | ARG | 456 | 47.424 | −19.698 | 82.719  | 1.00 | 42.00 |

TABLE 1-continued

The structural coordinates of an exemplary stabilized form of gp120 at atomic resolution

| ATOM | 2061 | CG | ARG | 456 | 48.889 | −19.811 | 83.063 | 1.00 | 44.96 |
|---|---|---|---|---|---|---|---|---|---|
| ATOM | 2062 | CD | ARG | 456 | 49.323 | −21.250 | 82.973 | 1.00 | 47.06 |
| ATOM | 2063 | NE | ARG | 456 | 49.147 | −21.774 | 81.621 | 1.00 | 49.39 |
| ATOM | 2064 | CZ | ARG | 456 | 50.117 | −21.842 | 80.714 | 1.00 | 50.82 |
| ATOM | 2065 | NH1 | ARG | 456 | 49.857 | −22.331 | 79.506 | 1.00 | 52.13 |
| ATOM | 2066 | NH2 | ARG | 456 | 51.348 | −21.439 | 81.019 | 1.00 | 49.94 |
| ATOM | 2067 | C | ARG | 456 | 47.664 | −17.389 | 81.825 | 1.00 | 42.48 |
| ATOM | 2068 | O | ARG | 456 | 47.665 | −17.626 | 80.624 | 1.00 | 41.96 |
| ATOM | 2069 | N | ASP | 457 | 48.333 | −16.371 | 82.362 | 1.00 | 44.50 |
| ATOM | 2070 | CA | ASP | 457 | 49.124 | −15.451 | 81.541 | 1.00 | 46.62 |
| ATOM | 2071 | CB | ASP | 457 | 49.969 | −14.515 | 82.414 | 1.00 | 45.79 |
| ATOM | 2072 | CG | ASP | 457 | 49.169 | −13.352 | 82.978 | 1.00 | 46.16 |
| ATOM | 2073 | OD1 | ASP | 457 | 49.798 | −12.434 | 83.549 | 1.00 | 44.86 |
| ATOM | 2074 | OD2 | ASP | 457 | 47.921 | −13.355 | 82.853 | 1.00 | 44.91 |
| ATOM | 2075 | C | ASP | 457 | 50.051 | −16.199 | 80.597 | 1.00 | 48.50 |
| ATOM | 2076 | O | ASP | 457 | 49.941 | −16.088 | 79.378 | 1.00 | 48.45 |
| ATOM | 2077 | N | GLY | 458 | 50.975 | −16.959 | 81.168 | 1.00 | 51.31 |
| ATOM | 2078 | CA | GLY | 458 | 51.898 | −17.712 | 80.346 | 1.00 | 54.51 |
| ATOM | 2079 | C | GLY | 458 | 52.751 | −16.795 | 79.499 | 1.00 | 57.29 |
| ATOM | 2080 | O | GLY | 458 | 53.043 | −15.659 | 79.886 | 1.00 | 56.35 |
| ATOM | 2081 | N | GLY | 459 | 53.145 | −17.288 | 78.332 | 1.00 | 60.01 |
| ATOM | 2082 | CA | GLY | 459 | 53.980 | −16.494 | 77.454 | 1.00 | 63.76 |
| ATOM | 2083 | C | GLY | 459 | 55.443 | −16.727 | 77.769 | 1.00 | 66.68 |
| ATOM | 2084 | O | GLY | 459 | 55.830 | −16.889 | 78.932 | 1.00 | 66.19 |
| ATOM | 2085 | N | ASN | 460 | 56.254 | −16.735 | 76.716 | 1.00 | 69.80 |
| ATOM | 2086 | CA | ASN | 460 | 57.694 | −16.954 | 76.813 | 1.00 | 73.18 |
| ATOM | 2087 | CB | ASN | 460 | 58.357 | −16.575 | 75.486 | 1.00 | 73.04 |
| ATOM | 2088 | CG | ASN | 460 | 57.866 | −17.426 | 74.325 | 1.00 | 73.09 |
| ATOM | 2089 | OD1 | ASN | 460 | 56.884 | −18.161 | 74.450 | 1.00 | 73.18 |
| ATOM | 2090 | ND2 | ASN | 460 | 58.543 | −17.323 | 73.186 | 1.00 | 72.64 |
| ATOM | 2091 | C | ASN | 460 | 58.409 | −16.242 | 77.965 | 1.00 | 75.44 |
| ATOM | 2092 | O | ASN | 460 | 58.412 | −15.010 | 78.062 | 1.00 | 75.19 |
| ATOM | 2093 | N | SER | 461 | 59.021 | −17.051 | 78.828 | 1.00 | 77.97 |
| ATOM | 2094 | CA | SER | 461 | 59.771 | −16.582 | 79.987 | 1.00 | 80.75 |
| ATOM | 2095 | CB | SER | 461 | 58.858 | −15.820 | 80.955 | 1.00 | 80.97 |
| ATOM | 2096 | OG | SER | 461 | 59.608 | −15.227 | 82.007 | 1.00 | 81.02 |
| ATOM | 2097 | C | SER | 461 | 60.368 | −17.804 | 80.689 | 1.00 | 82.74 |
| ATOM | 2098 | O | SER | 461 | 59.649 | −18.579 | 81.332 | 1.00 | 82.67 |
| ATOM | 2099 | N | ASN | 462 | 61.682 | −17.979 | 80.545 | 1.00 | 84.51 |
| ATOM | 2100 | CA | ASN | 462 | 62.399 | −19.101 | 81.160 | 1.00 | 85.75 |
| ATOM | 2101 | CB | ASN | 462 | 63.877 | −19.043 | 80.770 | 1.00 | 86.14 |
| ATOM | 2102 | CG | ASN | 462 | 64.408 | −17.626 | 80.735 | 1.00 | 86.77 |
| ATOM | 2103 | OD1 | ASN | 462 | 64.320 | −16.891 | 81.723 | 1.00 | 87.52 |
| ATOM | 2104 | ND2 | ASN | 462 | 64.963 | −17.230 | 79.594 | 1.00 | 86.09 |
| ATOM | 2105 | C | ASN | 462 | 62.248 | −19.078 | 82.681 | 1.00 | 85.99 |
| ATOM | 2106 | O | ASN | 462 | 62.664 | −20.014 | 83.377 | 1.00 | 86.05 |
| ATOM | 2107 | N | ASN | 463 | 61.648 | −17.992 | 83.172 | 1.00 | 85.36 |
| ATOM | 2108 | CA | ASN | 463 | 61.379 | −17.775 | 84.591 | 1.00 | 84.11 |
| ATOM | 2109 | CB | ASN | 463 | 60.737 | −16.395 | 84.774 | 1.00 | 86.07 |
| ATOM | 2110 | CG | ASN | 463 | 60.656 | −15.967 | 86.227 | 1.00 | 88.02 |
| ATOM | 2111 | OD1 | ASN | 463 | 60.296 | −16.757 | 87.101 | 1.00 | 90.17 |
| ATOM | 2112 | ND2 | ASN | 463 | 60.976 | −14.703 | 86.490 | 1.00 | 88.10 |
| ATOM | 2113 | C | ASN | 463 | 60.392 | −18.861 | 85.012 | 1.00 | 82.29 |
| ATOM | 2114 | O | ASN | 463 | 59.372 | −19.058 | 84.351 | 1.00 | 82.70 |
| ATOM | 2115 | N | GLU | 464 | 60.684 | −19.569 | 86.098 | 1.00 | 79.57 |
| ATOM | 2116 | CA | GLU | 464 | 59.788 | −20.631 | 86.542 | 1.00 | 76.54 |
| ATOM | 2117 | CB | GLU | 464 | 60.598 | −21.833 | 87.058 | 1.00 | 79.45 |
| ATOM | 2118 | CG | GLU | 464 | 61.323 | −22.608 | 85.943 | 1.00 | 82.50 |
| ATOM | 2119 | CD | GLU | 464 | 62.120 | −23.814 | 86.448 | 1.00 | 85.16 |
| ATOM | 2120 | OE1 | GLU | 464 | 62.812 | −24.457 | 85.620 | 1.00 | 85.88 |
| ATOM | 2121 | OE2 | GLU | 464 | 62.055 | −24.121 | 87.663 | 1.00 | 85.82 |
| ATOM | 2122 | C | GLU | 464 | 58.765 | −20.185 | 87.583 | 1.00 | 72.60 |
| ATOM | 2123 | O | GLU | 464 | 58.986 | −20.303 | 88.788 | 1.00 | 71.55 |
| ATOM | 2124 | N | SER | 465 | 57.639 | −19.677 | 87.081 | 1.00 | 68.78 |
| ATOM | 2125 | CA | SER | 465 | 56.516 | −19.200 | 87.893 | 1.00 | 64.10 |
| ATOM | 2126 | CB | SER | 465 | 56.918 | −17.974 | 88.715 | 1.00 | 63.31 |
| ATOM | 2127 | OG | SER | 465 | 57.130 | −16.853 | 87.880 | 1.00 | 60.85 |
| ATOM | 2128 | C | SER | 465 | 55.356 | −18.818 | 86.968 | 1.00 | 60.87 |
| ATOM | 2129 | O | SER | 465 | 55.526 | −18.016 | 86.049 | 1.00 | 59.72 |
| ATOM | 2130 | N | GLU | 466 | 54.184 | −19.397 | 87.215 | 1.00 | 57.26 |
| ATOM | 2131 | CA | GLU | 466 | 52.994 | −19.126 | 86.410 | 1.00 | 53.95 |
| ATOM | 2132 | CB | GLU | 466 | 52.200 | −20.413 | 86.211 | 1.00 | 54.65 |
| ATOM | 2133 | CG | GLU | 466 | 52.956 | −21.470 | 85.438 | 1.00 | 56.85 |
| ATOM | 2134 | CD | GLU | 466 | 53.221 | −21.049 | 84.011 | 1.00 | 57.73 |
| ATOM | 2135 | OE1 | GLU | 466 | 54.153 | −21.608 | 83.395 | 1.00 | 58.80 |
| ATOM | 2136 | OE2 | GLU | 466 | 52.492 | −20.165 | 83.506 | 1.00 | 57.31 |
| ATOM | 2137 | C | GLU | 466 | 52.110 | −18.087 | 87.080 | 1.00 | 51.49 |
| ATOM | 2138 | O | GLU | 466 | 52.057 | −18.015 | 88.306 | 1.00 | 51.94 |

TABLE 1-continued

The structural coordinates of an exemplary stabilized form of gp120 at atomic resolution

| | | | | | | | | | |
|---|---|---|---|---|---|---|---|---|---|
| ATOM | 2139 | N | ILE | 467 | 51.419 | −17.276 | 86.283 | 1.00 | 47.68 |
| ATOM | 2140 | CA | ILE | 467 | 50.543 | −16.254 | 86.850 | 1.00 | 44.16 |
| ATOM | 2141 | CB | ILE | 467 | 50.903 | −14.837 | 86.354 | 1.00 | 42.54 |
| ATOM | 2142 | CG2 | ILE | 467 | 50.189 | −13.805 | 87.209 | 1.00 | 41.04 |
| ATOM | 2143 | CG1 | ILE | 467 | 52.410 | −14.601 | 86.454 | 1.00 | 41.74 |
| ATOM | 2144 | CD1 | ILE | 467 | 52.829 | −13.208 | 86.044 | 1.00 | 40.72 |
| ATOM | 2145 | C | ILE | 467 | 49.100 | −16.539 | 86.466 | 1.00 | 42.71 |
| ATOM | 2146 | O | ILE | 467 | 48.817 | −16.864 | 85.315 | 1.00 | 43.08 |
| ATOM | 2147 | N | PHE | 468 | 48.187 | −16.421 | 87.423 | 1.00 | 39.98 |
| ATOM | 2148 | CA | PHE | 468 | 46.793 | −16.684 | 87.129 | 1.00 | 38.70 |
| ATOM | 2149 | CB | PHE | 468 | 46.347 | −17.953 | 87.827 | 1.00 | 39.01 |
| ATOM | 2150 | CG | PHE | 468 | 47.216 | −19.127 | 87.541 | 1.00 | 40.09 |
| ATOM | 2151 | CD1 | PHE | 468 | 48.465 | −19.243 | 88.145 | 1.00 | 40.16 |
| ATOM | 2152 | CD2 | PHE | 468 | 46.789 | −20.127 | 86.670 | 1.00 | 41.47 |
| ATOM | 2153 | CE1 | PHE | 468 | 49.280 | −20.334 | 87.891 | 1.00 | 40.98 |
| ATOM | 2154 | CE2 | PHE | 468 | 47.596 | −21.229 | 86.404 | 1.00 | 42.44 |
| ATOM | 2155 | CZ | PHE | 468 | 48.847 | −21.333 | 87.018 | 1.00 | 42.97 |
| ATOM | 2156 | C | PHE | 468 | 45.863 | −15.552 | 87.515 | 1.00 | 38.30 |
| ATOM | 2157 | O | PHE | 468 | 46.022 | −14.928 | 88.563 | 1.00 | 39.47 |
| ATOM | 2158 | N | ARG | 469 | 44.876 | −15.305 | 86.664 | 1.00 | 36.77 |
| ATOM | 2159 | CA | ARG | 469 | 43.912 | −14.250 | 86.897 | 1.00 | 35.74 |
| ATOM | 2160 | CB | ARG | 469 | 44.139 | −13.121 | 85.907 | 1.00 | 34.66 |
| ATOM | 2161 | CG | ARG | 469 | 45.560 | −12.642 | 85.831 | 1.00 | 33.62 |
| ATOM | 2162 | CD | ARG | 469 | 45.735 | −11.760 | 84.620 | 1.00 | 33.99 |
| ATOM | 2163 | NE | ARG | 469 | 47.111 | −11.330 | 84.426 | 1.00 | 32.62 |
| ATOM | 2164 | CZ | ARG | 469 | 47.721 | −10.426 | 85.179 | 1.00 | 32.46 |
| ATOM | 2165 | NH1 | ARG | 469 | 47.083 | −9.851 | 86.182 | 1.00 | 32.30 |
| ATOM | 2166 | NH2 | ARG | 469 | 48.968 | −10.089 | 84.918 | 1.00 | 33.90 |
| ATOM | 2167 | C | ARG | 469 | 42.522 | −14.811 | 86.690 | 1.00 | 35.90 |
| ATOM | 2168 | O | ARG | 469 | 42.344 | −15.782 | 85.968 | 1.00 | 37.30 |
| ATOM | 2169 | N | PRO | 470 | 41.512 | −14.196 | 87.316 | 1.00 | 36.11 |
| ATOM | 2170 | CD | PRO | 470 | 41.626 | −13.004 | 88.173 | 1.00 | 37.74 |
| ATOM | 2171 | CA | PRO | 470 | 40.117 | −14.628 | 87.205 | 1.00 | 35.55 |
| ATOM | 2172 | CB | PRO | 470 | 39.425 | −13.835 | 88.306 | 1.00 | 37.42 |
| ATOM | 2173 | CG | PRO | 470 | 40.181 | −12.546 | 88.299 | 1.00 | 37.79 |
| ATOM | 2174 | C | PRO | 470 | 39.572 | −14.304 | 85.826 | 1.00 | 34.84 |
| ATOM | 2175 | O | PRO | 470 | 39.664 | −13.163 | 85.350 | 1.00 | 32.79 |
| ATOM | 2176 | N | GLY | 471 | 39.009 | −15.318 | 85.182 | 1.00 | 34.39 |
| ATOM | 2177 | CA | GLY | 471 | 38.481 | −15.126 | 83.849 | 1.00 | 34.12 |
| ATOM | 2178 | C | GLY | 471 | 37.014 | −15.447 | 83.762 | 1.00 | 33.66 |
| ATOM | 2179 | O | GLY | 471 | 36.250 | −15.157 | 84.681 | 1.00 | 32.21 |
| ATOM | 2180 | N | GLY | 472 | 36.630 | −16.054 | 82.646 | 1.00 | 34.79 |
| ATOM | 2181 | CA | GLY | 472 | 35.242 | −16.408 | 82.433 | 1.00 | 36.19 |
| ATOM | 2182 | C | GLY | 472 | 34.526 | −15.361 | 81.600 | 1.00 | 37.07 |
| ATOM | 2183 | O | GLY | 472 | 35.141 | −14.417 | 81.090 | 1.00 | 37.63 |
| ATOM | 2184 | N | GLY | 473 | 33.218 | −15.516 | 81.471 | 1.00 | 36.43 |
| ATOM | 2185 | CA | GLY | 473 | 32.451 | −14.578 | 80.687 | 1.00 | 36.25 |
| ATOM | 2186 | C | GLY | 473 | 31.703 | −15.393 | 79.669 | 1.00 | 37.28 |
| ATOM | 2187 | O | GLY | 473 | 30.653 | −14.982 | 79.179 | 1.00 | 37.79 |
| ATOM | 2188 | N | ASP | 474 | 32.253 | −16.562 | 79.351 | 1.00 | 37.46 |
| ATOM | 2189 | CA | ASP | 474 | 31.620 | −17.455 | 78.396 | 1.00 | 38.13 |
| ATOM | 2190 | CB | ASP | 474 | 32.666 | −18.142 | 77.528 | 1.00 | 39.46 |
| ATOM | 2191 | CG | ASP | 474 | 32.042 | −18.956 | 76.420 | 1.00 | 41.78 |
| ATOM | 2192 | OD1 | ASP | 474 | 30.863 | −19.345 | 76.567 | 1.00 | 41.80 |
| ATOM | 2193 | OD2 | ASP | 474 | 32.726 | −19.215 | 75.408 | 1.00 | 43.88 |
| ATOM | 2194 | C | ASP | 474 | 30.842 | −18.501 | 79.179 | 1.00 | 37.74 |
| ATOM | 2195 | O | ASP | 474 | 31.350 | −19.584 | 79.445 | 1.00 | 38.81 |
| ATOM | 2196 | N | MET | 475 | 29.609 | −18.166 | 79.543 | 1.00 | 37.28 |
| ATOM | 2197 | CA | MET | 475 | 28.741 | −19.049 | 80.318 | 1.00 | 36.81 |
| ATOM | 2198 | CB | MET | 475 | 27.297 | −18.559 | 80.213 | 1.00 | 36.74 |
| ATOM | 2199 | CG | MET | 475 | 26.718 | −18.082 | 81.529 | 1.00 | 37.69 |
| ATOM | 2200 | SD | MET | 475 | 27.926 | −17.234 | 82.557 | 1.00 | 38.71 |
| ATOM | 2201 | CE | MET | 475 | 28.119 | −15.706 | 81.638 | 1.00 | 38.89 |
| ATOM | 2202 | C | MET | 475 | 28.814 | −20.542 | 79.979 | 1.00 | 37.19 |
| ATOM | 2203 | O | MET | 475 | 28.382 | −21.382 | 80.773 | 1.00 | 37.30 |
| ATOM | 2204 | N | ARG | 476 | 29.353 | −20.878 | 78.809 | 1.00 | 36.64 |
| ATOM | 2205 | CA | ARG | 476 | 29.484 | −22.273 | 78.420 | 1.00 | 34.96 |
| ATOM | 2206 | CB | ARG | 476 | 29.919 | −22.392 | 76.973 | 1.00 | 37.33 |
| ATOM | 2207 | CG | ARG | 476 | 28.879 | −21.935 | 75.991 | 1.00 | 39.91 |
| ATOM | 2208 | CD | ARG | 476 | 29.264 | −22.348 | 74.595 | 1.00 | 43.35 |
| ATOM | 2209 | NE | ARG | 476 | 28.644 | −21.475 | 73.610 | 1.00 | 48.16 |
| ATOM | 2210 | CZ | ARG | 476 | 29.072 | −20.246 | 73.339 | 1.00 | 50.83 |
| ATOM | 2211 | NH1 | ARG | 476 | 30.130 | −19.751 | 73.978 | 1.00 | 50.44 |
| ATOM | 2212 | NH2 | ARG | 476 | 28.434 | −19.508 | 72.438 | 1.00 | 52.09 |
| ATOM | 2213 | C | ARG | 476 | 30.505 | −22.950 | 79.309 | 1.00 | 34.15 |
| ATOM | 2214 | O | ARG | 476 | 30.466 | −24.155 | 79.495 | 1.00 | 33.39 |
| ATOM | 2215 | N | ASP | 477 | 31.437 | −22.175 | 79.846 | 1.00 | 33.97 |
| ATOM | 2216 | CA | ASP | 477 | 32.428 | −22.731 | 80.748 | 1.00 | 34.21 |

TABLE 1-continued

The structural coordinates of an exemplary stabilized form of gp120 at atomic resolution

| ATOM | 2217 | CB  | ASP | 477 | 33.497 | −21.702 | 81.091 | 1.00 | 34.12 |
|------|------|-----|-----|-----|--------|---------|--------|------|-------|
| ATOM | 2218 | CG  | ASP | 477 | 34.475 | −21.478 | 79.971 | 1.00 | 35.39 |
| ATOM | 2219 | OD1 | ASP | 477 | 34.800 | −22.449 | 79.256 | 1.00 | 36.22 |
| ATOM | 2220 | OD2 | ASP | 477 | 34.937 | −20.326 | 79.823 | 1.00 | 37.07 |
| ATOM | 2221 | C   | ASP | 477 | 31.696 | −23.120 | 82.030 | 1.00 | 35.79 |
| ATOM | 2222 | O   | ASP | 477 | 31.977 | −24.157 | 82.640 | 1.00 | 36.61 |
| ATOM | 2223 | N   | ASN | 478 | 30.753 | −22.278 | 82.440 | 1.00 | 35.81 |
| ATOM | 2224 | CA  | ASN | 478 | 29.992 | −22.539 | 83.647 | 1.00 | 35.64 |
| ATOM | 2225 | CB  | ASN | 478 | 29.160 | −21.315 | 84.029 | 1.00 | 37.76 |
| ATOM | 2226 | CG  | ASN | 478 | 29.987 | −20.040 | 84.081 | 1.00 | 39.41 |
| ATOM | 2227 | OD1 | ASN | 478 | 29.613 | −19.070 | 84.748 | 1.00 | 40.06 |
| ATOM | 2228 | ND2 | ASN | 478 | 31.108 | −20.029 | 83.363 | 1.00 | 37.85 |
| ATOM | 2229 | C   | ASN | 478 | 29.096 | −23.756 | 83.478 | 1.00 | 34.88 |
| ATOM | 2230 | O   | ASN | 478 | 28.958 | −24.550 | 84.389 | 1.00 | 34.09 |
| ATOM | 2231 | N   | TRP | 479 | 28.479 | −23.906 | 82.316 | 1.00 | 34.86 |
| ATOM | 2232 | CA  | TRP | 479 | 27.641 | −25.070 | 82.078 | 1.00 | 36.03 |
| ATOM | 2233 | CB  | TRP | 479 | 26.892 | −24.932 | 80.760 | 1.00 | 37.78 |
| ATOM | 2234 | CG  | TRP | 479 | 26.218 | −23.624 | 80.555 | 1.00 | 40.26 |
| ATOM | 2235 | CD2 | TRP | 479 | 25.541 | −22.847 | 81.536 | 1.00 | 40.78 |
| ATOM | 2236 | CE2 | TRP | 479 | 25.028 | −21.702 | 80.883 | 1.00 | 41.01 |
| ATOM | 2237 | CE3 | TRP | 479 | 25.314 | −23.002 | 82.904 | 1.00 | 41.79 |
| ATOM | 2238 | CD1 | TRP | 479 | 26.095 | −22.943 | 79.374 | 1.00 | 41.62 |
| ATOM | 2239 | NE1 | TRP | 479 | 25.380 | −21.787 | 79.562 | 1.00 | 41.25 |
| ATOM | 2240 | CZ2 | TRP | 479 | 24.307 | −20.719 | 81.552 | 1.00 | 40.72 |
| ATOM | 2241 | CZ3 | TRP | 479 | 24.595 | −22.023 | 83.569 | 1.00 | 43.55 |
| ATOM | 2242 | CH2 | TRP | 479 | 24.099 | −20.894 | 82.889 | 1.00 | 42.51 |
| ATOM | 2243 | C   | TRP | 479 | 28.576 | −26.270 | 81.972 | 1.00 | 35.96 |
| ATOM | 2244 | O   | TRP | 479 | 28.297 | −27.346 | 82.476 | 1.00 | 37.65 |
| ATOM | 2245 | N   | ARG | 480 | 29.700 | −26.070 | 81.304 | 1.00 | 36.48 |
| ATOM | 2246 | CA  | ARG | 480 | 30.685 | −27.126 | 81.108 | 1.00 | 37.20 |
| ATOM | 2247 | CB  | ARG | 480 | 31.863 | −26.576 | 80.284 | 1.00 | 39.00 |
| ATOM | 2248 | CG  | ARG | 480 | 32.614 | −27.615 | 79.462 | 1.00 | 40.70 |
| ATOM | 2249 | CD  | ARG | 480 | 33.888 | −27.058 | 78.807 | 1.00 | 42.07 |
| ATOM | 2250 | NE  | ARG | 480 | 33.624 | −25.883 | 77.995 | 1.00 | 41.84 |
| ATOM | 2251 | CZ  | ARG | 480 | 32.745 | −25.850 | 77.002 | 1.00 | 41.61 |
| ATOM | 2252 | NH1 | ARG | 480 | 32.044 | −26.937 | 76.691 | 1.00 | 41.31 |
| ATOM | 2253 | NH2 | ARG | 480 | 32.552 | −24.720 | 76.337 | 1.00 | 41.06 |
| ATOM | 2254 | C   | ARG | 480 | 31.202 | −27.706 | 82.428 | 1.00 | 36.72 |
| ATOM | 2255 | O   | ARG | 480 | 31.560 | −28.869 | 82.495 | 1.00 | 37.82 |
| ATOM | 2256 | N   | SER | 481 | 31.236 | −26.899 | 83.479 | 1.00 | 36.72 |
| ATOM | 2257 | CA  | SER | 481 | 31.738 | −27.367 | 84.765 | 1.00 | 37.00 |
| ATOM | 2258 | CB  | SER | 481 | 32.088 | −26.182 | 85.645 | 1.00 | 36.50 |
| ATOM | 2259 | OG  | SER | 481 | 30.897 | −25.619 | 86.144 | 1.00 | 33.89 |
| ATOM | 2260 | C   | SER | 481 | 30.742 | −28.243 | 85.516 | 1.00 | 37.55 |
| ATOM | 2261 | O   | SER | 481 | 31.024 | −28.717 | 86.616 | 1.00 | 36.47 |
| ATOM | 2262 | N   | GLU | 482 | 29.575 | −28.453 | 84.933 | 1.00 | 38.59 |
| ATOM | 2263 | CA  | GLU | 482 | 28.572 | −29.269 | 85.583 | 1.00 | 40.68 |
| ATOM | 2264 | CB  | GLU | 482 | 27.350 | −28.418 | 85.922 | 1.00 | 42.64 |
| ATOM | 2265 | CG  | GLU | 482 | 27.521 | −27.504 | 87.131 | 1.00 | 44.81 |
| ATOM | 2266 | CD  | GLU | 482 | 26.957 | −28.100 | 88.412 | 1.00 | 46.18 |
| ATOM | 2267 | OE1 | GLU | 482 | 25.726 | −28.318 | 88.481 | 1.00 | 47.32 |
| ATOM | 2268 | OE2 | GLU | 482 | 27.744 | −28.348 | 89.353 | 1.00 | 46.06 |
| ATOM | 2269 | C   | GLU | 482 | 28.163 | −30.428 | 84.697 | 1.00 | 41.36 |
| ATOM | 2270 | O   | GLU | 482 | 27.733 | −31.472 | 85.188 | 1.00 | 43.64 |
| ATOM | 2271 | N   | LEU | 483 | 28.304 | −30.255 | 83.391 | 1.00 | 40.45 |
| ATOM | 2272 | CA  | LEU | 483 | 27.919 | −31.303 | 82.459 | 1.00 | 40.92 |
| ATOM | 2273 | CB  | LEU | 483 | 27.182 | −30.673 | 81.283 | 1.00 | 40.20 |
| ATOM | 2274 | CG  | LEU | 483 | 25.928 | −29.921 | 81.723 | 1.00 | 40.80 |
| ATOM | 2275 | CD1 | LEU | 483 | 25.420 | −29.072 | 80.587 | 1.00 | 41.63 |
| ATOM | 2276 | CD2 | LEU | 483 | 24.874 | −30.909 | 82.175 | 1.00 | 41.17 |
| ATOM | 2277 | C   | LEU | 483 | 29.096 | −32.132 | 81.951 | 1.00 | 41.69 |
| ATOM | 2278 | O   | LEU | 483 | 28.931 | −33.000 | 81.092 | 1.00 | 41.28 |
| ATOM | 2279 | N   | TYR | 484 | 30.282 | −31.880 | 82.492 | 1.00 | 41.67 |
| ATOM | 2280 | CA  | TYR | 484 | 31.463 | −32.598 | 82.050 | 1.00 | 42.77 |
| ATOM | 2281 | CB  | TYR | 484 | 32.684 | −32.103 | 82.830 | 1.00 | 42.89 |
| ATOM | 2282 | CG  | TYR | 484 | 32.695 | −32.515 | 84.277 | 1.00 | 43.93 |
| ATOM | 2283 | CD1 | TYR | 484 | 33.244 | −33.735 | 84.668 | 1.00 | 44.09 |
| ATOM | 2284 | CE1 | TYR | 484 | 33.210 | −34.148 | 86.000 | 1.00 | 43.91 |
| ATOM | 2285 | CD2 | TYR | 484 | 32.113 | −31.714 | 85.255 | 1.00 | 43.24 |
| ATOM | 2286 | CE2 | TYR | 484 | 32.074 | −32.121 | 86.588 | 1.00 | 42.95 |
| ATOM | 2287 | CZ  | TYR | 484 | 32.624 | −33.337 | 86.950 | 1.00 | 42.55 |
| ATOM | 2288 | OH  | TYR | 484 | 32.605 | −33.739 | 88.263 | 1.00 | 43.56 |
| ATOM | 2289 | C   | TYR | 484 | 31.316 | −34.120 | 82.176 | 1.00 | 43.44 |
| ATOM | 2290 | O   | TYR | 484 | 31.810 | −34.877 | 81.327 | 1.00 | 42.64 |
| ATOM | 2291 | N   | LYS | 485 | 30.622 | −34.562 | 83.221 | 1.00 | 43.25 |
| ATOM | 2292 | CA  | LYS | 485 | 30.424 | −35.989 | 83.449 | 1.00 | 44.97 |
| ATOM | 2293 | CB  | LYS | 485 | 30.249 | −36.265 | 84.946 | 1.00 | 46.94 |
| ATOM | 2294 | CG  | LYS | 485 | 29.083 | −35.540 | 85.606 | 1.00 | 49.26 |

TABLE 1-continued

The structural coordinates of an exemplary stabilized form of gp120 at atomic resolution

| ATOM | 2295 | CD | LYS | 485 | 29.109 | −35.779 | 87.115 | 1.00 | 53.35 |
|---|---|---|---|---|---|---|---|---|---|
| ATOM | 2296 | CE | LYS | 485 | 28.091 | −34.913 | 87.862 | 1.00 | 55.98 |
| ATOM | 2297 | NZ | LYS | 485 | 28.190 | −35.067 | 89.350 | 1.00 | 55.85 |
| ATOM | 2298 | C | LYS | 485 | 29.230 | −36.557 | 82.686 | 1.00 | 44.79 |
| ATOM | 2299 | O | LYS | 485 | 28.637 | −37.547 | 83.105 | 1.00 | 45.03 |
| ATOM | 2300 | N | TYR | 486 | 28.876 | −35.931 | 81.568 | 1.00 | 43.62 |
| ATOM | 2301 | CA | TYR | 486 | 27.750 | −36.389 | 80.767 | 1.00 | 41.82 |
| ATOM | 2302 | CB | TYR | 486 | 26.523 | −35.492 | 80.970 | 1.00 | 38.82 |
| ATOM | 2303 | CG | TYR | 486 | 25.915 | −35.521 | 82.350 | 1.00 | 36.43 |
| ATOM | 2304 | CD1 | TYR | 486 | 26.240 | −34.550 | 83.299 | 1.00 | 37.04 |
| ATOM | 2305 | CE1 | TYR | 486 | 25.677 | −34.577 | 84.576 | 1.00 | 36.71 |
| ATOM | 2306 | CD2 | TYR | 486 | 25.011 | −36.514 | 82.709 | 1.00 | 34.16 |
| ATOM | 2307 | CE2 | TYR | 486 | 24.445 | −36.550 | 83.979 | 1.00 | 33.33 |
| ATOM | 2308 | CZ | TYR | 486 | 24.777 | −35.583 | 84.904 | 1.00 | 34.49 |
| ATOM | 2309 | OH | TYR | 486 | 24.220 | −35.624 | 86.158 | 1.00 | 34.00 |
| ATOM | 2310 | C | TYR | 486 | 28.089 | −36.382 | 79.291 | 1.00 | 42.66 |
| ATOM | 2311 | O | TYR | 486 | 29.078 | −35.796 | 78.866 | 1.00 | 44.53 |
| ATOM | 2312 | N | LYS | 487 | 27.249 | −37.041 | 78.509 | 1.00 | 43.23 |
| ATOM | 2313 | CA | LYS | 487 | 27.413 | −37.090 | 77.070 | 1.00 | 43.39 |
| ATOM | 2314 | CB | LYS | 487 | 28.638 | −37.915 | 76.670 | 1.00 | 42.59 |
| ATOM | 2315 | CG | LYS | 487 | 28.399 | −39.401 | 76.615 | 1.00 | 42.82 |
| ATOM | 2316 | CD | LYS | 487 | 29.518 | −40.088 | 75.855 | 1.00 | 45.58 |
| ATOM | 2317 | CE | LYS | 487 | 29.612 | −39.594 | 74.405 | 1.00 | 46.48 |
| ATOM | 2318 | NZ | LYS | 487 | 30.745 | −40.213 | 73.638 | 1.00 | 44.44 |
| ATOM | 2319 | C | LYS | 487 | 26.149 | −37.724 | 76.527 | 1.00 | 43.48 |
| ATOM | 2320 | O | LYS | 487 | 25.597 | −38.640 | 77.128 | 1.00 | 43.29 |
| ATOM | 2321 | N | VAL | 488 | 25.682 | −37.217 | 75.400 | 1.00 | 44.12 |
| ATOM | 2322 | CA | VAL | 488 | 24.475 | −37.729 | 74.790 | 1.00 | 45.91 |
| ATOM | 2323 | CB | VAL | 488 | 23.558 | −36.554 | 74.409 | 1.00 | 44.11 |
| ATOM | 2324 | CG1 | VAL | 488 | 24.209 | −35.720 | 73.338 | 1.00 | 44.27 |
| ATOM | 2325 | CG2 | VAL | 488 | 22.214 | −37.056 | 73.966 | 1.00 | 44.39 |
| ATOM | 2326 | C | VAL | 488 | 24.864 | −38.554 | 73.557 | 1.00 | 48.36 |
| ATOM | 2327 | O | VAL | 488 | 25.888 | −38.290 | 72.927 | 1.00 | 48.88 |
| ATOM | 2328 | N | VAL | 489 | 24.070 | −39.570 | 73.223 | 1.00 | 51.09 |
| ATOM | 2329 | CA | VAL | 489 | 24.383 | −40.403 | 72.060 | 1.00 | 53.62 |
| ATOM | 2330 | CB | VAL | 489 | 25.341 | −41.573 | 72.438 | 1.00 | 53.16 |
| ATOM | 2331 | CG1 | VAL | 489 | 24.659 | −42.513 | 73.409 | 1.00 | 51.07 |
| ATOM | 2332 | CG2 | VAL | 489 | 25.783 | −42.316 | 71.178 | 1.00 | 52.29 |
| ATOM | 2333 | C | VAL | 489 | 23.161 | −40.983 | 71.344 | 1.00 | 55.28 |
| ATOM | 2334 | O | VAL | 489 | 22.115 | −41.249 | 71.956 | 1.00 | 55.15 |
| ATOM | 2335 | N | LYS | 490 | 23.317 | −41.163 | 70.033 | 1.00 | 56.80 |
| ATOM | 2336 | CA | LYS | 490 | 22.272 | −41.708 | 69.179 | 1.00 | 58.05 |
| ATOM | 2337 | CB | LYS | 490 | 22.757 | −41.833 | 67.729 | 1.00 | 59.78 |
| ATOM | 2338 | CG | LYS | 490 | 23.172 | −40.539 | 67.031 | 1.00 | 63.37 |
| ATOM | 2339 | CD | LYS | 490 | 24.493 | −39.974 | 67.570 | 1.00 | 66.32 |
| ATOM | 2340 | CE | LYS | 490 | 25.132 | −38.975 | 66.597 | 1.00 | 66.85 |
| ATOM | 2341 | NZ | LYS | 490 | 24.183 | −37.926 | 66.111 | 1.00 | 68.56 |
| ATOM | 2342 | C | LYS | 490 | 21.928 | −43.094 | 69.671 | 1.00 | 57.96 |
| ATOM | 2343 | O | LYS | 490 | 22.825 | −43.917 | 69.873 | 1.00 | 58.39 |
| ATOM | 2344 | N | ILE | 491 | 20.642 | −43.364 | 69.868 | 1.00 | 57.59 |
| ATOM | 2345 | CA | ILE | 491 | 20.237 | −44.697 | 70.303 | 1.00 | 56.42 |
| ATOM | 2346 | CB | ILE | 491 | 18.861 | −44.685 | 70.982 | 1.00 | 53.57 |
| ATOM | 2347 | CG2 | ILE | 491 | 18.641 | −45.994 | 71.698 | 1.00 | 52.55 |
| ATOM | 2348 | CG1 | ILE | 491 | 18.776 | −43.545 | 71.983 | 1.00 | 52.06 |
| ATOM | 2349 | CD1 | ILE | 491 | 17.409 | −43.403 | 72.594 | 1.00 | 50.94 |
| ATOM | 2350 | C | ILE | 491 | 20.144 | −45.570 | 69.045 | 1.00 | 57.42 |
| ATOM | 2351 | O | ILE | 491 | 19.728 | −45.038 | 67.989 | 1.00 | 57.28 |
| ATOM | 2352 | OXT | ILE | 491 | 20.478 | −46.769 | 69.127 | 1.00 | 58.91 |
| END | | | | | | | | | |

VII. Crystals of gp120 with an Extended V3 Loop

The present disclosure further relates to the crystal structure of gp120 in which the V3 loop is in an extended conformation. The present disclosure also relates to the crystals obtained from a gp120 polypeptide with an extended V3 loop. The three-dimensional coordinates of a gp120 polypeptide with an extended V3 loop, three-dimensional structures of models of a gp120 polypeptide with an extended V3 loop, and uses of these models. The amino acid sequence of a gp120 polypeptide with an extended V3 loop variant is set forth as SEQ ID NO: 2.

The structure of a gp120 polypeptide with an extended V3 loop was solved in complex with the X5 Fab and the d1d2 domain of the CD4 receptor. Analysis of the structure revealed that the V3 loop was present in an elongated conformation that was previously not seen in other complexes involving the gp120 protein. An advantageous feature of this crystal structure over previous structures is the organization of the V3 loop in an elongated conformation, compatible with the elicitation of immunodominant antibody response. Table 2 provides the atomic coordinates of the crystal structure of the polypeptide disclosed in SEQ ID NO: 2.

TABLE 2

The structural coordinates of an exemplary gp120 with an extended V3 loop

| | | | | | | | | | | |
|---|---|---|---|---|---|---|---|---|---|---|
| ATOM | 1 | N | VAL | G | 84 | 83.090 | −158.764 | 98.727 | 1.00 | 133.29 |
| ATOM | 2 | CA | VAL | G | 84 | 84.569 | −158.842 | 98.897 | 1.00 | 133.95 |
| ATOM | 3 | C | VAL | G | 84 | 85.258 | −158.165 | 97.714 | 1.00 | 134.16 |
| ATOM | 4 | O | VAL | G | 84 | 85.855 | −158.828 | 96.866 | 1.00 | 134.41 |
| ATOM | 5 | CB | VAL | G | 84 | 85.039 | −160.312 | 98.978 | 1.00 | 134.07 |
| ATOM | 6 | CG1 | VAL | G | 84 | 86.507 | −160.372 | 99.373 | 1.00 | 134.72 |
| ATOM | 7 | CG2 | VAL | G | 84 | 84.181 | −161.078 | 99.974 | 1.00 | 132.76 |
| ATOM | 8 | N | VAL | G | 85 | 85.169 | −156.839 | 97.667 | 1.00 | 134.17 |
| ATOM | 9 | CA | VAL | G | 85 | 85.767 | −156.061 | 96.587 | 1.00 | 133.97 |
| ATOM | 10 | C | VAL | G | 85 | 87.243 | −155.768 | 96.832 | 1.00 | 134.16 |
| ATOM | 11 | O | VAL | G | 85 | 87.711 | −155.788 | 97.971 | 1.00 | 134.47 |
| ATOM | 12 | CB | VAL | G | 85 | 85.026 | −154.715 | 96.401 | 1.00 | 133.69 |
| ATOM | 13 | CG1 | VAL | G | 85 | 85.141 | −153.883 | 97.666 | 1.00 | 133.08 |
| ATOM | 14 | CG2 | VAL | G | 85 | 85.601 | −153.958 | 95.213 | 1.00 | 133.51 |
| ATOM | 15 | N | LEU | G | 86 | 87.971 | −155.505 | 95.751 | 1.00 | 134.10 |
| ATOM | 16 | CA | LEU | G | 86 | 89.392 | −155.192 | 95.827 | 1.00 | 134.30 |
| ATOM | 17 | C | LEU | G | 86 | 89.724 | −154.045 | 94.874 | 1.00 | 134.27 |
| ATOM | 18 | O | LEU | G | 86 | 90.077 | −154.264 | 93.714 | 1.00 | 134.21 |
| ATOM | 19 | CB | LEU | G | 86 | 90.235 | −156.426 | 95.483 | 1.00 | 134.49 |
| ATOM | 20 | CG | LEU | G | 86 | 90.134 | −157.616 | 96.446 | 1.00 | 134.44 |
| ATOM | 21 | CD1 | LEU | G | 86 | 88.803 | −158.331 | 96.264 | 1.00 | 134.35 |
| ATOM | 22 | CD2 | LEU | G | 86 | 91.277 | −158.581 | 96.183 | 1.00 | 134.28 |
| ATOM | 23 | N | GLU | G | 87 | 89.663 | −152.780 | 95.269 | 1.00 | 136.00 |
| ATOM | 24 | CA | GLU | G | 87 | 89.975 | −151.658 | 94.374 | 1.00 | 136.69 |
| ATOM | 25 | C | GLU | G | 87 | 91.472 | −151.398 | 94.342 | 1.00 | 137.59 |
| ATOM | 26 | O | GLU | G | 87 | 92.122 | −151.341 | 95.383 | 1.00 | 138.06 |
| ATOM | 27 | CB | GLU | G | 87 | 89.285 | −150.383 | 94.827 | 1.00 | 135.94 |
| ATOM | 28 | CG | GLU | G | 87 | 87.799 | −150.526 | 94.988 | 1.00 | 136.55 |
| ATOM | 29 | CD | GLU | G | 87 | 87.274 | −149.713 | 96.220 | 1.00 | 137.15 |
| ATOM | 30 | OE1 | GLU | G | 87 | 88.011 | −149.739 | 97.285 | 1.00 | 138.80 |
| ATOM | 31 | OE2 | GLU | G | 87 | 86.143 | −149.072 | 96.141 | 1.00 | 137.57 |
| ATOM | 32 | N | ASN | G | 88 | 91.857 | −151.247 | 93.247 | 1.00 | 136.70 |
| ATOM | 33 | CA | ASN | G | 88 | 93.272 | −150.981 | 92.995 | 1.00 | 137.44 |
| ATOM | 34 | C | ASN | G | 88 | 93.532 | −149.487 | 92.827 | 1.00 | 138.14 |
| ATOM | 35 | O | ASN | G | 88 | 93.615 | −148.984 | 91.707 | 1.00 | 138.46 |
| ATOM | 36 | CB | ASN | G | 88 | 93.735 | −151.732 | 91.741 | 1.00 | 137.16 |
| ATOM | 37 | CG | ASN | G | 88 | 95.046 | −151.199 | 91.192 | 1.00 | 137.46 |
| ATOM | 38 | OD1 | ASN | G | 88 | 96.022 | −151.042 | 91.924 | 1.00 | 137.34 |
| ATOM | 39 | ND2 | ASN | G | 88 | 95.074 | −150.921 | 89.892 | 1.00 | 138.00 |
| ATOM | 40 | N | VAL | G | 89 | 93.664 | −148.778 | 93.944 | 1.00 | 138.65 |
| ATOM | 41 | CA | VAL | G | 89 | 93.906 | −147.342 | 93.893 | 1.00 | 138.82 |
| ATOM | 42 | C | VAL | G | 89 | 94.756 | −146.842 | 95.059 | 1.00 | 139.51 |
| ATOM | 43 | O | VAL | G | 89 | 94.835 | −147.483 | 96.108 | 1.00 | 139.82 |
| ATOM | 44 | CB | VAL | G | 89 | 92.570 | −146.564 | 93.877 | 1.00 | 138.22 |
| ATOM | 45 | CG1 | VAL | G | 89 | 91.797 | −146.834 | 95.158 | 1.00 | 137.56 |
| ATOM | 46 | CG2 | VAL | G | 89 | 92.830 | −145.076 | 93.703 | 1.00 | 137.89 |
| ATOM | 47 | N | THR | G | 90 | 95.394 | −145.693 | 94.856 | 1.00 | 139.18 |
| ATOM | 48 | CA | THR | G | 90 | 96.233 | −145.076 | 95.874 | 1.00 | 138.77 |
| ATOM | 49 | C | THR | G | 90 | 95.355 | −144.357 | 96.903 | 1.00 | 137.61 |
| ATOM | 50 | O | THR | G | 90 | 94.887 | −143.241 | 96.671 | 1.00 | 137.17 |
| ATOM | 51 | CB | THR | G | 90 | 97.224 | −144.075 | 95.229 | 1.00 | 139.07 |
| ATOM | 52 | OG1 | THR | G | 90 | 97.906 | −143.340 | 96.252 | 1.00 | 139.89 |
| ATOM | 53 | CG2 | THR | G | 90 | 96.490 | −143.113 | 94.303 | 1.00 | 138.94 |
| ATOM | 54 | N | GLU | G | 91 | 95.133 | −145.015 | 98.038 | 1.00 | 136.88 |
| ATOM | 55 | CA | GLU | G | 91 | 94.302 | −144.480 | 99.117 | 1.00 | 136.34 |
| ATOM | 56 | C | GLU | G | 91 | 94.989 | −143.439 | 99.999 | 1.00 | 136.12 |
| ATOM | 57 | O | GLU | G | 91 | 95.991 | −143.730 | 100.653 | 1.00 | 136.07 |
| ATOM | 58 | CB | GLU | G | 91 | 93.806 | −145.627 | 100.002 | 1.00 | 135.71 |
| ATOM | 59 | CG | GLU | G | 91 | 92.609 | −146.385 | 99.457 | 1.00 | 134.03 |
| ATOM | 60 | CD | GLU | G | 91 | 91.293 | −145.844 | 99.980 | 1.00 | 132.56 |
| ATOM | 61 | OE1 | GLU | G | 91 | 90.982 | −144.661 | 99.725 | 1.00 | 131.44 |
| ATOM | 62 | OE2 | GLU | G | 91 | 90.568 | −146.606 | 100.653 | 1.00 | 131.61 |
| ATOM | 63 | N | HIS | G | 92 | 94.430 | −142.231 | 100.027 | 1.00 | 135.50 |
| ATOM | 64 | CA | HIS | G | 92 | 94.973 | −141.145 | 100.838 | 1.00 | 134.96 |
| ATOM | 65 | C | HIS | G | 92 | 94.490 | −141.268 | 102.282 | 1.00 | 133.04 |
| ATOM | 66 | O | HIS | G | 92 | 93.411 | −141.798 | 102.537 | 1.00 | 133.15 |
| ATOM | 67 | CB | HIS | G | 92 | 94.541 | −139.793 | 100.266 | 1.00 | 138.44 |
| ATOM | 68 | CG | HIS | G | 92 | 95.064 | −139.522 | 98.889 | 1.00 | 142.66 |
| ATOM | 69 | ND1 | HIS | G | 92 | 94.870 | −138.319 | 98.245 | 1.00 | 144.46 |
| ATOM | 70 | CD2 | HIS | G | 92 | 95.775 | −140.296 | 98.035 | 1.00 | 143.67 |
| ATOM | 71 | CE1 | HIS | G | 92 | 95.441 | −138.362 | 97.054 | 1.00 | 145.80 |
| ATOM | 72 | NE2 | HIS | G | 92 | 95.997 | −139.551 | 96.902 | 1.00 | 145.38 |
| ATOM | 73 | N | PHE | G | 93 | 95.289 | −140.768 | 103.221 | 1.00 | 130.39 |
| ATOM | 74 | CA | PHE | G | 93 | 94.950 | −140.836 | 104.640 | 1.00 | 126.69 |
| ATOM | 75 | C | PHE | G | 93 | 95.478 | −139.628 | 105.413 | 1.00 | 125.30 |
| ATOM | 76 | O | PHE | G | 93 | 96.479 | −139.026 | 105.033 | 1.00 | 125.23 |
| ATOM | 77 | CB | PHE | G | 93 | 95.534 | −142.115 | 105.247 | 1.00 | 125.14 |
| ATOM | 78 | CG | PHE | G | 93 | 94.502 | −143.095 | 105.721 | 1.00 | 123.03 |

TABLE 2-continued

The structural coordinates of an exemplary gp120 with an extended V3 loop

| ATOM | 79  | CD1 | PHE | G | 93  | 93.494  | −143.538 | 104.871 | 1.00 | 122.34 |
|------|-----|-----|-----|---|-----|---------|----------|---------|------|--------|
| ATOM | 80  | CD2 | PHE | G | 93  | 94.558  | −143.600 | 107.013 | 1.00 | 122.41 |
| ATOM | 81  | CE1 | PHE | G | 93  | 92.556  | −144.470 | 105.304 | 1.00 | 121.87 |
| ATOM | 82  | CE2 | PHE | G | 93  | 93.626  | −144.532 | 107.456 | 1.00 | 121.75 |
| ATOM | 83  | CZ  | PHE | G | 93  | 92.623  | −144.969 | 106.599 | 1.00 | 121.40 |
| ATOM | 84  | N   | ASN | G | 94  | 94.800  | −139.283 | 106.502 | 1.00 | 123.37 |
| ATOM | 85  | CA  | ASN | G | 94  | 95.207  | −138.158 | 107.336 | 1.00 | 121.13 |
| ATOM | 86  | C   | ASN | G | 94  | 94.643  | −138.370 | 108.735 | 1.00 | 120.97 |
| ATOM | 87  | O   | ASN | G | 94  | 93.696  | −139.136 | 108.918 | 1.00 | 121.62 |
| ATOM | 88  | CB  | ASN | G | 94  | 94.677  | −136.839 | 106.762 | 1.00 | 118.89 |
| ATOM | 89  | CG  | ASN | G | 94  | 95.603  | −135.670 | 107.034 | 1.00 | 116.56 |
| ATOM | 90  | OD1 | ASN | G | 94  | 96.617  | −135.501 | 106.358 | 1.00 | 115.47 |
| ATOM | 91  | ND2 | ASN | G | 94  | 95.266  | −134.863 | 108.033 | 1.00 | 115.47 |
| ATOM | 92  | N   | MET | G | 95  | 95.217  | −137.687 | 109.719 | 1.00 | 120.03 |
| ATOM | 93  | CA  | MET | G | 95  | 94.754  | −137.820 | 111.094 | 1.00 | 119.35 |
| ATOM | 94  | C   | MET | G | 95  | 94.581  | −136.459 | 111.751 | 1.00 | 118.97 |
| ATOM | 95  | O   | MET | G | 95  | 93.918  | −136.332 | 112.780 | 1.00 | 118.34 |
| ATOM | 96  | CB  | MET | G | 95  | 95.750  | −138.658 | 111.900 | 1.00 | 119.23 |
| ATOM | 97  | CG  | MET | G | 95  | 97.163  | −138.093 | 111.906 | 1.00 | 119.40 |
| ATOM | 98  | SD  | MET | G | 95  | 98.323  | −139.128 | 112.817 | 1.00 | 118.08 |
| ATOM | 99  | CE  | MET | G | 95  | 98.176  | −138.435 | 114.461 | 1.00 | 119.02 |
| ATOM | 100 | N   | TRP | G | 96  | 95.175  | −135.438 | 111.144 | 1.00 | 119.91 |
| ATOM | 101 | CA  | TRP | G | 96  | 95.102  | −134.087 | 111.683 | 1.00 | 121.52 |
| ATOM | 102 | C   | TRP | G | 96  | 93.868  | −133.346 | 111.184 | 1.00 | 123.34 |
| ATOM | 103 | O   | TRP | G | 96  | 93.242  | −132.601 | 111.935 | 1.00 | 123.67 |
| ATOM | 104 | CB  | TRP | G | 96  | 96.371  | −133.312 | 111.323 | 1.00 | 120.30 |
| ATOM | 105 | CG  | TRP | G | 96  | 97.616  | −134.122 | 111.530 | 1.00 | 119.93 |
| ATOM | 106 | CD1 | TRP | G | 96  | 98.257  | −134.889 | 110.599 | 1.00 | 119.95 |
| ATOM | 107 | CD2 | TRP | G | 96  | 98.326  | −134.309 | 112.761 | 1.00 | 119.57 |
| ATOM | 108 | NE1 | TRP | G | 96  | 99.321  | −135.544 | 111.174 | 1.00 | 119.53 |
| ATOM | 109 | CE2 | TRP | G | 96  | 99.387  | −135.204 | 112.498 | 1.00 | 119.10 |
| ATOM | 110 | CE3 | TRP | G | 96  | 98.170  | −133.805 | 114.058 | 1.00 | 119.39 |
| ATOM | 111 | CZ2 | TRP | G | 96  | 100.285 | −135.611 | 113.490 | 1.00 | 118.59 |
| ATOM | 112 | CZ3 | TRP | G | 96  | 99.064  | −134.210 | 115.043 | 1.00 | 117.94 |
| ATOM | 113 | CH2 | TRP | G | 96  | 100.109 | −135.103 | 114.751 | 1.00 | 117.96 |
| ATOM | 114 | N   | LYS | G | 97  | 93.519  | −133.549 | 109.919 | 1.00 | 125.13 |
| ATOM | 115 | CA  | LYS | G | 97  | 92.338  | −132.906 | 109.350 | 1.00 | 127.15 |
| ATOM | 116 | C   | LYS | G | 97  | 91.243  | −133.960 | 109.235 | 1.00 | 127.03 |
| ATOM | 117 | O   | LYS | G | 97  | 90.591  | −134.084 | 108.201 | 1.00 | 127.49 |
| ATOM | 118 | CB  | LYS | G | 97  | 92.656  | −132.324 | 107.965 | 1.00 | 128.56 |
| ATOM | 119 | CG  | LYS | G | 97  | 92.419  | −130.817 | 107.836 | 1.00 | 130.40 |
| ATOM | 120 | CD  | LYS | G | 97  | 93.554  | −129.998 | 108.449 | 1.00 | 131.70 |
| ATOM | 121 | CE  | LYS | G | 97  | 94.673  | −129.727 | 107.447 | 1.00 | 132.45 |
| ATOM | 122 | NZ  | LYS | G | 97  | 94.251  | −128.765 | 106.387 | 1.00 | 132.15 |
| ATOM | 123 | N   | ASN | G | 98  | 91.056  | −134.719 | 110.309 | 1.00 | 127.04 |
| ATOM | 124 | CA  | ASN | G | 98  | 90.060  | −135.781 | 110.347 | 1.00 | 127.06 |
| ATOM | 125 | C   | ASN | G | 98  | 88.846  | −135.370 | 111.174 | 1.00 | 126.76 |
| ATOM | 126 | O   | ASN | G | 98  | 88.979  | −134.956 | 112.325 | 1.00 | 127.98 |
| ATOM | 127 | CB  | ASN | G | 98  | 90.692  | −137.051 | 110.924 | 1.00 | 126.57 |
| ATOM | 128 | CG  | ASN | G | 98  | 89.763  | −138.242 | 110.877 | 1.00 | 125.98 |
| ATOM | 129 | OD1 | ASN | G | 98  | 88.791  | −138.254 | 110.124 | 1.00 | 126.75 |
| ATOM | 130 | ND2 | ASN | G | 98  | 90.067  | −139.262 | 111.670 | 1.00 | 125.44 |
| ATOM | 131 | N   | ASP | G | 99  | 87.665  | −135.494 | 110.580 | 1.00 | 125.41 |
| ATOM | 132 | CA  | ASP | G | 99  | 86.426  | −135.125 | 111.251 | 1.00 | 124.29 |
| ATOM | 133 | C   | ASP | G | 99  | 86.042  | −136.161 | 112.303 | 1.00 | 122.94 |
| ATOM | 134 | O   | ASP | G | 99  | 85.313  | −135.865 | 113.253 | 1.00 | 123.21 |
| ATOM | 135 | CB  | ASP | G | 99  | 85.309  | −134.984 | 110.213 | 1.00 | 125.07 |
| ATOM | 136 | CG  | ASP | G | 99  | 84.039  | −134.383 | 110.792 | 1.00 | 125.46 |
| ATOM | 137 | OD1 | ASP | G | 99  | 83.255  | −135.132 | 111.407 | 1.00 | 125.32 |
| ATOM | 138 | OD2 | ASP | G | 99  | 83.839  | −133.158 | 110.637 | 1.00 | 125.35 |
| ATOM | 139 | N   | MET | G | 100 | 86.548  | −137.376 | 112.128 | 1.00 | 121.29 |
| ATOM | 140 | CA  | MET | G | 100 | 86.264  | −138.472 | 113.044 | 1.00 | 120.02 |
| ATOM | 141 | C   | MET | G | 100 | 86.815  | −138.176 | 114.432 | 1.00 | 119.25 |
| ATOM | 142 | O   | MET | G | 100 | 86.282  | −138.649 | 115.436 | 1.00 | 118.87 |
| ATOM | 143 | CB  | MET | G | 100 | 86.879  | −139.768 | 112.510 | 1.00 | 119.67 |
| ATOM | 144 | CG  | MET | G | 100 | 86.385  | −141.023 | 113.205 | 1.00 | 120.23 |
| ATOM | 145 | SD  | MET | G | 100 | 87.433  | −142.456 | 112.875 | 1.00 | 121.05 |
| ATOM | 146 | CE  | MET | G | 100 | 86.737  | −143.078 | 111.340 | 1.00 | 122.33 |
| ATOM | 147 | N   | VAL | G | 101 | 87.887  | −137.395 | 114.482 | 1.00 | 118.47 |
| ATOM | 148 | CA  | VAL | G | 101 | 88.514  | −137.038 | 115.748 | 1.00 | 117.12 |
| ATOM | 149 | C   | VAL | G | 101 | 87.713  | −135.967 | 116.472 | 1.00 | 115.61 |
| ATOM | 150 | O   | VAL | G | 101 | 87.466  | −136.072 | 117.671 | 1.00 | 114.97 |
| ATOM | 151 | CB  | VAL | G | 101 | 89.943  | −136.515 | 115.529 | 1.00 | 117.83 |
| ATOM | 152 | CG1 | VAL | G | 101 | 90.577  | −136.163 | 116.863 | 1.00 | 119.14 |
| ATOM | 153 | CG2 | VAL | G | 101 | 90.770  | −137.564 | 114.807 | 1.00 | 118.81 |
| ATOM | 154 | N   | GLU | G | 102 | 87.305  | −134.938 | 115.738 | 1.00 | 115.04 |
| ATOM | 155 | CA  | GLU | G | 102 | 86.523  | −133.862 | 116.330 | 1.00 | 115.24 |
| ATOM | 156 | C   | GLU | G | 102 | 85.146  | −134.344 | 116.762 | 1.00 | 114.28 |

TABLE 2-continued

The structural coordinates of an exemplary gp120 with an extended V3 loop

| ATOM | 157 | O | GLU | G | 102 | 84.557 | −133.812 | 117.702 | 1.00 | 113.48 |
|---|---|---|---|---|---|---|---|---|---|---|
| ATOM | 158 | CB | GLU | G | 102 | 86.367 | −132.695 | 115.347 | 1.00 | 116.69 |
| ATOM | 159 | CG | GLU | G | 102 | 87.576 | −131.763 | 115.267 | 1.00 | 118.95 |
| ATOM | 160 | CD | GLU | G | 102 | 88.647 | −132.239 | 114.301 | 1.00 | 120.98 |
| ATOM | 161 | OE1 | GLU | G | 102 | 88.576 | −131.886 | 113.102 | 1.00 | 121.42 |
| ATOM | 162 | OE2 | GLU | G | 102 | 89.561 | −132.969 | 114.738 | 1.00 | 121.86 |
| ATOM | 163 | N | GLN | G | 103 | 84.634 | −135.357 | 116.076 | 1.00 | 114.05 |
| ATOM | 164 | CA | GLN | G | 103 | 83.319 | −135.893 | 116.395 | 1.00 | 114.16 |
| ATOM | 165 | C | GLN | G | 103 | 83.404 | −136.708 | 117.681 | 1.00 | 113.15 |
| ATOM | 166 | O | GLN | G | 103 | 82.510 | −136.657 | 118.525 | 1.00 | 113.27 |
| ATOM | 167 | CB | GLN | G | 103 | 82.824 | −136.756 | 115.230 | 1.00 | 116.01 |
| ATOM | 168 | CG | GLN | G | 103 | 81.313 | −136.831 | 115.089 | 1.00 | 118.46 |
| ATOM | 169 | CD | GLN | G | 103 | 80.887 | −137.109 | 113.660 | 1.00 | 120.20 |
| ATOM | 170 | OE1 | GLN | G | 103 | 81.169 | −138.173 | 113.109 | 1.00 | 121.62 |
| ATOM | 171 | NE2 | GLN | G | 103 | 80.208 | −136.143 | 113.048 | 1.00 | 120.70 |
| ATOM | 172 | N | MET | G | 104 | 84.497 | −137.450 | 117.823 | 1.00 | 112.25 |
| ATOM | 173 | CA | MET | G | 104 | 84.730 | −138.274 | 119.004 | 1.00 | 111.54 |
| ATOM | 174 | C | MET | G | 104 | 84.838 | −137.376 | 120.232 | 1.00 | 112.25 |
| ATOM | 175 | O | MET | G | 104 | 84.313 | −137.689 | 121.299 | 1.00 | 112.78 |
| ATOM | 176 | CB | MET | G | 104 | 86.028 | −139.071 | 118.840 | 1.00 | 110.90 |
| ATOM | 177 | CG | MET | G | 104 | 86.435 | −139.867 | 120.071 | 1.00 | 109.19 |
| ATOM | 178 | SD | MET | G | 104 | 85.518 | −141.402 | 120.304 | 1.00 | 108.60 |
| ATOM | 179 | CE | MET | G | 104 | 86.816 | −142.479 | 120.947 | 1.00 | 106.86 |
| ATOM | 180 | N | GLN | G | 105 | 85.530 | −136.256 | 120.063 | 1.00 | 112.10 |
| ATOM | 181 | CA | GLN | G | 105 | 85.726 | −135.286 | 121.134 | 1.00 | 111.89 |
| ATOM | 182 | C | GLN | G | 105 | 84.399 | −134.844 | 121.744 | 1.00 | 112.91 |
| ATOM | 183 | O | GLN | G | 105 | 84.246 | −134.807 | 122.963 | 1.00 | 113.09 |
| ATOM | 184 | CB | GLN | G | 105 | 86.475 | −134.064 | 120.588 | 1.00 | 110.93 |
| ATOM | 185 | CG | GLN | G | 105 | 86.461 | −132.848 | 121.498 | 1.00 | 108.92 |
| ATOM | 186 | CD | GLN | G | 105 | 87.579 | −132.849 | 122.518 | 1.00 | 108.26 |
| ATOM | 187 | OE1 | GLN | G | 105 | 87.613 | −132.002 | 123.408 | 1.00 | 108.65 |
| ATOM | 188 | NE2 | GLN | G | 105 | 88.505 | −133.792 | 122.388 | 1.00 | 108.60 |
| ATOM | 189 | N | GLU | G | 106 | 83.443 | −134.516 | 120.882 | 1.00 | 113.95 |
| ATOM | 190 | CA | GLU | G | 106 | 82.123 | −134.062 | 121.310 | 1.00 | 114.14 |
| ATOM | 191 | C | GLU | G | 106 | 81.423 | −135.064 | 122.216 | 1.00 | 112.47 |
| ATOM | 192 | O | GLU | G | 106 | 80.694 | −134.683 | 123.129 | 1.00 | 111.33 |
| ATOM | 193 | CB | GLU | G | 106 | 81.240 | −133.790 | 120.085 | 1.00 | 117.22 |
| ATOM | 194 | CG | GLU | G | 106 | 81.847 | −132.829 | 119.069 | 1.00 | 121.88 |
| ATOM | 195 | CD | GLU | G | 106 | 81.831 | −131.385 | 119.534 | 1.00 | 124.83 |
| ATOM | 196 | OE1 | GLU | G | 106 | 80.725 | −130.827 | 119.702 | 1.00 | 127.31 |
| ATOM | 197 | OE2 | GLU | G | 106 | 82.922 | −130.809 | 119.731 | 1.00 | 125.75 |
| ATOM | 198 | N | ASP | G | 107 | 81.651 | −136.347 | 121.961 | 1.00 | 112.07 |
| ATOM | 199 | CA | ASP | G | 107 | 81.025 | −137.407 | 122.739 | 1.00 | 112.28 |
| ATOM | 200 | C | ASP | G | 107 | 81.683 | −137.674 | 124.079 | 1.00 | 110.45 |
| ATOM | 201 | O | ASP | G | 107 | 81.034 | −138.143 | 125.012 | 1.00 | 110.76 |
| ATOM | 202 | CB | ASP | G | 107 | 80.989 | −138.693 | 121.918 | 1.00 | 114.84 |
| ATOM | 203 | CG | ASP | G | 107 | 79.945 | −138.646 | 120.814 | 1.00 | 117.49 |
| ATOM | 204 | OD1 | ASP | G | 107 | 78.775 | −138.970 | 121.099 | 1.00 | 120.99 |
| ATOM | 205 | OD2 | ASP | G | 107 | 80.294 | −138.268 | 119.674 | 1.00 | 117.70 |
| ATOM | 206 | N | ILE | G | 108 | 82.972 | −137.386 | 124.181 | 1.00 | 108.33 |
| ATOM | 207 | CA | ILE | G | 108 | 83.680 | −137.603 | 125.432 | 1.00 | 106.57 |
| ATOM | 208 | C | ILE | G | 108 | 83.295 | −136.515 | 126.419 | 1.00 | 104.72 |
| ATOM | 209 | O | ILE | G | 108 | 83.130 | −136.771 | 127.611 | 1.00 | 105.07 |
| ATOM | 210 | CB | ILE | G | 108 | 85.194 | −137.592 | 125.199 | 1.00 | 107.34 |
| ATOM | 211 | CG1 | ILE | G | 108 | 85.570 | −138.780 | 124.303 | 1.00 | 106.62 |
| ATOM | 212 | CG2 | ILE | G | 108 | 85.931 | −137.666 | 126.532 | 1.00 | 107.53 |
| ATOM | 213 | CD1 | ILE | G | 108 | 86.711 | −138.511 | 123.364 | 1.00 | 106.38 |
| ATOM | 214 | N | ILE | G | 109 | 83.140 | −135.301 | 125.909 | 1.00 | 102.38 |
| ATOM | 215 | CA | ILE | G | 109 | 82.755 | −134.174 | 126.740 | 1.00 | 100.25 |
| ATOM | 216 | C | ILE | G | 109 | 81.357 | −134.416 | 127.284 | 1.00 | 99.75 |
| ATOM | 217 | O | ILE | G | 109 | 81.073 | −134.128 | 128.443 | 1.00 | 100.09 |
| ATOM | 218 | CB | ILE | G | 109 | 82.758 | −132.871 | 125.925 | 1.00 | 99.79 |
| ATOM | 219 | CG1 | ILE | G | 109 | 84.181 | −132.570 | 125.447 | 1.00 | 98.40 |
| ATOM | 220 | CG2 | ILE | G | 109 | 82.219 | −131.728 | 126.764 | 1.00 | 99.76 |
| ATOM | 221 | CD1 | ILE | G | 109 | 84.271 | −131.441 | 124.449 | 1.00 | 97.98 |
| ATOM | 222 | N | SER | G | 110 | 80.493 | −134.963 | 126.436 | 1.00 | 99.49 |
| ATOM | 223 | CA | SER | G | 110 | 79.120 | −135.258 | 126.819 | 1.00 | 99.12 |
| ATOM | 224 | C | SER | G | 110 | 79.098 | −136.336 | 127.897 | 1.00 | 99.07 |
| ATOM | 225 | O | SER | G | 110 | 78.261 | −136.317 | 128.797 | 1.00 | 98.54 |
| ATOM | 226 | CB | SER | G | 110 | 78.329 | −135.732 | 125.601 | 1.00 | 99.18 |
| ATOM | 227 | OG | SER | G | 110 | 76.996 | −136.053 | 125.961 | 1.00 | 99.12 |
| ATOM | 228 | N | LEU | G | 111 | 80.029 | −137.276 | 127.793 | 1.00 | 99.33 |
| ATOM | 229 | CA | LEU | G | 111 | 80.135 | −138.364 | 128.755 | 1.00 | 100.48 |
| ATOM | 230 | C | LEU | G | 111 | 80.790 | −137.873 | 130.041 | 1.00 | 101.49 |
| ATOM | 231 | O | LEU | G | 111 | 80.609 | −138.458 | 131.109 | 1.00 | 101.29 |
| ATOM | 232 | CB | LEU | G | 111 | 80.952 | −139.511 | 128.155 | 1.00 | 100.12 |
| ATOM | 233 | CG | LEU | G | 111 | 80.176 | −140.676 | 127.531 | 1.00 | 100.14 |
| ATOM | 234 | CD1 | LEU | G | 111 | 80.992 | −141.321 | 126.426 | 1.00 | 100.57 |

TABLE 2-continued

The structural coordinates of an exemplary gp120 with an extended V3 loop

| ATOM | 235 | CD2 | LEU | G | 111 | 79.843 | −141.684 | 128.621 | 1.00 | 100.82 |
|---|---|---|---|---|---|---|---|---|---|---|
| ATOM | 236 | N | TRP | G | 112 | 81.553 | −136.791 | 129.928 | 1.00 | 103.03 |
| ATOM | 237 | CA | TRP | G | 112 | 82.238 | −136.210 | 131.076 | 1.00 | 104.23 |
| ATOM | 238 | C | TRP | G | 112 | 81.265 | −135.378 | 131.896 | 1.00 | 105.45 |
| ATOM | 239 | O | TRP | G | 112 | 81.329 | −135.357 | 133.122 | 1.00 | 106.05 |
| ATOM | 240 | CB | TRP | G | 112 | 83.402 | −135.326 | 130.612 | 1.00 | 103.46 |
| ATOM | 241 | CG | TRP | G | 112 | 84.730 | −135.748 | 131.159 | 1.00 | 102.75 |
| ATOM | 242 | CD1 | TRP | G | 112 | 85.403 | −136.903 | 130.881 | 1.00 | 103.42 |
| ATOM | 243 | CD2 | TRP | G | 112 | 85.550 | −135.017 | 132.080 | 1.00 | 101.80 |
| ATOM | 244 | NE1 | TRP | G | 112 | 86.593 | −136.936 | 131.570 | 1.00 | 103.39 |
| ATOM | 245 | CE2 | TRP | G | 112 | 86.708 | −135.792 | 132.313 | 1.00 | 101.79 |
| ATOM | 246 | CE3 | TRP | G | 112 | 85.418 | −133.783 | 132.730 | 1.00 | 100.62 |
| ATOM | 247 | CZ2 | TRP | G | 112 | 87.730 | −135.371 | 133.171 | 1.00 | 100.65 |
| ATOM | 248 | CZ3 | TRP | G | 112 | 86.435 | −133.366 | 133.582 | 1.00 | 100.30 |
| ATOM | 249 | CH2 | TRP | G | 112 | 87.576 | −134.160 | 133.793 | 1.00 | 100.15 |
| ATOM | 250 | N | ASP | G | 113 | 80.361 | −134.693 | 131.207 | 1.00 | 106.82 |
| ATOM | 251 | CA | ASP | G | 113 | 79.376 | −133.862 | 131.879 | 1.00 | 108.44 |
| ATOM | 252 | C | ASP | G | 113 | 78.342 | −134.672 | 132.643 | 1.00 | 108.41 |
| ATOM | 253 | O | ASP | G | 113 | 77.709 | −134.157 | 133.563 | 1.00 | 108.64 |
| ATOM | 254 | CB | ASP | G | 113 | 78.673 | −132.951 | 130.875 | 1.00 | 110.86 |
| ATOM | 255 | CG | ASP | G | 113 | 79.477 | −131.700 | 130.566 | 1.00 | 113.42 |
| ATOM | 256 | OD1 | ASP | G | 113 | 79.640 | −130.866 | 131.479 | 1.00 | 116.27 |
| ATOM | 257 | OD2 | ASP | G | 113 | 79.955 | −131.560 | 129.420 | 1.00 | 115.26 |
| ATOM | 258 | N | GLN | G | 114 | 78.160 | −135.936 | 132.273 | 1.00 | 107.17 |
| ATOM | 259 | CA | GLN | G | 114 | 77.188 | −136.766 | 132.974 | 1.00 | 106.10 |
| ATOM | 260 | C | GLN | G | 114 | 77.874 | −137.744 | 133.923 | 1.00 | 103.76 |
| ATOM | 261 | O | GLN | G | 114 | 77.242 | −138.651 | 134.461 | 1.00 | 104.43 |
| ATOM | 262 | CB | GLN | G | 114 | 76.300 | −137.527 | 131.980 | 1.00 | 109.06 |
| ATOM | 263 | CG | GLN | G | 114 | 77.005 | −138.596 | 131.161 | 1.00 | 113.60 |
| ATOM | 264 | CD | GLN | G | 114 | 76.029 | −139.502 | 130.422 | 1.00 | 116.46 |
| ATOM | 265 | OE1 | GLN | G | 114 | 75.346 | −139.076 | 129.488 | 1.00 | 118.64 |
| ATOM | 266 | NE2 | GLN | G | 114 | 75.951 | −140.758 | 130.850 | 1.00 | 116.28 |
| ATOM | 267 | N | SER | G | 115 | 79.172 | −137.543 | 134.127 | 1.00 | 100.33 |
| ATOM | 268 | CA | SER | G | 115 | 79.956 | −138.393 | 135.014 | 1.00 | 96.91 |
| ATOM | 269 | C | SER | G | 115 | 80.706 | −137.560 | 136.051 | 1.00 | 93.15 |
| ATOM | 270 | O | SER | G | 115 | 80.543 | −137.758 | 137.255 | 1.00 | 93.21 |
| ATOM | 271 | CB | SER | G | 115 | 80.946 | −139.233 | 134.203 | 1.00 | 99.27 |
| ATOM | 272 | OG | SER | G | 115 | 80.275 | −140.234 | 133.457 | 1.00 | 102.68 |
| ATOM | 273 | N | LEU | G | 116 | 81.527 | −136.629 | 135.581 | 1.00 | 88.46 |
| ATOM | 274 | CA | LEU | G | 116 | 82.290 | −135.766 | 136.475 | 1.00 | 84.39 |
| ATOM | 275 | C | LEU | G | 116 | 81.741 | −134.347 | 136.459 | 1.00 | 82.46 |
| ATOM | 276 | O | LEU | G | 116 | 81.977 | −133.591 | 135.519 | 1.00 | 82.86 |
| ATOM | 277 | CB | LEU | G | 116 | 83.767 | −135.750 | 136.068 | 1.00 | 83.85 |
| ATOM | 278 | CG | LEU | G | 116 | 84.646 | −136.857 | 136.656 | 1.00 | 82.12 |
| ATOM | 279 | CD1 | LEU | G | 116 | 85.974 | −136.902 | 135.922 | 1.00 | 82.50 |
| ATOM | 280 | CD2 | LEU | G | 116 | 84.854 | −136.596 | 138.144 | 1.00 | 80.96 |
| ATOM | 281 | N | LYS | G | 117 | 81.000 | −133.995 | 137.503 | 1.00 | 80.71 |
| ATOM | 282 | CA | LYS | G | 117 | 80.407 | −132.668 | 137.619 | 1.00 | 80.17 |
| ATOM | 283 | C | LYS | G | 117 | 81.100 | −131.822 | 138.683 | 1.00 | 77.80 |
| ATOM | 284 | O | LYS | G | 117 | 81.342 | −132.288 | 139.797 | 1.00 | 77.93 |
| ATOM | 285 | CB | LYS | G | 117 | 78.921 | −132.780 | 137.955 | 1.00 | 82.16 |
| ATOM | 286 | CG | LYS | G | 117 | 77.997 | −133.018 | 136.772 | 1.00 | 85.17 |
| ATOM | 287 | CD | LYS | G | 117 | 76.551 | −132.954 | 137.242 | 1.00 | 87.66 |
| ATOM | 288 | CE | LYS | G | 117 | 75.607 | −132.504 | 136.137 | 1.00 | 90.61 |
| ATOM | 289 | NZ | LYS | G | 117 | 74.283 | −132.090 | 136.692 | 1.00 | 87.92 |
| ATOM | 290 | N | PRO | G | 118 | 81.420 | −130.558 | 138.355 | 1.00 | 75.68 |
| ATOM | 291 | CA | PRO | G | 118 | 82.088 | −129.645 | 139.284 | 1.00 | 74.22 |
| ATOM | 292 | C | PRO | G | 118 | 81.059 | −129.021 | 140.206 | 1.00 | 73.71 |
| ATOM | 293 | O | PRO | G | 118 | 79.881 | −128.947 | 139.863 | 1.00 | 75.64 |
| ATOM | 294 | CB | PRO | G | 118 | 82.709 | −128.596 | 138.358 | 1.00 | 73.60 |
| ATOM | 295 | CG | PRO | G | 118 | 82.659 | −129.228 | 136.975 | 1.00 | 74.73 |
| ATOM | 296 | CD | PRO | G | 118 | 81.352 | −129.945 | 137.022 | 1.00 | 75.01 |
| ATOM | 297 | N | CYS | G | 119 | 81.481 | −128.570 | 141.377 | 1.00 | 73.04 |
| ATOM | 298 | CA | CYS | G | 119 | 80.517 | −127.953 | 142.264 | 1.00 | 73.80 |
| ATOM | 299 | C | CYS | G | 119 | 80.324 | −126.491 | 141.888 | 1.00 | 72.46 |
| ATOM | 300 | O | CYS | G | 119 | 79.284 | −125.907 | 142.171 | 1.00 | 73.82 |
| ATOM | 301 | CB | CYS | G | 119 | 80.944 | −128.105 | 143.722 | 1.00 | 77.08 |
| ATOM | 302 | SG | CYS | G | 119 | 79.924 | −129.360 | 144.564 | 1.00 | 86.22 |
| ATOM | 303 | N | VAL | G | 120 | 81.326 | −125.907 | 141.241 | 1.00 | 69.39 |
| ATOM | 304 | CA | VAL | G | 120 | 81.247 | −124.524 | 140.795 | 1.00 | 66.24 |
| ATOM | 305 | C | VAL | G | 120 | 81.939 | −124.437 | 139.445 | 1.00 | 66.78 |
| ATOM | 306 | O | VAL | G | 120 | 83.008 | −125.008 | 139.260 | 1.00 | 67.35 |
| ATOM | 307 | CB | VAL | G | 120 | 81.964 | −123.562 | 141.757 | 1.00 | 65.45 |
| ATOM | 308 | CG1 | VAL | G | 120 | 81.757 | −122.128 | 141.292 | 1.00 | 64.25 |
| ATOM | 309 | CG2 | VAL | G | 120 | 81.448 | −123.745 | 143.167 | 1.00 | 65.16 |
| ATOM | 310 | N | LYS | G | 121 | 81.321 | −123.744 | 138.498 | 1.00 | 68.69 |
| ATOM | 311 | CA | LYS | G | 121 | 81.903 | −123.590 | 137.170 | 1.00 | 71.74 |
| ATOM | 312 | C | LYS | G | 121 | 82.060 | −122.128 | 136.796 | 1.00 | 74.27 |

TABLE 2-continued

The structural coordinates of an exemplary gp120 with an extended V3 loop

| ATOM | 313 | O | LYS | G | 121 | 81.131 | −121.337 | 136.959 | 1.00 | 76.19 |
|---|---|---|---|---|---|---|---|---|---|---|
| ATOM | 314 | CB | LYS | G | 121 | 81.033 | −124.260 | 136.099 | 1.00 | 72.94 |
| ATOM | 315 | CG | LYS | G | 121 | 81.448 | −125.664 | 135.700 | 1.00 | 75.20 |
| ATOM | 316 | CD | LYS | G | 121 | 80.779 | −126.073 | 134.387 | 1.00 | 77.11 |
| ATOM | 317 | CE | LYS | G | 121 | 81.061 | −127.533 | 134.049 | 1.00 | 78.09 |
| ATOM | 318 | NZ | LYS | G | 121 | 80.615 | −127.906 | 132.674 | 1.00 | 79.45 |
| ATOM | 319 | N | LEU | G | 122 | 83.233 | −121.767 | 136.290 | 1.00 | 76.38 |
| ATOM | 320 | CA | LEU | G | 122 | 83.473 | −120.394 | 135.863 | 1.00 | 79.17 |
| ATOM | 321 | C | LEU | G | 122 | 83.757 | −120.376 | 134.371 | 1.00 | 81.74 |
| ATOM | 322 | O | LEU | G | 122 | 84.701 | −121.010 | 133.905 | 1.00 | 82.55 |
| ATOM | 323 | CB | LEU | G | 122 | 84.657 | −119.785 | 136.611 | 1.00 | 79.45 |
| ATOM | 324 | CG | LEU | G | 122 | 84.274 | −118.875 | 137.779 | 1.00 | 78.85 |
| ATOM | 325 | CD1 | LEU | G | 122 | 83.608 | −119.695 | 138.873 | 1.00 | 77.90 |
| ATOM | 326 | CD2 | LEU | G | 122 | 85.521 | −118.189 | 138.306 | 1.00 | 79.94 |
| ATOM | 327 | N | THR | G | 123 | 82.938 | −119.641 | 133.629 | 1.00 | 85.43 |
| ATOM | 328 | CA | THR | G | 123 | 83.092 | −119.563 | 132.186 | 1.00 | 90.13 |
| ATOM | 329 | C | THR | G | 123 | 83.058 | −118.134 | 131.670 | 1.00 | 93.59 |
| ATOM | 330 | O | THR | G | 123 | 82.259 | −117.321 | 132.126 | 1.00 | 94.38 |
| ATOM | 331 | CB | THR | G | 123 | 81.968 | −120.333 | 131.489 | 1.00 | 91.32 |
| ATOM | 332 | OG1 | THR | G | 123 | 81.834 | −121.630 | 132.076 | 1.00 | 93.24 |
| ATOM | 333 | CG2 | THR | G | 123 | 82.256 | −120.494 | 130.011 | 1.00 | 91.25 |
| ATOM | 334 | N | PRO | G | 124 | 83.927 | −117.810 | 130.700 | 1.00 | 97.34 |
| ATOM | 335 | CA | PRO | G | 124 | 83.953 | −116.456 | 130.148 | 1.00 | 100.80 |
| ATOM | 336 | C | PRO | G | 124 | 82.656 | −116.141 | 129.415 | 1.00 | 103.51 |
| ATOM | 337 | O | PRO | G | 124 | 82.392 | −116.686 | 128.346 | 1.00 | 104.31 |
| ATOM | 338 | CB | PRO | G | 124 | 85.163 | −116.493 | 129.211 | 1.00 | 100.91 |
| ATOM | 339 | CG | PRO | G | 124 | 86.068 | −117.489 | 129.882 | 1.00 | 100.12 |
| ATOM | 340 | CD | PRO | G | 124 | 85.075 | −118.584 | 130.199 | 1.00 | 98.73 |
| ATOM | 341 | N | LEU | G | 125 | 81.838 | −115.271 | 129.994 | 1.00 | 107.90 |
| ATOM | 342 | CA | LEU | G | 125 | 80.575 | −114.898 | 129.366 | 1.00 | 112.76 |
| ATOM | 343 | C | LEU | G | 125 | 80.861 | −113.904 | 128.250 | 1.00 | 116.09 |
| ATOM | 344 | O | LEU | G | 125 | 80.624 | −112.709 | 128.406 | 1.00 | 116.30 |
| ATOM | 345 | CB | LEU | G | 125 | 79.648 | −114.256 | 130.398 | 1.00 | 113.40 |
| ATOM | 346 | CG | LEU | G | 125 | 78.192 | −114.016 | 129.992 | 1.00 | 113.32 |
| ATOM | 347 | CD1 | LEU | G | 125 | 77.403 | −115.309 | 130.161 | 1.00 | 114.30 |
| ATOM | 348 | CD2 | LEU | G | 125 | 77.599 | −112.929 | 130.874 | 1.00 | 114.10 |
| ATOM | 349 | N | CYS | G | 126 | 81.378 | −114.395 | 127.128 | 1.00 | 119.58 |
| ATOM | 350 | CA | CYS | G | 126 | 81.708 | −113.515 | 126.016 | 1.00 | 122.95 |
| ATOM | 351 | C | CYS | G | 126 | 80.573 | −113.191 | 125.057 | 1.00 | 125.81 |
| ATOM | 352 | O | CYS | G | 126 | 80.494 | −113.734 | 123.953 | 1.00 | 126.35 |
| ATOM | 353 | CB | CYS | G | 126 | 82.901 | −114.067 | 125.236 | 1.00 | 122.36 |
| ATOM | 354 | SG | CYS | G | 126 | 84.494 | −113.726 | 126.046 | 1.00 | 121.90 |
| ATOM | 355 | N | VAL | G | 127 | 79.696 | −112.296 | 125.497 | 1.00 | 129.15 |
| ATOM | 356 | CA | VAL | G | 127 | 78.566 | −111.852 | 124.693 | 1.00 | 131.76 |
| ATOM | 357 | C | VAL | G | 127 | 78.834 | −110.393 | 124.326 | 1.00 | 132.26 |
| ATOM | 358 | O | VAL | G | 127 | 79.182 | −109.582 | 125.187 | 1.00 | 132.30 |
| ATOM | 359 | CB | VAL | G | 127 | 77.241 | −111.952 | 125.483 | 1.00 | 132.38 |
| ATOM | 360 | CG1 | VAL | G | 127 | 77.304 | −111.072 | 126.721 | 1.00 | 133.33 |
| ATOM | 361 | CG2 | VAL | G | 127 | 76.075 | −111.553 | 124.595 | 1.00 | 133.20 |
| ATOM | 362 | N | GLY | G | 128 | 78.684 | −110.063 | 123.048 | 1.00 | 131.94 |
| ATOM | 363 | CA | GLY | G | 128 | 78.941 | −108.702 | 122.614 | 1.00 | 131.82 |
| ATOM | 364 | C | GLY | G | 128 | 80.436 | −108.454 | 122.541 | 1.00 | 131.76 |
| ATOM | 365 | O | GLY | G | 128 | 81.051 | −108.049 | 123.527 | 1.00 | 131.75 |
| ATOM | 366 | N | ALA | G | 129 | 81.009 | −108.709 | 121.367 | 1.00 | 131.69 |
| ATOM | 367 | CA | ALA | G | 129 | 82.439 | −108.541 | 121.102 | 1.00 | 131.75 |
| ATOM | 368 | C | ALA | G | 129 | 83.240 | −107.898 | 122.232 | 1.00 | 132.17 |
| ATOM | 369 | O | ALA | G | 129 | 84.144 | −108.523 | 122.787 | 1.00 | 132.86 |
| ATOM | 370 | CB | ALA | G | 129 | 82.632 | −107.748 | 119.819 | 1.00 | 131.22 |
| ATOM | 371 | N | GLY | G | 130 | 82.913 | −106.649 | 122.558 | 1.00 | 131.78 |
| ATOM | 372 | CA | GLY | G | 130 | 83.615 | −105.949 | 123.621 | 1.00 | 130.67 |
| ATOM | 373 | C | GLY | G | 130 | 84.005 | −106.869 | 124.763 | 1.00 | 130.19 |
| ATOM | 374 | O | GLY | G | 130 | 83.255 | −107.782 | 125.104 | 1.00 | 130.65 |
| ATOM | 375 | N | SER | G | 195 | 85.182 | −106.632 | 125.341 | 1.00 | 128.61 |
| ATOM | 376 | CA | SER | G | 195 | 85.705 | −107.429 | 126.454 | 1.00 | 126.30 |
| ATOM | 377 | C | SER | G | 195 | 84.590 | −108.085 | 127.275 | 1.00 | 125.16 |
| ATOM | 378 | O | SER | G | 195 | 83.538 | −107.483 | 127.495 | 1.00 | 125.28 |
| ATOM | 379 | CB | SER | G | 195 | 86.570 | −106.538 | 127.345 | 1.00 | 125.36 |
| ATOM | 380 | OG | SER | G | 195 | 87.524 | −105.831 | 126.567 | 1.00 | 121.97 |
| ATOM | 381 | N | CYS | G | 196 | 84.830 | −109.311 | 127.740 | 1.00 | 122.96 |
| ATOM | 382 | CA | CYS | G | 196 | 83.821 | −110.058 | 128.490 | 1.00 | 120.58 |
| ATOM | 383 | C | CYS | G | 196 | 83.992 | −110.143 | 130.010 | 1.00 | 118.42 |
| ATOM | 384 | O | CYS | G | 196 | 84.973 | −109.664 | 130.580 | 1.00 | 117.88 |
| ATOM | 385 | CB | CYS | G | 196 | 83.720 | −111.480 | 127.931 | 1.00 | 120.97 |
| ATOM | 386 | SG | CYS | G | 196 | 84.469 | −111.710 | 126.286 | 1.00 | 122.59 |
| ATOM | 387 | N | ASP | G | 197 | 83.008 | −110.771 | 130.649 | 1.00 | 115.33 |
| ATOM | 388 | CA | ASP | G | 197 | 82.992 | −110.960 | 132.095 | 1.00 | 112.91 |
| ATOM | 389 | C | ASP | G | 197 | 82.935 | −112.461 | 132.366 | 1.00 | 111.21 |
| ATOM | 390 | O | ASP | G | 197 | 82.951 | −113.257 | 131.431 | 1.00 | 111.48 |

TABLE 2-continued

The structural coordinates of an exemplary gp120 with an extended V3 loop

| | | | | | | | | | | |
|---|---|---|---|---|---|---|---|---|---|---|
| ATOM | 391 | CB | ASP | G | 197 | 81.766 | −110.273 | 132.701 | 1.00 | 114.40 |
| ATOM | 392 | CG | ASP | G | 197 | 81.916 | −110.021 | 134.191 | 1.00 | 116.21 |
| ATOM | 393 | OD1 | ASP | G | 197 | 82.826 | −109.253 | 134.563 | 1.00 | 118.31 |
| ATOM | 394 | OD2 | ASP | G | 197 | 81.132 | −110.590 | 134.980 | 1.00 | 116.81 |
| ATOM | 395 | N | THR | G | 198 | 82.848 | −112.849 | 133.633 | 1.00 | 108.94 |
| ATOM | 396 | CA | THR | G | 198 | 82.796 | −114.265 | 133.987 | 1.00 | 106.71 |
| ATOM | 397 | C | THR | G | 198 | 81.395 | −114.729 | 134.392 | 1.00 | 104.11 |
| ATOM | 398 | O | THR | G | 198 | 80.627 | −113.974 | 134.988 | 1.00 | 105.56 |
| ATOM | 399 | CB | THR | G | 198 | 83.760 | −114.574 | 135.144 | 1.00 | 108.19 |
| ATOM | 400 | OG1 | THR | G | 198 | 83.441 | −113.738 | 136.263 | 1.00 | 109.13 |
| ATOM | 401 | CG2 | THR | G | 198 | 85.190 | −114.315 | 134.729 | 1.00 | 108.79 |
| ATOM | 402 | N | SER | G | 199 | 81.071 | −115.978 | 134.068 | 1.00 | 101.10 |
| ATOM | 403 | CA | SER | G | 199 | 79.765 | −116.555 | 134.395 | 1.00 | 98.61 |
| ATOM | 404 | C | SER | G | 199 | 79.905 | −117.657 | 135.444 | 1.00 | 96.43 |
| ATOM | 405 | O | SER | G | 199 | 80.584 | −118.661 | 135.216 | 1.00 | 96.37 |
| ATOM | 406 | CB | SER | G | 199 | 79.113 | −117.124 | 133.130 | 1.00 | 98.18 |
| ATOM | 407 | OG | SER | G | 199 | 77.821 | −117.635 | 133.406 | 1.00 | 96.50 |
| ATOM | 408 | N | VAL | G | 200 | 79.247 | −117.479 | 136.584 | 1.00 | 92.80 |
| ATOM | 409 | CA | VAL | G | 200 | 79.331 | −118.454 | 137.664 | 1.00 | 89.88 |
| ATOM | 410 | C | VAL | G | 200 | 78.074 | −119.310 | 137.797 | 1.00 | 87.32 |
| ATOM | 411 | O | VAL | G | 200 | 76.954 | −118.798 | 137.747 | 1.00 | 86.48 |
| ATOM | 412 | CB | VAL | G | 200 | 79.568 | −117.749 | 139.012 | 1.00 | 90.70 |
| ATOM | 413 | CG1 | VAL | G | 200 | 80.051 | −118.755 | 140.045 | 1.00 | 90.81 |
| ATOM | 414 | CG2 | VAL | G | 200 | 80.568 | −116.621 | 138.831 | 1.00 | 91.35 |
| ATOM | 415 | N | ILE | G | 201 | 78.270 | −120.614 | 137.976 | 1.00 | 84.68 |
| ATOM | 416 | CA | ILE | G | 201 | 77.164 | −121.552 | 138.132 | 1.00 | 81.86 |
| ATOM | 417 | C | ILE | G | 201 | 77.483 | −122.552 | 139.234 | 1.00 | 79.73 |
| ATOM | 418 | O | ILE | G | 201 | 78.516 | −123.210 | 139.197 | 1.00 | 79.56 |
| ATOM | 419 | CB | ILE | G | 201 | 76.904 | −122.366 | 136.840 | 1.00 | 82.08 |
| ATOM | 420 | CG1 | ILE | G | 201 | 76.600 | −121.432 | 135.666 | 1.00 | 85.27 |
| ATOM | 421 | CG2 | ILE | G | 201 | 75.733 | −123.311 | 137.055 | 1.00 | 78.87 |
| ATOM | 422 | CD1 | ILE | G | 201 | 77.830 | −120.796 | 135.047 | 1.00 | 89.69 |
| ATOM | 423 | N | THR | G | 202 | 76.600 | −122.667 | 140.216 | 1.00 | 78.11 |
| ATOM | 424 | CA | THR | G | 202 | 76.812 | −123.613 | 141.299 | 1.00 | 79.05 |
| ATOM | 425 | C | THR | G | 202 | 75.852 | −124.794 | 141.137 | 1.00 | 80.92 |
| ATOM | 426 | O | THR | G | 202 | 74.653 | −124.609 | 140.906 | 1.00 | 81.00 |
| ATOM | 427 | CB | THR | G | 202 | 76.575 | −122.964 | 142.667 | 1.00 | 78.00 |
| ATOM | 428 | OG1 | THR | G | 202 | 75.243 | −122.452 | 142.725 | 1.00 | 79.43 |
| ATOM | 429 | CG2 | THR | G | 202 | 77.549 | −121.842 | 142.901 | 1.00 | 77.99 |
| ATOM | 430 | N | GLN | G | 203 | 76.384 | −126.007 | 141.249 | 1.00 | 81.69 |
| ATOM | 431 | CA | GLN | G | 203 | 75.571 | −127.207 | 141.104 | 1.00 | 81.90 |
| ATOM | 432 | C | GLN | G | 203 | 76.077 | −128.353 | 141.977 | 1.00 | 83.87 |
| ATOM | 433 | O | GLN | G | 203 | 77.208 | −128.325 | 142.457 | 1.00 | 84.27 |
| ATOM | 434 | CB | GLN | G | 203 | 75.548 | −127.628 | 139.635 | 1.00 | 80.36 |
| ATOM | 435 | CG | GLN | G | 203 | 76.918 | −127.643 | 138.979 | 1.00 | 79.24 |
| ATOM | 436 | CD | GLN | G | 203 | 76.859 | −128.040 | 137.514 | 1.00 | 80.19 |
| ATOM | 437 | OE1 | GLN | G | 203 | 76.167 | −127.412 | 136.714 | 1.00 | 79.78 |
| ATOM | 438 | NE2 | GLN | G | 203 | 77.589 | −129.090 | 137.157 | 1.00 | 80.36 |
| ATOM | 439 | N | ALA | G | 204 | 75.232 | −129.359 | 142.181 | 1.00 | 86.42 |
| ATOM | 440 | CA | ALA | G | 204 | 75.593 | −130.514 | 143.003 | 1.00 | 87.19 |
| ATOM | 441 | C | ALA | G | 204 | 76.718 | −131.315 | 142.355 | 1.00 | 87.49 |
| ATOM | 442 | O | ALA | G | 204 | 76.692 | −131.563 | 141.156 | 1.00 | 85.76 |
| ATOM | 443 | CB | ALA | G | 204 | 74.366 | −131.405 | 143.209 | 1.00 | 86.04 |
| ATOM | 444 | N | CYS | G | 205 | 77.702 | −131.728 | 143.149 | 1.00 | 89.57 |
| ATOM | 445 | CA | CYS | G | 205 | 78.808 | −132.510 | 142.609 | 1.00 | 93.38 |
| ATOM | 446 | C | CYS | G | 205 | 79.087 | −133.832 | 143.328 | 1.00 | 96.85 |
| ATOM | 447 | O | CYS | G | 205 | 79.822 | −133.876 | 144.314 | 1.00 | 96.56 |
| ATOM | 448 | CB | CYS | G | 205 | 80.083 | −131.668 | 142.558 | 1.00 | 92.11 |
| ATOM | 449 | SG | CYS | G | 205 | 80.806 | −131.144 | 144.146 | 1.00 | 93.23 |
| ATOM | 450 | N | PRO | G | 206 | 78.506 | −134.938 | 142.826 | 1.00 | 100.89 |
| ATOM | 451 | CA | PRO | G | 206 | 78.691 | −136.266 | 143.416 | 1.00 | 105.01 |
| ATOM | 452 | C | PRO | G | 206 | 80.095 | −136.768 | 143.099 | 1.00 | 109.65 |
| ATOM | 453 | O | PRO | G | 206 | 80.606 | −136.538 | 142.004 | 1.00 | 110.64 |
| ATOM | 454 | CB | PRO | G | 206 | 77.621 | −137.107 | 142.719 | 1.00 | 103.87 |
| ATOM | 455 | CG | PRO | G | 206 | 76.607 | −136.099 | 142.253 | 1.00 | 102.48 |
| ATOM | 456 | CD | PRO | G | 206 | 77.497 | −135.000 | 141.757 | 1.00 | 102.04 |
| ATOM | 457 | N | LYS | G | 207 | 80.719 | −137.456 | 144.044 | 1.00 | 114.22 |
| ATOM | 458 | CA | LYS | G | 207 | 82.064 | −137.960 | 143.823 | 1.00 | 119.19 |
| ATOM | 459 | C | LYS | G | 207 | 82.101 | −139.371 | 143.241 | 1.00 | 123.01 |
| ATOM | 460 | O | LYS | G | 207 | 82.701 | −140.267 | 143.830 | 1.00 | 124.82 |
| ATOM | 461 | CB | LYS | G | 207 | 82.851 | −137.922 | 145.139 | 1.00 | 119.60 |
| ATOM | 462 | CG | LYS | G | 207 | 83.462 | −136.565 | 145.466 | 1.00 | 119.01 |
| ATOM | 463 | CD | LYS | G | 207 | 84.876 | −136.473 | 144.916 | 1.00 | 118.82 |
| ATOM | 464 | CE | LYS | G | 207 | 85.454 | −135.076 | 145.044 | 1.00 | 117.77 |
| ATOM | 465 | NZ | LYS | G | 207 | 84.868 | −134.134 | 144.051 | 1.00 | 116.94 |
| ATOM | 466 | N | ILE | G | 208 | 81.466 | −139.574 | 142.091 | 1.00 | 127.08 |
| ATOM | 467 | CA | ILE | G | 208 | 81.482 | −140.893 | 141.466 | 1.00 | 131.24 |
| ATOM | 468 | C | ILE | G | 208 | 82.668 | −141.008 | 140.512 | 1.00 | 132.68 |

TABLE 2-continued

The structural coordinates of an exemplary gp120 with an extended V3 loop

| ATOM | 469 | O | ILE | G | 208 | 83.143 | −140.004 | 139.984 | 1.00 | 133.21 |
|---|---|---|---|---|---|---|---|---|---|---|
| ATOM | 470 | CB | ILE | G | 208 | 80.184 | −141.174 | 140.682 | 1.00 | 132.20 |
| ATOM | 471 | CG1 | ILE | G | 208 | 79.995 | −140.133 | 139.584 | 1.00 | 132.98 |
| ATOM | 472 | CG2 | ILE | G | 208 | 78.995 | −141.165 | 141.622 | 1.00 | 132.23 |
| ATOM | 473 | CD1 | ILE | G | 208 | 78.847 | −140.446 | 138.655 | 1.00 | 134.64 |
| ATOM | 474 | N | SER | G | 209 | 83.138 | −142.234 | 140.295 | 1.00 | 134.15 |
| ATOM | 475 | CA | SER | G | 209 | 84.284 | −142.480 | 139.429 | 1.00 | 135.70 |
| ATOM | 476 | C | SER | G | 209 | 83.970 | −142.546 | 137.938 | 1.00 | 137.12 |
| ATOM | 477 | O | SER | G | 209 | 83.009 | −143.192 | 137.517 | 1.00 | 138.29 |
| ATOM | 478 | CB | SER | G | 209 | 84.979 | −143.779 | 139.850 | 1.00 | 134.98 |
| ATOM | 479 | OG | SER | G | 209 | 84.086 | −144.875 | 139.771 | 1.00 | 135.08 |
| ATOM | 480 | N | PHE | G | 210 | 84.798 | −141.869 | 137.146 | 1.00 | 137.24 |
| ATOM | 481 | CA | PHE | G | 210 | 84.660 | −141.858 | 135.694 | 1.00 | 137.12 |
| ATOM | 482 | C | PHE | G | 210 | 85.467 | −143.033 | 135.152 | 1.00 | 138.23 |
| ATOM | 483 | O | PHE | G | 210 | 86.687 | −142.950 | 135.018 | 1.00 | 138.35 |
| ATOM | 484 | CB | PHE | G | 210 | 85.200 | −140.546 | 135.121 | 1.00 | 136.15 |
| ATOM | 485 | CG | PHE | G | 210 | 85.309 | −140.538 | 133.623 | 1.00 | 135.14 |
| ATOM | 486 | CD1 | PHE | G | 210 | 84.170 | −140.630 | 132.828 | 1.00 | 134.46 |
| ATOM | 487 | CD2 | PHE | G | 210 | 86.550 | −140.429 | 133.003 | 1.00 | 134.03 |
| ATOM | 488 | CE1 | PHE | G | 210 | 84.266 | −140.612 | 131.436 | 1.00 | 133.36 |
| ATOM | 489 | CE2 | PHE | G | 210 | 86.657 | −140.409 | 131.614 | 1.00 | 133.27 |
| ATOM | 490 | CZ | PHE | G | 210 | 85.513 | −140.499 | 130.829 | 1.00 | 133.06 |
| ATOM | 491 | N | GLU | G | 211 | 84.774 | −144.126 | 134.852 | 1.00 | 139.29 |
| ATOM | 492 | CA | GLU | G | 211 | 85.408 | −145.342 | 134.347 | 1.00 | 140.31 |
| ATOM | 493 | C | GLU | G | 211 | 85.710 | −145.289 | 132.849 | 1.00 | 140.01 |
| ATOM | 494 | O | GLU | G | 211 | 84.856 | −144.906 | 132.049 | 1.00 | 139.77 |
| ATOM | 495 | CB | GLU | G | 211 | 84.515 | −146.543 | 134.648 | 1.00 | 141.10 |
| ATOM | 496 | CG | GLU | G | 211 | 84.410 | −146.875 | 136.128 | 1.00 | 143.21 |
| ATOM | 497 | CD | GLU | G | 211 | 83.070 | −147.479 | 136.492 | 1.00 | 144.76 |
| ATOM | 498 | OE1 | GLU | G | 211 | 82.970 | −148.106 | 137.568 | 1.00 | 145.16 |
| ATOM | 499 | OE2 | GLU | G | 211 | 82.114 | −147.317 | 135.704 | 1.00 | 146.11 |
| ATOM | 500 | N | PRO | G | 212 | 86.933 | −145.685 | 132.452 | 1.00 | 139.56 |
| ATOM | 501 | CA | PRO | G | 212 | 87.358 | −145.686 | 131.050 | 1.00 | 139.07 |
| ATOM | 502 | C | PRO | G | 212 | 86.618 | −146.766 | 130.271 | 1.00 | 138.18 |
| ATOM | 503 | O | PRO | G | 212 | 87.206 | −147.771 | 129.876 | 1.00 | 138.23 |
| ATOM | 504 | CB | PRO | G | 212 | 88.858 | −145.974 | 131.143 | 1.00 | 139.58 |
| ATOM | 505 | CG | PRO | G | 212 | 89.224 | −145.516 | 132.532 | 1.00 | 139.85 |
| ATOM | 506 | CD | PRO | G | 212 | 88.063 | −146.041 | 133.324 | 1.00 | 139.87 |
| ATOM | 507 | N | ILE | G | 213 | 85.327 | −146.555 | 130.049 | 1.00 | 136.58 |
| ATOM | 508 | CA | ILE | G | 213 | 84.515 | −147.525 | 129.329 | 1.00 | 134.44 |
| ATOM | 509 | C | ILE | G | 213 | 84.844 | −147.553 | 127.836 | 1.00 | 133.16 |
| ATOM | 510 | O | ILE | G | 213 | 84.751 | −146.535 | 127.154 | 1.00 | 133.40 |
| ATOM | 511 | CB | ILE | G | 213 | 83.025 | −147.221 | 129.538 | 1.00 | 134.18 |
| ATOM | 512 | CG1 | ILE | G | 213 | 82.170 | −148.233 | 128.780 | 1.00 | 133.60 |
| ATOM | 513 | CG2 | ILE | G | 213 | 82.728 | −145.797 | 129.093 | 1.00 | 134.56 |
| ATOM | 514 | CD1 | ILE | G | 213 | 80.713 | −148.192 | 129.175 | 1.00 | 134.43 |
| ATOM | 515 | N | PRO | G | 214 | 85.234 | −148.730 | 127.316 | 1.00 | 131.77 |
| ATOM | 516 | CA | PRO | G | 214 | 85.590 | −148.929 | 125.907 | 1.00 | 130.01 |
| ATOM | 517 | C | PRO | G | 214 | 84.603 | −148.292 | 124.933 | 1.00 | 128.02 |
| ATOM | 518 | O | PRO | G | 214 | 83.390 | −148.418 | 125.097 | 1.00 | 126.87 |
| ATOM | 519 | CB | PRO | G | 214 | 85.637 | −150.449 | 125.787 | 1.00 | 130.90 |
| ATOM | 520 | CG | PRO | G | 214 | 86.169 | −150.848 | 127.130 | 1.00 | 131.42 |
| ATOM | 521 | CD | PRO | G | 214 | 85.294 | −150.012 | 128.043 | 1.00 | 131.68 |
| ATOM | 522 | N | ILE | G | 215 | 85.131 | −147.609 | 123.922 | 1.00 | 126.22 |
| ATOM | 523 | CA | ILE | G | 215 | 84.297 | −146.949 | 122.928 | 1.00 | 124.39 |
| ATOM | 524 | C | ILE | G | 215 | 84.606 | −147.439 | 121.517 | 1.00 | 123.82 |
| ATOM | 525 | O | ILE | G | 215 | 85.758 | −147.432 | 121.089 | 1.00 | 123.83 |
| ATOM | 526 | CB | ILE | G | 215 | 84.498 | −145.419 | 122.972 | 1.00 | 124.52 |
| ATOM | 527 | CG1 | ILE | G | 215 | 83.798 | −144.853 | 124.204 | 1.00 | 124.66 |
| ATOM | 528 | CG2 | ILE | G | 215 | 83.946 | −144.775 | 121.712 | 1.00 | 123.95 |
| ATOM | 529 | CD1 | ILE | G | 215 | 82.301 | −145.085 | 124.207 | 1.00 | 126.40 |
| ATOM | 530 | N | HIS | G | 216 | 83.567 | −147.855 | 120.801 | 1.00 | 122.91 |
| ATOM | 531 | CA | HIS | G | 216 | 83.707 | −148.337 | 119.436 | 1.00 | 122.26 |
| ATOM | 532 | C | HIS | G | 216 | 83.005 | −147.378 | 118.487 | 1.00 | 122.82 |
| ATOM | 533 | O | HIS | G | 216 | 81.782 | −147.263 | 118.512 | 1.00 | 122.59 |
| ATOM | 534 | CB | HIS | G | 216 | 83.064 | −149.719 | 119.279 | 1.00 | 121.11 |
| ATOM | 535 | CG | HIS | G | 216 | 83.602 | −150.756 | 120.212 | 1.00 | 120.49 |
| ATOM | 536 | ND1 | HIS | G | 216 | 84.919 | −151.164 | 120.198 | 1.00 | 120.39 |
| ATOM | 537 | CD2 | HIS | G | 216 | 82.988 | −151.501 | 121.161 | 1.00 | 120.37 |
| ATOM | 538 | CE1 | HIS | G | 216 | 85.091 | −152.118 | 121.096 | 1.00 | 120.82 |
| ATOM | 539 | NE2 | HIS | G | 216 | 83.935 | −152.341 | 121.694 | 1.00 | 120.97 |
| ATOM | 540 | N | TYR | G | 217 | 83.767 | −146.678 | 117.657 | 1.00 | 124.13 |
| ATOM | 541 | CA | TYR | G | 217 | 83.154 | −145.780 | 116.686 | 1.00 | 126.48 |
| ATOM | 542 | C | TYR | G | 217 | 82.753 | −146.675 | 115.523 | 1.00 | 129.20 |
| ATOM | 543 | O | TYR | G | 217 | 83.591 | −147.022 | 114.699 | 1.00 | 129.59 |
| ATOM | 544 | CB | TYR | G | 217 | 84.159 | −144.736 | 116.202 | 1.00 | 124.57 |
| ATOM | 545 | CG | TYR | G | 217 | 83.551 | −143.677 | 115.308 | 1.00 | 123.48 |
| ATOM | 546 | CD1 | TYR | G | 217 | 82.990 | −142.522 | 115.849 | 1.00 | 123.73 |

TABLE 2-continued

The structural coordinates of an exemplary gp120 with an extended V3 loop

| ATOM | 547 | CD2 | TYR | G | 217 | 83.531 | −143.831 | 113.921 | 1.00 | 123.00 |
| --- | --- | --- | --- | --- | --- | --- | --- | --- | --- | --- |
| ATOM | 548 | CE1 | TYR | G | 217 | 82.427 | −141.541 | 115.033 | 1.00 | 123.68 |
| ATOM | 549 | CE2 | TYR | G | 217 | 82.969 | −142.858 | 113.096 | 1.00 | 123.64 |
| ATOM | 550 | CZ | TYR | G | 217 | 82.420 | −141.715 | 113.658 | 1.00 | 123.44 |
| ATOM | 551 | OH | TYR | G | 217 | 81.865 | −140.755 | 112.843 | 1.00 | 122.11 |
| ATOM | 552 | N | CYS | G | 218 | 81.486 | −147.070 | 115.462 | 1.00 | 132.82 |
| ATOM | 553 | CA | CYS | G | 218 | 81.054 | −147.947 | 114.380 | 1.00 | 136.36 |
| ATOM | 554 | C | CYS | G | 218 | 80.480 | −147.158 | 113.202 | 1.00 | 137.85 |
| ATOM | 555 | O | CYS | G | 218 | 80.050 | −146.011 | 113.357 | 1.00 | 138.46 |
| ATOM | 556 | CB | CYS | G | 218 | 79.996 | −148.934 | 114.866 | 1.00 | 137.77 |
| ATOM | 557 | SG | CYS | G | 218 | 80.410 | −149.952 | 116.317 | 1.00 | 141.47 |
| ATOM | 558 | N | ALA | G | 219 | 80.464 | −147.790 | 112.031 | 1.00 | 138.84 |
| ATOM | 559 | CA | ALA | G | 219 | 79.953 | −147.180 | 110.806 | 1.00 | 139.87 |
| ATOM | 560 | C | ALA | G | 219 | 78.437 | −147.322 | 110.652 | 1.00 | 140.76 |
| ATOM | 561 | O | ALA | G | 219 | 77.887 | −148.416 | 110.788 | 1.00 | 140.94 |
| ATOM | 562 | CB | ALA | G | 219 | 80.656 | −147.793 | 109.599 | 1.00 | 139.80 |
| ATOM | 563 | N | PRO | G | 220 | 77.747 | −146.211 | 110.347 | 1.00 | 141.32 |
| ATOM | 564 | CA | PRO | G | 220 | 76.292 | −146.186 | 110.168 | 1.00 | 142.02 |
| ATOM | 565 | C | PRO | G | 220 | 75.880 | −146.886 | 108.878 | 1.00 | 142.66 |
| ATOM | 566 | O | PRO | G | 220 | 76.725 | −147.227 | 108.052 | 1.00 | 143.05 |
| ATOM | 567 | CB | PRO | G | 220 | 75.973 | −144.688 | 110.128 | 1.00 | 141.53 |
| ATOM | 568 | CG | PRO | G | 220 | 77.147 | −144.054 | 110.841 | 1.00 | 141.13 |
| ATOM | 569 | CD | PRO | G | 220 | 78.287 | −144.845 | 110.277 | 1.00 | 140.75 |
| ATOM | 570 | N | ALA | G | 221 | 74.580 | −147.099 | 108.708 | 1.00 | 143.48 |
| ATOM | 571 | CA | ALA | G | 221 | 74.079 | −147.743 | 107.503 | 1.00 | 143.71 |
| ATOM | 572 | C | ALA | G | 221 | 74.302 | −146.806 | 106.325 | 1.00 | 142.82 |
| ATOM | 573 | O | ALA | G | 221 | 73.748 | −145.708 | 106.284 | 1.00 | 142.96 |
| ATOM | 574 | CB | ALA | G | 221 | 72.603 | −148.056 | 107.654 | 1.00 | 144.82 |
| ATOM | 575 | N | GLY | G | 222 | 75.115 | −147.243 | 105.370 | 1.00 | 140.94 |
| ATOM | 576 | CA | GLY | G | 222 | 75.396 | −146.417 | 104.209 | 1.00 | 138.32 |
| ATOM | 577 | C | GLY | G | 222 | 76.792 | −145.835 | 104.279 | 1.00 | 136.29 |
| ATOM | 578 | O | GLY | G | 222 | 77.201 | −145.050 | 103.424 | 1.00 | 136.34 |
| ATOM | 579 | N | PHE | G | 223 | 77.526 | −146.238 | 105.311 | 1.00 | 134.39 |
| ATOM | 580 | CA | PHE | G | 223 | 78.890 | −145.777 | 105.537 | 1.00 | 132.34 |
| ATOM | 581 | C | PHE | G | 223 | 79.777 | −146.927 | 106.001 | 1.00 | 130.44 |
| ATOM | 582 | O | PHE | G | 223 | 79.291 | −147.921 | 106.542 | 1.00 | 130.04 |
| ATOM | 583 | CB | PHE | G | 223 | 78.894 | −144.670 | 106.592 | 1.00 | 132.84 |
| ATOM | 584 | CG | PHE | G | 223 | 78.252 | −143.397 | 106.134 | 1.00 | 133.73 |
| ATOM | 585 | CD1 | PHE | G | 223 | 78.935 | −142.528 | 105.292 | 1.00 | 133.66 |
| ATOM | 586 | CD2 | PHE | G | 223 | 76.967 | −143.061 | 106.547 | 1.00 | 134.47 |
| ATOM | 587 | CE1 | PHE | G | 223 | 78.352 | −141.337 | 104.868 | 1.00 | 134.19 |
| ATOM | 588 | CE2 | PHE | G | 223 | 76.371 | −141.871 | 106.128 | 1.00 | 135.20 |
| ATOM | 589 | CZ | PHE | G | 223 | 77.067 | −141.007 | 105.287 | 1.00 | 135.04 |
| ATOM | 590 | N | ALA | G | 224 | 81.081 | −146.784 | 105.788 | 1.00 | 128.35 |
| ATOM | 591 | CA | ALA | G | 224 | 82.038 | −147.806 | 106.189 | 1.00 | 126.17 |
| ATOM | 592 | C | ALA | G | 224 | 83.350 | −147.160 | 106.618 | 1.00 | 124.72 |
| ATOM | 593 | O | ALA | G | 224 | 83.741 | −146.125 | 106.083 | 1.00 | 124.65 |
| ATOM | 594 | CB | ALA | G | 224 | 82.280 | −148.763 | 105.033 | 1.00 | 126.68 |
| ATOM | 595 | N | ILE | G | 225 | 84.028 | −147.771 | 107.583 | 1.00 | 122.82 |
| ATOM | 596 | CA | ILE | G | 225 | 85.296 | −147.238 | 108.062 | 1.00 | 121.00 |
| ATOM | 597 | C | ILE | G | 225 | 86.481 | −148.096 | 107.630 | 1.00 | 119.79 |
| ATOM | 598 | O | ILE | G | 225 | 86.477 | −149.316 | 107.801 | 1.00 | 119.03 |
| ATOM | 599 | CB | ILE | G | 225 | 85.293 | −147.094 | 109.603 | 1.00 | 121.03 |
| ATOM | 600 | CG1 | ILE | G | 225 | 84.767 | −148.369 | 110.258 | 1.00 | 120.98 |
| ATOM | 601 | CG2 | ILE | G | 225 | 84.438 | −145.910 | 110.010 | 1.00 | 120.24 |
| ATOM | 602 | CD1 | ILE | G | 225 | 85.843 | −149.311 | 110.722 | 1.00 | 120.08 |
| ATOM | 603 | N | LEU | G | 226 | 87.488 | −147.442 | 107.061 | 1.00 | 118.45 |
| ATOM | 604 | CA | LEU | G | 226 | 88.692 | −148.108 | 106.575 | 1.00 | 117.87 |
| ATOM | 605 | C | LEU | G | 226 | 89.778 | −148.170 | 107.644 | 1.00 | 117.93 |
| ATOM | 606 | O | LEU | G | 226 | 90.048 | −147.181 | 108.320 | 1.00 | 117.78 |
| ATOM | 607 | CB | LEU | G | 226 | 89.233 | −147.360 | 105.355 | 1.00 | 117.84 |
| ATOM | 608 | CG | LEU | G | 226 | 88.416 | −147.465 | 104.067 | 1.00 | 117.99 |
| ATOM | 609 | CD1 | LEU | G | 226 | 88.412 | −146.134 | 103.329 | 1.00 | 117.75 |
| ATOM | 610 | CD2 | LEU | G | 226 | 89.000 | −148.571 | 103.202 | 1.00 | 118.64 |
| ATOM | 611 | N | LYS | G | 227 | 90.405 | −149.333 | 107.784 | 1.00 | 118.28 |
| ATOM | 612 | CA | LYS | G | 227 | 91.465 | −149.518 | 108.766 | 1.00 | 119.16 |
| ATOM | 613 | C | LYS | G | 227 | 92.802 | −149.761 | 108.070 | 1.00 | 120.69 |
| ATOM | 614 | O | LYS | G | 227 | 93.016 | −150.822 | 107.486 | 1.00 | 121.36 |
| ATOM | 615 | CB | LYS | G | 227 | 91.137 | −150.710 | 109.674 | 1.00 | 117.69 |
| ATOM | 616 | CG | LYS | G | 227 | 92.124 | −150.907 | 110.812 | 1.00 | 116.17 |
| ATOM | 617 | CD | LYS | G | 227 | 92.021 | −152.297 | 111.418 | 1.00 | 115.50 |
| ATOM | 618 | CE | LYS | G | 227 | 93.166 | −152.535 | 112.389 | 1.00 | 114.84 |
| ATOM | 619 | NZ | LYS | G | 227 | 93.253 | −153.948 | 112.850 | 1.00 | 113.75 |
| ATOM | 620 | N | CYS | G | 228 | 93.701 | −148.782 | 108.125 | 1.00 | 122.52 |
| ATOM | 621 | CA | CYS | G | 228 | 95.013 | −148.931 | 107.494 | 1.00 | 124.88 |
| ATOM | 622 | C | CYS | G | 228 | 95.858 | −149.909 | 108.317 | 1.00 | 125.15 |
| ATOM | 623 | O | CYS | G | 228 | 96.285 | −149.591 | 109.427 | 1.00 | 125.31 |
| ATOM | 624 | CB | CYS | G | 228 | 95.704 | −147.560 | 107.380 | 1.00 | 127.78 |

TABLE 2-continued

The structural coordinates of an exemplary gp120 with an extended V3 loop

| ATOM | 625 | SG | CYS | G | 228 | 97.401 | −147.576 | 106.702 | 1.00 | 132.08 |
|---|---|---|---|---|---|---|---|---|---|---|
| ATOM | 626 | N | ASN | G | 229 | 96.082 | −151.103 | 107.768 | 1.00 | 125.50 |
| ATOM | 627 | CA | ASN | G | 229 | 96.859 | −152.135 | 108.452 | 1.00 | 126.07 |
| ATOM | 628 | C | ASN | G | 229 | 98.350 | −152.104 | 108.155 | 1.00 | 126.43 |
| ATOM | 629 | O | ASN | G | 229 | 99.019 | −153.135 | 108.224 | 1.00 | 126.40 |
| ATOM | 630 | CB | ASN | G | 229 | 96.331 | −153.533 | 108.114 | 1.00 | 127.05 |
| ATOM | 631 | CG | ASN | G | 229 | 95.052 | −153.874 | 108.855 | 1.00 | 128.07 |
| ATOM | 632 | OD1 | ASN | G | 229 | 93.960 | −153.472 | 108.455 | 1.00 | 129.09 |
| ATOM | 633 | ND2 | ASN | G | 229 | 95.185 | −154.612 | 109.953 | 1.00 | 128.62 |
| ATOM | 634 | N | ASP | G | 230 | 98.873 | −150.931 | 107.822 | 1.00 | 127.09 |
| ATOM | 635 | CA | ASP | G | 230 | 100.298 | −150.803 | 107.541 | 1.00 | 128.18 |
| ATOM | 636 | C | ASP | G | 230 | 101.112 | −151.040 | 108.808 | 1.00 | 129.06 |
| ATOM | 637 | O | ASP | G | 230 | 100.792 | −150.501 | 109.867 | 1.00 | 129.47 |
| ATOM | 638 | CB | ASP | G | 230 | 100.611 | −149.413 | 106.994 | 1.00 | 128.04 |
| ATOM | 639 | CG | ASP | G | 230 | 100.772 | −149.400 | 105.486 | 1.00 | 128.21 |
| ATOM | 640 | OD1 | ASP | G | 230 | 99.829 | −149.813 | 104.784 | 1.00 | 129.16 |
| ATOM | 641 | OD2 | ASP | G | 230 | 101.844 | −148.972 | 105.012 | 1.00 | 127.80 |
| ATOM | 642 | N | LYS | G | 231 | 102.174 | −151.832 | 108.693 | 1.00 | 130.19 |
| ATOM | 643 | CA | LYS | G | 231 | 103.034 | −152.142 | 109.833 | 1.00 | 131.50 |
| ATOM | 644 | C | LYS | G | 231 | 103.705 | −150.890 | 110.406 | 1.00 | 132.11 |
| ATOM | 645 | O | LYS | G | 231 | 103.862 | −150.762 | 111.620 | 1.00 | 132.26 |
| ATOM | 646 | CB | LYS | G | 231 | 104.103 | −153.164 | 109.420 | 1.00 | 131.22 |
| ATOM | 647 | CG | LYS | G | 231 | 103.545 | −154.525 | 108.994 | 1.00 | 131.29 |
| ATOM | 648 | CD | LYS | G | 231 | 102.981 | −155.296 | 110.185 | 1.00 | 131.06 |
| ATOM | 649 | CE | LYS | G | 231 | 102.249 | −156.559 | 109.747 | 1.00 | 130.17 |
| ATOM | 650 | NZ | LYS | G | 231 | 101.640 | −157.279 | 110.904 | 1.00 | 128.78 |
| ATOM | 651 | N | THR | G | 232 | 104.100 | −149.970 | 109.531 | 1.00 | 132.72 |
| ATOM | 652 | CA | THR | G | 232 | 104.750 | −148.738 | 109.960 | 1.00 | 133.16 |
| ATOM | 653 | C | THR | G | 232 | 104.170 | −147.577 | 109.173 | 1.00 | 133.64 |
| ATOM | 654 | O | THR | G | 232 | 104.627 | −147.283 | 108.072 | 1.00 | 134.29 |
| ATOM | 655 | CB | THR | G | 232 | 106.264 | −148.791 | 109.698 | 1.00 | 133.30 |
| ATOM | 656 | OG1 | THR | G | 232 | 106.807 | −149.976 | 110.286 | 1.00 | 133.19 |
| ATOM | 657 | CG2 | THR | G | 232 | 106.956 | −147.583 | 110.304 | 1.00 | 134.01 |
| ATOM | 658 | N | PHE | G | 233 | 103.162 | −146.923 | 109.741 | 1.00 | 133.70 |
| ATOM | 659 | CA | PHE | G | 233 | 102.506 | −145.798 | 109.086 | 1.00 | 134.07 |
| ATOM | 660 | C | PHE | G | 233 | 102.979 | −144.482 | 109.689 | 1.00 | 133.22 |
| ATOM | 661 | O | PHE | G | 233 | 103.185 | −144.394 | 110.897 | 1.00 | 133.97 |
| ATOM | 662 | CB | PHE | G | 233 | 100.990 | −145.927 | 109.240 | 1.00 | 135.95 |
| ATOM | 663 | CG | PHE | G | 233 | 100.211 | −145.067 | 108.293 | 1.00 | 138.56 |
| ATOM | 664 | CD1 | PHE | G | 233 | 100.413 | −145.170 | 106.922 | 1.00 | 139.24 |
| ATOM | 665 | CD2 | PHE | G | 233 | 99.267 | −144.163 | 108.766 | 1.00 | 139.44 |
| ATOM | 666 | CE1 | PHE | G | 233 | 99.687 | −144.386 | 106.031 | 1.00 | 140.27 |
| ATOM | 667 | CE2 | PHE | G | 233 | 98.534 | −143.372 | 107.885 | 1.00 | 140.80 |
| ATOM | 668 | CZ | PHE | G | 233 | 98.744 | −143.485 | 106.513 | 1.00 | 140.90 |
| ATOM | 669 | N | ASN | G | 234 | 103.137 | −143.455 | 108.857 | 1.00 | 132.11 |
| ATOM | 670 | CA | ASN | G | 234 | 103.606 | −142.163 | 109.353 | 1.00 | 131.12 |
| ATOM | 671 | C | ASN | G | 234 | 102.497 | −141.209 | 109.789 | 1.00 | 130.16 |
| ATOM | 672 | O | ASN | G | 234 | 102.776 | −140.083 | 110.195 | 1.00 | 130.18 |
| ATOM | 673 | CB | ASN | G | 234 | 104.479 | −141.463 | 108.305 | 1.00 | 131.40 |
| ATOM | 674 | CG | ASN | G | 234 | 103.667 | −140.844 | 107.184 | 1.00 | 131.18 |
| ATOM | 675 | OD1 | ASN | G | 234 | 103.832 | −139.666 | 106.859 | 1.00 | 130.27 |
| ATOM | 676 | ND2 | ASN | G | 234 | 102.791 | −141.636 | 106.581 | 1.00 | 130.32 |
| ATOM | 677 | N | GLY | G | 235 | 101.246 | −141.649 | 109.711 | 1.00 | 128.79 |
| ATOM | 678 | CA | GLY | G | 235 | 100.152 | −140.784 | 110.119 | 1.00 | 127.79 |
| ATOM | 679 | C | GLY | G | 235 | 99.372 | −140.177 | 108.967 | 1.00 | 127.12 |
| ATOM | 680 | O | GLY | G | 235 | 98.186 | −140.456 | 108.808 | 1.00 | 126.69 |
| ATOM | 681 | N | LYS | G | 236 | 100.023 | −139.334 | 108.171 | 1.00 | 126.63 |
| ATOM | 682 | CA | LYS | G | 236 | 99.361 | −138.704 | 107.031 | 1.00 | 126.89 |
| ATOM | 683 | C | LYS | G | 236 | 100.036 | −139.113 | 105.726 | 1.00 | 128.87 |
| ATOM | 684 | O | LYS | G | 236 | 101.238 | −139.357 | 105.693 | 1.00 | 129.74 |
| ATOM | 685 | CB | LYS | G | 236 | 99.386 | −137.177 | 107.169 | 1.00 | 124.81 |
| ATOM | 686 | CG | LYS | G | 236 | 100.774 | −136.597 | 107.412 | 1.00 | 122.07 |
| ATOM | 687 | CD | LYS | G | 236 | 100.770 | −135.068 | 107.512 | 1.00 | 120.19 |
| ATOM | 688 | CE | LYS | G | 236 | 100.766 | −134.390 | 106.146 | 1.00 | 118.90 |
| ATOM | 689 | NZ | LYS | G | 236 | 100.848 | −132.901 | 106.254 | 1.00 | 116.47 |
| ATOM | 690 | N | GLY | G | 237 | 99.254 | −139.183 | 104.654 | 1.00 | 130.44 |
| ATOM | 691 | CA | GLY | G | 237 | 99.797 | −139.569 | 103.364 | 1.00 | 132.18 |
| ATOM | 692 | C | GLY | G | 237 | 99.066 | −140.755 | 102.767 | 1.00 | 133.46 |
| ATOM | 693 | O | GLY | G | 237 | 97.921 | −141.018 | 103.138 | 1.00 | 134.02 |
| ATOM | 694 | N | PRO | G | 238 | 99.693 | −141.487 | 101.838 | 1.00 | 133.68 |
| ATOM | 695 | CA | PRO | G | 238 | 99.075 | −142.651 | 101.200 | 1.00 | 133.81 |
| ATOM | 696 | C | PRO | G | 238 | 99.297 | −143.951 | 101.985 | 1.00 | 133.94 |
| ATOM | 697 | O | PRO | G | 238 | 100.427 | −144.267 | 102.353 | 1.00 | 133.93 |
| ATOM | 698 | CB | PRO | G | 238 | 99.759 | −142.702 | 99.827 | 1.00 | 133.77 |
| ATOM | 699 | CG | PRO | G | 238 | 100.463 | −141.336 | 99.685 | 1.00 | 134.36 |
| ATOM | 700 | CD | PRO | G | 238 | 100.886 | −141.069 | 101.093 | 1.00 | 134.13 |
| ATOM | 701 | N | CYS | G | 239 | 98.228 | −144.703 | 102.245 | 1.00 | 134.81 |
| ATOM | 702 | CA | CYS | G | 239 | 98.361 | −145.976 | 102.959 | 1.00 | 136.32 |

TABLE 2-continued

The structural coordinates of an exemplary gp120 with an extended V3 loop

| | | | | | | | | | | |
|---|---|---|---|---|---|---|---|---|---|---|
| ATOM | 703 | C | CYS | G | 239 | 98.399 | −147.104 | 101.926 | 1.00 | 136.72 |
| ATOM | 704 | O | CYS | G | 239 | 97.640 | −147.086 | 100.958 | 1.00 | 136.38 |
| ATOM | 705 | CB | CYS | G | 239 | 97.187 | −146.196 | 103.935 | 1.00 | 136.44 |
| ATOM | 706 | SG | CYS | G | 239 | 97.192 | −147.860 | 104.696 | 1.00 | 136.59 |
| ATOM | 707 | N | LYS | G | 240 | 99.274 | −148.086 | 102.136 | 1.00 | 138.05 |
| ATOM | 708 | CA | LYS | G | 240 | 99.405 | −149.212 | 101.207 | 1.00 | 139.87 |
| ATOM | 709 | C | LYS | G | 240 | 98.342 | −150.286 | 101.428 | 1.00 | 139.47 |
| ATOM | 710 | O | LYS | G | 240 | 97.436 | −150.447 | 100.613 | 1.00 | 139.04 |
| ATOM | 711 | CB | LYS | G | 240 | 100.802 | −149.837 | 101.324 | 1.00 | 141.13 |
| ATOM | 712 | CG | LYS | G | 240 | 101.941 | −148.901 | 100.918 | 1.00 | 142.81 |
| ATOM | 713 | CD | LYS | G | 240 | 103.310 | −149.526 | 101.173 | 1.00 | 143.74 |
| ATOM | 714 | CE | LYS | G | 240 | 104.429 | −148.549 | 100.835 | 1.00 | 143.78 |
| ATOM | 715 | NZ | LYS | G | 240 | 105.786 | −149.103 | 101.110 | 1.00 | 143.33 |
| ATOM | 716 | N | ASN | G | 241 | 98.458 | −151.020 | 102.530 | 1.00 | 139.54 |
| ATOM | 717 | CA | ASN | G | 241 | 97.499 | −152.070 | 102.850 | 1.00 | 139.69 |
| ATOM | 718 | C | ASN | G | 241 | 96.445 | −151.535 | 103.811 | 1.00 | 139.92 |
| ATOM | 719 | O | ASN | G | 241 | 96.774 | −151.092 | 104.908 | 1.00 | 139.69 |
| ATOM | 720 | CB | ASN | G | 241 | 98.207 | −153.257 | 103.505 | 1.00 | 139.80 |
| ATOM | 721 | CG | ASN | G | 241 | 97.305 | −154.468 | 103.640 | 1.00 | 140.13 |
| ATOM | 722 | OD1 | ASN | G | 241 | 97.503 | −155.314 | 104.512 | 1.00 | 139.63 |
| ATOM | 723 | ND2 | ASN | G | 241 | 96.312 | −154.563 | 102.763 | 1.00 | 139.93 |
| ATOM | 724 | N | VAL | G | 242 | 95.182 | −151.588 | 103.405 | 1.00 | 139.96 |
| ATOM | 725 | CA | VAL | G | 242 | 94.098 | −151.102 | 104.249 | 1.00 | 140.28 |
| ATOM | 726 | C | VAL | G | 242 | 92.840 | −151.950 | 104.097 | 1.00 | 140.63 |
| ATOM | 727 | O | VAL | G | 242 | 92.326 | −152.114 | 102.991 | 1.00 | 141.19 |
| ATOM | 728 | CB | VAL | G | 242 | 93.759 | −149.631 | 103.905 | 1.00 | 140.31 |
| ATOM | 729 | CG1 | VAL | G | 242 | 93.609 | −149.479 | 102.400 | 1.00 | 139.72 |
| ATOM | 730 | CG2 | VAL | G | 242 | 92.476 | −149.210 | 104.607 | 1.00 | 140.48 |
| ATOM | 731 | N | SER | G | 243 | 92.350 | −152.486 | 105.211 | 1.00 | 140.58 |
| ATOM | 732 | CA | SER | G | 243 | 91.149 | −153.322 | 105.211 | 1.00 | 140.55 |
| ATOM | 733 | C | SER | G | 243 | 89.925 | −152.489 | 105.588 | 1.00 | 140.69 |
| ATOM | 734 | O | SER | G | 243 | 90.002 | −151.264 | 105.656 | 1.00 | 140.64 |
| ATOM | 735 | CB | SER | G | 243 | 91.308 | −154.467 | 106.213 | 1.00 | 140.83 |
| ATOM | 736 | OG | SER | G | 243 | 91.381 | −153.972 | 107.536 | 1.00 | 140.52 |
| ATOM | 737 | N | THR | G | 244 | 88.804 | −153.157 | 105.845 | 1.00 | 141.03 |
| ATOM | 738 | CA | THR | G | 244 | 87.582 | −152.460 | 106.212 | 1.00 | 141.52 |
| ATOM | 739 | C | THR | G | 244 | 86.765 | −153.217 | 107.244 | 1.00 | 142.08 |
| ATOM | 740 | O | THR | G | 244 | 86.149 | −154.231 | 106.927 | 1.00 | 141.97 |
| ATOM | 741 | CB | THR | G | 244 | 86.683 | −152.231 | 104.983 | 1.00 | 141.57 |
| ATOM | 742 | OG1 | THR | G | 244 | 87.375 | −151.421 | 104.032 | 1.00 | 142.02 |
| ATOM | 743 | CG2 | THR | G | 244 | 85.395 | −151.532 | 105.384 | 1.00 | 140.17 |
| ATOM | 744 | N | VAL | G | 245 | 86.769 | −152.726 | 108.476 | 1.00 | 142.71 |
| ATOM | 745 | CA | VAL | G | 245 | 86.005 | −153.338 | 109.549 | 1.00 | 143.44 |
| ATOM | 746 | C | VAL | G | 245 | 84.747 | −152.503 | 109.763 | 1.00 | 143.75 |
| ATOM | 747 | O | VAL | G | 245 | 84.627 | −151.413 | 109.204 | 1.00 | 143.15 |
| ATOM | 748 | CB | VAL | G | 245 | 86.821 | −153.377 | 110.853 | 1.00 | 144.12 |
| ATOM | 749 | CG1 | VAL | G | 245 | 87.881 | −154.460 | 110.778 | 1.00 | 144.77 |
| ATOM | 750 | CG2 | VAL | G | 245 | 87.479 | −152.032 | 111.086 | 1.00 | 144.53 |
| ATOM | 751 | N | GLN | G | 246 | 83.808 | −153.006 | 110.557 | 1.00 | 144.36 |
| ATOM | 752 | CA | GLN | G | 246 | 82.577 | −152.266 | 110.799 | 1.00 | 144.77 |
| ATOM | 753 | C | GLN | G | 246 | 82.652 | −151.364 | 112.024 | 1.00 | 144.15 |
| ATOM | 754 | O | GLN | G | 246 | 82.087 | −150.272 | 112.025 | 1.00 | 143.24 |
| ATOM | 755 | CB | GLN | G | 246 | 81.392 | −153.227 | 110.918 | 1.00 | 146.20 |
| ATOM | 756 | CG | GLN | G | 246 | 81.220 | −154.117 | 109.699 | 1.00 | 148.95 |
| ATOM | 757 | CD | GLN | G | 246 | 81.195 | −153.327 | 108.400 | 1.00 | 150.00 |
| ATOM | 758 | OE1 | GLN | G | 246 | 80.344 | −152.461 | 108.202 | 1.00 | 150.67 |
| ATOM | 759 | NE2 | GLN | G | 246 | 82.136 | −153.623 | 107.510 | 1.00 | 149.89 |
| ATOM | 760 | N | CYS | G | 247 | 83.338 | −151.814 | 113.069 | 1.00 | 143.81 |
| ATOM | 761 | CA | CYS | G | 247 | 83.474 | −150.999 | 114.274 | 1.00 | 143.17 |
| ATOM | 762 | C | CYS | G | 247 | 84.949 | −150.785 | 114.595 | 1.00 | 142.65 |
| ATOM | 763 | O | CYS | G | 247 | 85.796 | −151.613 | 114.255 | 1.00 | 142.71 |
| ATOM | 764 | CB | CYS | G | 247 | 82.810 | −151.662 | 115.485 | 1.00 | 142.99 |
| ATOM | 765 | SG | CYS | G | 247 | 80.988 | −151.740 | 115.542 | 1.00 | 143.43 |
| ATOM | 766 | N | THR | G | 248 | 85.247 | −149.676 | 115.262 | 1.00 | 141.73 |
| ATOM | 767 | CA | THR | G | 248 | 86.613 | −149.336 | 115.640 | 1.00 | 140.76 |
| ATOM | 768 | C | THR | G | 248 | 87.070 | −150.095 | 116.883 | 1.00 | 140.31 |
| ATOM | 769 | O | THR | G | 248 | 86.258 | −150.456 | 117.731 | 1.00 | 140.20 |
| ATOM | 770 | CB | THR | G | 248 | 86.725 | −147.838 | 115.923 | 1.00 | 140.39 |
| ATOM | 771 | OG1 | THR | G | 248 | 86.168 | −147.112 | 114.824 | 1.00 | 141.14 |
| ATOM | 772 | CG2 | THR | G | 248 | 88.169 | −147.433 | 116.094 | 1.00 | 140.10 |
| ATOM | 773 | N | HIS | G | 249 | 88.375 | −150.325 | 116.991 | 1.00 | 139.86 |
| ATOM | 774 | CA | HIS | G | 249 | 88.932 | −151.035 | 118.138 | 1.00 | 139.38 |
| ATOM | 775 | C | HIS | G | 249 | 88.597 | −150.355 | 119.464 | 1.00 | 137.88 |
| ATOM | 776 | O | HIS | G | 249 | 88.282 | −149.167 | 119.501 | 1.00 | 138.46 |
| ATOM | 777 | CB | HIS | G | 249 | 90.449 | −151.170 | 117.990 | 1.00 | 140.83 |
| ATOM | 778 | CG | HIS | G | 249 | 90.872 | −152.257 | 117.049 | 1.00 | 143.17 |
| ATOM | 779 | ND1 | HIS | G | 249 | 90.448 | −152.316 | 115.739 | 1.00 | 143.35 |
| ATOM | 780 | CD2 | HIS | G | 249 | 91.689 | −153.323 | 117.227 | 1.00 | 143.40 |

TABLE 2-continued

The structural coordinates of an exemplary gp120 with an extended V3 loop

| ATOM | 781 | CE1 | HIS | G | 249 | 90.986 | −153.371 | 115.151 | 1.00 | 143.13 |
|---|---|---|---|---|---|---|---|---|---|---|
| ATOM | 782 | NE2 | HIS | G | 249 | 91.743 | −153.998 | 116.032 | 1.00 | 143.09 |
| ATOM | 783 | N | GLY | G | 250 | 88.672 | −151.119 | 120.550 | 1.00 | 135.79 |
| ATOM | 784 | CA | GLY | G | 250 | 88.359 | −150.585 | 121.865 | 1.00 | 132.31 |
| ATOM | 785 | C | GLY | G | 250 | 89.255 | −149.450 | 122.328 | 1.00 | 129.65 |
| ATOM | 786 | O | GLY | G | 250 | 90.404 | −149.674 | 122.714 | 1.00 | 129.34 |
| ATOM | 787 | N | ILE | G | 251 | 88.723 | −148.232 | 122.302 | 1.00 | 126.82 |
| ATOM | 788 | CA | ILE | G | 251 | 89.464 | −147.053 | 122.729 | 1.00 | 123.65 |
| ATOM | 789 | C | ILE | G | 251 | 89.083 | −146.696 | 124.159 | 1.00 | 121.43 |
| ATOM | 790 | O | ILE | G | 251 | 87.906 | −146.528 | 124.468 | 1.00 | 121.14 |
| ATOM | 791 | CB | ILE | G | 251 | 89.145 | −145.841 | 121.836 | 1.00 | 123.65 |
| ATOM | 792 | CG1 | ILE | G | 251 | 89.420 | −146.199 | 120.375 | 1.00 | 124.47 |
| ATOM | 793 | CG2 | ILE | G | 251 | 89.983 | −144.643 | 122.259 | 1.00 | 122.65 |
| ATOM | 794 | CD1 | ILE | G | 251 | 90.843 | −146.656 | 120.116 | 1.00 | 125.76 |
| ATOM | 795 | N | ARG | G | 252 | 90.082 | −146.581 | 125.025 | 1.00 | 119.23 |
| ATOM | 796 | CA | ARG | G | 252 | 89.857 | −146.237 | 126.422 | 1.00 | 117.32 |
| ATOM | 797 | C | ARG | G | 252 | 89.886 | −144.713 | 126.553 | 1.00 | 114.89 |
| ATOM | 798 | O | ARG | G | 252 | 90.918 | −144.088 | 126.322 | 1.00 | 114.47 |
| ATOM | 799 | CB | ARG | G | 252 | 90.959 | −146.854 | 127.291 | 1.00 | 119.04 |
| ATOM | 800 | CG | ARG | G | 252 | 91.398 | −148.252 | 126.860 | 1.00 | 120.89 |
| ATOM | 801 | CD | ARG | G | 252 | 90.441 | −149.350 | 127.320 | 1.00 | 123.64 |
| ATOM | 802 | NE | ARG | G | 252 | 90.658 | −149.735 | 128.715 | 1.00 | 125.39 |
| ATOM | 803 | CZ | ARG | G | 252 | 90.032 | −150.741 | 129.319 | 1.00 | 125.75 |
| ATOM | 804 | NH1 | ARG | G | 252 | 89.145 | −151.468 | 128.653 | 1.00 | 126.03 |
| ATOM | 805 | NH2 | ARG | G | 252 | 90.296 | −151.025 | 130.589 | 1.00 | 124.96 |
| ATOM | 806 | N | PRO | G | 253 | 88.749 | −144.093 | 126.923 | 1.00 | 113.15 |
| ATOM | 807 | CA | PRO | G | 253 | 88.674 | −142.635 | 127.073 | 1.00 | 112.07 |
| ATOM | 808 | C | PRO | G | 253 | 89.467 | −142.080 | 128.254 | 1.00 | 111.17 |
| ATOM | 809 | O | PRO | G | 253 | 88.925 | −141.891 | 129.346 | 1.00 | 111.86 |
| ATOM | 810 | CB | PRO | G | 253 | 87.178 | −142.389 | 127.228 | 1.00 | 111.80 |
| ATOM | 811 | CG | PRO | G | 253 | 86.754 | −143.589 | 128.011 | 1.00 | 112.54 |
| ATOM | 812 | CD | PRO | G | 253 | 87.441 | −144.700 | 127.232 | 1.00 | 113.08 |
| ATOM | 813 | N | VAL | G | 254 | 90.746 | −141.807 | 128.022 | 1.00 | 109.24 |
| ATOM | 814 | CA | VAL | G | 254 | 91.622 | −141.274 | 129.057 | 1.00 | 106.74 |
| ATOM | 815 | C | VAL | G | 254 | 92.049 | −139.851 | 128.722 | 1.00 | 106.15 |
| ATOM | 816 | O | VAL | G | 254 | 92.714 | −139.615 | 127.712 | 1.00 | 105.35 |
| ATOM | 817 | CB | VAL | G | 254 | 92.894 | −142.136 | 129.198 | 1.00 | 106.43 |
| ATOM | 818 | CG1 | VAL | G | 254 | 93.815 | −141.539 | 130.252 | 1.00 | 105.45 |
| ATOM | 819 | CG2 | VAL | G | 254 | 92.516 | −143.559 | 129.568 | 1.00 | 105.32 |
| ATOM | 820 | N | VAL | G | 255 | 91.659 | −138.906 | 129.567 | 1.00 | 105.48 |
| ATOM | 821 | CA | VAL | G | 255 | 92.020 | −137.511 | 129.363 | 1.00 | 104.38 |
| ATOM | 822 | C | VAL | G | 255 | 93.205 | −137.137 | 130.244 | 1.00 | 102.82 |
| ATOM | 823 | O | VAL | G | 255 | 93.042 | −136.827 | 131.423 | 1.00 | 103.17 |
| ATOM | 824 | CB | VAL | G | 255 | 90.835 | −136.573 | 129.684 | 1.00 | 103.63 |
| ATOM | 825 | CG1 | VAL | G | 255 | 89.960 | −136.398 | 128.452 | 1.00 | 102.60 |
| ATOM | 826 | CG2 | VAL | G | 255 | 90.013 | −137.153 | 130.821 | 1.00 | 103.74 |
| ATOM | 827 | N | SER | G | 256 | 94.399 | −137.177 | 129.664 | 1.00 | 101.35 |
| ATOM | 828 | CA | SER | G | 256 | 95.619 | −136.849 | 130.391 | 1.00 | 100.45 |
| ATOM | 829 | C | SER | G | 256 | 96.587 | −136.050 | 129.530 | 1.00 | 99.76 |
| ATOM | 830 | O | SER | G | 256 | 96.492 | −136.053 | 128.304 | 1.00 | 99.01 |
| ATOM | 831 | CB | SER | G | 256 | 96.298 | −138.133 | 130.875 | 1.00 | 100.56 |
| ATOM | 832 | OG | SER | G | 256 | 96.534 | −139.020 | 129.799 | 1.00 | 100.95 |
| ATOM | 833 | N | THR | G | 257 | 97.529 | −135.379 | 130.182 | 1.00 | 99.86 |
| ATOM | 834 | CA | THR | G | 257 | 98.513 | −134.566 | 129.479 | 1.00 | 100.65 |
| ATOM | 835 | C | THR | G | 257 | 99.914 | −135.174 | 129.524 | 1.00 | 101.63 |
| ATOM | 836 | O | THR | G | 257 | 100.217 | −136.011 | 130.380 | 1.00 | 101.64 |
| ATOM | 837 | CB | THR | G | 257 | 98.581 | −133.145 | 130.078 | 1.00 | 99.95 |
| ATOM | 838 | OG1 | THR | G | 257 | 98.775 | −133.230 | 131.496 | 1.00 | 97.28 |
| ATOM | 839 | CG2 | THR | G | 257 | 97.307 | −132.392 | 129.795 | 1.00 | 100.77 |
| ATOM | 840 | N | GLN | G | 258 | 100.762 | −134.744 | 128.591 | 1.00 | 101.38 |
| ATOM | 841 | CA | GLN | G | 258 | 102.140 | −135.218 | 128.506 | 1.00 | 101.30 |
| ATOM | 842 | C | GLN | G | 258 | 102.259 | −136.706 | 128.194 | 1.00 | 101.52 |
| ATOM | 843 | O | GLN | G | 258 | 102.841 | −137.083 | 127.180 | 1.00 | 101.61 |
| ATOM | 844 | CB | GLN | G | 258 | 102.879 | −134.899 | 129.807 | 1.00 | 102.03 |
| ATOM | 845 | CG | GLN | G | 258 | 102.869 | −133.420 | 130.152 | 1.00 | 104.23 |
| ATOM | 846 | CD | GLN | G | 258 | 103.675 | −133.098 | 131.394 | 1.00 | 105.40 |
| ATOM | 847 | OE1 | GLN | G | 258 | 103.500 | −133.721 | 132.440 | 1.00 | 106.32 |
| ATOM | 848 | NE2 | GLN | G | 258 | 104.560 | −132.114 | 131.286 | 1.00 | 107.50 |
| ATOM | 849 | N | LEU | G | 259 | 101.713 | −137.546 | 129.068 | 1.00 | 101.69 |
| ATOM | 850 | CA | LEU | G | 259 | 101.768 | −138.993 | 128.881 | 1.00 | 102.17 |
| ATOM | 851 | C | LEU | G | 259 | 100.423 | −139.538 | 128.414 | 1.00 | 102.41 |
| ATOM | 852 | O | LEU | G | 259 | 99.373 | −139.022 | 128.788 | 1.00 | 102.52 |
| ATOM | 853 | CB | LEU | G | 259 | 102.160 | −139.681 | 130.196 | 1.00 | 101.92 |
| ATOM | 854 | CG | LEU | G | 259 | 103.530 | −139.358 | 130.810 | 1.00 | 101.73 |
| ATOM | 855 | CD1 | LEU | G | 259 | 103.500 | −139.663 | 132.298 | 1.00 | 99.97 |
| ATOM | 856 | CD2 | LEU | G | 259 | 104.617 | −140.161 | 130.111 | 1.00 | 101.60 |
| ATOM | 857 | N | LEU | G | 260 | 100.465 | −140.582 | 127.593 | 1.00 | 102.49 |
| ATOM | 858 | CA | LEU | G | 260 | 99.251 | −141.217 | 127.088 | 1.00 | 102.67 |

TABLE 2-continued

The structural coordinates of an exemplary gp120 with an extended V3 loop

| | | | | | | | | | | |
|---|---|---|---|---|---|---|---|---|---|---|
| ATOM | 859 | C | LEU | G | 260 | 99.110 | −142.568 | 127.778 | 1.00 | 103.61 |
| ATOM | 860 | O | LEU | G | 260 | 99.966 | −143.437 | 127.621 | 1.00 | 103.69 |
| ATOM | 861 | CB | LEU | G | 260 | 99.353 | −141.409 | 125.576 | 1.00 | 101.68 |
| ATOM | 862 | CG | LEU | G | 260 | 99.448 | −140.122 | 124.752 | 1.00 | 101.95 |
| ATOM | 863 | CD1 | LEU | G | 260 | 99.953 | −140.434 | 123.355 | 1.00 | 104.05 |
| ATOM | 864 | CD2 | LEU | G | 260 | 98.086 | −139.457 | 124.703 | 1.00 | 102.22 |
| ATOM | 865 | N | LEU | G | 261 | 98.030 | −142.748 | 128.533 | 1.00 | 105.17 |
| ATOM | 866 | CA | LEU | G | 261 | 97.815 | −143.991 | 129.276 | 1.00 | 106.41 |
| ATOM | 867 | C | LEU | G | 261 | 96.661 | −144.836 | 128.744 | 1.00 | 107.21 |
| ATOM | 868 | O | LEU | G | 261 | 95.708 | −144.314 | 128.167 | 1.00 | 106.94 |
| ATOM | 869 | CB | LEU | G | 261 | 97.549 | −143.661 | 130.743 | 1.00 | 105.72 |
| ATOM | 870 | CG | LEU | G | 261 | 98.232 | −142.392 | 131.272 | 1.00 | 104.79 |
| ATOM | 871 | CD1 | LEU | G | 261 | 97.660 | −142.057 | 132.637 | 1.00 | 105.02 |
| ATOM | 872 | CD2 | LEU | G | 261 | 99.741 | −142.577 | 131.340 | 1.00 | 103.55 |
| ATOM | 873 | N | ASN | G | 262 | 96.752 | −146.147 | 128.959 | 1.00 | 108.66 |
| ATOM | 874 | CA | ASN | G | 262 | 95.724 | −147.091 | 128.515 | 1.00 | 110.01 |
| ATOM | 875 | C | ASN | G | 262 | 95.280 | −146.877 | 127.074 | 1.00 | 112.35 |
| ATOM | 876 | O | ASN | G | 262 | 94.183 | −146.376 | 126.822 | 1.00 | 113.39 |
| ATOM | 877 | CB | ASN | G | 262 | 94.502 | −147.021 | 129.432 | 1.00 | 108.26 |
| ATOM | 878 | CG | ASN | G | 262 | 94.817 | −147.452 | 130.846 | 1.00 | 107.34 |
| ATOM | 879 | OD1 | ASN | G | 262 | 95.692 | −148.294 | 131.054 | 1.00 | 106.57 |
| ATOM | 880 | ND2 | ASN | G | 262 | 94.093 | −146.901 | 131.819 | 1.00 | 107.98 |
| ATOM | 881 | N | GLY | G | 263 | 96.129 | −147.276 | 126.132 | 1.00 | 114.75 |
| ATOM | 882 | CA | GLY | G | 263 | 95.801 | −147.115 | 124.728 | 1.00 | 117.52 |
| ATOM | 883 | C | GLY | G | 263 | 96.326 | −148.237 | 123.856 | 1.00 | 119.64 |
| ATOM | 884 | O | GLY | G | 263 | 96.747 | −149.284 | 124.354 | 1.00 | 119.72 |
| ATOM | 885 | N | SER | G | 264 | 96.308 | −148.008 | 122.547 | 1.00 | 121.07 |
| ATOM | 886 | CA | SER | G | 264 | 96.771 | −148.992 | 121.578 | 1.00 | 122.04 |
| ATOM | 887 | C | SER | G | 264 | 98.291 | −149.038 | 121.482 | 1.00 | 123.78 |
| ATOM | 888 | O | SER | G | 264 | 98.949 | −148.003 | 121.362 | 1.00 | 123.31 |
| ATOM | 889 | CB | SER | G | 264 | 96.178 | −148.678 | 120.201 | 1.00 | 120.42 |
| ATOM | 890 | OG | SER | G | 264 | 96.593 | −149.632 | 119.242 | 1.00 | 120.43 |
| ATOM | 891 | N | LEU | G | 265 | 98.844 | −150.244 | 121.540 | 1.00 | 126.40 |
| ATOM | 892 | CA | LEU | G | 265 | 100.286 | −150.421 | 121.448 | 1.00 | 129.15 |
| ATOM | 893 | C | LEU | G | 265 | 100.693 | −150.823 | 120.037 | 1.00 | 130.72 |
| ATOM | 894 | O | LEU | G | 265 | 99.983 | −151.573 | 119.368 | 1.00 | 130.95 |
| ATOM | 895 | CB | LEU | G | 265 | 100.764 | −151.493 | 122.433 | 1.00 | 130.79 |
| ATOM | 896 | CG | LEU | G | 265 | 100.641 | −151.191 | 123.929 | 1.00 | 132.07 |
| ATOM | 897 | CD1 | LEU | G | 265 | 99.572 | −152.079 | 124.562 | 1.00 | 132.65 |
| ATOM | 898 | CD2 | LEU | G | 265 | 101.988 | −151.433 | 124.590 | 1.00 | 131.38 |
| ATOM | 899 | N | ALA | G | 266 | 101.838 | −150.322 | 119.586 | 1.00 | 132.23 |
| ATOM | 900 | CA | ALA | G | 266 | 102.339 | −150.651 | 118.259 | 1.00 | 134.12 |
| ATOM | 901 | C | ALA | G | 266 | 102.910 | −152.065 | 118.269 | 1.00 | 135.84 |
| ATOM | 902 | O | ALA | G | 266 | 103.783 | −152.381 | 119.077 | 1.00 | 136.72 |
| ATOM | 903 | CB | ALA | G | 266 | 103.413 | −149.656 | 117.848 | 1.00 | 133.87 |
| ATOM | 904 | N | GLU | G | 267 | 102.417 | −152.911 | 117.370 | 1.00 | 137.31 |
| ATOM | 905 | CA | GLU | G | 267 | 102.878 | −154.294 | 117.286 | 1.00 | 138.28 |
| ATOM | 906 | C | GLU | G | 267 | 104.287 | −154.420 | 116.704 | 1.00 | 138.43 |
| ATOM | 907 | O | GLU | G | 267 | 104.941 | −155.449 | 116.877 | 1.00 | 138.51 |
| ATOM | 908 | CB | GLU | G | 267 | 101.913 | −155.128 | 116.435 | 1.00 | 139.08 |
| ATOM | 909 | CG | GLU | G | 267 | 101.055 | −156.140 | 117.199 | 1.00 | 140.98 |
| ATOM | 910 | CD | GLU | G | 267 | 100.029 | −155.491 | 118.109 | 1.00 | 142.29 |
| ATOM | 911 | OE1 | GLU | G | 267 | 100.397 | −155.083 | 119.230 | 1.00 | 143.33 |
| ATOM | 912 | OE2 | GLU | G | 267 | 98.855 | −155.381 | 117.696 | 1.00 | 142.39 |
| ATOM | 913 | N | GLU | G | 268 | 104.752 | −153.384 | 116.011 | 1.00 | 138.17 |
| ATOM | 914 | CA | GLU | G | 268 | 106.084 | −153.414 | 115.408 | 1.00 | 137.57 |
| ATOM | 915 | C | GLU | G | 268 | 107.102 | −152.595 | 116.197 | 1.00 | 136.57 |
| ATOM | 916 | O | GLU | G | 268 | 107.669 | −153.080 | 117.175 | 1.00 | 135.78 |
| ATOM | 917 | CB | GLU | G | 268 | 106.017 | −152.915 | 113.959 | 1.00 | 137.43 |
| ATOM | 918 | CG | GLU | G | 268 | 105.211 | −153.810 | 113.019 | 1.00 | 137.50 |
| ATOM | 919 | CD | GLU | G | 268 | 105.925 | −155.107 | 112.673 | 1.00 | 136.95 |
| ATOM | 920 | OE1 | GLU | G | 268 | 106.938 | −155.053 | 111.943 | 1.00 | 136.48 |
| ATOM | 921 | OE2 | GLU | G | 268 | 105.474 | −156.178 | 113.133 | 1.00 | 135.94 |
| ATOM | 922 | N | GLU | G | 269 | 107.332 | −151.358 | 115.767 | 1.00 | 136.24 |
| ATOM | 923 | CA | GLU | G | 269 | 108.289 | −150.478 | 116.434 | 1.00 | 135.49 |
| ATOM | 924 | C | GLU | G | 269 | 107.654 | −149.157 | 116.855 | 1.00 | 134.06 |
| ATOM | 925 | O | GLU | G | 269 | 106.488 | −148.888 | 116.558 | 1.00 | 133.72 |
| ATOM | 926 | CB | GLU | G | 269 | 109.470 | −150.193 | 115.500 | 1.00 | 136.19 |
| ATOM | 927 | CG | GLU | G | 269 | 110.272 | −151.422 | 115.099 | 1.00 | 136.58 |
| ATOM | 928 | CD | GLU | G | 269 | 111.252 | −151.862 | 116.170 | 1.00 | 136.55 |
| ATOM | 929 | OE1 | GLU | G | 269 | 112.182 | −151.086 | 116.479 | 1.00 | 136.08 |
| ATOM | 930 | OE2 | GLU | G | 269 | 111.095 | −152.982 | 116.700 | 1.00 | 136.04 |
| ATOM | 931 | N | VAL | G | 270 | 108.431 | −148.335 | 117.553 | 1.00 | 132.32 |
| ATOM | 932 | CA | VAL | G | 270 | 107.958 | −147.031 | 117.994 | 1.00 | 130.76 |
| ATOM | 933 | C | VAL | G | 270 | 107.775 | −146.124 | 116.783 | 1.00 | 129.81 |
| ATOM | 934 | O | VAL | G | 270 | 108.685 | −145.973 | 115.968 | 1.00 | 130.00 |
| ATOM | 935 | CB | VAL | G | 270 | 108.966 | −146.377 | 118.966 | 1.00 | 131.35 |
| ATOM | 936 | CG1 | VAL | G | 270 | 108.937 | −144.860 | 118.811 | 1.00 | 131.66 |

TABLE 2-continued

The structural coordinates of an exemplary gp120 with an extended V3 loop

| ATOM | 937 | CG2 | VAL | G | 270 | 108.621 | −146.755 | 120.395 | 1.00 | 130.81 |
|---|---|---|---|---|---|---|---|---|---|---|
| ATOM | 938 | N | VAL | G | 271 | 106.598 | −145.520 | 116.668 | 1.00 | 128.20 |
| ATOM | 939 | CA | VAL | G | 271 | 106.313 | −144.636 | 115.547 | 1.00 | 126.00 |
| ATOM | 940 | C | VAL | G | 271 | 105.937 | −143.226 | 115.975 | 1.00 | 123.76 |
| ATOM | 941 | O | VAL | G | 271 | 104.888 | −143.009 | 116.581 | 1.00 | 123.89 |
| ATOM | 942 | CB | VAL | G | 271 | 105.168 | −145.198 | 114.680 | 1.00 | 127.31 |
| ATOM | 943 | CG1 | VAL | G | 271 | 105.713 | −146.225 | 113.699 | 1.00 | 127.47 |
| ATOM | 944 | CG2 | VAL | G | 271 | 104.117 | −145.838 | 115.573 | 1.00 | 128.06 |
| ATOM | 945 | N | ILE | G | 272 | 106.804 | −142.272 | 115.656 | 1.00 | 121.03 |
| ATOM | 946 | CA | ILE | G | 272 | 106.572 | −140.872 | 115.990 | 1.00 | 118.57 |
| ATOM | 947 | C | ILE | G | 272 | 105.975 | −140.139 | 114.795 | 1.00 | 116.72 |
| ATOM | 948 | O | ILE | G | 272 | 106.352 | −140.394 | 113.652 | 1.00 | 116.74 |
| ATOM | 949 | CB | ILE | G | 272 | 107.887 | −140.177 | 116.415 | 1.00 | 118.70 |
| ATOM | 950 | CG1 | ILE | G | 272 | 109.042 | −140.617 | 115.512 | 1.00 | 119.92 |
| ATOM | 951 | CG2 | ILE | G | 272 | 108.203 | −140.507 | 117.860 | 1.00 | 118.21 |
| ATOM | 952 | CD1 | ILE | G | 272 | 109.082 | −139.944 | 114.157 | 1.00 | 120.90 |
| ATOM | 953 | N | ARG | G | 273 | 105.040 | −139.232 | 115.052 | 1.00 | 114.52 |
| ATOM | 954 | CA | ARG | G | 273 | 104.405 | −138.500 | 113.967 | 1.00 | 112.62 |
| ATOM | 955 | C | ARG | G | 273 | 103.923 | −137.100 | 114.334 | 1.00 | 112.88 |
| ATOM | 956 | O | ARG | G | 273 | 103.487 | −136.845 | 115.455 | 1.00 | 113.04 |
| ATOM | 957 | CB | ARG | G | 273 | 103.254 | −139.339 | 113.401 | 1.00 | 110.31 |
| ATOM | 958 | CG | ARG | G | 273 | 102.587 | −140.260 | 114.417 | 1.00 | 106.44 |
| ATOM | 959 | CD | ARG | G | 273 | 102.311 | −141.625 | 113.795 | 1.00 | 104.49 |
| ATOM | 960 | NE | ARG | G | 273 | 101.683 | −142.560 | 114.726 | 1.00 | 102.80 |
| ATOM | 961 | CZ | ARG | G | 273 | 101.400 | −143.826 | 114.433 | 1.00 | 101.53 |
| ATOM | 962 | NH1 | ARG | G | 273 | 101.691 | −144.310 | 113.234 | 1.00 | 99.91 |
| ATOM | 963 | NH2 | ARG | G | 273 | 100.825 | −144.607 | 115.337 | 1.00 | 100.38 |
| ATOM | 964 | N | SER | G | 274 | 104.018 | −136.199 | 113.363 | 1.00 | 113.32 |
| ATOM | 965 | CA | SER | G | 274 | 103.618 | −134.810 | 113.531 | 1.00 | 114.33 |
| ATOM | 966 | C | SER | G | 274 | 103.131 | −134.296 | 112.184 | 1.00 | 115.69 |
| ATOM | 967 | O | SER | G | 274 | 103.519 | −134.816 | 111.140 | 1.00 | 115.97 |
| ATOM | 968 | CB | SER | G | 274 | 104.814 | −133.974 | 114.003 | 1.00 | 114.12 |
| ATOM | 969 | OG | SER | G | 274 | 104.457 | −132.617 | 114.198 | 1.00 | 114.92 |
| ATOM | 970 | N | ASP | G | 275 | 102.285 | −133.274 | 112.205 | 1.00 | 117.50 |
| ATOM | 971 | CA | ASP | G | 275 | 101.764 | −132.718 | 110.966 | 1.00 | 119.82 |
| ATOM | 972 | C | ASP | G | 275 | 102.906 | −132.161 | 110.109 | 1.00 | 122.54 |
| ATOM | 973 | O | ASP | G | 275 | 102.898 | −132.283 | 108.885 | 1.00 | 123.77 |
| ATOM | 974 | CB | ASP | G | 275 | 100.742 | −131.626 | 111.284 | 1.00 | 119.48 |
| ATOM | 975 | CG | ASP | G | 275 | 99.978 | −131.168 | 110.059 | 1.00 | 119.15 |
| ATOM | 976 | OD1 | ASP | G | 275 | 100.457 | −130.241 | 109.380 | 1.00 | 119.47 |
| ATOM | 977 | OD2 | ASP | G | 275 | 98.907 | −131.748 | 109.774 | 1.00 | 119.52 |
| ATOM | 978 | N | ASN | G | 276 | 103.885 | −131.547 | 110.766 | 1.00 | 124.54 |
| ATOM | 979 | CA | ASN | G | 276 | 105.053 | −130.984 | 110.095 | 1.00 | 126.17 |
| ATOM | 980 | C | ASN | G | 276 | 106.182 | −130.957 | 111.116 | 1.00 | 126.16 |
| ATOM | 981 | O | ASN | G | 276 | 106.209 | −130.097 | 111.996 | 1.00 | 127.07 |
| ATOM | 982 | CB | ASN | G | 276 | 104.764 | −129.565 | 109.575 | 1.00 | 127.69 |
| ATOM | 983 | CG | ASN | G | 276 | 105.951 | −128.957 | 108.826 | 1.00 | 130.48 |
| ATOM | 984 | OD1 | ASN | G | 276 | 106.983 | −128.684 | 109.436 | 1.00 | 131.45 |
| ATOM | 985 | ND2 | ASN | G | 276 | 105.817 | −128.752 | 107.512 | 1.00 | 133.41 |
| ATOM | 986 | N | PHE | G | 277 | 107.098 | −131.915 | 111.001 | 1.00 | 125.51 |
| ATOM | 987 | CA | PHE | G | 277 | 108.223 | −132.013 | 111.917 | 1.00 | 124.73 |
| ATOM | 988 | C | PHE | G | 277 | 109.164 | −130.820 | 111.885 | 1.00 | 124.32 |
| ATOM | 989 | O | PHE | G | 277 | 109.851 | −130.543 | 112.869 | 1.00 | 124.52 |
| ATOM | 990 | CB | PHE | G | 277 | 109.021 | −133.282 | 111.645 | 1.00 | 124.97 |
| ATOM | 991 | CG | PHE | G | 277 | 108.616 | −134.440 | 112.498 | 1.00 | 124.70 |
| ATOM | 992 | CD1 | PHE | G | 277 | 107.662 | −135.352 | 112.061 | 1.00 | 124.33 |
| ATOM | 993 | CD2 | PHE | G | 277 | 109.177 | −134.606 | 113.758 | 1.00 | 125.19 |
| ATOM | 994 | CE1 | PHE | G | 277 | 107.274 | −136.416 | 112.872 | 1.00 | 124.54 |
| ATOM | 995 | CE2 | PHE | G | 277 | 108.797 | −135.661 | 114.575 | 1.00 | 125.18 |
| ATOM | 996 | CZ | PHE | G | 277 | 107.843 | −136.568 | 114.132 | 1.00 | 124.26 |
| ATOM | 997 | N | THR | G | 278 | 109.205 | −130.113 | 110.763 | 1.00 | 123.74 |
| ATOM | 998 | CA | THR | G | 278 | 110.082 | −128.954 | 110.660 | 1.00 | 123.33 |
| ATOM | 999 | C | THR | G | 278 | 109.545 | −127.821 | 111.522 | 1.00 | 122.48 |
| ATOM | 1000 | O | THR | G | 278 | 110.298 | −126.961 | 111.974 | 1.00 | 122.37 |
| ATOM | 1001 | CB | THR | G | 278 | 110.194 | −128.471 | 109.208 | 1.00 | 123.77 |
| ATOM | 1002 | OG1 | THR | G | 278 | 110.512 | −129.583 | 108.363 | 1.00 | 122.39 |
| ATOM | 1003 | CG2 | THR | G | 278 | 111.299 | −127.432 | 109.076 | 1.00 | 124.71 |
| ATOM | 1004 | N | ASN | G | 279 | 108.237 | −127.836 | 111.752 | 1.00 | 121.41 |
| ATOM | 1005 | CA | ASN | G | 279 | 107.588 | −126.823 | 112.569 | 1.00 | 120.64 |
| ATOM | 1006 | C | ASN | G | 279 | 107.553 | −127.290 | 114.019 | 1.00 | 119.86 |
| ATOM | 1007 | O | ASN | G | 279 | 107.075 | −128.384 | 114.316 | 1.00 | 119.77 |
| ATOM | 1008 | CB | ASN | G | 279 | 106.168 | −126.570 | 112.060 | 1.00 | 122.36 |
| ATOM | 1009 | CG | ASN | G | 279 | 105.527 | −125.362 | 112.703 | 1.00 | 123.19 |
| ATOM | 1010 | OD1 | ASN | G | 279 | 106.104 | −124.276 | 112.716 | 1.00 | 124.95 |
| ATOM | 1011 | ND2 | ASN | G | 279 | 104.322 | −125.540 | 113.228 | 1.00 | 123.66 |
| ATOM | 1012 | N | ASN | G | 280 | 108.059 | −126.451 | 114.917 | 1.00 | 118.87 |
| ATOM | 1013 | CA | ASN | G | 280 | 108.107 | −126.780 | 116.336 | 1.00 | 118.01 |
| ATOM | 1014 | C | ASN | G | 280 | 106.785 | −126.592 | 117.075 | 1.00 | 117.08 |

TABLE 2-continued

The structural coordinates of an exemplary gp120 with an extended V3 loop

| | | | | | | | | | | |
|---|---|---|---|---|---|---|---|---|---|---|
| ATOM | 1015 | O | ASN | G | 280 | 106.615 | −127.104 | 118.181 | 1.00 | 117.55 |
| ATOM | 1016 | CB | ASN | G | 280 | 109.187 | −125.943 | 117.019 | 1.00 | 118.90 |
| ATOM | 1017 | CG | ASN | G | 280 | 109.006 | −124.457 | 116.781 | 1.00 | 119.84 |
| ATOM | 1018 | OD1 | ASN | G | 280 | 108.992 | −124.001 | 115.638 | 1.00 | 119.58 |
| ATOM | 1019 | ND2 | ASN | G | 280 | 108.865 | −123.694 | 117.859 | 1.00 | 121.00 |
| ATOM | 1020 | N | ALA | G | 281 | 105.851 | −125.862 | 116.472 | 1.00 | 115.19 |
| ATOM | 1021 | CA | ALA | G | 281 | 104.557 | −125.612 | 117.102 | 1.00 | 112.13 |
| ATOM | 1022 | C | ALA | G | 281 | 103.663 | −126.842 | 117.077 | 1.00 | 109.69 |
| ATOM | 1023 | O | ALA | G | 281 | 102.802 | −127.010 | 117.937 | 1.00 | 109.86 |
| ATOM | 1024 | CB | ALA | G | 281 | 103.859 | −124.453 | 116.409 | 1.00 | 113.29 |
| ATOM | 1025 | N | LYS | G | 282 | 103.865 | −127.693 | 116.078 | 1.00 | 106.77 |
| ATOM | 1026 | CA | LYS | G | 282 | 103.078 | −128.911 | 115.939 | 1.00 | 104.34 |
| ATOM | 1027 | C | LYS | G | 282 | 103.510 | −129.937 | 116.979 | 1.00 | 102.27 |
| ATOM | 1028 | O | LYS | G | 282 | 104.699 | −130.197 | 117.147 | 1.00 | 101.74 |
| ATOM | 1029 | CB | LYS | G | 282 | 103.260 | −129.495 | 114.534 | 1.00 | 104.78 |
| ATOM | 1030 | CG | LYS | G | 282 | 102.841 | −128.579 | 113.392 | 1.00 | 105.16 |
| ATOM | 1031 | CD | LYS | G | 282 | 101.326 | −128.507 | 113.226 | 1.00 | 107.10 |
| ATOM | 1032 | CE | LYS | G | 282 | 100.956 | −127.757 | 111.947 | 1.00 | 107.70 |
| ATOM | 1033 | NZ | LYS | G | 282 | 99.493 | −127.777 | 111.657 | 1.00 | 108.40 |
| ATOM | 1034 | N | THR | G | 283 | 102.542 | −130.523 | 117.671 | 1.00 | 100.94 |
| ATOM | 1035 | CA | THR | G | 283 | 102.848 | −131.514 | 118.693 | 1.00 | 100.59 |
| ATOM | 1036 | C | THR | G | 283 | 103.256 | −132.850 | 118.076 | 1.00 | 99.16 |
| ATOM | 1037 | O | THR | G | 283 | 102.777 | −133.227 | 117.003 | 1.00 | 98.27 |
| ATOM | 1038 | CB | THR | G | 283 | 101.643 | −131.751 | 119.620 | 1.00 | 102.18 |
| ATOM | 1039 | OG1 | THR | G | 283 | 100.523 | −132.185 | 118.843 | 1.00 | 103.66 |
| ATOM | 1040 | CG2 | THR | G | 283 | 101.276 | −130.478 | 120.352 | 1.00 | 102.55 |
| ATOM | 1041 | N | ILE | G | 284 | 104.135 | −133.567 | 118.767 | 1.00 | 97.96 |
| ATOM | 1042 | CA | ILE | G | 284 | 104.616 | −134.855 | 118.292 | 1.00 | 97.14 |
| ATOM | 1043 | C | ILE | G | 284 | 104.064 | −136.005 | 119.123 | 1.00 | 97.31 |
| ATOM | 1044 | O | ILE | G | 284 | 104.344 | −136.110 | 120.318 | 1.00 | 97.07 |
| ATOM | 1045 | CB | ILE | G | 284 | 106.157 | −134.899 | 118.331 | 1.00 | 96.52 |
| ATOM | 1046 | CG1 | ILE | G | 284 | 106.714 | −133.841 | 117.375 | 1.00 | 96.20 |
| ATOM | 1047 | CG2 | ILE | G | 284 | 106.656 | −136.293 | 117.964 | 1.00 | 96.59 |
| ATOM | 1048 | CD1 | ILE | G | 284 | 108.195 | −133.608 | 117.509 | 1.00 | 96.44 |
| ATOM | 1049 | N | ILE | G | 285 | 103.276 | −136.863 | 118.485 | 1.00 | 98.01 |
| ATOM | 1050 | CA | ILE | G | 285 | 102.685 | −138.013 | 119.158 | 1.00 | 99.80 |
| ATOM | 1051 | C | ILE | G | 285 | 103.602 | −139.229 | 119.071 | 1.00 | 101.17 |
| ATOM | 1052 | O | ILE | G | 285 | 103.975 | −139.661 | 117.980 | 1.00 | 100.52 |
| ATOM | 1053 | CB | ILE | G | 285 | 101.312 | −138.386 | 118.537 | 1.00 | 99.80 |
| ATOM | 1054 | CG1 | ILE | G | 285 | 100.246 | −137.372 | 118.961 | 1.00 | 100.25 |
| ATOM | 1055 | CG2 | ILE | G | 285 | 100.903 | −139.782 | 118.977 | 1.00 | 100.16 |
| ATOM | 1056 | CD1 | ILE | G | 285 | 100.455 | −135.980 | 118.409 | 1.00 | 102.53 |
| ATOM | 1057 | N | VAL | G | 286 | 103.955 | −139.782 | 120.224 | 1.00 | 103.62 |
| ATOM | 1058 | CA | VAL | G | 286 | 104.831 | −140.943 | 120.282 | 1.00 | 106.86 |
| ATOM | 1059 | C | VAL | G | 286 | 104.055 | −142.192 | 120.683 | 1.00 | 109.26 |
| ATOM | 1060 | O | VAL | G | 286 | 103.311 | −142.176 | 121.663 | 1.00 | 109.45 |
| ATOM | 1061 | CB | VAL | G | 286 | 105.953 | −140.727 | 121.314 | 1.00 | 107.59 |
| ATOM | 1062 | CG1 | VAL | G | 286 | 106.960 | −141.865 | 121.236 | 1.00 | 108.43 |
| ATOM | 1063 | CG2 | VAL | G | 286 | 106.621 | −139.385 | 121.074 | 1.00 | 107.25 |
| ATOM | 1064 | N | GLN | G | 287 | 104.222 | −143.270 | 119.923 | 1.00 | 112.10 |
| ATOM | 1065 | CA | GLN | G | 287 | 103.540 | −144.527 | 120.225 | 1.00 | 115.20 |
| ATOM | 1066 | C | GLN | G | 287 | 104.575 | −145.549 | 120.675 | 1.00 | 116.64 |
| ATOM | 1067 | O | GLN | G | 287 | 105.564 | −145.779 | 119.982 | 1.00 | 117.12 |
| ATOM | 1068 | CB | GLN | G | 287 | 102.803 | −145.057 | 118.992 | 1.00 | 116.06 |
| ATOM | 1069 | CG | GLN | G | 287 | 101.378 | −145.514 | 119.275 | 1.00 | 117.17 |
| ATOM | 1070 | CD | GLN | G | 287 | 100.932 | −146.653 | 118.378 | 1.00 | 117.46 |
| ATOM | 1071 | OE1 | GLN | G | 287 | 101.086 | −146.600 | 117.158 | 1.00 | 116.74 |
| ATOM | 1072 | NE2 | GLN | G | 287 | 100.366 | −147.692 | 118.984 | 1.00 | 117.73 |
| ATOM | 1073 | N | LEU | G | 288 | 104.338 | −146.170 | 121.825 | 1.00 | 119.08 |
| ATOM | 1074 | CA | LEU | G | 288 | 105.270 | −147.150 | 122.375 | 1.00 | 122.20 |
| ATOM | 1075 | C | LEU | G | 288 | 104.788 | −148.588 | 122.203 | 1.00 | 124.20 |
| ATOM | 1076 | O | LEU | G | 288 | 103.594 | −148.867 | 122.309 | 1.00 | 124.85 |
| ATOM | 1077 | CB | LEU | G | 288 | 105.479 | −146.874 | 123.862 | 1.00 | 121.50 |
| ATOM | 1078 | CG | LEU | G | 288 | 105.844 | −145.433 | 124.231 | 1.00 | 121.43 |
| ATOM | 1079 | CD1 | LEU | G | 288 | 105.637 | −145.233 | 125.720 | 1.00 | 122.39 |
| ATOM | 1080 | CD2 | LEU | G | 288 | 107.281 | −145.134 | 123.832 | 1.00 | 123.19 |
| ATOM | 1081 | N | LYS | G | 289 | 105.721 | −149.503 | 121.953 | 1.00 | 126.07 |
| ATOM | 1082 | CA | LYS | G | 289 | 105.380 | −150.912 | 121.782 | 1.00 | 127.42 |
| ATOM | 1083 | C | LYS | G | 289 | 105.478 | −151.682 | 123.097 | 1.00 | 127.68 |
| ATOM | 1084 | O | LYS | G | 289 | 104.856 | −152.732 | 123.258 | 1.00 | 126.88 |
| ATOM | 1085 | CB | LYS | G | 289 | 106.285 | −151.552 | 120.723 | 1.00 | 128.03 |
| ATOM | 1086 | CG | LYS | G | 289 | 107.441 | −150.673 | 120.252 | 1.00 | 129.35 |
| ATOM | 1087 | CD | LYS | G | 289 | 108.782 | −151.209 | 120.736 | 1.00 | 130.44 |
| ATOM | 1088 | CE | LYS | G | 289 | 109.966 | −150.519 | 120.051 | 1.00 | 130.23 |
| ATOM | 1089 | NZ | LYS | G | 289 | 110.464 | −149.301 | 120.754 | 1.00 | 131.22 |
| ATOM | 1090 | N | GLU | G | 290 | 106.263 | −151.159 | 124.033 | 1.00 | 128.43 |
| ATOM | 1091 | CA | GLU | G | 290 | 106.416 | −151.788 | 125.341 | 1.00 | 128.96 |
| ATOM | 1092 | C | GLU | G | 290 | 105.619 | −150.998 | 126.375 | 1.00 | 127.87 |

TABLE 2-continued

The structural coordinates of an exemplary gp120 with an extended V3 loop

| | | | | | | | | | | |
|---|---|---|---|---|---|---|---|---|---|---|
| ATOM | 1093 | O | GLU | G | 290 | 105.837 | −149.800 | 126.553 | 1.00 | 127.30 |
| ATOM | 1094 | CB | GLU | G | 290 | 107.894 | −151.843 | 125.744 | 1.00 | 131.22 |
| ATOM | 1095 | CG | GLU | G | 290 | 108.714 | −152.872 | 124.974 | 1.00 | 134.12 |
| ATOM | 1096 | CD | GLU | G | 290 | 110.117 | −153.047 | 125.532 | 1.00 | 135.56 |
| ATOM | 1097 | OE1 | GLU | G | 290 | 110.924 | −152.097 | 125.442 | 1.00 | 136.25 |
| ATOM | 1098 | OE2 | GLU | G | 290 | 110.412 | −154.138 | 126.064 | 1.00 | 135.63 |
| ATOM | 1099 | N | SER | G | 291 | 104.697 | −151.673 | 127.052 | 1.00 | 126.04 |
| ATOM | 1100 | CA | SER | G | 291 | 103.856 | −151.030 | 128.053 | 1.00 | 124.60 |
| ATOM | 1101 | C | SER | G | 291 | 104.589 | −150.693 | 129.344 | 1.00 | 124.35 |
| ATOM | 1102 | O | SER | G | 291 | 105.113 | −151.577 | 130.025 | 1.00 | 125.69 |
| ATOM | 1103 | CB | SER | G | 291 | 102.656 | −151.922 | 128.379 | 1.00 | 123.78 |
| ATOM | 1104 | OG | SER | G | 291 | 103.084 | −153.161 | 128.915 | 1.00 | 123.88 |
| ATOM | 1105 | N | VAL | G | 292 | 104.615 | −149.408 | 129.679 | 1.00 | 123.16 |
| ATOM | 1106 | CA | VAL | G | 292 | 105.263 | −148.941 | 130.898 | 1.00 | 121.87 |
| ATOM | 1107 | C | VAL | G | 292 | 104.192 | −148.750 | 131.968 | 1.00 | 121.23 |
| ATOM | 1108 | O | VAL | G | 292 | 103.399 | −147.813 | 131.897 | 1.00 | 120.89 |
| ATOM | 1109 | CB | VAL | G | 292 | 105.968 | −147.595 | 130.662 | 1.00 | 121.78 |
| ATOM | 1110 | CG1 | VAL | G | 292 | 106.742 | −147.191 | 131.907 | 1.00 | 121.71 |
| ATOM | 1111 | CG2 | VAL | G | 292 | 106.886 | −147.697 | 129.461 | 1.00 | 120.71 |
| ATOM | 1112 | N | GLU | G | 293 | 104.169 | −149.640 | 132.952 | 1.00 | 120.89 |
| ATOM | 1113 | CA | GLU | G | 293 | 103.178 | −149.574 | 134.015 | 1.00 | 121.29 |
| ATOM | 1114 | C | GLU | G | 293 | 103.474 | −148.476 | 135.031 | 1.00 | 121.55 |
| ATOM | 1115 | O | GLU | G | 293 | 104.568 | −148.408 | 135.591 | 1.00 | 121.80 |
| ATOM | 1116 | CB | GLU | G | 293 | 103.086 | −150.933 | 134.723 | 1.00 | 121.08 |
| ATOM | 1117 | CG | GLU | G | 293 | 102.116 | −150.988 | 135.893 | 1.00 | 121.19 |
| ATOM | 1118 | CD | GLU | G | 293 | 101.966 | −152.394 | 136.445 | 1.00 | 122.13 |
| ATOM | 1119 | OE1 | GLU | G | 293 | 102.946 | −153.167 | 136.371 | 1.00 | 122.07 |
| ATOM | 1120 | OE2 | GLU | G | 293 | 100.876 | −152.722 | 136.961 | 1.00 | 123.25 |
| ATOM | 1121 | N | ILE | G | 294 | 102.493 | −147.610 | 135.258 | 1.00 | 121.87 |
| ATOM | 1122 | CA | ILE | G | 294 | 102.637 | −146.524 | 136.217 | 1.00 | 121.70 |
| ATOM | 1123 | C | ILE | G | 294 | 101.621 | −146.720 | 137.333 | 1.00 | 121.42 |
| ATOM | 1124 | O | ILE | G | 294 | 100.433 | −146.917 | 137.076 | 1.00 | 121.27 |
| ATOM | 1125 | CB | ILE | G | 294 | 102.418 | −145.160 | 135.536 | 1.00 | 122.02 |
| ATOM | 1126 | CG1 | ILE | G | 294 | 102.578 | −144.033 | 136.557 | 1.00 | 122.87 |
| ATOM | 1127 | CG2 | ILE | G | 294 | 101.048 | −145.125 | 134.884 | 1.00 | 121.44 |
| ATOM | 1128 | CD1 | ILE | G | 294 | 102.714 | −142.660 | 135.931 | 1.00 | 122.60 |
| ATOM | 1129 | N | ASN | G | 295 | 102.097 | −146.674 | 138.573 | 1.00 | 121.00 |
| ATOM | 1130 | CA | ASN | G | 295 | 101.238 | −146.874 | 139.736 | 1.00 | 121.44 |
| ATOM | 1131 | C | ASN | G | 295 | 101.204 | −145.674 | 140.677 | 1.00 | 121.01 |
| ATOM | 1132 | O | ASN | G | 295 | 102.134 | −145.462 | 141.457 | 1.00 | 121.03 |
| ATOM | 1133 | CB | ASN | G | 295 | 101.710 | −148.103 | 140.517 | 1.00 | 122.74 |
| ATOM | 1134 | CG | ASN | G | 295 | 101.810 | −149.344 | 139.651 | 1.00 | 122.92 |
| ATOM | 1135 | OD1 | ASN | G | 295 | 100.819 | −149.793 | 139.075 | 1.00 | 122.88 |
| ATOM | 1136 | ND2 | ASN | G | 295 | 103.011 | −149.905 | 139.555 | 1.00 | 122.92 |
| ATOM | 1137 | N | CYS | G | 296 | 100.124 | −144.901 | 140.605 | 1.00 | 120.25 |
| ATOM | 1138 | CA | CYS | G | 296 | 99.960 | −143.728 | 141.456 | 1.00 | 118.86 |
| ATOM | 1139 | C | CYS | G | 296 | 98.928 | −144.045 | 142.537 | 1.00 | 117.99 |
| ATOM | 1140 | O | CYS | G | 296 | 97.835 | −144.528 | 142.236 | 1.00 | 117.00 |
| ATOM | 1141 | CB | CYS | G | 296 | 99.466 | −142.537 | 140.636 | 1.00 | 119.34 |
| ATOM | 1142 | SG | CYS | G | 296 | 100.316 | −142.227 | 139.052 | 1.00 | 119.64 |
| ATOM | 1143 | N | THR | G | 297 | 99.268 | −143.765 | 143.791 | 1.00 | 117.75 |
| ATOM | 1144 | CA | THR | G | 297 | 98.356 | −144.042 | 144.895 | 1.00 | 117.96 |
| ATOM | 1145 | C | THR | G | 297 | 98.386 | −142.956 | 145.967 | 1.00 | 117.03 |
| ATOM | 1146 | O | THR | G | 297 | 99.224 | −142.055 | 145.933 | 1.00 | 115.96 |
| ATOM | 1147 | CB | THR | G | 297 | 98.692 | −145.394 | 145.560 | 1.00 | 118.94 |
| ATOM | 1148 | OG1 | THR | G | 297 | 99.992 | −145.325 | 146.159 | 1.00 | 120.18 |
| ATOM | 1149 | CG2 | THR | G | 297 | 98.688 | −146.509 | 144.524 | 1.00 | 119.76 |
| ATOM | 1150 | N | ARG | G | 298 | 97.459 | −143.050 | 146.916 | 1.00 | 116.66 |
| ATOM | 1151 | CA | ARG | G | 298 | 97.369 | −142.092 | 148.010 | 1.00 | 116.73 |
| ATOM | 1152 | C | ARG | G | 298 | 96.753 | −142.780 | 149.228 | 1.00 | 118.95 |
| ATOM | 1153 | O | ARG | G | 298 | 95.710 | −143.426 | 149.124 | 1.00 | 118.61 |
| ATOM | 1154 | CB | ARG | G | 298 | 96.521 | −140.888 | 147.585 | 1.00 | 114.49 |
| ATOM | 1155 | CG | ARG | G | 298 | 96.550 | −139.720 | 148.564 | 1.00 | 112.45 |
| ATOM | 1156 | CD | ARG | G | 298 | 95.473 | −139.831 | 149.632 | 1.00 | 110.20 |
| ATOM | 1157 | NE | ARG | G | 298 | 94.138 | −139.603 | 149.085 | 1.00 | 108.71 |
| ATOM | 1158 | CZ | ARG | G | 298 | 93.026 | −139.566 | 149.812 | 1.00 | 107.87 |
| ATOM | 1159 | NH1 | ARG | G | 298 | 93.082 | −139.742 | 151.125 | 1.00 | 107.98 |
| ATOM | 1160 | NH2 | ARG | G | 298 | 91.857 | −139.349 | 149.227 | 1.00 | 107.62 |
| ATOM | 1161 | N | PRO | G | 299 | 97.402 | −142.651 | 150.399 | 1.00 | 121.18 |
| ATOM | 1162 | CA | PRO | G | 299 | 96.984 | −143.233 | 151.681 | 1.00 | 123.48 |
| ATOM | 1163 | C | PRO | G | 299 | 95.484 | −143.182 | 151.977 | 1.00 | 125.98 |
| ATOM | 1164 | O | PRO | G | 299 | 94.700 | −142.658 | 151.186 | 1.00 | 126.15 |
| ATOM | 1165 | CB | PRO | G | 299 | 97.805 | −142.442 | 152.691 | 1.00 | 123.50 |
| ATOM | 1166 | CG | PRO | G | 299 | 99.092 | −142.253 | 151.958 | 1.00 | 122.94 |
| ATOM | 1167 | CD | PRO | G | 299 | 98.621 | −141.841 | 150.576 | 1.00 | 121.50 |
| ATOM | 1168 | N | ASN | G | 300 | 95.092 | −143.724 | 153.127 | 1.00 | 127.96 |
| ATOM | 1169 | CA | ASN | G | 300 | 93.684 | −143.752 | 153.502 | 1.00 | 130.21 |
| ATOM | 1170 | C | ASN | G | 300 | 93.364 | −143.237 | 154.905 | 1.00 | 131.51 |

TABLE 2-continued

The structural coordinates of an exemplary gp120 with an extended V3 loop

| ATOM | 1171 | O | ASN | G | 300 | 93.985 | −142.292 | 155.394 | 1.00 | 131.18 |
|---|---|---|---|---|---|---|---|---|---|---|
| ATOM | 1172 | CB | ASN | G | 300 | 93.137 | −145.173 | 153.341 | 1.00 | 130.07 |
| ATOM | 1173 | CG | ASN | G | 300 | 93.919 | −146.194 | 154.142 | 1.00 | 130.57 |
| ATOM | 1174 | OD1 | ASN | G | 300 | 95.139 | −146.299 | 154.015 | 1.00 | 130.10 |
| ATOM | 1175 | ND2 | ASN | G | 300 | 93.216 | −146.958 | 154.969 | 1.00 | 131.18 |
| ATOM | 1176 | N | GLN | G | 301 | 92.384 | −143.877 | 155.537 | 1.00 | 133.80 |
| ATOM | 1177 | CA | GLN | G | 301 | 91.912 | −143.514 | 156.871 | 1.00 | 135.82 |
| ATOM | 1178 | C | GLN | G | 301 | 92.716 | −144.156 | 158.004 | 1.00 | 137.01 |
| ATOM | 1179 | O | GLN | G | 301 | 92.448 | −143.903 | 159.180 | 1.00 | 136.35 |
| ATOM | 1180 | CB | GLN | G | 301 | 90.436 | −143.911 | 157.001 | 1.00 | 135.35 |
| ATOM | 1181 | CG | GLN | G | 301 | 89.724 | −143.404 | 158.248 | 1.00 | 135.28 |
| ATOM | 1182 | CD | GLN | G | 301 | 89.563 | −141.897 | 158.258 | 1.00 | 134.83 |
| ATOM | 1183 | OE1 | GLN | G | 301 | 89.785 | −141.230 | 157.247 | 1.00 | 134.19 |
| ATOM | 1184 | NE2 | GLN | G | 301 | 89.160 | −141.353 | 159.402 | 1.00 | 133.96 |
| ATOM | 1185 | N | ASN | G | 302 | 93.701 | −144.979 | 157.656 | 1.00 | 138.83 |
| ATOM | 1186 | CA | ASN | G | 302 | 94.522 | −145.651 | 158.662 | 1.00 | 140.81 |
| ATOM | 1187 | C | ASN | G | 302 | 95.302 | −144.706 | 159.574 | 1.00 | 141.45 |
| ATOM | 1188 | O | ASN | G | 302 | 96.112 | −145.155 | 160.387 | 1.00 | 141.13 |
| ATOM | 1189 | CB | ASN | G | 302 | 95.494 | −146.633 | 157.997 | 1.00 | 141.80 |
| ATOM | 1190 | CG | ASN | G | 302 | 94.851 | −147.975 | 157.690 | 1.00 | 143.04 |
| ATOM | 1191 | OD1 | ASN | G | 302 | 94.307 | −148.632 | 158.579 | 1.00 | 142.23 |
| ATOM | 1192 | ND2 | ASN | G | 302 | 94.919 | −148.392 | 156.431 | 1.00 | 142.70 |
| ATOM | 1193 | N | THR | G | 303 | 95.063 | −143.404 | 159.440 | 1.00 | 142.24 |
| ATOM | 1194 | CA | THR | G | 303 | 95.745 | −142.423 | 160.278 | 1.00 | 142.95 |
| ATOM | 1195 | C | THR | G | 303 | 95.430 | −142.755 | 161.734 | 1.00 | 143.18 |
| ATOM | 1196 | O | THR | G | 303 | 96.274 | −143.285 | 162.457 | 1.00 | 143.28 |
| ATOM | 1197 | CB | THR | G | 303 | 95.263 | −140.990 | 159.969 | 1.00 | 143.28 |
| ATOM | 1198 | OG1 | THR | G | 303 | 95.502 | −140.691 | 158.588 | 1.00 | 143.23 |
| ATOM | 1199 | CG2 | THR | G | 303 | 96.006 | −139.980 | 160.831 | 1.00 | 144.01 |
| ATOM | 1200 | N | ARG | G | 304 | 94.208 | −142.441 | 162.154 | 1.00 | 143.39 |
| ATOM | 1201 | CA | ARG | G | 304 | 93.762 | −142.731 | 163.512 | 1.00 | 143.68 |
| ATOM | 1202 | C | ARG | G | 304 | 92.770 | −143.886 | 163.431 | 1.00 | 143.18 |
| ATOM | 1203 | O | ARG | G | 304 | 92.051 | −144.019 | 162.441 | 1.00 | 143.86 |
| ATOM | 1204 | CB | ARG | G | 304 | 93.108 | −141.495 | 164.138 | 1.00 | 144.11 |
| ATOM | 1205 | CG | ARG | G | 304 | 94.084 | −140.349 | 164.381 | 1.00 | 145.32 |
| ATOM | 1206 | CD | ARG | G | 304 | 95.261 | −140.809 | 165.238 | 1.00 | 147.31 |
| ATOM | 1207 | NE | ARG | G | 304 | 96.271 | −139.770 | 165.421 | 1.00 | 147.56 |
| ATOM | 1208 | CZ | ARG | G | 304 | 97.419 | −139.953 | 166.067 | 1.00 | 147.68 |
| ATOM | 1209 | NH1 | ARG | G | 304 | 97.706 | −141.136 | 166.593 | 1.00 | 146.72 |
| ATOM | 1210 | NH2 | ARG | G | 304 | 98.283 | −138.953 | 166.187 | 1.00 | 146.63 |
| ATOM | 1211 | N | LYS | G | 305 | 92.728 | −144.722 | 164.464 | 1.00 | 141.97 |
| ATOM | 1212 | CA | LYS | G | 305 | 91.836 | −145.874 | 164.442 | 1.00 | 140.98 |
| ATOM | 1213 | C | LYS | G | 305 | 90.851 | −145.964 | 165.606 | 1.00 | 140.38 |
| ATOM | 1214 | O | LYS | G | 305 | 89.921 | −146.771 | 165.565 | 1.00 | 140.91 |
| ATOM | 1215 | CB | LYS | G | 305 | 92.668 | −147.159 | 164.384 | 1.00 | 141.00 |
| ATOM | 1216 | CG | LYS | G | 305 | 91.930 | −148.361 | 163.818 | 1.00 | 140.99 |
| ATOM | 1217 | CD | LYS | G | 305 | 91.633 | −148.169 | 162.338 | 1.00 | 141.06 |
| ATOM | 1218 | CE | LYS | G | 305 | 90.967 | −149.397 | 161.741 | 1.00 | 141.85 |
| ATOM | 1219 | NZ | LYS | G | 305 | 90.730 | −149.243 | 160.279 | 1.00 | 140.37 |
| ATOM | 1220 | N | SER | G | 306 | 91.042 | −145.149 | 166.638 | 1.00 | 139.15 |
| ATOM | 1221 | CA | SER | G | 306 | 90.143 | −145.193 | 167.788 | 1.00 | 137.47 |
| ATOM | 1222 | C | SER | G | 306 | 89.922 | −143.845 | 168.466 | 1.00 | 136.43 |
| ATOM | 1223 | O | SER | G | 306 | 90.820 | −143.005 | 168.518 | 1.00 | 136.13 |
| ATOM | 1224 | CB | SER | G | 306 | 90.663 | −146.198 | 168.818 | 1.00 | 137.39 |
| ATOM | 1225 | OG | SER | G | 306 | 90.732 | −147.502 | 168.267 | 1.00 | 136.71 |
| ATOM | 1226 | N | ILE | G | 307 | 88.713 | −143.654 | 168.985 | 1.00 | 135.40 |
| ATOM | 1227 | CA | ILE | G | 307 | 88.345 | −142.424 | 169.678 | 1.00 | 135.12 |
| ATOM | 1228 | C | ILE | G | 307 | 87.998 | −142.771 | 171.124 | 1.00 | 133.50 |
| ATOM | 1229 | O | ILE | G | 307 | 87.697 | −143.924 | 171.433 | 1.00 | 133.64 |
| ATOM | 1230 | CB | ILE | G | 307 | 87.122 | −141.754 | 169.013 | 1.00 | 135.24 |
| ATOM | 1231 | CG1 | ILE | G | 307 | 87.410 | −141.505 | 167.531 | 1.00 | 136.04 |
| ATOM | 1232 | CG2 | ILE | G | 307 | 86.802 | −140.437 | 169.709 | 1.00 | 135.56 |
| ATOM | 1233 | CD1 | ILE | G | 307 | 86.248 | −140.899 | 166.770 | 1.00 | 137.26 |
| ATOM | 1234 | N | HIS | G | 308 | 88.042 | −141.777 | 172.005 | 1.00 | 132.91 |
| ATOM | 1235 | CA | HIS | G | 308 | 87.739 | −141.997 | 173.416 | 1.00 | 132.86 |
| ATOM | 1236 | C | HIS | G | 308 | 86.709 | −141.003 | 173.946 | 1.00 | 130.36 |
| ATOM | 1237 | O | HIS | G | 308 | 86.915 | −139.791 | 173.887 | 1.00 | 130.34 |
| ATOM | 1238 | CB | HIS | G | 308 | 89.023 | −141.899 | 174.244 | 1.00 | 133.35 |
| ATOM | 1239 | CG | HIS | G | 308 | 90.081 | −142.878 | 173.836 | 1.00 | 134.57 |
| ATOM | 1240 | ND1 | HIS | G | 308 | 90.588 | −142.935 | 172.557 | 1.00 | 135.10 |
| ATOM | 1241 | CD2 | HIS | G | 308 | 90.726 | −143.837 | 174.541 | 1.00 | 134.82 |
| ATOM | 1242 | CE1 | HIS | G | 308 | 91.501 | −143.889 | 172.490 | 1.00 | 135.21 |
| ATOM | 1243 | NE2 | HIS | G | 308 | 91.604 | −144.451 | 173.680 | 1.00 | 134.93 |
| ATOM | 1244 | N | ILE | G | 309 | 85.593 | −141.524 | 174.451 | 1.00 | 129.66 |
| ATOM | 1245 | CA | ILE | G | 309 | 84.535 | −140.678 | 174.996 | 1.00 | 132.96 |
| ATOM | 1246 | C | ILE | G | 309 | 84.853 | −140.335 | 176.442 | 1.00 | 129.06 |
| ATOM | 1247 | O | ILE | G | 309 | 85.368 | −141.163 | 177.189 | 1.00 | 130.20 |
| ATOM | 1248 | CB | ILE | G | 309 | 83.150 | −141.381 | 174.982 | 1.00 | 129.80 |

TABLE 2-continued

The structural coordinates of an exemplary gp120 with an extended V3 loop

| ATOM | 1249 | CG1 | ILE | G | 309 | 82.794 | −141.842 | 173.567 | 1.00 | 129.99 |
|---|---|---|---|---|---|---|---|---|---|---|
| ATOM | 1250 | CG2 | ILE | G | 309 | 82.079 | −140.427 | 175.513 | 1.00 | 129.45 |
| ATOM | 1251 | CD1 | ILE | G | 309 | 82.707 | −140.721 | 172.551 | 1.00 | 131.16 |
| ATOM | 1252 | N | AGLY | G | 312 | 84.519 | −139.106 | 176.817 | 0.50 | 130.34 |
| ATOM | 1253 | N | BGLY | G | 312 | 84.580 | −139.093 | 176.821 | 0.50 | 130.54 |
| ATOM | 1254 | CA | AGLY | G | 312 | 84.745 | −138.635 | 178.168 | 0.50 | 130.62 |
| ATOM | 1255 | CA | BGLY | G | 312 | 84.870 | −138.668 | 178.175 | 0.50 | 132.03 |
| ATOM | 1256 | C | AGLY | G | 312 | 83.667 | −137.629 | 178.521 | 0.50 | 130.49 |
| ATOM | 1257 | C | BGLY | G | 312 | 84.057 | −137.472 | 178.615 | 0.50 | 132.56 |
| ATOM | 1258 | O | AGLY | G | 312 | 83.395 | −136.719 | 177.734 | 0.50 | 129.55 |
| ATOM | 1259 | O | BGLY | G | 312 | 83.971 | −136.469 | 177.901 | 0.50 | 132.01 |
| ATOM | 1260 | N | APRO | G | 313 | 83.028 | −137.767 | 179.695 | 0.50 | 130.44 |
| ATOM | 1261 | N | BPRO | G | 313 | 83.443 | −137.553 | 179.805 | 0.50 | 133.04 |
| ATOM | 1262 | CA | APRO | G | 313 | 81.972 | −136.840 | 180.115 | 0.50 | 131.53 |
| ATOM | 1263 | CA | BPRO | G | 313 | 82.628 | −136.463 | 180.344 | 0.50 | 134.04 |
| ATOM | 1264 | C | APRO | G | 313 | 82.413 | −135.375 | 180.098 | 0.50 | 132.66 |
| ATOM | 1265 | C | BPRO | G | 313 | 83.434 | −135.170 | 180.483 | 0.50 | 134.58 |
| ATOM | 1266 | O | APRO | G | 313 | 81.581 | −134.468 | 180.030 | 0.50 | 132.16 |
| ATOM | 1267 | O | BPRO | G | 313 | 84.184 | −134.985 | 181.445 | 0.50 | 133.93 |
| ATOM | 1268 | CB | APRO | G | 313 | 81.618 | −137.333 | 181.522 | 0.50 | 130.68 |
| ATOM | 1269 | CB | BPRO | G | 313 | 82.148 | −137.021 | 181.686 | 0.50 | 133.44 |
| ATOM | 1270 | CG | APRO | G | 313 | 82.890 | −137.969 | 181.999 | 0.50 | 130.40 |
| ATOM | 1271 | CG | BPRO | G | 313 | 83.237 | −137.955 | 182.081 | 0.50 | 133.35 |
| ATOM | 1272 | CD | APRO | G | 313 | 83.349 | −138.718 | 180.774 | 0.50 | 130.35 |
| ATOM | 1273 | CD | BPRO | G | 313 | 83.569 | −138.649 | 180.783 | 0.50 | 133.12 |
| ATOM | 1274 | N | AGLY | G | 314 | 83.726 | −135.158 | 180.147 | 0.50 | 133.78 |
| ATOM | 1275 | N | BGLY | G | 314 | 83.279 | −134.282 | 179.508 | 0.50 | 135.23 |
| ATOM | 1276 | CA | AGLY | G | 314 | 84.259 | −133.808 | 180.140 | 0.50 | 135.11 |
| ATOM | 1277 | CA | BGLY | G | 314 | 84.005 | −133.028 | 179.539 | 0.50 | 136.68 |
| ATOM | 1278 | C | AGLY | G | 314 | 85.185 | −133.514 | 178.973 | 0.50 | 136.46 |
| ATOM | 1279 | C | BGLY | G | 314 | 85.217 | −133.071 | 178.633 | 0.50 | 137.64 |
| ATOM | 1280 | O | AGLY | G | 314 | 85.779 | −132.436 | 178.916 | 0.50 | 136.65 |
| ATOM | 1281 | O | BGLY | G | 314 | 86.040 | −132.151 | 178.641 | 0.50 | 137.68 |
| ATOM | 1282 | N | AARG | G | 315 | 85.317 | −134.464 | 178.047 | 0.50 | 137.71 |
| ATOM | 1283 | N | BARG | G | 315 | 85.330 | −134.146 | 177.855 | 0.50 | 138.87 |
| ATOM | 1284 | CA | AARG | G | 315 | 86.179 | −134.280 | 176.881 | 0.50 | 138.32 |
| ATOM | 1285 | CA | BARG | G | 315 | 86.445 | −134.302 | 176.934 | 0.50 | 139.12 |
| ATOM | 1286 | C | AARG | G | 315 | 86.103 | −135.394 | 175.835 | 0.50 | 139.46 |
| ATOM | 1287 | C | BARG | G | 315 | 86.339 | −135.478 | 175.969 | 0.50 | 140.02 |
| ATOM | 1288 | O | AARG | G | 315 | 85.308 | −136.326 | 175.960 | 0.50 | 140.02 |
| ATOM | 1289 | O | BARG | G | 315 | 85.746 | −136.513 | 176.268 | 0.50 | 140.48 |
| ATOM | 1290 | CB | AARG | G | 315 | 87.634 | −134.069 | 177.327 | 0.50 | 138.97 |
| ATOM | 1291 | CB | BARG | G | 315 | 87.766 | −134.388 | 177.707 | 0.50 | 140.03 |
| ATOM | 1292 | CG | AARG | G | 315 | 88.095 | −134.926 | 178.501 | 0.50 | 138.68 |
| ATOM | 1293 | CG | BARG | G | 315 | 87.860 | −135.517 | 178.714 | 0.50 | 140.27 |
| ATOM | 1294 | CD | AARG | G | 315 | 89.381 | −134.354 | 179.103 | 0.50 | 138.38 |
| ATOM | 1295 | CD | BARG | G | 315 | 89.207 | −135.465 | 179.420 | 0.50 | 140.88 |
| ATOM | 1296 | NE | AARG | G | 315 | 89.824 | −135.078 | 180.294 | 0.50 | 138.70 |
| ATOM | 1297 | NE | BARG | G | 315 | 89.349 | −136.496 | 180.445 | 0.50 | 140.22 |
| ATOM | 1298 | CZ | AARG | G | 315 | 90.845 | −134.703 | 181.062 | 0.50 | 138.42 |
| ATOM | 1299 | CZ | BARG | G | 315 | 90.422 | −136.637 | 181.219 | 0.50 | 139.80 |
| ATOM | 1300 | NH1 | AARG | G | 315 | 91.530 | −133.607 | 180.768 | 0.50 | 138.28 |
| ATOM | 1301 | NH1 | BARG | G | 315 | 91.454 | −135.813 | 181.085 | 0.50 | 138.98 |
| ATOM | 1302 | NH2 | AARG | G | 315 | 91.181 | −135.424 | 182.125 | 0.50 | 138.35 |
| ATOM | 1303 | NH2 | BARG | G | 315 | 90.466 | −137.604 | 182.126 | 0.50 | 138.56 |
| ATOM | 1304 | N | ALA | G | 316 | 86.934 | −135.273 | 174.800 | 1.00 | 144.80 |
| ATOM | 1305 | CA | ALA | G | 316 | 86.989 | −136.226 | 173.690 | 1.00 | 143.79 |
| ATOM | 1306 | C | ALA | G | 316 | 88.432 | −136.339 | 173.191 | 1.00 | 146.46 |
| ATOM | 1307 | O | ALA | G | 316 | 89.285 | −135.522 | 173.549 | 1.00 | 147.07 |
| ATOM | 1308 | CB | ALA | G | 316 | 86.065 | −135.774 | 172.553 | 1.00 | 144.31 |
| ATOM | 1309 | N | PHE | G | 317 | 88.701 | −137.350 | 172.366 | 1.00 | 149.66 |
| ATOM | 1310 | CA | PHE | G | 317 | 90.048 | −137.578 | 171.852 | 1.00 | 151.88 |
| ATOM | 1311 | C | PHE | G | 317 | 90.071 | −137.825 | 170.343 | 1.00 | 152.98 |
| ATOM | 1312 | O | PHE | G | 317 | 89.095 | −138.305 | 169.765 | 1.00 | 153.44 |
| ATOM | 1313 | CB | PHE | G | 317 | 90.693 | −138.774 | 172.565 | 1.00 | 151.95 |
| ATOM | 1314 | CG | PHE | G | 317 | 90.978 | −138.541 | 174.025 | 1.00 | 152.25 |
| ATOM | 1315 | CD1 | PHE | G | 317 | 89.940 | −138.387 | 174.940 | 1.00 | 151.95 |
| ATOM | 1316 | CD2 | PHE | G | 317 | 92.290 | −138.486 | 174.487 | 1.00 | 152.28 |
| ATOM | 1317 | CE1 | PHE | G | 317 | 90.204 | −138.181 | 176.293 | 1.00 | 151.79 |
| ATOM | 1318 | CE2 | PHE | G | 317 | 92.565 | −138.281 | 175.838 | 1.00 | 152.38 |
| ATOM | 1319 | CZ | PHE | G | 317 | 91.519 | −138.129 | 176.742 | 1.00 | 152.23 |
| ATOM | 1320 | N | TYR | G | 318 | 91.199 | −137.492 | 169.720 | 1.00 | 154.53 |
| ATOM | 1321 | CA | TYR | G | 318 | 91.406 | −137.676 | 168.283 | 1.00 | 155.71 |
| ATOM | 1322 | C | TYR | G | 318 | 90.427 | −136.911 | 167.391 | 1.00 | 155.64 |
| ATOM | 1323 | O | TYR | G | 318 | 89.646 | −137.520 | 166.659 | 1.00 | 155.52 |
| ATOM | 1324 | CB | TYR | G | 318 | 91.340 | −139.165 | 167.919 | 1.00 | 156.48 |
| ATOM | 1325 | CG | TYR | G | 318 | 92.267 | −140.063 | 168.711 | 1.00 | 157.82 |
| ATOM | 1326 | CD1 | TYR | G | 318 | 92.044 | −140.309 | 170.065 | 1.00 | 158.34 |

TABLE 2-continued

The structural coordinates of an exemplary gp120 with an extended V3 loop

| | | | | | | | | | | |
|---|---|---|---|---|---|---|---|---|---|---|
| ATOM | 1327 | CD2 | TYR | G | 318 | 93.353 | −140.689 | 168.099 | 1.00 | 158.59 |
| ATOM | 1328 | CE1 | TYR | G | 318 | 92.875 | −141.159 | 170.791 | 1.00 | 158.85 |
| ATOM | 1329 | CE2 | TYR | G | 318 | 94.192 | −141.542 | 168.817 | 1.00 | 159.15 |
| ATOM | 1330 | CZ | TYR | G | 318 | 93.945 | −141.772 | 170.162 | 1.00 | 159.22 |
| ATOM | 1331 | OH | TYR | G | 318 | 94.765 | −142.615 | 170.877 | 1.00 | 159.77 |
| ATOM | 1332 | N | THR | G | 319 | 90.474 | −135.583 | 167.440 | 1.00 | 155.30 |
| ATOM | 1333 | CA | THR | G | 319 | 89.589 | −134.763 | 166.616 | 1.00 | 155.09 |
| ATOM | 1334 | C | THR | G | 319 | 90.251 | −133.430 | 166.269 | 1.00 | 154.62 |
| ATOM | 1335 | O | THR | G | 319 | 89.683 | −132.611 | 165.545 | 1.00 | 153.91 |
| ATOM | 1336 | CB | THR | G | 319 | 88.246 | −134.485 | 167.334 | 1.00 | 155.83 |
| ATOM | 1337 | OG1 | THR | G | 319 | 87.669 | −135.722 | 167.771 | 1.00 | 156.26 |
| ATOM | 1338 | CG2 | THR | G | 319 | 87.265 | −133.797 | 166.389 | 1.00 | 155.64 |
| ATOM | 1339 | N | THR | G | 320 | 91.460 | −133.223 | 166.783 | 1.00 | 154.50 |
| ATOM | 1340 | CA | THR | G | 320 | 92.199 | −131.990 | 166.532 | 1.00 | 154.03 |
| ATOM | 1341 | C | THR | G | 320 | 93.278 | −132.162 | 165.463 | 1.00 | 153.67 |
| ATOM | 1342 | O | THR | G | 320 | 94.420 | −131.734 | 165.646 | 1.00 | 153.56 |
| ATOM | 1343 | CB | THR | G | 320 | 92.867 | −131.467 | 167.823 | 1.00 | 154.73 |
| ATOM | 1344 | OG1 | THR | G | 320 | 93.762 | −132.462 | 168.338 | 1.00 | 154.90 |
| ATOM | 1345 | CG2 | THR | G | 320 | 91.814 | −131.143 | 168.874 | 1.00 | 154.48 |
| ATOM | 1346 | N | GLY | G | 321 | 92.912 | −132.791 | 164.350 | 1.00 | 152.75 |
| ATOM | 1347 | CA | GLY | G | 321 | 93.861 | −132.995 | 163.270 | 1.00 | 151.08 |
| ATOM | 1348 | C | GLY | G | 321 | 94.014 | −131.729 | 162.449 | 1.00 | 150.38 |
| ATOM | 1349 | O | GLY | G | 321 | 93.119 | −131.365 | 161.685 | 1.00 | 149.77 |
| ATOM | 1350 | N | GLU | G | 322 | 95.150 | −131.056 | 162.605 | 1.00 | 149.39 |
| ATOM | 1351 | CA | GLU | G | 322 | 95.405 | −129.814 | 161.884 | 1.00 | 148.29 |
| ATOM | 1352 | C | GLU | G | 322 | 96.649 | −129.909 | 161.008 | 1.00 | 147.73 |
| ATOM | 1353 | O | GLU | G | 322 | 96.564 | −130.249 | 159.827 | 1.00 | 146.53 |
| ATOM | 1354 | CB | GLU | G | 322 | 95.572 | −128.662 | 162.877 | 1.00 | 148.27 |
| ATOM | 1355 | CG | GLU | G | 322 | 94.503 | −128.616 | 163.956 | 1.00 | 148.79 |
| ATOM | 1356 | CD | GLU | G | 322 | 94.707 | −127.471 | 164.928 | 1.00 | 148.76 |
| ATOM | 1357 | OE1 | GLU | G | 322 | 95.819 | −127.354 | 165.485 | 1.00 | 148.26 |
| ATOM | 1358 | OE2 | GLU | G | 322 | 93.753 | −126.693 | 165.138 | 1.00 | 148.68 |
| ATOM | 1359 | N | ILE | G | 322A | 97.801 | −129.607 | 161.603 | 1.00 | 147.61 |
| ATOM | 1360 | CA | ILE | G | 322A | 99.087 | −129.634 | 160.910 | 1.00 | 147.08 |
| ATOM | 1361 | C | ILE | G | 322A | 98.968 | −129.223 | 159.444 | 1.00 | 146.30 |
| ATOM | 1362 | O | ILE | G | 322A | 98.978 | −130.067 | 158.548 | 1.00 | 145.89 |
| ATOM | 1363 | CB | ILE | G | 322A | 99.755 | −131.036 | 161.003 | 1.00 | 147.76 |
| ATOM | 1364 | CG1 | ILE | G | 322A | 98.807 | −132.120 | 160.480 | 1.00 | 148.35 |
| ATOM | 1365 | CG2 | ILE | G | 322A | 100.149 | −131.324 | 162.446 | 1.00 | 147.20 |
| ATOM | 1366 | CD1 | ILE | G | 322A | 99.408 | −133.513 | 160.469 | 1.00 | 146.09 |
| ATOM | 1367 | N | ILE | G | 323 | 98.854 | −127.917 | 159.214 | 1.00 | 145.42 |
| ATOM | 1368 | CA | ILE | G | 323 | 98.728 | −127.370 | 157.865 | 1.00 | 144.18 |
| ATOM | 1369 | C | ILE | G | 323 | 99.759 | −127.991 | 156.928 | 1.00 | 143.58 |
| ATOM | 1370 | O | ILE | G | 323 | 100.878 | −127.492 | 156.799 | 1.00 | 143.84 |
| ATOM | 1371 | CB | ILE | G | 323 | 98.919 | −125.833 | 157.864 | 1.00 | 143.68 |
| ATOM | 1372 | CG1 | ILE | G | 323 | 97.919 | −125.179 | 158.823 | 1.00 | 142.95 |
| ATOM | 1373 | CG2 | ILE | G | 323 | 98.743 | −125.285 | 156.452 | 1.00 | 142.76 |
| ATOM | 1374 | CD1 | ILE | G | 323 | 96.462 | −125.431 | 158.476 | 1.00 | 141.08 |
| ATOM | 1375 | N | GLY | G | 324 | 99.371 | −129.082 | 156.275 | 1.00 | 142.21 |
| ATOM | 1376 | CA | GLY | G | 324 | 100.273 | −129.759 | 155.363 | 1.00 | 139.77 |
| ATOM | 1377 | C | GLY | G | 324 | 99.607 | −130.172 | 154.067 | 1.00 | 137.92 |
| ATOM | 1378 | O | GLY | G | 324 | 98.645 | −129.543 | 153.622 | 1.00 | 137.70 |
| ATOM | 1379 | N | ASP | G | 325 | 100.119 | −131.238 | 153.461 | 1.00 | 136.00 |
| ATOM | 1380 | CA | ASP | G | 325 | 99.579 | −131.735 | 152.203 | 1.00 | 133.50 |
| ATOM | 1381 | C | ASP | G | 325 | 98.873 | −133.076 | 152.378 | 1.00 | 131.01 |
| ATOM | 1382 | O | ASP | G | 325 | 99.517 | −134.125 | 152.420 | 1.00 | 130.01 |
| ATOM | 1383 | CB | ASP | G | 325 | 100.701 | −131.883 | 151.168 | 1.00 | 134.89 |
| ATOM | 1384 | CG | ASP | G | 325 | 101.463 | −130.587 | 150.937 | 1.00 | 135.71 |
| ATOM | 1385 | OD1 | ASP | G | 325 | 100.829 | −129.577 | 150.563 | 1.00 | 136.06 |
| ATOM | 1386 | OD2 | ASP | G | 325 | 102.698 | −130.580 | 151.125 | 1.00 | 134.58 |
| ATOM | 1387 | N | ILE | G | 326 | 97.549 | −133.035 | 152.488 | 1.00 | 129.15 |
| ATOM | 1388 | CA | ILE | G | 326 | 96.752 | −134.248 | 152.636 | 1.00 | 127.17 |
| ATOM | 1389 | C | ILE | G | 326 | 96.181 | −134.612 | 151.270 | 1.00 | 125.06 |
| ATOM | 1390 | O | ILE | G | 326 | 95.556 | −135.660 | 151.097 | 1.00 | 123.58 |
| ATOM | 1391 | CB | ILE | G | 326 | 95.585 | −134.060 | 153.642 | 1.00 | 128.41 |
| ATOM | 1392 | CG1 | ILE | G | 326 | 94.645 | −132.942 | 153.173 | 1.00 | 129.82 |
| ATOM | 1393 | CG2 | ILE | G | 326 | 96.140 | −133.766 | 155.028 | 1.00 | 127.42 |
| ATOM | 1394 | CD1 | ILE | G | 326 | 95.235 | −131.542 | 153.236 | 1.00 | 130.42 |
| ATOM | 1395 | N | ARG | G | 327 | 96.405 | −133.725 | 150.305 | 1.00 | 123.14 |
| ATOM | 1396 | CA | ARG | G | 327 | 95.941 | −133.924 | 148.939 | 1.00 | 121.11 |
| ATOM | 1397 | C | ARG | G | 327 | 97.147 | −134.327 | 148.100 | 1.00 | 120.61 |
| ATOM | 1398 | O | ARG | G | 327 | 97.188 | −134.076 | 146.897 | 1.00 | 120.79 |
| ATOM | 1399 | CB | ARG | G | 327 | 95.358 | −132.627 | 148.372 | 1.00 | 120.85 |
| ATOM | 1400 | CG | ARG | G | 327 | 94.459 | −131.843 | 149.317 | 1.00 | 118.55 |
| ATOM | 1401 | CD | ARG | G | 327 | 93.929 | −130.592 | 148.622 | 1.00 | 116.19 |
| ATOM | 1402 | NE | ARG | G | 327 | 93.320 | −129.641 | 149.549 | 1.00 | 114.20 |
| ATOM | 1403 | CZ | ARG | G | 327 | 92.253 | −129.896 | 150.299 | 1.00 | 112.97 |
| ATOM | 1404 | NH1 | ARG | G | 327 | 91.661 | −131.080 | 150.241 | 1.00 | 112.39 |

TABLE 2-continued

The structural coordinates of an exemplary gp120 with an extended V3 loop

| ATOM | 1405 | NH2 | ARG | G | 327 | 91.777 | −128.963 | 151.111 | 1.00 | 111.25 |
|---|---|---|---|---|---|---|---|---|---|---|
| ATOM | 1406 | N | GLN | G | 328 | 98.134 | −134.943 | 148.743 | 1.00 | 120.56 |
| ATOM | 1407 | CA | GLN | G | 328 | 99.349 | −135.363 | 148.056 | 1.00 | 120.47 |
| ATOM | 1408 | C | GLN | G | 328 | 99.300 | −136.818 | 147.602 | 1.00 | 120.52 |
| ATOM | 1409 | O | GLN | G | 328 | 98.731 | −137.676 | 148.278 | 1.00 | 119.31 |
| ATOM | 1410 | CB | GLN | G | 328 | 100.564 | −135.158 | 148.965 | 1.00 | 120.86 |
| ATOM | 1411 | CG | GLN | G | 328 | 101.888 | −135.560 | 148.330 | 1.00 | 121.32 |
| ATOM | 1412 | CD | GLN | G | 328 | 103.053 | −135.494 | 149.302 | 1.00 | 121.93 |
| ATOM | 1413 | OE1 | GLN | G | 328 | 104.192 | −135.792 | 148.942 | 1.00 | 121.20 |
| ATOM | 1414 | NE2 | GLN | G | 328 | 102.771 | −135.104 | 150.541 | 1.00 | 121.27 |
| ATOM | 1415 | N | ALA | G | 329 | 99.909 | −137.081 | 146.451 | 1.00 | 120.97 |
| ATOM | 1416 | CA | ALA | G | 329 | 99.961 | −138.422 | 145.883 | 1.00 | 121.52 |
| ATOM | 1417 | C | ALA | G | 329 | 101.311 | −138.622 | 145.204 | 1.00 | 122.43 |
| ATOM | 1418 | O | ALA | G | 329 | 102.079 | −137.673 | 145.043 | 1.00 | 122.38 |
| ATOM | 1419 | CB | ALA | G | 329 | 98.836 | −138.606 | 144.877 | 1.00 | 121.15 |
| ATOM | 1420 | N | HIS | G | 330 | 101.600 | −139.858 | 144.811 | 1.00 | 123.54 |
| ATOM | 1421 | CA | HIS | G | 330 | 102.861 | −140.168 | 144.150 | 1.00 | 124.36 |
| ATOM | 1422 | C | HIS | G | 330 | 102.701 | −141.357 | 143.210 | 1.00 | 124.92 |
| ATOM | 1423 | O | HIS | G | 330 | 101.851 | −142.221 | 143.431 | 1.00 | 124.23 |
| ATOM | 1424 | CB | HIS | G | 330 | 103.943 | −140.473 | 145.189 | 1.00 | 124.54 |
| ATOM | 1425 | CG | HIS | G | 330 | 103.653 | −141.680 | 146.028 | 1.00 | 125.33 |
| ATOM | 1426 | ND1 | HIS | G | 330 | 102.556 | −141.764 | 146.858 | 1.00 | 125.66 |
| ATOM | 1427 | CD2 | HIS | G | 330 | 104.317 | −142.852 | 146.162 | 1.00 | 125.46 |
| ATOM | 1428 | CE1 | HIS | G | 330 | 102.556 | −142.937 | 147.467 | 1.00 | 125.67 |
| ATOM | 1429 | NE2 | HIS | G | 330 | 103.614 | −143.617 | 147.061 | 1.00 | 125.50 |
| ATOM | 1430 | N | CYS | G | 331 | 103.519 | −141.392 | 142.162 | 1.00 | 125.98 |
| ATOM | 1431 | CA | CYS | G | 331 | 103.471 | −142.479 | 141.187 | 1.00 | 127.16 |
| ATOM | 1432 | C | CYS | G | 331 | 104.763 | −143.292 | 141.212 | 1.00 | 129.17 |
| ATOM | 1433 | O | CYS | G | 331 | 105.756 | −142.883 | 141.814 | 1.00 | 129.56 |
| ATOM | 1434 | CB | CYS | G | 331 | 103.263 | −141.931 | 139.777 | 1.00 | 124.83 |
| ATOM | 1435 | SG | CYS | G | 331 | 101.784 | −140.903 | 139.514 | 1.00 | 121.39 |
| ATOM | 1436 | N | ASN | G | 332 | 104.744 | −144.441 | 140.542 | 1.00 | 131.21 |
| ATOM | 1437 | CA | ASN | G | 332 | 105.907 | −145.317 | 140.491 | 1.00 | 133.03 |
| ATOM | 1438 | C | ASN | G | 332 | 106.019 | −146.059 | 139.161 | 1.00 | 132.94 |
| ATOM | 1439 | O | ASN | G | 332 | 105.054 | −146.665 | 138.696 | 1.00 | 133.74 |
| ATOM | 1440 | CB | ASN | G | 332 | 105.845 | −146.346 | 141.625 | 1.00 | 135.06 |
| ATOM | 1441 | CG | ASN | G | 332 | 106.883 | −146.090 | 142.699 | 1.00 | 138.61 |
| ATOM | 1442 | OD1 | ASN | G | 332 | 108.036 | −145.797 | 142.379 | 1.00 | 140.34 |
| ATOM | 1443 | ND2 | ASN | G | 332 | 106.492 | −146.199 | 143.969 | 1.00 | 141.14 |
| ATOM | 1444 | N | ILE | G | 333 | 107.205 | −146.016 | 138.562 | 1.00 | 132.27 |
| ATOM | 1445 | CA | ILE | G | 333 | 107.458 | −146.705 | 137.305 | 1.00 | 131.40 |
| ATOM | 1446 | C | ILE | G | 333 | 108.827 | −147.371 | 137.344 | 1.00 | 131.17 |
| ATOM | 1447 | O | ILE | G | 333 | 109.685 | −146.991 | 138.138 | 1.00 | 130.59 |
| ATOM | 1448 | CB | ILE | G | 333 | 107.438 | −145.738 | 136.110 | 1.00 | 130.99 |
| ATOM | 1449 | CG1 | ILE | G | 333 | 108.336 | −144.541 | 136.416 | 1.00 | 131.41 |
| ATOM | 1450 | CG2 | ILE | G | 333 | 106.013 | −145.321 | 135.796 | 1.00 | 130.08 |
| ATOM | 1451 | CD1 | ILE | G | 333 | 108.808 | −143.797 | 135.194 | 1.00 | 130.71 |
| ATOM | 1452 | N | SER | G | 334 | 109.027 | −148.362 | 136.482 | 1.00 | 130.80 |
| ATOM | 1453 | CA | SER | G | 334 | 110.298 | −149.071 | 136.417 | 1.00 | 130.47 |
| ATOM | 1454 | C | SER | G | 334 | 111.379 | −148.202 | 135.781 | 1.00 | 129.18 |
| ATOM | 1455 | O | SER | G | 334 | 111.253 | −147.785 | 134.630 | 1.00 | 128.30 |
| ATOM | 1456 | CB | SER | G | 334 | 110.137 | −150.366 | 135.620 | 1.00 | 131.53 |
| ATOM | 1457 | OG | SER | G | 334 | 109.185 | −151.224 | 136.226 | 1.00 | 134.33 |
| ATOM | 1458 | N | ARG | G | 335 | 112.441 | −147.938 | 136.537 | 1.00 | 128.40 |
| ATOM | 1459 | CA | ARG | G | 335 | 113.550 | −147.114 | 136.062 | 1.00 | 127.88 |
| ATOM | 1460 | C | ARG | G | 335 | 114.232 | −147.713 | 134.831 | 1.00 | 127.39 |
| ATOM | 1461 | O | ARG | G | 335 | 114.594 | −146.992 | 133.901 | 1.00 | 125.90 |
| ATOM | 1462 | CB | ARG | G | 335 | 114.588 | −146.944 | 137.174 | 1.00 | 128.63 |
| ATOM | 1463 | CG | ARG | G | 335 | 115.721 | −145.986 | 136.839 | 1.00 | 130.03 |
| ATOM | 1464 | CD | ARG | G | 335 | 115.354 | −144.549 | 137.175 | 1.00 | 131.46 |
| ATOM | 1465 | NE | ARG | G | 335 | 116.464 | −143.631 | 136.927 | 1.00 | 133.64 |
| ATOM | 1466 | CZ | ARG | G | 335 | 116.796 | −143.164 | 135.728 | 1.00 | 135.08 |
| ATOM | 1467 | NH1 | ARG | G | 335 | 116.102 | −143.521 | 134.655 | 1.00 | 135.62 |
| ATOM | 1468 | NH2 | ARG | G | 335 | 117.828 | −142.340 | 135.600 | 1.00 | 136.66 |
| ATOM | 1469 | N | ALA | G | 336 | 114.409 | −149.030 | 134.831 | 1.00 | 127.56 |
| ATOM | 1470 | CA | ALA | G | 336 | 115.060 | −149.712 | 133.717 | 1.00 | 127.56 |
| ATOM | 1471 | C | ALA | G | 336 | 114.193 | −149.726 | 132.462 | 1.00 | 127.53 |
| ATOM | 1472 | O | ALA | G | 336 | 114.702 | −149.613 | 131.347 | 1.00 | 127.19 |
| ATOM | 1473 | CB | ALA | G | 336 | 115.419 | −151.140 | 134.121 | 1.00 | 127.32 |
| ATOM | 1474 | N | LYS | G | 337 | 112.884 | −149.870 | 132.653 | 1.00 | 127.34 |
| ATOM | 1475 | CA | LYS | G | 337 | 111.929 | −149.897 | 131.547 | 1.00 | 126.12 |
| ATOM | 1476 | C | LYS | G | 337 | 111.697 | −148.511 | 130.952 | 1.00 | 125.19 |
| ATOM | 1477 | O | LYS | G | 337 | 111.525 | −148.370 | 129.742 | 1.00 | 125.25 |
| ATOM | 1478 | CB | LYS | G | 337 | 110.590 | −150.483 | 132.019 | 1.00 | 125.26 |
| ATOM | 1479 | CG | LYS | G | 337 | 110.486 | −152.006 | 131.948 | 1.00 | 125.56 |
| ATOM | 1480 | CD | LYS | G | 337 | 110.195 | −152.482 | 130.524 | 1.00 | 125.22 |
| ATOM | 1481 | CE | LYS | G | 337 | 110.096 | −154.003 | 130.442 | 1.00 | 125.33 |
| ATOM | 1482 | NZ | LYS | G | 337 | 109.878 | −154.486 | 129.045 | 1.00 | 122.70 |

TABLE 2-continued

The structural coordinates of an exemplary gp120 with an extended V3 loop

| ATOM | 1483 | N    | TRP | G | 338 | 111.693 | −147.488 | 131.802 | 1.00 | 123.88 |
|------|------|------|-----|---|-----|---------|----------|---------|------|--------|
| ATOM | 1484 | CA   | TRP | G | 338 | 111.471 | −146.120 | 131.343 | 1.00 | 122.35 |
| ATOM | 1485 | C    | TRP | G | 338 | 112.656 | −145.584 | 130.551 | 1.00 | 122.08 |
| ATOM | 1486 | O    | TRP | G | 338 | 112.482 | −144.934 | 129.521 | 1.00 | 121.22 |
| ATOM | 1487 | CB   | TRP | G | 338 | 111.188 | −145.199 | 132.535 | 1.00 | 121.06 |
| ATOM | 1488 | CG   | TRP | G | 338 | 111.092 | −143.744 | 132.172 | 1.00 | 119.31 |
| ATOM | 1489 | CD1  | TRP | G | 338 | 111.853 | −142.726 | 132.669 | 1.00 | 119.14 |
| ATOM | 1490 | CD2  | TRP | G | 338 | 110.185 | −143.145 | 131.235 | 1.00 | 118.77 |
| ATOM | 1491 | NE1  | TRP | G | 338 | 111.479 | −141.531 | 132.103 | 1.00 | 119.01 |
| ATOM | 1492 | CE2  | TRP | G | 338 | 110.458 | −141.758 | 131.220 | 1.00 | 118.35 |
| ATOM | 1493 | CE3  | TRP | G | 338 | 109.170 | −143.644 | 130.409 | 1.00 | 118.58 |
| ATOM | 1494 | CZ2  | TRP | G | 338 | 109.751 | −140.864 | 130.408 | 1.00 | 117.90 |
| ATOM | 1495 | CZ3  | TRP | G | 338 | 108.467 | −142.753 | 129.601 | 1.00 | 118.02 |
| ATOM | 1496 | CH2  | TRP | G | 338 | 108.763 | −141.378 | 129.609 | 1.00 | 117.53 |
| ATOM | 1497 | N    | ASN | G | 339 | 113.860 | −145.865 | 131.034 | 1.00 | 122.65 |
| ATOM | 1498 | CA   | ASN | G | 339 | 115.068 | −145.399 | 130.367 | 1.00 | 123.64 |
| ATOM | 1499 | C    | ASN | G | 339 | 115.247 | −146.081 | 129.015 | 1.00 | 122.72 |
| ATOM | 1500 | O    | ASN | G | 339 | 115.779 | −145.490 | 128.079 | 1.00 | 120.87 |
| ATOM | 1501 | CB   | ASN | G | 339 | 116.292 | −145.661 | 131.249 | 1.00 | 126.14 |
| ATOM | 1502 | CG   | ASN | G | 339 | 117.430 | −144.705 | 130.960 | 1.00 | 128.79 |
| ATOM | 1503 | OD1  | ASN | G | 339 | 117.338 | −143.511 | 131.247 | 1.00 | 129.26 |
| ATOM | 1504 | ND2  | ASN | G | 339 | 118.508 | −145.223 | 130.384 | 1.00 | 130.45 |
| ATOM | 1505 | N    | ASP | G | 340 | 114.805 | −147.331 | 128.922 | 1.00 | 122.55 |
| ATOM | 1506 | CA   | ASP | G | 340 | 114.913 | −148.080 | 127.676 | 1.00 | 122.48 |
| ATOM | 1507 | C    | ASP | G | 340 | 113.925 | −147.552 | 126.654 | 1.00 | 121.75 |
| ATOM | 1508 | O    | ASP | G | 340 | 114.254 | −147.398 | 125.482 | 1.00 | 121.24 |
| ATOM | 1509 | CB   | ASP | G | 340 | 114.651 | −149.569 | 127.913 | 1.00 | 123.36 |
| ATOM | 1510 | CG   | ASP | G | 340 | 115.932 | −150.373 | 128.021 | 1.00 | 124.46 |
| ATOM | 1511 | OD1  | ASP | G | 340 | 116.606 | −150.547 | 126.987 | 1.00 | 124.57 |
| ATOM | 1512 | OD2  | ASP | G | 340 | 116.263 | −150.820 | 129.138 | 1.00 | 124.24 |
| ATOM | 1513 | N    | THR | G | 341 | 112.709 | −147.277 | 127.107 | 1.00 | 121.23 |
| ATOM | 1514 | CA   | THR | G | 341 | 111.678 | −146.760 | 126.223 | 1.00 | 120.37 |
| ATOM | 1515 | C    | THR | G | 341 | 112.005 | −145.321 | 125.864 | 1.00 | 120.04 |
| ATOM | 1516 | O    | THR | G | 341 | 111.571 | −144.813 | 124.833 | 1.00 | 119.85 |
| ATOM | 1517 | CB   | THR | G | 341 | 110.292 | −146.798 | 126.885 | 1.00 | 119.50 |
| ATOM | 1518 | OG1  | THR | G | 341 | 110.387 | −146.310 | 128.227 | 1.00 | 118.81 |
| ATOM | 1519 | CG2  | THR | G | 341 | 109.738 | −148.202 | 126.892 | 1.00 | 119.32 |
| ATOM | 1520 | N    | LEU | G | 342 | 112.780 | −144.668 | 126.719 | 1.00 | 118.58 |
| ATOM | 1521 | CA   | LEU | G | 342 | 113.172 | −143.285 | 126.488 | 1.00 | 117.21 |
| ATOM | 1522 | C    | LEU | G | 342 | 114.214 | −143.283 | 125.372 | 1.00 | 117.06 |
| ATOM | 1523 | O    | LEU | G | 342 | 114.277 | −142.363 | 124.557 | 1.00 | 116.61 |
| ATOM | 1524 | CB   | LEU | G | 342 | 113.757 | −142.700 | 127.780 | 1.00 | 116.17 |
| ATOM | 1525 | CG   | LEU | G | 342 | 113.453 | −141.242 | 128.147 | 1.00 | 115.99 |
| ATOM | 1526 | CD1  | LEU | G | 342 | 113.803 | −141.014 | 129.608 | 1.00 | 115.86 |
| ATOM | 1527 | CD2  | LEU | G | 342 | 114.230 | −140.299 | 127.247 | 1.00 | 115.38 |
| ATOM | 1528 | N    | LYS | G | 343 | 115.021 | −144.340 | 125.341 | 1.00 | 117.43 |
| ATOM | 1529 | CA   | LYS | G | 343 | 116.071 | −144.497 | 124.340 | 1.00 | 117.14 |
| ATOM | 1530 | C    | LYS | G | 343 | 115.481 | −144.739 | 122.957 | 1.00 | 116.27 |
| ATOM | 1531 | O    | LYS | G | 343 | 115.931 | −144.159 | 121.970 | 1.00 | 114.89 |
| ATOM | 1532 | CB   | LYS | G | 343 | 116.988 | −145.668 | 124.720 | 1.00 | 118.24 |
| ATOM | 1533 | CG   | LYS | G | 343 | 118.124 | −145.916 | 123.741 | 1.00 | 119.11 |
| ATOM | 1534 | CD   | LYS | G | 343 | 118.999 | −147.081 | 124.184 | 1.00 | 118.05 |
| ATOM | 1535 | CE   | LYS | G | 343 | 120.143 | −147.321 | 123.205 | 1.00 | 117.07 |
| ATOM | 1536 | NZ   | LYS | G | 343 | 121.015 | −148.456 | 123.624 | 1.00 | 118.22 |
| ATOM | 1537 | N    | GLN | G | 344 | 114.466 | −145.594 | 122.890 | 1.00 | 115.18 |
| ATOM | 1538 | CA   | GLN | G | 344 | 113.828 | −145.899 | 121.617 | 1.00 | 114.37 |
| ATOM | 1539 | C    | GLN | G | 344 | 113.146 | −144.685 | 121.009 | 1.00 | 114.01 |
| ATOM | 1540 | O    | GLN | G | 344 | 112.888 | −144.642 | 119.807 | 1.00 | 113.70 |
| ATOM | 1541 | CB   | GLN | G | 344 | 112.838 | −147.051 | 121.780 | 1.00 | 113.68 |
| ATOM | 1542 | CG   | GLN | G | 344 | 113.519 | −148.414 | 121.728 | 1.00 | 114.75 |
| ATOM | 1543 | CD   | GLN | G | 344 | 113.191 | −149.300 | 122.912 | 1.00 | 115.83 |
| ATOM | 1544 | OE1  | GLN | G | 344 | 112.072 | −149.795 | 123.044 | 1.00 | 116.37 |
| ATOM | 1545 | NE2  | GLN | G | 344 | 114.172 | −149.505 | 123.784 | 1.00 | 116.57 |
| ATOM | 1546 | N    | ILE | G | 345 | 112.858 | −143.694 | 121.839 | 1.00 | 113.81 |
| ATOM | 1547 | CA   | ILE | G | 345 | 112.241 | −142.472 | 121.349 | 1.00 | 113.74 |
| ATOM | 1548 | C    | ILE | G | 345 | 113.341 | −141.701 | 120.641 | 1.00 | 114.51 |
| ATOM | 1549 | O    | ILE | G | 345 | 113.143 | −141.157 | 119.555 | 1.00 | 114.50 |
| ATOM | 1550 | CB   | ILE | G | 345 | 111.689 | −141.630 | 122.513 | 1.00 | 113.46 |
| ATOM | 1551 | CG1  | ILE | G | 345 | 110.481 | −142.345 | 123.133 | 1.00 | 113.45 |
| ATOM | 1552 | CG2  | ILE | G | 345 | 111.291 | −140.246 | 122.018 | 1.00 | 112.53 |
| ATOM | 1553 | CD1  | ILE | G | 345 | 109.980 | −141.716 | 124.407 | 1.00 | 114.16 |
| ATOM | 1554 | N    | VAL | G | 346 | 114.509 | −141.680 | 121.271 | 1.00 | 115.23 |
| ATOM | 1555 | CA   | VAL | G | 346 | 115.670 | −140.996 | 120.729 | 1.00 | 116.13 |
| ATOM | 1556 | C    | VAL | G | 346 | 116.128 | −141.657 | 119.439 | 1.00 | 116.56 |
| ATOM | 1557 | O    | VAL | G | 346 | 116.491 | −140.980 | 118.476 | 1.00 | 115.69 |
| ATOM | 1558 | CB   | VAL | G | 346 | 116.836 | −141.021 | 121.727 | 1.00 | 116.71 |
| ATOM | 1559 | CG1  | VAL | G | 346 | 118.063 | −140.394 | 121.104 | 1.00 | 116.76 |
| ATOM | 1560 | CG2  | VAL | G | 346 | 116.444 | −140.284 | 122.999 | 1.00 | 117.56 |

TABLE 2-continued

The structural coordinates of an exemplary gp120 with an extended V3 loop

| ATOM | 1561 | N   | ILE | G | 347 | 116.105 | −142.984 | 119.423 | 1.00 | 116.67 |
|------|------|-----|-----|---|-----|---------|----------|---------|------|--------|
| ATOM | 1562 | CA  | ILE | G | 347 | 116.513 | −143.735 | 118.246 | 1.00 | 117.05 |
| ATOM | 1563 | C   | ILE | G | 347 | 115.693 | −143.356 | 117.022 | 1.00 | 117.43 |
| ATOM | 1564 | O   | ILE | G | 347 | 116.235 | −143.207 | 115.928 | 1.00 | 117.11 |
| ATOM | 1565 | CB  | ILE | G | 347 | 116.366 | −145.248 | 118.488 | 1.00 | 118.09 |
| ATOM | 1566 | CG1 | ILE | G | 347 | 117.391 | −145.700 | 119.527 | 1.00 | 118.82 |
| ATOM | 1567 | CG2 | ILE | G | 347 | 116.546 | −146.012 | 117.186 | 1.00 | 117.63 |
| ATOM | 1568 | CD1 | ILE | G | 347 | 118.828 | −145.515 | 119.081 | 1.00 | 120.24 |
| ATOM | 1569 | N   | LYS | G | 348 | 114.387 | −143.199 | 117.215 | 1.00 | 118.10 |
| ATOM | 1570 | CA  | LYS | G | 348 | 113.492 | −142.836 | 116.125 | 1.00 | 119.28 |
| ATOM | 1571 | C   | LYS | G | 348 | 113.477 | −141.331 | 115.880 | 1.00 | 120.01 |
| ATOM | 1572 | O   | LYS | G | 348 | 113.158 | −140.883 | 114.780 | 1.00 | 119.90 |
| ATOM | 1573 | CB  | LYS | G | 348 | 112.069 | −143.326 | 116.416 | 1.00 | 119.85 |
| ATOM | 1574 | CG  | LYS | G | 348 | 111.895 | −144.844 | 116.394 | 1.00 | 120.97 |
| ATOM | 1575 | CD  | LYS | G | 348 | 112.020 | −145.410 | 114.980 | 1.00 | 122.36 |
| ATOM | 1576 | CE  | LYS | G | 348 | 111.989 | −146.937 | 114.982 | 1.00 | 123.02 |
| ATOM | 1577 | NZ  | LYS | G | 348 | 112.225 | −147.510 | 113.623 | 1.00 | 121.99 |
| ATOM | 1578 | N   | LEU | G | 349 | 113.815 | −140.550 | 116.903 | 1.00 | 120.97 |
| ATOM | 1579 | CA  | LEU | G | 349 | 113.837 | −139.098 | 116.757 | 1.00 | 122.27 |
| ATOM | 1580 | C   | LEU | G | 349 | 115.045 | −138.660 | 115.947 | 1.00 | 124.05 |
| ATOM | 1581 | O   | LEU | G | 349 | 114.973 | −137.710 | 115.170 | 1.00 | 124.00 |
| ATOM | 1582 | CB  | LEU | G | 349 | 113.876 | −138.406 | 118.122 | 1.00 | 121.94 |
| ATOM | 1583 | CG  | LEU | G | 349 | 112.543 | −138.095 | 118.810 | 1.00 | 122.12 |
| ATOM | 1584 | CD1 | LEU | G | 349 | 112.808 | −137.386 | 120.131 | 1.00 | 122.10 |
| ATOM | 1585 | CD2 | LEU | G | 349 | 111.696 | −137.209 | 117.900 | 1.00 | 122.34 |
| ATOM | 1586 | N   | ARG | G | 350 | 116.161 | −139.356 | 116.134 | 1.00 | 126.82 |
| ATOM | 1587 | CA  | ARG | G | 350 | 117.382 | −139.020 | 115.411 | 1.00 | 129.77 |
| ATOM | 1588 | C   | ARG | G | 350 | 117.297 | −139.583 | 114.004 | 1.00 | 130.79 |
| ATOM | 1589 | O   | ARG | G | 350 | 118.100 | −139.246 | 113.138 | 1.00 | 130.39 |
| ATOM | 1590 | CB  | ARG | G | 350 | 118.618 | −139.578 | 116.136 | 1.00 | 131.03 |
| ATOM | 1591 | CG  | ARG | G | 350 | 118.728 | −141.100 | 116.172 | 1.00 | 134.23 |
| ATOM | 1592 | CD  | ARG | G | 350 | 119.545 | −141.557 | 117.385 | 1.00 | 136.50 |
| ATOM | 1593 | NE  | ARG | G | 350 | 120.947 | −141.131 | 117.377 | 1.00 | 137.14 |
| ATOM | 1594 | CZ  | ARG | G | 350 | 121.944 | −141.836 | 116.849 | 1.00 | 137.25 |
| ATOM | 1595 | NH1 | ARG | G | 350 | 121.700 | −143.008 | 116.276 | 1.00 | 136.86 |
| ATOM | 1596 | NH2 | ARG | G | 350 | 123.190 | −141.381 | 116.914 | 1.00 | 136.51 |
| ATOM | 1597 | N   | GLU | G | 351 | 116.307 | −140.440 | 113.783 | 1.00 | 131.73 |
| ATOM | 1598 | CA  | GLU | G | 351 | 116.108 | −141.051 | 112.477 | 1.00 | 131.78 |
| ATOM | 1599 | C   | GLU | G | 351 | 115.426 | −140.024 | 111.574 | 1.00 | 131.64 |
| ATOM | 1600 | O   | GLU | G | 351 | 115.425 | −140.150 | 110.352 | 1.00 | 130.89 |
| ATOM | 1601 | CB  | GLU | G | 351 | 115.250 | −142.319 | 112.618 | 1.00 | 132.20 |
| ATOM | 1602 | CG  | GLU | G | 351 | 115.735 | −143.503 | 111.787 | 1.00 | 133.83 |
| ATOM | 1603 | CD  | GLU | G | 351 | 114.933 | −144.778 | 112.033 | 1.00 | 134.12 |
| ATOM | 1604 | OE1 | GLU | G | 351 | 114.970 | −145.303 | 113.165 | 1.00 | 133.27 |
| ATOM | 1605 | OE2 | GLU | G | 351 | 114.267 | −145.261 | 111.092 | 1.00 | 133.23 |
| ATOM | 1606 | N   | GLN | G | 352 | 114.851 | −138.998 | 112.197 | 1.00 | 131.55 |
| ATOM | 1607 | CA  | GLN | G | 352 | 114.174 | −137.930 | 111.469 | 1.00 | 131.20 |
| ATOM | 1608 | C   | GLN | G | 352 | 115.029 | −136.667 | 111.583 | 1.00 | 131.74 |
| ATOM | 1609 | O   | GLN | G | 352 | 115.015 | −135.810 | 110.703 | 1.00 | 131.22 |
| ATOM | 1610 | CB  | GLN | G | 352 | 112.775 | −137.684 | 112.055 | 1.00 | 129.40 |
| ATOM | 1611 | CG  | GLN | G | 352 | 111.683 | −137.483 | 111.010 | 1.00 | 128.29 |
| ATOM | 1612 | CD  | GLN | G | 352 | 111.760 | −136.141 | 110.302 | 1.00 | 128.13 |
| ATOM | 1613 | OE1 | GLN | G | 352 | 111.325 | −136.007 | 109.158 | 1.00 | 128.02 |
| ATOM | 1614 | NE2 | GLN | G | 352 | 112.296 | −135.137 | 110.986 | 1.00 | 127.02 |
| ATOM | 1615 | N   | PHE | G | 353 | 115.781 | −136.567 | 112.675 | 1.00 | 132.98 |
| ATOM | 1616 | CA  | PHE | G | 353 | 116.654 | −135.423 | 112.911 | 1.00 | 135.12 |
| ATOM | 1617 | C   | PHE | G | 353 | 118.045 | −135.862 | 113.357 | 1.00 | 136.10 |
| ATOM | 1618 | O   | PHE | G | 353 | 118.362 | −135.841 | 114.547 | 1.00 | 136.53 |
| ATOM | 1619 | CB  | PHE | G | 353 | 116.054 | −134.490 | 113.969 | 1.00 | 135.78 |
| ATOM | 1620 | CG  | PHE | G | 353 | 114.963 | −133.605 | 113.447 | 1.00 | 137.46 |
| ATOM | 1621 | CD1 | PHE | G | 353 | 113.645 | −133.786 | 113.853 | 1.00 | 137.80 |
| ATOM | 1622 | CD2 | PHE | G | 353 | 115.255 | −132.586 | 112.544 | 1.00 | 137.80 |
| ATOM | 1623 | CE1 | PHE | G | 353 | 112.631 | −132.963 | 113.365 | 1.00 | 138.59 |
| ATOM | 1624 | CE2 | PHE | G | 353 | 114.249 | −131.759 | 112.050 | 1.00 | 138.17 |
| ATOM | 1625 | CZ  | PHE | G | 353 | 112.935 | −131.948 | 112.461 | 1.00 | 138.87 |
| ATOM | 1626 | N   | GLU | G | 354 | 118.871 | −136.261 | 112.397 | 1.00 | 137.05 |
| ATOM | 1627 | CA  | GLU | G | 354 | 120.224 | −136.707 | 112.687 | 1.00 | 137.91 |
| ATOM | 1628 | C   | GLU | G | 354 | 121.203 | −135.540 | 112.616 | 1.00 | 137.70 |
| ATOM | 1629 | O   | GLU | G | 354 | 120.881 | −134.475 | 112.085 | 1.00 | 137.66 |
| ATOM | 1630 | CB  | GLU | G | 354 | 120.615 | −137.825 | 111.716 | 1.00 | 138.86 |
| ATOM | 1631 | CG  | GLU | G | 354 | 121.921 | −138.512 | 112.053 | 1.00 | 139.85 |
| ATOM | 1632 | CD  | GLU | G | 354 | 122.022 | −138.871 | 113.521 | 1.00 | 140.14 |
| ATOM | 1633 | OE1 | GLU | G | 354 | 121.152 | −139.618 | 114.017 | 1.00 | 140.78 |
| ATOM | 1634 | OE2 | GLU | G | 354 | 122.976 | −138.403 | 114.175 | 1.00 | 139.52 |
| ATOM | 1635 | N   | ASN | G | 355 | 122.406 | −135.754 | 113.142 | 1.00 | 137.40 |
| ATOM | 1636 | CA  | ASN | G | 355 | 123.425 | −134.703 | 113.192 | 1.00 | 136.85 |
| ATOM | 1637 | C   | ASN | G | 355 | 122.937 | −133.573 | 114.098 | 1.00 | 136.44 |
| ATOM | 1638 | O   | ASN | G | 355 | 123.254 | −132.412 | 113.913 | 1.00 | 137.04 |

TABLE 2-continued

The structural coordinates of an exemplary gp120 with an extended V3 loop

| ATOM | 1639 | CB | ASN | G | 355 | 123.740 | −134.195 | 111.776 | 1.00 | 136.54 |
|---|---|---|---|---|---|---|---|---|---|---|
| ATOM | 1640 | CG | ASN | G | 355 | 124.508 | −135.220 | 110.949 | 1.00 | 135.79 |
| ATOM | 1641 | OD1 | ASN | G | 355 | 124.035 | −136.328 | 110.725 | 1.00 | 135.13 |
| ATOM | 1642 | ND2 | ASN | G | 355 | 125.715 | −134.853 | 110.514 | 1.00 | 135.21 |
| ATOM | 1643 | N | LYS | G | 357 | 122.152 | −133.950 | 115.096 | 1.00 | 135.07 |
| ATOM | 1644 | CA | LYS | G | 357 | 121.606 | −133.017 | 116.079 | 1.00 | 133.42 |
| ATOM | 1645 | C | LYS | G | 357 | 121.698 | −133.716 | 117.421 | 1.00 | 131.94 |
| ATOM | 1646 | O | LYS | G | 357 | 121.977 | −134.913 | 117.471 | 1.00 | 131.61 |
| ATOM | 1647 | CB | LYS | G | 357 | 120.137 | −132.700 | 115.770 | 1.00 | 133.82 |
| ATOM | 1648 | CG | LYS | G | 357 | 119.862 | −132.151 | 114.378 | 1.00 | 134.32 |
| ATOM | 1649 | CD | LYS | G | 357 | 119.821 | −130.635 | 114.369 | 1.00 | 135.18 |
| ATOM | 1650 | CE | LYS | G | 357 | 119.478 | −130.113 | 112.987 | 1.00 | 135.74 |
| ATOM | 1651 | NZ | LYS | G | 357 | 119.344 | −128.636 | 112.997 | 1.00 | 135.57 |
| ATOM | 1652 | N | THR | G | 358 | 121.466 | −132.974 | 118.499 | 1.00 | 130.25 |
| ATOM | 1653 | CA | THR | G | 358 | 121.499 | −133.557 | 119.832 | 1.00 | 128.54 |
| ATOM | 1654 | C | THR | G | 358 | 120.142 | −133.485 | 120.532 | 1.00 | 127.66 |
| ATOM | 1655 | O | THR | G | 358 | 119.636 | −132.395 | 120.811 | 1.00 | 127.33 |
| ATOM | 1656 | CB | THR | G | 358 | 122.531 | −132.868 | 120.749 | 1.00 | 127.87 |
| ATOM | 1657 | OG1 | THR | G | 358 | 123.852 | −133.126 | 120.269 | 1.00 | 127.40 |
| ATOM | 1658 | CG2 | THR | G | 358 | 122.406 | −133.397 | 122.167 | 1.00 | 127.41 |
| ATOM | 1659 | N | ILE | G | 359 | 119.558 | −134.647 | 120.813 | 1.00 | 126.20 |
| ATOM | 1660 | CA | ILE | G | 359 | 118.258 | −134.718 | 121.480 | 1.00 | 125.26 |
| ATOM | 1661 | C | ILE | G | 359 | 118.360 | −134.591 | 123.005 | 1.00 | 124.58 |
| ATOM | 1662 | O | ILE | G | 359 | 118.904 | −135.468 | 123.681 | 1.00 | 124.63 |
| ATOM | 1663 | CB | ILE | G | 359 | 117.528 | −136.050 | 121.154 | 1.00 | 124.56 |
| ATOM | 1664 | CG1 | ILE | G | 359 | 117.243 | −136.142 | 119.654 | 1.00 | 124.71 |
| ATOM | 1665 | CG2 | ILE | G | 359 | 116.212 | −136.130 | 121.922 | 1.00 | 124.84 |
| ATOM | 1666 | CD1 | ILE | G | 359 | 118.474 | −136.371 | 118.804 | 1.00 | 124.99 |
| ATOM | 1667 | N | VAL | G | 360 | 117.816 | −133.503 | 123.541 | 1.00 | 123.68 |
| ATOM | 1668 | CA | VAL | G | 360 | 117.841 | −133.248 | 124.977 | 1.00 | 122.86 |
| ATOM | 1669 | C | VAL | G | 360 | 116.417 | −133.181 | 125.520 | 1.00 | 122.77 |
| ATOM | 1670 | O | VAL | G | 360 | 115.532 | −132.627 | 124.874 | 1.00 | 122.31 |
| ATOM | 1671 | CB | VAL | G | 360 | 118.535 | −131.907 | 125.278 | 1.00 | 122.10 |
| ATOM | 1672 | CG1 | VAL | G | 360 | 118.861 | −131.806 | 126.759 | 1.00 | 121.81 |
| ATOM | 1673 | CG2 | VAL | G | 360 | 119.783 | −131.772 | 124.427 | 1.00 | 122.35 |
| ATOM | 1674 | N | PHE | G | 361 | 116.201 | −133.746 | 126.702 | 1.00 | 122.89 |
| ATOM | 1675 | CA | PHE | G | 361 | 114.881 | −133.744 | 127.323 | 1.00 | 122.88 |
| ATOM | 1676 | C | PHE | G | 361 | 114.852 | −132.840 | 128.544 | 1.00 | 123.80 |
| ATOM | 1677 | O | PHE | G | 361 | 115.619 | −133.024 | 129.490 | 1.00 | 124.18 |
| ATOM | 1678 | CB | PHE | G | 361 | 114.486 | −135.169 | 127.705 | 1.00 | 121.54 |
| ATOM | 1679 | CG | PHE | G | 361 | 114.075 | −136.008 | 126.536 | 1.00 | 120.64 |
| ATOM | 1680 | CD1 | PHE | G | 361 | 112.802 | −135.884 | 125.995 | 1.00 | 121.67 |
| ATOM | 1681 | CD2 | PHE | G | 361 | 114.967 | −136.901 | 125.954 | 1.00 | 120.34 |
| ATOM | 1682 | CE1 | PHE | G | 361 | 112.419 | −136.638 | 124.889 | 1.00 | 122.25 |
| ATOM | 1683 | CE2 | PHE | G | 361 | 114.596 | −137.660 | 124.847 | 1.00 | 120.52 |
| ATOM | 1684 | CZ | PHE | G | 361 | 113.319 | −137.528 | 124.314 | 1.00 | 121.45 |
| ATOM | 1685 | N | ASN | G | 362 | 113.954 | −131.864 | 128.516 | 1.00 | 124.73 |
| ATOM | 1686 | CA | ASN | G | 362 | 113.837 | −130.906 | 129.602 | 1.00 | 125.55 |
| ATOM | 1687 | C | ASN | G | 362 | 112.401 | −130.831 | 130.118 | 1.00 | 124.88 |
| ATOM | 1688 | O | ASN | G | 362 | 111.485 | −131.370 | 129.499 | 1.00 | 124.87 |
| ATOM | 1689 | CB | ASN | G | 362 | 114.294 | −129.537 | 129.097 | 1.00 | 127.19 |
| ATOM | 1690 | CG | ASN | G | 362 | 114.691 | −128.608 | 130.215 | 1.00 | 130.61 |
| ATOM | 1691 | OD1 | ASN | G | 362 | 113.874 | −128.287 | 131.083 | 1.00 | 131.85 |
| ATOM | 1692 | ND2 | ASN | G | 362 | 115.948 | −128.168 | 130.199 | 1.00 | 133.40 |
| ATOM | 1693 | N | HIS | G | 363 | 112.207 | −130.159 | 131.248 | 1.00 | 124.22 |
| ATOM | 1694 | CA | HIS | G | 363 | 110.878 | −130.014 | 131.826 | 1.00 | 123.37 |
| ATOM | 1695 | C | HIS | G | 363 | 110.003 | −129.081 | 130.986 | 1.00 | 122.33 |
| ATOM | 1696 | O | HIS | G | 363 | 110.445 | −128.552 | 129.965 | 1.00 | 123.35 |
| ATOM | 1697 | CB | HIS | G | 363 | 110.986 | −129.485 | 133.261 | 1.00 | 123.55 |
| ATOM | 1698 | CG | HIS | G | 363 | 111.789 | −128.228 | 133.388 | 1.00 | 123.69 |
| ATOM | 1699 | ND1 | HIS | G | 363 | 111.430 | −127.051 | 132.769 | 1.00 | 123.31 |
| ATOM | 1700 | CD2 | HIS | G | 363 | 112.933 | −127.966 | 134.063 | 1.00 | 124.89 |
| ATOM | 1701 | CE1 | HIS | G | 363 | 112.319 | −126.118 | 133.056 | 1.00 | 123.86 |
| ATOM | 1702 | NE2 | HIS | G | 363 | 113.242 | −126.646 | 133.839 | 1.00 | 125.14 |
| ATOM | 1703 | N | SER | G | 364 | 108.763 | −128.876 | 131.419 | 1.00 | 119.87 |
| ATOM | 1704 | CA | SER | G | 364 | 107.853 | −128.002 | 130.691 | 1.00 | 117.00 |
| ATOM | 1705 | C | SER | G | 364 | 108.279 | −126.547 | 130.857 | 1.00 | 115.19 |
| ATOM | 1706 | O | SER | G | 364 | 108.577 | −126.102 | 131.964 | 1.00 | 115.16 |
| ATOM | 1707 | CB | SER | G | 364 | 106.422 | −128.192 | 131.192 | 1.00 | 116.69 |
| ATOM | 1708 | OG | SER | G | 364 | 105.495 | −127.562 | 130.324 | 1.00 | 116.92 |
| ATOM | 1709 | N | SER | G | 365 | 108.307 | −125.811 | 129.752 | 1.00 | 113.25 |
| ATOM | 1710 | CA | SER | G | 365 | 108.711 | −124.411 | 129.770 | 1.00 | 112.58 |
| ATOM | 1711 | C | SER | G | 365 | 107.797 | −123.480 | 130.566 | 1.00 | 112.63 |
| ATOM | 1712 | O | SER | G | 365 | 108.216 | −122.389 | 130.949 | 1.00 | 113.24 |
| ATOM | 1713 | CB | SER | G | 365 | 108.848 | −123.897 | 128.341 | 1.00 | 112.43 |
| ATOM | 1714 | OG | SER | G | 365 | 107.754 | −124.318 | 127.550 | 1.00 | 112.84 |
| ATOM | 1715 | N | GLY | G | 366 | 106.559 | −123.895 | 130.823 | 1.00 | 112.08 |
| ATOM | 1716 | CA | GLY | G | 366 | 105.661 | −123.044 | 131.591 | 1.00 | 111.71 |

TABLE 2-continued

The structural coordinates of an exemplary gp120 with an extended V3 loop

| ATOM | 1717 | C | GLY | G | 366 | 104.224 | −123.031 | 131.111 | 1.00 | 111.01 |
|------|------|------|-----|---|-----|---------|----------|---------|------|--------|
| ATOM | 1718 | O | GLY | G | 366 | 103.920 | −123.550 | 130.041 | 1.00 | 111.21 |
| ATOM | 1719 | N | GLY | G | 367 | 103.339 | −122.439 | 131.908 | 1.00 | 110.29 |
| ATOM | 1720 | CA | GLY | G | 367 | 101.935 | −122.374 | 131.538 | 1.00 | 109.86 |
| ATOM | 1721 | C | GLY | G | 367 | 101.013 | −122.876 | 132.633 | 1.00 | 109.09 |
| ATOM | 1722 | O | GLY | G | 367 | 101.382 | −122.880 | 133.806 | 1.00 | 110.03 |
| ATOM | 1723 | N | ASP | G | 368 | 99.810 | −123.300 | 132.255 | 1.00 | 107.77 |
| ATOM | 1724 | CA | ASP | G | 368 | 98.847 | −123.813 | 133.219 | 1.00 | 106.93 |
| ATOM | 1725 | C | ASP | G | 368 | 99.347 | −125.117 | 133.825 | 1.00 | 105.42 |
| ATOM | 1726 | O | ASP | G | 368 | 99.888 | −125.969 | 133.122 | 1.00 | 105.22 |
| ATOM | 1727 | CB | ASP | G | 368 | 97.490 | −124.046 | 132.551 | 1.00 | 109.08 |
| ATOM | 1728 | CG | ASP | G | 368 | 96.754 | −122.749 | 132.246 | 1.00 | 110.72 |
| ATOM | 1729 | OD1 | ASP | G | 368 | 96.346 | −122.063 | 133.204 | 1.00 | 112.84 |
| ATOM | 1730 | OD2 | ASP | G | 368 | 96.587 | −122.420 | 131.052 | 1.00 | 110.53 |
| ATOM | 1731 | N | PRO | G | 369 | 99.161 | −125.290 | 135.143 | 1.00 | 104.21 |
| ATOM | 1732 | CA | PRO | G | 369 | 99.587 | −126.484 | 135.874 | 1.00 | 103.74 |
| ATOM | 1733 | C | PRO | G | 369 | 99.165 | −127.797 | 135.227 | 1.00 | 102.96 |
| ATOM | 1734 | O | PRO | G | 369 | 99.756 | −128.842 | 135.495 | 1.00 | 103.69 |
| ATOM | 1735 | CB | PRO | G | 369 | 98.955 | −126.279 | 137.243 | 1.00 | 104.51 |
| ATOM | 1736 | CG | PRO | G | 369 | 99.051 | −124.796 | 137.406 | 1.00 | 104.97 |
| ATOM | 1737 | CD | PRO | G | 369 | 98.530 | −124.330 | 136.063 | 1.00 | 104.21 |
| ATOM | 1738 | N | GLU | G | 370 | 98.148 | −127.745 | 134.376 | 1.00 | 101.68 |
| ATOM | 1739 | CA | GLU | G | 370 | 97.676 | −128.949 | 133.707 | 1.00 | 100.29 |
| ATOM | 1740 | C | GLU | G | 370 | 98.665 | −129.450 | 132.663 | 1.00 | 99.24 |
| ATOM | 1741 | O | GLU | G | 370 | 98.741 | −130.650 | 132.396 | 1.00 | 100.20 |
| ATOM | 1742 | CB | GLU | G | 370 | 96.316 | −128.699 | 133.049 | 1.00 | 101.70 |
| ATOM | 1743 | CG | GLU | G | 370 | 95.129 | −128.747 | 134.007 | 1.00 | 101.29 |
| ATOM | 1744 | CD | GLU | G | 370 | 94.927 | −127.459 | 134.790 | 1.00 | 101.71 |
| ATOM | 1745 | OE1 | GLU | G | 370 | 94.058 | −127.440 | 135.687 | 1.00 | 101.10 |
| ATOM | 1746 | OE2 | GLU | G | 370 | 95.628 | −126.465 | 134.508 | 1.00 | 102.45 |
| ATOM | 1747 | N | ILE | G | 371 | 99.424 | −128.532 | 132.077 | 1.00 | 97.76 |
| ATOM | 1748 | CA | ILE | G | 371 | 100.401 | −128.891 | 131.058 | 1.00 | 96.84 |
| ATOM | 1749 | C | ILE | G | 371 | 101.755 | −129.144 | 131.702 | 1.00 | 95.29 |
| ATOM | 1750 | O | ILE | G | 371 | 102.455 | −130.104 | 131.369 | 1.00 | 94.66 |
| ATOM | 1751 | CB | ILE | G | 371 | 100.563 | −127.756 | 130.041 | 1.00 | 96.73 |
| ATOM | 1752 | CG1 | ILE | G | 371 | 99.189 | −127.193 | 129.678 | 1.00 | 96.23 |
| ATOM | 1753 | CG2 | ILE | G | 371 | 101.254 | −128.276 | 128.792 | 1.00 | 98.30 |
| ATOM | 1754 | CD1 | ILE | G | 371 | 99.236 | −125.769 | 129.192 | 1.00 | 96.31 |
| ATOM | 1755 | N | VAL | G | 372 | 102.111 | −128.273 | 132.637 | 1.00 | 92.31 |
| ATOM | 1756 | CA | VAL | G | 372 | 103.376 | −128.378 | 133.340 | 1.00 | 89.48 |
| ATOM | 1757 | C | VAL | G | 372 | 103.503 | −129.702 | 134.081 | 1.00 | 87.73 |
| ATOM | 1758 | O | VAL | G | 372 | 104.586 | −130.277 | 134.150 | 1.00 | 88.58 |
| ATOM | 1759 | CB | VAL | G | 372 | 103.533 | −127.237 | 134.352 | 1.00 | 89.89 |
| ATOM | 1760 | CG1 | VAL | G | 372 | 104.936 | −127.246 | 134.926 | 1.00 | 91.74 |
| ATOM | 1761 | CG2 | VAL | G | 372 | 103.233 | −125.906 | 133.683 | 1.00 | 89.58 |
| ATOM | 1762 | N | MET | G | 373 | 102.395 | −130.187 | 134.631 | 1.00 | 86.24 |
| ATOM | 1763 | CA | MET | G | 373 | 102.411 | −131.444 | 135.364 | 1.00 | 86.32 |
| ATOM | 1764 | C | MET | G | 373 | 101.540 | −132.498 | 134.689 | 1.00 | 86.85 |
| ATOM | 1765 | O | MET | G | 373 | 100.541 | −132.174 | 134.051 | 1.00 | 86.82 |
| ATOM | 1766 | CB | MET | G | 373 | 101.930 | −131.220 | 136.805 | 1.00 | 86.15 |
| ATOM | 1767 | CG | MET | G | 373 | 102.616 | −130.059 | 137.512 | 1.00 | 85.92 |
| ATOM | 1768 | SD | MET | G | 373 | 103.120 | −130.448 | 139.200 | 1.00 | 87.98 |
| ATOM | 1769 | CE | MET | G | 373 | 101.830 | −129.658 | 140.161 | 1.00 | 88.57 |
| ATOM | 1770 | N | HIS | G | 374 | 101.930 | −133.762 | 134.823 | 1.00 | 87.56 |
| ATOM | 1771 | CA | HIS | G | 374 | 101.161 | −134.857 | 134.244 | 1.00 | 88.76 |
| ATOM | 1772 | C | HIS | G | 374 | 99.810 | −134.931 | 134.944 | 1.00 | 90.65 |
| ATOM | 1773 | O | HIS | G | 374 | 99.699 | −135.514 | 136.019 | 1.00 | 93.49 |
| ATOM | 1774 | CB | HIS | G | 374 | 101.905 | −136.181 | 134.422 | 1.00 | 87.35 |
| ATOM | 1775 | CG | HIS | G | 374 | 101.079 | −137.385 | 134.096 | 1.00 | 85.69 |
| ATOM | 1776 | ND1 | HIS | G | 374 | 100.563 | −137.614 | 132.839 | 1.00 | 85.77 |
| ATOM | 1777 | CD2 | HIS | G | 374 | 100.677 | −138.425 | 134.863 | 1.00 | 85.18 |
| ATOM | 1778 | CE1 | HIS | G | 374 | 99.881 | −138.745 | 132.845 | 1.00 | 87.31 |
| ATOM | 1779 | NE2 | HIS | G | 374 | 99.934 | −139.257 | 134.061 | 1.00 | 86.65 |
| ATOM | 1780 | N | SER | G | 375 | 98.788 | −134.346 | 134.330 | 1.00 | 91.35 |
| ATOM | 1781 | CA | SER | G | 375 | 97.454 | −134.327 | 134.918 | 1.00 | 91.01 |
| ATOM | 1782 | C | SER | G | 375 | 96.531 | −135.438 | 134.431 | 1.00 | 90.01 |
| ATOM | 1783 | O | SER | G | 375 | 96.426 | −135.685 | 133.233 | 1.00 | 90.38 |
| ATOM | 1784 | CB | SER | G | 375 | 96.796 | −132.978 | 134.636 | 1.00 | 93.11 |
| ATOM | 1785 | OG | SER | G | 375 | 96.788 | −132.708 | 133.244 | 1.00 | 93.88 |
| ATOM | 1786 | N | PHE | G | 376 | 95.860 | −136.101 | 135.368 | 1.00 | 90.06 |
| ATOM | 1787 | CA | PHE | G | 376 | 94.920 | −137.166 | 135.037 | 1.00 | 93.27 |
| ATOM | 1788 | C | PHE | G | 376 | 93.895 | −137.317 | 136.156 | 1.00 | 95.94 |
| ATOM | 1789 | O | PHE | G | 376 | 94.034 | −136.702 | 137.212 | 1.00 | 95.54 |
| ATOM | 1790 | CB | PHE | G | 376 | 95.649 | −138.495 | 134.805 | 1.00 | 92.86 |
| ATOM | 1791 | CG | PHE | G | 376 | 96.283 | −139.076 | 136.037 | 1.00 | 93.02 |
| ATOM | 1792 | CD1 | PHE | G | 376 | 97.542 | −138.660 | 136.454 | 1.00 | 93.40 |
| ATOM | 1793 | CD2 | PHE | G | 376 | 95.628 | −140.065 | 136.766 | 1.00 | 92.09 |
| ATOM | 1794 | CE1 | PHE | G | 376 | 98.144 | −139.223 | 137.581 | 1.00 | 93.87 |

TABLE 2-continued

The structural coordinates of an exemplary gp120 with an extended V3 loop

| ATOM | 1795 | CE2 | PHE | G | 376 | 96.218 | −140.634 | 137.892 | 1.00 | 92.28 |
|---|---|---|---|---|---|---|---|---|---|---|
| ATOM | 1796 | CZ | PHE | G | 376 | 97.479 | −140.214 | 138.300 | 1.00 | 94.05 |
| ATOM | 1797 | N | ASN | G | 377 | 92.870 | −138.132 | 135.930 | 1.00 | 99.59 |
| ATOM | 1798 | CA | ASN | G | 377 | 91.825 | −138.327 | 136.931 | 1.00 | 104.81 |
| ATOM | 1799 | C | ASN | G | 377 | 91.355 | −139.774 | 137.059 | 1.00 | 107.26 |
| ATOM | 1800 | O | ASN | G | 377 | 91.034 | −140.429 | 136.068 | 1.00 | 107.33 |
| ATOM | 1801 | CB | ASN | G | 377 | 90.625 | −137.442 | 136.598 | 1.00 | 107.57 |
| ATOM | 1802 | CG | ASN | G | 377 | 90.145 | −137.635 | 135.176 | 1.00 | 110.35 |
| ATOM | 1803 | OD1 | ASN | G | 377 | 90.827 | −137.256 | 134.223 | 1.00 | 112.46 |
| ATOM | 1804 | ND2 | ASN | G | 377 | 88.974 | −138.242 | 135.023 | 1.00 | 111.65 |
| ATOM | 1805 | N | CYS | G | 378 | 91.313 | −140.259 | 138.296 | 1.00 | 110.71 |
| ATOM | 1806 | CA | CYS | G | 378 | 90.878 | −141.621 | 138.595 | 1.00 | 113.87 |
| ATOM | 1807 | C | CYS | G | 378 | 90.247 | −141.634 | 139.988 | 1.00 | 114.07 |
| ATOM | 1808 | O | CYS | G | 378 | 90.894 | −141.266 | 140.966 | 1.00 | 113.69 |
| ATOM | 1809 | CB | CYS | G | 378 | 92.069 | −142.601 | 138.540 | 1.00 | 116.89 |
| ATOM | 1810 | SG | CYS | G | 378 | 93.430 | −142.309 | 139.720 | 1.00 | 121.15 |
| ATOM | 1811 | N | GLY | G | 379 | 88.985 | −142.047 | 140.080 | 1.00 | 113.75 |
| ATOM | 1812 | CA | GLY | G | 379 | 88.320 | −142.076 | 141.373 | 1.00 | 112.55 |
| ATOM | 1813 | C | GLY | G | 379 | 87.547 | −140.800 | 141.651 | 1.00 | 111.47 |
| ATOM | 1814 | O | GLY | G | 379 | 86.731 | −140.736 | 142.570 | 1.00 | 112.00 |
| ATOM | 1815 | N | GLY | G | 380 | 87.809 | −139.776 | 140.849 | 1.00 | 109.49 |
| ATOM | 1816 | CA | GLY | G | 380 | 87.123 | −138.513 | 141.024 | 1.00 | 107.11 |
| ATOM | 1817 | C | GLY | G | 380 | 88.074 | −137.401 | 141.410 | 1.00 | 105.53 |
| ATOM | 1818 | O | GLY | G | 380 | 87.672 | −136.246 | 141.521 | 1.00 | 106.59 |
| ATOM | 1819 | N | GLU | G | 381 | 89.342 | −137.743 | 141.611 | 1.00 | 102.89 |
| ATOM | 1820 | CA | GLU | G | 381 | 90.339 | −136.749 | 141.989 | 1.00 | 100.20 |
| ATOM | 1821 | C | GLU | G | 381 | 91.269 | −136.414 | 140.832 | 1.00 | 97.39 |
| ATOM | 1822 | O | GLU | G | 381 | 91.658 | −137.291 | 140.062 | 1.00 | 97.65 |
| ATOM | 1823 | CB | GLU | G | 381 | 91.165 | −137.252 | 143.174 | 1.00 | 101.99 |
| ATOM | 1824 | CG | GLU | G | 381 | 90.341 | −137.669 | 144.376 | 1.00 | 104.32 |
| ATOM | 1825 | CD | GLU | G | 381 | 89.409 | −136.574 | 144.853 | 1.00 | 106.86 |
| ATOM | 1826 | OE1 | GLU | G | 381 | 89.884 | −135.439 | 145.071 | 1.00 | 108.66 |
| ATOM | 1827 | OE2 | GLU | G | 381 | 88.201 | −136.853 | 145.014 | 1.00 | 108.04 |
| ATOM | 1828 | N | PHE | G | 382 | 91.629 | −135.140 | 140.719 | 1.00 | 93.73 |
| ATOM | 1829 | CA | PHE | G | 382 | 92.513 | −134.697 | 139.648 | 1.00 | 89.57 |
| ATOM | 1830 | C | PHE | G | 382 | 93.963 | −134.629 | 140.104 | 1.00 | 88.33 |
| ATOM | 1831 | O | PHE | G | 382 | 94.338 | −133.753 | 140.882 | 1.00 | 88.16 |
| ATOM | 1832 | CB | PHE | G | 382 | 92.073 | −133.326 | 139.134 | 1.00 | 86.63 |
| ATOM | 1833 | CG | PHE | G | 382 | 90.700 | −133.321 | 138.523 | 1.00 | 84.43 |
| ATOM | 1834 | CD1 | PHE | G | 382 | 89.570 | −133.512 | 139.313 | 1.00 | 82.70 |
| ATOM | 1835 | CD2 | PHE | G | 382 | 90.536 | −133.130 | 137.155 | 1.00 | 83.85 |
| ATOM | 1836 | CE1 | PHE | G | 382 | 88.298 | −133.513 | 138.749 | 1.00 | 80.29 |
| ATOM | 1837 | CE2 | PHE | G | 382 | 89.268 | −133.130 | 136.584 | 1.00 | 82.03 |
| ATOM | 1838 | CZ | PHE | G | 382 | 88.149 | −133.321 | 137.383 | 1.00 | 80.22 |
| ATOM | 1839 | N | PHE | G | 383 | 94.777 | −135.555 | 139.607 | 1.00 | 87.21 |
| ATOM | 1840 | CA | PHE | G | 383 | 96.190 | −135.607 | 139.965 | 1.00 | 86.08 |
| ATOM | 1841 | C | PHE | G | 383 | 97.049 | −134.663 | 139.136 | 1.00 | 85.60 |
| ATOM | 1842 | O | PHE | G | 383 | 96.735 | −134.368 | 137.984 | 1.00 | 85.11 |
| ATOM | 1843 | CB | PHE | G | 383 | 96.727 | −137.032 | 139.805 | 1.00 | 85.28 |
| ATOM | 1844 | CG | PHE | G | 383 | 96.120 | −138.022 | 140.755 | 1.00 | 85.57 |
| ATOM | 1845 | CD1 | PHE | G | 383 | 94.790 | −138.408 | 140.627 | 1.00 | 85.90 |
| ATOM | 1846 | CD2 | PHE | G | 383 | 96.880 | −138.571 | 141.782 | 1.00 | 85.81 |
| ATOM | 1847 | CE1 | PHE | G | 383 | 94.226 | −139.327 | 141.508 | 1.00 | 85.70 |
| ATOM | 1848 | CE2 | PHE | G | 383 | 96.326 | −139.489 | 142.667 | 1.00 | 85.26 |
| ATOM | 1849 | CZ | PHE | G | 383 | 94.997 | −139.868 | 142.530 | 1.00 | 84.70 |
| ATOM | 1850 | N | TYR | G | 384 | 98.135 | −134.190 | 139.736 | 1.00 | 85.21 |
| ATOM | 1851 | CA | TYR | G | 384 | 99.071 | −133.295 | 139.061 | 1.00 | 86.70 |
| ATOM | 1852 | C | TYR | G | 384 | 100.504 | −133.685 | 139.415 | 1.00 | 89.54 |
| ATOM | 1853 | O | TYR | G | 384 | 101.132 | −133.047 | 140.255 | 1.00 | 90.93 |
| ATOM | 1854 | CB | TYR | G | 384 | 98.812 | −131.845 | 139.473 | 1.00 | 85.32 |
| ATOM | 1855 | CG | TYR | G | 384 | 97.548 | −131.256 | 138.895 | 1.00 | 83.12 |
| ATOM | 1856 | CD1 | TYR | G | 384 | 96.321 | −131.416 | 139.533 | 1.00 | 82.42 |
| ATOM | 1857 | CD2 | TYR | G | 384 | 97.579 | −130.555 | 137.690 | 1.00 | 81.60 |
| ATOM | 1858 | CE1 | TYR | G | 384 | 95.153 | −130.891 | 138.983 | 1.00 | 82.41 |
| ATOM | 1859 | CE2 | TYR | G | 384 | 96.422 | −130.029 | 137.132 | 1.00 | 81.05 |
| ATOM | 1860 | CZ | TYR | G | 384 | 95.214 | −130.200 | 137.782 | 1.00 | 81.32 |
| ATOM | 1861 | OH | TYR | G | 384 | 94.070 | −129.681 | 137.223 | 1.00 | 78.86 |
| ATOM | 1862 | N | CYS | G | 385 | 101.010 | −134.733 | 138.764 | 1.00 | 93.00 |
| ATOM | 1863 | CA | CYS | G | 385 | 102.358 | −135.249 | 139.016 | 1.00 | 96.10 |
| ATOM | 1864 | C | CYS | G | 385 | 103.432 | −134.478 | 138.255 | 1.00 | 98.98 |
| ATOM | 1865 | O | CYS | G | 385 | 103.284 | −134.196 | 137.064 | 1.00 | 100.31 |
| ATOM | 1866 | CB | CYS | G | 385 | 102.448 | −136.727 | 138.625 | 1.00 | 96.17 |
| ATOM | 1867 | SG | CYS | G | 385 | 101.237 | −137.831 | 139.415 | 1.00 | 97.03 |
| ATOM | 1868 | N | ASN | G | 386 | 104.522 | −134.158 | 138.944 | 1.00 | 101.88 |
| ATOM | 1869 | CA | ASN | G | 386 | 105.630 | −133.416 | 138.351 | 1.00 | 105.68 |
| ATOM | 1870 | C | ASN | G | 386 | 106.483 | −134.318 | 137.460 | 1.00 | 109.06 |
| ATOM | 1871 | O | ASN | G | 386 | 107.126 | −135.249 | 137.940 | 1.00 | 110.00 |
| ATOM | 1872 | CB | ASN | G | 386 | 106.488 | −132.802 | 139.464 | 1.00 | 104.65 |

TABLE 2-continued

The structural coordinates of an exemplary gp120 with an extended V3 loop

| ATOM | 1873 | CG  | ASN | G | 386 | 107.278 | −131.592 | 138.997 | 1.00 | 104.49 |
| ---- | ---- | --- | --- | - | --- | ------- | -------- | ------- | ---- | ------ |
| ATOM | 1874 | OD1 | ASN | G | 386 | 107.793 | −130.826 | 139.811 | 1.00 | 105.86 |
| ATOM | 1875 | ND2 | ASN | G | 386 | 107.380 | −131.417 | 137.682 | 1.00 | 103.57 |
| ATOM | 1876 | N   | SER | G | 387 | 106.489 | −134.033 | 136.161 | 1.00 | 112.28 |
| ATOM | 1877 | CA  | SER | G | 387 | 107.255 | −134.828 | 135.204 | 1.00 | 115.20 |
| ATOM | 1878 | C   | SER | G | 387 | 108.613 | −134.207 | 134.897 | 1.00 | 117.38 |
| ATOM | 1879 | O   | SER | G | 387 | 109.080 | −134.244 | 133.756 | 1.00 | 118.83 |
| ATOM | 1880 | CB  | SER | G | 387 | 106.468 | −134.982 | 133.901 | 1.00 | 114.78 |
| ATOM | 1881 | OG  | SER | G | 387 | 106.259 | −133.722 | 133.290 | 1.00 | 115.93 |
| ATOM | 1882 | N   | ALA | G | 388 | 109.242 | −133.635 | 135.916 | 1.00 | 118.94 |
| ATOM | 1883 | CA  | ALA | G | 388 | 110.543 | −133.004 | 135.747 | 1.00 | 120.08 |
| ATOM | 1884 | C   | ALA | G | 388 | 111.650 | −134.046 | 135.640 | 1.00 | 120.63 |
| ATOM | 1885 | O   | ALA | G | 388 | 112.518 | −133.955 | 134.776 | 1.00 | 121.23 |
| ATOM | 1886 | CB  | ALA | G | 388 | 110.821 | −132.064 | 136.915 | 1.00 | 120.48 |
| ATOM | 1887 | N   | GLN | G | 389 | 111.612 | −135.038 | 136.523 | 1.00 | 121.07 |
| ATOM | 1888 | CA  | GLN | G | 389 | 112.616 | −136.094 | 136.531 | 1.00 | 121.87 |
| ATOM | 1889 | C   | GLN | G | 389 | 112.436 | −137.082 | 135.383 | 1.00 | 121.47 |
| ATOM | 1890 | O   | GLN | G | 389 | 113.415 | −137.619 | 134.864 | 1.00 | 122.53 |
| ATOM | 1891 | CB  | GLN | G | 389 | 112.584 | −136.833 | 137.870 | 1.00 | 123.58 |
| ATOM | 1892 | CG  | GLN | G | 389 | 111.184 | −137.051 | 138.405 | 1.00 | 127.91 |
| ATOM | 1893 | CD  | GLN | G | 389 | 111.168 | −137.823 | 139.708 | 1.00 | 130.19 |
| ATOM | 1894 | OE1 | GLN | G | 389 | 111.948 | −137.547 | 140.620 | 1.00 | 132.91 |
| ATOM | 1895 | NE2 | GLN | G | 389 | 110.266 | −138.791 | 139.806 | 1.00 | 131.56 |
| ATOM | 1896 | N   | LEU | G | 390 | 111.189 | −137.319 | 134.987 | 1.00 | 120.77 |
| ATOM | 1897 | CA  | LEU | G | 390 | 110.899 | −138.241 | 133.892 | 1.00 | 119.93 |
| ATOM | 1898 | C   | LEU | G | 390 | 111.556 | −137.810 | 132.589 | 1.00 | 119.16 |
| ATOM | 1899 | O   | LEU | G | 390 | 112.076 | −138.639 | 131.843 | 1.00 | 119.29 |
| ATOM | 1900 | CB  | LEU | G | 390 | 109.392 | −138.349 | 133.667 | 1.00 | 120.27 |
| ATOM | 1901 | CG  | LEU | G | 390 | 108.609 | −139.237 | 134.633 | 1.00 | 120.93 |
| ATOM | 1902 | CD1 | LEU | G | 390 | 107.122 | −139.075 | 134.385 | 1.00 | 122.76 |
| ATOM | 1903 | CD2 | LEU | G | 390 | 109.028 | −140.682 | 134.437 | 1.00 | 121.13 |
| ATOM | 1904 | N   | PHE | G | 391 | 111.525 | −136.512 | 132.312 | 1.00 | 117.95 |
| ATOM | 1905 | CA  | PHE | G | 391 | 112.116 | −135.993 | 131.088 | 1.00 | 116.69 |
| ATOM | 1906 | C   | PHE | G | 391 | 113.329 | −135.117 | 131.375 | 1.00 | 116.29 |
| ATOM | 1907 | O   | PHE | G | 391 | 113.311 | −133.915 | 131.123 | 1.00 | 116.61 |
| ATOM | 1908 | CB  | PHE | G | 391 | 111.076 | −135.193 | 130.296 | 1.00 | 115.47 |
| ATOM | 1909 | CG  | PHE | G | 391 | 109.902 | −136.012 | 129.830 | 1.00 | 113.79 |
| ATOM | 1910 | CD1 | PHE | G | 391 | 108.889 | −136.372 | 130.713 | 1.00 | 112.00 |
| ATOM | 1911 | CD2 | PHE | G | 391 | 109.814 | −136.430 | 128.504 | 1.00 | 113.65 |
| ATOM | 1912 | CE1 | PHE | G | 391 | 107.806 | −137.138 | 130.284 | 1.00 | 111.30 |
| ATOM | 1913 | CE2 | PHE | G | 391 | 108.735 | −137.197 | 128.066 | 1.00 | 112.65 |
| ATOM | 1914 | CZ  | PHE | G | 391 | 107.730 | −137.550 | 128.959 | 1.00 | 111.37 |
| ATOM | 1915 | N   | ASN | G | 392 | 114.386 | −135.730 | 131.900 | 1.00 | 116.37 |
| ATOM | 1916 | CA  | ASN | G | 392 | 115.614 | −135.010 | 132.219 | 1.00 | 116.90 |
| ATOM | 1917 | C   | ASN | G | 392 | 116.832 | −135.861 | 131.881 | 1.00 | 117.22 |
| ATOM | 1918 | O   | ASN | G | 392 | 117.371 | −136.552 | 132.746 | 1.00 | 117.20 |
| ATOM | 1919 | CB  | ASN | G | 392 | 115.653 | −134.660 | 133.710 | 1.00 | 117.23 |
| ATOM | 1920 | CG  | ASN | G | 392 | 116.788 | −133.711 | 134.059 | 1.00 | 117.04 |
| ATOM | 1921 | OD1 | ASN | G | 392 | 117.373 | −133.793 | 135.141 | 1.00 | 116.31 |
| ATOM | 1922 | ND2 | ASN | G | 392 | 117.091 | −132.792 | 133.148 | 1.00 | 115.97 |
| ATOM | 1923 | N   | SER | G | 393 | 117.264 | −135.811 | 130.628 | 1.00 | 117.25 |
| ATOM | 1924 | CA  | SER | G | 393 | 118.420 | −136.587 | 130.199 | 1.00 | 117.84 |
| ATOM | 1925 | C   | SER | G | 393 | 118.898 | −136.099 | 128.838 | 1.00 | 118.76 |
| ATOM | 1926 | O   | SER | G | 393 | 118.091 | −135.750 | 127.979 | 1.00 | 118.46 |
| ATOM | 1927 | CB  | SER | G | 393 | 118.059 | −138.076 | 130.130 | 1.00 | 117.40 |
| ATOM | 1928 | OG  | SER | G | 393 | 116.915 | −138.287 | 129.323 | 1.00 | 117.90 |
| ATOM | 1929 | N   | THR | G | 394 | 120.213 | −136.069 | 128.648 | 1.00 | 120.79 |
| ATOM | 1930 | CA  | THR | G | 394 | 120.788 | −135.615 | 127.390 | 1.00 | 122.12 |
| ATOM | 1931 | C   | THR | G | 394 | 121.239 | −136.811 | 126.565 | 1.00 | 123.64 |
| ATOM | 1932 | O   | THR | G | 394 | 121.846 | −137.738 | 127.096 | 1.00 | 123.04 |
| ATOM | 1933 | CB  | THR | G | 394 | 122.003 | −134.711 | 127.640 | 1.00 | 121.38 |
| ATOM | 1934 | OG1 | THR | G | 394 | 121.701 | −133.792 | 128.694 | 1.00 | 121.49 |
| ATOM | 1935 | CG2 | THR | G | 394 | 122.347 | −133.924 | 126.390 | 1.00 | 120.33 |
| ATOM | 1936 | N   | TRP | G | 395 | 120.938 | −136.791 | 125.271 | 1.00 | 125.53 |
| ATOM | 1937 | CA  | TRP | G | 395 | 121.324 | −137.885 | 124.389 | 1.00 | 127.71 |
| ATOM | 1938 | C   | TRP | G | 395 | 122.040 | −137.385 | 123.138 | 1.00 | 130.76 |
| ATOM | 1939 | O   | TRP | G | 395 | 121.444 | −136.713 | 122.296 | 1.00 | 130.73 |
| ATOM | 1940 | CB  | TRP | G | 395 | 120.092 | −138.696 | 123.976 | 1.00 | 124.98 |
| ATOM | 1941 | CG  | TRP | G | 395 | 119.330 | −139.263 | 125.127 | 1.00 | 122.80 |
| ATOM | 1942 | CD1 | TRP | G | 395 | 118.578 | −138.573 | 126.032 | 1.00 | 122.44 |
| ATOM | 1943 | CD2 | TRP | G | 395 | 119.259 | −140.641 | 125.511 | 1.00 | 121.88 |
| ATOM | 1944 | NE1 | TRP | G | 395 | 118.041 | −139.435 | 126.957 | 1.00 | 122.03 |
| ATOM | 1945 | CE2 | TRP | G | 395 | 118.442 | −140.710 | 126.662 | 1.00 | 121.61 |
| ATOM | 1946 | CE3 | TRP | G | 395 | 119.804 | −141.823 | 124.995 | 1.00 | 122.03 |
| ATOM | 1947 | CZ2 | TRP | G | 395 | 118.159 | −141.918 | 127.308 | 1.00 | 121.03 |
| ATOM | 1948 | CZ3 | TRP | G | 395 | 119.521 | −143.024 | 125.638 | 1.00 | 121.12 |
| ATOM | 1949 | CH2 | TRP | G | 395 | 118.705 | −143.061 | 126.782 | 1.00 | 120.35 |
| ATOM | 1950 | N   | ASN | G | 396 | 123.322 | −137.722 | 123.023 | 1.00 | 134.68 |

TABLE 2-continued

The structural coordinates of an exemplary gp120 with an extended V3 loop

| ATOM | 1951 | CA | ASN | G | 396 | 124.132 | −137.319 | 121.877 | 1.00 | 138.49 |
|---|---|---|---|---|---|---|---|---|---|---|
| ATOM | 1952 | C | ASN | G | 396 | 125.278 | −138.306 | 121.699 | 1.00 | 140.34 |
| ATOM | 1953 | O | ASN | G | 396 | 126.028 | −138.237 | 120.723 | 1.00 | 140.16 |
| ATOM | 1954 | CB | ASN | G | 396 | 124.702 | −135.914 | 122.091 | 1.00 | 139.54 |
| ATOM | 1955 | CG | ASN | G | 396 | 125.710 | −135.858 | 123.225 | 1.00 | 140.48 |
| ATOM | 1956 | OD1 | ASN | G | 396 | 125.396 | −136.194 | 124.367 | 1.00 | 140.41 |
| ATOM | 1957 | ND2 | ASN | G | 396 | 126.929 | −135.431 | 122.914 | 1.00 | 139.91 |
| ATOM | 1958 | N | ASN | G | 397 | 125.405 | −139.223 | 122.653 | 1.00 | 142.71 |
| ATOM | 1959 | CA | ASN | G | 397 | 126.461 | −140.225 | 122.616 | 1.00 | 145.52 |
| ATOM | 1960 | C | ASN | G | 397 | 126.235 | −141.263 | 123.712 | 1.00 | 147.30 |
| ATOM | 1961 | O | ASN | G | 397 | 126.975 | −141.314 | 124.696 | 1.00 | 147.83 |
| ATOM | 1962 | CB | ASN | G | 397 | 127.820 | −139.546 | 122.804 | 1.00 | 145.45 |
| ATOM | 1963 | CG | ASN | G | 397 | 128.980 | −140.452 | 122.449 | 1.00 | 146.09 |
| ATOM | 1964 | OD1 | ASN | G | 397 | 130.135 | −140.031 | 122.478 | 1.00 | 147.69 |
| ATOM | 1965 | ND2 | ASN | G | 397 | 128.680 | −141.700 | 122.109 | 1.00 | 146.44 |
| ATOM | 1966 | N | ASN | G | 401 | 125.206 | −142.087 | 123.536 | 1.00 | 148.95 |
| ATOM | 1967 | CA | ASN | G | 401 | 124.874 | −143.125 | 124.505 | 1.00 | 150.19 |
| ATOM | 1968 | C | ASN | G | 401 | 124.087 | −144.258 | 123.850 | 1.00 | 151.32 |
| ATOM | 1969 | O | ASN | G | 401 | 122.864 | −144.187 | 123.729 | 1.00 | 151.15 |
| ATOM | 1970 | CB | ASN | G | 401 | 124.057 | −142.526 | 125.654 | 1.00 | 149.72 |
| ATOM | 1971 | CG | ASN | G | 401 | 123.716 | −143.547 | 126.723 | 1.00 | 150.07 |
| ATOM | 1972 | OD1 | ASN | G | 401 | 123.043 | −144.543 | 126.455 | 1.00 | 150.13 |
| ATOM | 1973 | ND2 | ASN | G | 401 | 124.180 | −143.304 | 127.943 | 1.00 | 150.04 |
| ATOM | 1974 | N | THR | G | 402 | 124.798 | −145.301 | 123.431 | 1.00 | 152.32 |
| ATOM | 1975 | CA | THR | G | 402 | 124.171 | −146.452 | 122.790 | 1.00 | 152.72 |
| ATOM | 1976 | C | THR | G | 402 | 124.884 | −147.746 | 123.178 | 1.00 | 152.78 |
| ATOM | 1977 | O | THR | G | 402 | 125.762 | −148.222 | 122.457 | 1.00 | 152.62 |
| ATOM | 1978 | CB | THR | G | 402 | 124.193 | −146.315 | 121.249 | 1.00 | 152.55 |
| ATOM | 1979 | OG1 | THR | G | 402 | 123.528 | −145.105 | 120.864 | 1.00 | 152.61 |
| ATOM | 1980 | CG2 | THR | G | 402 | 123.489 | −147.498 | 120.597 | 1.00 | 152.80 |
| ATOM | 1981 | N | GLU | G | 403 | 124.503 | −148.307 | 124.322 | 1.00 | 153.02 |
| ATOM | 1982 | CA | GLU | G | 403 | 125.102 | −149.547 | 124.806 | 1.00 | 153.40 |
| ATOM | 1983 | C | GLU | G | 403 | 124.013 | −150.508 | 125.281 | 1.00 | 153.32 |
| ATOM | 1984 | O | GLU | G | 403 | 123.311 | −151.112 | 124.468 | 1.00 | 152.98 |
| ATOM | 1985 | CB | GLU | G | 403 | 126.074 | −149.251 | 125.952 | 1.00 | 153.38 |
| ATOM | 1986 | CG | GLU | G | 403 | 126.971 | −150.422 | 126.323 | 1.00 | 154.46 |
| ATOM | 1987 | CD | GLU | G | 403 | 127.851 | −150.127 | 127.522 | 1.00 | 155.23 |
| ATOM | 1988 | OE1 | GLU | G | 403 | 128.568 | −149.104 | 127.499 | 1.00 | 155.71 |
| ATOM | 1989 | OE2 | GLU | G | 403 | 127.828 | −150.921 | 128.486 | 1.00 | 155.97 |
| ATOM | 1990 | N | GLY | G | 404 | 123.875 | −150.647 | 126.597 | 1.00 | 153.51 |
| ATOM | 1991 | CA | GLY | G | 404 | 122.862 | −151.531 | 127.148 | 1.00 | 153.40 |
| ATOM | 1992 | C | GLY | G | 404 | 123.409 | −152.822 | 127.728 | 1.00 | 153.73 |
| ATOM | 1993 | O | GLY | G | 404 | 123.831 | −153.715 | 126.991 | 1.00 | 153.69 |
| ATOM | 1994 | N | SER | G | 405 | 123.400 | −152.922 | 129.054 | 1.00 | 153.35 |
| ATOM | 1995 | CA | SER | G | 405 | 123.888 | −154.112 | 129.745 | 1.00 | 152.70 |
| ATOM | 1996 | C | SER | G | 405 | 123.183 | −154.291 | 131.086 | 1.00 | 152.14 |
| ATOM | 1997 | O | SER | G | 405 | 122.394 | −155.221 | 131.259 | 1.00 | 151.89 |
| ATOM | 1998 | CB | SER | G | 405 | 125.401 | −154.021 | 129.962 | 1.00 | 152.88 |
| ATOM | 1999 | OG | SER | G | 405 | 126.096 | −154.051 | 128.728 | 1.00 | 152.70 |
| ATOM | 2000 | N | ASN | G | 406 | 123.473 | −153.398 | 132.031 | 1.00 | 151.38 |
| ATOM | 2001 | CA | ASN | G | 406 | 122.864 | −153.445 | 133.359 | 1.00 | 150.36 |
| ATOM | 2002 | C | ASN | G | 406 | 123.489 | −152.410 | 134.294 | 1.00 | 149.65 |
| ATOM | 2003 | O | ASN | G | 406 | 124.666 | −152.503 | 134.641 | 1.00 | 149.18 |
| ATOM | 2004 | CB | ASN | G | 406 | 123.020 | −154.842 | 133.970 | 1.00 | 150.31 |
| ATOM | 2005 | CG | ASN | G | 406 | 122.212 | −155.018 | 135.243 | 1.00 | 150.00 |
| ATOM | 2006 | OD1 | ASN | G | 406 | 122.418 | −154.308 | 136.227 | 1.00 | 150.04 |
| ATOM | 2007 | ND2 | ASN | G | 406 | 121.284 | −155.970 | 135.228 | 1.00 | 148.55 |
| ATOM | 2008 | N | ASN | G | 407 | 122.691 | −151.425 | 134.696 | 1.00 | 149.20 |
| ATOM | 2009 | CA | ASN | G | 407 | 123.153 | −150.371 | 135.596 | 1.00 | 148.98 |
| ATOM | 2010 | C | ASN | G | 407 | 122.039 | −149.959 | 136.557 | 1.00 | 148.75 |
| ATOM | 2011 | O | ASN | G | 407 | 120.905 | −149.720 | 136.141 | 1.00 | 148.64 |
| ATOM | 2012 | CB | ASN | G | 407 | 123.622 | −149.154 | 134.792 | 1.00 | 148.85 |
| ATOM | 2013 | CG | ASN | G | 407 | 124.837 | −149.454 | 133.934 | 1.00 | 148.15 |
| ATOM | 2014 | OD1 | ASN | G | 407 | 125.883 | −149.861 | 134.440 | 1.00 | 147.21 |
| ATOM | 2015 | ND2 | ASN | G | 407 | 124.704 | −149.252 | 132.627 | 1.00 | 146.76 |
| ATOM | 2016 | N | THR | G | 408 | 122.372 | −149.876 | 137.843 | 1.00 | 148.42 |
| ATOM | 2017 | CA | THR | G | 408 | 121.400 | −149.505 | 138.866 | 1.00 | 147.81 |
| ATOM | 2018 | C | THR | G | 408 | 121.620 | −148.095 | 139.413 | 1.00 | 147.62 |
| ATOM | 2019 | O | THR | G | 408 | 122.740 | −147.710 | 139.750 | 1.00 | 147.36 |
| ATOM | 2020 | CB | THR | G | 408 | 121.433 | −150.503 | 140.047 | 1.00 | 147.47 |
| ATOM | 2021 | OG1 | THR | G | 408 | 121.128 | −151.820 | 139.570 | 1.00 | 146.97 |
| ATOM | 2022 | CG2 | THR | G | 408 | 120.415 | −150.110 | 141.110 | 1.00 | 147.04 |
| ATOM | 2023 | N | GLU | G | 409 | 120.532 | −147.333 | 139.497 | 1.00 | 147.14 |
| ATOM | 2024 | CA | GLU | G | 409 | 120.563 | −145.965 | 140.005 | 1.00 | 146.36 |
| ATOM | 2025 | C | GLU | G | 409 | 119.161 | −145.527 | 140.417 | 1.00 | 145.32 |
| ATOM | 2026 | O | GLU | G | 409 | 118.354 | −145.122 | 139.579 | 1.00 | 145.40 |
| ATOM | 2027 | CB | GLU | G | 409 | 121.116 | −145.012 | 138.938 | 1.00 | 146.73 |
| ATOM | 2028 | CG | GLU | G | 409 | 120.856 | −143.531 | 139.211 | 1.00 | 147.62 |

TABLE 2-continued

The structural coordinates of an exemplary gp120 with an extended V3 loop

| ATOM | 2029 | CD  | GLU | G | 409 | 121.396 | −143.060 | 140.552 | 1.00 | 148.32 |
|------|------|-----|-----|---|-----|---------|----------|---------|------|--------|
| ATOM | 2030 | OE1 | GLU | G | 409 | 121.186 | −141.875 | 140.891 | 1.00 | 147.74 |
| ATOM | 2031 | OE2 | GLU | G | 409 | 122.029 | −143.866 | 141.267 | 1.00 | 149.23 |
| ATOM | 2032 | N   | GLY | G | 410 | 118.878 | −145.613 | 141.713 | 1.00 | 143.74 |
| ATOM | 2033 | CA  | GLY | G | 410 | 117.570 | −145.228 | 142.210 | 1.00 | 141.66 |
| ATOM | 2034 | C   | GLY | G | 410 | 116.524 | −146.283 | 141.903 | 1.00 | 140.56 |
| ATOM | 2035 | O   | GLY | G | 410 | 115.851 | −146.210 | 140.874 | 1.00 | 140.48 |
| ATOM | 2036 | N   | ASN | G | 412 | 116.401 | −147.261 | 142.799 | 1.00 | 138.86 |
| ATOM | 2037 | CA  | ASN | G | 412 | 115.446 | −148.363 | 142.670 | 1.00 | 136.44 |
| ATOM | 2038 | C   | ASN | G | 412 | 114.351 | −148.049 | 141.651 | 1.00 | 134.58 |
| ATOM | 2039 | O   | ASN | G | 412 | 114.474 | −148.377 | 140.470 | 1.00 | 133.27 |
| ATOM | 2040 | CB  | ASN | G | 412 | 114.818 | −148.658 | 144.038 | 1.00 | 137.07 |
| ATOM | 2041 | CG  | ASN | G | 412 | 114.127 | −150.009 | 144.090 | 1.00 | 138.01 |
| ATOM | 2042 | OD1 | ASN | G | 412 | 113.251 | −150.306 | 143.279 | 1.00 | 138.79 |
| ATOM | 2043 | ND2 | ASN | G | 412 | 114.519 | −150.835 | 145.055 | 1.00 | 137.47 |
| ATOM | 2044 | N   | THR | G | 413 | 113.283 | −147.412 | 142.121 | 1.00 | 132.39 |
| ATOM | 2045 | CA  | THR | G | 413 | 112.167 | −147.028 | 141.264 | 1.00 | 129.59 |
| ATOM | 2046 | C   | THR | G | 413 | 111.876 | −145.553 | 141.502 | 1.00 | 127.51 |
| ATOM | 2047 | O   | THR | G | 413 | 111.733 | −145.116 | 142.645 | 1.00 | 127.21 |
| ATOM | 2048 | CB  | THR | G | 413 | 110.899 | −147.848 | 141.575 | 1.00 | 129.45 |
| ATOM | 2049 | OG1 | THR | G | 413 | 110.560 | −147.703 | 142.959 | 1.00 | 130.30 |
| ATOM | 2050 | CG2 | THR | G | 413 | 111.125 | −149.319 | 141.259 | 1.00 | 129.33 |
| ATOM | 2051 | N   | ILE | G | 414 | 111.792 | −144.788 | 140.418 | 1.00 | 125.10 |
| ATOM | 2052 | CA  | ILE | G | 414 | 111.543 | −143.356 | 140.515 | 1.00 | 122.12 |
| ATOM | 2053 | C   | ILE | G | 414 | 110.120 | −143.022 | 140.958 | 1.00 | 119.27 |
| ATOM | 2054 | O   | ILE | G | 414 | 109.151 | −143.618 | 140.489 | 1.00 | 118.60 |
| ATOM | 2055 | CB  | ILE | G | 414 | 111.838 | −142.653 | 139.169 | 1.00 | 121.95 |
| ATOM | 2056 | CG1 | ILE | G | 414 | 111.801 | −141.138 | 139.358 | 1.00 | 122.52 |
| ATOM | 2057 | CG2 | ILE | G | 414 | 110.830 | −143.086 | 138.118 | 1.00 | 121.32 |
| ATOM | 2058 | CD1 | ILE | G | 414 | 112.797 | −140.620 | 140.384 | 1.00 | 122.64 |
| ATOM | 2059 | N   | THR | G | 415 | 110.003 | −142.060 | 141.866 | 1.00 | 115.70 |
| ATOM | 2060 | CA  | THR | G | 415 | 108.704 | −141.642 | 142.387 | 1.00 | 111.52 |
| ATOM | 2061 | C   | THR | G | 415 | 108.362 | −140.206 | 141.981 | 1.00 | 109.61 |
| ATOM | 2062 | O   | THR | G | 415 | 109.175 | −139.293 | 142.141 | 1.00 | 109.81 |
| ATOM | 2063 | CB  | THR | G | 415 | 108.676 | −141.739 | 143.923 | 1.00 | 110.78 |
| ATOM | 2064 | OG1 | THR | G | 415 | 109.874 | −141.165 | 144.460 | 1.00 | 110.36 |
| ATOM | 2065 | CG2 | THR | G | 415 | 108.569 | −143.179 | 144.369 | 1.00 | 109.69 |
| ATOM | 2066 | N   | LEU | G | 416 | 107.150 | −140.018 | 141.463 | 1.00 | 106.18 |
| ATOM | 2067 | CA  | LEU | G | 416 | 106.684 | −138.706 | 141.012 | 1.00 | 103.07 |
| ATOM | 2068 | C   | LEU | G | 416 | 105.914 | −137.919 | 142.070 | 1.00 | 101.81 |
| ATOM | 2069 | O   | LEU | G | 416 | 104.998 | −138.443 | 142.708 | 1.00 | 101.50 |
| ATOM | 2070 | CB  | LEU | G | 416 | 105.775 | −138.847 | 139.791 | 1.00 | 101.73 |
| ATOM | 2071 | CG  | LEU | G | 416 | 106.344 | −139.279 | 138.433 | 1.00 | 101.54 |
| ATOM | 2072 | CD1 | LEU | G | 416 | 107.506 | −138.367 | 138.062 | 1.00 | 100.93 |
| ATOM | 2073 | CD2 | LEU | G | 416 | 106.797 | −140.724 | 138.497 | 1.00 | 102.75 |
| ATOM | 2074 | N   | PRO | G | 417 | 106.269 | −136.638 | 142.261 | 1.00 | 100.49 |
| ATOM | 2075 | CA  | PRO | G | 417 | 105.601 | −135.778 | 143.242 | 1.00 | 99.11  |
| ATOM | 2076 | C   | PRO | G | 417 | 104.244 | −135.385 | 142.674 | 1.00 | 97.27  |
| ATOM | 2077 | O   | PRO | G | 417 | 104.181 | −134.634 | 141.706 | 1.00 | 96.57  |
| ATOM | 2078 | CB  | PRO | G | 417 | 106.539 | −134.573 | 143.338 | 1.00 | 99.33  |
| ATOM | 2079 | CG  | PRO | G | 417 | 107.875 | −135.120 | 142.895 | 1.00 | 100.96 |
| ATOM | 2080 | CD  | PRO | G | 417 | 107.462 | −135.964 | 141.726 | 1.00 | 101.14 |
| ATOM | 2081 | N   | CYS | G | 418 | 103.158 | −135.878 | 143.255 | 1.00 | 96.07  |
| ATOM | 2082 | CA  | CYS | G | 418 | 101.840 | −135.543 | 142.722 | 1.00 | 95.36  |
| ATOM | 2083 | C   | CYS | G | 418 | 100.974 | −134.814 | 143.737 | 1.00 | 94.31  |
| ATOM | 2084 | O   | CYS | G | 418 | 101.186 | −134.933 | 144.941 | 1.00 | 93.95  |
| ATOM | 2085 | CB  | CYS | G | 418 | 101.124 | −136.816 | 142.273 | 1.00 | 96.19  |
| ATOM | 2086 | SG  | CYS | G | 418 | 100.205 | −136.655 | 140.711 | 1.00 | 99.96  |
| ATOM | 2087 | N   | ARG | G | 419 | 99.992  | −134.065 | 143.243 | 1.00 | 93.30  |
| ATOM | 2088 | CA  | ARG | G | 419 | 99.085  | −133.325 | 144.112 | 1.00 | 92.31  |
| ATOM | 2089 | C   | ARG | G | 419 | 97.658  | −133.284 | 143.571 | 1.00 | 90.72  |
| ATOM | 2090 | O   | ARG | G | 419 | 97.433  | −132.982 | 142.396 | 1.00 | 90.53  |
| ATOM | 2091 | CB  | ARG | G | 419 | 99.596  | −131.890 | 144.314 | 1.00 | 93.73  |
| ATOM | 2092 | CG  | ARG | G | 419 | 98.698  | −131.006 | 145.181 | 1.00 | 95.93  |
| ATOM | 2093 | CD  | ARG | G | 419 | 99.220  | −129.571 | 145.236 | 1.00 | 99.25  |
| ATOM | 2094 | NE  | ARG | G | 419 | 98.204  | −128.611 | 145.670 | 1.00 | 100.53 |
| ATOM | 2095 | CZ  | ARG | G | 419 | 97.837  | −128.412 | 146.933 | 1.00 | 100.92 |
| ATOM | 2096 | NH1 | ARG | G | 419 | 98.402  | −129.102 | 147.916 | 1.00 | 100.24 |
| ATOM | 2097 | NH2 | ARG | G | 419 | 96.900  | −127.517 | 147.214 | 1.00 | 100.94 |
| ATOM | 2098 | N   | ILE | G | 420 | 96.699  | −133.601 | 144.436 | 1.00 | 88.67  |
| ATOM | 2099 | CA  | ILE | G | 420 | 95.283  | −133.579 | 144.078 | 1.00 | 86.76  |
| ATOM | 2100 | C   | ILE | G | 420 | 94.765  | −132.157 | 144.276 | 1.00 | 86.13  |
| ATOM | 2101 | O   | ILE | G | 420 | 95.033  | −131.530 | 145.302 | 1.00 | 86.62  |
| ATOM | 2102 | CB  | ILE | G | 420 | 94.463  | −134.540 | 144.969 | 1.00 | 85.30  |
| ATOM | 2103 | CG1 | ILE | G | 420 | 94.795  | −135.997 | 144.627 | 1.00 | 84.63  |
| ATOM | 2104 | CG2 | ILE | G | 420 | 92.977  | −134.295 | 144.768 | 1.00 | 85.53  |
| ATOM | 2105 | CD1 | ILE | G | 420 | 96.188  | −136.429 | 145.018 | 1.00 | 84.54  |
| ATOM | 2106 | N   | LYS | G | 421 | 94.021  | −131.645 | 143.302 | 1.00 | 84.49  |

TABLE 2-continued

The structural coordinates of an exemplary gp120 with an extended V3 loop

| ATOM | 2107 | CA | LYS | G | 421 | 93.523 | −130.279 | 143.400 | 1.00 | 83.10 |
| ATOM | 2108 | C | LYS | G | 421 | 92.006 | −130.151 | 143.259 | 1.00 | 83.34 |
| ATOM | 2109 | O | LYS | G | 421 | 91.341 | −131.023 | 142.702 | 1.00 | 83.53 |
| ATOM | 2110 | CB | LYS | G | 421 | 94.224 | −129.405 | 142.343 | 1.00 | 82.25 |
| ATOM | 2111 | CG | LYS | G | 421 | 95.756 | −129.478 | 142.395 | 1.00 | 82.29 |
| ATOM | 2112 | CD | LYS | G | 421 | 96.428 | −128.598 | 141.347 | 1.00 | 81.95 |
| ATOM | 2113 | CE | LYS | G | 421 | 97.882 | −128.375 | 141.743 | 1.00 | 84.09 |
| ATOM | 2114 | NZ | LYS | G | 421 | 98.489 | −127.187 | 141.078 | 1.00 | 83.94 |
| ATOM | 2115 | N | GLN | G | 422 | 91.471 | −129.045 | 143.768 | 1.00 | 83.63 |
| ATOM | 2116 | CA | GLN | G | 422 | 90.040 | −128.764 | 143.702 | 1.00 | 82.61 |
| ATOM | 2117 | C | GLN | G | 422 | 89.728 | −127.802 | 142.565 | 1.00 | 80.65 |
| ATOM | 2118 | O | GLN | G | 422 | 88.823 | −128.044 | 141.770 | 1.00 | 78.92 |
| ATOM | 2119 | CB | GLN | G | 422 | 89.553 | −128.181 | 145.033 | 1.00 | 84.13 |
| ATOM | 2120 | CG | GLN | G | 422 | 89.286 | −129.228 | 146.109 | 1.00 | 88.24 |
| ATOM | 2121 | CD | GLN | G | 422 | 88.821 | −128.620 | 147.421 | 1.00 | 91.10 |
| ATOM | 2122 | OE1 | GLN | G | 422 | 89.614 | −128.054 | 148.174 | 1.00 | 92.63 |
| ATOM | 2123 | NE2 | GLN | G | 422 | 87.527 | −128.731 | 147.699 | 1.00 | 91.83 |
| ATOM | 2124 | N | ILE | G | 423 | 90.474 | −126.706 | 142.493 | 1.00 | 79.69 |
| ATOM | 2125 | CA | ILE | G | 423 | 90.276 | −125.734 | 141.431 | 1.00 | 79.70 |
| ATOM | 2126 | C | ILE | G | 423 | 91.021 | −126.251 | 140.208 | 1.00 | 79.36 |
| ATOM | 2127 | O | ILE | G | 423 | 92.238 | −126.436 | 140.240 | 1.00 | 81.30 |
| ATOM | 2128 | CB | ILE | G | 423 | 90.807 | −124.356 | 141.858 | 1.00 | 79.75 |
| ATOM | 2129 | CG1 | ILE | G | 423 | 89.917 | −123.811 | 142.982 | 1.00 | 80.64 |
| ATOM | 2130 | CG2 | ILE | G | 423 | 90.841 | −123.411 | 140.668 | 1.00 | 79.15 |
| ATOM | 2131 | CD1 | ILE | G | 423 | 90.446 | −122.563 | 143.643 | 1.00 | 83.89 |
| ATOM | 2132 | N | ILE | G | 424 | 90.275 | −126.493 | 139.138 | 1.00 | 78.23 |
| ATOM | 2133 | CA | ILE | G | 424 | 90.833 | −127.038 | 137.915 | 1.00 | 77.77 |
| ATOM | 2134 | C | ILE | G | 424 | 90.580 | −126.185 | 136.690 | 1.00 | 77.60 |
| ATOM | 2135 | O | ILE | G | 424 | 89.543 | −125.539 | 136.576 | 1.00 | 78.36 |
| ATOM | 2136 | CB | ILE | G | 424 | 90.208 | −128.401 | 137.631 | 1.00 | 78.68 |
| ATOM | 2137 | CG1 | ILE | G | 424 | 90.294 | −129.256 | 138.885 | 1.00 | 80.96 |
| ATOM | 2138 | CG2 | ILE | G | 424 | 90.893 | −129.069 | 136.451 | 1.00 | 80.04 |
| ATOM | 2139 | CD1 | ILE | G | 424 | 89.310 | −130.360 | 138.897 | 1.00 | 85.27 |
| ATOM | 2140 | N | ASN | G | 425 | 91.533 | −126.182 | 135.766 | 1.00 | 78.21 |
| ATOM | 2141 | CA | ASN | G | 425 | 91.356 | −125.444 | 134.521 | 1.00 | 79.38 |
| ATOM | 2142 | C | ASN | G | 425 | 90.717 | −126.445 | 133.562 | 1.00 | 81.00 |
| ATOM | 2143 | O | ASN | G | 425 | 91.281 | −127.506 | 133.291 | 1.00 | 82.92 |
| ATOM | 2144 | CB | ASN | G | 425 | 92.697 | −124.946 | 133.978 | 1.00 | 78.48 |
| ATOM | 2145 | CG | ASN | G | 425 | 93.007 | −123.526 | 134.408 | 1.00 | 79.22 |
| ATOM | 2146 | OD1 | ASN | G | 425 | 92.243 | −122.601 | 134.123 | 1.00 | 78.79 |
| ATOM | 2147 | ND2 | ASN | G | 425 | 94.136 | −123.341 | 135.080 | 1.00 | 80.19 |
| ATOM | 2148 | N | MET | G | 426 | 89.534 | −126.112 | 133.057 | 1.00 | 82.44 |
| ATOM | 2149 | CA | MET | G | 426 | 88.803 | −127.010 | 132.169 | 1.00 | 83.15 |
| ATOM | 2150 | C | MET | G | 426 | 89.441 | −127.260 | 130.810 | 1.00 | 82.81 |
| ATOM | 2151 | O | MET | G | 426 | 89.996 | −126.349 | 130.194 | 1.00 | 81.41 |
| ATOM | 2152 | CB | MET | G | 426 | 87.378 | −126.496 | 131.982 | 1.00 | 84.29 |
| ATOM | 2153 | CG | MET | G | 426 | 86.668 | −126.263 | 133.303 | 1.00 | 83.67 |
| ATOM | 2154 | SD | MET | G | 426 | 84.893 | −126.182 | 133.114 | 1.00 | 83.84 |
| ATOM | 2155 | CE | MET | G | 426 | 84.500 | −127.928 | 133.137 | 1.00 | 84.40 |
| ATOM | 2156 | N | TRP | G | 427 | 89.355 | −128.509 | 130.353 | 1.00 | 82.00 |
| ATOM | 2157 | CA | TRP | G | 427 | 89.909 | −128.910 | 129.063 | 1.00 | 81.18 |
| ATOM | 2158 | C | TRP | G | 427 | 88.857 | −128.872 | 127.963 | 1.00 | 80.45 |
| ATOM | 2159 | O | TRP | G | 427 | 89.182 | −128.678 | 126.793 | 1.00 | 80.26 |
| ATOM | 2160 | CB | TRP | G | 427 | 90.501 | −130.323 | 129.142 | 1.00 | 81.81 |
| ATOM | 2161 | CG | TRP | G | 427 | 89.522 | −131.397 | 129.531 | 1.00 | 82.28 |
| ATOM | 2162 | CD1 | TRP | G | 427 | 89.242 | −131.834 | 130.794 | 1.00 | 82.98 |
| ATOM | 2163 | CD2 | TRP | G | 427 | 88.708 | −132.181 | 128.646 | 1.00 | 81.40 |
| ATOM | 2164 | NE1 | TRP | G | 427 | 88.310 | −132.843 | 130.751 | 1.00 | 82.68 |
| ATOM | 2165 | CE2 | TRP | G | 427 | 87.964 | −133.076 | 129.447 | 1.00 | 81.58 |
| ATOM | 2166 | CE3 | TRP | G | 427 | 88.536 | −132.213 | 127.256 | 1.00 | 80.71 |
| ATOM | 2167 | CZ2 | TRP | G | 427 | 87.061 | −133.996 | 128.902 | 1.00 | 81.39 |
| ATOM | 2168 | CZ3 | TRP | G | 427 | 87.637 | −133.130 | 126.715 | 1.00 | 80.74 |
| ATOM | 2169 | CH2 | TRP | G | 427 | 86.912 | −134.007 | 127.539 | 1.00 | 80.83 |
| ATOM | 2170 | N | GLN | G | 428 | 87.596 | −129.059 | 128.341 | 1.00 | 80.48 |
| ATOM | 2171 | CA | GLN | G | 428 | 86.509 | −129.047 | 127.370 | 1.00 | 80.94 |
| ATOM | 2172 | C | GLN | G | 428 | 86.367 | −127.664 | 126.752 | 1.00 | 80.28 |
| ATOM | 2173 | O | GLN | G | 428 | 86.432 | −127.507 | 125.534 | 1.00 | 80.34 |
| ATOM | 2174 | CB | GLN | G | 428 | 85.192 | −129.450 | 128.033 | 1.00 | 82.24 |
| ATOM | 2175 | CG | GLN | G | 428 | 85.271 | −130.727 | 128.850 | 1.00 | 84.02 |
| ATOM | 2176 | CD | GLN | G | 428 | 85.490 | −130.459 | 130.327 | 1.00 | 85.70 |
| ATOM | 2177 | OE1 | GLN | G | 428 | 86.450 | −129.794 | 130.718 | 1.00 | 86.37 |
| ATOM | 2178 | NE2 | GLN | G | 428 | 84.593 | −130.976 | 131.157 | 1.00 | 88.20 |
| ATOM | 2179 | N | GLU | G | 429 | 86.168 | −126.661 | 127.599 | 1.00 | 79.28 |
| ATOM | 2180 | CA | GLU | G | 429 | 86.028 | −125.290 | 127.128 | 1.00 | 79.36 |
| ATOM | 2181 | C | GLU | G | 429 | 86.891 | −124.365 | 127.975 | 1.00 | 77.22 |
| ATOM | 2182 | O | GLU | G | 429 | 87.281 | −124.718 | 129.088 | 1.00 | 77.49 |
| ATOM | 2183 | CB | GLU | G | 429 | 84.558 | −124.850 | 127.196 | 1.00 | 82.15 |
| ATOM | 2184 | CG | GLU | G | 429 | 84.005 | −124.666 | 128.603 | 1.00 | 82.38 |

TABLE 2-continued

The structural coordinates of an exemplary gp120 with an extended V3 loop

| ATOM | 2185 | CD | GLU | G | 429 | 82.538 | −124.263 | 128.606 | 1.00 | 83.05 |
|---|---|---|---|---|---|---|---|---|---|---|
| ATOM | 2186 | OE1 | GLU | G | 429 | 82.199 | −123.225 | 127.998 | 1.00 | 81.83 |
| ATOM | 2187 | OE2 | GLU | G | 429 | 81.723 | −124.988 | 129.215 | 1.00 | 83.79 |
| ATOM | 2188 | N | VAL | G | 430 | 87.199 | −123.187 | 127.449 | 1.00 | 74.05 |
| ATOM | 2189 | CA | VAL | G | 430 | 88.009 | −122.237 | 128.193 | 1.00 | 72.33 |
| ATOM | 2190 | C | VAL | G | 430 | 87.291 | −121.876 | 129.491 | 1.00 | 72.05 |
| ATOM | 2191 | O | VAL | G | 430 | 86.126 | −121.489 | 129.473 | 1.00 | 73.40 |
| ATOM | 2192 | CB | VAL | G | 430 | 88.240 | −120.955 | 127.377 | 1.00 | 72.15 |
| ATOM | 2193 | CG1 | VAL | G | 430 | 89.157 | −120.012 | 128.135 | 1.00 | 70.59 |
| ATOM | 2194 | CG2 | VAL | G | 430 | 88.826 | −121.304 | 126.022 | 1.00 | 72.50 |
| ATOM | 2195 | N | GLY | G | 431 | 87.983 | −122.013 | 130.616 | 1.00 | 71.44 |
| ATOM | 2196 | CA | GLY | G | 431 | 87.367 | −121.693 | 131.891 | 1.00 | 70.65 |
| ATOM | 2197 | C | GLY | G | 431 | 87.947 | −122.483 | 133.046 | 1.00 | 69.99 |
| ATOM | 2198 | O | GLY | G | 431 | 88.954 | −123.168 | 132.884 | 1.00 | 72.09 |
| ATOM | 2199 | N | LYS | G | 432 | 87.319 | −122.386 | 134.214 | 1.00 | 68.32 |
| ATOM | 2200 | CA | LYS | G | 432 | 87.785 | −123.103 | 135.397 | 1.00 | 66.54 |
| ATOM | 2201 | C | LYS | G | 432 | 86.663 | −123.912 | 136.026 | 1.00 | 64.43 |
| ATOM | 2202 | O | LYS | G | 432 | 85.510 | −123.822 | 135.611 | 1.00 | 66.65 |
| ATOM | 2203 | CB | LYS | G | 432 | 88.344 | −122.123 | 136.434 | 1.00 | 68.76 |
| ATOM | 2204 | CG | LYS | G | 432 | 89.580 | −121.362 | 135.973 | 1.00 | 71.24 |
| ATOM | 2205 | CD | LYS | G | 432 | 90.008 | −120.336 | 137.012 | 1.00 | 72.43 |
| ATOM | 2206 | CE | LYS | G | 432 | 91.167 | −119.486 | 136.515 | 1.00 | 74.60 |
| ATOM | 2207 | NZ | LYS | G | 432 | 92.391 | −120.287 | 136.230 | 1.00 | 76.20 |
| ATOM | 2208 | N | ALA | G | 433 | 87.008 | −124.700 | 137.036 | 1.00 | 61.60 |
| ATOM | 2209 | CA | ALA | G | 433 | 86.031 | −125.529 | 137.721 | 1.00 | 60.62 |
| ATOM | 2210 | C | ALA | G | 433 | 86.467 | −125.778 | 139.156 | 1.00 | 61.66 |
| ATOM | 2211 | O | ALA | G | 433 | 87.655 | −125.757 | 139.464 | 1.00 | 65.08 |
| ATOM | 2212 | CB | ALA | G | 433 | 85.872 | −126.850 | 136.989 | 1.00 | 59.62 |
| ATOM | 2213 | N | MET | G | 434 | 85.495 | −126.019 | 140.027 | 1.00 | 61.86 |
| ATOM | 2214 | CA | MET | G | 434 | 85.756 | −126.272 | 141.439 | 1.00 | 62.17 |
| ATOM | 2215 | C | MET | G | 434 | 85.099 | −127.572 | 141.885 | 1.00 | 63.75 |
| ATOM | 2216 | O | MET | G | 434 | 83.884 | −127.727 | 141.762 | 1.00 | 65.83 |
| ATOM | 2217 | CB | MET | G | 434 | 85.203 | −125.123 | 142.283 | 1.00 | 61.94 |
| ATOM | 2218 | CG | MET | G | 434 | 84.957 | −125.495 | 143.737 | 1.00 | 62.90 |
| ATOM | 2219 | SD | MET | G | 434 | 86.262 | −125.005 | 144.862 | 1.00 | 64.78 |
| ATOM | 2220 | CE | MET | G | 434 | 85.342 | −123.924 | 145.974 | 1.00 | 64.90 |
| ATOM | 2221 | N | TYR | G | 435 | 85.890 | −128.501 | 142.413 | 1.00 | 63.38 |
| ATOM | 2222 | CA | TYR | G | 435 | 85.343 | −129.777 | 142.874 | 1.00 | 61.59 |
| ATOM | 2223 | C | TYR | G | 435 | 85.401 | −129.929 | 144.388 | 1.00 | 62.48 |
| ATOM | 2224 | O | TYR | G | 435 | 86.030 | −129.129 | 145.079 | 1.00 | 62.27 |
| ATOM | 2225 | CB | TYR | G | 435 | 86.079 | −130.945 | 142.219 | 1.00 | 58.59 |
| ATOM | 2226 | CG | TYR | G | 435 | 85.750 | −131.133 | 140.759 | 1.00 | 54.66 |
| ATOM | 2227 | CD1 | TYR | G | 435 | 86.207 | −130.237 | 139.798 | 1.00 | 52.26 |
| ATOM | 2228 | CD2 | TYR | G | 435 | 84.967 | −132.206 | 140.340 | 1.00 | 57.11 |
| ATOM | 2229 | CE1 | TYR | G | 435 | 85.893 | −130.406 | 138.453 | 1.00 | 54.48 |
| ATOM | 2230 | CE2 | TYR | G | 435 | 84.646 | −132.384 | 138.999 | 1.00 | 57.17 |
| ATOM | 2231 | CZ | TYR | G | 435 | 85.110 | −131.482 | 138.062 | 1.00 | 55.72 |
| ATOM | 2232 | OH | TYR | G | 435 | 84.781 | −131.663 | 136.738 | 1.00 | 55.13 |
| ATOM | 2233 | N | ALA | G | 436 | 84.747 | −130.967 | 144.897 | 1.00 | 64.73 |
| ATOM | 2234 | CA | ALA | G | 436 | 84.713 | −131.229 | 146.331 | 1.00 | 69.52 |
| ATOM | 2235 | C | ALA | G | 436 | 86.048 | −131.755 | 146.862 | 1.00 | 73.34 |
| ATOM | 2236 | O | ALA | G | 436 | 86.882 | −132.251 | 146.104 | 1.00 | 74.12 |
| ATOM | 2237 | CB | ALA | G | 436 | 83.598 | −132.225 | 146.645 | 1.00 | 68.49 |
| ATOM | 2238 | N | PRO | G | 437 | 86.266 | −131.648 | 148.184 | 1.00 | 77.56 |
| ATOM | 2239 | CA | PRO | G | 437 | 87.501 | −132.114 | 148.818 | 1.00 | 80.89 |
| ATOM | 2240 | C | PRO | G | 437 | 87.721 | −133.611 | 148.599 | 1.00 | 85.07 |
| ATOM | 2241 | O | PRO | G | 437 | 86.766 | −134.365 | 148.413 | 1.00 | 86.90 |
| ATOM | 2242 | CB | PRO | G | 437 | 87.285 | −131.754 | 150.285 | 1.00 | 79.74 |
| ATOM | 2243 | CG | PRO | G | 437 | 86.421 | −130.527 | 150.197 | 1.00 | 78.93 |
| ATOM | 2244 | CD | PRO | G | 437 | 85.409 | −130.972 | 149.171 | 1.00 | 77.85 |
| ATOM | 2245 | N | PRO | G | 438 | 88.988 | −134.058 | 148.617 | 1.00 | 88.61 |
| ATOM | 2246 | CA | PRO | G | 438 | 89.362 | −135.460 | 148.416 | 1.00 | 91.38 |
| ATOM | 2247 | C | PRO | G | 438 | 88.540 | −136.458 | 149.225 | 1.00 | 95.06 |
| ATOM | 2248 | O | PRO | G | 438 | 88.062 | −136.149 | 150.318 | 1.00 | 94.95 |
| ATOM | 2249 | CB | PRO | G | 438 | 90.840 | −135.467 | 148.790 | 1.00 | 89.15 |
| ATOM | 2250 | CG | PRO | G | 438 | 91.284 | −134.125 | 148.301 | 1.00 | 87.77 |
| ATOM | 2251 | CD | PRO | G | 438 | 90.189 | −133.240 | 148.859 | 1.00 | 88.31 |
| ATOM | 2252 | N | ILE | G | 439 | 88.379 | −137.655 | 148.672 | 1.00 | 99.51 |
| ATOM | 2253 | CA | ILE | G | 439 | 87.615 | −138.713 | 149.320 | 1.00 | 105.19 |
| ATOM | 2254 | C | ILE | G | 439 | 88.361 | −139.228 | 150.546 | 1.00 | 110.13 |
| ATOM | 2255 | O | ILE | G | 439 | 89.590 | −139.212 | 150.581 | 1.00 | 110.70 |
| ATOM | 2256 | CB | ILE | G | 439 | 87.395 | −139.884 | 148.354 | 1.00 | 104.20 |
| ATOM | 2257 | CG1 | ILE | G | 439 | 87.009 | −139.347 | 146.973 | 1.00 | 103.55 |
| ATOM | 2258 | CG2 | ILE | G | 439 | 86.297 | −140.795 | 148.882 | 1.00 | 104.68 |
| ATOM | 2259 | CD1 | ILE | G | 439 | 87.025 | −140.395 | 145.894 | 1.00 | 105.15 |
| ATOM | 2260 | N | ARG | G | 440 | 87.613 | −139.688 | 151.544 | 1.00 | 116.12 |
| ATOM | 2261 | CA | ARG | G | 440 | 88.200 | −140.192 | 152.779 | 1.00 | 122.02 |
| ATOM | 2262 | C | ARG | G | 440 | 89.016 | −141.478 | 152.623 | 1.00 | 124.42 |

TABLE 2-continued

The structural coordinates of an exemplary gp120 with an extended V3 loop

| ATOM | 2263 | O | ARG | G | 440 | 90.028 | −141.660 | 153.300 | 1.00 | 125.60 |
|---|---|---|---|---|---|---|---|---|---|---|
| ATOM | 2264 | CB | ARG | G | 440 | 87.096 | −140.376 | 153.833 | 1.00 | 124.40 |
| ATOM | 2265 | CG | ARG | G | 440 | 85.821 | −141.037 | 153.316 | 1.00 | 128.47 |
| ATOM | 2266 | CD | ARG | G | 440 | 85.962 | −142.547 | 153.275 | 1.00 | 132.51 |
| ATOM | 2267 | NE | ARG | G | 440 | 85.509 | −143.111 | 152.007 | 1.00 | 135.84 |
| ATOM | 2268 | CZ | ARG | G | 440 | 85.710 | −144.374 | 151.643 | 1.00 | 137.31 |
| ATOM | 2269 | NH1 | ARG | G | 440 | 86.354 | −145.200 | 152.456 | 1.00 | 137.16 |
| ATOM | 2270 | NH2 | ARG | G | 440 | 85.275 | −144.810 | 150.467 | 1.00 | 136.49 |
| ATOM | 2271 | N | GLY | G | 441 | 88.592 | −142.358 | 151.721 | 1.00 | 125.98 |
| ATOM | 2272 | CA | GLY | G | 441 | 89.305 | −143.609 | 151.521 | 1.00 | 127.56 |
| ATOM | 2273 | C | GLY | G | 441 | 90.602 | −143.502 | 150.739 | 1.00 | 128.74 |
| ATOM | 2274 | O | GLY | G | 441 | 91.025 | −142.412 | 150.347 | 1.00 | 128.11 |
| ATOM | 2275 | N | GLN | G | 442 | 91.230 | −144.653 | 150.518 | 1.00 | 129.91 |
| ATOM | 2276 | CA | GLN | G | 442 | 92.483 | −144.745 | 149.780 | 1.00 | 130.78 |
| ATOM | 2277 | C | GLN | G | 442 | 92.234 | −144.787 | 148.275 | 1.00 | 131.13 |
| ATOM | 2278 | O | GLN | G | 442 | 91.299 | −145.438 | 147.805 | 1.00 | 130.50 |
| ATOM | 2279 | CB | GLN | G | 442 | 93.251 | −145.997 | 150.219 | 1.00 | 132.26 |
| ATOM | 2280 | CG | GLN | G | 442 | 93.839 | −146.801 | 149.072 | 1.00 | 134.25 |
| ATOM | 2281 | CD | GLN | G | 442 | 95.123 | −147.506 | 149.454 | 1.00 | 135.13 |
| ATOM | 2282 | OE1 | GLN | G | 442 | 95.125 | −148.447 | 150.248 | 1.00 | 136.02 |
| ATOM | 2283 | NE2 | GLN | G | 442 | 96.233 | −147.040 | 148.897 | 1.00 | 134.96 |
| ATOM | 2284 | N | ILE | G | 443 | 93.084 | −144.096 | 147.524 | 1.00 | 131.67 |
| ATOM | 2285 | CA | ILE | G | 443 | 92.961 | −144.041 | 146.073 | 1.00 | 132.30 |
| ATOM | 2286 | C | ILE | G | 443 | 94.142 | −144.725 | 145.398 | 1.00 | 131.73 |
| ATOM | 2287 | O | ILE | G | 443 | 95.271 | −144.238 | 145.452 | 1.00 | 131.38 |
| ATOM | 2288 | CB | ILE | G | 443 | 92.890 | −142.582 | 145.591 | 1.00 | 133.10 |
| ATOM | 2289 | CG1 | ILE | G | 443 | 91.729 | −141.871 | 146.291 | 1.00 | 133.63 |
| ATOM | 2290 | CG2 | ILE | G | 443 | 92.701 | −142.535 | 144.080 | 1.00 | 134.13 |
| ATOM | 2291 | CD1 | ILE | G | 443 | 91.703 | −140.384 | 146.055 | 1.00 | 133.79 |
| ATOM | 2292 | N | ARG | G | 444 | 93.874 | −145.856 | 144.759 | 1.00 | 131.74 |
| ATOM | 2293 | CA | ARG | G | 444 | 94.909 | −146.629 | 144.078 | 1.00 | 131.48 |
| ATOM | 2294 | C | ARG | G | 444 | 94.593 | −146.714 | 142.583 | 1.00 | 129.69 |
| ATOM | 2295 | O | ARG | G | 444 | 93.492 | −147.113 | 142.205 | 1.00 | 129.68 |
| ATOM | 2296 | CB | ARG | G | 444 | 94.964 | −148.037 | 144.693 | 1.00 | 133.90 |
| ATOM | 2297 | CG | ARG | G | 444 | 96.261 | −148.390 | 145.433 | 1.00 | 136.43 |
| ATOM | 2298 | CD | ARG | G | 444 | 96.037 | −149.515 | 146.449 | 1.00 | 138.19 |
| ATOM | 2299 | NE | ARG | G | 444 | 97.247 | −150.283 | 146.748 | 1.00 | 139.51 |
| ATOM | 2300 | CZ | ARG | G | 444 | 98.290 | −149.830 | 147.441 | 1.00 | 140.29 |
| ATOM | 2301 | NH1 | ARG | G | 444 | 98.294 | −148.595 | 147.929 | 1.00 | 140.09 |
| ATOM | 2302 | NH2 | ARG | G | 444 | 99.338 | −150.619 | 147.647 | 1.00 | 140.64 |
| ATOM | 2303 | N | CYS | G | 445 | 95.543 | −146.334 | 141.732 | 1.00 | 127.32 |
| ATOM | 2304 | CA | CYS | G | 445 | 95.316 | −146.391 | 140.286 | 1.00 | 124.83 |
| ATOM | 2305 | C | CYS | G | 445 | 96.544 | −146.962 | 139.558 | 1.00 | 123.33 |
| ATOM | 2306 | O | CYS | G | 445 | 97.684 | −146.679 | 139.926 | 1.00 | 123.02 |
| ATOM | 2307 | CB | CYS | G | 445 | 94.974 | −144.987 | 139.740 | 1.00 | 124.31 |
| ATOM | 2308 | SG | CYS | G | 445 | 93.684 | −144.087 | 140.680 | 1.00 | 124.41 |
| ATOM | 2309 | N | SER | G | 446 | 96.299 | −147.780 | 138.536 | 1.00 | 121.97 |
| ATOM | 2310 | CA | SER | G | 446 | 97.366 | −148.402 | 137.752 | 1.00 | 119.88 |
| ATOM | 2311 | C | SER | G | 446 | 97.031 | −148.373 | 136.262 | 1.00 | 117.92 |
| ATOM | 2312 | O | SER | G | 446 | 95.924 | −148.733 | 135.859 | 1.00 | 117.72 |
| ATOM | 2313 | CB | SER | G | 446 | 97.574 | −149.853 | 138.202 | 1.00 | 120.03 |
| ATOM | 2314 | OG | SER | G | 446 | 96.407 | −150.627 | 137.986 | 1.00 | 120.27 |
| ATOM | 2315 | N | SER | G | 447 | 97.994 | −147.955 | 135.448 | 1.00 | 114.74 |
| ATOM | 2316 | CA | SER | G | 447 | 97.790 | −147.875 | 134.008 | 1.00 | 112.04 |
| ATOM | 2317 | C | SER | G | 447 | 99.096 | −148.079 | 133.241 | 1.00 | 108.70 |
| ATOM | 2318 | O | SER | G | 447 | 100.182 | −147.987 | 133.812 | 1.00 | 108.62 |
| ATOM | 2319 | CB | SER | G | 447 | 97.173 | −146.518 | 133.655 | 1.00 | 113.67 |
| ATOM | 2320 | OG | SER | G | 447 | 97.856 | −145.468 | 134.314 | 1.00 | 114.63 |
| ATOM | 2321 | N | ASN | G | 448 | 98.975 | −148.359 | 131.946 | 1.00 | 104.80 |
| ATOM | 2322 | CA | ASN | G | 448 | 100.127 | −148.587 | 131.084 | 1.00 | 101.05 |
| ATOM | 2323 | C | ASN | G | 448 | 100.392 | −147.407 | 130.161 | 1.00 | 98.08 |
| ATOM | 2324 | O | ASN | G | 448 | 99.549 | −147.048 | 129.342 | 1.00 | 97.79 |
| ATOM | 2325 | CB | ASN | G | 448 | 99.908 | −149.848 | 130.235 | 1.00 | 102.67 |
| ATOM | 2326 | CG | ASN | G | 448 | 100.039 | −151.126 | 131.038 | 1.00 | 103.58 |
| ATOM | 2327 | OD1 | ASN | G | 448 | 101.140 | −151.519 | 131.422 | 1.00 | 103.71 |
| ATOM | 2328 | ND2 | ASN | G | 448 | 98.912 | −151.781 | 131.299 | 1.00 | 103.79 |
| ATOM | 2329 | N | ILE | G | 449 | 101.566 | −146.804 | 130.294 | 1.00 | 94.94 |
| ATOM | 2330 | CA | ILE | G | 449 | 101.935 | −145.676 | 129.449 | 1.00 | 92.96 |
| ATOM | 2331 | C | ILE | G | 449 | 102.228 | −146.206 | 128.054 | 1.00 | 92.14 |
| ATOM | 2332 | O | ILE | G | 449 | 103.343 | −146.635 | 127.757 | 1.00 | 91.85 |
| ATOM | 2333 | CB | ILE | G | 449 | 103.182 | −144.975 | 129.987 | 1.00 | 93.15 |
| ATOM | 2334 | CG1 | ILE | G | 449 | 102.947 | −144.584 | 131.449 | 1.00 | 94.25 |
| ATOM | 2335 | CG2 | ILE | G | 449 | 103.494 | −143.747 | 129.141 | 1.00 | 91.79 |
| ATOM | 2336 | CD1 | ILE | G | 449 | 104.181 | −144.084 | 132.146 | 1.00 | 94.95 |
| ATOM | 2337 | N | THR | G | 450 | 101.214 | −146.178 | 127.201 | 1.00 | 91.70 |
| ATOM | 2338 | CA | THR | G | 450 | 101.349 | −146.681 | 125.845 | 1.00 | 92.19 |
| ATOM | 2339 | C | THR | G | 450 | 101.910 | −145.647 | 124.876 | 1.00 | 91.91 |
| ATOM | 2340 | O | THR | G | 450 | 102.164 | −145.955 | 123.714 | 1.00 | 92.23 |

TABLE 2-continued

The structural coordinates of an exemplary gp120 with an extended V3 loop

| ATOM | 2341 | CB | THR | G | 450 | 99.992 | −147.171 | 125.312 | 1.00 | 92.87 |
| --- | --- | --- | --- | --- | --- | --- | --- | --- | --- | --- |
| ATOM | 2342 | OG1 | THR | G | 450 | 99.044 | −146.101 | 125.374 | 1.00 | 94.60 |
| ATOM | 2343 | CG2 | THR | G | 450 | 99.480 | −148.328 | 126.147 | 1.00 | 91.70 |
| ATOM | 2344 | N | GLY | G | 451 | 102.101 | −144.421 | 125.350 | 1.00 | 92.40 |
| ATOM | 2345 | CA | GLY | G | 451 | 102.631 | −143.373 | 124.493 | 1.00 | 93.12 |
| ATOM | 2346 | C | GLY | G | 451 | 102.795 | −142.059 | 125.232 | 1.00 | 93.74 |
| ATOM | 2347 | O | GLY | G | 451 | 102.551 | −141.983 | 126.434 | 1.00 | 94.94 |
| ATOM | 2348 | N | LEU | G | 452 | 103.208 | −141.020 | 124.516 | 1.00 | 93.32 |
| ATOM | 2349 | CA | LEU | G | 452 | 103.394 | −139.708 | 125.121 | 1.00 | 94.48 |
| ATOM | 2350 | C | LEU | G | 452 | 103.370 | −138.597 | 124.077 | 1.00 | 96.43 |
| ATOM | 2351 | O | LEU | G | 452 | 103.383 | −138.862 | 122.875 | 1.00 | 97.24 |
| ATOM | 2352 | CB | LEU | G | 452 | 104.717 | −139.660 | 125.898 | 1.00 | 94.99 |
| ATOM | 2353 | CG | LEU | G | 452 | 105.989 | −140.116 | 125.174 | 1.00 | 94.35 |
| ATOM | 2354 | CD1 | LEU | G | 452 | 107.082 | −139.061 | 125.305 | 1.00 | 93.41 |
| ATOM | 2355 | CD2 | LEU | G | 452 | 106.447 | −141.441 | 125.767 | 1.00 | 94.53 |
| ATOM | 2356 | N | LEU | G | 453 | 103.339 | −137.353 | 124.546 | 1.00 | 97.31 |
| ATOM | 2357 | CA | LEU | G | 453 | 103.312 | −136.191 | 123.662 | 1.00 | 97.97 |
| ATOM | 2358 | C | LEU | G | 453 | 104.537 | −135.317 | 123.900 | 1.00 | 99.02 |
| ATOM | 2359 | O | LEU | G | 453 | 104.923 | −135.080 | 125.044 | 1.00 | 98.34 |
| ATOM | 2360 | CB | LEU | G | 453 | 102.045 | −135.374 | 123.919 | 1.00 | 100.23 |
| ATOM | 2361 | CG | LEU | G | 453 | 100.710 | −136.088 | 123.684 | 1.00 | 102.44 |
| ATOM | 2362 | CD1 | LEU | G | 453 | 99.780 | −135.831 | 124.857 | 1.00 | 104.66 |
| ATOM | 2363 | CD2 | LEU | G | 453 | 100.089 | −135.602 | 122.384 | 1.00 | 104.74 |
| ATOM | 2364 | N | LEU | G | 454 | 105.144 | −134.835 | 122.821 | 1.00 | 101.32 |
| ATOM | 2365 | CA | LEU | G | 454 | 106.335 | −133.995 | 122.925 | 1.00 | 104.16 |
| ATOM | 2366 | C | LEU | G | 454 | 106.287 | −132.786 | 122.002 | 1.00 | 105.43 |
| ATOM | 2367 | O | LEU | G | 454 | 105.683 | −132.829 | 120.935 | 1.00 | 104.92 |
| ATOM | 2368 | CB | LEU | G | 454 | 107.587 | −134.810 | 122.590 | 1.00 | 107.11 |
| ATOM | 2369 | CG | LEU | G | 454 | 108.124 | −135.787 | 123.640 | 1.00 | 109.52 |
| ATOM | 2370 | CD1 | LEU | G | 454 | 109.036 | −136.808 | 122.980 | 1.00 | 110.38 |
| ATOM | 2371 | CD2 | LEU | G | 454 | 108.870 | −135.011 | 124.718 | 1.00 | 110.90 |
| ATOM | 2372 | N | THR | G | 455 | 106.940 | −131.710 | 122.423 | 1.00 | 107.87 |
| ATOM | 2373 | CA | THR | G | 455 | 107.007 | −130.483 | 121.639 | 1.00 | 111.93 |
| ATOM | 2374 | C | THR | G | 455 | 108.450 | −129.979 | 121.669 | 1.00 | 113.34 |
| ATOM | 2375 | O | THR | G | 455 | 108.941 | −129.532 | 122.708 | 1.00 | 113.32 |
| ATOM | 2376 | CB | THR | G | 455 | 106.087 | −129.392 | 122.216 | 1.00 | 112.59 |
| ATOM | 2377 | OG1 | THR | G | 455 | 106.172 | −129.403 | 123.643 | 1.00 | 113.78 |
| ATOM | 2378 | CG2 | THR | G | 455 | 104.650 | −129.615 | 121.796 | 1.00 | 113.67 |
| ATOM | 2379 | N | ARG | G | 456 | 109.126 | −130.057 | 120.526 | 1.00 | 115.82 |
| ATOM | 2380 | CA | ARG | G | 456 | 110.520 | −129.638 | 120.426 | 1.00 | 117.80 |
| ATOM | 2381 | C | ARG | G | 456 | 110.714 | −128.126 | 120.336 | 1.00 | 118.96 |
| ATOM | 2382 | O | ARG | G | 456 | 109.853 | −127.405 | 119.834 | 1.00 | 118.29 |
| ATOM | 2383 | CB | ARG | G | 456 | 111.177 | −130.305 | 119.212 | 1.00 | 117.97 |
| ATOM | 2384 | CG | ARG | G | 456 | 110.748 | −129.740 | 117.864 | 1.00 | 119.08 |
| ATOM | 2385 | CD | ARG | G | 456 | 111.533 | −130.384 | 116.728 | 1.00 | 119.35 |
| ATOM | 2386 | NE | ARG | G | 456 | 111.439 | −129.607 | 115.496 | 1.00 | 119.68 |
| ATOM | 2387 | CZ | ARG | G | 456 | 112.130 | −128.496 | 115.257 | 1.00 | 119.75 |
| ATOM | 2388 | NH1 | ARG | G | 456 | 112.977 | −128.027 | 116.165 | 1.00 | 120.37 |
| ATOM | 2389 | NH2 | ARG | G | 456 | 111.968 | −127.847 | 114.112 | 1.00 | 119.93 |
| ATOM | 2390 | N | ASP | G | 457 | 111.860 | −127.656 | 120.823 | 1.00 | 119.85 |
| ATOM | 2391 | CA | ASP | G | 457 | 112.189 | −126.233 | 120.793 | 1.00 | 120.75 |
| ATOM | 2392 | C | ASP | G | 457 | 112.749 | −125.857 | 119.427 | 1.00 | 122.23 |
| ATOM | 2393 | O | ASP | G | 457 | 113.723 | −126.451 | 118.964 | 1.00 | 122.14 |
| ATOM | 2394 | CB | ASP | G | 457 | 113.226 | −125.903 | 121.869 | 1.00 | 120.14 |
| ATOM | 2395 | CG | ASP | G | 457 | 112.739 | −126.229 | 123.267 | 1.00 | 120.03 |
| ATOM | 2396 | OD1 | ASP | G | 457 | 113.374 | −125.778 | 124.243 | 1.00 | 119.43 |
| ATOM | 2397 | OD2 | ASP | G | 457 | 111.721 | −126.943 | 123.378 | 1.00 | 119.90 |
| ATOM | 2398 | N | GLY | G | 458 | 112.139 | −124.865 | 118.787 | 1.00 | 123.91 |
| ATOM | 2399 | CA | GLY | G | 458 | 112.597 | −124.440 | 117.475 | 1.00 | 126.39 |
| ATOM | 2400 | C | GLY | G | 458 | 113.689 | −123.387 | 117.531 | 1.00 | 128.56 |
| ATOM | 2401 | O | GLY | G | 458 | 114.703 | −123.567 | 118.205 | 1.00 | 128.30 |
| ATOM | 2402 | N | GLY | G | 459 | 113.487 | −122.284 | 116.817 | 1.00 | 130.42 |
| ATOM | 2403 | CA | GLY | G | 459 | 114.472 | −121.222 | 116.807 | 1.00 | 132.58 |
| ATOM | 2404 | C | GLY | G | 459 | 115.502 | −121.403 | 115.712 | 1.00 | 134.70 |
| ATOM | 2405 | O | GLY | G | 459 | 116.070 | −122.485 | 115.552 | 1.00 | 134.58 |
| ATOM | 2406 | N | ILE | G | 460 | 115.751 | −120.338 | 114.959 | 1.00 | 137.83 |
| ATOM | 2407 | CA | ILE | G | 460 | 116.726 | −120.379 | 113.875 | 1.00 | 140.76 |
| ATOM | 2408 | C | ILE | G | 460 | 118.138 | −120.321 | 114.468 | 1.00 | 142.81 |
| ATOM | 2409 | O | ILE | G | 460 | 119.123 | −120.606 | 113.792 | 1.00 | 142.92 |
| ATOM | 2410 | CB | ILE | G | 460 | 116.497 | −119.194 | 112.903 | 1.00 | 140.96 |
| ATOM | 2411 | CG1 | ILE | G | 460 | 116.933 | −119.570 | 111.484 | 1.00 | 141.22 |
| ATOM | 2412 | CG2 | ILE | G | 460 | 117.259 | −117.970 | 113.383 | 1.00 | 141.19 |
| ATOM | 2413 | CD1 | ILE | G | 460 | 118.421 | −119.766 | 111.310 | 1.00 | 140.88 |
| ATOM | 2414 | N | ASN | G | 461 | 118.223 | −119.963 | 115.746 | 1.00 | 145.09 |
| ATOM | 2415 | CA | ASN | G | 461 | 119.506 | −119.878 | 116.443 | 1.00 | 147.66 |
| ATOM | 2416 | C | ASN | G | 461 | 120.070 | −121.289 | 116.632 | 1.00 | 149.02 |
| ATOM | 2417 | O | ASN | G | 461 | 119.393 | −122.161 | 117.178 | 1.00 | 148.11 |
| ATOM | 2418 | CB | ASN | G | 461 | 119.309 | −119.186 | 117.800 | 1.00 | 148.39 |

TABLE 2-continued

The structural coordinates of an exemplary gp120 with an extended V3 loop

| ATOM | 2419 | CG  | ASN | G | 461 | 120.581 | −118.560 | 118.329 | 1.00 | 149.53 |
| ATOM | 2420 | OD1 | ASN | G | 461 | 121.509 | −119.257 | 118.737 | 1.00 | 149.19 |
| ATOM | 2421 | ND2 | ASN | G | 461 | 120.631 | −117.233 | 118.323 | 1.00 | 148.79 |
| ATOM | 2422 | N   | GLU | G | 462 | 121.303 | −121.511 | 116.179 | 1.00 | 151.28 |
| ATOM | 2423 | CA  | GLU | G | 462 | 121.931 | −122.826 | 116.284 | 1.00 | 153.22 |
| ATOM | 2424 | C   | GLU | G | 462 | 122.706 | −123.073 | 117.578 | 1.00 | 153.57 |
| ATOM | 2425 | O   | GLU | G | 462 | 123.216 | −122.143 | 118.202 | 1.00 | 153.46 |
| ATOM | 2426 | CB  | GLU | G | 462 | 122.859 | −123.067 | 115.085 | 1.00 | 153.86 |
| ATOM | 2427 | CG  | GLU | G | 462 | 124.074 | −122.139 | 114.989 | 1.00 | 156.71 |
| ATOM | 2428 | CD  | GLU | G | 462 | 123.763 | −120.798 | 114.342 | 1.00 | 157.61 |
| ATOM | 2429 | OE1 | GLU | G | 462 | 123.171 | −119.922 | 115.006 | 1.00 | 157.89 |
| ATOM | 2430 | OE2 | GLU | G | 462 | 124.110 | −120.625 | 113.154 | 1.00 | 158.13 |
| ATOM | 2431 | N   | ASN | G | 463 | 122.794 | −124.342 | 117.965 | 1.00 | 153.66 |
| ATOM | 2432 | CA  | ASN | G | 463 | 123.507 | −124.735 | 119.172 | 1.00 | 153.40 |
| ATOM | 2433 | C   | ASN | G | 463 | 123.918 | −126.200 | 119.044 | 1.00 | 152.49 |
| ATOM | 2434 | O   | ASN | G | 463 | 124.772 | −126.690 | 119.784 | 1.00 | 152.48 |
| ATOM | 2435 | CB  | ASN | G | 463 | 122.608 | −124.525 | 120.400 | 1.00 | 154.12 |
| ATOM | 2436 | CG  | ASN | G | 463 | 123.375 | −124.598 | 121.707 | 1.00 | 155.58 |
| ATOM | 2437 | OD1 | ASN | G | 463 | 123.613 | −125.679 | 122.245 | 1.00 | 156.54 |
| ATOM | 2438 | ND2 | ASN | G | 463 | 123.780 | −123.439 | 122.217 | 1.00 | 156.41 |
| ATOM | 2439 | N   | GLY | G | 464 | 123.311 | −126.886 | 118.081 | 1.00 | 150.94 |
| ATOM | 2440 | CA  | GLY | G | 464 | 123.614 | −128.286 | 117.858 | 1.00 | 149.00 |
| ATOM | 2441 | C   | GLY | G | 464 | 122.693 | −129.184 | 118.658 | 1.00 | 147.53 |
| ATOM | 2442 | O   | GLY | G | 464 | 122.652 | −130.397 | 118.450 | 1.00 | 147.66 |
| ATOM | 2443 | N   | THR | G | 465 | 121.937 | −128.577 | 119.566 | 1.00 | 145.51 |
| ATOM | 2444 | CA  | THR | G | 465 | 121.012 | −129.311 | 120.416 | 1.00 | 142.98 |
| ATOM | 2445 | C   | THR | G | 465 | 119.561 | −128.931 | 120.146 | 1.00 | 140.93 |
| ATOM | 2446 | O   | THR | G | 465 | 119.208 | −127.752 | 120.074 | 1.00 | 140.82 |
| ATOM | 2447 | CB  | THR | G | 465 | 121.305 | −129.042 | 121.903 | 1.00 | 143.71 |
| ATOM | 2448 | OG1 | THR | G | 465 | 121.216 | −127.633 | 122.153 | 1.00 | 144.71 |
| ATOM | 2449 | CG2 | THR | G | 465 | 122.691 | −129.520 | 122.266 | 1.00 | 143.31 |
| ATOM | 2450 | N   | GLU | G | 466 | 118.730 | −129.951 | 119.981 | 1.00 | 137.84 |
| ATOM | 2451 | CA  | GLU | G | 466 | 117.304 | −129.762 | 119.750 | 1.00 | 134.60 |
| ATOM | 2452 | C   | GLU | G | 466 | 116.586 | −130.315 | 120.976 | 1.00 | 132.23 |
| ATOM | 2453 | O   | GLU | G | 466 | 116.495 | −131.530 | 121.155 | 1.00 | 131.65 |
| ATOM | 2454 | CB  | GLU | G | 466 | 116.866 | −130.515 | 118.492 | 1.00 | 134.81 |
| ATOM | 2455 | CG  | GLU | G | 466 | 117.430 | −129.969 | 117.182 | 1.00 | 135.55 |
| ATOM | 2456 | CD  | GLU | G | 466 | 116.756 | −128.681 | 116.729 | 1.00 | 136.34 |
| ATOM | 2457 | OE1 | GLU | G | 466 | 117.195 | −128.100 | 115.711 | 1.00 | 136.05 |
| ATOM | 2458 | OE2 | GLU | G | 466 | 115.785 | −128.250 | 117.386 | 1.00 | 137.26 |
| ATOM | 2459 | N   | ILE | G | 467 | 116.080 | −129.417 | 121.814 | 1.00 | 129.25 |
| ATOM | 2460 | CA  | ILE | G | 467 | 115.400 | −129.801 | 123.047 | 1.00 | 126.01 |
| ATOM | 2461 | C   | ILE | G | 467 | 113.989 | −130.338 | 122.826 | 1.00 | 123.54 |
| ATOM | 2462 | O   | ILE | G | 467 | 113.261 | −129.848 | 121.966 | 1.00 | 122.31 |
| ATOM | 2463 | CB  | ILE | G | 467 | 115.299 | −128.602 | 124.008 | 1.00 | 125.82 |
| ATOM | 2464 | CG1 | ILE | G | 467 | 116.509 | −127.686 | 123.827 | 1.00 | 125.39 |
| ATOM | 2465 | CG2 | ILE | G | 467 | 115.262 | −129.091 | 125.449 | 1.00 | 124.63 |
| ATOM | 2466 | CD1 | ILE | G | 467 | 117.829 | −128.361 | 124.104 | 1.00 | 125.46 |
| ATOM | 2467 | N   | PHE | G | 468 | 113.609 | −131.345 | 123.610 | 1.00 | 121.29 |
| ATOM | 2468 | CA  | PHE | G | 468 | 112.277 | −131.939 | 123.518 | 1.00 | 119.38 |
| ATOM | 2469 | C   | PHE | G | 468 | 111.562 | −131.923 | 124.866 | 1.00 | 117.84 |
| ATOM | 2470 | O   | PHE | G | 468 | 111.904 | −132.687 | 125.768 | 1.00 | 118.28 |
| ATOM | 2471 | CB  | PHE | G | 468 | 112.360 | −133.382 | 123.005 | 1.00 | 119.43 |
| ATOM | 2472 | CG  | PHE | G | 468 | 112.625 | −133.488 | 121.533 | 1.00 | 119.45 |
| ATOM | 2473 | CD1 | PHE | G | 468 | 113.909 | −133.319 | 121.028 | 1.00 | 119.08 |
| ATOM | 2474 | CD2 | PHE | G | 468 | 111.584 | −133.738 | 120.645 | 1.00 | 119.65 |
| ATOM | 2475 | CE1 | PHE | G | 468 | 114.154 | −133.397 | 119.660 | 1.00 | 119.36 |
| ATOM | 2476 | CE2 | PHE | G | 468 | 111.818 | −133.817 | 119.274 | 1.00 | 119.82 |
| ATOM | 2477 | CZ  | PHE | G | 468 | 113.105 | −133.647 | 118.781 | 1.00 | 119.73 |
| ATOM | 2478 | N   | ARG | G | 469 | 110.564 | −131.053 | 124.991 | 1.00 | 115.90 |
| ATOM | 2479 | CA  | ARG | G | 469 | 109.789 | −130.924 | 126.224 | 1.00 | 113.44 |
| ATOM | 2480 | C   | ARG | G | 469 | 108.427 | −131.610 | 126.079 | 1.00 | 112.22 |
| ATOM | 2481 | O   | ARG | G | 469 | 107.896 | −131.719 | 124.975 | 1.00 | 112.65 |
| ATOM | 2482 | CB  | ARG | G | 469 | 109.598 | −129.441 | 126.557 | 1.00 | 113.09 |
| ATOM | 2483 | CG  | ARG | G | 469 | 110.898 | −128.670 | 126.770 | 1.00 | 111.90 |
| ATOM | 2484 | CD  | ARG | G | 469 | 110.656 | −127.167 | 126.817 | 1.00 | 111.27 |
| ATOM | 2485 | NE  | ARG | G | 469 | 111.891 | −126.413 | 127.024 | 1.00 | 110.94 |
| ATOM | 2486 | CZ  | ARG | G | 469 | 112.337 | −126.009 | 128.210 | 1.00 | 111.59 |
| ATOM | 2487 | NH1 | ARG | G | 469 | 111.650 | −126.282 | 129.311 | 1.00 | 111.63 |
| ATOM | 2488 | NH2 | ARG | G | 469 | 113.474 | −125.331 | 128.297 | 1.00 | 111.19 |
| ATOM | 2489 | N   | PRO | G | 470 | 107.846 | −132.080 | 127.196 | 1.00 | 110.32 |
| ATOM | 2490 | CA  | PRO | G | 470 | 106.544 | −132.757 | 127.180 | 1.00 | 109.56 |
| ATOM | 2491 | C   | PRO | G | 470 | 105.415 | −131.804 | 126.802 | 1.00 | 109.38 |
| ATOM | 2492 | O   | PRO | G | 470 | 105.184 | −130.810 | 127.487 | 1.00 | 109.40 |
| ATOM | 2493 | CB  | PRO | G | 470 | 106.404 | −133.268 | 128.615 | 1.00 | 108.27 |
| ATOM | 2494 | CG  | PRO | G | 470 | 107.830 | −133.391 | 129.083 | 1.00 | 109.61 |
| ATOM | 2495 | CD  | PRO | G | 470 | 108.422 | −132.120 | 128.547 | 1.00 | 110.06 |
| ATOM | 2496 | N   | GLY | G | 471 | 104.716 | −132.104 | 125.712 | 1.00 | 109.49 |

TABLE 2-continued

The structural coordinates of an exemplary gp120 with an extended V3 loop

| ATOM | 2497 | CA | GLY | G | 471 | 103.619 | −131.252 | 125.285 | 1.00 | 109.11 |
|---|---|---|---|---|---|---|---|---|---|---|
| ATOM | 2498 | C | GLY | G | 471 | 102.315 | −131.685 | 125.924 | 1.00 | 108.92 |
| ATOM | 2499 | O | GLY | G | 471 | 102.257 | −131.939 | 127.126 | 1.00 | 108.60 |
| ATOM | 2500 | N | GLY | G | 472 | 101.265 | −131.772 | 125.119 | 1.00 | 109.42 |
| ATOM | 2501 | CA | GLY | G | 472 | 99.979 | −132.193 | 125.638 | 1.00 | 110.45 |
| ATOM | 2502 | C | GLY | G | 472 | 99.070 | −131.040 | 126.004 | 1.00 | 111.45 |
| ATOM | 2503 | O | GLY | G | 472 | 99.502 | −129.891 | 126.097 | 1.00 | 111.96 |
| ATOM | 2504 | N | GLY | G | 473 | 97.796 | −131.351 | 126.209 | 1.00 | 111.01 |
| ATOM | 2505 | CA | GLY | G | 473 | 96.835 | −130.322 | 126.562 | 1.00 | 110.43 |
| ATOM | 2506 | C | GLY | G | 473 | 95.576 | −130.471 | 125.741 | 1.00 | 109.88 |
| ATOM | 2507 | O | GLY | G | 473 | 94.491 | −130.678 | 126.277 | 1.00 | 109.70 |
| ATOM | 2508 | N | ASP | G | 474 | 95.730 | −130.366 | 124.428 | 1.00 | 109.83 |
| ATOM | 2509 | CA | ASP | G | 474 | 94.608 | −130.513 | 123.516 | 1.00 | 110.37 |
| ATOM | 2510 | C | ASP | G | 474 | 94.250 | −131.993 | 123.454 | 1.00 | 110.43 |
| ATOM | 2511 | O | ASP | G | 474 | 95.003 | −132.796 | 122.907 | 1.00 | 110.70 |
| ATOM | 2512 | CB | ASP | G | 474 | 94.996 | −129.990 | 122.135 | 1.00 | 111.19 |
| ATOM | 2513 | CG | ASP | G | 474 | 93.885 | −130.137 | 121.121 | 1.00 | 111.06 |
| ATOM | 2514 | OD1 | ASP | G | 474 | 92.726 | −129.834 | 121.465 | 1.00 | 110.92 |
| ATOM | 2515 | OD2 | ASP | G | 474 | 94.180 | −130.541 | 119.977 | 1.00 | 111.81 |
| ATOM | 2516 | N | MET | G | 475 | 93.102 | −132.346 | 124.024 | 1.00 | 109.99 |
| ATOM | 2517 | CA | MET | G | 475 | 92.659 | −133.732 | 124.061 | 1.00 | 108.99 |
| ATOM | 2518 | C | MET | G | 475 | 92.325 | −134.343 | 122.706 | 1.00 | 108.30 |
| ATOM | 2519 | O | MET | G | 475 | 91.989 | −135.524 | 122.634 | 1.00 | 108.27 |
| ATOM | 2520 | CB | MET | G | 475 | 91.454 | −133.873 | 124.992 | 1.00 | 110.06 |
| ATOM | 2521 | CG | MET | G | 475 | 91.742 | −133.498 | 126.443 | 1.00 | 110.69 |
| ATOM | 2522 | SD | MET | G | 475 | 93.014 | −134.548 | 127.161 | 1.00 | 111.79 |
| ATOM | 2523 | CE | MET | G | 475 | 93.387 | −133.671 | 128.688 | 1.00 | 111.72 |
| ATOM | 2524 | N | ARG | G | 476 | 92.409 | −133.560 | 121.633 | 1.00 | 107.84 |
| ATOM | 2525 | CA | ARG | G | 476 | 92.113 | −134.093 | 120.302 | 1.00 | 107.39 |
| ATOM | 2526 | C | ARG | G | 476 | 93.218 | −135.060 | 119.904 | 1.00 | 105.79 |
| ATOM | 2527 | O | ARG | G | 476 | 92.979 | −136.056 | 119.224 | 1.00 | 105.68 |
| ATOM | 2528 | CB | ARG | G | 476 | 92.034 | −132.961 | 119.271 | 1.00 | 108.90 |
| ATOM | 2529 | CG | ARG | G | 476 | 90.927 | −131.951 | 119.512 | 1.00 | 110.95 |
| ATOM | 2530 | CD | ARG | G | 476 | 91.060 | −130.754 | 118.578 | 1.00 | 112.58 |
| ATOM | 2531 | NE | ARG | G | 476 | 90.086 | −129.707 | 118.883 | 1.00 | 114.24 |
| ATOM | 2532 | CZ | ARG | G | 476 | 90.079 | −128.499 | 118.323 | 1.00 | 115.25 |
| ATOM | 2533 | NH1 | ARG | G | 476 | 90.997 | −128.170 | 117.422 | 1.00 | 114.91 |
| ATOM | 2534 | NH2 | ARG | G | 476 | 89.151 | −127.616 | 118.668 | 1.00 | 115.36 |
| ATOM | 2535 | N | ASP | G | 477 | 94.430 | −134.748 | 120.345 | 1.00 | 103.73 |
| ATOM | 2536 | CA | ASP | G | 477 | 95.599 | −135.558 | 120.051 | 1.00 | 101.54 |
| ATOM | 2537 | C | ASP | G | 477 | 95.552 | −136.903 | 120.752 | 1.00 | 99.60 |
| ATOM | 2538 | O | ASP | G | 477 | 96.155 | −137.864 | 120.286 | 1.00 | 98.87 |
| ATOM | 2539 | CB | ASP | G | 477 | 96.863 | −134.813 | 120.473 | 1.00 | 103.36 |
| ATOM | 2540 | CG | ASP | G | 477 | 96.918 | −133.399 | 119.918 | 1.00 | 105.17 |
| ATOM | 2541 | OD1 | ASP | G | 477 | 96.905 | −133.252 | 118.680 | 1.00 | 105.96 |
| ATOM | 2542 | OD2 | ASP | G | 477 | 96.965 | −132.441 | 120.720 | 1.00 | 106.74 |
| ATOM | 2543 | N | ASN | G | 478 | 94.844 | −136.972 | 121.875 | 1.00 | 98.58 |
| ATOM | 2544 | CA | ASN | G | 478 | 94.741 | −138.220 | 122.628 | 1.00 | 98.61 |
| ATOM | 2545 | C | ASN | G | 478 | 93.974 | −139.286 | 121.862 | 1.00 | 99.30 |
| ATOM | 2546 | O | ASN | G | 478 | 94.303 | −140.468 | 121.926 | 1.00 | 99.94 |
| ATOM | 2547 | CB | ASN | G | 478 | 94.058 | −137.984 | 123.977 | 1.00 | 97.49 |
| ATOM | 2548 | CG | ASN | G | 478 | 94.911 | −137.180 | 124.928 | 1.00 | 96.81 |
| ATOM | 2549 | OD1 | ASN | G | 478 | 95.228 | −136.022 | 124.666 | 1.00 | 95.84 |
| ATOM | 2550 | ND2 | ASN | G | 478 | 95.289 | −137.792 | 126.044 | 1.00 | 97.25 |
| ATOM | 2551 | N | TRP | G | 479 | 92.945 | −138.861 | 121.141 | 1.00 | 99.87 |
| ATOM | 2552 | CA | TRP | G | 479 | 92.131 | −139.788 | 120.370 | 1.00 | 100.66 |
| ATOM | 2553 | C | TRP | G | 479 | 92.738 | −139.936 | 118.980 | 1.00 | 102.34 |
| ATOM | 2554 | O | TRP | G | 479 | 92.442 | −140.887 | 118.259 | 1.00 | 102.87 |
| ATOM | 2555 | CB | TRP | G | 479 | 90.692 | −139.267 | 120.263 | 1.00 | 98.97 |
| ATOM | 2556 | CG | TRP | G | 479 | 90.253 | −138.426 | 121.434 | 1.00 | 96.33 |
| ATOM | 2557 | CD1 | TRP | G | 479 | 89.768 | −137.150 | 121.384 | 1.00 | 94.67 |
| ATOM | 2558 | CD2 | TRP | G | 479 | 90.275 | −138.791 | 122.823 | 1.00 | 94.42 |
| ATOM | 2559 | NE1 | TRP | G | 479 | 89.491 | −136.696 | 122.651 | 1.00 | 92.78 |
| ATOM | 2560 | CE2 | TRP | G | 479 | 89.795 | −137.680 | 123.553 | 1.00 | 92.98 |
| ATOM | 2561 | CE3 | TRP | G | 479 | 90.660 | −139.944 | 123.520 | 1.00 | 93.84 |
| ATOM | 2562 | CZ2 | TRP | G | 479 | 89.681 | −137.691 | 124.948 | 1.00 | 92.68 |
| ATOM | 2563 | CZ3 | TRP | G | 479 | 90.547 | −139.954 | 124.910 | 1.00 | 93.85 |
| ATOM | 2564 | CH2 | TRP | G | 479 | 90.063 | −138.831 | 125.606 | 1.00 | 93.88 |
| ATOM | 2565 | N | ARG | G | 480 | 93.588 | −138.984 | 118.607 | 1.00 | 103.86 |
| ATOM | 2566 | CA | ARG | G | 480 | 94.246 | −139.015 | 117.304 | 1.00 | 105.08 |
| ATOM | 2567 | C | ARG | G | 480 | 95.281 | −140.125 | 117.271 | 1.00 | 105.26 |
| ATOM | 2568 | O | ARG | G | 480 | 95.594 | −140.668 | 116.215 | 1.00 | 105.84 |
| ATOM | 2569 | CB | ARG | G | 480 | 94.922 | −137.670 | 117.013 | 1.00 | 106.56 |
| ATOM | 2570 | CG | ARG | G | 480 | 94.125 | −136.768 | 116.090 | 1.00 | 107.60 |
| ATOM | 2571 | CD | ARG | G | 480 | 94.632 | −135.333 | 116.100 | 1.00 | 109.95 |
| ATOM | 2572 | NE | ARG | G | 480 | 93.740 | −134.452 | 115.346 | 1.00 | 114.38 |
| ATOM | 2573 | CZ | ARG | G | 480 | 93.766 | −133.122 | 115.392 | 1.00 | 117.10 |
| ATOM | 2574 | NH1 | ARG | G | 480 | 94.645 | −132.492 | 116.162 | 1.00 | 118.14 |

TABLE 2-continued

The structural coordinates of an exemplary gp120 with an extended V3 loop

| ATOM | 2575 | NH2 | ARG | G | 480 | 92.901 | −132.421 | 114.671 | 1.00 | 119.32 |
|------|------|-----|-----|---|-----|--------|----------|---------|------|--------|
| ATOM | 2576 | N | SER | G | 481 | 95.807 | −140.461 | 118.440 | 1.00 | 105.09 |
| ATOM | 2577 | CA | SER | G | 481 | 96.810 | −141.506 | 118.545 | 1.00 | 105.78 |
| ATOM | 2578 | C | SER | G | 481 | 96.169 | −142.872 | 118.346 | 1.00 | 106.98 |
| ATOM | 2579 | O | SER | G | 481 | 96.853 | −143.854 | 118.069 | 1.00 | 107.51 |
| ATOM | 2580 | CB | SER | G | 481 | 97.483 | −141.448 | 119.918 | 1.00 | 105.86 |
| ATOM | 2581 | OG | SER | G | 481 | 96.531 | −141.636 | 120.949 | 1.00 | 102.63 |
| ATOM | 2582 | N | GLU | G | 482 | 94.850 | −142.925 | 118.487 | 1.00 | 108.44 |
| ATOM | 2583 | CA | GLU | G | 482 | 94.112 | −144.173 | 118.341 | 1.00 | 110.31 |
| ATOM | 2584 | C | GLU | G | 482 | 93.359 | −144.249 | 117.016 | 1.00 | 111.16 |
| ATOM | 2585 | O | GLU | G | 482 | 93.213 | −145.324 | 116.438 | 1.00 | 111.61 |
| ATOM | 2586 | CB | GLU | G | 482 | 93.123 | −144.327 | 119.501 | 1.00 | 110.81 |
| ATOM | 2587 | CG | GLU | G | 482 | 93.759 | −144.254 | 120.883 | 1.00 | 110.72 |
| ATOM | 2588 | CD | GLU | G | 482 | 94.577 | −145.485 | 121.225 | 1.00 | 110.51 |
| ATOM | 2589 | OE1 | GLU | G | 482 | 93.977 | −146.563 | 121.425 | 1.00 | 109.50 |
| ATOM | 2590 | OE2 | GLU | G | 482 | 95.819 | −145.375 | 121.292 | 1.00 | 110.56 |
| ATOM | 2591 | N | LEU | G | 483 | 92.883 | −143.103 | 116.540 | 1.00 | 111.84 |
| ATOM | 2592 | CA | LEU | G | 483 | 92.130 | −143.046 | 115.294 | 1.00 | 112.60 |
| ATOM | 2593 | C | LEU | G | 483 | 92.979 | −142.608 | 114.107 | 1.00 | 113.68 |
| ATOM | 2594 | O | LEU | G | 483 | 92.449 | −142.122 | 113.108 | 1.00 | 114.27 |
| ATOM | 2595 | CB | LEU | G | 483 | 90.949 | −142.083 | 115.440 | 1.00 | 112.17 |
| ATOM | 2596 | CG | LEU | G | 483 | 89.872 | −142.442 | 116.469 | 1.00 | 111.13 |
| ATOM | 2597 | CD1 | LEU | G | 483 | 88.927 | −141.266 | 116.650 | 1.00 | 110.76 |
| ATOM | 2598 | CD2 | LEU | G | 483 | 89.115 | −143.677 | 116.003 | 1.00 | 111.73 |
| ATOM | 2599 | N | TYR | G | 484 | 94.292 | −142.782 | 114.206 | 1.00 | 114.79 |
| ATOM | 2600 | CA | TYR | G | 484 | 95.186 | −142.383 | 113.125 | 1.00 | 115.54 |
| ATOM | 2601 | C | TYR | G | 484 | 95.019 | −143.284 | 111.912 | 1.00 | 115.88 |
| ATOM | 2602 | O | TYR | G | 484 | 95.102 | −142.827 | 110.774 | 1.00 | 115.90 |
| ATOM | 2603 | CB | TYR | G | 484 | 96.644 | −142.409 | 113.602 | 1.00 | 115.90 |
| ATOM | 2604 | CG | TYR | G | 484 | 97.250 | −143.791 | 113.733 | 1.00 | 116.80 |
| ATOM | 2605 | CD1 | TYR | G | 484 | 98.038 | −144.328 | 112.714 | 1.00 | 116.77 |
| ATOM | 2606 | CD2 | TYR | G | 484 | 97.042 | −144.560 | 114.878 | 1.00 | 118.01 |
| ATOM | 2607 | CE1 | TYR | G | 484 | 98.608 | −145.597 | 112.836 | 1.00 | 117.84 |
| ATOM | 2608 | CE2 | TYR | G | 484 | 97.606 | −145.828 | 115.008 | 1.00 | 118.60 |
| ATOM | 2609 | CZ | TYR | G | 484 | 98.388 | −146.339 | 113.985 | 1.00 | 118.39 |
| ATOM | 2610 | OH | TYR | G | 484 | 98.956 | −147.587 | 114.115 | 1.00 | 118.31 |
| ATOM | 2611 | N | LYS | G | 485 | 94.780 | −144.566 | 112.160 | 1.00 | 116.57 |
| ATOM | 2612 | CA | LYS | G | 485 | 94.606 | −145.525 | 111.082 | 1.00 | 117.94 |
| ATOM | 2613 | C | LYS | G | 485 | 93.136 | −145.765 | 110.752 | 1.00 | 119.33 |
| ATOM | 2614 | O | LYS | G | 485 | 92.749 | −146.883 | 110.413 | 1.00 | 119.55 |
| ATOM | 2615 | CB | LYS | G | 485 | 95.282 | −146.851 | 111.451 | 1.00 | 116.62 |
| ATOM | 2616 | CG | LYS | G | 485 | 94.855 | −147.425 | 112.794 | 1.00 | 114.79 |
| ATOM | 2617 | CD | LYS | G | 485 | 95.577 | −148.736 | 113.075 | 1.00 | 113.85 |
| ATOM | 2618 | CE | LYS | G | 485 | 95.207 | −149.299 | 114.438 | 1.00 | 112.32 |
| ATOM | 2619 | NZ | LYS | G | 485 | 95.894 | −150.593 | 114.708 | 1.00 | 112.53 |
| ATOM | 2620 | N | TYR | G | 486 | 92.321 | −144.718 | 110.849 | 1.00 | 121.24 |
| ATOM | 2621 | CA | TYR | G | 486 | 90.895 | −144.831 | 110.549 | 1.00 | 123.65 |
| ATOM | 2622 | C | TYR | G | 486 | 90.356 | −143.638 | 109.763 | 1.00 | 125.80 |
| ATOM | 2623 | O | TYR | G | 486 | 90.761 | −142.499 | 109.986 | 1.00 | 126.52 |
| ATOM | 2624 | CB | TYR | G | 486 | 90.077 | −144.979 | 111.836 | 1.00 | 122.26 |
| ATOM | 2625 | CG | TYR | G | 486 | 90.279 | −146.286 | 112.559 | 1.00 | 120.89 |
| ATOM | 2626 | CD1 | TYR | G | 486 | 91.272 | −146.426 | 113.527 | 1.00 | 120.39 |
| ATOM | 2627 | CD2 | TYR | G | 486 | 89.478 | −147.389 | 112.271 | 1.00 | 120.13 |
| ATOM | 2628 | CE1 | TYR | G | 486 | 91.461 | −147.636 | 114.192 | 1.00 | 119.39 |
| ATOM | 2629 | CE2 | TYR | G | 486 | 89.660 | −148.600 | 112.927 | 1.00 | 119.78 |
| ATOM | 2630 | CZ | TYR | G | 486 | 90.651 | −148.717 | 113.885 | 1.00 | 119.20 |
| ATOM | 2631 | OH | TYR | G | 486 | 90.829 | −149.916 | 114.531 | 1.00 | 118.81 |
| ATOM | 2632 | N | LYS | G | 487 | 89.433 | −143.912 | 108.848 | 1.00 | 127.78 |
| ATOM | 2633 | CA | LYS | G | 487 | 88.820 | −142.869 | 108.041 | 1.00 | 129.98 |
| ATOM | 2634 | C | LYS | G | 487 | 87.421 | −143.315 | 107.641 | 1.00 | 131.14 |
| ATOM | 2635 | O | LYS | G | 487 | 87.261 | −144.328 | 106.959 | 1.00 | 131.65 |
| ATOM | 2636 | CB | LYS | G | 487 | 89.660 | −142.592 | 106.786 | 1.00 | 130.89 |
| ATOM | 2637 | CG | LYS | G | 487 | 89.250 | −141.325 | 106.044 | 1.00 | 132.86 |
| ATOM | 2638 | CD | LYS | G | 487 | 90.086 | −141.091 | 104.791 | 1.00 | 134.47 |
| ATOM | 2639 | CE | LYS | G | 487 | 89.712 | −139.769 | 104.131 | 1.00 | 134.86 |
| ATOM | 2640 | NZ | LYS | G | 487 | 90.540 | −139.468 | 102.931 | 1.00 | 133.70 |
| ATOM | 2641 | N | VAL | G | 488 | 86.408 | −142.571 | 108.072 | 1.00 | 132.54 |
| ATOM | 2642 | CA | VAL | G | 488 | 85.031 | −142.915 | 107.737 | 1.00 | 134.39 |
| ATOM | 2643 | C | VAL | G | 488 | 84.808 | −142.655 | 106.245 | 1.00 | 135.42 |
| ATOM | 2644 | O | VAL | G | 488 | 85.382 | −141.719 | 105.682 | 1.00 | 135.33 |
| ATOM | 2645 | CB | VAL | G | 488 | 84.047 | −142.072 | 108.571 | 1.00 | 134.46 |
| ATOM | 2646 | CG1 | VAL | G | 488 | 84.146 | −140.608 | 108.170 | 1.00 | 134.65 |
| ATOM | 2647 | CG2 | VAL | G | 488 | 82.638 | −142.599 | 108.401 | 1.00 | 134.22 |
| ATOM | 2648 | N | VAL | G | 489 | 83.982 | −143.470 | 105.600 | 1.00 | 137.04 |
| ATOM | 2649 | CA | VAL | G | 489 | 83.762 | −143.293 | 104.173 | 1.00 | 139.05 |
| ATOM | 2650 | C | VAL | G | 489 | 82.330 | −143.585 | 103.707 | 1.00 | 140.08 |
| ATOM | 2651 | O | VAL | G | 489 | 81.606 | −144.357 | 104.338 | 1.00 | 140.02 |
| ATOM | 2652 | CB | VAL | G | 489 | 84.732 | −144.207 | 103.383 | 1.00 | 139.34 |

TABLE 2-continued

The structural coordinates of an exemplary gp120 with an extended V3 loop

| ATOM | 2653 | CG1 | VAL | G | 489 | 83.998 | −145.432 | 102.860 | 1.00 | 140.18 |
|---|---|---|---|---|---|---|---|---|---|---|
| ATOM | 2654 | CG2 | VAL | G | 489 | 85.385 | −143.422 | 102.267 | 1.00 | 139.74 |
| ATOM | 2655 | N | LYS | G | 490 | 81.934 | −142.966 | 102.597 | 1.00 | 142.79 |
| ATOM | 2656 | CA | LYS | G | 490 | 80.607 | −143.179 | 102.032 | 1.00 | 145.45 |
| ATOM | 2657 | C | LYS | G | 490 | 80.669 | −144.502 | 101.281 | 1.00 | 147.18 |
| ATOM | 2658 | O | LYS | G | 490 | 81.655 | −144.786 | 100.598 | 1.00 | 146.18 |
| ATOM | 2659 | CB | LYS | G | 490 | 80.247 | −142.036 | 101.070 | 1.00 | 145.83 |
| ATOM | 2660 | CG | LYS | G | 490 | 78.752 | −141.852 | 100.807 | 1.00 | 146.99 |
| ATOM | 2661 | CD | LYS | G | 490 | 78.501 | −140.629 | 99.928 | 1.00 | 148.09 |
| ATOM | 2662 | CE | LYS | G | 490 | 77.034 | −140.213 | 99.934 | 1.00 | 148.60 |
| ATOM | 2663 | NZ | LYS | G | 490 | 76.795 | −138.971 | 99.143 | 1.00 | 149.62 |
| ATOM | 2664 | N | ILE | G | 491 | 79.626 | −145.312 | 101.399 | 1.00 | 149.88 |
| ATOM | 2665 | CA | ILE | G | 491 | 79.617 | −146.604 | 100.731 | 1.00 | 153.14 |
| ATOM | 2666 | C | ILE | G | 491 | 79.546 | −146.484 | 99.202 | 1.00 | 154.50 |
| ATOM | 2667 | O | ILE | G | 491 | 78.688 | −147.084 | 98.550 | 1.00 | 154.54 |
| ATOM | 2668 | CB | ILE | G | 491 | 78.451 | −147.475 | 101.262 | 1.00 | 153.49 |
| ATOM | 2669 | CG1 | ILE | G | 491 | 78.722 | −148.946 | 100.955 | 1.00 | 154.55 |
| ATOM | 2670 | CG2 | ILE | G | 491 | 77.126 | −147.000 | 100.685 | 1.00 | 153.61 |
| ATOM | 2671 | CD1 | ILE | G | 491 | 79.857 | −149.529 | 101.778 | 1.00 | 154.67 |
| ATOM | 2672 | N | GLU | G | 492 | 80.465 | −145.699 | 98.645 | 1.00 | 156.47 |
| ATOM | 2673 | CA | GLU | G | 492 | 80.561 | −145.474 | 97.201 | 1.00 | 158.38 |
| ATOM | 2674 | C | GLU | G | 492 | 81.994 | −145.101 | 96.827 | 1.00 | 159.02 |
| ATOM | 2675 | O | GLU | G | 492 | 82.890 | −145.919 | 97.028 | 1.00 | 158.59 |
| ATOM | 2676 | CB | GLU | G | 492 | 79.624 | −144.345 | 96.762 | 1.00 | 159.61 |
| ATOM | 2677 | CG | GLU | G | 492 | 78.521 | −144.781 | 95.808 | 1.00 | 162.25 |
| ATOM | 2678 | CD | GLU | G | 492 | 77.654 | −143.621 | 95.352 | 1.00 | 162.67 |
| ATOM | 2679 | OE1 | GLU | G | 492 | 78.173 | −142.729 | 94.645 | 1.00 | 163.05 |
| ATOM | 2680 | OE2 | GLU | G | 492 | 76.455 | −143.599 | 95.704 | 1.00 | 162.15 |
| ATOM | 2681 | OXT | GLU | G | 492 | 82.208 | −143.994 | 96.336 | 1.00 | 158.19 |
| TER | 2682 | | GLU | G | 492 | | | | | |
| END | | | | | | | | | | |

The present disclosure also provides for a machine-readable data storage medium which comprises a data storage material encoded with machine readable data defined by the structure coordinates of a stabilized gp120 polypeptide or gp120 polypeptide with an extended V3 loop as define in Table 1 or Table 2 respectively, or a subset thereof, such as at least about 5, such at least about 10, at least about 20, at least about 30, at least at least about 40, at least about 50, at least about 60, at least about 70, at least about 80, at least about 90, at least about 100, at least about 150, at least about 200, at least about 250, at least about 300, at least about 350, at least about 400, at least about 450, at least about 500 or more atoms of the structure, such as defined by the coordinates of Table 1 or Table 2.

Those of skill in the art will understand that a set of structure coordinates for a gp120 polypeptide, for example a stabilized gp120 polypeptide, a gp120 polypeptide with an extended V3 loop, or a portion thereof, is a relative set of points that define a shape in three dimensions. Thus, it is possible that an entirely different set of coordinates could define a similar or identical shape. Moreover, slight variations in the individual coordinates will have little effect on overall shape. The variations in coordinates discussed above may be generated because of mathematical manipulations of the structure coordinates. For example, the structure coordinates set forth in Table 1 or Table 2, or a portion thereof could be manipulated by crystallographic permutations of the structure coordinates, fractionalization of the structure coordinates; integer additions or subtractions to sets of the structure coordinates, deletion of a portion of the coordinates, inversion of the structure coordinates, or any combination of the above.

This disclosure further provides systems, such as computer systems, intended to generate structures and/or perform rational drug or compound design for an antigenic compound capable of eliciting an immune response in a subject. The system can contain one or more or all of: atomic co-ordinate data according to Table 1, Table 2, or a subset thereof and the Figures derived therefrom by homology modeling, the data defining the three-dimensional structure of a gp120 or at least one sub-domain thereof, or structure factor data for gp120, the structure factor data being derivable from the atomic co-ordinate data of Table 1 or Table 2 or a subset thereof and the Figures. This disclosure also involves computer readable media with: atomic co-ordinate data according to Table 1, Table 2 or a subset thereof and/or the Figures or derived therefrom by homology modeling, the data defining the three-dimensional structure of a gp120 or at least one sub-domain thereof; or structure factor data for a gp120, the structure factor data being derivable from the atomic co-ordinate data of Table 1, Table 2, or a subset thereof and/or the Figures. By providing such computer readable media, the atomic co-ordinate data can be routinely accessed to the gp120 or a sub-domain thereof. For example RASMOL (Sayle et al., TIBS vol. 20 (1995), 374) is a publicly available software package which allows access and analysis of atomic co-ordinate data for structural determination and/or rational drug design. Structure factor data, which are derivable from atomic co-ordinate data (see, for example, Blundell et al., in *Protein Crystallography*, Academic Press, NY, London and San Francisco (1976)), are particularly useful for calculating electron density maps, for example, difference Fourier electron density maps. Thus, there are additional uses for the computer readable media and/or computer systems and/or atomic co-ordinate data and additional reasons to provide them to users.

VIII. Identification of Immunogens

The crystals of this disclosure and particularly the atomic structure coordinates obtained from these crystals are particularly useful for identifying compounds elicit neutralizing antibodies, for example CD4BS and CD4i antibodies. The compounds identified are useful in eliciting antibodies to gp120, such as antibodies to lentivirus, such as SIV, or HIV, for example HIV-1 or HIV-2.

The crystal structure of a stabilized form of gp120 or a gp120 with the V3 loop in the extended conformation allows a novel approach for drug or compound discovery, identification, and design of compounds that mimic the antigenic surfaces of gp120 that bind neutralizing antibodies. Such compound can be useful as immunogens to illicit an immune response to HIV when administered to a subject, for example by eliciting anti-HIV antibodies, such as neutralizing antibodies, for example CD4BD or CD4i antibodies. Compounds that elicit anti-HIV antibodies are useful in diagnosis, treatment, or prevention of HIV-1 in a subject in need thereof.

The disclosure provides a computer-based method of rational drug, compound design, or identification which comprises: providing the structure of a stabilized form of gp120 (for example as defined by the coordinates or a subset of the coordinates in Table 1 and/or in the Figures) or a gp120 with the V3 loop in the extended conformation (for example as defined by the coordinates or subset of the coordinates in Table 2 and/or in the Figures); providing a structure of a candidate compound; and fitting the structure of the candidate compound to the structure of the stabilized form of gp120 (for example as defined by the coordinates or a subset of the coordinates in Table 1 and/or in the Figures) or the gp120 with the V3 loop in the extended conformation (for example as defined by the coordinates or a subset of the coordinates in Table 2 and/or in the Figures.

In certain embodiments, the coordinates of atoms of interest of the stabilized form of gp120 or the gp120 with the V3 loop in the extended conformation in the vicinity of the antigenic surface are used to model the antigenic surface to which as antibody binds, such as a neutralizing antibody, for example a CD4i or CD4BS antibody. These coordinates may be used to define a space which is then screened "in silico" against a candidate compound. Thus, the disclosure provides a computer-based method of rational drug or compound design or identification which comprises: providing the coordinates of at least two atoms of Table 1 or Table 2; providing the structure of a candidate compound; and fitting the structure of the candidate to the coordinates of at least two atoms of Table 1 or Table 2.

In practice, it may be desirable to model a sufficient number of atoms of the stabilized form of gp120 or the gp120 with the V3 loop in the extended conformation as defined by the coordinates of Table 1 or Table 2 which represent the active site or binding region. Thus, there can be provided the coordinates of at least about 5, such at least about 10, at least about 20, at least about 30, at least at least about 40, at least about 50, at least about 60, at least about 70, at least about 80, at least about 90, at least about 100, at least about 150, at least about 200, at least about 250, at least about 300, at least about 350, at least about 400, at least about 450, or at least about 500 atoms of the structure.

The methods disclosed herein can employ a sub-domain, region, or fragment of interest of the stabilized form of gp120 or the gp120 with the extended V3 loop which is in the vicinity of the antigenic surface, and providing a computer-based method for identifying or rationally designing a compound or drug, such as an immunogen which includes: providing the coordinates of at least a sub-domain, region, or fragment of the stabilized form of gp120 or the gp120 with the extended V3 loop; providing the structure of a candidate compound that mimics the antigenic surface of the gp120 with the extended V3 loop; and fitting the structure of the candidate compound to the coordinates of the stabilized form of gp120 or the gp120 with the extended V3 loop sub-domain, region, or fragment provided. A "sub-domain", "region", or "fragment" can mean at least one, for example, one, two, three, four, or more, element(s) of secondary structure of particular regions of the stabilized form of gp120 or the gp120 with the extended V3 loop gp120 with the extended V3 loop, and includes those set forth in Table 1 and Table 2.

These methods can optionally include synthesizing the candidate compound, (such as an immunogen) and/or administering the candidate compound to an animal capable of eliciting antibodies and testing whether the candidate compound elicits anti-HIV antibodies. Compounds which elicit anti-HIV antibodies are useful for diagnostic purposes, as well as for immunogenic, immunological or even vaccine compositions, as well as pharmaceutical compositions.

In some embodiments, the candidate compound is designed from the gp120 amino acid sequence, for example an amino acid sequence is assembled to provide a candidate compound, for example by synthesizing the amino acid sequence or producing a nucleic acid encoding the candidate compound.

The step of providing the structure of a candidate compound may involve selecting the candidate compound by computationally screening a database of compounds for surface similarity with an epitope on the stabilized form of gp120 or the gp120 with the extended V3 loop. For example, a 3-D descriptor for the candidate compound may be derived, the descriptor including geometric and functional constraints derived from the architecture and chemical nature of the epitope. The descriptor may then be used to interrogate the compound database, a candidate compound being a compound that has a good match to the features of the descriptor. In effect, the descriptor can be a type of virtual pharmacophore.

The determination of the three-dimensional structure of the gp120 with the extended V3 loop provides a basis for the design of new and specific compounds that are useful for eliciting an immune response. For example, from knowing the three-dimensional structure the stabilized form of gp120 or the gp120 with the extended V3 loop, computer modeling programs may be used to design or identify different molecules expected to interact with possible or confirmed active sites such as binding sites or other structural or functional features of neutralizing antibodies.

By way of example, a compound that potentially mimics the antigenic surface of the stabilized form of gp120 or the gp120 with the extended V3 loop can be examined through the use of computer modeling using a docking program such as GRAM, DOCK or AUTODOCK (see for example, Walters et al. *Drug Discovery Today,* 3(4):160-178, 1998; Dunbrack et al. *Folding and Design* 2:27-42, 1997). This procedure can include computer fitting of potential immunogens to ascertain how well the shape and the chemical structure of the potential binder will mimic the antigenic surface. Various other computer programs such as AMBER or CHARM may be used to further refine the dynamic and electrostatic characteristics of a candidate compound. Programs such as GRID (Goodford, *J. Med. Chem,* 28:849-57, 1985) may also be used to analyze the antigenic surfaces to predict immunogenic compounds. Alternatively, computer-assisted, manual examination can be used to predict immunogenic compounds from antigenic surfaces.

IX. Stabilized gp120 Polypeptides as Crystallization Tools

One problem with the formation of crystals containing wild-type gp120 is that conformationally variable molecules are not amenable to crystallization. For an ordered crystal to form the molecules forming the crystal must be essential locked in place. Molecules that are unstable or "floppy" such as wild-type gp120 must overcome large entropic ($\Delta S$) costs to form a crystal lattice. By using conformationally stabilized forms of gp120 this entropic cost of becoming ordered is lessened and crystals form more easily. Those skilled in the art can take advantage of this by crystallizing their complex of interest with a stabilized form of gp120. For example, stabilized forms of gp120 can be used to crystallize previously uncrystallizable broadly neutralizing antibodies. In one embodiment, the broadly neutralizing antibody does not induce conformational stabilization as measured by $-T\Delta S$ of less than 28 kcal/mol upon antibody binding to gp120. The use of broadly neutralizing antibodies is disclosed, for example, in Burton, Nature Re. 2:706-713, 2002, herein incorporated by reference. One example of how this can be accomplished is by forming complexes of a stabilized form of gp120 and the antibody of interest in the presence of CD4.

The following examples are provided to illustrate certain particular features and/or embodiments. These examples should not be construed to limit the invention to the particular features or embodiments described.

EXAMPLES

Example 1

Structure-Assisted Stabilization of gp120 in its CD4-Bound Conformation

This example describes the methods used to design stabilized forms of gp120 disclosed herein.

Thermodynamic analysis showed that the conformation of gp120 prior to CD4 binding was highly flexible (Myszka et al., *Proc Natl Acad Sci USA.* 97(16):9026-31, 2000). The CD4-bound state of gp120 consists of an inner domain (containing the N and C termini), an outer domain, and a four-stranded bridging sheet minidomain. Two-thirds of the CD4 contact surface is with the outer domain, the remaining one-third with the bridging sheet. In the unliganded state, the inner domain is radically altered, with most of its secondary structural elements repositioned. The bridging sheet is pulled apart with the two β-hairpins of the sheet separated by 20 Å. The outer domain, by contrast, remains virtually unchanged.

An initial series of mutants was constructed and analyzed. Initial antigenic analysis suggested that a single mutation, 375 S to W, was able to partially stabilize gp120 in the CD4-bound state. Thermodynamic analysis (ITC) confirmed this result, showing that the entropy ($-T\Delta S$) of gp120 binding to CD4 had reduced from 40 kcal/mol to roughly 25 kcal/mol (Xiang et al., *J Virol.* 76(19):9888-99, 2002).

To further reduce the entropy of CD4 binding to a range typical of antibody recognition (5-10 kcal/mol), precise characterization was used to confirm the mutational stabilization of conformation including: (1) crystallographic determination of the gp120 mutant structure (2) isothermotitration calorimetric analysis of the entropy of CD4 binding, and (3) precise surface-plasmon resonance analysis of the on/off rates of antibodies to the modified gp120 glycoproteins. This design cycle is shown in FIG. 1. Initial isothermotitration calorimetry demonstrated that cavity-filling mutants, such as 375 S to W, did not significantly reduce the entropy of CD4 gp120 binding in the context of core HXBc2.

Figure 2:
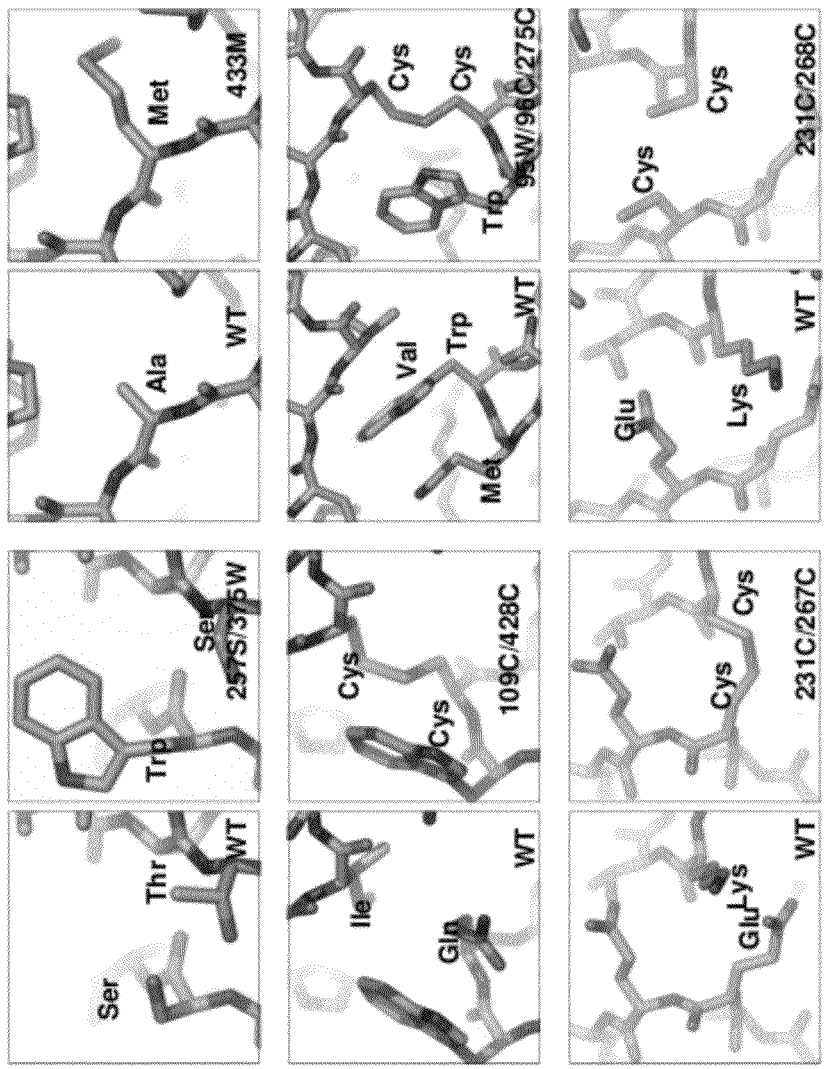
FIG. 2 is a set of computer generated images. The images show the modeled structures of wild-type gp120 compared with cavity-filling and double cysteine mutants. Each pair of panels shows the HXBc2 core wild-type structure (left panels) and the mutant structure (right panels). Data ranged from minimum Bragg spacings of 1.9 A to 2.5 A.
Figure 3:
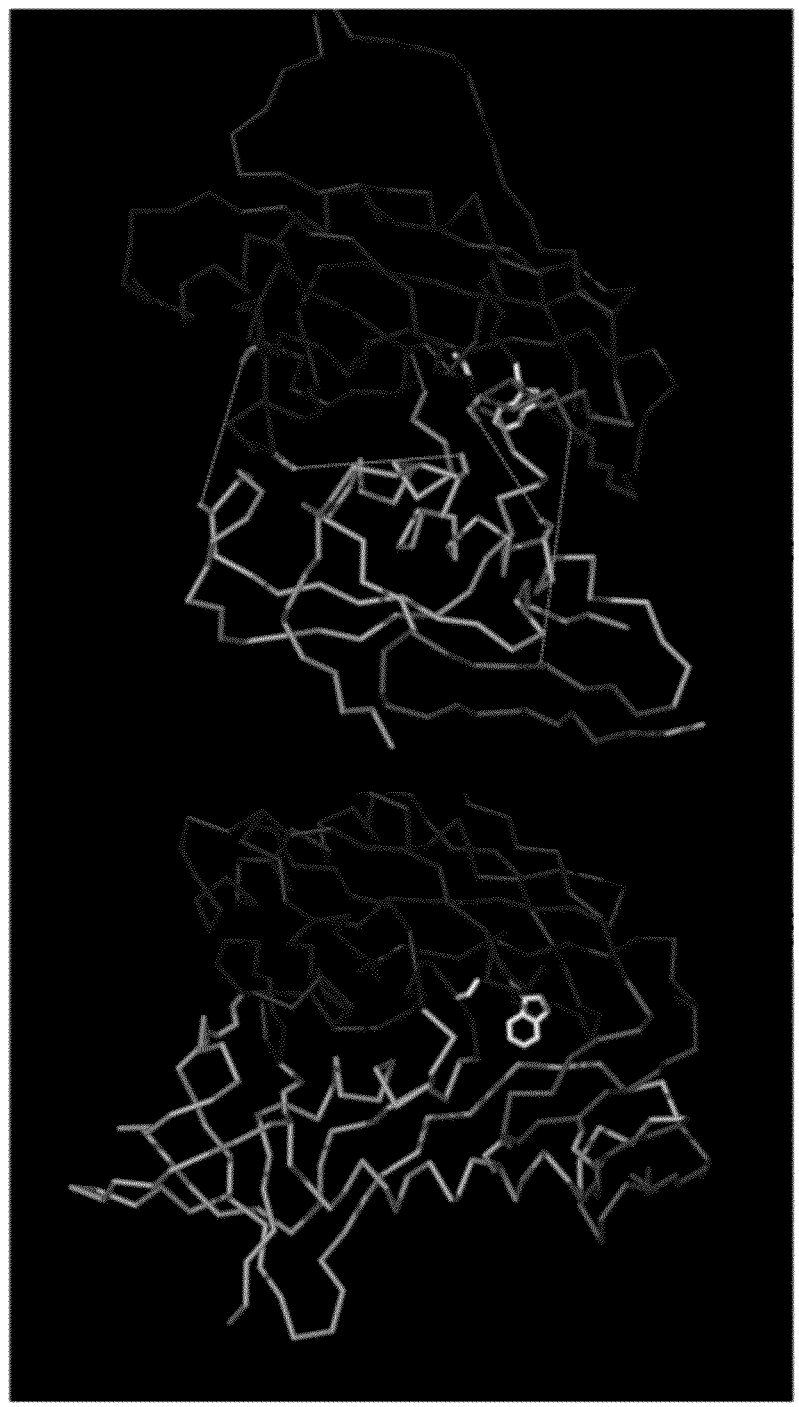
FIG. 3 is a set of computer generated images. The images show the positions of conformationally st represent the surface of gp120 and V3 color-coded according to the properties of the underlying atoms. Column 2 shows the molecular surface colored according to the sequence variability of the underlying amino acids for Clade B, with variable regions in purple and conserved regions in white. Columns 3 and 4 show the mutational effect of varying amino acids on CCR5 binding (column 3) or on the binding of sulfated CCR5 Nterminal peptides (column 4). Black defines surfaces that were not tested, yellow regions that when altered do not affect binding, and green areas where alterations significantly affect binding. Column 5 depicts the electrostatic potential at the solvent accessible surface, with blue showing electropositive, red electronegative, and white apolar. Column 6 depicts the gp120 surface with modeled N-linked glycans [(Nacetylglucosamine) 2(mannose)3 cores] in orange-yellow, with the 301 glycan highlighted in purple. The molecular surface corresponding to positions "11" and "25", suggested to be important in distinguishing between CXCR4 and CCR5, are highlighted, as well as residue 440 which sequence analysis indicates is also of some significance in this regard.

Additional cavity-filling mutations and five different disulfides were modeled. The cavity-filling mutants increased hydrophobic interactions at domain interfaces. The disulfides either tied together the inner domain, outer domain and bridging sheet, or were internal to the bridging sheet. Crystallographic analysis on five of these disulfides showed that four of them formed disulfide bonds. Two of these showed minimal perturbation in structure: 96-275 which tied together the inner and outer domain, 109-428 which tied together the bridging sheet and outer domain. The 231-267 disulfide, which tied together the inner domain and outer domain and the 123-431 disulfide, which tied together two strands of the bridging sheet, both showed local perturbations of structure. The potential disulfide formed by mutating 231 to C and 268 to C did not form (FIG. 2). The recently solved crystal structure of the unliganded gp120 core from SIV (Chen et al, Structure, 13(2):197-211, 2005) allowed the position of each disulfide to be modeled in the unliganded structure (FIG. 3). This mapping showed that even a single disulfide would be incompatible with the conformation of the unliganded gp120 seen in the SIV crystal structure (Table 3).

TABLE 3

Relative disulfide distances in the CD4-bound conformation and in the unliganded SIV conformation.

| Category Category | HIV Mutation HIV Mutation | SIV Equivalent SIV Equivalent | Cα-Cα Distance (Å) HIV | Cα-Cα Distance (Å) SIV |
|---|---|---|---|---|
| S-S | 96-275 | 78-290 | 6.4 | 21.9 |
| S-S | 109-428 | 91-441 | 6.1 | 16.2 |
| S-S | 123-431 | 105-444 | 4.4 | 23.5 |
| S-S | 231-267 | 245-282 | 6.0 | 16.8 |
| Cavity | 257/375 | 271/391 | 5.2 | 5.6 |

In the core context, each single inter-domain disulfide reduced the entropy of CD4 interaction by roughly 10 kcal/mol, as measured by isothermotitration calorimetry (ITC). Combinations of disulfides were tested. Two disulfide combinations showed similar antigenic phenotypes suggesting a partially stabilized gp120 conformation; ITC analysis for several of the different two disulfide combinations showed the entropy of CD4 interaction was reduced by roughly 20 kcal/mol. Combinations of three and four disulfides were also tested, although most of these only expressed poorly, perhaps due to complications of folding so many cysteines into the correct disulfide bonds. Removal of additional core disulfide (such as the second conserved disulfide in the V1/V2 region) and stabilization of the V3 region may enhance folding. A summary of the qualitative Biacore and ITC results for 17 mutants is shown in Table 4.

TABLE 4

| Qualitative BIACORE on Supernatant and ITC results | | | | | | | | | | | | | | | | | | | |
|---|---|---|---|---|---|---|---|---|---|---|---|---|---|---|---|---|---|---|---|
| Mutant | Mutant location | | | | | | | CD4/CD4i | | | CD4BS | | | | | | | | DSC/$T_M$ |
| Name | C2 | C3 | C1S1 | S2 | S3 | S4 | S5 | CD4 | 17B | M6 | b12 | F105 | F91 | 15e | m14 | m18 | SS folding | °C. |
| WT core* | | | | | | | | A | A | A | AA | AA | AA | AA | AA | AA | 0 FFFF | 50.6 |
| 2a* | x | | | | | | | AAA | AA | AA | AA | N | N | A/N | A/N | AA | 0 FFFF | 50.6 |

TABLE 4-continued

Qualitative BIACORE on Supernatant and ITC results

| Mutant Name | \multicolumn{7}{c}{Mutant location} | \multicolumn{3}{c}{CD4/CD4i} | \multicolumn{7}{c}{CD4BS} | SS | folding | DSC/$T_M$ °C. |
|---|---|---|---|---|---|---|---|---|---|---|---|---|---|---|---|---|---|---|---|
| | C2 | C3 | C1S1 | S2 | S3 | S4 | S5 | CD4 | 17B | M6 | b12 | F105 | F91 | 15e | m14 | m18 | | | |
| 4-0* | x | | | | | | x | AAA | AA | AA | AA | N | N | A/N | A/N | AA | 0 | FFFF | 55.7 |
| 4a* | x | | | x | | | | A | A | nd | A/N | N | N | N | N | A | 1 | FFF | 53.8 |
| 4b* | x | | | | | x | | A | A | nd | AA | N | A/N | N | N | AA | 1 | FFF | 56.4 |
| 4c* | x | | | X | | | | A | A | nd | A | N | N | N | N | AA | 1 | FFF | |
| 5mut | x | | x | | | | | A | A | nd | A | N | N | N | N | AA | 1 | FFF | |
| 6a* | x | x | x | | | | | A | A | nd | AA | N | A | N | N | AA | 1 | FFF | |
| 6b | x | | | x | | x | | AA | A | nd | N | N | N | N | N | N | 2 | FFF | 59.0 |
| 8a | x | x | x | | | x | | AA | A | nd | A | N | N | N | N | AA | 2 | F | |
| 8b* | x | x | x | x | | | | AA | A | nd | A | N | N | N | N | A/N | 2 | FF | |
| 9a | x | x | | x | X | x | | A | N | N | A/N | N | N | N | N | N | 3 | F/N | |
| 8c | x | | | x | X | x | | A | A | A | A/N | N | N | N | N | N | 3 | F/N | |
| 10a | x | x | x | x | | x | | N | N | nd | N | N | N | N | N | N | 3 | N | |
| 9b | x | | x | | X | x | | A | A | A | A/N | N | N | N | N | AA | 3 | F/N | |
| 10c | x | x | x | | X | x | | A | N | N | A/N | N | N | N | N | AA | 3 | F/N | |
| 9c* | x | | x | x | X | | | AA | AA | AAA | A | N | N | N | N | A/N | 3 | F | |
| 10b | x | x | x | x | X | | | A | A | A/N | A | N | N | N | N | A/N | 3 | F/N | |
| 11a | x | | x | x | X | x | | A | A | A | A | N | N | N | N | N | 4 | F/N | |

Note:
Cavity-filling mutants: C1: M95W, C2: T257S/S375W; C3: A433M;
Disulfide bond mutants: S1: W96C/V275C; S2: I109C/Q428C; S3: T123C/G431C; S4: K231C/E267C; S5: K231C/E268C Qualitative Biacore analysis and ITC of conformationally stabilized mutants. Biacore analyses were carried out on transfected cell supernatants or with purified protein at 10 ug/ml. Yellow rows represent mutants with structures determined by X-ray crystallography. "A" indicates binding, "F" indicates folding, and "N" indicates no binding or folding. The mutants are indicated with the wildtype residue and position followed by the substituted residue as follows, C1:M95W; C2:T275S/S375W; C3:A433M; S1:W96C/V275C; S2:I109C/Q428C; S3:T123C/G431C; S4K231C/E267C, for example A433M means that a methionine has been substituted for an alanine to create a C3 mutant protein.

Quantitative surface-plasmon resonance characterization of the binding of the various mutants to CD4, to 17b in the absence of CD4 and to 17b in the presence of CD4 allowed the degree of conformational stabilization to be assessed (Table 5).

greatly increased the "on-rate" of binding, with little effect on the off-rate. This indicated that 17b cannot bind to its site, without the conformational change induced by CD4. In contrast, the initial binding even of CD4 must occur without the conformational change.

Surface-plasmon resonance (SPR) experiments were performed on a Biacore biosensor system at 25° C. Antibody (17b or m6 for the CD4i antibodies; F105, b12, 1.5e, etc. for CD4BS antibodies; b3, b3, b11 etc. for Fab fragments of CD4BS antibodies; and 2-domain CD4 for CD4) were immobilized on research grade CM5 sensor chips using the recommended standard amine coupling. Binding experiments were carried out in HBSP buffer (10 mM HEPES, pH 7.4, 150 mM NaCl and 0.005% surfactant P-20).

During the association phase, gp120 were passed over the buffer-equilibrated chip surface at a rate of 30 ul/min. After the association phase, bound analytes were allowed to disso-

TABLE 5

Quantitative Surface-Plasmon Resonance Characterization of Mutant gp120 Kinetic Parameters.

| Mutant | CD4 | | | 17b without CD4 | | | 17b with CD4 | | | CD4 |
|---|---|---|---|---|---|---|---|---|---|---|
| | on | off | KD | on | off | KD | on | off | KD | Induction |
| WT core | 4.95E+04 | 1.46E−03 | 2.95E−08 | 9.81E+03 | 4.33E−03 | 4.41E−07 | 7.84E+05 | 2.07E−03 | 2.64E−09 | 7.99E+01 |
| 2a | 1.19E+05 | 1.78E−04 | 1.49E−09 | 1.03E+05 | 1.66E−02 | 1.61E−07 | 1.62E+06 | 9.98E−03 | 6.14E−09 | 1.57E+01 |
| 4-0 | 1.10E+05 | 1.39E−04 | 1.26E−09 | 1.54E+05 | 0.0196 | 1.28E−07 | 1.76E+06 | 0.0101 | 5.73E−09 | 1.14E+01 |
| 4a | 1.23E+05 | 2.81E−04 | 2.28E−09 | 3.75E+05 | 0.0212 | 5.66E−08 | 2.51E+06 | 0.014 | 5.56E−09 | 6.69E+00 |
| 4b | 1.08E+05 | 1.62E−04 | 1.50E−09 | 1.06E+05 | 0.0192 | 1.81E−07 | 1.48E+06 | 0.01 | 6.76E−09 | 1.40E+01 |
| 4c | 1.07E+05 | 1.20E−04 | 1.12E−09 | 2.98E+05 | 0.0114 | 3.82E−08 | 2.05E+06 | 9.14E−03 | 4.45E−09 | 6.88E+00 |
| 5mut | 3.08E+04 | 4.14E−04 | 1.35E−08 | 7.06E+04 | 0.0168 | 2.37E−07 | 1.31E+06 | 1.02E−02 | 7.78E−09 | 1.86E+01 |
| 6a | 6.56E+04 | 4.47E−04 | 6.82E−09 | 8.94E+04 | 8.42E−03 | 9.41E−08 | 2.83E+05 | 7.46E−03 | 2.64E−08 | 3.17E+00 |
| 6b | 7.89E+04 | 3.08E−04 | 3.91E−09 | 2.08E+05 | 0.0225 | 1.08E−07 | 9.27E+05 | 0.0126 | 1.36E−08 | 4.46E+00 |
| 8a | 141000 | 0.00062 | 4.4E−09 | 354000 | 0.00712 | 2.01E−08 | 240000 | 0.0106 | 4.42E−08 | 0.677966 |
| 8b | 83000 | 0.000484 | 5.83E−09 | 135000 | 0.00403 | 3.01E−08 | 310000 | 0.0151 | 4.88E−08 | 2.296296 |
| 9c | 6.78E+04 | 1.45E−04 | 2.14E−09 | 1.04E+06 | 0.011 | 1.05E−08 | 1.28E+06 | 8.53E−03 | 6.69E−09 | 1.23E+00 |

CD4-on rate did not change much, indicating that initial CD4 occurs without conformational stabilization. The off-rate did decrease relative to wild-type, however, indicating that once CD4 bound, the conformational change was able to lock CD4 into place. A very different effect was seen with the CD4i antibody 17b. With 17b, conformational stabilization ciate for 5 min. The chip surface was then regenerated by two 25 ul injections of 10 mM Glycine/HCl (pH 3.0) at a flow rate of 50 ul/min. Association and dissociation values were calculated by numerical integration and global fitting to a 1:1 interaction model using BIAevaluation 3.0 software (Biacore, Inc.)

Example 2

Atomic Level Structure Determination of gp120

This example describes the methods used to obtain crystals of a gp120 with an extended V3 loop.

Variational Crystallization and Robotic Screening

To increase the probability of obtaining crystals suitable for X-ray structural analysis, 13 different complexes of HIV-1 envelope glycoprotein gp120 core with intact V3 were prepared and screened for crystallization. To ensure that gp120 was in its coreceptor binding conformation, all complexes contained CD4 (2-domain).

1) Protein Production, Purification, and Complex Preparation

Constructs of core+V3 gp120 from clade B HIV-1 isolates, YU2, JR-FL, and HXBc2, were prepared as previously described (Wu et al., Nature 384:179, 1996; Grundner et al., Virology 330:233, 2004). Truncations of the N-terminus, C-terminus, and substitution of the tripeptide GAG for the V1/V2 region were identical to those previously described (Grundner et al., Virology 330:233, 2004). Wild-type isolates were used for YU2 and HXBc2. For JR-FL, a functional 2-glycan deletion variant was used with mutations, 301N/Q and 388T/A (Koch et al., Virology 313:387, 2003). This CCR5-using JR-FL variant was more susceptible to neutralization by CD4-binding site antibodies, but not to CD4-induced antibodies (Koch et al., Virology 313: 387, 2003. Constructs were expressed in Drosophila Schneider 2 cells under an inducible metallothionein promoter. The 2-domain CD4 (d1d2), antigen-binding fragments (Fabs) and single-chain variable fragments (scFv) of CD4-induced (CD4i) antibodies, 17b, 48d, 412d, m6, m9 and X5, were prepared as previously described (Ryu et al., Nature 348:419, 1990; Kwong et al., J. Biol. Chem. 274:4115, 1999; Huang et al., Proc. Natl. Acad. Sci. USA 101:2706, 2004; Zhang et al., J. Mol. Biol. 335:209, 2004; Moulard et al., Proc. Natl. Acad. Sci. USA 99:6913, 2002). Preparations of gp120 complexes followed procedures that were essentially the same as previously described (Kwong et al., J. Biol. Chem. 274:4115, 1999). Briefly, glycans were removed by digestion with endoglycosidases H and D to leave only the protein proximal N-acetylglucosamine and 1,6 fucose residues. The 2-domain CD4 was added, the binary complexes passed through a concanavalin A column to remove any gp120 proteins with uncleaved N-linked glycan, and the complexes further purified by gel filtration (Hiload 26/60 Superdex S200 prep grad, Amersham). Fab or scFv of CD4-induced (CD4i) antibodies were added and the ternary complexes purified by Superdex S200 chromatography. Purified complexes in 0.35 M NaCl, 2.5 mM Tris pH 7.0, 0.02% NaN3 were concentrated to 5-8 mg/ml. The following complexes were made (specified by strain of core+V3 gp120:soluble CD4 domain fragment: CD4-induced antibody type and fragment):

JR-FL:d1d2:17b Fab
JR-FL:d1d2:48d Fab
JR-FL:d1d2:412d Fab
JR-FL:d1d2:X5 Fab
JR-FL:d1d2
YU2:d1d2:48d Fab
YU2:d1d2:X5 Fab
HXBc2:d1d2:17b Fab
HXBc2:d1d2:48d Fab
HXBc2:d1d2:412d Fab
HXBc2:d1d2:X5 Fab
HXBc2:d1d2:m6 scFv
HXBc2:d1d2:m9 scFv

2) Robotic Screening of Crystallization Conditions

The gp120 complexes were screened robotically using vapor-diffusion sitting droplets composed of 50 nl protein combined with 50 nl crystallization solution (Lesley et al., Proc. Natl. Acad. Sci. USA 99:11664, 2002). 576 different commercially available crystallization solutions were used in each screen. JRFL complexes were screened with Hampton Research Screen I/II, Emerald Wizard Screen I/II, Emerald Wizard Cryo Screen I/II, Hampton Crystal Screen Cryo, Hampton PEG/Ion Screen, Hampton Grid Screens (ammonium sulfate, PEG 6000, MPD, and PEG/LiCl), and Syrrx Polymer Screen. YU2 and HXBc2 complexes were screened in the same manner except that the Hampton Research Index screen was substituted for the Emerald Wizard Cryo Screens. Pictures of crystallization drops were taken at 0, 1, 3, 7, 14, and 21 days after set-up, and the images inspected visually for protein crystals.

3) Crystallization Optimization

Initial crystals observed from robotic screens were reproduced and optimized manually using vapor-diffusion hanging droplets. A total of eight different crystal forms were grown to sizes suitable for testing diffraction quality. While most of the crystals diffracted to at best only 6-10 Å, one crystal consisting of JR-FL:d1d2:X5 Fab diffracted to at least 5 Å and was chosen for further optimization. Larger single crystals were produced by macroseeding (Thaller et al., J. Mol. Biol. 147: 465, 1981): 1.5 µl of 5 mg/ml JR-FL:d1d2:X5 Fab was mixed with an equal volume of 1.3 M ammonium sulfate and placed over a 0.5 ml reservoir of 1.3 M ammonium sulfate; after 30 minutes, a single crystal was transferred directly to the droplet. Macroseeded crystals grew to 0.1×0.1×0.2 mm in 5-7 days.

Example 3

Structure Determination of gp120 with an Extended V3 Loop

This example describes the methods used to determine the structure of a gp120 with an extended loop to atomic resolution.

Data Collection

Crystals were dehydrated (Heras et al., Structure 11:139, 2003) over 3 M ammonium sulfate reservoirs for 2-3 days. Dehydrated crystals were cross-linked over 20 µl of 1.5% glutaraldehyde for 1.5 hr using the procedure of Lusty (Lusty, J. Appl. Cryst. 32:106, 1999), transferred to a cryoprotectant solution containing 2 M ammonium sulfate, 60% (w/v) xylitol, 10% (w/v) erythritol and 5% (v/v) ethylene glycol for 1-2 minutes, covered with paratone-N, loop mounted, and flash-cooled to 100° K. for data collection. X-ray data were collected at a wavelength of 1.00 Å, using the intense 3rd generation undulator beam-line (SER-CAT) at the Advanced Photon Source, and processed and reduced with HKL2000 (Otwinowski and Minor, Methods Enymol. 276:307, 1997). The crystals were found to belong to space group P622 and to contain one complex per asymmetric unit. The diffraction was anisotropic, with stronger diffraction along the 6-fold axis. The crystal structure of JR-FL:d1d2:X5 Fab was solved by molecular replacement with CNS (Brunger et al., Acta Crystallogr. D 54:905, 1998). For gp120:CD4, a binary search model was constructed from YU2 core gp120 complexed to d1d2 as extracted from the previously determined ternary complex with 17b (pdb accession number, 1RZK) (Kwong et al., Structure 8:1329, 2000), with gp120 N-terminus (residues 83-86) and V4 region (residues 399-406) deleted. For X5 Fab, the structure of free X5 was used (pdb accession number, 1RHH) (Darbha et al., *Biochemistry* 43:1410, 2004). Cross-rotation and translation search with 15-4 Å data yielded Patterson correlation coefficients of 22.3% and 31.1% for YU2core:d1d2 and X5 Fab, respectively. The combined solution gave a Patterson correlation coefficient of 51.7%. By using the programs, O (Jones et al., *Acta Crystallogr. A* 47:110, 1991) for model building and CNS (Brunger et al., *Acta Crystallogr. D*54:905, 1998) for refinement, side-chains of the initial models were corrected, and the models subjected to torsion angle simulated annealing with slow cooling. Iterative manual fittings were carried out in B-value sharpened maps ($-75$ Å$^2$; 2Fo-Fc) to enhance visual recognition of protein sidechain definition. Refinement in CNS, however, used unsharpened data, with strong 3 geometric constraints to maintain idealized stereochemistry. Statistics summarizing the X-ray crystallographic data and refinement are shown in Table 6.

TABLE 6

X-ray crystallographic data and refinement statistics

Data collection

Space group P622
Molecules per ASU 1
Wavelength, Å 1.00
Unit cell dimensions a = b = 226.0 Å, c = 98.0 Å
Resolution, Å* 50-3.30 (3.71-3.55, 3.55-3.42, 3.42-3.30)
Completeness, %* 86.6 (91.4, 50.7, 20.9)
No. of total reflections 186,823
No. of unique reflections 19,372
Redundancy* 9.6 (5.1, 4.3, 3.1)
I/σ* 26.2 (2.3, 1.5, 1.3)
Rsym, %*, ‡ 8.2 (38.8, 47.3, 50.5)
Refinement statistics (|F| > 0 σ)

Resolution, Å 20.0-3.30
No. of reflections 19,364
Rcryst, %*, § 31.7
Rfree, %*, §, || 34.7
Rmsd bond length, Å 0.0043#
Rmsd bond angles, ° 0.978#
Luzzatti error, Å 0.64
Average B-value, Å2 125
Ramachandran plot
Most favored, % 83.3
Additionally allowed, % 15.8
Generously allowed, % 0.8
Disallowed, % 0.1

*Values in parentheses are for the last three highest resolution shells.
‡ Rsym = Σ|I − <I>|/Σ<I>, where I is the observed intensity, and <I> is the average intensity of multiple observations of symmetry related reflections.
§ R = Σhkl||Fobs| − |Fcalc||/Σhkl|Fobs|
|| Rfree is calculated from 10% of the reflections excluded from refinement.
The geometry was tightly restrained, as this was observed to improve the Rfree.

Model Analysis

All superpositions were performed using lsqkab in CCP4 (Collaborative Computational Project, *Acta Crystallogr. D*50:760, 1994). Molecular surface interactions were calculated using MS (Connolly, *J. Mol. Graph.* 11:139, 1993). Figures were prepared using PyMOL (DeLano Scientific, San Carlos, Calif., 2002) and GRASP (Nicholls et al, *Proteins Struct. Funct. Genet.* 11:281, 1991).

Glycan Modeling

Asn-(N-acetylglucosamine)2(mannose)3 N-linked sugar cores were modeled following procedures described previously for the HXBc2 core (Wyatt et al., *Nature* 393:705, 1998). Briefly, JR-FL core with V3 and the HXBc2 core with modeled glycan were superimposed. Conserved sites of Nlinked glycan were transferred, and other sites were built manually, including glycans at 301 and 386. The core was fixed and the Asn and attached glycan were subjected to molecular dynamics.

Sequence Analysis

Analyses were carried out with only sequences with complete V3, limited to one sequence per individual, extracted from the Los Alamos HIV sequence database (www.hiv.lanl. gov/content/hiv-db.) for all M group sequences that had coreceptor usage specified as either CCR5 or CXCR4. The B clade subset of the M group had the most coreceptor usage information for a single clade, and so it was also analyzed separately. Alignments were made from constant to variable regions, with the β-turn (GPGR analog) of the tip forced into alignment. The Shannon entropy (Shannon, *Bell System Tech.* 27:379, 1948) was calculated for each site, treating gaps inserted to maintain alignment and distinct amino acids as characters, and statistical analysis of the variation at each site comparing R5 and X4 viruses was performed by using a Monte Carlo randomization of the two data sets (Korber et al., *J. Virol.* 68:7467, 1994), with a Bonferroni correction to contend with multiple tests. An entropy score is actually a simple measure of the information content of a data set: when considered in this context, as a measure of amino acid diversity in the column of an alignment, it has the virtue of capturing both the range and distribution of observed amino acids. Zero indicates absolute conservation, and a score of 4.4 indicates complete randomness.

Example 4

This example describes the analysis of the structural details of a gp120 with an extended loop.

The third variable region (V3) of the HIV-1 gp120 envelope glycoprotein is immunodominant and contains features essential for coreceptor binding. Disclosed herein is the structure of the V3 loop in the context of an HIV-1 gp120 core complexed to the CD4 receptor and to the X5 antibody at 3.5 angstrom resolution. Binding of gp120 to cell-surface CD4 positions V3 so that its coreceptor-binding tip protrudes 30 angstroms from the core toward the target cell membrane. The extended nature and antibody accessibility of V3 explain its immunodominance. Snapshots of the gp120 entry mechanism have been visualized through crystal structures of unliganded and CD4-bound states (Chen et al., *Nature* 433:834, 2005; Kwong et al., *Nature* 393:648, 1998). Prior to this disclosure an essential component of the coreceptor binding site, the third variable region (V3), was been absent from structural characterizations of the gp120 core. The structure of V3 in the context of core gp120 bound to CD4, described herein, reveals the entire coreceptor binding site. The V3 appears to act as a molecular hook, not only for snaring coreceptor but also for modulating subunit associations within the viral spike. Its extended nature is compatible with the elicitation of an immunodominant antibody response and the generation of broadly neutralizing antibodies to V3 epitopes.

Figure 5:
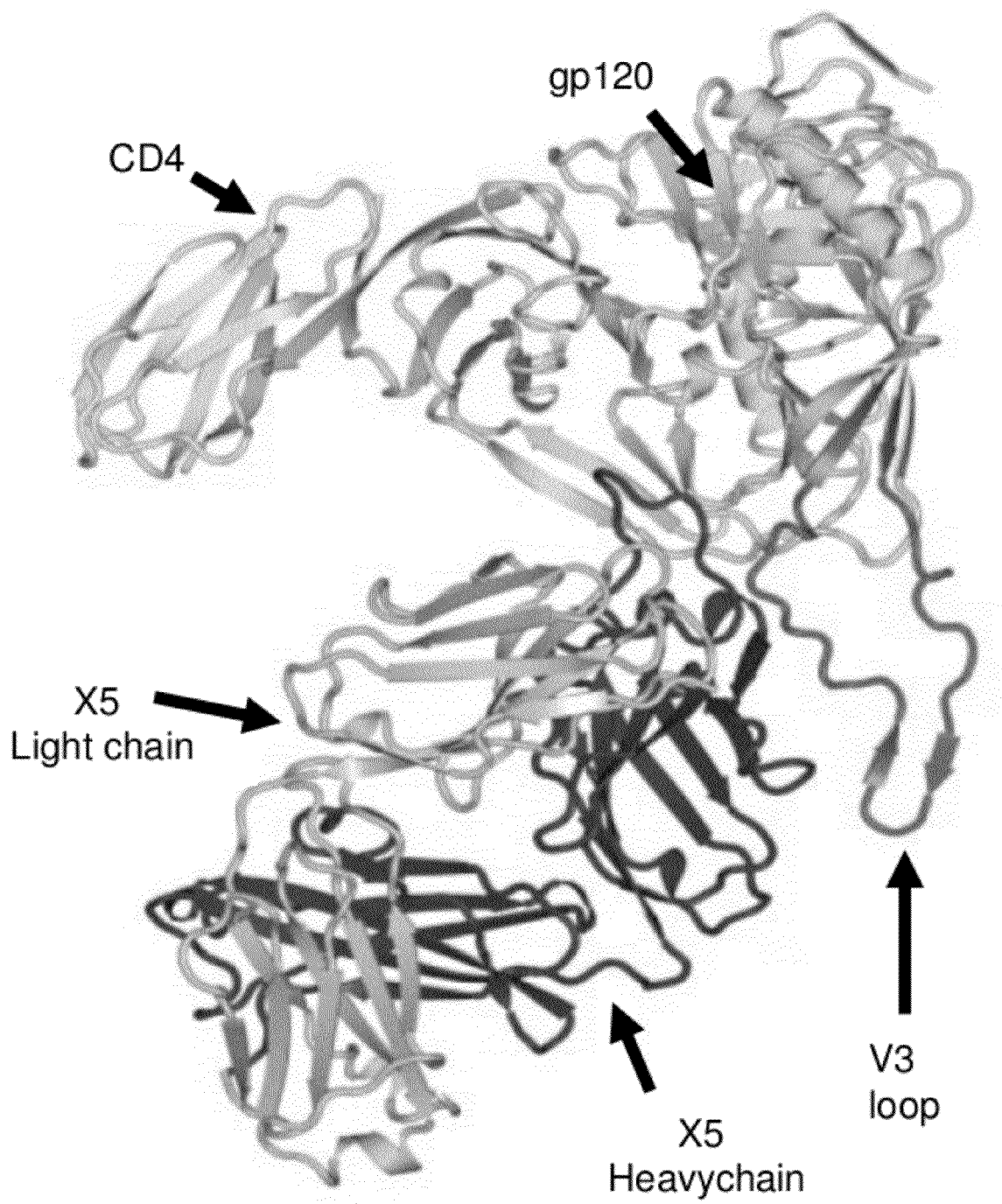

The extreme glycosylation and conformational flexibility of gp120 inhibit crystallization. Variational crystallization and various technologies adapted from structural genomics were used to obtain crystals suitable for x-ray structural analysis (Kwong et al., *J. Biol. Chem.* 274:4115, 1999; Stevens and Wilson, *Science* 293:519 (2001). The gp120 core with V3 from JR-FL The crystallized JR-FL was derived from a JR-FL variant with two point mutants, Asn301Gln and Thr388Ala. These mutations removed two Nlinked glycans, and the resultant virus was more sensitive to neutralization but was otherwise functional (Koch et al., *Virology* 313:387, 2003), when complexed to CD4 (two domain) and the antigen-binding fragment (Fab) of the X5 antibody (Koch et al., *Virology* 313:387, 2003), formed hexagonal crystals that diffracted to approximately 3.5 Å resolution with x-rays provided by an Advanced Photon Source undulator beam line (SER-CAT) (Table 5). The structure was solved by molecular replacement and is shown in FIG. 5.

Figure 6:
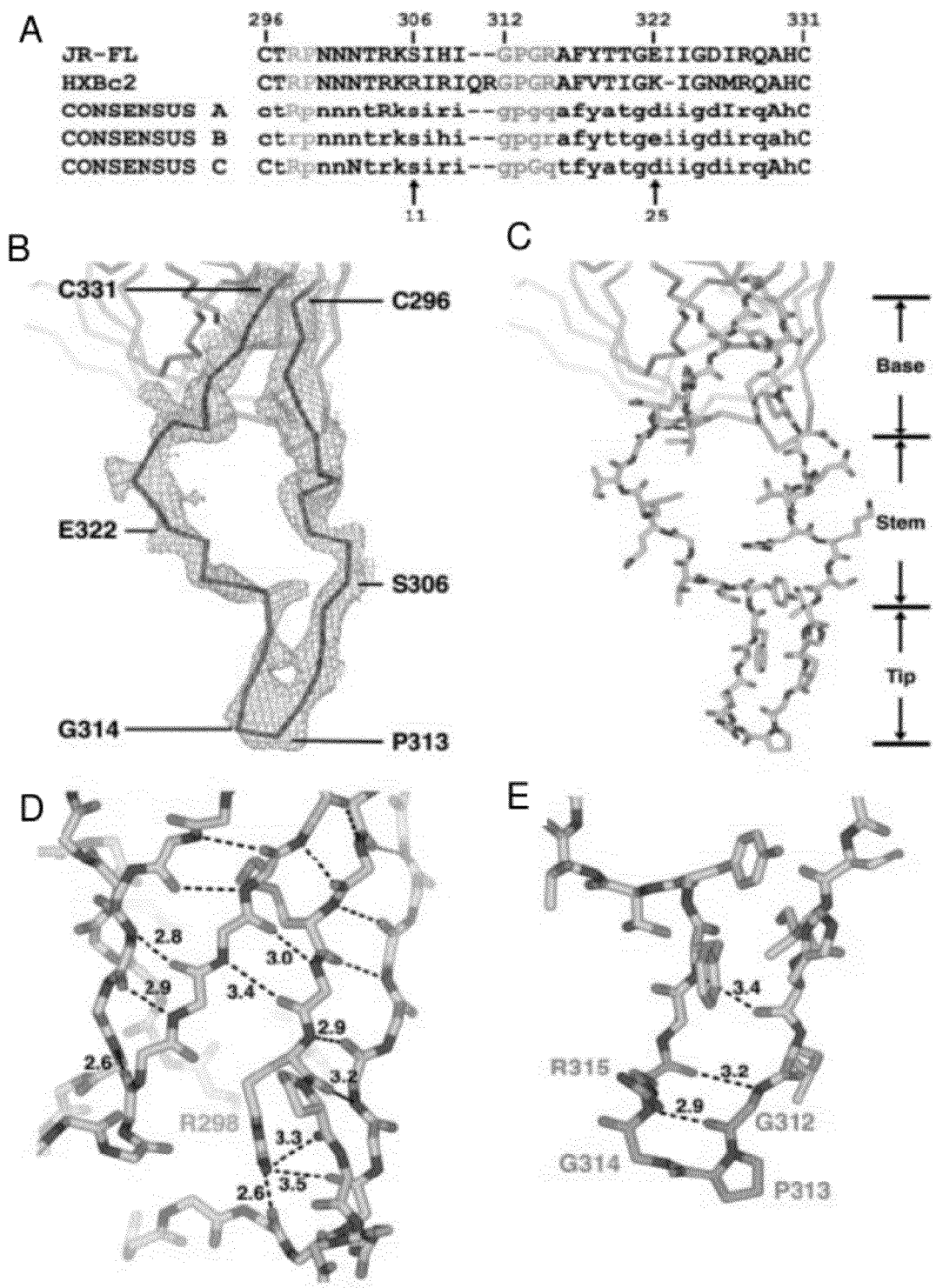
Figure 9:
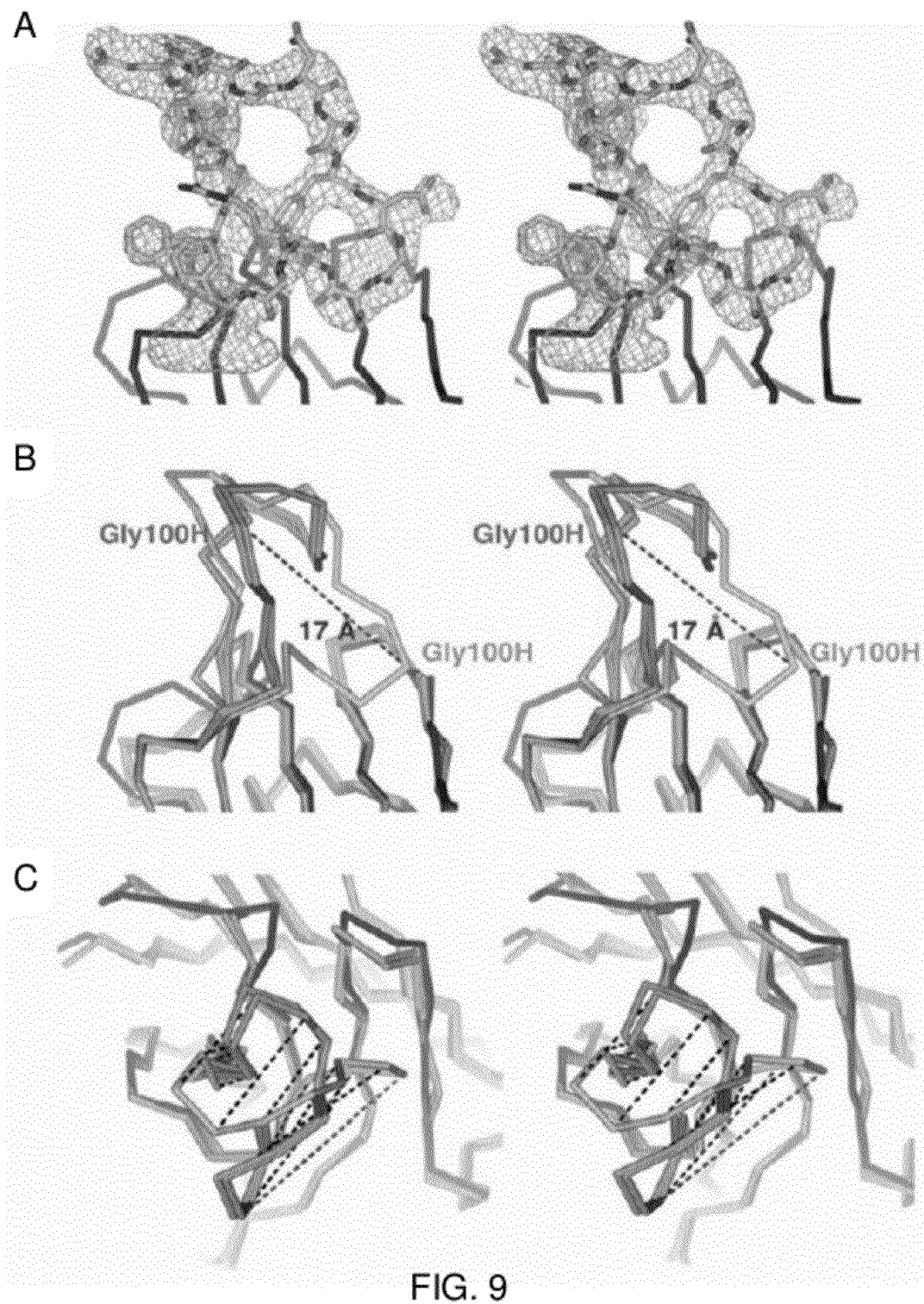
Figure 10:
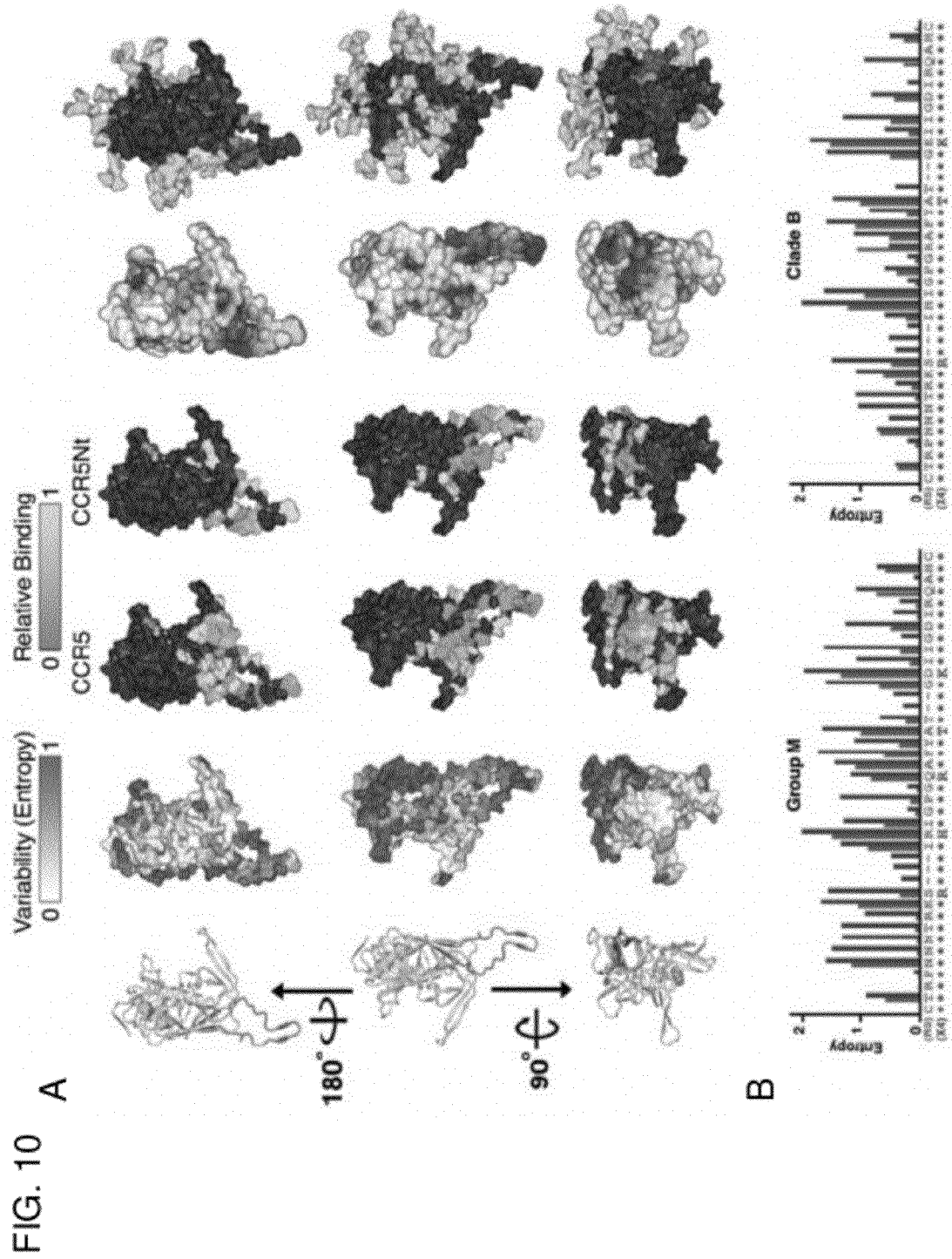
FIG. 10 (B) V3 sequence variation. The sequence variation was quantified (see methods) and is expressed as an entropy score: a score of zero indicates absolute conservation, a score of 4.4 indicates complete randomness. The V3 in B clade viruses which use CCR5 is comparable in terms of overall variation with other regions of gp120. The median entropy of each position within V3 is 0.21, and the interquartile range is 0-0.59. If one excludes the named variable domains, the rest of gp120 has a median entropy of 0.2, with an interquartile range of 0.-0.44. There is no statistical difference between these two distributions (Wilcoxon rank-sum p value=0.14). In contrast, V1, V2, V4 and V5 are much more variable (median entropy=1.24, interquartile range 0.67-1.70, p value compared to V3, <10-9.) Graphed in red and blue, respectively, are the position-dependent entropy score from 242 CCR5-using isolates (R5) and 47 CXCR4-using isolates (X4). Twenty positions were found to be significantly more variable in X4 than R5 viruses after correction for multiple tests. In particular, the N-linked glycosylation site (NNT) is highly conserved in R5 viruses, with 238/242 viruses reported to be R5 in the Los Alamos database carrying the potential glycosylation site at position 301, whereas only 17/47 X4 viruses retain the site (p<<10-10). This glycan has been previously observed to influence overall neutralization sensitivity. Finally, insertions were found with higher frequency in X4 viruses. The consensus R5 and X4 sequences are shown. The entropy scores from 64 R5 and 19 X4 Clade B isolates are shown, along with the respective consensus sequences. Asterisks denote where the consensus X4 sequence is the same as the consensus R5 sequence.
Figure 12:
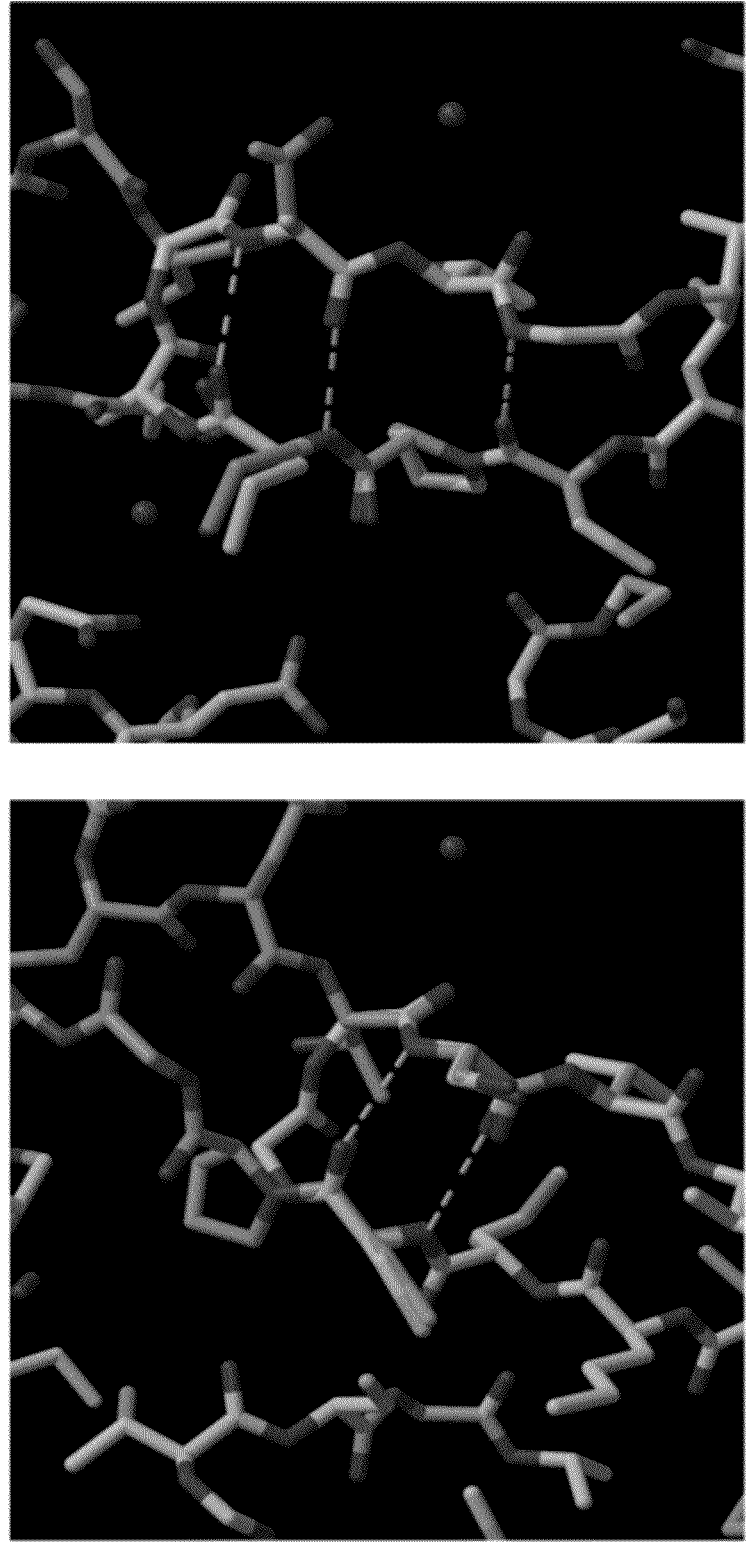
FIG. 12 is a set of computer generated images showing the modeled structure of the V1/2 for HXBc2 9c mutant.
Figure 16A:
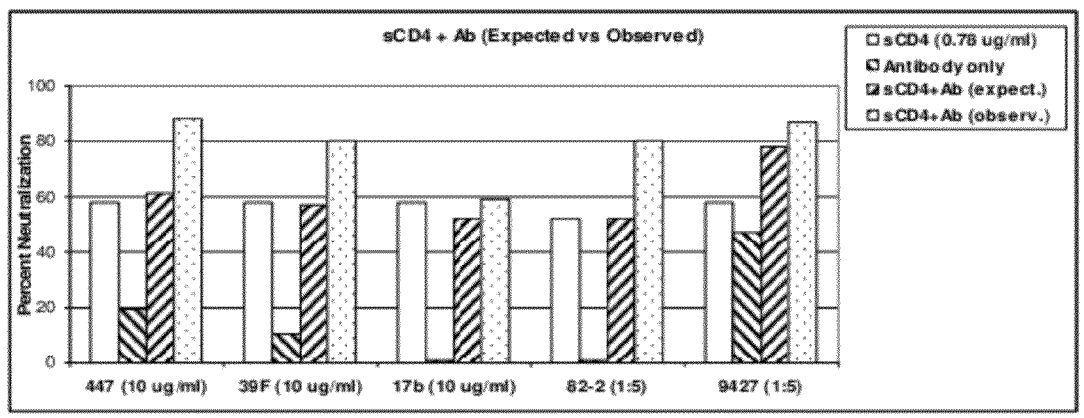
FIG. 16A is a bar graph showing the percent neutralization by sCD4 triggering of the V3 loop epitope. Data shown are percent neutralization of pseudovirus YU2 by the monoclonal antibodies (mAb) or sera listed under each set of bar graphs. The white bar shows neutralization by sCD4 alone. The first hatched bar shows neutralization by the specified antibody alone. The second hatched bar shows the calculated (expected) neutralization by a combination of sCD4 and the specified antibody. The stippled bar shows the observed (actual) neutralization by the combination of sCD4 and the specified antibody. 447 and 39F are anti-V3 mAbs. 17b is a mAb to the co-receptor binding site. 82-2 is an individual guinea pig sera derived from immunization with dCFIdV12 (BaL). 9427 is an individual baboon sera derived from immunization with gp140GCN-4 (YU2). Observed is measured percent neutralization with sCD4+Antibody. Expected=calculated additive effect of the two antibodies assuming they act independently. This effect is the product of the fraction remaining virus for each Ab; e.g. an antibody that produces 50% neutralization leaves 0.5 virus remaining. A second antibody with 50% neutralization would reduce that by 50%, leaving 0.25 fraction remaining virus. Thus, the effect of the two antibodies is 0.5×0.5=0.25. And 0.25 remaining is 75% neutralization.
Figure 16B:
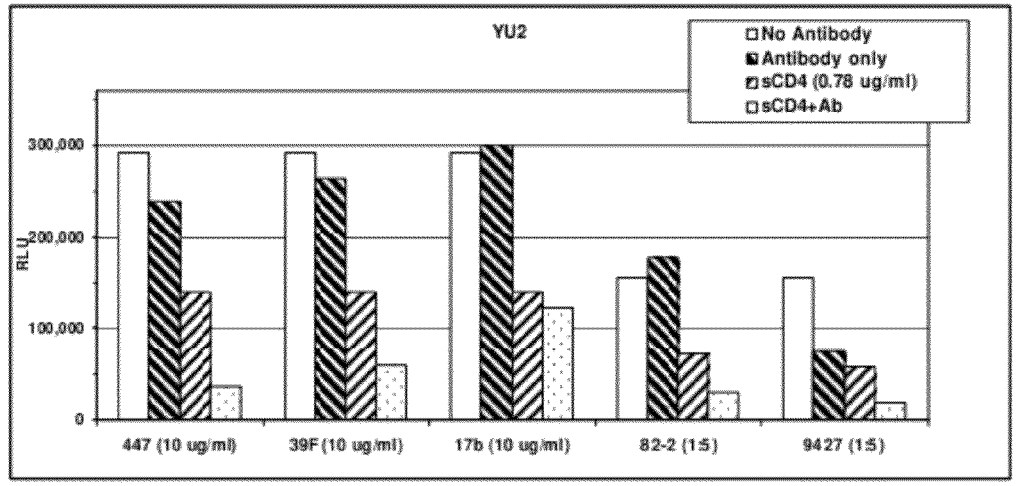
FIG. 16B is a bar graph of the actual luciferase (RLU) data plotted in FIG. 16A. The figure legend describes each bar. The antibodies and sera used are as described for FIG. 16A.
Figures 16C, 16D, 16E:
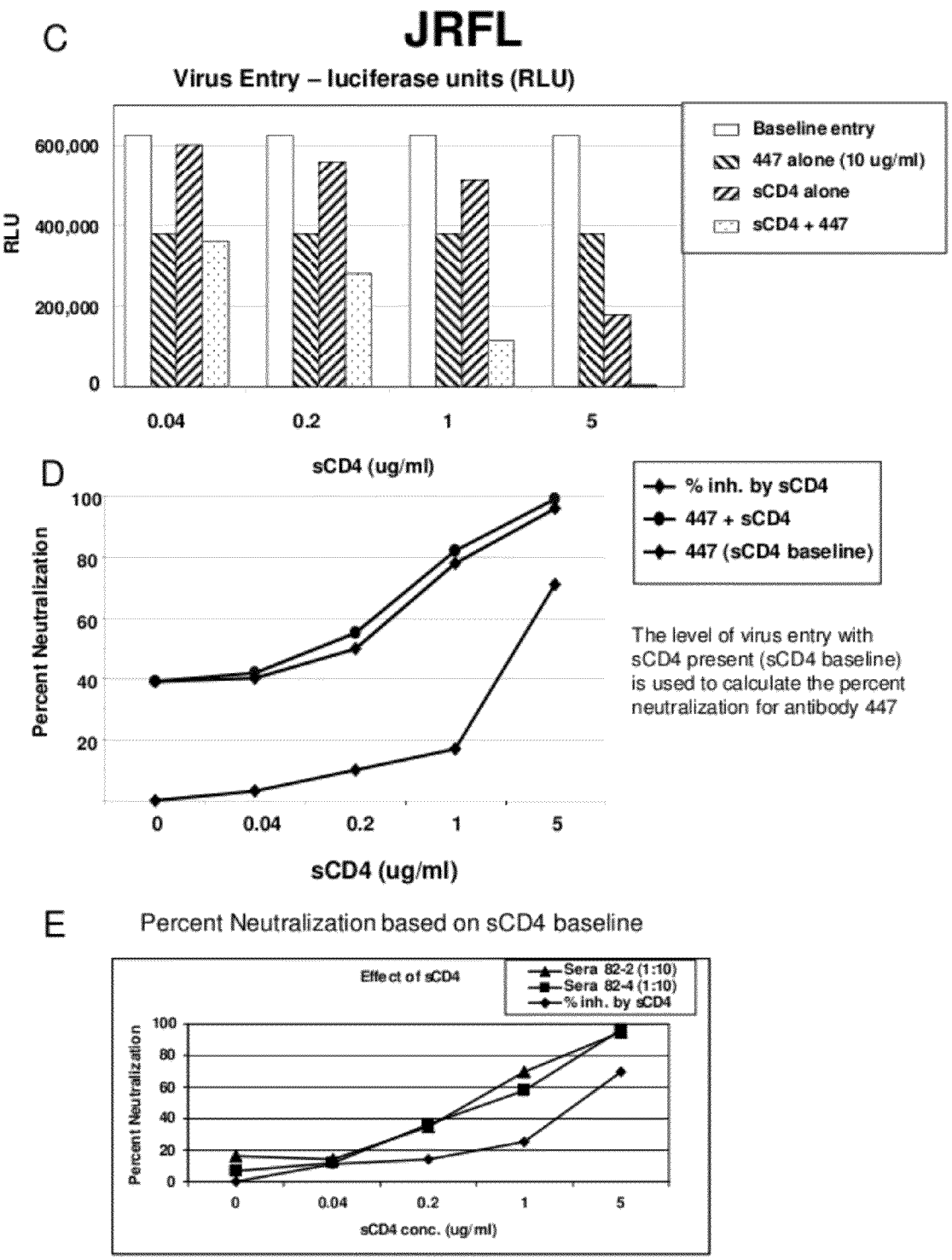
FIG. 16C is a bar graph of the actual luciferase (RLU) data for HIV strain JRFL. The antibodies tested are indicated.
FIG. 16E is a line graph of the neutralization of JRFL by two guinea pig sera as shown (▲, ■). The diamonds (♦) show the effect of sCD4 alone. The line graphs show the neutralization of each sera, calculated based on the virus entry with sCD4 present.
Figure 16F:
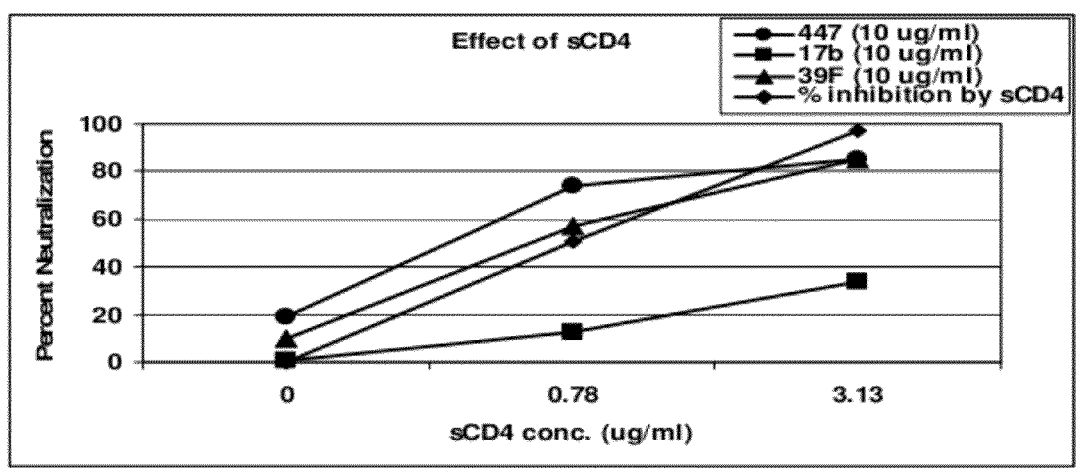
FIG. 16F is a line graph of the neutralization of YU2 by mAbs 447, 17b, and 39F.
Figure 16G:
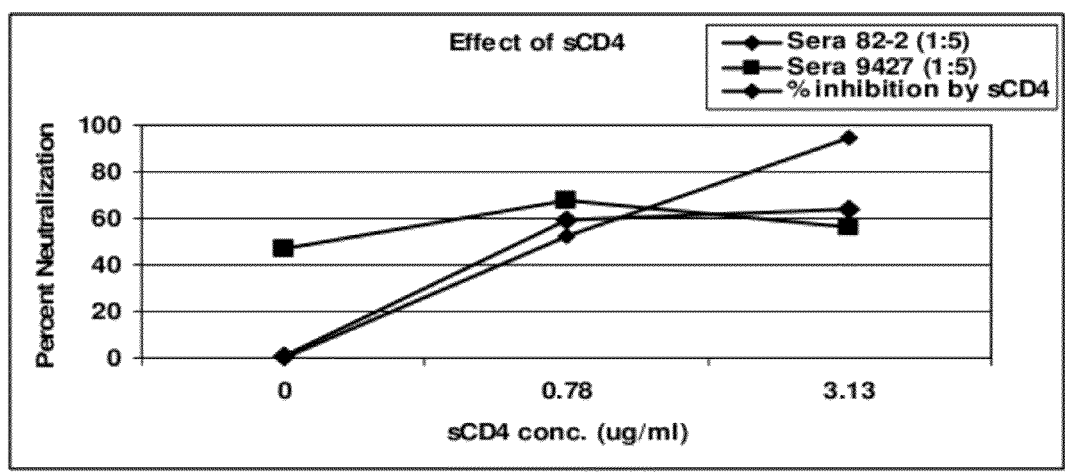
FIG. 16G is a line graph of the neutralization of YU2 by the two animal sera that were described in FIG. 16A.
Figure 16H:
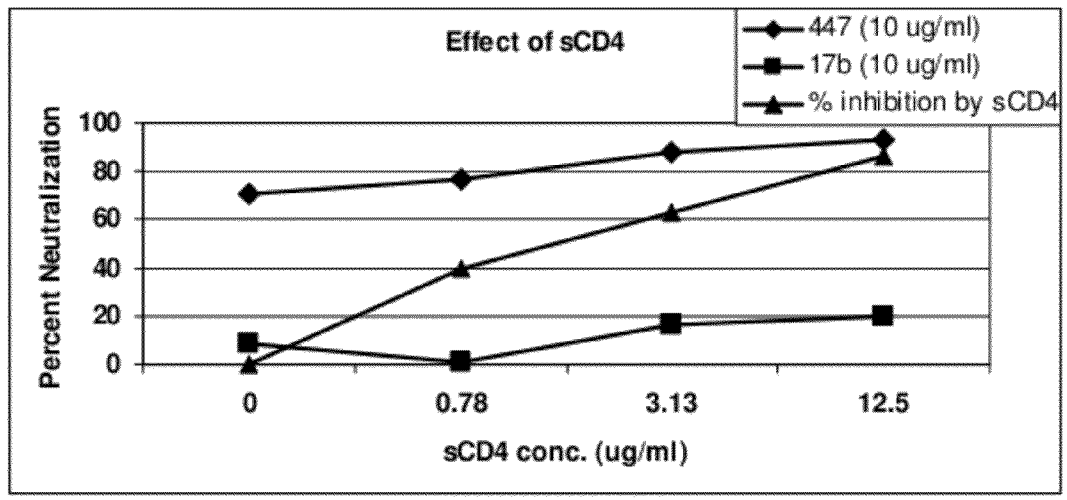
FIG. 16 is a set a plots of neutralization data for various HIV isolates in the presence and absence of CD4, showing the effect of CD4 triggering on viral neutralization.
FIG. 16I is a line graph of the neutralization of virus 6535 by two guinea pig sera as shown (♦, ■). The diamonds (♦) show the effect of sCD4 alone.
FIG. 16J is a line graph of the neutralization of virus ADA by mAbs 447.
FIG. 16K is a line graph of the neutralization of virus ADA by two guinea pig sera as shown (♦, ■).
FIG. 16L is a line graph of the neutralization of the clade C virus TV1 by mAbs 447 and 17b.
FIG. 16M is a line graph of the neutralization of the clade C virus TV1 by guinea pig sera derived from animals immunized with clade C dCFI Env.
FIG. 16N is a line graph of the neutralization of the clade C virus ZA12 by mAb 17b.
FIG. 16O is a line graph of the neutralization of the clade C virus ZA12 by guinea pig sera derived from animals immunized with clade C dCFI Env.
FIG. 16P is a line graph of the neutralization of the clade C virus Z109 by mAbs 447 and 17b.
FIG. 16Q is a line graph of the neutralization of the clade C virus Z109 by guinea pig sera derived from animals immunized with clade C dCFI Env.
Figure 16I:
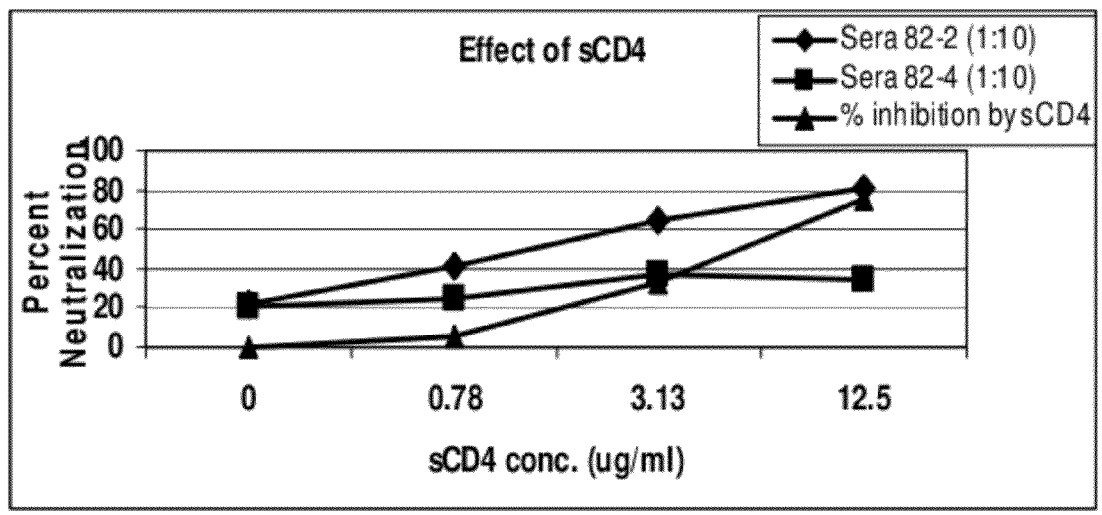
Figure 16L:
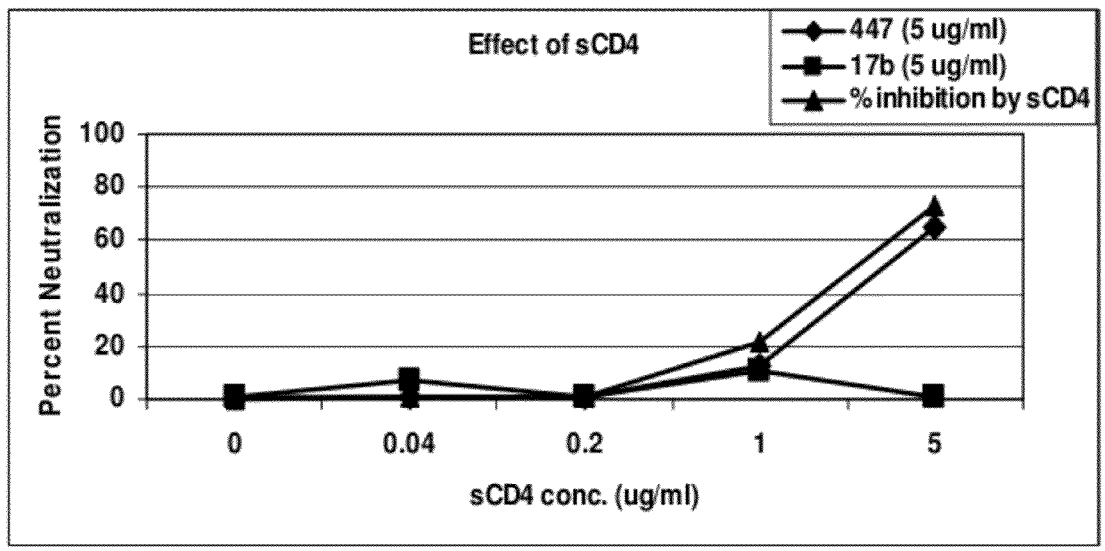
Figure 16M:
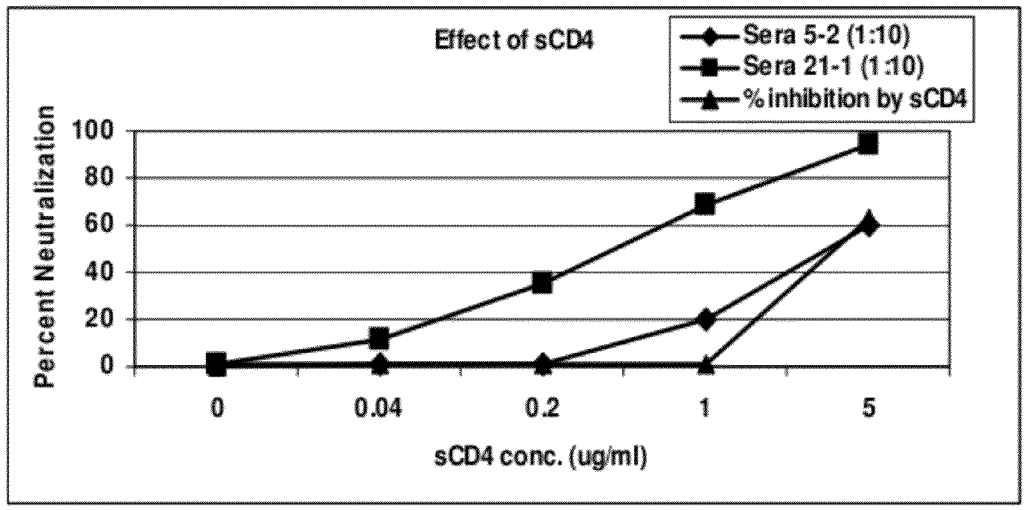
Figure 16P:
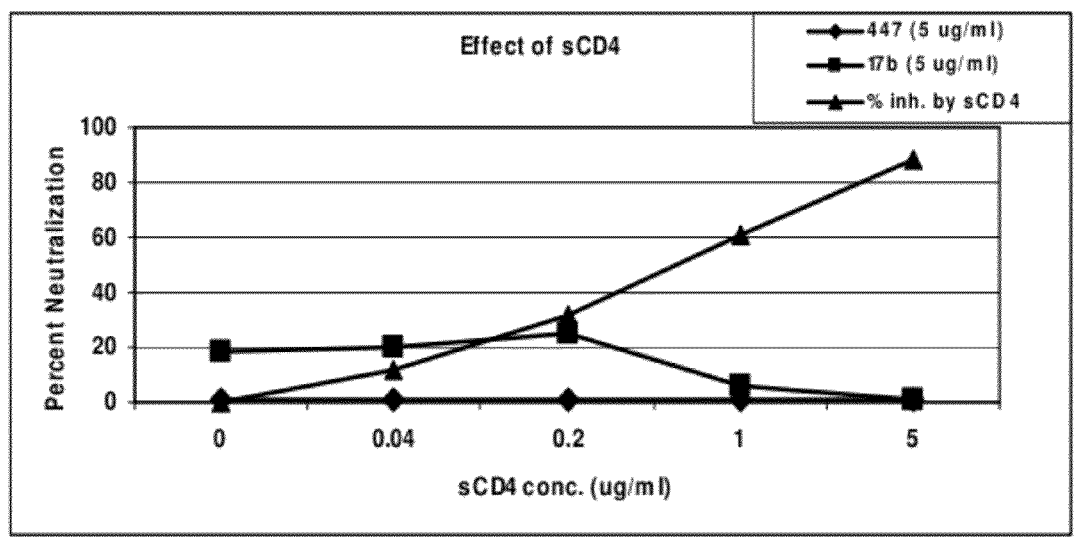
Figure 16Q:
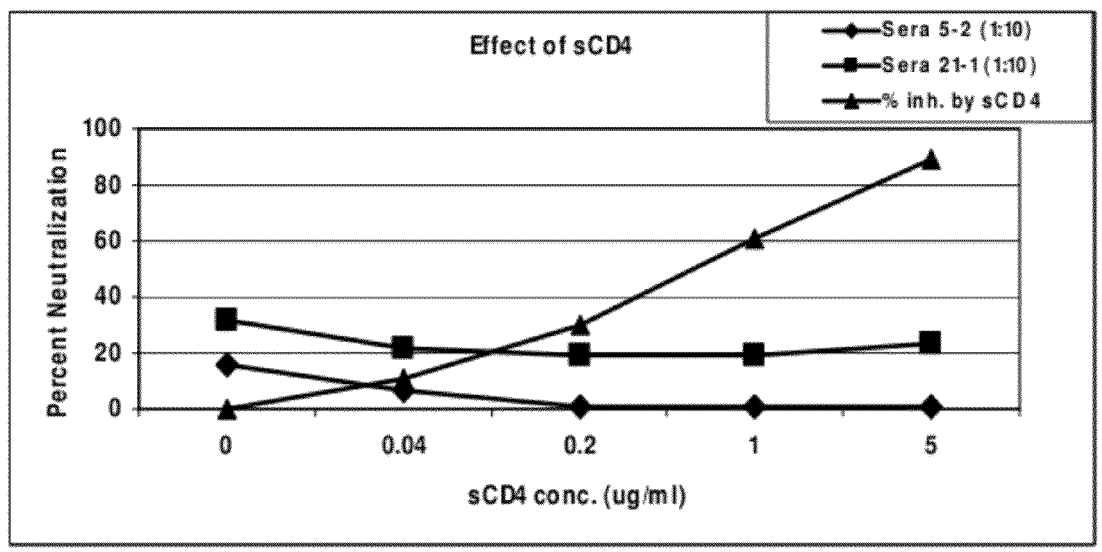

The overall assembly of CD4, X5, and core gp120 resembled the previously determined individual structures of CD4 (Ryu et al., Nature 34:419, 1990; Wang et al., Nature 348:411, 1990) and of free X5 (Darbha et al., Biochemistry 43:1410, 2004) as well as the complex of core gp120 bound to CD4 (Kwong et al., Nature 393:648, 1998; Kwong et al., Structure 8:1329, 2000). For core gp120, some differences were observed in the variable loops and also at the N terminus, regions where variations in gp120 have previously been observed (Chen et al., Nature 433:834, 2005; Kwong et al., Nature 393:648, 1998; Kwong et al., Structure 8:1329, 2000; Huang et al., Structure 13:755, 2005). Structural resemblance was maintained around the base of V3, indicating that the previous truncation (Chen et al., Nature 433:834, 2005; Kwong et al., Nature 393:648, 1998; Kwong et al., Structure 8:1329, 2000; Huang et al., Structure 13:755, 2005) did not distort this region of the core. In X5, a large structural difference was observed for the third complementarity determining loop of the X5 heavy chain (CDR H3). Comparison of the refined structures of free X5 (Darbha et al., Biochemistry 43:1410, 2004) and bound X5 showed Cα movements of up to 17 Å, one of the largest induced fits observed for an antibody (FIG. 9). The gp120 envelope protein is composed of inner and outer domains, named for their expected orientation in the oligomeric viral spike (Kwong et al., Nature 393:648, 1998). V3 emanates from neighboring staves of the stacked double barrel that makes up the outer domain; it is almost 50 Å long from the disulfide bridge at its base to its conserved tip, but is otherwise only 15 Å wide and 5 Å deep (FIG. 6). Overall, it can be subdivided into three structural regions: a conserved base, which forms an integral portion of the core; a flexible stem, which extends away from the core; and a b-hairpin tip. In the crystal structure, the flexibility and position of the V3 tip may be influenced by a lattice contact, in which hydrogen bonds are made to the exposed backbone of the V3 b ribbon between Ile307 and Ile309. Tenuous sidechain contacts are also observed for the returning strand in the V3 stem with X5, as well as with V4 of a symmetry-related gp120 molecule, but these side-chain contacts are unlikely to influence its conformation. Features of gp120 important for coreceptor binding have been mapped by mutagenesis to two regions: (i) the V3 tip, and (ii) the gp120 core around the bridging sheet, the V3 base, and neighboring residues (Rizzuto et al., Science 280:1949, 1998; Rizzuto and Sodroski, AIDS Res. Hum. Retroviruses 16:741, 2000; Cormier et al., J. Virol. 75:5541, 2001; Cormier et al., J. Virol. 76:8953, 2002). Analysis of these two regions on this new structure indicates that they are conserved in both sequence and structure (FIGS. 10A and 11). The structural conservation of the V3 tip was surprising here in light of the apparent flexibility of the intervening stem, but we found the V3 tip to be strikingly similar in the context of the core, in antibody-V3 peptide complexes, and as a free peptide; such similarity is consistent with previous reports of recurring conformations for the V3 tip in antibody:peptide complexes (Stanfield et al., Virology 315: 159, 2003). The structure shows that conserved regions important for coreceptor binding are separated by 10 to 20 Å and by portions of the V3 stem with moderate to high sequence variation (FIG. 10). Emerging data on the structures of the coreceptors indicate that the regions identified as being important for binding gp120—the coreceptor N terminus and the second extracellular loop—may also be spatially separated (Klco, et al., Nat. Struct. Mol. Biol. 12:320, 2005).

Figure 7:
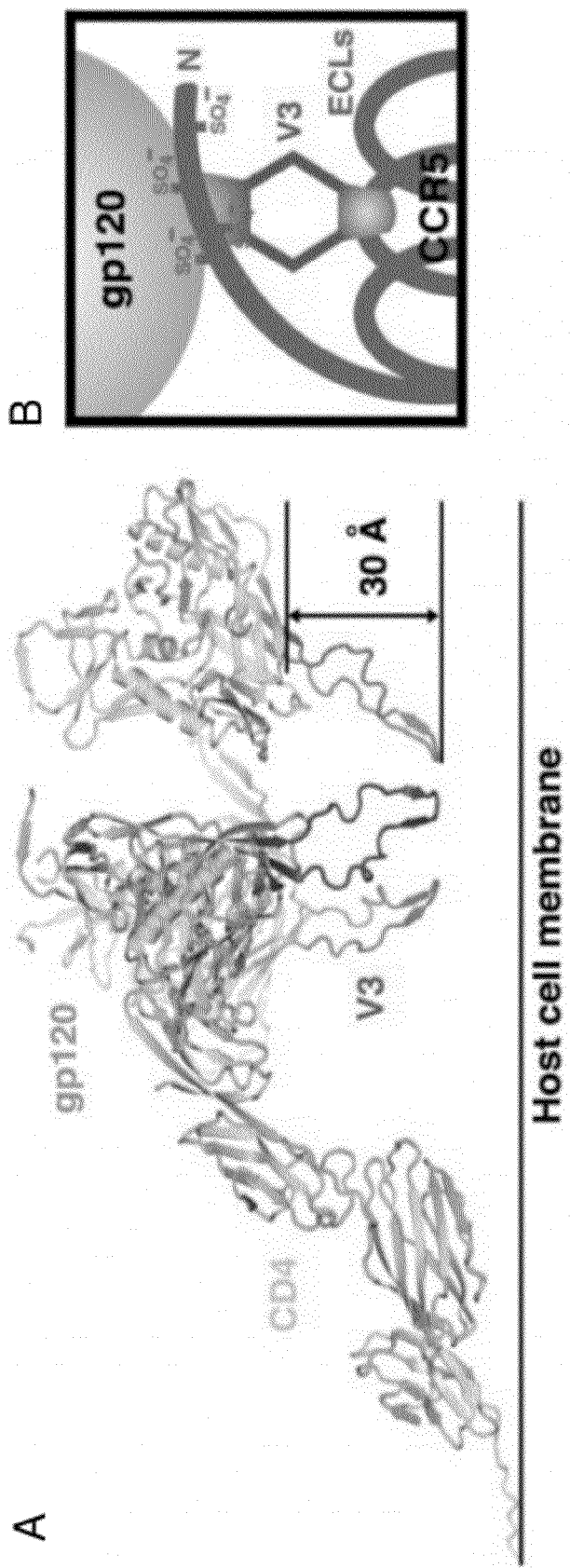
Figure 8:
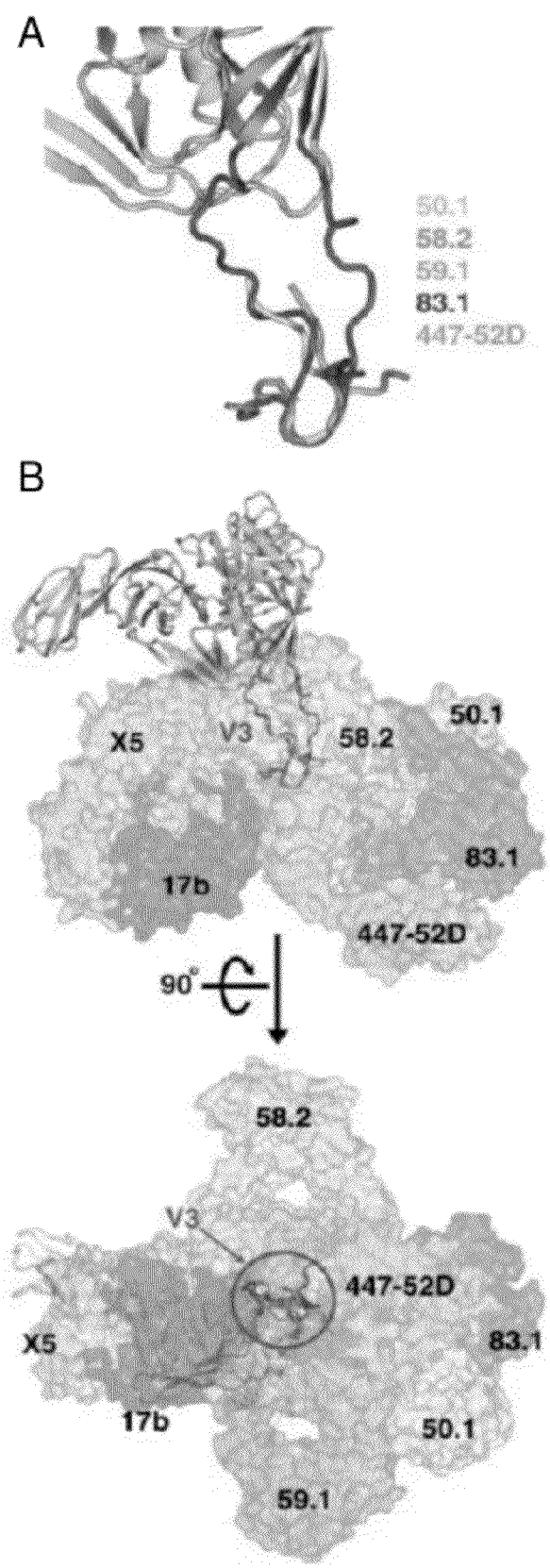

By integrating the two-site gp120 binding site on the coreceptor with the two-site coreceptor binding site that it is observe in the structure of V3 gp120 with an extended V3 loop, that the N terminus of the coreceptor reaches up and binds to the core and V3 base while the V3 tip of gp120 reaches down to interact with the second extracellular loop of the coreceptor (FIG. 7B). Support for this model comes from several sources: (i) Biochemical studies show that the binding of CCR5 Nterminal peptides to gp120 is affected by gp120 alterations only on the core and around the base of V3 (Cormier and Dragic, J. Virol. 76:8953, 2002); and (ii) small-molecule inhibitors of HIV entry that bind to the second extracellular loop of the coreceptor are observed to no longer affect mutant viruses with V3 truncations. Despite general tolerance of the V3 stem to changes in sequence, there is less tolerance for insertions or deletions than in other gp120 variable loops. Superimposition of the core gp120 V3 structure on the modeled gp120 core trimer that previously obtained by optimization of quantifiable surface parameters (Kwong, et al., J. Virol. 74:1961, 2000) orients gp120 in the context of both cell-surface CD4 and the target cell membrane. Such a superposition projects the highly conserved Pro-Gly of the V3 tip 30 Å toward the target cell membrane (FIG. 7A). Different coreceptors, primarily CXCR4 or CCR5, can support HIV-1 entry. Sequence analysis has defined an 11/25 rule: If the 11th or 25th positions of V3 are positively charged, viruses will use CXCR4; otherwise they use CCR5 (Resch et al., Virology 288:51, 2001). In addition, V3 sequences are more conserved for CCR5-using viruses (FIG. 10). The structure of the V3 loop disclosed herein shows that positions 11 and 25 (residues 306 and 322) are within the variable stem. They each project about the same distance away from the core but are separated by a Cα distance of 17 Å (FIG. 10). This separation suggests that positions 11 and 25 recognize different portions of the coreceptor. CD4 induces large conformational changes in gp120. Before CD4 binding, V3 may not protrude precisely as observed here for the CD4-triggered coreceptor binding state of gp120 (Sattentau and Moore, J. Exp. Med. 174:407, 1991; Werner and Levy, J. Virol. 67:2566, 1993). However, structural comparison of unliganded versus CD4-bound conformations of gp120 (Kwong et al., Nature 393:648, 1998; Hartley et al., AIDS Res. Hum. Retroviruses 21:171, 2005) reveals that the local conformation of the region of the outer domain from which V3 emanates is mostly unchanged. Thus, the extended structure of V3 that we observe here should be generally representative of V3. Immunization with gp120 or gp120/gp41 in various contexts may elicit an immune response in which HXB2CG virtually all of the neutralizing activity is directed at V3. The conformation of crystal and nuclear magnetic resonance structures of V3-reactive antibody-peptide complexes was examined for clues to this immunodominant response (FIG. 11). Although the conformation of V3 peptides in these antibody-peptide complexes varies somewhat, the Pro-Gly tip is more conserved. Superimposing the conserved tip in the peptides with the V3 tip in the core+V3 structure permits the V3 peptide-binding antibodies to be placed in the context of the gp120 core. The antibodies completely surround V3 (FIG. 8). Although the accessibility of V3 may be quite different on a primary isolate in its pre-CD4 trimeric state, the extended nature of V3 as disclosed herein, when coupled to mechanisms that cloak the rest of the HIV envelope from antibody binding (Wyatt and Sodroski, Science 280:1884, 1998; Wyatt et al., Nature 393:705, 1998; Wei et al., Nature 422:307, 2003), is consistent with its ability to generate an immunodominant response. The attributes observed for V3 (such as, high relative surface area, chemically reactive backbone, conformational flexibility, and overall extended nature) may allow V3 to serve as a general molecular hook. Before CD4 binding, these attributes would enhance the ability of V3 to grasp neighboring protomers on the viral spike. Such quaternary interactions would explain V3's influence on overall neutralization sensitivity, for example, its ability to transfer neutralization resistance from YU2 to HXBc2 (Sullivan et al., *J. Virol.* 72:6332, 1998). After CD4 binding, the coreceptor binding site forms and V3 would jut prominently toward the target cell membrane. In this context, binding at the V3 tip may act as a ripcord to initiate gp41-mediated fusion.

Example 5

Prime-Boost Immunization with Stabilized gp120 and gp140 Trimer

This example describes the "prime-boost" immunization scheme used to generate a heightened immune response in a subject.

Based on the biophysical characterization of gp120 stabilized in the CD4 bound conformation performed an immunization scheme was performed whereby HXBc2 strain wild-type or cysteine-stabilized core gp120 proteins were used to prime the immune response for subsequent immunization with soluble, stabilized trimeric YU2 strain gp140-foldon molecules (Yang et al. *J Virol.* 76(9):4634-42, 2002). B-cells primed by the stabilized cores were primed for epitopes displayed preferentially only on the stabilized HX core CD4 binding site, or to other stabilized surfaces, efficiently presented only by the cysteine-stabilized cores.

Boosting with the gp140 trimeric molecules "immuno-focuses" primed B cells on shared and conserved determinants between the two immunogens and altering strains would not boost B cells directed at HX- or YU2-specific epitopes. Thus, the only B-cells boosted selectively by the trimer would be those that could bind efficiently both the stabilized core as well as the trimer. Thus, stabilized cores can stimulate B cells that could induce the CD4-bound or the b12 conformation in the gp140 trimers.

Figure 4A:
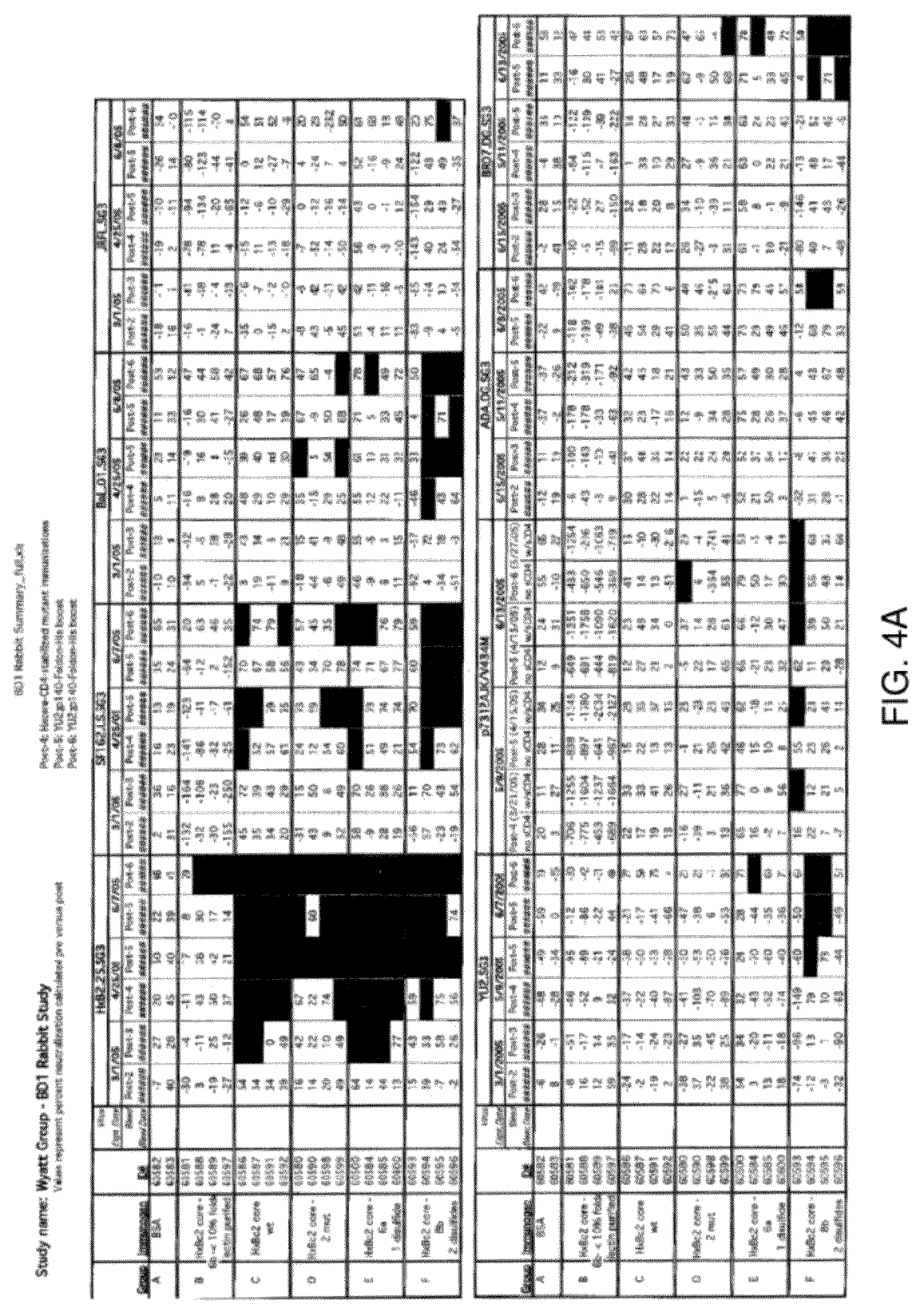
Figure 4B:
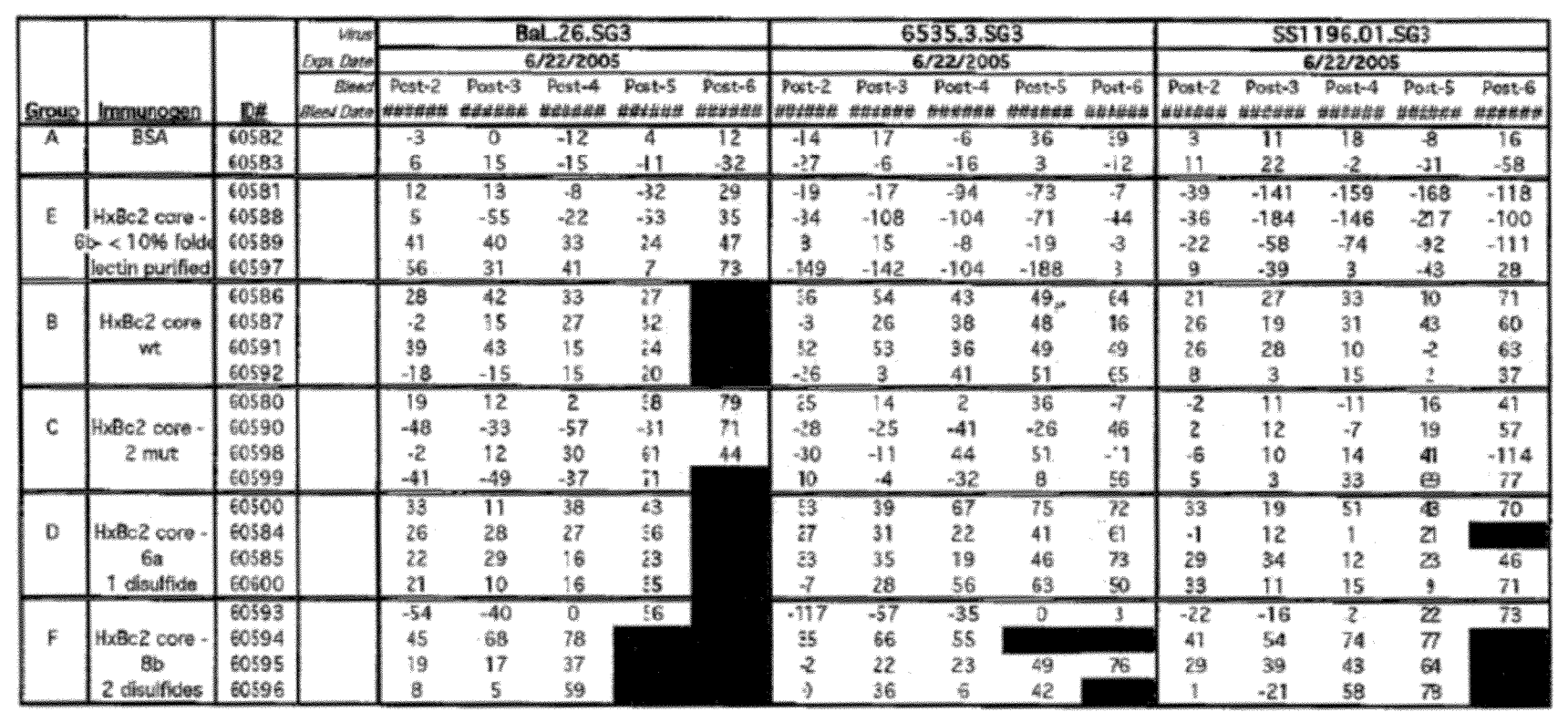
Figures 4D, 4E, 4F, 4G, 4H, 4I, 4J, 4K:
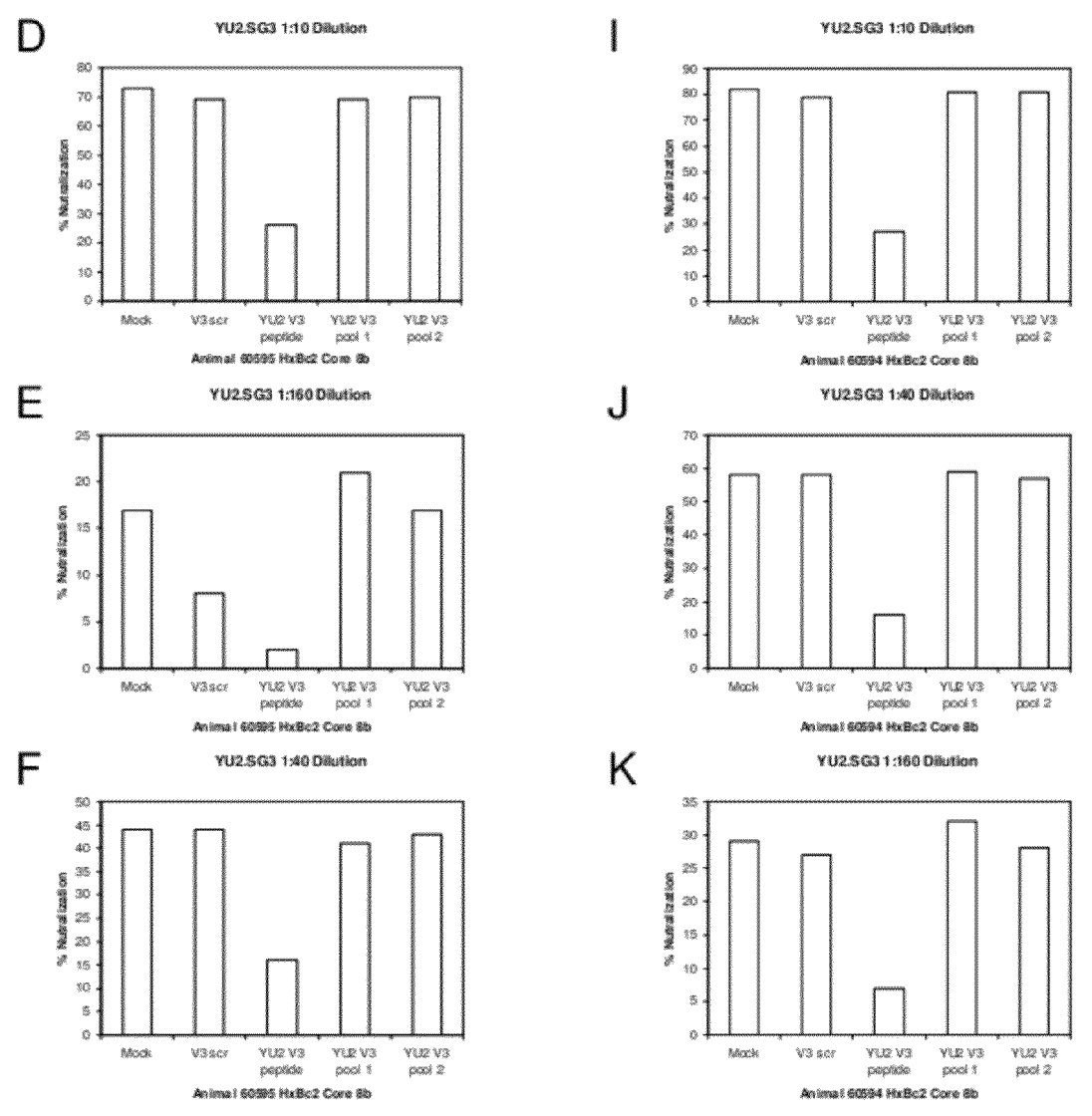
Figures 4G, 4H, 4I, 4J, 4K, 4L, 4M:
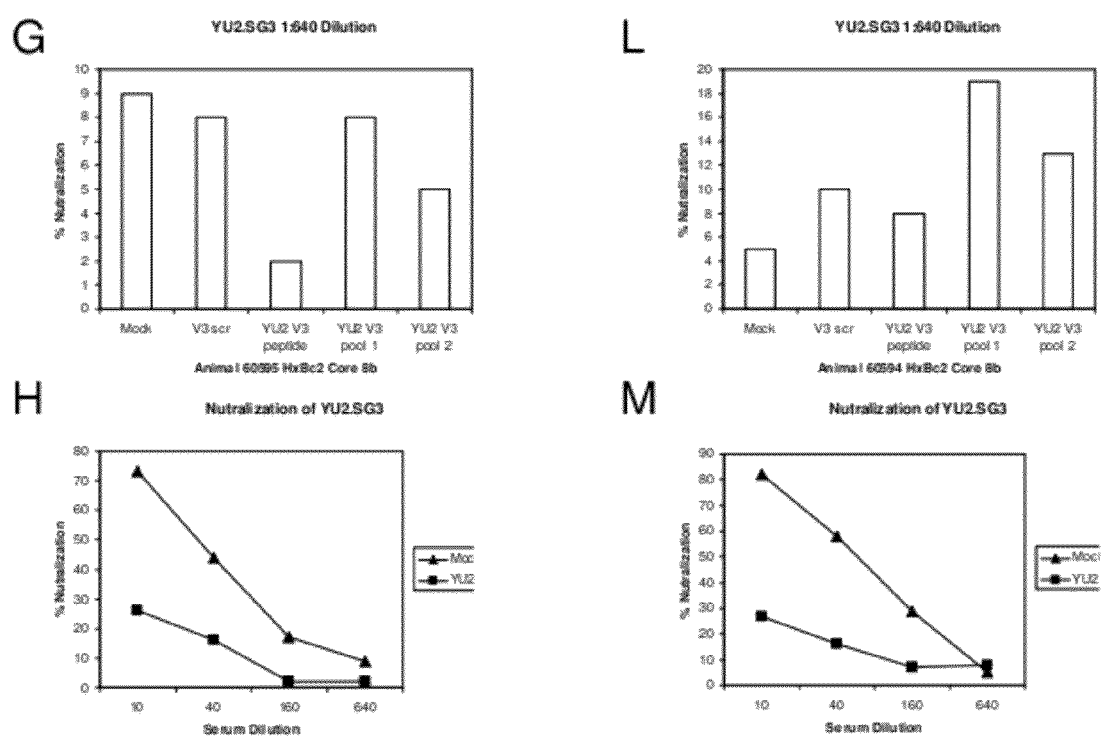

Based upon this scheme, HIV gp120 core and trimer proteins were expressed by transient transfection of 293 cells with the relevant plasmid DNA. Soluble proteins were purified from culture supernatants by affinity chromatography and maintained in PBS, pH 7.4. Each rabbit was injected at two sites by the intramuscular route in the hind leg with 50 ug of protein emulsified at 1:1 ratio in GSK AS01B adjuvant in a total volume of 1 ml. The rabbits were inoculated four times with emulsified HX wild-type or stabilized core proteins followed by two injections with the emulsified YU2 gp140 trimeric proteins. Inoculations were performed at approximate four week intervals and the immune sera were collected ten days following each injection. The presence of high-titer anti-gp120 antibodies were confirmed by ELISA. The ability to neutralize viral particles derived from selected HIV strains was determined in a luciferase-based HIV entry assay. Virus was incubated with pre- or post-immune sera and the percent neutralization in the immune sera was calculated as the decrease in entry relative to virus incubated with pre-immune sera or an irrelevant BSA protein-emulsified control. The tabulated results of the immunogenicity-neutralization are shown in FIG. 4A-B.

Example 6

Virus Neutralization

This example describes the neutralization of various HIV isolates with CD4 induced triggering.
Construction of DNA and Recombinant Adenoviruses Plasmid DNA and Ad5-based first-generation (ΔE1, ΔE3) recombinant adenoviruses expressing different V loop deletions of gp140(ΔCFI) were constructed. HIV envelope genes encoding gp145(ΔCFI) (BaL) (Genbank accession No. M68893), gp145(ΔCFI) (clade C) (Genbank accession No. AF286227), gp145(ΔCFI) (CN54) (Genbank accession No. AX149771), and gp145(ΔCFI) (clade A) (Genbank accession No. U08794) were synthesized using human-preferred codons. gp145(ΔCFI)(B)(V3/C/1AB) and gp145(ΔCFI)(B)(V3/A/1AB) were made by replacing Bal V3 loop with shortened clade C V3(1AB) and clade A V3(1AB) sequences respectively.
Vaccination Guinea pigs were intramuscularly immunized with 500 µg (in 400 µl PBS) of the gp145 version of plasmid DNA at week 0, 2, and 6. At week 14, the guinea pigs were boosted with $10^{11}$ particles (in 400 µl PBS) of recombinant replication defective adenovirus (rAd) expressing the corresponding gp140 version of the protein. Serum was collected at week –2 and week 16, aliquotted, and frozen at –20° C.
Virus Neutralization Assay Single round of infection HIV-1 Env pseudoviruses were prepared by cotransfecting 293T cells with an Env expression plasmid containing a full gp160 env gene and an env-deficient HIV-1 backbone vector (pSG3ΔEnv). Virus-containing culture supernatants were harvested 2 days after transfection, centrifuged and filtered through 0.45-micron filter, and stored at –80° C. Pseudovirus neutralization was measured as a function of Tat-induced luciferase reporter gene expression after a single round of infection in TZM-bl cells. TZM-bl cells express CD4, CXCR4 and CCR5 and contain and integrated reporter gene for firefly luciferase under the control of an HIV-1 LTR. The level of viral infection was quantified by measurement of relative luciferase units (RLU) that are directly proportion to the amount of virus inputs. Briefly, 40 ul of virus was incubated for 30 minutes at 37° C. with serial dilutions of test serum samples (10 ul) in duplicate wells of a 96-well flat bottom culture plate. The final serum dilution was defined at the point of incubation with virus supernatant. 10,000 TZM-bl cells were then added to each well in a total volume of 20 ul and plates were incubated overnight at 37° C. in a 5% CO2 incubator. One set of eight wells received mock antibody followed by virus and cells (controls wells for virus entry) and a set of eight wells received cells with mock virus (to control for luciferase background). Viral input was set at a multiplicity of infection (moi) of approximately 0.1, which generally results in 100,000 to 400,000 RLU. After over night incubation, 150 ul of fresh medium was added to each well and incubated for 24 hours at 37° C. in a 5% $CO_2$ incubator. To determine RLU, cell culture medium was aspirated from wells followed by addition of 50 ul of cell lysis buffer (Promega, Madison, Wis.). 30 ul of cell lysate was transferred to wells of a black Optiplate (PerkinElmer) for measurement of luminescence using a Perkin-Elmer Victor-light luminometer that injects 50 ul of luciferase substrate reagent to each well just prior to reading RLU. To test for sCD4 triggering, two-domain sCD4 was added to the virus just prior to the addition of sera.

Example 7

Identification of Immunogenic Fragments of gp120

This example describes the selection of immunogenic fragments of stabilized gp120.

A nucleic acid molecule encoding a stabilized p120 fragment is expressed in a host using standard techniques (see above; see Sambrook et al., Molecular Cloning; A Laboratory Manual, Cold Spring Harbor Press, Cold Spring Harbor, N.Y.: 1989). Preferable gp120 fragment is expressed such that the gp120 fragment can be isolated or purified in sufficient quantity. The stabilized gp120 fragment that are expressed are analyzed by various techniques known in the art, such as immunoblot, and ELISA, and for binding to CD4 and mAbs directed to the CD4 binding site, for example the b12 antibody.

To determine the antigenic potential of stabilized p120 fragments, subjects such as mice, rabbits or other suitable subjects are immunized with stabilized p120 fragments. Sera from such immunized subjects are tested for antibody activity for example by ELISA with the expressed polypeptide. They are also tested in a CD4 binding assay, for example by qualitative biacore, and the binding of neutralizing antibodies, for example by using the b12 antibody. Thus, antigenic fragments of stabilized forms are selected to archive broadly reactive neutralizing antibody responses.

Example 8

Conformational Masking of Stabilized Immunogens

This example describes the strategies to mask portions of a stabilized gp120 polypeptide from non-neutralizing antibodies.

The polypeptide "new 9c" as set forth as SEQ ID NO: 1 includes residues at the base of the V3 loop, and restores recognition of the core by the CD4-induced antibodies, such as 17b. Individual and combination glycan mutations were designed in the context of the stabilized gp120 polypeptides disclosed herein (for example, such as set forth in SEQ ID NO: 2 or encoded by SEQ ID NO: 4-18) to prevent the elicitation of non-neutralizing antibodies. Using site-directed mutagenesis, specific Asn and Ser/Thr residues are incorporated into the 8b core. The Asn-X-Ser/Thr residues mediate the attachment of glycans to the designated asparagine residues by mammalian cell glycosylating enzymes in the endoplasmic reticulum. This scheme is used to mask the immunogenic but non-neutralizing surfaces present in gp120.

Typically, wild-type gp120 cores elicit antibodies in rabbits that bind more efficiently to the core proteins than to full length gp120 glycoproteins. It is likely that the cores, via their truncated loops and N- and C-termini, elicit antibodies to surfaces that are not exposed in monomeric gp120.

As another aspect of an overall strategy to optimize the stabilized core priming of a trimer boost, glycans are designed at selected densities on the stabilized core to dampen or eliminate unwanted core-specific responses based upon the 8b core-b12 structure disclosed herein. The optimized and proteins are expressed, purified, analyzed and tested for immunogenicity by themselves or in sequential prime-boost with the YU2 gp140 trimers.

To mask the surface recognized by 17b and other CD4-induced antibodies the following mutations were designed:

| Mutation 1 | Mutation 2 |
|---|---|
| a. R419N | K421S |
| b. I420N | Q422S |
| c. Q422N | I424T |
| d. I423N | N425T |
| and one additional mutant to add 2 glycans | | |
| e. R419N | K421S + I423N | N425T |

To mask surfaces other than the CD4 binding site, which includes the b12 epitope region, the following N-glycan addition sites were designed:

| Glycan | Location | Mutation 1 | Mutation 2 |
|---|---|---|---|
| 1 | 246 | Q246N | |
| 2 | 267 | E267N | E269T |
| 3 | 97 | K97N | D99T |
| 4 | 103 | Q103N | H105S |
| 5 | 92 | | N94T |
| 6 | 114 | Q114N | L116T |
| 7 | 222 | G222N | A224T |
| 8 | 201 | I201N | Q203T |
| 9 | 206 | P206N | V208T |
| 10 | 423 | I423N | N425T |
| 11 | 434 | M434N | A436S |
| 12 | 442 | Q442N | R444T |
| 13 | 210 | F210N | P212T |
| Density 2 | | | |
| 1 | 246 | Q246N | |
| 2 | 97 | K97N | D99T |
| 3 | 103 | Q103N | H105S |
| 4 | 201 | I201N | Q203T |
| 5 | 206 | P206N | V208T |
| 6 | 434 | M434N | A436S |
| 7 | 442 | Q442N | R444T |
| 8 | 210 | F210N | P212T |
| 9 | 114 | Q114N | L116T |
| Density 3 | | | |
| 1 | 206 | P206N | V208T |
| 2 | 442 | Q442N | R444T |
| 3 | 114 | Q114N | L116T |
| 4 | 246 | Q246N | |
| 5 | 434 | M434N | A436S |

Mutation 1 and Mutation 2 correspond to the N glycosylation consensus sequence: NxT/S where x is anything except proline. T is better than S for glycosylation. Blanks indicate positions where no mutations are necessary. These glysolated peptides are used to induce a immune response in a subject.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated immunogen comprising a HIV-1 gp120 polypeptide or immunogenic fragment thereof stabilized in a CD4-bound conformation by crosslinked cysteines, wherein the gp120polypeptide or immunogenic fragment thereof comprises cysteines for the amino acids in at least one of residue pairs 96 and 275; 109 and 428; 123 and 431; and 231 and 267, and amino acid substitutions at positions 257 and 375, and wherein the residue numbers correspond to amino acid positions in the amino acid sequence set forth as SEQ ID NO: 27.

2. The isolated immunogen of claim 1, having a substitution of serine for the amino acid at position 257 and a substitution of tryptophan for the amino acid at position 375.

3. The isolated immunogen of claim 1, further comprising an amino acid substitution at position 95, 433, or a combination thereof.

4. The isolated immunogen of claim 3, wherein the substitution at position 95 is a tryptophan substitution and the substitution at position 433 is a methionine substitution.

5. The isolated immunogen of claim 1, wherein the gp120 polypeptide or immunogenic fragment thereof is encoded by a nucleic acid sequence set forth as one of SEQ ID NOs: 4-9 and 11-18, or any degenerate variant of SEQ ID NOs: 4-9 and 11-18.

6. The isolated immunogen of claim 1, wherein the gp120 polypeptide or immunogenic fragment thereof is encoded by a nucleic acid sequence set forth as SEQ ID NO: 10, or a degenerate variant of SEQ ID NO: 10.

7. The isolated immunogen according to claim 1, wherein the gp120 polypeptide or immunogenic fragment thereof comprises the gp120 Hxbc core of SEQ ID NO: 20, having substitutions of cysteines for the amino acids at positions 96, 109, 275, and 428.

8. The isolated immunogen according to claim 1, wherein the gp120 polypeptide or immunogenic fragment thereof comprises the gp120 Hxbc core of SEQ ID NO: 20having substitutions of cysteines for the amino acids at positions 96, 109, 275, and 428, a tryptophan for the amino acid at position 95, a serine for the amino acid at position 257, a tryptophan for the amino acid at position 375, and a methionine for the amino acid at position 433.

9. The isolated immunogen according to claim 1, wherein the immunogenic fragment comprises residues 255-421 and 436-474 of gp120 covalently linked at residues 421 and 436.

10. The isolated immunogen according to claim 9, wherein residues 421 and 436 of the immunogenic fragment are covalently linked by a peptide linker.

11. The isolated immunogen according to claim 1, wherein the gp120 polypeptide comprises at least two pairs of crosslinked cysteine residues.

12. The isolated immunogen according to claim 1, wherein the gp120 polypeptide comprises at least three pairs of crosslinked cysteine residues.

13. The isolated immunogen according to claim 1, wherein the gp120 polypeptide comprises at least four pairs of crosslinked cysteine residues.

14. The isolated immunogen according to claim 1, wherein the immunogen is further covalently linked to a carrier, Toll like receptor ligand, dendritic cell, or B cell targeting moiety.

15. The isolated immunogen according to claim 1, wherein the immunogen is glycosylated.

16. The isolated immunogen according to claim 15, wherein the immunogen is glycosylated at one or more of amino acid residue positions 92, 97, 103, 114, 201, 206, 210, 222, 246, 267, 419, 420, 422, 423, 434, or 442 of the gp120 polypeptide.

17. A composition comprising the immunogen of claim 1 and a pharmaceutically acceptable carrier.

18. A method for generating an immune response in a subject, comprising administering to the subject a therapeutically effective amount of the immunogen of claim 1, thereby generating the immune response.

19. The method of claim 18, further comprising administering a therapeutically effective amount of a polypeptide comprising:
 a) a monomeric or trimeric gp140 polypeptide;
 b) an monomeric or trimeric gp120 polypeptide; or
 c) a soluble form of CD4; or
 d) any combination of a-c, above.

20. The method of claim 18, wherein the subject is a human subject.

* * * * *

SEQUENCE LISTING

<160> NUMBER OF SEQ ID NOS: 27

<210> SEQ ID NO 1
<211> LENGTH: 324
<212> TYPE: PRT
<213> ORGANISM: Human immunodeficiency virus type 1

<400> SEQUENCE: 1

```
Val Val Leu Val Asn Val Thr Glu Asn Phe Asn Trp Cys Lys Asn Asp
1               5                  10                 15

Met Val Glu Gln Met His Glu Asp Ile Cys Ser Leu Trp Asp Gln Ser
            20                 25                 30

Leu Lys Pro Cys Val Lys Leu Cys Pro Leu Ala Gly Ala Thr Ser Val
            35                 40                 45

Ile Thr Gln Ala Cys Pro Lys Val Ser Phe Glu Pro Ile Pro Ile His
 50                 55                 60

Tyr Cys Ala Pro Ala Gly Phe Ala Ile Leu Lys Cys Asn Asn Lys Thr
 65                 70                 75                 80

Phe Asn Gly Thr Gly Pro Cys Thr Asn Val Ser Thr Val Gln Cys Thr
                85                 90                 95

His Gly Ile Arg Pro Val Val Ser Ser Gln Leu Leu Leu Asn Gly Ser
                100                105                110

Leu Ala Glu Glu Glu Val Val Ile Arg Ser Cys Asn Phe Thr Asp Asn
                115                120                125

Ala Lys Thr Ile Ile Val Gln Leu Asn Thr Ser Val Glu Ile Asn Cys
    130                135                140

Thr Arg Pro Asn Asn Gly Ser Gly Ser Gly Asn Met Arg Gln
145                150                155                160

Ala His Cys Asn Ile Ser Arg Ala Lys Trp Asn Asn Thr Leu Lys Gln
                165                170                175

Ile Ala Ser Lys Leu Arg Glu Gln Phe Gly Asn Asn Lys Thr Ile Ile
                180                185                190

Phe Lys Gln Ser Ser Gly Gly Asp Pro Glu Ile Val Thr His Trp Phe
    195                200                205

Asn Cys Gly Gly Glu Phe Phe Tyr Cys Asn Ser Thr Gln Leu Phe Asn
    210                215                220

Ser Thr Trp Phe Asn Ser Thr Trp Ser Thr Glu Gly Ser Asn Asn Thr
225                230                235                240

Glu Gly Ser Asp Thr Ile Thr Leu Pro Cys Arg Ile Lys Gln Ile Ile
                245                250                255

Asn Met Trp Cys Lys Val Cys Lys Ala Met Tyr Ala Pro Pro Ile Ser
                260                265                270

Gly Gln Ile Arg Cys Ser Ser Asn Ile Thr Gly Leu Leu Leu Thr Arg
                275                280                285

Asp Gly Gly Asn Ser Asn Asn Glu Ser Glu Ile Phe Arg Pro Gly Gly
    290                295                300

Gly Asp Met Arg Asp Asn Trp Arg Ser Glu Leu Tyr Lys Tyr Lys Val
305                310                315                320

Val Lys Ile Glu

<210> SEQ ID NO 2
<211> LENGTH: 344
<212> TYPE: PRT
<213> ORGANISM: Human immunodeficiency virus type 1

<400> SEQUENCE: 2

Gly Ala Arg Ser Glu Val Val Leu Glu Asn Val Thr Glu His Phe Asn
1               5                  10                 15

Met Trp Lys Asn Asp Met Val Glu Gln Met Gln Glu Asp Ile Ile Ser
            20                 25                 30

Leu Trp Asp Gln Ser Leu Lys Pro Cys Val Lys Leu Thr Pro Leu Cys
            35                 40                 45
```

```
Val Gly Ala Gly Ser Cys Asp Thr Ser Val Ile Thr Gln Ala Cys Pro
 50                  55                  60

Lys Ile Ser Phe Glu Pro Ile Pro Ile His Tyr Cys Ala Pro Ala Gly
 65                  70                  75                  80

Phe Ala Ile Leu Lys Cys Asn Asp Lys Thr Phe Asn Gly Lys Gly Pro
                 85                  90                  95

Cys Lys Asn Val Ser Thr Val Gln Cys Thr His Gly Ile Arg Pro Val
            100                 105                 110

Val Ser Thr Gln Leu Leu Leu Asn Gly Ser Leu Ala Glu Glu Glu Val
            115                 120                 125

Val Ile Arg Ser Asp Asn Phe Thr Asn Ala Lys Thr Ile Ile Val
        130                 135                 140

Gln Leu Lys Glu Ser Val Glu Ile Asn Cys Thr Arg Pro Asn Gln Asn
145                 150                 155                 160

Thr Arg Lys Ser Ile His Ile Gly Pro Gly Arg Ala Phe Tyr Thr Thr
                165                 170                 175

Gly Glu Ile Ile Gly Asp Ile Arg Gln Ala His Cys Asn Ile Ser Arg
                180                 185                 190

Ala Lys Trp Asn Asp Thr Leu Lys Gln Ile Val Ile Lys Leu Arg Glu
            195                 200                 205

Gln Phe Glu Asn Lys Thr Ile Val Phe Asn His Ser Ser Gly Gly Asp
            210                 215                 220

Pro Glu Ile Val Met His Ser Phe Asn Cys Gly Gly Glu Phe Phe Tyr
225                 230                 235                 240

Cys Asn Ser Ala Gln Leu Phe Asn Ser Thr Trp Asn Asn Asn Thr Glu
                245                 250                 255

Gly Ser Asn Asn Thr Glu Gly Ser Thr Ile Thr Leu Pro Cys Arg Ile
                260                 265                 270

Lys Gln Ile Ile Asn Met Trp Gln Glu Val Gly Lys Ala Met Tyr Ala
            275                 280                 285

Pro Pro Ile Arg Gly Gln Ile Arg Cys Ser Ser Asn Ile Thr Gly Leu
            290                 295                 300

Leu Leu Thr Arg Asp Gly Gly Ile Asn Glu Asn Gly Thr Glu Ile Phe
305                 310                 315                 320

Arg Pro Gly Gly Gly Asp Met Arg Asp Asn Trp Arg Ser Glu Leu Tyr
                325                 330                 335

Lys Tyr Lys Val Val Lys Ile Glu
            340

<210> SEQ ID NO 3
<211> LENGTH: 1053
<212> TYPE: DNA
<213> ORGANISM: Human immunodeficiency virus type 1

<400> SEQUENCE: 3
atgaagagag ggctctgctg tgtgctgctg ctgtgtggag cagtcttcgt ttcgcccagc      60
caggaaatcc atgcccgatt cagaagagga gccagatctg aggtggtgct ggtgaacgtg     120
accgagaact tcaacatgtg gaagaacgac atggtggagc agatgcacga ggacatcatc     180
agcctgtggg accagagcct gaagccctgc gtgaagctga ccccctgtg cgtgggcgcc      240 ggcagctgca caccagcgt gatcacccag gcctgcccca ggtgagcttc gagcccatc       300 cccatccact actgcgcccc cgccggcttc gccatcctga gtgcaacaa caagaccttc      360 aacggcaccg cccctgcac caacgtgagc accgtgcagt gcacccacgg catccgcccc      420
gtggtgagca gtcagctgct gctgaacggc agcctggccg aggaggaggt ggtgatccgc     480
```

```
agcgtgaact tcaccgacaa cgccaagacc atcatcgtgc agctgaacac cagcgtggag    540
atcaactgca ccggcgccgg ccactgcaac atcgcccgcg ccaagtggaa caacaccctg    600
aagcagatcg ccagcaagct gcgcgagcag ttcggcaaca caagaccat catcttcaag     660 cagagcagcg gcggcgaccc cgagatcgtg acccactggt tcaactgcgg cggcgagttc    720
ttctactgca acagcaccca gctgttcaac agcacctggt tcaacagcac ctggagcacc    780
gagggcagca acaacaccga gggcagcgac accatcaccc tgccctgccg catcaagcag    840
atcatcaaca tgtggcagaa ggtgggcaag gccatgtacg cccccccat cagcggccag     900 atccgctgca gcagcaacat caccggcctg ctgctgaccc gcgacggcgg caacagcaac    960
aacgagagcg agatcttccg tccgggcggc ggcgacatgc gcgacaactg gcgcagcgag    1020
ctgtacaagt acaaggtggt gaagatcgag tga                                 1053

<210> SEQ ID NO 4
<211> LENGTH: 1053
<212> TYPE: DNA
<213> ORGANISM: Human immunodeficiency virus type 1

<400> SEQUENCE: 4
atgaagagag ggctctgctg tgtgctgctg ctgtgtggag cagtcttcgt ttcgcccagc     60
caggaaatcc atgcccgatt cagaagagga gccagatctg aggtggtgct ggtgaacgtg    120
accgagaact tcaacatgtg gaagaacgac atggtggagc agatgcacga ggacatctgt    180
agcctgtggg accagagcct gaagccctgc gtgaagctga ccccctgtg cgtgggcgcc    240 ggcagctgca acaccagcgt gatcacccag gcctgcccca aggtgagctt cgagcccatc    300
cccatccact actgcgcccc cgccggcttc gccatcctga gtgcaacaa caagaccttc    360 aacggcaccg gccctgcac caacgtgagc accgtgcagt gcacccacgg catccgcccc    420
gtggtgagca gtcagctgct gctgaacggc agcctggccg aggaggaggt ggtgatccgc    480
agcgtgaact tcaccgacaa cgccaagacc atcatcgtgc agctgaacac cagcgtggag    540
atcaactgca ccggcgccgg ccactgcaac atcgcccgcg ccaagtggaa caacaccctg    600
aagcagatcg ccagcaagct gcgcgagcag ttcggcaaca caagaccat catcttcaag     660 cagagcagcg gcggcgaccc cgagatcgtg acccactggt tcaactgcgg cggcgagttc    720
ttctactgca acagcaccca gctgttcaac agcacctggt tcaacagcac ctggagcacc    780
gagggcagca acaacaccga gggcagcgac accatcaccc tgccctgccg catcaagcag    840
atcatcaaca tgtggtgtaa ggtgggcaag gccatgtacg cccccccat cagcggccag     900 atccgctgca gcagcaacat caccggcctg ctgctgaccc gcgacggcgg caacagcaac    960
aacgagagcg agatcttccg tccgggcggc ggcgacatgc gcgacaactg gcgcagcgag    1020
ctgtacaagt acaaggtggt gaagatcgag tga                                 1053

<210> SEQ ID NO 5
<211> LENGTH: 1053
<212> TYPE: DNA
<213> ORGANISM: Human immunodeficiency virus type 1

<400> SEQUENCE: 5
atgaagagag ggctctgctg tgtgctgctg ctgtgtggag cagtcttcgt ttcgcccagc     60
caggaaatcc atgcccgatt cagaagagga gccagatctg aggtggtgct ggtgaacgtg    120
accgagaact tcaacatgtg gaagaacgac atggtggagc agatgcacga ggacatcatc    180
agcctgtggg accagagcct gaagccctgc gtgaagctga ccccctgtg cgtgggcgcc    240
```

```
ggcagctgca acaccagcgt gatcacccag gcctgcccca aggtgagctt cgagcccatc    300
cccatccact actgcgcccc cgccggcttc gccatcctga agtgcaacaa ctgtaccttc    360
aacggtaccg gcccctgcac caacgtgagc accgtgcagt gcacccacgg catccgcccc    420
gtggtgagca gtcagctgct gctgaacggc agcctggcat gcgaggaggt ggtgatccgc    480
agcgtgaact tcaccgacaa cgccaagacc atcatcgtgc agctgaacac cagcgtggag    540
atcaactgca ccggcgccgg ccactgcaac atcgcccgcg ccaagtggaa caacaccctg    600
aagcagatcg ccagcaagct gcgcgagcag ttcggcaaca acaagaccat catcttcaag    660
cagagcagcg gcggcgaccc cgagatcgtg acccactggt tcaactgcgg cggcgagttc    720
ttctactgca acagcaccca gctgttcaac agcacctggt tcaacagcac ctggagcacc    780
gagggcagca acaaccga gggcagcgac accatcaccc tgccctgccg catcaagcag    840
atcatcaaca tgtggcagaa ggtgggcaag gccatgtacg cccccccat cagcggccag    900 atccgctgca gcagcaacat caccggcctg ctgctgaccc gcgacggcgg caacagcaac    960
aacgagagcg agatcttccg tccgggcggc ggcgacatgc gcgacaactg gcgcagcgag   1020
ctgtacaagt acaaggtggt gaagatcgag tga                               1053

<210> SEQ ID NO 6
<211> LENGTH: 1053
<212> TYPE: DNA
<213> ORGANISM: Human immunodeficiency virus type 1

<400> SEQUENCE: 6
atgaagagag ggctctgctg tgtgctgctg ctgtgtggag cagtcttcgt ttcgcccagc     60
caggaaatcc atgcccgatt cagaagagga gccagatctg aggtggtgct ggtgaacgtg    120
accgagaact tcaacatgtg gaagaacgac atggtggagc agatgcacga ggacatcatc    180
agcctgtggg accagagcct gaagccctgc gtgaagctgt gtcccctgtg cgtgggcgcc    240
ggcagctgca acaccagcgt gatcacccag gcctgcccca aggtgagctt cgagcccatc    300
cccatccact actgcgcccc cgccggcttc gccatcctga agtgcaacaa caagaccttc    360
aacggcaccg gcccctgcac caacgtgagc accgtgcagt gcacccacgg catccgcccc    420
gtggtgagca gtcagctgct gctgaacggc agcctggccg aggaggaggt ggtgatccgc    480
agcgtgaact tcaccgacaa cgccaagacc atcatcgtgc agctgaacac cagcgtggag    540
atcaactgca ccggcgccgg ccactgcaac atcgcccgcg ccaagtggaa caacaccctg    600
aagcagatcg ccagcaagct gcgcgagcag ttcggcaaca acaagaccat catcttcaag    660
cagagcagcg gcggcgaccc cgagatcgtg acccactggt tcaactgcgg cggcgagttc    720
ttctactgca acagcaccca gctgttcaac agcacctggt tcaacagcac ctggagcacc    780
gagggcagca acaaccga gggcagcgac accatcaccc tgccctgccg catcaagcag    840
atcatcaaca tgtggcagaa ggtgtgtaag gccatgtacg cccccccat cagcggccag    900 atccgctgca gcagcaacat caccggcctg ctgctgaccc gcgacggcgg caacagcaac    960
aacgagagcg agatcttccg tccgggcggc ggcgacatgc gcgacaactg gcgcagcgag   1020
ctgtacaagt acaaggtggt gaagatcgag tga                               1053

<210> SEQ ID NO 7
<211> LENGTH: 1053
<212> TYPE: DNA
<213> ORGANISM: Human immunodeficiency virus type 1

<400> SEQUENCE: 7
```

```
atgaagagag ggctctgctg tgtgctgctg ctgtgtggag cagtcttcgt ttcgcccagc      60
caggaaatcc atgcccgatt cagaagagga gccagatctg aggtggtgct ggtgaacgtg     120
accgagaact tcaactggtg caagaacgac atggtggagc agatgcacga ggacatctgt    180
agcctgtggg accagagcct gaagccctgc gtgaagctga ccccctgtg cgtgggcgcc     240
ggcagctgca acaccagcgt gatcacccag gcctgcccca aggtgagctt cgagcccatc    300
cccatccact actgcgcccc cgccggcttc gccatcctga agtgcaacaa caagaccttc    360
aacggcaccg cccctgcac caacgtgagc accgtgcagt gcacccacgg catccgcccc     420
gtggtgagca gtcagctgct gctgaacggc agcctggccg aggaggaggt ggtgatcaga    480
tcttgcaact tcaccgacaa cgccaagacc atcatcgtgc agctgaacac cagcgtggag    540
atcaactgca ccggcgccgg ccactgcaac atcgcccgcg ccaagtggaa caacaccctg    600
aagcagatcg ccagcaagct gcgcgagcag ttcggcaaca acaagaccat catcttcaag    660
cagagcagcg gcggcgaccc cgagatcgtg acccactggt tcaactgcgg cggcgagttc    720
ttctactgca cagcaccca gctgttcaac agcacctggt tcaacagcac ctggagcacc    780
gagggcagca acaaccga gggcagcgac accatcaccc tgccctgccg catcaagcag     840
atcattaata tgtggtgtaa ggtgggcaag atgatgtacg cccccccat cagcggccag    900
atccgctgca gcagcaacat caccggcctg ctgctgaccc cgacggcgg caacagcaac   960
aacgagagcg agatcttccg tccgggcggc ggcgacatgc gcgacaactg gcgcagcgag  1020
ctgtacaagt acaaggtggt gaagatcgag tga                              1053

<210> SEQ ID NO 8
<211> LENGTH: 1053
<212> TYPE: DNA
<213> ORGANISM: Human immunodeficiency virus type 1

<400> SEQUENCE: 8
atgaagagag ggctctgctg tgtgctgctg ctgtgtggag cagtcttcgt ttcgcccagc     60
caggaaatcc atgcccgatt cagaagagga gccagatctg aggtggtgct ggtgaacgtg    120
accgagaact tcaacatgtg gaagaacgac atggtggagc agatgcacga ggacatctgt   180
agcctgtggg accagagcct gaagccctgc gtgaagctga ccccctgtg cgtgggcgcc    240
ggcagctgca acaccagcgt gatcacccag gcctgcccca aggtgagctt cgagcccatc   300
cccatccact actgcgcccc cgccggcttc gccatcctga agtgcaacaa ctgtaccttc   360
aacggtaccg cccctgcac caacgtgagc accgtgcagt gcacccacgg catccgcccc    420
gtggtgagca gtcagctgct gctgaacggc agcctggcat gcgaggaggt ggtgatccgc   480
agcgtgaact tcaccgacaa cgccaagacc atcatcgtgc agctgaacac cagcgtggag   540
atcaactgca ccggcgccgg ccactgcaac atcgcccgcg ccaagtggaa caacaccctg   600
aagcagatcg ccagcaagct gcgcgagcag ttcggcaaca acaagaccat catcttcaag   660
cagagcagcg gcggcgaccc cgagatcgtg acccactggt tcaactgcgg cggcgagttc   720
ttctactgca cagcaccca gctgttcaac agcacctggt tcaacagcac ctggagcacc   780
gagggcagca acaaccga gggcagcgac accatcaccc tgccctgccg catcaagcag    840
atcattaata tgtggtgtaa ggtgggcaag gccatgtacg cccccccat cagcggccag    900
atccgctgca gcagcaacat caccggcctg ctgctgaccc cgacggcgg caacagcaac   960
aacgagagcg agatcttccg tccgggcggc ggcgacatgc gcgacaactg gcgcagcgag  1020
ctgtacaagt acaaggtggt gaagatcgag tga                              1053
```

<210> SEQ ID NO 9
<211> LENGTH: 1053
<212> TYPE: DNA
<213> ORGANISM: Human immunodeficiency virus type 1

<400> SEQUENCE: 9

| | | | | | |
|---|---|---|---|---|---|
| atgaagagag | ggctctgctg | tgtgctgctg | ctgtgtggag | cagtcttcgt | ttcgcccagc | 60 |
| caggaaatcc | atgcccgatt | cagaagagga | gccagatctg | aggtggtgct | ggtgaacgtg | 120 |
| accgagaact | tcaactggtg | caagaacgac | atggtggagc | agatgcacga | ggacatcatc | 180 |
| agcctgtggg | accagagcct | gaagccctgc | gtgaagctga | ccccctgtg | cgtgggcgcc | 240 |
| ggcagctgca | acaccagcgt | gatcacccag | gcctgcccca | aggtgagctt | cgagcccatc | 300 |
| cccatccact | actgcgcccc | cgccggcttc | gccatcctga | agtgcaacaa | ctgtaccttc | 360 |
| aacggtaccg | cccctgcac | caacgtgagc | accgtgcagt | gcacccacgg | catccgcccc | 420 |
| gtggtgagca | gtcagctgct | gctgaacgg | agcctggcat | gcgaggaggt | ggtgatcaga | 480 |
| tcttgcaact | tcaccgacaa | cgccaagacc | atcatcgtgc | agctgaacac | cagcgtggag | 540 |
| atcaactgca | ccggcgccgg | ccactgcaac | atcgcccgcg | ccaagtggaa | caacaccctg | 600 |
| aagcagatcg | ccagcaagct | gcgcgagcag | ttcggcaaca | caagaccat | catcttcaag | 660 |
| cagagcagcg | gcggcgaccc | cgagatcgtg | acccactggt | tcaactgcgg | cggcgagttc | 720 |
| ttctactgca | acagcaccca | gctgttcaac | agcacctggt | tcaacagcac | ctggagcacc | 780 |
| gagggcagca | acaacaccga | gggcagcgac | accatcaccc | tgccctgccg | catcaagcag | 840 |
| atcatcaata | tgtggcagaa | ggtgggcaag | atgatgtacg | ccccccccat | cagcggccag | 900 |
| atccgctgca | gcagcaacat | caccggcctg | ctgctgaccc | gcgacggcgg | caacagcaac | 960 |
| aacgagagcg | agatcttccg | tccgggcggc | ggcgacatgc | gcgacaactg | gcgcagcgag | 1020 |
| ctgtacaagt | acaaggtggt | gaagatcgag | tga | | | 1053 |

<210> SEQ ID NO 10
<211> LENGTH: 1053
<212> TYPE: DNA
<213> ORGANISM: Human immunodeficiency virus type 1

<400> SEQUENCE: 10

| | | | | | |
|---|---|---|---|---|---|
| atgaagagag | ggctctgctg | tgtgctgctg | ctgtgtggag | cagtcttcgt | ttcgcccagc | 60 |
| caggaaatcc | atgcccgatt | cagaagagga | gccagatctg | aggtggtgct | ggtgaacgtg | 120 |
| accgagaact | tcaactggtg | caagaacgac | atggtggagc | agatgcacga | ggacatctgt | 180 |
| agcctgtggg | accagagcct | gaagccctgc | gtgaagctga | ccccctgtg | cgtgggcgcc | 240 |
| ggcagctgca | acaccagcgt | gatcacccag | gcctgcccca | aggtgagctt | cgagcccatc | 300 |
| cccatccact | actgcgcccc | cgccggcttc | gccatcctga | agtgcaacaa | caagaccttc | 360 |
| aacggcaccg | cccctgcac | caacgtgagc | accgtgcagt | gcacccacgg | catccgcccc | 420 |
| gtggtgagca | gtcagctgct | gctgaacggc | agcctggccg | aggaggaggt | ggtgatcaga | 480 |
| tcttgcaact | tcaccgacaa | cgccaagacc | atcatcgtgc | agctgaacac | cagcgtggag | 540 |
| atcaactgca | ccggcgccgg | ccactgcaac | atcgcccgcg | ccaagtggaa | caacaccctg | 600 |
| aagcagatcg | ccagcaagct | gcgcgagcag | ttcggcaaca | caagaccat | catcttcaag | 660 |
| cagagcagcg | gcggcgaccc | cgagatcgtg | acccactggt | tcaactgcgg | cggcgagttc | 720 |
| ttctactgca | acagcaccca | gctgttcaac | agcacctggt | tcaacagcac | ctggagcacc | 780 |
| gagggcagca | acaacaccga | gggcagcgac | accatcaccc | tgccctgccg | catcaagcag | 840 |

| | |
|---|---:|
| atcattaata tgtggtgtaa ggtgggcaag atgatgtacg cccccccat cagcggccag | 900 |
| atccgctgca gcagcaacat caccggcctg ctgctgaccc gcgacggcgg caacagcaac | 960 |
| aacgagagcg agatcttccg tccgggcggc ggcgacatgc gcgacaactg gcgcagcgag | 1020 |
| ctgtacaagt acaaggtggt gaagatcgag tga | 1053 |

<210> SEQ ID NO 11
<211> LENGTH: 1053
<212> TYPE: DNA
<213> ORGANISM: Human immunodeficiency virus type 1

<400> SEQUENCE: 11

| | |
|---|---:|
| atgaagagag ggctctgctg tgtgctgctg ctgtgtggag cagtcttcgt ttcgcccagc | 60 |
| caggaaatcc atgcccgatt cagaagagga gccagatctg aggtggtgct ggtgaacgtg | 120 |
| accgagaact tcaacatgtg gaagaacgac atggtggagc agatgcacga ggacatctgt | 180 |
| agcctgtggg accagagcct gaagccctgc gtgaagcttt gtccctgtg cgtgggcgcc | 240 |
| ggcagctgca acaccagcgt gatcacccag gcctgcccca aggtgagctt cgagcccatc | 300 |
| cccatccact actgcgcccc cgccggcttc gccatcctga gtgcaacaa ctgtaccttc | 360 |
| aacggtaccg gcccctgcac caacgtgagc accgtgcagt gcacccacgg catccgcccc | 420 |
| gtggtgagca gtcagctgct gctgaacggc agcctggcat gcgaggaggt ggtgatccgc | 480 |
| agcgtgaact tcaccgacaa cgccaagacc atcatcgtgc agctgaacac cagcgtggag | 540 |
| atcaactgca ccggcgccgg ccactgcaac atcgcccgcg ccaagtggaa caacaccctg | 600 |
| aagcagatcg ccagcaagct gcgcgagcag ttcggcaaca acaagaccat catcttcaag | 660 |
| cagagcagcg gcggcgaccc cgagatcgtg acccactggt tcaactgcgg cggcgagttc | 720 |
| ttctactgca acagcacccc gctgttcaac agcacctggt tcaacagcac ctggagcacc | 780 |
| gagggcagca caacaccga gggcagcgac accatcaccc tgccctgccg catcaagcag | 840 |
| atcattaata tgtggtgtaa ggtgtgtaag gccatgtacg cccccccat cagcggccag | 900 |
| atccgctgca gcagcaacat caccggcctg ctgctgaccc gcgacggcgg caacagcaac | 960 |
| aacgagagcg agatcttccg tccgggcggc ggcgacatgc gcgacaactg gcgcagcgag | 1020 |
| ctgtacaagt acaaggtggt gaagatcgag tga | 1053 |

<210> SEQ ID NO 12
<211> LENGTH: 1053
<212> TYPE: DNA
<213> ORGANISM: Human immunodeficiency virus type 1

<400> SEQUENCE: 12

| | |
|---|---:|
| atgaagagag ggctctgctg tgtgctgctg ctgtgtggag cagtcttcgt ttcgcccagc | 60 |
| caggaaatcc atgc

| | | |
|---|---|---|
| aagcagatcg ccagcaagct gcgcgagcag ttcggcaaca acaagaccat catcttcaag | 660 | |
| cagagcagcg gcggcgaccc cgagatcgtg acccactggt tcaactgcgg cggcgagttc | 720 | |
| ttctactgca acagcaccca gctgttcaac agcacctggt tcaacagcac ctggagcacc | 780 | |
| gagggcagca acaaccga gggcagcgac accatcaccc tgccctgccg catcaagcag | 840 | |
| atcattaata tgtggtgtaa ggtgtgtaag atgatgtacg ccccccgat atcaggccag | 900 | |
| atccgctgca gcagcaacat caccggcctg ctgctgaccc gcgacggcgg caacagcaac | 960 | |
| aacgagagcg agatcttccg tccgggcggc ggcgacatgc gcgacaactg gcgcagcgag | 1020 | |
| ctgtacaagt acaaggtggt gaagatcgag tga | 1053 | |

<210> SEQ ID NO 13
<211> LENGTH: 1053
<212> TYPE: DNA
<213> ORGANISM: Human immunodeficiency virus type 1

<400> SEQUENCE: 13

| | | |
|---|---|---|
| atgaagagag ggctctgctg tgtgctgctg ctgtgtggag cagtcttcgt ttcgcccagc | 60 | |
| caggaaatcc atgcccgatt cagaagagga gccagatctg aggtggtgct ggtgaacgtg | 120 | |
| accgagaact tcaactggtg caagaacgac atggtggagc agatgcacga ggacatcatc | 180 | |
| agcctgtggg accagagcct gaagccctgc gtgaagcttt gtcccctgtg cgtgggcgcc | 240 | |
| ggcagctgca acaccagcgt gatcacccag gcctgcccca aggtgagctt cgagcccatc | 300 | |
| cccatccact actgcgcccc cgccggcttc gccatcctga agtgcaacaa ctgtaccttc | 360 | |
| aacggtaccg cccctgcac caacgtgagc accgtgcagt gcacccacgg catccgcccc | 420 | |
| gtggtgagca gtcagctgct gctgaacggc agcctggcat gcgaggaggt ggtgatcaga | 480 | |
| tcttgcaact tcaccgacaa cgccaagacc atcatcgtgc agctgaacac cagcgtggag | 540 | |
| atcaactgca ccggcgccgg ccactgcaac atcgcccgcg ccaagtggaa caacaccctg | 600 | |
| aagcagatcg ccagcaagct gcgcgagcag ttcggcaaca acaagaccat catcttcaag | 660 | |
| cagagcagcg gcggcgaccc cgagatcgtg acccactggt tcaactgcgg cggcgagttc | 720 | |
| ttctactgca acagcaccca gctgttcaac agcacctggt tcaacagcac ctggagcacc | 780 | |
| gagggcagca acaaccga gggcagcgac accatcaccc tgccctgccg catcaagcag | 840 | |
| atcatcaaca tgtggcagaa ggtgtgtaag gccatgtacg ccccccccat cagcggccag | 900 | |
| atccgctgca gcagcaacat caccggcctg ctgctgaccc gcgacggcgg caacagcaac | 960 | |
| aacgagagcg agatcttccg tccgggcggc ggcgacatgc gcgacaactg gcgcagcgag | 1020 | |
| ctgtacaagt acaaggtggt gaagatcgag tga | 1053 | |

<210> SEQ ID NO 14
<211> LENGTH: 1053
<212> TYPE: DNA
<213> ORGANISM: Human immunodeficiency virus type 1

<400> SEQUENCE: 14

| | | |
|---|---|---|
| atgaagagag ggctctgctg tgtgctgctg ctgtgtggag cagtcttcgt ttcgcccagc | 60 | |
| caggaaatcc atgcccgatt cagaagagga gccagatctg aggtggtgct ggtgaacgtg | 120 | |
| accgagaact tcaactggtg caagaacgac atggtggagc agatgcacga ggacatctgt | 180 | |
| agcctgtggg accagagcct gaagccctgc gtgaagctgt gtcccctgtg cgtgggcgcc | 240 | |
| ggcagctgca acaccagcgt gatcacccag gcctgcccca aggtgagctt cgagcccatc | 300 | |
| cccatccact actgcgcccc cgctggcttc gccatcctga agtgcaacaa caagaccttc | 360 | |

| | |
|---|---|
| aacggcaccg gcccctgcac caacgtgagc accgtgcagt gcacccacgg catccgcccc | 420 |
| gtggtgagca gtcagctgct gctgaacggc agcctggccg aggaggaggt ggtgatcaga | 480 |
| tcttgcaact tcaccgacaa cgccaagacc atcatcgtgc agctgaacac cagcgtggag | 540 |
| atcaactgca ccggcgccgg ccactgcaac atcgcccgcg ccaagtggaa caacaccctg | 600 |
| aagcagatcg ccagcaagct gcgcgagcag ttcggcaaca acaagaccat catcttcaag | 660 |
| cagagcagcg gcggcgaccc cgagatcgtg acccactggt tcaactgcgg cggcgagttc | 720 |
| ttctactgca acagcaccca gctgttcaac agcacctggt tcaacagcac ctggagcacc | 780 |
| gagggcagca acaaccccga gggcagcgac accatcaccc tgccctgccg catcaagcag | 840 |
| atcatcaaca tgtggtgtaa ggtgtgtaag gccatgtacg ccccccccat cagcggccag | 900 |
| atccgctgca gcagcaacat caccggcctg ctgctgaccc gcgacggcgg caacagcaac | 960 |
| aacgagagcg agatcttccg tccgggcggc ggcgacatgc gcgacaactg gcgcagcgag | 1020 |
| ctgtacaagt acaaggtggt gaagatcgag tga | 1053 |

<210> SEQ ID NO 15
<211> LENGTH: 1053
<212> TYPE: DNA
<213> ORGANISM: Human immunodeficiency virus type 1

<400> SEQUENCE: 15

| | |
|---|---|
| atgaagagag ggctctgctg tgtgctgctg ctgtgtggag cagtcttcgt ttcgcccagc | 60 |
| caggaaatcc atgcccgatt cagaagagga gccagatctg aggtggtgct ggtgaacgtg | 120 |
| accgagaact tcaactggtg caagaacgac atggtggagc agatgcacga ggacatctgt | 180 |
| agcctgtggg accagagcct gaagccctgc gtgaagctga cccccctgtg cgtgggcgcc | 240 |
| ggcagctgca acaccagcgt gatcacccag gcctgcccca aggtgagctt cgagcccatc | 300 |
| cccatccact actgcgcccc cgccggcttc gccatcctga gtgcaacaa ctgtaccttc | 360 |
| aacggtaccg gcccctgcac caacgtgagc accgtgcagt gcacccacgg catccgcccc | 420 |
| gtggtgagca gtcagctgct gctgaacggc agcctggcat gcgaggaggt ggtgatcaga | 480 |
| tcttgcaact tcaccgacaa cgccaagacc atcatcgtgc agctgaacac cagcgtggag | 540 |
| atcaactgca ccggcgccgg ccactgcaac atcgcccgcg ccaagtggaa caacaccctg | 600 |
| aagcagatcg ccagcaagct gcgcgagcag ttcggcaaca acaagaccat catcttcaag | 660 |
| cagagcagcg gcggcgaccc cgagatcgtg acccactggt tcaactgcgg cggcgagttc | 720 |
| ttctactgca acagcaccca gctgttcaac agcacctggt tcaacagcac ctggagcacc | 780 |
| gagggcagca acaaccccga gggcagcgac accatcaccc tgccctgccg catcaagcag | 840 |
| atcattaata tgtggtgtaa ggtgggcaag atgatgtacg ccccccccat cagcggccag | 900 |
| atccgctgca gcagcaacat caccggcctg ctgctgaccc gcgacggcgg caacagcaac | 960 |
| aacgagagcg agatcttccg tccgggcggc ggcgacatgc gcgacaactg gcgcagcgag | 1020 |
| ctgtacaagt acaaggtggt gaagatcgag tga | 1053 |

<210> SEQ ID NO 16
<211> LENGTH: 1054
<212> TYPE: DNA
<213> ORGANISM: Human immunodeficiency virus type 1

<400> SEQUENCE: 16

| | |
|---|---|
| atgaagagag ggctctgctg tgtgctgctg ctgtgtggag cagtcttcgt ttcgcccagc | 60 |
| caggaaatcc atgcccgatt cagaagagga gccagatctg aggtggtgct ggtgaacgtg | 120 |

```
accgagaact tcaactggtg caagaacgac atggtggagc agatgcacga ggacatctgt     180
agcctgtggg accagagcct gaagccctgc gtgaagctgt gtccctgtg cgtgggcgcc     240 ggcagctgca acaccagcgt gatcacccag gcctgcccca aggtgagctt cgagcccatc     300
cccatccact actgcgcccc cgctggcttc gccatcctga agtgcaacaa caagaccttc     360
aacggcaccg cccctgcac caacgtgagc accgtgcagt gcacccacgg catccgcccc     420
gtggtgagca gtcagctgct gctgaacggc agcctggccg aggaggaggt ggtgatcaga     480
tcttgcaact tcaccgacaa cgccaagacc atcatcgtgc agctgaacac cagcgtggag     540
atcaactgca ccggcgccgg ccactgcaac atcgcccgcg ccaagtggaa caacaccctg     600
aagcagatcg ccagcaagct gcgcgagcag ttcggcaaca acaagaccat catcttcaag     660
cagagcagcg gcggcgaccc cgagatcgtg acccactggt tcaactgcgg cggcgagttc     720
ttctactgca acagcaccca gctgttcaac agcacctggt tcaacagcac ctggagcacc     780
gagggcagca acaacaccga gggcagcgac accatcaccc tgccctgccg catcaagcag     840
atcatcaaca tgtggtgtaa ggtgtgtaag atgatgtacg ccccccccat cagcggccag     900
atccgctgca gcagcaacat caccggcctg ctgctgaccc gcgacggcgg caacagcaac     960
aacgagagcg agatcttccg tccgggcggc ggcgacatgc gcgacaactg gcgcagcgag    1020
ctgtacaagt acaaggtggt gaagatcgag tgag                                1054

<210> SEQ ID NO 17
<211> LENGTH: 1053
<212> TYPE: DNA
<213> ORGANISM: Human immunodeficiency virus type 1

<400> SEQUENCE: 17
atgaagagag ggctctgctg tgtgctgctg ctgtgtggag cagtcttcgt ttcgcccagc      60
caggaaatcc atgcccgatt cagaagagga gccagatctg aggtggtgct ggtgaacgtg     120
accgagaact tcaactggtg caagaacgac atggtggagc agatgcacga ggacatcatc     180
agcctgtggg accagagcct gaagccctgc gtgaagcttt gtccctgtg cgtgggcgcc     240 ggcagctgca acaccagcgt gatcacccag gcctgcccca aggtgagctt cgagcccatc     300
cccatccact actgcgcccc cgccggcttc gccatcctga agtgcaacaa ctgtaccttc     360
aacggtaccg cccctgcac caacgtgagc accgtgcagt gcacccacgg catccgcccc     420
gtggtgagca gtcagctgct gctgaacggc agcctggcat gcgaggaggt ggtgatcaga     480
tcttgcaact tcaccgacaa cgccaagacc atcatcgtgc agctgaacac cagcgtggag     540
atcaactgca ccggcgccgg ccactgcaac atcgcccgcg ccaagtggaa caacaccctg     600
aagcagatcg ccagcaagct gcgcgagcag ttcggcaaca acaagaccat catcttcaag     660
cagagcagcg gcggcgaccc cgagatcgtg acccactggt tcaactgcgg cggcgagttc     720
ttctactgca acagcaccca gctgttcaac agcacctggt tcaacagcac ctggagcacc     780
gagggcagca acaacaccga gggcagcgac accatcaccc tgccctgccg catcaagcag     840
atcatcaata tgtggcagaa ggtgtgtaag gccatgtacg ccccccccat cagcggccag     900
atccgctgca gcagcaacat caccggcctg ctgctgaccc gcgacggcgg caacagcaac     960
aacgagagcg agatcttccg tccgggcggc ggcgacatgc gcgacaactg gcgcagcgag    1020
ctgtacaagt acaaggtggt gaagatcgag tga                                 1053

<210> SEQ ID NO 18
<211> LENGTH: 1053
```

<212> TYPE: DNA
<213> ORGANISM: Human immunodeficiency virus type 1

<400> SEQUENCE: 18
atgaagagag ggctctgctg tgtgctgctg ctgtgtggag cagtcttcgt ttcgcccagc 60
caggaaatcc atgcccgatt cagaagagga gccagatctg aggtggtgct ggtgaacgtg 120
accgagaact tcaactggtg caagaacgac atggtggagc agatgcacga ggacatctgt 180
agcctgtggg accagagcct gaagccctgc gtgaagctgt gtcccctgtg cgtgggcgcc 240
ggcagctgca acaccagcgt gatcacccag gcctgcccca aggtgagctt cgagcccatc 300
cccatccact actgcgcccc cgccggcttc gccatcctga agtgcaacaa ctgtaccttc 360
aacggtaccg gcccctgcac caacgtgagc accgtgcagt gcacccacgg catccgcccc 420
gtggtgagca gtcagctgct gctgaacggc agcctggcat gcgaggaggt ggtgatcaga 480
tcttgcaact tcaccgacaa cgccaagacc atcatcgtgc agctgaacac cagcgtggag 540
atcaactgca ccggcgccgg ccactgcaac atcgcccgcg ccaagtggaa caacaccctg 600
aagcagatcg ccagcaagct gcgcgagcag ttcggcaaca acaagaccat catcttcaag 660
cagagcagcg gcggcgaccc cgagatcgtg acccactggt tcaactgcgg cggcgagttc 720
ttctactgca acagcaccca gctgttcaac agcacctggt tcaacagcac ctggagcacc 780
gagggcagca acaacaccga gggcagcgac accatcaccc tgccctgccg catcaagcag 840
atcatcaaca tgtggtgtaa ggtgtgtaag gccatgtacg ccccccccat cagcggccag 900
atccgctgca gcagcaacat caccggcctg ctgctgaccc gcgacggcgg caacagcaac 960
aacgagagcg agatcttccg tccgggcggc ggcgacatgc gcgacaactg gcgcagcgag 1020
ctgtacaagt acaaggtggt gaagatcgag tga 1053

<210> SEQ ID NO 19
<211> LENGTH: 1053
<212> TYPE: DNA
<213> ORGANISM: Human immunodeficiency virus type 1

<400> SEQUENCE: 19
atgaagagag ggctctgctg tgtgctgctg ctgtgtggag cagtcttcgt ttcgcccagc 60
caggaaatcc atgcccgatt cagaagagga gccagatctg aggtggtgct ggtgaacgtg 120
accgagaact tcaacatgtg gaagaacgac atggtggagc agatgcacga ggacatcatc 180
agcctgtggg accagagcct gaagccctgc gtgaagctga ccccccctgtg cgtgggcgcc 240
ggcagctgca acaccagcgt gatcacccag gcctgcccca aggtgagctt cgagcccatc 300
cccatccact actgcgcccc cgccggcttc gccatcctga agtgcaacaa caagaccttc 360
aacggcaccg gcccctgcac caacgtgagc accgtgcagt gcacccacgg catccgcccc 420
gtggtgagca cccagctgct gctgaacggc agcctggccg aggaggaggt ggtgatccgc 480
agcgtgaact tcaccgacaa cgccaagacc atcatcgtgc agctgaacac cagcgtggag 540
atcaactgca ccggcgccgg ccactgcaac atcgcccgcg ccaagtggaa caacaccctg 600
aagcagatcg ccagcaagct gcgcgagcag ttcggcaaca acaagaccat catcttcaag 660
cagagcagcg gcggcgaccc cgagatcgtg acccacagct tcaactgcgg cggcgagttc 720
ttctactgca acagcaccca gctgttcaac agcacctggt tcaacagcac ctggagcacc 780
gagggcagca acaacaccga gggcagcgac accatcaccc tgccctgccg catcaagcag 840
atcatcaaca tgtggcagaa ggtgggcaag gccatgtacg ccccccccat cagcggccag 900
atccgctgca gcagcaacat caccggcctg ctgctgaccc gcgacggcgg caacagcaac 960
aacgagagcg agatcttccg tccgggcggc ggcgacatgc gcgacaactg gcgcagcgag    1020
ctgtacaagt acaaggtggt gaagatcgag tga                                 1053

<210> SEQ ID NO 20
<211> LENGTH: 317
<212> TYPE: PRT
<213> ORGANISM: Human immunodeficiency virus type 1

<400> SEQUENCE: 20

Glu Val Val Leu Val Asn Val Thr Glu Asn Phe Asn Met Trp Lys Asn
1               5                   10                  15

Asp Met Val Glu Gln Met His Glu Asp Ile Ile Ser Leu Trp Asp Gln
            20                  25                  30

Ser Leu Lys Pro Cys Val Lys Leu Thr Pro Leu Cys Val Gly Ala Gly
        35                  40                  45

Ser Cys Asn Thr Ser Val Ile Thr Gln Ala Cys Pro Lys Val Ser Phe
    50                  55                  60

Glu Pro Ile Pro Ile His Tyr Cys Ala Pro Ala Gly Phe Ala Ile Leu
65                  70                  75                  80

Lys Cys Asn Asn Lys Thr Phe Asn Gly Thr Gly Pro Cys Thr Asn Val
                85                  90                  95

Ser Thr Val Gln Cys Thr His Gly Ile Arg Pro Val Val Ser Thr Gln
            100                 105                 110

Leu Leu Leu Asn Gly Ser Leu Ala Glu Glu Val Val Ile Arg Ser
        115                 120                 125

Val Asn Phe Thr Asp Asn Ala Lys Thr Ile Ile Val Gln Leu Asn Thr
    130                 135                 140

Ser Val Glu Ile Asn Cys Thr Gly Ala Gly His Cys Asn Ile Ser Arg
145                 150                 155                 160

Ala Lys Trp Asn Asn Thr Leu Lys Gln Ile Ala Ser Lys Leu Arg Glu
                165                 170                 175

Gln Phe Gly Asn Asn Lys Thr Ile Ile Phe Lys Gln Ser Ser Gly Gly
            180                 185                 190

Asp Pro Glu Ile Val Thr His Ser Phe Asn Cys Gly Gly Glu Phe Phe
        195                 200                 205

Tyr Cys Asn Ser Thr Gln Leu Phe Asn Ser Thr Trp Phe Asn Ser Thr
    210                 215                 220

Trp Ser Thr Glu Gly Ser Asn Asn Thr Glu Gly Ser Asp Thr Ile Thr
225                 230                 235                 240

Leu Pro Cys Arg Ile Lys Gln Ile Ile Asn Met Trp Gln Lys Val Gly
                245                 250                 255

Lys Ala Met Tyr Ala Pro Pro Ile Ser Gly Gln Ile Arg Cys Ser Ser
            260                 265                 270

Asn Ile Thr Gly Leu Leu Leu Thr Arg Asp Gly Gly Asn Ser Asn Asn
        275                 280                 285

Glu Ser Glu Ile Phe Arg Pro Gly Gly Gly Asp Met Arg Asp Asn Trp
    290                 295                 300

Arg Ser Glu Leu Tyr Lys Tyr Lys Val Val Lys Ile Glu
305                 310                 315

<210> SEQ ID NO 21
<211> LENGTH: 35
<212> TYPE: PRT
<213> ORGANISM: Human immunodeficiency virus type 1

<400> SEQUENCE: 21

```
Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 22
<211> LENGTH: 36
<212> TYPE: PRT
<213> ORGANISM: Human immunodeficiency virus type 1

<400> SEQUENCE: 22

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

<210> SEQ ID NO 23
<211> LENGTH: 35
<212> TYPE: PRT
<213> ORGANISM: Human immunodeficiency virus type 1

<400> SEQUENCE: 23

Cys Thr Arg Pro Asn Asn Asn Thr Arg Lys Ser Ile Arg Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 24
<211> LENGTH: 35
<212> TYPE: PRT
<213> ORGANISM: Human immunodeficiency virus type 1

<400> SEQUENCE: 24

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 25
<211> LENGTH: 35
<212> TYPE: PRT
<213> ORGANISM: Human immunodeficiency virus type 1

<400> SEQUENCE: 25

Cys Thr Arg Pro Asn Asn Asn Thr Arg Lys Ser Ile Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 26
```

<211> LENGTH: 1077
<212> TYPE: DNA
<213> ORGANISM: Human immunodeficiency virus type 1

<400> SEQUENCE: 26

```
atgaagagag ggctctgctg tgtgctgctg ctgtgtggag cagtcttcgt ttcgcccagc    60
caggaaatcc atgcccgatt cagaagagga gccagatctg aggtggtgct ggtgaacgtg   120
accgagaact tcaactggtg caagaacgac atggtggagc agatgcacga ggacatctgt   180
agcctgtggg accagagcct gaagccctgc gtgaagctgt gtcctctggc cggcgccacc   240
agcgtgatca cccaggcctg ccccaaggtg agcttcgagc ccatccccat ccactactgc   300
gcccccgctg gcttcgccat cctgaagtgc aacaacaaga ccttcaacgg caccggcccc   360
tgcaccaacg tgagcaccgt gcagtgcacc cacggcatcc gccccgtggt gagcagtcag   420
ctgctgctga acggcagcct ggccgaggag gaggtggtga tcagatcttg caacttcacc   480
gacaacgcca agaccatcat cgtgcagctg aacaccagcg tggagatcaa ctgcaccccgc  540
cccaacaacg gcggcagcgg cagcggcggc aacatgcgcc aggcccactg caacatcagc   600
cgcgccaagt ggaacaacac cctgaagcag atcgccagca gctgcgcga gcagttcggc   660
aacaacaaga ccatcatctt caagcagagc agcggcggcg accccgagat cgtgacccac   720
tggttcaact gcggcggcga gttcttctac tgcaacagca cccagctgtt caacagcacc   780
tggttcaaca gcacctggag caccgagggc agcaacaaca ccgagggcag cgacaccatc   840
accctgccct gccgcatcaa gcagatcatc aacatgtggt gtaaggtgtg taaggccatg   900
tacgccccc ccatcagcgg ccagatccgc tgcagcagca acatcaccgg cctgctgctg   960
acccgcgacg gcggcaacag caacaacgag agcgagatct ccgtccgggg cggcggcgac  1020
atgcgcgaca ctggcgcag cgagctgtac aagtacaagg tggtgaagat cgagtga     1077
```

<210> SEQ ID NO 27
<211> LENGTH: 478
<212> TYPE: PRT
<213> ORGANISM: Human immunodeficiency virus

<400> SEQUENCE: 27

```
Leu Trp Val Thr Val Tyr Tyr Gly Val Pro Val Trp Lys Glu Ala Thr
 1               5                  10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Val Leu Val Asn Val Thr Glu Asn Phe Asn Met Trp Lys
    50                  55                  60

Asn Asp Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Ser Leu
                85                  90                  95

Lys Cys Thr Asp Leu Lys Asn Asp Thr Asn Thr Asn Ser Ser Ser Gly
            100                 105                 110

Arg Met Ile Met Glu Lys Gly Glu Ile Lys Asn Cys Ser Phe Asn Ile
        115                 120                 125

Ser Thr Ser Ile Arg Gly Lys Val Gln Lys Glu Tyr Ala Phe Phe Tyr
    130                 135                 140

Lys Leu Asp Ile Ile Pro Ile Asp Asn Asp Thr Thr Ser Tyr Lys Leu
145                 150                 155                 160
```

-continued

```
Thr Ser Cys Asn Thr Ser Val Ile Thr Gln Ala Cys Pro Lys Val Ser
            165                 170                 175

Phe Glu Pro Ile Pro Ile His Tyr Cys Ala Pro Ala Gly Phe Ala Ile
            180                 185                 190

Leu Lys Cys Asn Asn Lys Thr Phe Asn Gly Thr Gly Pro Cys Thr Asn
            195                 200                 205

Val Ser Thr Val Gln Cys Thr His Gly Ile Arg Pro Val Val Ser Thr
            210                 215                 220

Gln Leu Leu Leu Asn Gly Ser Leu Ala Glu Glu Glu Val Val Ile Arg
225                 230                 235                 240

Ser Val Asn Phe Thr Asp Asn Ala Lys Thr Ile Ile Val Gln Leu Asn
            245                 250                 255

Thr Ser Val Glu Ile Asn Cys Thr Arg Pro Asn Asn Asn Thr Arg Lys
            260                 265                 270

Arg Ile Arg Ile Gln Arg Gly Pro Gly Arg Ala Phe Val Thr Ile Gly
            275                 280                 285

Lys Ile Gly Asn Met Arg Gln Ala His Cys Asn Ile Ser Arg Ala Lys
            290                 295                 300

Trp Asn Asn Thr Leu Lys Gln Ile Ala Ser Lys Leu Arg Glu Gln Phe
305                 310                 315                 320

Gly Asn Asn Lys Thr Ile Ile Phe Lys Gln Ser Ser Gly Gly Asp Pro
            325                 330                 335

Glu Ile Val Thr His Ser Phe Asn Cys Gly Gly Glu Phe Phe Tyr Cys
            340                 345                 350

Asn Ser Thr Gln Leu Phe Asn Ser Thr Trp Phe Asn Ser Thr Trp Ser
            355                 360                 365

Thr Glu Gly Ser Asn Asn Thr Glu Gly Ser Asp Thr Ile Thr Leu Pro
            370                 375                 380

Cys Arg Ile Lys Gln Ile Ile Asn Met Trp Gln Lys Val Gly Lys Ala
385                 390                 395                 400

Met Tyr Ala Pro Pro Ile Ser Gly Gln Ile Arg Cys Ser Ser Asn Ile
            405                 410                 415

Thr Gly Leu Leu Leu Thr Arg Asp Gly Gly Asn Ser Asn Asn Glu Ser
            420                 425                 430

Glu Ile Phe Arg Pro Gly Gly Gly Asp Met Arg Asp Asn Trp Arg Ser
            435                 440                 445

Glu Leu Tyr Lys Tyr Lys Val Val Lys Ile Glu Pro Leu Gly Val Ala
            450                 455                 460

Pro Thr Lys Ala Lys Arg Arg Val Val Gln Arg Glu Lys Arg
465                 470                 475
```